US011230571B2

United States Patent
Le Hir de Fallois et al.

(10) Patent No.: US 11,230,571 B2
(45) Date of Patent: *Jan. 25, 2022

(54) ANTHELMINTIC DEPSIPEPTIDE COMPOUNDS

(71) Applicant: BOEHRINGER INGELHEIM ANIMAL HEALTH USA INC., Duluth, GA (US)

(72) Inventors: Loic Le Hir de Fallois, Atlanta, GA (US); Greg Pacofsky, Raleigh, NC (US); Alan Long, Flowery Branch, GA (US); Charles Q. Meng, Grayson, GA (US); Hyoung Ik Lee, Cary, NC (US)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/392,412

(22) Filed: Apr. 23, 2019

(65) Prior Publication Data

US 2019/0248840 A1    Aug. 15, 2019

Related U.S. Application Data

(62) Division of application No. 15/378,219, filed on Dec. 14, 2016, now Pat. No. 10,344,056.

(60) Provisional application No. 62/272,040, filed on Dec. 28, 2015.

(51) Int. Cl.
| | |
|---|---|
| *C07K 11/02* | (2006.01) |
| *A61K 38/15* | (2006.01) |
| *A61K 45/06* | (2006.01) |
| *A61P 33/00* | (2006.01) |
| *A61P 33/10* | (2006.01) |
| *A61P 43/00* | (2006.01) |
| *C07D 413/14* | (2006.01) |
| *A01N 43/72* | (2006.01) |
| *C07D 273/00* | (2006.01) |

(52) U.S. Cl.
CPC .............. *C07K 11/02* (2013.01); *A01N 43/72* (2013.01); *A61K 38/15* (2013.01); *A61K 45/06* (2013.01); *C07D 273/00* (2013.01); *C07D 413/14* (2013.01)

(58) Field of Classification Search
CPC ........ A01N 43/72; A61K 38/15; A61K 45/06; A61P 33/00; A61P 33/10; A61P 43/00; C07D 273/00; C07D 413/14; C07K 11/02
See application file for complete search history.

(56) References Cited

U.S. PATENT DOCUMENTS

| | | | |
|---|---|---|---|
| 5,116,815 A | 5/1992 | Takagi et al. | |
| 5,514,773 A | 5/1996 | Nishiyama et al. | |
| 5,589,503 A | 12/1996 | Mencke et al. | |
| 5,646,244 A | 7/1997 | Nishiyama et al. | |
| 5,717,063 A | 2/1998 | Scherkenbeck et al. | |
| 5,747,448 A | 5/1998 | Ohyama et al. | |
| 5,777,075 A | 7/1998 | Scherkenbeck et al. | |
| 5,856,346 A | 1/1999 | Nishiyama et al. | |
| 5,874,530 A | 2/1999 | Scherkenbeck et al. | |
| 6,159,932 A | 12/2000 | Mencke et al. | |
| 6,235,875 B1 | 5/2001 | Yamanishi et al. | |
| 6,265,537 B1 | 7/2001 | Jeschke et al. | |
| 6,329,338 B1 | 12/2001 | Sakanata et al. | |
| 6,355,615 B1 | 3/2002 | Dyker et al. | |
| 6,468,966 B1 | 10/2002 | Scherkenbeck et al. | |
| 6,630,569 B1 | 10/2003 | Jeschke et al. | |
| 6,828,300 B2 | 12/2004 | Dyker et al. | |
| 6,900,176 B2 | 5/2005 | Dyker et al. | |
| 7,763,583 B2 | 7/2010 | Kanikanti et al. | |
| 7,914,816 B2 | 3/2011 | Kalbe et al. | |
| 8,440,612 B2 | 5/2013 | Greif et al. | |
| 8,440,613 B2 | 5/2013 | Harder et al. | |
| 2003/0125244 A1 | 7/2003 | Kaibe et al. | |
| 2004/0115483 A1 | 6/2004 | Kaibe et al. | |
| 2009/0215678 A1 | 8/2009 | Bach et al. | |
| 2011/0046072 A1 | 2/2011 | Kanikanti et al. | |
| 2011/0201550 A1 | 8/2011 | Harder et al. | |
| 2012/0302496 A1 | 11/2012 | Harder et al. | |
| 2014/0371139 A1 | 12/2014 | Kanikanti et al. | |
| 2015/0166608 A1 | 6/2015 | Mitomi et al. | |

FOREIGN PATENT DOCUMENTS

| | | |
|---|---|---|
| AU | 768910 B2 | 1/2004 |
| CA | 2876387 A1 | 12/2013 |
| EP | 0626375 A1 | 11/1994 |

(Continued)

OTHER PUBLICATIONS

Merriam-Webster Online Dictionary, (Prevent, Available online at: https://www.merriam-webster.com/dictionary/prevent, accessed on Jan. 29, 2020. (Year: 2020).*

N'Guessan et al., Bioorg. Med. Chem., 25, 2017, 6695-6706 (Year: 2017).*

Endoparasite from https://www.esccap.org/parasites/Endoparasites/1/, pp. 1-13. Accessed Mar. 15, 2021. (Year: 2021).*

Krucken et al., "Anthelmintic cyclooctadepsipeptides: complex in structure and mode of action", Trends in Parasitology, 2012, vol. 28, No. 9, pp. 385-394.

Harder et al., "Cyclooctadepsipeptides—an anthelmintically active class of compounds exhibiting a novel mode of action", International Journal of Antimicrobial Agents, 2003, vol. 22, No. 3, pp. 318-331.

(Continued)

*Primary Examiner* — Julie Ha
(74) *Attorney, Agent, or Firm* — John Ezcurra

(57) ABSTRACT

The present invention provides cyclic depsipeptide compounds of formula (I) and compositions comprising the compounds that are effective against parasites that harm animals, including humans. The compounds and compositions may be used for combating parasites in or on animals including mammals and birds. The invention also provides for an improved method for eradicating, controlling and preventing parasite infestation in animals, including birds and mammals.

28 Claims, No Drawings

(56) References Cited

FOREIGN PATENT DOCUMENTS

| EP | 0634408 A1 | 1/1995 |
|---|---|---|
| EP | 0662326 A2 | 7/1995 |
| EP | 0685469 A1 | 12/1995 |
| WO | 9947506 A1 | 9/1999 |
| WO | 00/69425 A2 | 11/2000 |
| WO | 2012/028556 A1 | 3/2012 |
| WO | 2013092558 A1 | 6/2013 |
| WO | 2016/187534 A1 | 11/2016 |

OTHER PUBLICATIONS

Scherkenbeck et al., "PF1022A—A Novel Anthelmintic Cyclooctadepsipeptide. Modification and Exchange of the N-Methyl Leucine Residues", Bioorganic and Medicinal Chemistry Letters, 1998, No. 8, pp. 1035-1040.
Ohyama et al., "Structure-activity relationship of anthelmintic cyclooctadepsipeptides", Biosci., Biotechnol., Biochem., 2011, vol. 75, No. 7, pp. 1354-1363.
Yanai et al., "Para-position derivatives of fungal anthelmintic cyclodepsipeptides engineered with Streptomyces venezuelae antibiotic biosynthetic genes", Nature Biotechnology, 2004, vol. 22, No. 7, pp. 848-855.
Dyker et al., "Chimeric cyclodepsipeptides as mimetics for the anthelmintic PF1022A", Bioorganic & Medicinal Chemistry Letters, 2004, vol. 14, pp. 6129-6132.
Jeschke et al., "Influence of the cyclooctadepsipeptides PF1022A and PF1022E as natural products on the design of semi-synthetic anthelmintics such as emodepside". Parasitology Research, 2005, 97, S11-S16.
Dutton and Lee, "Epsilon-lactam analogs of the anthelmintic cyclodepsipeptide PF1022A", Tetrahedron Letters, 1998, vol. 39, No. 30, pp. 5313-5316.
Jeschke et al., "Synthesis of anthelmintically active N-methylated amidoxime analogues of the cyclic octadepsipeptide PF1022A", Pest Management Science, 2002, vol. 58, No. 12, pp. 1205-1215.
B. Lee, "Generation of a small library of cyclodepsipeptide PF1022A analogues using a cyclization-Cleavage method with oxime resin", Bioorganic & Medicinal Chemistry Letters, 2002, vol. 12, No. 3, pp. 353-356.
Muller et al., "In vitro Synthesis of New Cyclodepsipeptides of the PF1022-Type: Probing the a-D-Hydroxy Acid Tolerance of PF1022 Synthetase", ChemBioChem, 2009, vol. 10, No. 2, pp. 323-328.
Scherkenbeck et al., "Synthesis, conformational studies and anthelmintic activity of a constrained PF1022A analogue", Pesticide Science, 1999, vol. 55, pp. 457-461.
Dutton & Lee, "Restricted Conformation Analogues of an Anthelmintic Cyclodepsipeptide", Journal of Medicinal Chemistry, 2003, vol. 46, No. 11, pp. 2057-2073.
Biswas et al., "Oxyazapeptides: synthesis, structure determination, and conformational analysis", Journal of Organic Chemistry, 2013, vol. 78, No. 17, pp. 8502-8509.
Scherkenbeck et al., "PF1022A and Related Cyclodepsipeptides—A Novel Class of Anthelmintics", Current Topics in Medicinal Chemistry, 2002, vol. 2, No. 7, pp. 759-777.
Jeschke et al., "Synthesis and anthelmintic activity of cyclohexadepsipeptides with cyclohexylmethyl side chains", Bioorganic & Medicinal Chemistry Letters, 2007, vol. 17, pp. 3690-3695.
Jeschke et al., "Synthesis and anthelmintic activity of thioamide analogues of cyclic octadepsipeptides such as PF1022A", Pest Management Science, 2001, vol. 57, pp. 1000-1006.
Scherkenbeck et al., "Azadepsipeptides: Synthesis and Evaluation of a Novel Class of Peptidomimetics", Journal of Organic Chemistry, 2001, vol. 66, pp. 3760-3766.
Sivanathan, Sivatharushan, and Jurgen Scherkenbeck. "Cyclodepsipeptides: A rich source of biologically active compounds for drug research." Molecules 19.8 (2014): 12368-12420.

* cited by examiner

ANTHELMINTIC DEPSIPEPTIDE COMPOUNDS

CROSS REFERENCE TO RELATED APPLICATIONS

This application is a divisional application of Ser. No. 15/378,219 filed on Dec. 14, 2016, now U.S. Pat. No. 10,344,056, which claims the benefit of U.S. Provisional Application No. 62/272,040 filed on Dec. 28, 2015, both of which are herein incorporated by reference.

FIELD OF THE INVENTION

The present invention is directed to new anthelmintic depsipeptides compounds with improved activity against endoparasites and ectoparasites. The invention is also directed to compositions comprising the compounds and methods and uses of the compounds for eradicating, controlling, and preventing a parasite infestation and/or infection in animals. The compounds of the invention may be administered to animals, particularly mammals, fish and birds, to prevent or treat parasitic infections and/or infestations.

BACKGROUND OF THE INVENTION

Animals, including mammals (including humans), fish and birds, are often susceptible to parasite infestations and infections. These parasites may be ectoparasites, such as fleas and ticks. Animals also suffer from endoparasitic infections including, for example, helminthiasis which is most frequently caused by a group of parasitic worms described as nematodes or roundworms. These parasites cause severe economic losses in pigs, sheep, horses, and cattle as well as affecting domestic animals and poultry. Other parasites which occur in the gastrointestinal tract of animals and humans include *Ancylostoma, Necator, Ascaris, Strongyloides, Trichinella, Capillaria, Toxocara, Toxascaris, Trichuris, Enterobius* and parasites which are found in the blood or other tissues and organs such as filarial worms and the extra intestinal stages of *Strongyloides, Toxocara* and *Trichinella*.

One type of endoparasite which seriously harms mammals is *Dirofilaria immitis*, also known as Heartworm. Other filarial endoparasites include *Dirofilaria repens* and *Dirofilaria honkongensis*, which can also infect humans. The most common hosts are dogs and cats but other mammals such as ferrets and raccoons may also be infected. Heartworms go throughout several life stages before they become adults infecting the pulmonary artery of the host mammal. The worms require the mosquito as an intermediate host to complete their life cycle. The period between the initial infection when the dog is bitten by a mosquito and the maturation of the worms into adults living in the heart and pulmonary arteries is six to seven months in dogs and is known as the "prepatent period". L3 larvae migrate during blood feeding of the mosquito to the tip of the mosquito's mouth parts (labium), leave the mosquito and are deposited on the skin of the dog where they then migrate through the bite wound into the host. Most L3 larvae molt to fourth-stage larvae (L4s) in canine subcutaneous tissues within 1-3 days after infection. Then, they migrate to the muscles of the chest and abdomen, and 45 to 60 days after infection, molt to the fifth stage (L5, immature adult). Between 75 and 120 days after infection, these immature heartworms then enter the bloodstream and are carried through the heart to reside in the pulmonary artery. Around seven months after infection, *Dirofilaria immitis* adults reach maturity and sexually reproduce in the pulmonary arteries and right ventricle. Adult males are around 15 cm in length, and females are around 25 cm in length and their normal life span as adults is calculated to be about 5 years.

Heartworm infection is a severe and life-threatening disease. Canine heartworm infection is preventable and prophylaxis treatment is a priority in heartworm endemic areas. Treatment of mature heartworm infection with an adulticide (e.g. melarsomine dihydrochloride) is costly and can cause serious adverse side effects, thus prevention by monthly administration of drugs that interrupt larvae development is widely used. The goal of marketed heartworm preventive therapies in dogs is to prevent the development of the parasite to adult heartworms by interrupting the *Dirofilaria immitis* life cycle post-infection.

The macrocyclic lactones (MLs, e.g. ivermectin, milbemycin oxime, moxidectin, and selamectin) are the most commonly used chemoprophylaxis agents and are administered at monthly or six-month intervals. These drugs have been effective against *Dirofilaria immitis* infective third-stage larvae (L3) deposited by the mosquito as well as maturing fourth-stage larvae (L4). When administered monthly, MLs kill L3 and L4 larvae acquired within the previous 30 days, and thus prevent disease caused by adult worms. MLs can also be used monthly in infected dogs to suppress reproduction in adult worms and remove microfilariae, thereby reducing transmission and gradually causing the attrition of adult worms (Vet Parasitol 2005 Oct. 24 133(2-3) 197-206).

In recent years, an increased number of lack of efficacy (LOE) cases have been reported, in which dogs develop mature heartworm infections despite receiving monthly prophylactic doses of macrocyclic lactones drugs. For example, Atkins et al, (Veterinary Parasitology 206 (2014) 106-113) recently reported that an increasing number of cases of dogs that tested heartworm antigen positive while receiving heartworm preventive medication which suggests that some populations of *Dirofilaria immitis* have developed selectional resistance to heartworm preventives (American Heartworm Society, 2010. *Heartworm Preventive Resistance. Is it Possible*, vol. 37. Bulletin of the American Heartworm Society, pp. 5.). Thus, there is an ongoing need to develop new anthelmintic agents with improved activity against *Dirofilaria immitis* and other endoparasites.

Various parasiticides exist in the art for treating endoparasites infections in animals. In addition to the macrocyclic lactones, cyclic depsipeptides with antiparasitic activity are known. PF1022A is a 24-membered cyclic depsipeptide isolated from the fungus *Mycelia sterilia* by Sasaki et al. (see *J. Antibiotics* 45: 692-697 (1992)) has been found to exhibit broad anthelmintic activity against a variety of endoparasites in vivo with low toxicity. These compounds are described, for example, in U.S. Pat. Nos. 5,514,773; 5,747,448; 5,646,244; 5,874,530; among others, which are incorporated herein by reference. Emodepside is a semi synthetic analog of PF1022A containing a morpholine group at the para position of the phenyl lactate groups. Emodepside is a potent anthelmintic used in combination with praziquantel in the product Profender® for the treatment of parasitic worms in cats and dogs. Recently, Scherkenbeck et al., described the synthesis of analogs of PF1022A in which the phenyl group in the phenyl lactate moieties of the molecule were substituted with heteroaromatic groups (*Letters in Organic Chemistry*, 2016, 13, 441-445). However, the antiparasitic activity of PF1022A and emodepside is not satisfactory for the treatment of certain parasites, especially for the control of *Dirofilaria immitis* in mammals to prevent the establishment of Heartworm disease. Thus, there is a need in the art for more effective antiparasitic agents for treatment and protection of animals, e.g. mammals, fish and birds against parasites, in particular internal parasites including nematodes and filarial worms such as Heartworm.

It is expressly noted that citation or identification of any document in this application is not an admission that such document is available as prior art to the present invention. Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

SUMMARY OF THE INVENTION

The invention provides novel and inventive cyclic depsipeptide compounds with superior anthelmintic activity and possibly also superior activity against ectoparasites in certain embodiments. In addition the invention provides compositions comprising the novel depsipeptide compounds and methods for the treatment and prevention of parasitic infection and possibly infestation of animals using the compounds. In certain embodiments, the cyclic depsipeptide compounds of formula (I) may be used to treat parasitic infections in humans.

In one embodiment, the present invention provides cyclic depsipeptide compounds of formula (I) shown below:

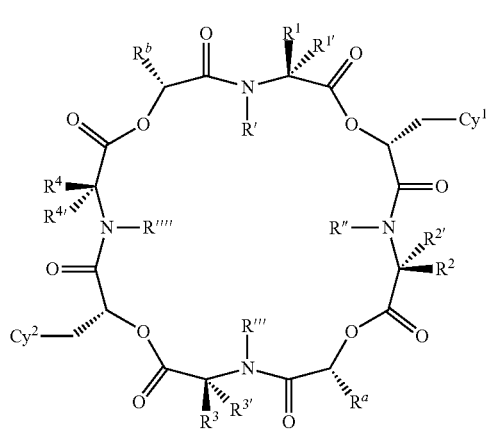

(I)

or a pharmaceutically or veterinarily acceptable salt thereof, wherein the meanings of variables $R^1$, $R^{1'}$, $R^2$, $R^{2'}$, $R^3$, $R^{3'}$, $R^4$, $R^{4'}$ $Cy^1$, $Cy^2$, $R^a$, $R^b$, R', R'', R''' and R'''' are as described below. The invention also provides veterinary compositions comprising the inventive compounds, or salts thereof, in combination with a pharmaceutically acceptable carrier or diluent.

The compounds of the invention are intended to encompass racemic mixtures, specific stereoisomers and tautomeric forms of the compound. Another aspect of the invention is a salt form of the compound of the invention.

The inventive compounds and compositions comprising the compounds are highly effective for the treatment and prophylaxis of internal parasites in animals including mammals, fish and birds, and in particular, humans, cats, dogs, horses, chickens, pigs, sheep and cattle with the aim of ridding these hosts of all the endoparasites commonly encountered by mammals, fish and birds.

In one embodiment, the compounds and compositions of the invention are highly effective against endoparasites, such as filariae (e.g. Heartworm), hookworms, whipworms and roundworms of the digestive tract of animals (including humans). In certain embodiments, the compounds and compositions of the invention are effective against *Dirofilaria immitis* (Heartworm) isolates that are less sensitive to treatment with macrocyclic lactones. In another embodiment, the novel and inventive depsipeptides of the invention are effective for treating and preventing infections of animals with nematodes that are less sensitive to treatment with commercially available or known macrocyclic lactone active agents.

In certain embodiments, the invention provides compositions comprising a combination of a novel depsipeptide of the invention in combination with at least a second active agent, which broadens the scope of protection afforded to animals against endoparasites and possibly also ectoparasites.

The present invention is also directed to methods for the treatment and prevention of a parasitic infection or infestation in an animal comprising administering at least one of the compounds of formula (I) of the invention to the animal. Also included in the present invention are uses of the compounds for the treatment and/or prevention of a parasitic infections and infestations in animals and the use of the compounds in the preparation of a medicament for the treatment and/or prevention of a parasitic infection in an animal.

It is an object of the invention to not encompass within the invention any previously known product, process of making the product, or method of using the product such that the Applicants reserve the right to this invention and hereby disclose a disclaimer of any previously known product, process, or method.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law; e.g., they allow for elements not explicitly recited, but exclude elements that are found in the prior art or that affect a basic or novel characteristic of the invention.

These and other embodiments are disclosed or are obvious from, and encompassed by, the following Detailed Description.

DETAILED DESCRIPTION

The present invention provides novel and inventive cyclic depsipeptide compounds of formula (I) having parasiticidal activity against endoparasites and also against ectoparasites in certain embodiments, or veterinarily salts thereof, and compositions comprising the compounds or salts for the treatment or prevention of parasitic infestations and/or infection in an animal Also provided are methods for the treatment or prevention of parasitic infestations and/or infection in animals, comprising administering an effective amount of the depsipeptide compound of the invention, or a salt thereof, to the animal.

The novel and inventive cyclic depsipeptide of formula (I) described herein and their pharmaceutically acceptable salts are particularly effective for controlling endoparasites. Endoparasites include, but are not limited to, nematodes (such as roundworms, hookworms, and whipworms) and filarial worms such as *Dirofilaria immitis* (Heartworm). In certain embodiments, the novel cyclic depsipeptides of the invention have been found to have significantly higher efficacy against endoparasites compared with known cyclic depsipeptides including PF1022A and emodepside. In other embodiments, the novel cyclic depsipeptides of the invention have also been surprisingly found to have an improved safety profile (lower toxicity to mammals) compared to cyclic depsipeptides of the prior art such as PF1022A and emodepside. Furthermore, it has been discovered that the novel cyclic depsipeptides of the invention are significantly more resistant to metabolic modification in the body of animals so that they maintain at a higher concentration in the host animal's body and a higher level of activity against internal parasites for a longer duration of time.

In one embodiment, the cyclic depsipeptides of the invention have been found to be highly effective against filarial worms such as *Dirofilaria immitis* (microfilarial and larval stages), including isolates of the parasite that are less sensitive to treatment with macrocyclic lactones. In other embodiments, the compounds of the invention are effective against endoparasites that are not effectively controlled by the known cyclic depsipeptides such as PF1022A and emodepside.

In another embodiment, the cyclic depsipeptides of the invention have been found to have activity against ectoparasites such as fleas and ticks. Thus, in certain embodiments the cyclic depsipeptides may have endectocidal activity against both internal and external parasites.

The invention includes at least the following features:

(a) In one embodiment, the invention provides novel cyclic depsipeptide compounds of formula (I), or pharmaceutically or veterinarily acceptable salts thereof, which are active endoparasites and in some cases also active against ectoparasites;

(b) veterinary and pharmaceutical compositions comprising a parasiticidally effective amount of the cyclic depsipeptide compounds of formula (I), or a pharmaceutically or veterinarily salts thereof, in combination with a pharmaceutically or veterinarily acceptable carrier or diluent;

(c) veterinary and pharmaceutical compositions comprising a parasiticidally effective amount of the cyclic depsipeptide compounds of the invention, or pharmaceutically or veterinarily acceptable salts thereof, in combination with one more other active agents and a pharmaceutically or veterinarily acceptable carrier or diluent;

(d) methods for treating a parasitic infestation/infection in or on an animal are provided comprising administering a parasiticidally effective amount of a cyclic depsipeptide compound of formula (I), or a pharmaceutically or veterinarily acceptable salts thereof, to the animal in need thereof;

(e) methods for the prevention of a parasitic infestation/infection of an animal, which comprise administering a parasiticidally effective amount of a cyclic depsipeptide compound of formula (I), or pharmaceutically or veterinarily acceptable salts thereof, with one or more additional active agents, to the animal in need thereof;

(f) use of the cyclic depsipeptide compounds of formula (I), or pharmaceutically or veterinarily acceptable salts thereof, for the treatment or prevention of a parasitic infection and possibly also a parasitic infestation in an animal;

(g) use of the cyclic depsipeptide compounds of formula (I), or pharmaceutically or veterinarily acceptable salts thereof, in the manufacture of a medicament for the treatment or prevention of a parasitic infection in an animal; and (h) processes for the preparation of the compounds of formula (I).

Definitions

Terms used herein will have their customary meanings in the art unless specified. The organic moieties mentioned in the definitions of the variables of the cyclic depsipeptide formula (I) are like the term halogen—i.e., collective terms for individual listings of the individual group members—fluoro, chloro, bromo and iodo in with respect to halogen. The prefix $C_n$-$C_m$ indicates in each case the possible number of carbon atoms in the group.

The term "alkyl" refers to saturated straight, branched, primary, secondary or tertiary hydrocarbons, including those having 1 to 12 atoms. In some embodiments, alkyl groups will include $C_1$-$C_{10}$, $C_1$-$C_8$, $C_1$-$C_6$, $C_1$-$C_4$ or $C_1$-$C_3$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Preferably, unless otherwise indicated, when the "alkyl" group is a substituent on another substituent, the alkyl group is unsubstituted. Moreover, preferably unless otherwise indicated, "alkyl" in the context of the alkyl component of: alkylamino, di(alkyl)amino, alkoxy, alkoxyalkoxy, alkyl ester, haloalkoxy, alkylthio, thioalkyl, alkylthioalkyl, haloalkylthio, heteroalkyl, hydroxyalkyl, alkoxyalkyl, alkylsulfinyl, haloalkylsulfinyl, alkylsulfonyl, haloalkylsulfonyl, trialkylsilyl, etc., means alkyl as defined above, wherein the alkyl component is not further substituted.

Carbocyclic groups are cyclic groups composed exclusively of carbon. The carbocyclic groups include both aromatic rings such as phenyl and non-aromatic rings such as cyclohexyl and include those with 3 to 14 carbon atoms having single or multiple fused rings.

Cyclic alkyl groups, which are encompassed by alkyls, may be referred to as "cycloalkyl" and include those with 3 to 10 carbon atoms having single or multiple fused rings. Non-limiting examples of cycloalkyl groups include adamantyl, cyclopropyl, cyclobutyl, cyclopentyl, cyclohexyl, cycloheptyl, cyclooctyl and the like. Preferably, unless otherwise indicated, when the "cycloalkyl" group is a substituent on another substituent, the cycloalkyl group is unsubstituted.

The alkyl and cycloalkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamoyl, ester, phosphonyl, phosphinyl, phosphoryl, phosphine, thioester, thioether, acid halide, anhydride, oxime, hydrazine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., Protective Groups in Organic Synthesis, John Wiley and Sons, Third Edition, 1999, hereby incorporated by reference.

The term "alkenyl" refers to both straight and branched carbon chains which have at least one carbon-carbon double bond. Preferably, unless otherwise indicated, when the "alkenyl" group is a substituent on another substituent, the alkyl group is unsubstituted. In some embodiments, alkenyl groups may include $C_2$-$C_{12}$ alkenyl groups. In other embodiments, alkenyl includes $C_2$-$C_{10}$, $C_2$-$C_8$, $C_2$-$C_6$ or $C_2$-$C_4$ alkenyl groups. In one embodiment of alkenyl, the number of double bonds is 1-3; in another embodiment of alkenyl, the number of double bonds is one. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Cycloalkenyl" refers to monovalent cyclic alkenyl groups of from 4 to 10 carbon atoms, preferably 5 to 8 carbon atoms, having single or multiple fused rings which fused rings may or may not be cycloalkenyl provided that the point of attachment is to a cycloalkenyl ring atom. Examples of cycloalkenyl groups include, by way of example, cyclopenten-4-yl, cyclooctene-5-yl and the like. Alkenyl and cycloalkenyl groups may be unsubstituted or substituted with one or more substituents as described for alkyl above.

"Alkynyl" refers to both straight and branched carbon chains which have at least one carbon-carbon triple bond. Preferably, unless otherwise indicated, when the "alkynyl" group is a substituent on another substituent, the alkynyl group is unsubstituted. In one embodiment of alkynyl, the number of triple bonds is 1-3; in another embodiment of alkynyl, the number of triple bonds is one. In some embodiments, alkynyl groups include from 2 to 12 carbon atoms.

In other embodiments, alkynyl groups may include $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "fluoroalkyl" as used herein refers to an alkyl in which one or more of the hydrogen atoms is replaced with fluorine atoms, for example difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

"Alkoxy" refers to alkyl-O—, wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

"Aryl" refers to a monovalent aromatic carbocyclic group of from 6 to 14 carbon atoms having a single ring or multiple fused rings. Aryl groups include, but are not limited to, phenyl, biphenyl, and naphthyl. In some embodiments aryl includes tetrahydronaphthyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, halothio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, —SF$_5$, alkylamino, alkenylamino, alkynylamino, di(alkyl)amino, di(alkenyl)-amino, di(alkynyl)amino, or trialkylsilyl.

The term "aralkyl" refers to an aryl group that is bonded to the parent compound through a diradical alkylene bridge, (—CH$_2$—)$_n$, where n is 1-12 and where "aryl" is as defined above.

"Heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple fused rings provided that the point of attachment is through a heteroaryl ring atom. Examples of heteroaryls include pyridyl, pyridazinyl, pyrimidinyl, pyrazinyl, triazinyl, pyrrolyl, indolyl, quinolinyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, benzothiophenyl, imidazopyridyl, imidazopyrimidyl, or pyrrolopyrimidyl. Heteroaryl rings may be unsubstituted or substituted by one or more moieties as described for aryl above.

"Heterocyclyl," "heterocyclic" or "heterocyclo" refers to fully saturated or unsaturated, cyclic groups, for example, 3 to 7 membered monocyclic, 7 to 11 membered bicyclic, or 10 to 15 membered tricyclic ring systems, which have one or more oxygen, sulfur or nitrogen heteroatoms in ring, preferably 1 to 4 or 1 to 3 heteroatoms. The nitrogen and sulfur heteroatoms may optionally be oxidized and the nitrogen heteroatoms may optionally be quaternized. Unless otherwise indicated, the heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, aziridinyl, azetidinyl, oxetanyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

The term "alkylthio" refers to alkyl-S—, where "alkyl" is as defined above. In some embodiments, the alkyl component of the alkylthio group will include $C_1$-$C_{10}$, $C_1$-$C_8$, $C_1$-$C_6$ $C_1$-$C_4$ or $C_1$-$C_3$ alkyl groups. For example, $C_1$-$C_4$-alkylthio includes, but is not limited to, methylthio, ethylthio, propylthio, 1-methylethylthio, butylthio, 1-methylpropylthio, 2-methylpropylthio or 1,1-dimethylethylthio.

Similarly, the terms "haloalkylthio," "cycloalkylthio," "halocycloalkylthio" refer to the groups —S-haloalkyl, —S-cycloalkyl, and —S-halocycloalkyl, respectively, where the terms "haloalkyl," "cycloalkyl," and "halocycloalkyl" are as defined above.

The term "halothio" refers to groups of the formula $X_n$—S— where X is a halogen atom and n is 1, 3 or 5. The term "halothio" includes —SF$_5$.

The term "alkylsulfinyl" refers to the group alkyl-S(=O)—, where "alkyl" is as defined above. In some embodiments, the alkyl component in alkylsulfinyl groups will include $C_1$-$C_{12}$, $C_1$-$C_{10}$, $C_1$-$C_8$, $C_1$-$C_6$, $C_1$-$C_4$ or $C_1$-$C_3$ alkyl groups. Examples include, but are not limited to, —SO—CH$_3$, —SO—C$_2$H$_5$, n-propylsulfinyl, 1-methylethyl sulfinyl, n-butylsulfinyl, 1-methylpropylsulfinyl, 2-methylpropylsulfinyl, 1,1-dimethylethyl sulfinyl, n-pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethylbutyl sulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

Similarly, the terms "alkenylsulfinyl," "alkynylsulfinyl," "haloalkylsulfinyl," "haloalkenylsulfinyl," and "haloalkynylsulfinyl" refer to the groups alkenyl-S(=O)—, alkynyl-S(=O)—, and haloalkyl-S(=O)—, haloalkenyl-S(=O)—, and haloalkynyl-S(=O)—, where the terms "alkenyl," "alkynyl," "haloalkyl," "haloalkenyl," and "haloalkynyl" are as defined above.

The term "alkylsulfonyl" refers to the group alkyl-S(=O)$_2$—, where the term "alkyl" is as defined above. In some embodiments, the alkyl component in alkylsulfonyl groups will include $C_1$-$C_{12}$, $C_1$-$C_{10}$, $C_1$-$C_8$, $C_1$-$C_6$ or $C_1$-$C_4$ alkyl groups. Examples include, but are not limited to, —SO$_2$—CH$_3$, —SO$_2$—C$_2$H$_5$, n-propylsulfonyl, —SO$_2$—CH(CH$_3$)$_2$, n-butylsulfonyl, 1-methylpropylsulfonyl, 2-methylpropylsulfonyl, —SO$_2$—C(CH$_3$)$_3$, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutyl sulfonyl, 1,2-dimethylbutylsulfonyl, 1,3-dimethylbutyl sulfonyl, 2,2- dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropyl sulfonyl, 1-ethyl-1-methylpropyl sulfonyl or 1-ethyl-2-methylpropylsulfonyl and the like.

The terms "alkenylsulfonyl," "alkynylsulfonyl," "haloalkylsulfonyl," "haloalkenylsulfonyl," and "haloalkynylsulfonyl" refer to the groups alkenyl-S(=O)$_2$—, alkynyl-S(=O)$_2$—, and haloalkyl-S(=O)$_2$—, haloalkenyl-S(=O)$_2$—, and haloalkynyl-S(=O)$_2$—, where the terms "alkenyl," "alkynyl," "haloalkyl," "haloalkenyl," and "haloalkynyl" are as defined above.

The terms "alkylamino," "dialkylamino," "alkenylamino," "alkynylamino," "di(alkenyl)amino," and "di(alkynyl)amino" refer to the groups —NH(alkyl), —N(alkyl)$_2$, —NH(alkenyl), —NH(alkynyl), —N(alkenyl)$_2$ and —N(alkynyl)$_2$, where the terms "alkyl," "alkenyl," and "alkynyl" are as defined above. In some embodiments, the alkyl component in alkylamino or dialkylamino groups will include $C_1$-$C_{12}$, $C_1$-$C_{10}$, $C_1$-$C_8$, $C_1$-$C_6$ or $C_1$-$C_4$ alkyl groups.

Compounds of the Invention:

The compounds of the invention are 24-membered cyclic depsipeptide compounds which have potent activity against endoparasites such as nematodes and filarial worms (microfilarial and larval stages) and also against ectoparasites such as fleas and ticks. In one embodiment the invention provides cyclic depsipeptide compounds of formula (I), or a pharmaceutically or veterinarily acceptable salt thereof:

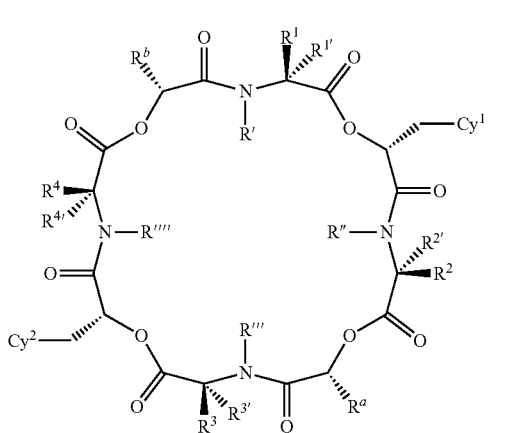

(I)

wherein:

$Cy^1$ and $Cy^2$ are independently aryl, carbocyclic, heteroaryl or heterocyclic, each of which may be optionally substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —NO$_2$, cycloalkyl, heteroalkyl, heterocyclyl, aryl and heteroaryl, wherein each cycloalkyl, heteroalkyl, heterocyclyl, aryl or heteroaryl substituents of $Cy^1$ and $Cy^2$ is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5OC(O)$—, $R^5C(O)O$—, $R^5C(O)NR^6$—, —CN and —NO$_2$;

$R^5$ and $R^6$ are independently hydrogen, alkyl, haloalkyl, thioalkyl, alkylthio, alkylthioalkyl, hydroxyalkyl, alkoxyalkyl, alkenyl, haloalkenyl, alkynyl, haloalkynyl, or the group —CH$_2$C(O)NHCH$_2$CF$_3$; or $R^5$ and $R^6$ together with the atom(s) to which they are bonded form a $C_3$-$C_6$ cyclic group;

R', R", R''' and R'''' are each independently hydrogen or $C_1$-$C_3$alkyl;

$R^a$ and $R^b$ are independently hydrogen, $C_1$-$C_3$alkyl or $C_1$-$C_3$haloalkyl; and (a) $R^1$ is a 3- to 6-membered carbocyclic or 3- to 6-membered heterocyclic ring or $R^1$ is $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or 3- to 6-membered heterocyclic ring or 3- to 8-membered carbocyclic or 3- to 8-membered heterocyclic ring may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{1'}$ is hydrogen or $C_1$-$C_3$alkyl; or $R^1$ and $R^{1'}$ together form a 2-6-membered carbon chain to form a ring; and $R^2$, $R^{2'}$, $R^3$, $R^{3'}$, $R^4$ and $R^{4'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino; or (b) $R^2$ is a 3- to 6-membered carbocyclic or 3- to 6-membered heterocyclic ring, or $R^2$ is $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or 3- to 6-membered heterocyclic ring or 3- to 8-membered carbocyclic or 3- to 8-membered heterocyclic ring may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{2'}$ is hydrogen or $C_1$-$C_3$alkyl; or $R^2$ and $R^{2'}$ together form a 2-6-membered carbon chain to form a ring; and $R^1$, $R^{1'}$, $R^3$, $R^{3'}$, $R^4$ and $R^{4'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino; or (c) $R^3$ is a 3- to 6-membered carbocyclic or 3- to 6-membered heterocyclic ring, or $R^3$ is $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic group; wherein said 3- to 6-membered carbocyclic or 3- to 6-membered heterocyclic ring or 3- to 8-membered carbocyclic or 3- to 8-membered heterocyclic ring may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^3$ is hydrogen or $C_1$-$C_3$alkyl; or $R^3$ and $R^{3'}$ together form a 2-6-membered carbon chain to form a ring; and $R^1$, $R^{1'}$, $R^2$, $R^{2'}$, $R^4$ and $R^{4'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino; or (d) $R^4$ is a 3- to 6-membered carbocyclic or 3- to 6-membered heterocyclic ring, or $R^4$ is $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or 3- to 6-membered heterocyclic ring or 3- to 8-membered carbocyclic or 3- to 8-membered heterocyclic ring may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{4'}$ is hydrogen or $C_1$-$C_3$alkyl; or $R^4$ and $R^{4'}$ together form a 2-6-membered carbon chain to form a ring; and $R^1$, $R^{1'}$, $R^2$, $R^{2'}$, $R^3$ and $R^{3'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino; or (e) $R^1$ and/or $R^2$ are each independently a 3- to 6-membered carbocyclic or 3- to 6-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or 3- to 6-membered heterocyclic ring(s) or 3- to 8-membered carbocyclic or 3- to 8-membered heterocyclic ring(s) may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{1'}$ and/or $R^{2'}$ are independently hydrogen or $C_1$-$C_3$alkyl; or $R^1$ and $R^{1'}$ together and/or $R^2$ and $R^{2'}$ together independently form a 2-6-membered carbon chain to form a ring; and $R^3$, $R^{3'}$, $R^4$ and $R^{4'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino; or (f) $R^1$ and/or $R^3$ are each independently a 3- to 6-membered carbocyclic or 3- to 6-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or 3- to 6-membered heterocyclic ring(s) or 3- to 8-membered carbocyclic or 3- to 8-membered heterocyclic ring(s) may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{1'}$ and/or $R^{3'}$ are independently hydrogen or $C_1$-$C_3$alkyl; or $R^1$ and $R^{1'}$ together and/or $R^3$ and $R^{3'}$ together independently form a 2-6-membered carbon chain to form a ring; and $R^2$, $R^{2'}$, $R^4$ and $R^{4'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino; or (g) $R^1$ and/or $R^4$ are each independently a 3- to 6-membered carbocyclic or 3- to 6-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or 3- to 6-membered heterocyclic ring(s) or 3- to 8-membered carbocyclic or 3- to 8-membered heterocyclic ring(s) may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{1'}$ and/or $R^{4'}$ are independently hydrogen or $C_1$-$C_3$alkyl; or $R^1$ and $R^{1'}$ together and/or $R^4$ and $R^{4'}$ together independently form a 2-6-membered carbon chain to form a ring; and $R^2$, $R^{2'}$, $R^3$ and $R^{3'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino; or (h) $R^2$ and/or $R^4$ are each independently a 3- to 6-membered carbocyclic or 3- to 6-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or 3- to 6-membered heterocyclic ring(s) or 3- to 8-membered carbocyclic or 3- to 8-membered heterocyclic ring(s) may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{2'}$ and/or $R^{4'}$ are independently hydrogen or $C_1$-$C_3$alkyl; or $R^2$ and $R^{2'}$ together and/or $R^4$ and $R^{4'}$ together independently form a 2-6-membered carbon chain to form a ring; and $R^1$, $R^{1'}$, $R^3$ and $R^{3'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino; or (i) $R^2$ and/or $R^3$ are each independently a 3- to 6-membered carbocyclic or 3- to 6-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or 3- to 6-membered heterocyclic ring(s) or 3- to 8-membered carbocyclic or 3- to 8-membered heterocyclic ring(s) may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{2'}$ and/or $R^{3'}$ are independently hydrogen or $C_1$-$C_3$alkyl; or $R^2$ and $R^{2'}$ together and/or $R^3$ and $R^{3'}$ together independently form a 2-6-membered carbon chain to form a ring; and $R^1$, $R^{1'}$, $R^4$ and $R^{4'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino; or (j) $R^3$ and/or $R^4$ are each independently a 3- to 6-membered carbocyclic or 3- to 6-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or 3- to 6-membered heterocyclic ring(s) or 3- to 8-membered carbocyclic or 3- to 8-membered heterocyclic ring(s) may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{3'}$ and/or $R^{4'}$ are independently hydrogen or $C_1$-$C_3$alkyl; or $R^3$ and $R^{3'}$ together and/or $R^4$ and $R^{4'}$ together independently form a 2-6-membered carbon chain to form a ring; and $R^1$, $R^{1'}$, $R^2$ and $R^{2'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino; or (k) $R^1$ and/or $R^2$ and/or $R^3$ are each independently a 3- to 6-membered carbocyclic or 3- to 6-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or 3- to 6-membered heterocyclic ring(s) or 3- to 8-membered carbocyclic or 3- to 8-membered heterocyclic ring(s) may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{1'}$ and/or $R^{2'}$ and/or $R^{3'}$ are independently hydrogen or $C_1$-$C_3$alkyl; or $R^1$ and $R^{1'}$ together and/or $R^2$ and $R^{2'}$ together and/or $R^3$ and $R^{3'}$ together independently form a 2-6-membered carbon chain to form a ring; and $R^4$ and $R^{4'}$ are independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino; or (l) $R^2$ and/or $R^3$ and/or $R^4$ are each independently a 3- to 6-membered carbocyclic or 3- to 6-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or 3- to 6-membered heterocyclic ring(s) or 3- to 8-membered carbocyclic or 3- to 8-membered heterocyclic ring(s) may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{2'}$ and/or $R^{3'}$ and/or $R^{4'}$ are independently hydrogen or $C_1$-$C_3$alkyl; or $R^2$ and $R^{2'}$ together and/or $R^3$ and $R^{3'}$ together and/or $R^4$ and $R^{4'}$ together independently form a 2-6-membered carbon chain to form a ring; and $R^1$ and $R^{1'}$ are independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino; or (m) $R^1$ and/or $R^3$ and/or $R^4$ are each independently a 3- to 6-membered carbocyclic or 3- to 6-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or 3- to 6-membered heterocyclic ring(s) or 3- to 8-membered carbocyclic or 3- to 8-membered heterocyclic ring(s) may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{1'}$ and/or $R^{3'}$ and/or $R^{4'}$ are independently hydrogen or $C_1$-$C_3$alkyl; or $R^1$ and $R^{1'}$ together and/or $R^3$ and $R^{3'}$ together and/or $R^4$ and $R^{4'}$ together independently form a 2-6-membered carbon chain to form a ring; and $R^2$ and $R^{2'}$ are independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino; or (n) $R^1$ and/or $R^2$ and/or $R^4$ are each independently a 3- to 6-membered carbocyclic or 3- to 6-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or 3- to 6-membered heterocyclic ring(s) or 3- to 8-membered carbocyclic or 3- to 8-membered heterocyclic ring(s) may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino and alkylamino and dialkylamino; and $R^{1'}$ and/or $R^{2'}$ and/or $R^{4'}$ are independently hydrogen or $C_1$-$C_3$alkyl; or $R^1$ and $R^{1'}$ together and/or $R^2$ and $R^{2'}$ together and/or $R^4$ and $R^{4'}$ together independently form a 2-6-membered carbon chain to form a ring; and $R^3$ and $R^{3'}$ are independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino; or (o) $R^1$ and/or $R^2$ and/or $R^3$ and/or $R^4$ are each independently a 3- to 6-membered carbocyclic or 3- to 6-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or 3- to 6-membered heterocyclic ring(s) or 3- to 8-membered carbocyclic or 3- to 8-membered heterocyclic ring(s) may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{1'}$ and/or $R^{2'}$ and/or $R^{3'}$ and/or $R^{4'}$ are independently hydrogen or $C_1$-$C_3$alkyl; or $R^1$ and $R^{1'}$ together and/or $R^2$ and $R^{2'}$ together and/or $R^3$ and $R^{3'}$ together and/or $R^4$ and $R^{4'}$ together independently form a 2-6-membered carbon chain to form a ring.

$Cy^1$ and $Cy^2$ Groups

In one embodiment, $Cy^1$ and $Cy^2$ are independently phenyl substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, R C(O)NR$^6$—, —CN, —NO$_2$, cycloalkyl, heteroalkyl, heterocyclyl, aryl and heteroaryl, wherein each cycloalkyl, heteroalkyl, heterocyclyl, aryl or heteroaryl substituent is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN and —NO$_2$; where $R^5$ and $R^6$ are as defined above. It will be appreciated that the substituents on the phenyl ring may be at any position of the ring including at the ortho, meta and para positions to the point of attachment to the macrocycle.

In another embodiment, $Cy^1$ and $Cy^2$ are independently phenyl, heteroaryl or heterocyclyl optionally independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —NO$_2$, cycloalkyl, heteroalkyl, heterocyclyl, aryl and heteroaryl, wherein each cycloalkyl, heteroalkyl, heterocyclyl, aryl or heteroaryl substituent is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN and —NO$_2$.

In another embodiment, $Cy^1$ and $Cy^2$ are independently 6-12 membered bicyclic aryl, 6-12 membered bicyclic heteroaryl or 6-12 membered bicyclic heterocyclyl groups, each of which is optionally substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —NO$_2$, cycloalkyl, heteroalkyl, heterocyclyl, aryl and heteroaryl, wherein each cycloalkyl, heteroalkyl, heterocyclyl, aryl or heteroaryl substituent is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN and —NO$_2$.

In another embodiment, $Cy^1$ and $Cy^2$ are independently bicyclic heterocyclic groups, each of which is optionally substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —NO$_2$, cycloalkyl, heteroalkyl, heterocyclyl, aryl or heteroaryl, wherein each cycloalkyl, heteroalkyl, heterocyclyl, aryl and heteroaryl substituent is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN and —NO$_2$.

In another embodiment, $Cy^1$ and $Cy^2$ are independently phenyl, biphenyl, naphthyl, tetrahydronaphthyl, phenylcyclopropyl, biphenylene (biphenylenyl), fluorene (fluorenyl), anthracene (anthracenyl), acenaphthene (acenaphthenyl), phenanthrene (phenanthrenyl) or indanyl, each of which optionally substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —NO$_2$, cycloalkyl, heteroalkyl, heterocyclyl, aryl and heteroaryl, wherein each cycloalkyl, heteroalkyl, heterocyclyl, aryl or heteroaryl substituent is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)-$, $R^5S(O)_2-$, $R^5C(O)-$, $R^5R^6NC(O)-$, $R^5R^6NC(O)NR^5-$, $R^5OC(O)-$, $R^5C(O)O-$, $R^5C(O)NR^6-$, $-CN$ and $-NO_2$.

In yet another embodiment, $Cy^1$ and $Cy^2$ are independently pyridyl, pyridazinyl, pyrimidinyl, pyrazinyl, triazinyl, pyrrolyl, indolyl, quinolinyl, isoquinolinyl, quinazolinyl, quinoxalinyl, furanyl, thiophenyl, pyrrolyl, imidazolyl, oxazolyl, isoxazolyl, thiazolyl, isothiazolyl, benzoxazolyl, benzothiazolyl, pyrazolyl, benzofuranyl, dihydrobenzofuranyl, benzothiophenyl, imidazopyridyl, imidazopyrimidyl or pyrrolopyrimidyl, each of which is optionally substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)-$, $R^5S(O)_2-$, $R^5C(O)-$, $R^5R^6NC(O)-$, $R^5R^6NC(O)NR^5-$, $R^5OC(O)-$, $R^5C(O)O-$, $R^5C(O)NR^6-$, $-CN$, $-NO_2$, cycloalkyl, heteroalkyl, heterocyclyl, aryl and heteroaryl, wherein each cycloalkyl, heteroalkyl, heterocyclyl, aryl or heteroaryl substituent is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)-$, $R^5S(O)_2-$, $R^5C(O)-$, $R^5R^6NC(O)-$, $R^5R^6NC(O)NR^5-$, $R^5OC(O)-$, $R^5C(O)O-$, $R^5C(O)NR^6-$, $-CN$ and $-NO_2$.

In another embodiment, $Cy^1$ and $Cy^2$ are independently pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuranyl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl or triazinyl, each of which is optionally independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)-$, $R^5S(O)_2-$, $R^5C(O)-$, $R^5R^6NC(O)-$, $R^5R^6NC(O)NR^5-$, $R^5OC(O)-$, $R^5C(O)O-$, $R C(O)NR^6-$, $-CN$, $-NO_2$, cycloalkyl, heteroalkyl, heterocyclyl, aryl and heteroaryl, wherein each cycloalkyl, heteroalkyl, heterocyclyl, aryl or heteroaryl substituent is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)-$, $R^5S(O)_2-$, $R^5C(O)-$, $R^5R^6NC(O)-$, $R^5R^6NC(O)NR^5-$, $R^5OC(O)-$, $R^5C(O)O-$, $R^5C(O)NR^6-$, $-CN$ and $-NO_2$.

In another embodiment, $Cy^1$ and $Cy^2$ are independently indolyl, isoindolyl, benzothiazolyl, benzoxazolyl, benz[d]isoxazolyl, benzotriazolyl, benzodioxolyl, benzothienyl, quinuclidinyl, quinazolinyl, quinoxalinyl, quinolinyl, isoquinolinyl, benzimidazolyl, benzopyranyl, indolizinyl, benzofuranyl, dihydrobenzofuranyl, chromonyl, coumarinyl, cinnolinyl, indazolyl, pyrrolopyridyl, phthalazinyl, 1,2,3-benzotriazinyl, 1,2,4-benzotriazinyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl or tetrahydroisoquinolinyl, each of which is optionally substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)-$, $R^5S(O)_2-$, $R^5C(O)-$, $R^5R^6NC(O)-$, $R^5R^6NC(O)NR^5-$, $R^5OC(O)-$, $R^5C(O)O-$, $R C(O)NR^6-$, $-CN$, $-NO_2$, cycloalkyl, heteroalkyl, heterocyclyl, aryl or heteroaryl, wherein each cycloalkyl, heteroalkyl, heterocyclyl, aryl or heteroaryl substituent is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)-$, $R^5S(O)_2-$, $R^5C(O)-$, $R^5R^6NC(O)-$, $R^5R^6NC(O)NR^5-$, $R^5OC(O)-$, $R^5C(O)O-$, $R^5C(O)NR^6-$, $-CN$ and $-NO_2$.

In one embodiment, $Cy^1$ and $Cy^2$ are independently phenyl substituted with heterocyclyl. In yet another embodiment, $Cy^1$ and $Cy^2$ are independently a 6-membered heteroaryl group substituted with heterocyclyl. In still another embodiment, $Cy^1$ and $Cy^2$ are independently heterocyclyl substituted with a heterocyclyl group. In yet another embodiment, $Cy^1$ and $Cy^2$ are independently phenyl, pyridinyl, pyridazinyl, pyrimidinyl, pyrazinyl or tetrazinyl, each of which is substituted with heterocyclyl.

In one embodiment, $Cy^1$ and $Cy^2$ are independently phenyl, pyridinyl, pyridazinyl, pyrimidinyl, pyrazinyl or tetrazinyl, each of which is substituted with morpholino, tetrahydropyran, tetrahydrofuran, pyrrolidino or piperidino, wherein said morpholino, tetrahydropyran, tetrahydrofuran, pyrrolidino or piperidino may be optionally substituted with one or more halogen, alkyl or haloalkyl.

In one embodiment, $Cy^1$ and $Cy^2$ are independently phenyl or a 5-membered or a 6-membered heteroaryl ring, each of which is optionally substituted with one or more halogen, hydroxy, alkoxy, haloalkoxy, alkylthio, haloalkylthio, thioamido, $-SF_5$, amino, alkylamino or dialkylamino.

In another embodiment, $Cy^1$ and $Cy^2$ are independently phenyl or a 5-membered or a 6-membered heteroaryl ring, each of which is optionally substituted with one or more alkyl, haloalkyl, alkenyl, haloalkenyl, alkynyl, haloalkynyl.

In another embodiment, $Cy^1$ and $Cy^2$ are independently phenyl or a 5-membered or a 6-membered heteroaryl ring, each of which is optionally substituted with one or more methyl, ethyl, propyl, isopropyl, butyl, isobutyl, tert-butyl, $CF_3$, $-CH_2CF_3$, $-CHFCF_3$ or $-CF_2CF_3$.

In another embodiment, $Cy^1$ and $Cy^2$ are independently phenyl or a 5-membered or a 6-membered heteroaryl ring, each of which is optionally substituted with fluoro, chloro, bromo or iodo.

In another embodiment, $Cy^1$ and $Cy^2$ are independently phenyl or a 5-membered or a 6-membered heteroaryl ring, each of which is optionally substituted with one or more hydroxy, methoxy, trifluoromethoxy, $-OCH_2CF_3$, $-OCHFCF_3$, $-OCF_2CF_3$, $-SCH_3$, $-SCF_3$, $-SCH_2CF_3$, $-SCHFCF_3$, $-SCF_2CF_3$, $-S(O)CH_3$, $-S(O)CF_3$, $-S(O)CH_2CF_3$, $-S(O)CHFCF_3$, $-S(O)CF_2CF_3$, $-S(O)_2CH_3$, $-S(O)_2CF_3$, $-S(O)_2CH_2CF_3$, $-S(O)_2CHFCF_3$, $-S(O)_2CF_2CF_3$ or $SF_5$.

In yet another embodiment, $Cy^1$ and $Cy^2$ are independently phenyl, thienyl, oxazolyl, thiazolyl, isothiazolyl, 1,3-

4-thiadazolyl, pyrazolyl, furyl, imidazolyl, pyrrolyl, pyridinyl, pyridazinyl, pyrimidinyl, pyrazinyl or tetrazinyl, each of which is optionally substituted with one or more halogen, hydroxy, alkoxy, haloalkoxy, alkylthio, haloalkylthio, thioamido, amino, alkylamino or dialkylamino.

In yet another embodiment, $Cy^1$ and $Cy^2$ are independently phenyl, thienyl, oxazolyl, thiazolyl, isothiazolyl, 1,3-4-thiadazolyl, pyrazolyl, furyl, imidazolyl, pyrrolyl, pyridinyl, pyridazinyl, pyrimidinyl, pyrazinyl or tetrazinyl, each of which is optionally substituted with one or more alkyl, haloalkyl, alkenyl, haloalkenyl, alkynyl or haloalkynyl.

In another embodiment, $Cy^1$ and $Cy^2$ are independently phenyl, a 5-membered or a 6-membered heteroaryl ring, each of which is optionally substituted with methyl, ethyl, propyl, isopropyl, butyl, isobutyl, tert-butyl, $CF_3$, —$CH_2CF_3$, —$CHFCF_3$ or —$CF_2CF_3$.

In yet another embodiment, $Cy^1$ and $Cy^2$ are independently phenyl, thienyl, oxazolyl, thiazolyl, isothiazolyl, 1,3-4-thiadazolyl, pyrazolyl, furyl, imidazolyl, pyrrolyl, pyridinyl, pyridazinyl, pyrimidinyl, pyrazinyl or tetrazinyl, each of which is optionally substituted with fluoro, chloro, bromo or iodo.

In yet another embodiment, $Cy^1$ and $Cy^2$ are independently phenyl, thienyl, oxazolyl, thiazolyl, isothiazolyl, 1,3-4-thiadazolyl, pyrazolyl, furyl, imidazolyl, pyrrolyl, pyridinyl, pyridazinyl, pyrimidinyl, pyrazinyl or tetrazinyl, each of which is optionally substituted with hydroxy, methoxy, trifluoromethoxy, —$OCH_2CF_3$, —$OCHFCF_3$, —$OCF_2CF_3$, —$SCH_3$, —$SCF_3$, —$SCH_2CF_3$, —$SCHFCF_3$, —$SCF_2CF_3$, —$S(O)CH_3$, —$S(O)CF_3$, —$S(O)CH_2CF_3$, —$S(O)CHFCF_3$, —$S(O)CF_2CF_3$, —$S(O)_2CH_3$, —$S(O)_2CF_3$, —$S(O)_2CH_2CF_3$, —$S(O)_2CHFCF_3$, —$S(O)_2CF_2CF_3$ or $SF_5$.

In another embodiment, $Cy^1$ and $Cy^2$ are independently phenyl substituted by $C_1$-$C_6$alkyl, $C_1$-$C_6$-haloalkyl, $C_1$-$C_3$alkoxy, $C_1$-$C_3$-haloalkoxy, $C_3$-$C_8$cycloalkyl, tetrahydropyranyl, morpholinyl or piperidinyl, wherein each $C_1$-$C_6$alkyl, $C_3$-$C_8$cycloalkyl, tetrahydropyranyl, morpholinyl or piperidinyl is optionally substituted by one or more halogen, $C_1$-$C_4$alkyl, $C_1$-$C_3$alkoxy, $C_1$-$C_3$haloalkoxy or $SF_5$.

In another embodiment, $Cy^1$ and $Cy^2$ are independently phenyl substituted by t-butyl, sec-butyl, isobutyl, isopropyl, trifluoromethyl, methoxy, ethoxy, propoxy, trifluoromethoxy, cyclopentyl, cyclohexyl, tetrahydropyranyl, morpholinyl or piperidinyl, wherein each t-butyl, sec-butyl, isobutyl, isopropyl, cyclopentyl, cyclohexyl, tetrahydropyranyl, morpholinyl or piperidinyl is optionally substituted by one or more halogen, $C_1$-$C_4$alkyl, $C_1$-$C_3$alkoxy, $C_1$-$C_3$haloalkoxy or $SF_5$.

In another embodiment, $Cy^1$ and $Cy^2$ are independently phenyl substituted by t-butyl, isopropyl, cyclohexyl, trifluoromethoxy, trifluoromethyl, tetrahydropyranyl, morpholinyl or piperidinyl, wherein each cyclohexyl, tetrahydropyranyl, morpholinyl or piperidinyl is optionally substituted by one or more halogen, $C_1$-$C_4$alkyl, $C_1$-$C_3$alkoxy, $C_1$-$C_3$haloalkoxy or $SF_5$.

In another embodiment, $Cy^1$ and $Cy^2$ are independently phenyl substituted by t-butyl, trifluoromethyl, trifluoromethoxy, cyclohexyl, tetrahydropyranyl, morpholinyl or piperidinyl, wherein each cyclohexyl, tetrahydropyranyl, morpholinyl or piperidinyl is optionally substituted by one or more fluoro.

In another embodiment, $Cy^1$ and $Cy^2$ are independently one of $R^1$ to $R^8$ shown below:

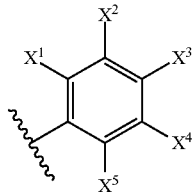
R1

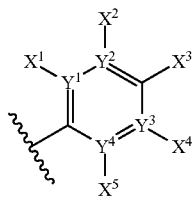
R2

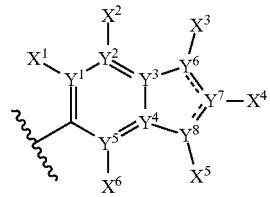
R3

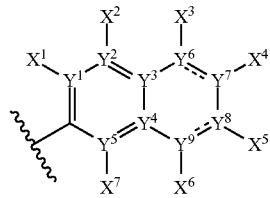
R4

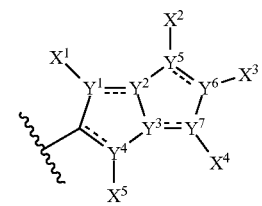
R5

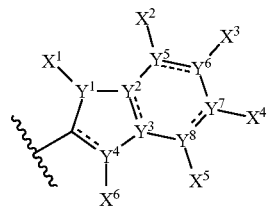
R6

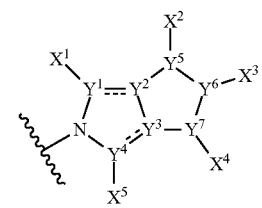
R7

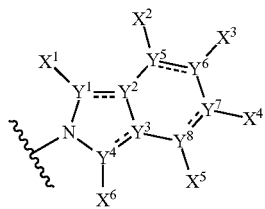
R8

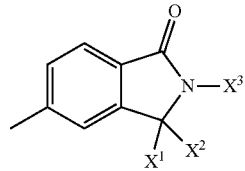
R9

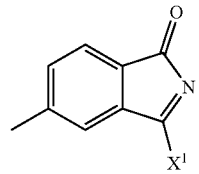
R10

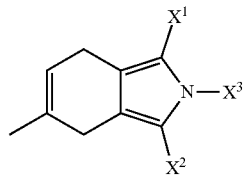
R11 wherein $Y^1$, $Y^2$, $Y^3$, $Y^4$, $Y^5$, $Y^6$, $Y^7$, $Y^8$ and $Y^9$ are each independently C, CH or N; and $X^1$, $X^2$, $X^3$, $X^4$, $X^5$, $X^6$ and $X^7$ are independently hydrogen, oxo, halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —$NO_2$, cycloalkyl, heteroalkyl, aryl or heteroaryl, wherein each cycloalkyl, heteroalkyl, aryl or heteroaryl substituent is optionally further substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN and —$NO_2$, where $R^5$ and $R^6$ are as defined above; and the dashed lines together with the solid lines, i.e. ---- represents single or double bonds.

In one embodiment, $Cy^1$ and $Cy^2$ are independently $R^1$ to $R^8$ wherein Y, $Y^2$, $Y^3$, $Y^4$, $Y^5$, $Y^6$, $Y^7$, $Y^8$ and $Y^9$ are each independently C, CH or N; and $X^1$, $X^2$, $X^3$, $X^4$, $X^5$, $X^6$ and $X^7$ are independently hydrogen, halogen, hydroxy, alkoxy, haloalkoxy, alkylthio, haloalkylthio, $R^5R^6NC(O)$—, $R^5R^6NC(O)NR^5$—, thioamido, amino, alkylamino or dialkylamino.

In another embodiment, $Cy^1$ and $Cy^2$ are independently $R^1$ to $R^8$ wherein $Y^1$, $Y^2$, $Y^3$, $Y^4$, $Y^5$, $Y^6$, $Y^7$, $Y^8$ and $Y^9$ are each independently C, CH or N; and $X^1$, $X^2$, $X^3$, $X^4$, $X^5$, $X^6$ and $X^7$ are independently hydrogen, alkyl, haloalkyl, alkenyl, haloalkenyl, alkynyl, haloalkynyl.

In another embodiment, $Cy^1$ and $Cy^2$ are independently $R^1$ to $R^8$ wherein $Y^1$, $Y^2$, $Y^3$, $Y^4$, Y, $Y^6$, $Y^7$, $Y^8$ and $Y^9$ are each independently C, CH or N; and $X^1$, $X^2$, $X^3$, $X^4$, $X^5$, $X^6$ and $X^7$ are independently hydrogen, methyl, ethyl, propyl, isopropyl, butyl, isobutyl, tert-butyl, $CF_3$, —$CH_2CF_3$, —$CHFCF_3$ or $CF_2CF_3$.

In another embodiment, $Cy^1$ and $Cy^2$ are independently $R^1$ to $R^8$ wherein $Y^1$, $Y^2$, $Y^3$, $Y^4$, Y, $Y^6$, $Y^7$, $Y^8$ and $Y^9$ are each independently C, CH or N; and $X^1$, $X^2$, $X^3$, $X^4$, $X^5$, $X^6$ and $X^7$ are independently hydrogen, fluoro, chloro, bromo or iodo.

In another embodiment, $Cy^1$ and $Cy^2$ are independently $R^1$ to $R^8$, wherein $Y^1$, $Y^2$, $Y^3$, $Y^4$, $Y^5$, $Y^6$, $Y^7$, $Y^8$ and $Y^9$ are each independently C, CH or N; and $X^1$, $X^2$, $X^3$, $X^4$, $X^5$, $X^6$ and $X^7$ are independently hydrogen, hydroxy, methoxy, trifluoromethoxy, —$OCH_2CF_3$, —$OCHFCF_3$, —$OCF_2CF_3$, methylthio, trifluoromethylthio, —$SCH_2CF_3$, —$SCHFCF_3$, —$SCF_2CF_3$ or $SF_5$.

In another embodiment, $Cy^1$ and $Cy^2$ are independently $R^9$ to $R^{11}$ shown below:

wherein $X^1$, $X^2$ and $X^3$ are independently hydrogen, halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —$NO_2$, cycloalkyl, heteroalkyl, aryl or heteroaryl, wherein $R^5$ and $R^6$ are as defined above, and wherein each cycloalkyl, heteroalkyl, aryl or heteroaryl is optionally further substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN and —$NO_2$.

In one embodiment, $Cy^1$ and $Cy^2$ are independently $R^9$ to $R^{11}$, wherein $X^1$, $X^2$ and $X^3$ are independently hydrogen, halogen, alkyl or haloalkyl. In another embodiment, $Cy^1$ and $Cy^2$ are independently $R^9$ to $R^{11}$, wherein $X^1$, $X^2$ and $X^3$ are independently hydrogen, fluoro, chloro, bromo or iodo. In another embodiment, $Cy^1$ and $Cy^2$ are independently $R^9$ to $R^{11}$, wherein $X^1$, $X^2$ and $X^3$ are independently hydrogen, methyl, ethyl, propyl, isopropyl, butyl, isobutyl, tert-butyl, $CF_3$, —$CH_2CF_3$, —$CHFCF_3$ or $CF_2CF_3$. In yet another embodiment, $Cy^1$ and $Cy^2$ are independently $R^9$ to $R^{11}$, wherein $X^1$, $X^2$ and $X^3$ are independently hydrogen, hydroxy, methoxy, trifluoromethoxy, —$OCH_2CF_3$, —$OCHFCF_3$, —$OCF_2CF_3$, methylthio, trifluoromethylthio, —$SCH_2CF_3$, —$SCHFCF_3$, —$SCF_2CF_3$ or $SF_5$.

In another embodiment, $Cy^1$ and/or $Cy^2$ are independently phenyl, p-morpholinophenyl, p-fluorophenyl, p-$OCF_3$-phenyl, p-$CF_3$-phenyl, 3,4,5-trifluoro-phenyl, p-tetrahydropyranyl-phenyl, 4-morpholino-2-pyridinyl, 4-morpholino-3-pyridinyl, p-thiosulfonylmorpholino-phenyl, p-$NH_2$-phenyl, p-S-tetrazolyl-phenyl, p-$NH_2$— phenyl, dihydrobenzofuranyl, 4-morpholinocyclohexyl, p-iodophenyl, p-bromophenyl, p-nitrophenyl and p-tert-butylphenyl.

In another embodiment, $Cy^1$ and $Cy^2$ are the groups shown in Table 1 below:

TABLE 1
| Cy¹ | Cy² |
|---|---|
| p-F—Ph | p-F—Ph |
| Ph | Ph |
| p-CF₃—Ph | p-CF₃—Ph |
| 3,4,5-tri-F—Ph | 3,4,5-tri-F—Ph |
| p-NH₂—Ph | p-NH₂—Ph |
| p-OCF₃—Ph | p-OCF₃—Ph |
| p-SCF₃—Ph | p-SCF₃—Ph |
| p-tBu—Ph | p-tBu—Ph |
| p-I—Ph | p-I—Ph |
| p-Br—Ph | p-Br—Ph |
| p-NO₂—Ph | p-NO₂—Ph |
| p-SF₅—Ph | p-SF₅—Ph |
| 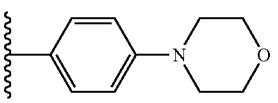 | 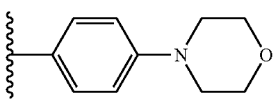 |
| 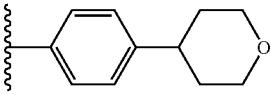 | 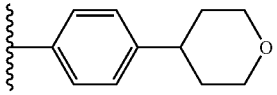 |
| 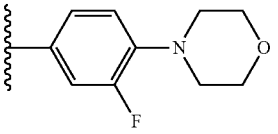 [SMILES: *c1ccc(N2CCOCC2)c(F)c1] | 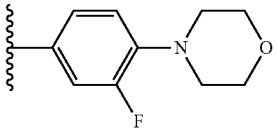 [SMILES: *c1ccc(N2CCOCC2)c(F)c1] |
| 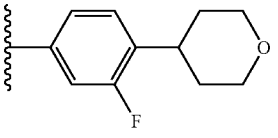 [SMILES: *c1ccc(C2CCOCC2)c(F)c1] | 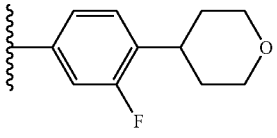 [SMILES: *c1ccc(C2CCOCC2)c(F)c1] |
| 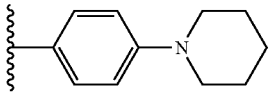 [SMILES: *c1ccc(N2CCCCC2)cc1] | 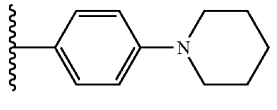 [SMILES: *c1ccc(N2CCCCC2)cc1] |
| 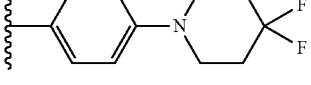 | 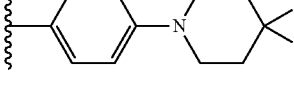 |
| 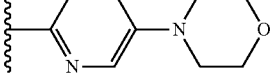 | 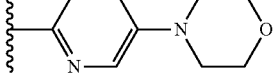 |
| 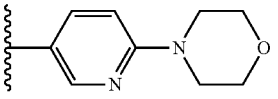 | 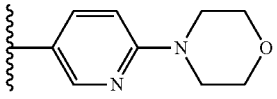 |
| 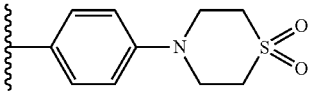 | 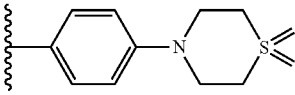 |
| 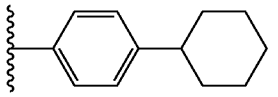 [SMILES: *c1ccc(C2CCCCC2)cc1] | 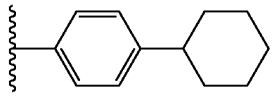 [SMILES: *c1ccc(C2CCCCC2)cc1] |

TABLE 1-continued

| Cy¹ | Cy² |
|---|---|
| 4-(4,4-difluorocyclohexyl)phenyl | 4-(4,4-difluorocyclohexyl)phenyl |
| | Ph |
| 4-(morpholin-4-yl)phenyl | |
| | p-I—Ph |
| 4-(1-methyl-1H-1,2,4-triazol-5-ylthio)phenyl | |
| 2,3-dihydrobenzofuran-5-yl | 2,3-dihydrobenzofuran-5-yl |
| 4-(1-methyl-1H-tetrazol-5-ylthio)phenyl | 4-(1-methyl-1H-tetrazol-5-ylthio)phenyl |
| 4-(morpholin-4-yl)cyclohexyl | 4-(morpholin-4-yl)cyclohexyl |
| | Ph |
| 4-(1-methyl-1H-tetrazol-5-ylthio)phenyl | |

$R^a$ and $R^b$ $R^a$ and $R^b$ may independently be hydrogen, $C_1$-$C_3$alkyl or $C_1$-$C_3$haloalkyl. In one embodiment, $R^a$ and $R^b$ are independently hydrogen or methyl. In another embodiment, $R^a$ and $R^b$ are independently hydrogen, methyl, ethyl or propyl. In another embodiment, $R^a$ and $R^b$ are independently hydrogen, methyl or $CF_3$. In still another embodiment, $R^a$ and $R^b$ are both methyl. In yet another embodiment, $R^a$ and $R^b$ are both hydrogen.

R', R", R'" and R""

In one embodiment, R', R", R'" and R"" are independently hydrogen or $C_1$-$C_3$alkyl. In another embodiment, R', R", R'" and R"" are independently hydrogen or methyl. In another embodiment, each of R', R", R'" and R"" are independently hydrogen, methyl or ethyl.

$R^1$, $R^{1'}$, $R^2$, $R^{2'}$, $R^3$, $R^{3'}$ $R^4$ and $R^{4'}$

It will be understood that the invention includes compounds wherein the various groups Cy¹ and Cy² described in the above embodiments are combined with any combination of $R^1$, $R^{1'}$, $R^2$, $R^{2'}$, $R^3$, $R^{3'}$ $R^4$ and $R^{4'}$ described above for formula (I) and in the embodiments described below.

In one embodiment of the invention, one of $R^1$ to $R^4$ is a 3- to 6-membered carbocyclic or a 3- to 6-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or 3- to 6-membered heterocyclic ring or 3- to 8-membered carbocyclic or 3- to 8-membered heterocyclic ring may be further substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, alkylsulfinyl, haloalkylsulfinyl, halothio, alkylsulfonyl, haloalkylsulfonyl, alkoxyalkoxy, oxo, cyano, amino, alkylamino and dialkylamino; while the others of $R^1$ to $R^4$ are independently $C_1$-$C_8$ alkyl, optionally independently substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In another embodiment, two of $R^1$ to $R^4$ are independently a 3- to 6-membered carbocyclic or 3- to 6-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or 3- to 6-membered heterocyclic ring(s) or 3- to 8-membered carbocyclic or 3- to 8-membered heterocyclic ring(s) may be further independently substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; while the other two of $R^1$ to $R^4$ are independently $C_1$-$C_8$ alkyl, optionally independently substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In another embodiment, $R^2$ and $R^4$ are independently a 3- to 6-membered carbocyclic or 3- to 6-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or 3- to 6-membered heterocyclic ring(s) or 3- to 8-membered carbocyclic or 3- to 8-membered heterocyclic ring(s) may be further independently substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^1$ and $R^3$ are independently $C_1$-$C_8$ alkyl, optionally independently substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino. In another embodiment, $R^1$ and $R^3$ are independently a 3- to 6-membered carbocyclic or 3- to 6-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or 3- to 6-membered heterocyclic ring(s) or 3- to 8-membered carbocyclic or 3- to 8-membered heterocyclic ring(s) may be further independently substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^2$ and $R^4$ are independently $C_1$-$C_8$ alkyl, optionally independently substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In yet another embodiment, three of $R^1$ to $R^4$ are independently a 3- to 6-membered carbocyclic or 3- to 6-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or 3- to 6-membered heterocyclic ring(s) or 3- to 8-membered carbocyclic or 3- to 8-membered heterocyclic ring(s) may be further independently substituted by one or more selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; while the other of $R^1$ to $R^4$ is $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In still another embodiment, all four of $R^1$ to $R^4$ are independently a 3- to 6-membered carbocyclic or 3- to 6-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or heterocyclic ring(s) or 3- to 8-membered carbocyclic or heterocyclic ring(s) may be further independently substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In one embodiment of the invention, one of $R^1$ to $R^4$ is a 3- to 5-membered carbocyclic or 3- to 5-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 5-membered carbocyclic or 3- to 5-membered heterocyclic ring or 3- to 8-membered carbocyclic or 3- to 8-membered heterocyclic ring may be further substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, alkylsulfinyl, haloalkylsulfinyl, halothio, alkylsulfonyl, haloalkylsulfonyl, alkoxyalkoxy, oxo, cyano, amino, alkylamino and dialkylamino; while the others of $R^1$ to $R^4$ are independently $C_1$-$C_8$ alkyl, optionally independently substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In another embodiment, two of $R^1$ to $R^4$ are independently a 3- to 5-membered carbocyclic or 3- to 5-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 5-membered carbocyclic or 3- to 5-membered heterocyclic ring(s) or 3- to 8-membered carbocyclic or 3- to 8-membered heterocyclic ring(s) may be further independently substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; while the other two of $R^1$ to $R^4$ are independently $C_1$-$C_8$ alkyl, optionally independently substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In another embodiment, $R^2$ and $R^4$ are independently a 3- to 5-membered carbocyclic or 3- to 5-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 5-membered carbocyclic or 3- to 5-membered heterocyclic ring(s) or 3- to 8-membered carbocyclic or 3- to 8-membered heterocyclic ring(s) may be further independently substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^1$ and $R^3$ are independently $C_1$-$C_8$ alkyl, optionally independently substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In yet another embodiment, $R^1$ and $R^3$ are independently a 3- to 5-membered carbocyclic or 3- to 5-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 5-membered carbocyclic or 3- to 5-membered heterocyclic ring(s) or 3- to 8-membered carbocyclic or 3- to 8-membered heterocyclic ring(s) may be further independently substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^2$ and $R^4$ are independently $C_1$-$C_8$ alkyl, optionally independently substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In yet another embodiment, three of $R^1$ to $R^4$ are independently a 3- to 5-membered carbocyclic or 3- to 5-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 5-membered carbocyclic or 3- to 5-membered heterocyclic ring(s) or 3- to 8-membered carbocyclic or 3- to 8-membered heterocyclic ring(s) may be further independently substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; while the other of $R^1$ to $R^4$ is $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In still another embodiment, all four of $R^1$ to $R^4$ are independently a 3- to 5-membered carbocyclic or 3- to 5-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 5-membered carbocyclic or 3- to 5-membered heterocyclic ring(s) or 3- to 8-membered carbocyclic or 3- to 8-membered heterocyclic ring(s) may be further independently substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment of the invention, one of $R^1$ to $R^4$ is a 3- or 4-membered carbocyclic or 3- or 4-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 6-membered carbocyclic or 3- to 6-membered heterocyclic ring; wherein said 3- or 4-membered carbocyclic or 3- or 4-membered heterocyclic ring or 3- to 6-membered carbocyclic or 3- to 6-membered heterocyclic ring may be further substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; while the others of $R^1$ to $R^4$ are independently $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment, two of $R^1$ to $R^4$ are independently a 3- or 4-membered carbocyclic or 3- or 4-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 6-membered carbocyclic or 3- to 6-membered heterocyclic ring; wherein said 3- or 4-membered carbocyclic or 3- or 4-membered heterocyclic ring(s) or 3- to 6-membered carbocyclic or 3- to 6-membered heterocyclic ring(s) may be further independently substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; while the other two of $R^1$ to $R^4$ are independently $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment, $R^2$ and $R^4$ are independently a 3- or 4-membered carbocyclic or 3- or 4-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 6-membered carbocyclic or 3- to 6-membered heterocyclic ring; wherein said 3- or 4-membered carbocyclic or 3- or 4-membered heterocyclic ring(s) or 3- to 6-membered carbocyclic or 3- to 6-membered heterocyclic ring(s) may be further independently substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^1$ and $R^3$ are independently $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In still another embodiment, $R^1$ and $R^3$ are independently a 3- or 4-membered carbocyclic or 3- or 4-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 6-membered carbocyclic or 3- to 6-membered heterocyclic ring; wherein said 3- or 4-membered carbocyclic or 3- or 4-membered heterocyclic ring(s) or 3- to 6-membered carbocyclic or 3- to 6-membered heterocyclic ring(s) may be further independently substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^2$ and $R^4$ are independently $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In yet another embodiment, three of $R^1$ to $R^4$ are independently a 3- or 4-membered carbocyclic or 3- or 4-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 6-membered carbocyclic or 3- to 6-membered heterocyclic ring; wherein said 3- or 4-membered carbocyclic or 3- or 4-membered heterocyclic ring(s) or 3- to 6-membered carbocyclic or 3- to 6-membered heterocyclic ring(s) may be further independently substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; while the other of $R^1$ to $R^4$ is $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In still another embodiment, all four of $R^1$ to $R^4$ are independently a 3- or 4-membered carbocyclic or 3- or 4-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 6-membered carbocyclic or 3- to 6-membered heterocyclic ring; wherein said 3- or 4-membered carbocyclic or 3- or 4-membered heterocyclic ring(s) or 3- to 6-membered carbocyclic or 3- to 6-membered heterocyclic ring(s) may be further substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment of the invention, one of $R^1$ to $R^4$ together with the corresponding $R^{1'}$ to $R^{4'}$ form a 2-6-membered carbon chain to form a ring which is optionally substituted by one or more halogen, $C_1$-$C_3$alkyl or $C_1$-$C_3$haloalkyl; and the others of $R^1$ to $R^4$ and $R^{1'}$ to $R^{4'}$ are independently hydrogen or $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment of the invention, two of $R^1$ to $R^4$ together with the corresponding $R^{1'}$ to $R^{4'}$ form a 2-6-membered carbon chain to form a ring which is optionally substituted by one or more halogen, $C_1$-$C_3$alkyl or $C_1$-$C_3$haloalkyl; and
the others of $R^1$ to $R^4$ and $R^{1'}$ to $R^{4'}$ are independently hydrogen or $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment of the invention, $R^2$ and $R^4$ together with the corresponding $R^{2'}$ and $R^{4'}$ independently form a 2-6-membered carbon chain to form a ring which is optionally substituted by one or more halogen, $C_1$-$C_3$alkyl or $C_1$-$C_3$haloalkyl; and
$R^1$, $R^{1'}$, $R^3$ and $R^{3'}$ are independently hydrogen or $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment of the invention, $R^1$ and $R^3$ together with the corresponding $R^{1'}$ and $R^{3'}$ independently form a 2-6-membered carbon chain to form a ring which is optionally substituted by one or more halogen, $C_1$-$C_3$alkyl or $C_1$-$C_3$haloalkyl; and
$R^2$, $R^{2'}$, $R^4$ and $R^{4'}$ are independently hydrogen or $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment of the invention, three of $R^1$ to $R^4$ together with the corresponding $R^{1'}$ to $R^{4'}$ form a 2-6-membered carbon chain to form a ring which is optionally substituted by one or more halogen, $C_1$-$C_3$alkyl or $C_1$-$C_3$haloalkyl; and
the others of $R^1$ to $R^4$ and $R^{1'}$ to $R^{4'}$ are independently hydrogen or $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment of the invention, all four of $R^1$ to $R^4$ together with the corresponding $R^{1'}$ to $R^{4'}$ form a 2-6-membered carbon chain to form a ring which is optionally substituted by one or more halogen, $C_1$-$C_3$alkyl or $C_1$-$C_3$haloalkyl.

In another embodiment of the invention, one of $R^1$ to $R^4$ is a cyclopropyl, cyclobutyl, cyclopentyl, cyclohexyl or phenyl ring or $C_1$-$C_3$ alkyl or $C_1$-$C_3$ haloalkyl, wherein the $C_1$-$C_3$ alkyl or $C_1$-$C_3$ haloalkyl is substituted by a 3- to 5-membered carbocyclic or 3- to 5-membered heterocyclic ring, wherein said cyclopropyl, cyclobutyl, cyclopentyl, cyclohexyl or phenyl ring or 3- to 5-membered carbocyclic or 3- to 5-membered heterocyclic ring may be further group substituted by one or more substituents selected from the group consisting of halogen, hydroxy, alkyl, haloalkyl, cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; while the others of $R^1$ to $R^4$ are independently $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In another embodiment, two of $R^1$ to $R^4$ are independently cyclopropyl, cyclobutyl, cyclopentyl, cyclohexyl or phenyl or $C_1$-$C_3$ alkyl or $C_1$-$C_3$ haloalkyl, wherein the $C_1$-$C_3$ alkyl or $C_1$-$C_3$ haloalkyl is substituted by a 3- to 5-membered carbocyclic or 3- to 5-membered heterocyclic ring, wherein said cyclopropyl, cyclobutyl, cyclopentyl, cyclohexyl or phenyl ring(s) or 3- to 5-membered carbocyclic or 3- to 5-membered heterocyclic ring(s) may be further independently substituted by one or more substituents selected from the group consisting of halogen, hydroxy, alkoxy, alkyl, haloalkyl, cycloalkyl, heterocyclyl, phenyl, heteroaryl, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; while the other two of $R^1$ to $R^4$ are independently $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In another embodiment, $R^2$ and $R^4$ are independently cyclopropyl, cyclobutyl, cyclopentyl, cyclohexyl or phenyl or $C_1$-$C_3$ alkyl or $C_1$-$C_3$ haloalkyl, wherein the $C_1$-$C_3$ alkyl or $C_1$-$C_3$ haloalkyl is substituted by a 3- to 5-membered carbocyclic or 3- to 5-membered heterocyclic ring, wherein said cyclopropyl, cyclobutyl, cyclopentyl, cyclohexyl or phenyl ring(s) or 3- to 5-membered carbocyclic or 3- to 5-membered heterocyclic ring(s) may be further independently substituted by one or more substituents selected from the group consisting of halogen, hydroxy, alkoxy, alkyl, haloalkyl, cycloalkyl, heterocyclyl, phenyl, heteroaryl, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^1$ and $R^3$ are independently $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In yet another embodiment, $R^1$ and $R^3$ are independently cyclopropyl, cyclobutyl, cyclopentyl, cyclohexyl or phenyl or $C_1$-$C_3$ alkyl or $C_1$-$C_3$ haloalkyl, wherein the $C_1$-$C_3$ alkyl or $C_1$-$C_3$ haloalkyl is substituted by a 3- to 5-membered carbocyclic or 3- to 5-membered heterocyclic ring, wherein said cyclopropyl, cyclobutyl, cyclopentyl, cyclohexyl or phenyl ring(s) or 3- to 5-membered carbocyclic or 3- to 5-membered heterocyclic ring(s) may be further independently substituted by one or more substituents selected from the group consisting of halogen, hydroxy, alkoxy, alkyl, haloalkyl, cycloalkyl, heterocyclyl, phenyl, heteroaryl, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^2$ and $R^4$ are independently $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In another embodiment, $R^2$ and $R^4$ are independently cyclopropyl, cyclobutyl, or phenyl; and $R^1$ and $R^3$ are independently $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In another embodiment, $R^1$ and $R^3$ are independently cyclopropyl, cyclobutyl, or phenyl; and $R^2$ and $R^4$ are independently $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In yet another embodiment, three of $R^1$ to $R^4$ are independently a cyclopropyl, cyclobutyl, cyclopentyl, cyclohexyl or phenyl or $C_1$-$C_3$ alkyl or $C_1$-$C_3$ haloalkyl, wherein the $C_1$-$C_3$ alkyl or $C_1$-$C_3$ haloalkyl is substituted by a 3- to 5-membered carbocyclic or 3- to 5-membered heterocyclic ring, wherein said cyclopropyl, cyclobutyl, cyclopentyl, cyclohexyl or phenyl ring(s) or 3- to 5-membered carbocyclic or 3- to 5-membered heterocyclic ring(s) may be further independently substituted by one or more substituents selected from the group consisting of halogen, hydroxy, alkyl, haloalkyl, cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; while the other of $R^1$ to $R^4$ is $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In still another embodiment, all four of $R^1$ to $R^4$ are independently cyclopropyl, cyclobutyl, cyclopentyl, cyclohexyl or phenyl or $C_1$-$C_3$ alkyl or $C_1$-$C_3$ haloalkyl, wherein the $C_1$-$C_3$ alkyl or $C_1$-$C_3$ haloalkyl is substituted by a 3- to 5-membered carbocyclic or 3- to 5-membered heterocyclic ring, wherein said cyclopropyl ring(s) or 3- to 5-membered carbocyclic or 3- to 5-membered heterocyclic ring(s) may be further independently substituted by one or more substituents selected from the group consisting of halogen, hydroxy, alkyl, haloalkyl, cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment of the invention, one of $R^1$ to $R^4$ together with the corresponding $R^{1'}$ to $R^{4'}$ form a 2-4-membered carbon chain to form a cyclopropyl, cyclobutyl or cyclopentyl ring, each of which is optionally substituted by one or more fluoro, methyl or trifluoromethyl; and the others of $R^1$ to $R^4$ and $R^{1'}$ to $R^{4'}$ are independently hydrogen or $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment of the invention, two of $R^1$ to $R^4$ together with the corresponding $R^{1'}$ to $R^{4'}$ form a 2-4-membered carbon chain to form a cyclopropyl, cyclobutyl or cyclopentyl ring, each of which is optionally substituted by one or more fluoro, methyl or trifluoromethyl; and the others of $R^1$ to $R^4$ and $R^{1'}$ to $R^{4'}$ are independently hydrogen or $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment of the invention, three of $R^1$ to $R^4$ together with the corresponding $R^{1'}$ to $R^{4'}$ form a 2-4-membered carbon chain to form a cyclopropyl, cyclobutyl or cyclopentyl ring, each of which is optionally substituted by one or more fluoro, methyl or trifluoromethyl; and the other $R^1$ to $R^4$ and corresponding $R^{1'}$ to $R^{4'}$ are independently hydrogen or $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment of the invention, one of $R^1$ to $R^4$ is a methylene (—$CH_2$—) or methylene substituted by one or two halogen atoms (—CHX— or —$CX_2$— where X is halogen) which are independently substituted by a 3- to 6-membered carbocyclic or 3- to 6-membered heterocyclic group (in other words methyl or methyl substituted by one or two halogen atoms, which is further substituted by a 3- to 6-membered carbocyclic or a 3- to 6-membered heterocyclic group), wherein said 3- to 6-membered carbocyclic or 3- to 6-membered heterocyclic group may be further substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; while the others of $R^1$ to $R^4$ are independently $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In another embodiment, two of $R^1$ to $R^4$ are independently methylene (—$CH_2$—) or methylene substituted by one or two halogen atoms (—CHX— or —$CX_2$— where X is halogen) which are independently substituted by a 3- to 6-membered carbocyclic or 3- to 6-membered heterocyclic group (in other words methyl or methyl substituted by one or two halogen atoms, each of which is independently further substituted by a 3- to 6-membered carbocyclic or a 3- to 6-membered heterocyclic group), wherein said 3- to 6-membered carbocyclic or 3- to 6-membered heterocyclic group may be further substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; while the other two of $R^1$ to $R^4$ are independently $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In another embodiment, $R^2$ and $R^4$ are independently methylene (—$CH_2$—) or methylene substituted by one or two halogen atoms (—CHX— or —$CX_2$— where X is halogen) which are independently substituted by a 3- to 6-membered carbocyclic or 3- to 6-membered heterocyclic group (in other words methyl or methyl substituted by one or two halogen atoms, each of which is independently further substituted by a 3- to 6-membered carbocyclic or a 3- to 6-membered heterocyclic group), wherein said 3- to 6-membered carbocyclic or 3- to 6-membered heterocyclic group may be further substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^1$ and $R^3$ are independently $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In another embodiment, $R^1$ and $R^3$ are independently methylene (—$CH_2$—) or methylene substituted by one or two halogen atoms (—CHX— or —$CX_2$— where X is halogen) which are independently substituted by a 3- to 6-membered carbocyclic or 3- to 6-membered heterocyclic group (in other words methyl or methyl substituted by one or two halogen atoms, each of which is independently further substituted by a 3- to 6-membered carbocyclic or a 3- to 6-membered heterocyclic group), wherein said 3- to 6-membered carbocyclic or 3- to 6-membered heterocyclic group may be further substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^2$ and $R^4$ are independently $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In yet another embodiment, three of $R^1$ to $R^4$ are independently methylene (—$CH_2$—) or methylene substituted by one or two halogen atoms (—CHX— or —$CX_2$— where X is halogen) which are independently substituted by a 3- to 6-membered 3- to 6-membered carbocyclic or 3- to 6-membered heterocyclic group (in other words methyl or methyl substituted by one or two halogen atoms, each of which is independently further substituted by a 3- to 6-membered carbocyclic or a 3- to 6-membered heterocyclic group), wherein said 3- to 6-membered carbocyclic or 3- to 6-membered heterocyclic group may be further independently substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; while the other of $R^1$ to $R^4$ is $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In still another embodiment, all four of $R^1$ to $R^4$ are independently methylene (—$CH_2$—) or methylene substituted by one or two halogen atoms (—CHX— or —$CX_2$— where X is halogen) which are independently substituted by a 3- to 6-membered carbocyclic or 3- to 6-membered heterocyclic group (in other words methyl or methyl substituted by one or two halogen atoms, each of which is independently further substituted by a 3- to 6-membered carbocyclic or 3- to 6-membered heterocyclic group), wherein said 3- to 6-membered carbocyclic or 3- to 6-membered heterocyclic group may be further independently substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment of the invention, one of $R^1$ to $R^4$ is a methylene (—$CH_2$—) or methylene substituted by one or two halogen atoms (—CHX— or —CX$_2$— where X is halogen) which is substituted by a carbocyclic or heterocyclic group selected from the group consisting of cyclopropyl, cyclobutyl, cyclopentyl, cyclopentenyl, phenyl, oxirane, oxetane, thiirane, thietane, aziridine, azetidine, pyrrolidine, pyrrole, thiophene, oxazole, isoxazole, isoxazoline, thiazole, isothiazole, 1,3,4-thiadiazole, pyrazole, imidazole, triazole, tetrazole, furan, tetrahydrofuran, and dihydrofuran (in other words methyl or methyl substituted by one or two halogen atoms, which is further substituted by one of said carbocyclic or heterocyclic groups), wherein said carbocyclic or heterocyclic group may be further independently substituted by one or more substituents selected from the group consisting of halogen, hydroxy, alkyl, haloalkyl, cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino while the others of $R^1$ to $R^4$ are $C_1$-$C_4$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In another embodiment, two of $R^1$ to $R^4$ are independently methylene (—CH$_2$—) or methylene substituted by one or two halogen atoms (—CHX— or —CX$_2$— where X is halogen) which are independently substituted by a carbocyclic or heterocyclic group selected from the group consisting of cyclopropyl, cyclobutyl, cyclopentyl, cyclopentenyl, phenyl, oxirane, oxetane, thiirane, thietane, aziridine, azetidine, pyrrolidine, pyrrole, thiophene, oxazole, isoxazole, isoxazoline, thiazole, isothiazole, 1,3,4-thiadiazole, pyrazole, imidazole, triazole, tetrazole, furan, tetrahydrofuran, and dihydrofuran (in other words methyl or methyl substituted by one or two halogen atoms, each of which is independently further substituted by said carbocyclic or heterocyclic groups), wherein said carbocyclic or heterocyclic group may be further independently substituted by one or more substituents selected from the group consisting of halogen, hydroxy, alkyl, haloalkyl, cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino while the others of $R^1$ to $R^4$ are $C_1$-$C_4$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment, $R^2$ and $R^4$ are independently methylene (—CH$_2$—) or methylene substituted by one or two halogen atoms (—CHX— or —CX$_2$— where X is halogen) which are independently substituted by a carbocyclic or heterocyclic group selected from the group consisting of cyclopropyl, cyclobutyl, cyclopentyl, cyclopentenyl, phenyl, oxirane, oxetane, thiirane, thietane, aziridine, azetidine, pyrrolidine, pyrrole, thiophene, oxazole, isoxazole, isoxazoline, thiazole, isothiazole, 1,3,4-thiadiazole, pyrazole, imidazole, triazole, tetrazole, furan, tetrahydrofuran, and dihydrofuran (in other words methyl or methyl substituted by one or two halogen atoms, each of which is independently further substituted by said carbocyclic or heterocyclic groups), wherein said carbocyclic or heterocyclic group may be further independently substituted by one or more substituents selected from the group consisting of halogen, hydroxy, alkyl, haloalkyl, cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^1$ and $R^3$ are independently $C_1$-$C_4$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment, $R^1$ and $R^3$ are independently methylene (—CH$_2$—) or methylene substituted by one or two halogen atoms (—CHX— or —CX$_2$— where X is halogen) which are independently substituted by a carbocyclic or heterocyclic group selected from the group consisting of cyclopropyl, cyclobutyl, cyclopentyl, cyclopentenyl, phenyl, oxirane, oxetane, thiirane, thietane, aziridine, azetidine, pyrrolidine, pyrrole, thiophene, oxazole, isoxazole, isoxazoline, thiazole, isothiazole, 1,3,4-thiadiazole, pyrazole, imidazole, triazole, tetrazole, furan, tetrahydrofuran, and dihydrofuran (in other words methyl or methyl substituted by one or two halogen atoms, each of which is independently further substituted by said carbocyclic or heterocyclic groups), wherein said carbocyclic or heterocyclic group may be further independently substituted by one or more substituents selected from the group consisting of halogen, hydroxy, alkyl, haloalkyl, cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^2$ and $R^4$ are independently $C_1$-$C_4$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In yet another embodiment, three of $R^1$ to $R^4$ are independently methylene (—CH$_2$—) or methylene substituted by one or two halogen atoms (—CHX— or —CX$_2$— where X is halogen) which are independently substituted by a carbocyclic or heterocyclic group selected from the group consisting of cyclopropyl, cyclobutyl, cyclopentyl, cyclopentenyl, phenyl, oxirane, oxetane, thiirane, thietane, aziridine, azetidine, pyrrolidine, pyrrole, thiophene, oxazole, isoxazole, isoxazoline, thiazole, isothiazole, 1,3,4-thiadiazole, pyrazole, imidazole, triazole, tetrazole, furan, tetrahydrofuran, and dihydrofuran (in other words methyl or methyl substituted by one or two halogen atoms, each of which is independently further substituted by said carbocyclic or heterocyclic groups), wherein said carbocyclic or heterocyclic group may be further independently substituted by one or more substituents selected from the group consisting of halogen, hydroxy, alkyl, haloalkyl, cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the others of $R^1$ to $R^4$ are $C_1$-$C_4$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In still another embodiment, all four of $R^1$ to $R^4$ are independently methylene (—CH$_2$—) or methylene substituted by one or two halogen atoms (—CHX— or —CX$_2$— where X is halogen) which are independently substituted by carbocyclic or heterocyclic group selected from the group consisting of cyclopropyl, cyclobutyl, cyclopentyl, cyclopentenyl, phenyl, oxirane, oxetane, thiirane, thietane, aziridine, azetidine, pyrrolidine, pyrrole, thiophene, oxazole, isoxazole, isoxazoline, thiazole, isothiazole, 1,3,4-thiadazole, pyrazole, imidazole, triazole, tetrazole, furan, tetrahydrofuran, and dihydrofuran (in other words methyl or methyl substituted by one or two halogen atoms, each of which is independently further substituted by said carbocyclic or heterocyclic groups), wherein said carbocyclic or heterocyclic group may be further independently substituted by one or more substituents selected from the group consisting of halogen, hydroxy, alkyl, haloalkyl, cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment of the invention, one of $R^1$ to $R^4$ together with the corresponding $R^{1'}$ to $R^{4'}$ form a 2- or 3-membered carbon chain to form a cyclopropyl or cyclobutyl ring which is optionally substituted by one or more fluoro, methyl or trifluoromethyl; and the others of $R^1$ to $R^4$ and $R^{1'}$ to $R^{4'}$ are independently hydrogen or $C_1$-$C_4$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment of the invention, two of $R^1$ to $R^4$ together with the corresponding $R^{1'}$ to $R^{4'}$ independently form a 2- or 3-membered carbon chain to form a cyclopropyl or cyclobutyl ring each of which is optionally substituted by one or more fluoro, methyl or trifluoromethyl; and the others of $R^1$ to $R^4$ and $R^{1'}$ to $R^{4'}$ are independently hydrogen or $C_1$-$C_4$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment of the invention, three of $R^1$ to $R^4$ together with the corresponding $R^{1'}$ to $R^{4'}$ independently form a 2- or 3-membered carbon chain to form a cyclopropyl or cyclobutyl ring, each of which is optionally substituted by one or more fluoro, methyl or trifluoromethyl; and the others of $R^1$ to $R^4$ and $R^{1'}$ to $R^{4'}$ are independently hydrogen or $C_1$-$C_4$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment of the invention, all four of $R^1$ to $R^4$ together with the corresponding $R^{1'}$ to $R^{4'}$ independently form a 2- or 3-membered carbon chain to form a cyclopropyl or cyclobutyl ring, each of which is optionally substituted by one or more fluoro, methyl or trifluoromethyl.

In still another embodiment, one of $R^1$ to $R^4$ is methylene (—$CH_2$—) or methylene substituted by one or two halogen atoms (—CHX— or —$CX_2$— where X is halogen) which are substituted by carbocyclic or heterocyclic group selected from the group consisting of naphthyl, indanyl, biphenyl, indolyl, isoindolyl, benzothiazolyl, benzoxazolyl, benz[d]isoxazolyl, benzotriazolyl, benzodioxolyl, benzothienyl, quinuclidinyl, quinazolinyl, quinoxalinyl, quinolinyl, isoquinolinyl, benzimidazolyl, benzopyranyl, indolizinyl, benzofuranyl, dihydrobenzofuranyl, chromonyl, coumarinyl, cinnolinyl, indazolyl, pyrrolopyridyl, phthalazinyl, 1,2,3-benzotriazinyl, 1,2,4-benzotriazinyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and tetrahydroisoquinolinyl (in other words methyl or methyl substituted by one or two halogen atoms, which is further substituted by one of said carbocyclic or heterocyclic groups), wherein said carbocyclic or heterocyclic group may be further independently substituted by one or more substituents selected from the group consisting of halogen, hydroxy, alkyl, haloalkyl, cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the others of $R^1$ to $R^4$ are $C_1$-$C_4$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In still another embodiment, two of $R^1$ to $R^4$ is methylene (—$CH_2$—) or methylene substituted by one or two halogen atoms (—CHX— or —$CX_2$— where X is halogen) which are independently substituted by carbocyclic or heterocyclic group selected from the group consisting of naphthyl, indanyl, biphenyl, indolyl, isoindolyl, benzothiazolyl, benzoxazolyl, benz[d]isoxazolyl, benzotriazolyl, benzodioxolyl, benzothienyl, quinuclidinyl, quinazolinyl, quinoxalinyl, quinolinyl, isoquinolinyl, benzimidazolyl, benzopyranyl, indolizinyl, benzofuranyl, dihydrobenzofuranyl, chromonyl, coumarinyl, cinnolinyl, indazolyl, pyrrolopyridyl, phthalazinyl, 1,2,3-benzotriazinyl, 1,2,4-benzotriazinyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and tetrahydroisoquinolinyl (in other words methyl or methyl substituted by one or two halogen atoms, each of which is independently further substituted by said carbocyclic or heterocyclic groups), wherein said carbocyclic or heterocyclic group may be further independently substituted by one or more substituents selected from the group consisting of halogen, hydroxy, alkyl, haloalkyl, cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the others of $R^1$ to $R^4$ are $C_1$-$C_4$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In still another embodiment, $R^2$ and $R^4$ are methylene (—$CH_2$—) or methylene substituted by one or two halogen atoms (—CHX— or —$CX_2$— where X is halogen) which are independently substituted by carbocyclic or heterocyclic group selected from the group consisting of naphthyl, indanyl, biphenyl, indolyl, isoindolyl, benzothiazolyl, benzoxazolyl, benz[d]isoxazolyl, benzotriazolyl, benzodioxolyl, benzothienyl, quinuclidinyl, quinazolinyl, quinoxalinyl, quinolinyl, isoquinolinyl, benzimidazolyl, benzopyranyl, indolizinyl, benzofuranyl, dihydrobenzofuranyl, chromonyl, coumarinyl, cinnolinyl, indazolyl, pyrrolopyridyl, phthalazinyl, 1,2,3-benzotriazinyl, 1,2,4-benzotriazinyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and tetrahydroisoquinolinyl (in other words methyl or methyl substituted by one or two halogen atoms, each of which is independently further substituted by said carbocyclic or heterocyclic groups), wherein said carbocyclic or heterocyclic group may be further independently substituted by one or more substituents selected from the group consisting of halogen, hydroxy, alkyl, haloalkyl, cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^1$ and $R^3$ are independently $C_1$-$C_4$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In still another embodiment, $R^1$ and $R^3$ are methylene (—$CH_2$—) or methylene substituted by one or two halogen atoms (—CHX— or —$CX_2$— where X is halogen) which are independently substituted by carbocyclic or heterocyclic group selected from the group consisting of naphthyl, indanyl, biphenyl, indolyl, isoindolyl, benzothiazolyl, benzoxazolyl, benz[d]isoxazolyl, benzotriazolyl, benzodioxolyl, benzothienyl, quinuclidinyl, quinazolinyl, quinoxalinyl, quinolinyl, isoquinolinyl, benzimidazolyl, benzopyranyl, indolizinyl, benzofuranyl, dihydrobenzofuranyl, chromonyl, coumarinyl, cinnolinyl, indazolyl, pyrrolopyridyl, phthalazinyl, 1,2,3-benzotriazinyl, 1,2,4-benzotriazinyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and tetrahydroisoquinolinyl (in other words methyl or methyl substituted by one or two halogen atoms, each of which is independently further substituted by said carbocyclic or heterocyclic groups), wherein said carbocyclic or heterocyclic group may be further independently substituted by one or more substituents selected from the group consisting of halogen, hydroxy, alkyl, haloalkyl, cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^2$ and $R^4$ are independently $C_1$-$C_4$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In still another embodiment, three of $R^1$ to $R^4$ are independently methylene (—$CH_2$—) or methylene substituted by one or two halogen atoms (—CHX— or —$CX_2$— where X is halogen) which are independently substituted by carbocyclic or heterocyclic group selected from the group consisting of naphthyl, indanyl, biphenyl, indolyl, isoindolyl, benzothiazolyl, benzoxazolyl, benz[d]isoxazolyl, benzotriazolyl, benzodioxolyl, benzothienyl, quinuclidinyl, quinazolinyl, quinoxalinyl, quinolinyl, isoquinolinyl, benzimidazolyl, benzopyranyl, indolizinyl, benzofuranyl, dihydrobenzofuranyl, chromonyl, coumarinyl, cinnolinyl, indazolyl, pyrrolopyridyl, phthalazinyl, 1,2,3-benzotriazinyl, 1,2,4-benzotriazinyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and tetrahydroisoquinolinyl (in other words methyl or methyl substituted by one or two halogen atoms, each of which is independently further substituted by said carbocyclic or heterocyclic groups), wherein said carbocyclic or heterocyclic group may be further independently substituted by one or more substituents selected from the group consisting of halogen, hydroxy, alkyl, haloalkyl, cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the other of $R^1$ to $R^4$ are $C_1$-$C_4$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In still another embodiment, all four of $R^1$ to $R^4$ are independently methylene (—$CH_2$—) or methylene substituted by one or two halogen atoms (—CHX— or —$CX_2$— where X is halogen) which are independently substituted by carbocyclic or heterocyclic group selected from the group consisting of naphthyl, indanyl, biphenyl, indolyl, isoindolyl, benzothiazolyl, benzoxazolyl, benz[d]isoxazolyl, benzotriazolyl, benzodioxolyl, benzothienyl, quinuclidinyl, quinazolinyl, quinoxalinyl, quinolinyl, isoquinolinyl, benzimidazolyl, benzopyranyl, indolizinyl, benzofuranyl, dihydrobenzofuranyl, chromonyl, coumarinyl, cinnolinyl, indazolyl, pyrrolopyridyl, phthalazinyl, 1,2,3-benzotriazinyl, 1,2,4-benzotriazinyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and tetrahydroisoquinolinyl (in other words methyl or methyl substituted by one or two halogen atoms, each of which is independently further substituted by said carbocyclic or heterocyclic groups), wherein said carbocyclic or heterocyclic group may be further independently substituted by one or more substituents selected from the group consisting of halogen, hydroxy, alkyl, haloalkyl, cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment of the invention, one of $R^1$ to $R^4$ is a methylene (—$CH_2$—) or methylene substituted by one or two halogen atoms (—CHX— or —$CX_2$— where X is halogen) which are substituted by a 3- to 6-membered carbocyclic or 3- to 6-membered heterocyclic group (in other words methyl or methyl substituted by one or two halogen atoms, which is further substituted by a 3- to 6-membered carbocyclic or a 3- to 6-membered heterocyclic group), wherein said 3- to 6-membered carbocyclic or 3- to 6-membered heterocyclic group may be further independently substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the others of $R^1$ to $R^4$ are independently 2-methylpropyl or 2,2-dimethylpropyl.

In another embodiment, two of $R^1$ to $R^4$ are independently methylene (—$CH_2$—) or methylene substituted by one or two halogen atoms (—CHX— or —$CX_2$— where X is halogen) which are independently substituted by a 3- to 6-membered carbocyclic or 3- to 6-membered heterocyclic group (in other words methyl or methyl substituted by one or two halogen atoms, each of which is independently further substituted by said 3- to 6-membered carbocyclic or 3- to 6-membered heterocyclic groups), wherein said 3- to 6-membered carbocyclic or 3- to 6-membered heterocyclic group may be further substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the other two of $R^1$ to $R^4$ are independently 2-methylpropyl or 2,2-dimethylpropyl.

In another embodiment, $R^2$ and $R^4$ are independently methylene (—$CH_2$—) or methylene substituted by one or two halogen atoms (—CHX— or —$CX_2$— where X is halogen) which are independently substituted by a 3- to 6-membered carbocyclic or 3- to 6-membered heterocyclic group (in other words methyl or methyl substituted by one or two halogen atoms, each of which is independently further substituted by said 3- to 6-membered carbocyclic or 3- to 6-membered heterocyclic groups), wherein said 3- to 6-membered carbocyclic or 3- to 6-membered heterocyclic group may be further substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^1$ and $R^3$ are independently 2-methylpropyl or 2,2-dimethylpropyl.

In another embodiment, $R^1$ and $R^3$ are independently methylene (—$CH_2$—) or methylene substituted by one or two halogen atoms (—CHX— or —$CX_2$— where X is halogen) which are independently substituted by a 3- to 6-membered carbocyclic or 3- to 6-membered heterocyclic group (in other words methyl or methyl substituted by one or two halogen atoms, each of which is independently further substituted by said 3- to 6-membered carbocyclic or 3- to 6-membered heterocyclic groups), wherein said 3- to 6-membered carbocyclic or 3- to 6-membered heterocyclic group may be further substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^2$ and $R^4$ are independently 2-methylpropyl or 2,2-dimethylpropyl.

In yet another embodiment, three of $R^1$ to $R^4$ are independently methylene (—$CH_2$—) or methylene substituted by one or two halogen atoms (—CHX— or —$CX_2$— where X is halogen) which are independently substituted by a 3- to 6-membered carbocyclic or 3- to 6-membered heterocyclic group (in other words methyl or methyl substituted by one or two halogen atoms, each of which is independently further substituted by said 3- to 6-membered carbocyclic or 3- to 6-membered heterocyclic group), wherein said 3- to 6-membered carbocyclic or 3- to 6-membered heterocyclic group may be further independently substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the other of $R^1$ to $R^4$ is 2-methylpropyl or 2,2-dimethylpropyl.

In another embodiment of the invention, one of $R^1$ to $R^4$ together with the corresponding $R^{1'}$ to $R^{4'}$ form a 2- or 3-membered carbon chain to form a cyclopropyl or cyclobutyl ring which is optionally substituted by one or more fluoro, methyl or trifluoromethyl; and the others of $R^1$ to $R^4$ and $R^{1'}$ to $R^{4'}$ are independently hydrogen, 2-methylpropyl or 2,2-dimethylpropyl.

In another embodiment of the invention, two of $R^1$ to $R^4$ together with the corresponding $R^{1'}$ to $R^{4'}$ independently form a 2- or 3-membered carbon chain to form a cyclopropyl or cyclobutyl ring, each of which is optionally independently substituted by one or more fluoro, methyl or trifluoromethyl; and the others of $R^1$ to $R^4$ and $R^{1'}$ to $R^{4'}$ are independently hydrogen, 2-methylpropyl or 2,2-dimethylpropyl.

In another embodiment of the invention, three of $R^1$ to $R^4$ together with the corresponding $R^{1'}$ to $R^{4'}$ independently form a 2- or 3-membered carbon chain to form a cyclopropyl or cyclobutyl ring, each of which is optionally independently substituted by one or more fluoro, methyl or trifluoromethyl; and the other of $R^1$ to $R^4$ and the corresponding $R^{1'}$ to $R^{4'}$ are independently hydrogen, 2-methylpropyl or 2,2-dimethylpropyl.

In another embodiment of the invention, one of $R^1$ to $R^4$ is a methylene (—$CH_2$—) or methylene substituted by one or two halogen atoms (—CHX— or —$CX_2$— where X is halogen) which is substituted by a 3- to 6-membered carbocyclic or 3- to 6-membered heterocyclic group (in other words methyl or methyl substituted by one or two halogen atoms, which is further substituted by a 3- to 6-membered carbocyclic or a 3- to 6-membered heterocyclic group), wherein said 3- to 6-membered carbocyclic or 3- to 6-membered heterocyclic group may be further independently substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the others of $R^1$ to $R^4$ are independently 2,2-dimethylpropyl or 2-methylpropyl substituted by one or more substituents selected from the group consisting of halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment, two of $R^1$ to $R^4$ are independently methylene (—$CH_2$—) or methylene substituted by one or two halogen atoms (—CHX— or —$CX_2$— where X is halogen) which are independently substituted by a 3- to 6-membered carbocyclic or 3- to 6-membered heterocyclic group (in other words methyl or methyl substituted by one or two halogen atoms, each of which is independently further substituted by a 3- to 6-membered carbocyclic or a 3- to 6-membered heterocyclic group), wherein said 3- to 6-membered carbocyclic or 3- to 6-membered heterocyclic groups may be further substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the other two of $R^1$ to $R^4$ are independently 2,2-dimethylpropyl or 2-methylpropyl substituted by one or more substituents selected from the group consisting of halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment, $R^2$ and $R^4$ are independently methylene (—$CH_2$—) or methylene substituted by one or two halogen atoms (—CHX— or —$CX_2$— where X is halogen) which are independently substituted by a 3- to 6-membered carbocyclic or 3- to 6-membered heterocyclic group (in other words methyl or methyl substituted by one or two halogen atoms, each of which is independently further substituted by a 3- to 6-membered carbocyclic or a 3- to 6-membered heterocyclic group), wherein said 3- to 6-membered carbocyclic or 3- to 6-membered heterocyclic groups may be further substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^1$ and $R^3$ are independently 2,2-dimethylpropyl or 2-methylpropyl substituted by one or more substituents selected from the group consisting of halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment, $R^1$ and $R^3$ are independently methylene (—$CH_2$—) or methylene substituted by one or two halogen atoms (—CHX— or —$CX_2$— where X is halogen) which are independently substituted by a 3- to 6-membered carbocyclic or 3- to 6-membered heterocyclic group (in other words methyl or methyl substituted by one or two halogen atoms, each of which is independently further substituted by a 3- to 6-membered carbocyclic or a 3- to 6-membered heterocyclic group), wherein said 3- to 6-membered carbocyclic or 3- to 6-membered heterocyclic groups may be further substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^2$ and $R^4$ are independently 2,2-dimethylpropyl or 2-methylpropyl substituted by one or more substituents selected from the group consisting of halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In yet another embodiment, three of $R^1$ to $R^4$ are independently methylene (—$CH_2$—) or methylene substituted by one or two halogen atoms (—CHX— or —$CX_2$— where X is halogen) which are independently substituted by a 3- to 6-membered carbocyclic or a 3- to 6-membered heterocyclic group, wherein said 3- to 6-membered carbocyclic or 3- to 6-membered heterocyclic groups may be further independently substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the other of $R^1$ to $R^4$ is 2,2-dimethylpropyl or 2-methylpropyl substituted by one or more substituents selected from the group consisting of halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In yet another embodiment, one of $R^1$ to $R^4$ is methylene (—$CH_2$—) or methylene substituted by one or two halogen atoms (—CHX— or —$CX_2$— where X is halogen) which is substituted by a carbocyclic or heterocyclic group selected from the group consisting of cyclopropyl, cyclobutyl, cyclopentyl, cyclopentenyl, phenyl, oxirane, oxetane, thiirane, thietane, aziridine, azetidine, pyrrolidine, pyrrole, thiophene, oxazole, isoxazole, isoxazoline, thiazole, isothiazole, 1,3,4-thiadiazole, pyrazole, imidazole, triazole, tetrazole, furan, tetrahydrofuran and dihydrofuran (in other words methyl or methyl substituted by one or two halogen atoms, which is independently further substituted by said carbocyclic or heterocyclic groups), wherein said carbocyclic or heterocyclic group may be further substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the others of $R^1$ to $R^4$ are independently 2,2-dimethylpropyl or 2-methylpropyl substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In yet another embodiment, two of $R^1$ to $R^4$ are independently methylene (—$CH_2$—) or methylene substituted by one or two halogen atoms (—CHX— or —$CX_2$— where X is halogen) which are independently substituted by a carbocyclic or heterocyclic group selected from the group consisting of cyclopropyl, cyclobutyl, cyclopentyl, cyclopentenyl, phenyl, oxirane, oxetane, thiirane, thietane, aziridine, azetidine, pyrrolidine, pyrrole, thiophene, oxazole, isoxazole, isoxazoline, thiazole, isothiazole, 1,3,4-thiadiazole, pyrazole, imidazole, triazole, tetrazole, furan, tetrahydrofuran and dihydrofuran (in other words methyl or methyl substituted by one or two halogen atoms, which is independently further substituted by said carbocyclic or heterocyclic groups), wherein said carbocyclic or heterocyclic groups may be further independently substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the others of $R^1$ to $R^4$ are independently 2,2-dimethylpropyl or 2-methylpropyl substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In yet another embodiment, $R^2$ and $R^4$ are independently methylene (—$CH_2$—) or methylene substituted by one or two halogen atoms (—CHX— or —$CX_2$— where X is halogen) which are independently substituted by a carbocyclic or heterocyclic group selected from the group consisting of cyclopropyl, cyclobutyl, cyclopentyl, cyclopentenyl, phenyl, oxirane, oxetane, thiirane, thietane, aziridine, azetidine, pyrrolidine, pyrrole, thiophene, oxazole, isoxazole, isoxazoline, thiazole, isothiazole, 1,3,4-thiadiazole, pyrazole, imidazole, triazole, tetrazole, furan, tetrahydrofuran and dihydrofuran (in other words methyl or methyl substituted by one or two halogen atoms, which is independently further substituted by said carbocyclic or heterocyclic groups), wherein said carbocyclic or heterocyclic groups may be further independently substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^1$ and $R^3$ are independently 2,2-dimethylpropyl or 2-methylpropyl substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In yet another embodiment, $R^1$ and $R^3$ are independently methylene ($-CH_2-$) or methylene substituted by one or two halogen atoms ($-CHX-$ or $-CX_2-$ where X is halogen) which are independently substituted by a carbocyclic or heterocyclic group selected from the group consisting of cyclopropyl, cyclobutyl, cyclopentyl, cyclopentenyl, phenyl, oxirane, oxetane, thiirane, thietane, aziridine, azetidine, pyrrolidine, pyrrole, thiophene, oxazole, isoxazole, isoxazoline, thiazole, isothiazole, 1,3,4-thiadazole, pyrazole, imidazole, triazole, tetrazole, furan, tetrahydrofuran and dihydrofuran (in other words methyl or methyl substituted by one or two halogen atoms, which is independently further substituted by said carbocyclic or heterocyclic groups), wherein said carbocyclic or heterocyclic groups may be further independently substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^2$ and $R^4$ are independently 2,2-dimethylpropyl or 2-methylpropyl substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In yet another embodiment, three of $R^1$ to $R^4$ are independently methylene ($-CH_2-$) or methylene substituted by one or two halogen atoms ($-CHX-$ or $-CX_2-$ where X is halogen) which are independently substituted by a carbocyclic or heterocyclic group selected from the group consisting of cyclopropyl, cyclobutyl, cyclopentyl, cyclopentenyl, phenyl, oxirane, oxetane, thiirane, thietane, aziridine, azetidine, pyrrolidine, pyrrole, thiophene, oxazole, isoxazole, isoxazoline, thiazole, isothiazole, 1,3,4-thiadazole, pyrazole, imidazole, triazole, tetrazole, furan, tetrahydrofuran and dihydrofuran (in other words methyl or methyl substituted by one or two halogen atoms, which is independently further substituted by said carbocyclic or heterocyclic groups), wherein said carbocyclic or heterocyclic groups may be further independently substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the other $R^1$ to $R^4$ is 2,2-dimethylpropyl or 2-methylpropyl substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In yet another embodiment, one of $R^1$ to $R^4$ are independently methylene ($-CH_2-$) or methylene substituted by one or two halogen atoms ($-CHX-$ or $-CX_2-$ where X is halogen) which is substituted by a carbocyclic or heterocyclic group selected from the group consisting of naphthyl, indanyl, biphenyl, indolyl, isoindolyl, benzothiazolyl, benzoxazolyl, benz[d]isoxazolyl, benzotriazolyl, benzodioxolyl, benzothienyl, quinuclidinyl, quinazolinyl, quinoxalinyl, quinolinyl, isoquinolinyl, benzimidazolyl, benzopyranyl, indolizinyl, benzofuranyl, dihydrobenzofuranyl, chromonyl, coumarinyl, cinnolinyl, indazolyl, pyrrolopyridyl, phthalazinyl, 1,2,3-benzotriazinyl, 1,2,4-benzotriazinyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and tetrahydroisoquinolinyl (in other words methyl or methyl substituted by one or two halogen atoms, which is independently further substituted by one of said carbocyclic or heterocyclic groups), wherein said carbocyclic or heterocyclic group may be further substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the others of $R^1$ to $R^4$ are independently 2,2-dimethylpropyl or 2-methylpropyl substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment, two of $R^1$ to $R^4$ are independently methylene ($-CH_2-$) or methylene substituted by one or two halogen atoms ($-CHX-$ or $-CX_2-$ where X is halogen) which are independently substituted by a carbocyclic or heterocyclic group selected from the group consisting of naphthyl, indanyl, biphenyl, indolyl, isoindolyl, benzothiazolyl, benzoxazolyl, benz[d]isoxazolyl, benzotriazolyl, benzodioxolyl, benzothienyl, quinuclidinyl, quinazolinyl, quinoxalinyl, quinolinyl, isoquinolinyl, benzimidazolyl, benzopyranyl, indolizinyl, benzofuranyl, dihydrobenzofuranyl, chromonyl, coumarinyl, cinnolinyl, indazolyl, pyrrolopyridyl, phthalazinyl, 1,2,3-benzotriazinyl, 1,2,4-benzotriazinyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and tetrahydroisoquinolinyl (in other words methyl or methyl substituted by one or two halogen atoms, each of which is independently further substituted by one of said carbocyclic or heterocyclic groups), wherein said carbocyclic or heterocyclic groups may be further independently substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the others of $R^1$ to $R^4$ are independently 2,2-dimethylpropyl or 2-methylpropyl substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment, $R^2$ and $R^4$ are independently methylene ($-CH_2-$) or methylene substituted by one or two halogen atoms ($-CHX-$ or $-CX_2-$ where X is halogen) which are independently substituted by a carbocyclic or heterocyclic group selected from the group consisting of naphthyl, indanyl, biphenyl, indolyl, isoindolyl, benzothiazolyl, benzoxazolyl, benz[d]isoxazolyl, benzotriazolyl, benzodioxolyl, benzothienyl, quinuclidinyl, quinazolinyl, quinoxalinyl, quinolinyl, isoquinolinyl, benzimidazolyl, benzopyranyl, indolizinyl, benzofuranyl, dihydrobenzofuranyl, chromonyl, coumarinyl, cinnolinyl, indazolyl, pyrrolopyridyl, phthalazinyl, 1,2,3-benzotriazinyl, 1,2,4-benzotriazinyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and tetrahydroisoquinolinyl (in other words methyl or methyl substituted by one or two halogen atoms, each of which is independently further substituted by one of said carbocyclic or heterocyclic groups), wherein said carbocyclic or heterocyclic groups may be further independently substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^1$ and $R^3$ are independently 2,2-dimethylpropyl or 2-methylpropyl substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment, $R^1$ and $R^3$ are independently methylene (—$CH_2$—) or methylene substituted by one or two halogen atoms (—CHX— or —$CX_2$— where X is halogen) which are independently substituted by a carbocyclic or heterocyclic group selected from the group consisting of naphthyl, indanyl, biphenyl, indolyl, isoindolyl, benzothiazolyl, benzoxazolyl, benz[d]isoxazolyl, benzotriazolyl, benzodioxolyl, benzothienyl, quinuclidinyl, quinazolinyl, quinoxalinyl, quinolinyl, isoquinolinyl, benzimidazolyl, benzopyranyl, indolizinyl, benzofuranyl, dihydrobenzofuranyl, chromonyl, coumarinyl, cinnolinyl, indazolyl, pyrrolopyridyl, phthalazinyl, 1,2,3-benzotriazinyl, 1,2,4-benzotriazinyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and tetrahydroisoquinolinyl (in other words methyl or methyl substituted by one or two halogen atoms, each of which is independently further substituted by one of said carbocyclic or heterocyclic groups), wherein said carbocyclic or heterocyclic groups may be further independently substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^2$ and $R^4$ are independently 2,2-dimethylpropyl or 2-methylpropyl substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In yet another embodiment, three of $R^1$ to $R^4$ are independently methylene (—$CH_2$—) or methylene substituted by one or two halogen atoms (—CHX— or —$CX_2$— where X is halogen) which are independently substituted by a carbocyclic or heterocyclic group selected from the group consisting of naphthyl, indanyl, biphenyl, indolyl, isoindolyl, benzothiazolyl, benzoxazolyl, benz[d]isoxazolyl, benzotriazolyl, benzodioxolyl, benzothienyl, quinuclidinyl, quinazolinyl, quinoxalinyl, quinolinyl, isoquinolinyl, benzimidazolyl, benzopyranyl, indolizinyl, benzofuranyl, dihydrobenzofuranyl, chromonyl, coumarinyl, cinnolinyl, indazolyl, pyrrolopyridyl, phthalazinyl, 1,2,3-benzotriazinyl, 1,2,4-benzotriazinyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and tetrahydroisoquinolinyl (in other words methyl or methyl substituted by one or two halogen atoms, each of which is independently further substituted by one of said carbocyclic or heterocyclic groups), wherein said carbocyclic or heterocyclic groups may be further substituted by one or more substituents selected from the group consisting of halogen, hydroxy, alkyl, haloalkyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the other $R^1$ to $R^4$ is 2,2-dimethylpropyl or 2-methylpropyl substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In another embodiment, all four of $R^1$ to $R^4$ are independently methylene (—$CH_2$—) or methylene substituted by one or two halogen atoms (—CHX— or —$CX_2$— where X is halogen) which are independently substituted by a carbocyclic or heterocyclic group selected from the group consisting of naphthyl, indanyl, biphenyl, indolyl, isoindolyl, benzothiazolyl, benzoxazolyl, benz[d]isoxazolyl, benzotriazolyl, benzodioxolyl, benzothienyl, quinuclidinyl, quinazolinyl, quinoxalinyl, quinolinyl, isoquinolinyl, benzimidazolyl, benzopyranyl, indolizinyl, benzofuranyl, dihydrobenzofuranyl, chromonyl, coumarinyl, cinnolinyl, indazolyl, pyrrolopyridyl, phthalazinyl, 1,2,3-benzotriazinyl, 1,2,4-benzotriazinyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and tetrahydroisoquinolinyl (in other words methyl or methyl substituted by one or two halogen atoms, each of which is independently further substituted by one of said carbocyclic or heterocyclic groups), wherein said carbocyclic or heterocyclic groups may be further substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment of the invention, one of $R^1$ to $R^4$ together with the corresponding $R^{1'}$ to $R^{4'}$ form a 2- or 3-membered carbon chain to form a cyclopropyl or cyclobutyl ring which is optionally substituted by one or more fluoro, methyl or trifluoromethyl; and the others of $R^1$ to $R^4$ and $R^{1'}$ to $R^{4'}$ are independently hydrogen, 2,2-dimethylpropyl or 2-methylpropyl substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment of the invention, two of $R^1$ to $R^4$ together with the corresponding $R^{1'}$ to $R^{4'}$ independently form a 2- or 3-membered carbon chain to form a cyclopropyl or cyclobutyl ring, each of which is optionally independently substituted by one or more fluoro, methyl or trifluoromethyl; and the others of $R^1$ to $R^4$ and $R^{1'}$ to $R^{4'}$ are independently hydrogen, 2,2-dimethylpropyl or 2-methylpropyl substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment of the invention, three of $R^1$ to $R^4$ together with the corresponding $R^{1'}$ to $R^{4'}$ independently form a 2- or 3-membered carbon chain to form a cyclopropyl or cyclobutyl ring, each of which is optionally independently substituted by one or more fluoro, methyl or trifluoromethyl; and the other of $R^1$ to $R^4$ and corresponding $R^{1'}$ to $R^{4'}$ are independently hydrogen, 2,2-dimethylpropyl or 2-methylpropyl substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In yet another embodiment, one of $R^1$ to $R^4$ is methylene (—$CH_2$—) or methylene substituted by one or two halogen atoms (—CHX— or —$CX_2$— where X is halogen) which is substituted by a carbocyclic or heterocyclic group selected from the group consisting of cyclopropyl, cyclobutyl, cyclopentyl, cyclopentenyl, phenyl, oxirane, oxetane, thiirane, thietane, aziridine, azetidine, pyrrolidine, pyrrole, thiophene, oxazole, isoxazole, isoxazoline, thiazole, isothiazole, 1,3,4-thiadazole, pyrazole, imidazole, triazole, tetrazole, furan, tetrahydrofuran and dihydrofuran (in other words methyl or methyl substituted by one or two halogen atoms, which is further substituted by one of said carbocyclic or heterocyclic groups), wherein said carbocyclic or heterocyclic group may be further substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the others of $R^1$ to $R^4$ are independently 2,2-dimethylpropyl or 2-methylpropyl substituted by one or more halogen.

In yet another embodiment, two of $R^1$ to $R^4$ are independently methylene (—$CH_2$—) or methylene substituted by one or two halogen atoms (—CHX— or —$CX_2$— where X is halogen) which are independently substituted by a carbocyclic or heterocyclic group selected from the group consisting of cyclopropyl, cyclobutyl, cyclopentyl, cyclopentenyl, phenyl, oxirane, oxetane, thiirane, thietane, aziridine, azetidine, pyrrolidine, pyrrole, thiophene, oxazole, isoxazole, isoxazoline, thiazole, isothiazole, 1,3,4-thiadazole, pyrazole, imidazole, triazole, tetrazole, furan, tetrahydrofuran and dihydrofuran (in other words methyl or methyl substituted by one or two halogen atoms, each of which is independently further substituted by one of said carbocyclic or heterocyclic groups), wherein said carbocyclic or heterocyclic groups may be further substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the others of $R^1$ to $R^4$ are independently 2,2-dimethylpropyl or 2-methylpropyl substituted by one or more halogen.

In yet another embodiment, $R^2$ and $R^4$ are independently methylene (—$CH_2$—) or methylene substituted by one or two halogen atoms (—CHX— or —$CX_2$— where X is halogen) which are independently substituted by a carbocyclic or heterocyclic group selected from the group consisting of cyclopropyl, cyclobutyl, cyclopentyl, cyclopentenyl, phenyl, oxirane, oxetane, thiirane, thietane, aziridine, azetidine, pyrrolidine, pyrrole, thiophene, oxazole, isoxazole, isoxazoline, thiazole, isothiazole, 1,3,4-thiadazole, pyrazole, imidazole, triazole, tetrazole, furan, tetrahydrofuran and dihydrofuran (in other words methyl or methyl substituted by one or two halogen atoms, each of which is independently further substituted by one of said carbocyclic or heterocyclic groups), wherein said carbocyclic or heterocyclic groups may be further substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^1$ and $R^3$ are independently 2,2-dimethylpropyl or 2-methylpropyl substituted by one or more halogen.

In yet another embodiment, $R^1$ and $R^3$ are independently methylene (—$CH_2$—) or methylene substituted by one or two halogen atoms (—CHX— or —$CX_2$— where X is halogen) which are independently substituted by a carbocyclic or heterocyclic group selected from the group consisting of cyclopropyl, cyclobutyl, cyclopentyl, cyclopentenyl, phenyl, oxirane, oxetane, thiirane, thietane, aziridine, azetidine, pyrrolidine, pyrrole, thiophene, oxazole, isoxazole, isoxazoline, thiazole, isothiazole, 1,3,4-thiadazole, pyrazole, imidazole, triazole, tetrazole, furan, tetrahydrofuran and dihydrofuran (in other words methyl or methyl substituted by one or two halogen atoms, each of which is independently further substituted by one of said carbocyclic or heterocyclic groups), wherein said carbocyclic or heterocyclic groups may be further substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^2$ and $R^4$ are independently 2,2-dimethylpropyl or 2-methylpropyl substituted by one or more halogen.

In yet another embodiment, three of $R^1$ to $R^4$ are independently methylene (—$CH_2$—) or methylene substituted by one or two halogen atoms (—CHX— or —$CX_2$— where X is halogen) which are independently substituted by a carbocyclic or heterocyclic group selected from the group consisting of cyclopropyl, cyclobutyl, cyclopentyl, cyclopentenyl, phenyl, oxirane, oxetane, thiirane, thietane, aziridine, azetidine, pyrrolidine, pyrrole, thiophene, oxazole, isoxazole, isoxazoline, thiazole, isothiazole, 1,3,4-thiadazole, pyrazole, imidazole, triazole, tetrazole, furan, tetrahydrofuran and dihydrofuran (in other words methyl or methyl substituted by one or two halogen atoms, each of which is independently further substituted by one of said carbocyclic or heterocyclic groups), wherein said carbocyclic or heterocyclic groups may be further independently substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the other of $R^1$ to $R^4$ is 2,2-dimethylpropyl or 2-methylpropyl substituted by one or more halogen.

In yet another embodiment, one of $R^1$ to $R^4$ is independently methylene (—$CH_2$—) or methylene substituted by one or two halogen atoms (—CHX— or —$CX_2$— where X is halogen) which is substituted by a carbocyclic or heterocyclic group selected from the group consisting of cyclopropyl, cyclobutyl, cyclopentyl, cyclopentenyl, phenyl, oxetane, pyrrole, tetrahydrofuran and dihydrofuran (in other words methyl or methyl substituted by one or two halogen atoms, which is further substituted by one of said carbocyclic or heterocyclic groups), wherein said carbocyclic or heterocyclic group may be further substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the others of $R^1$ to $R^4$ are independently 2,2-dimethylpropyl or 2-methylpropyl substituted by one or more fluorine.

In yet another embodiment, two of $R^1$ to $R^4$ are independently methylene (—$CH_2$—) or methylene substituted by one or two halogen atoms (—CHX— or —$CX_2$— where X is halogen) which are independently substituted by a carbocyclic or heterocyclic group selected from the group consisting of cyclopropyl, cyclobutyl, cyclopentyl, cyclopentenyl, phenyl, oxetane, pyrrole, tetrahydrofuran and dihydrofuran (in other words methyl or methyl substituted by one or two halogen atoms, each of which is independently further substituted by one of said carbocyclic or heterocyclic groups), wherein said carbocyclic or heterocyclic groups may be further independently substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the others of $R^1$ to $R^4$ are independently 2,2-dimethylpropyl or 2-methylpropyl, substituted by one or more fluorine.

In yet another embodiment, $R^2$ and $R^4$ are independently methylene (—$CH_2$—) or methylene substituted by one or two halogen atoms (—CHX— or —$CX_2$— where X is halogen) which are independently substituted by a carbocyclic or heterocyclic group selected from the group consisting of cyclopropyl, cyclobutyl, cyclopentyl, cyclopentenyl, phenyl, oxetane, pyrrole, tetrahydrofuran and dihydrofuran (in other words methyl or methyl substituted by one or two halogen atoms, each of which is independently further substituted by one of said carbocyclic or heterocyclic groups), wherein said carbocyclic or heterocyclic groups may be further independently substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^1$ and $R^3$ are independently 2,2-dimethylpropyl or 2-methylpropyl, substituted by one or more fluorine.

In yet another embodiment, $R^1$ and $R^3$ are independently methylene (—$CH_2$—) or methylene substituted by one or two halogen atoms (—CHX— or —$CX_2$— where X is halogen) which are independently substituted by a carbocyclic or heterocyclic group selected from the group consisting of cyclopropyl, cyclobutyl, cyclopentyl, cyclopentenyl, phenyl, oxetane, pyrrole, tetrahydrofuran and dihydrofuran (in other words methyl or methyl substituted by one or two halogen atoms, each of which is independently further substituted by one of said carbocyclic or heterocyclic groups), wherein said carbocyclic or heterocyclic groups may be further independently substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, haloalkylsulfonyl, alkoxyalkoxy, oxo, cyano, amino, alkylamino and dialkylamino; and $R^2$ and $R^4$ are independently 2,2-dimethylpropyl or 2-methylpropyl, substituted by one or more fluorine.

In yet another embodiment, three of $R^1$ to $R^4$ are independently methylene (—$CH_2$—) or methylene substituted by one or two halogen atoms (—CHX— or —$CX_2$— where X is halogen) which are independently substituted by a carbocyclic or heterocyclic group selected from the group consisting of cyclopropyl, cyclobutyl, cyclopentyl, cyclopentenyl, phenyl, oxetane, pyrrole, tetrahydrofuran and dihydrofuran (in other words methyl or methyl substituted by one or two halogen atoms, each of which is independently further substituted by one of said carbocyclic or heterocyclic groups), wherein said carbocyclic or heterocyclic groups may be further independently substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, while the other of $R^1$ to $R^4$ is 2,2-dimethylpropyl or 2-methylpropyl substituted by one or more fluorine.

In yet another embodiment, one of $R^1$ to $R^4$ is independently methylene (—$CH_2$—) or methylene substituted by one or two fluorine atoms (—CHF— or —$CF_2$—) which is substituted by a carbocyclic or heterocyclic group selected from the group consisting of cyclopropyl, cyclobutyl, cyclopentyl, cyclopentenyl, phenyl, oxetane, pyrrole, tetrahydrofuran and dihydrofuran (in other words methyl or methyl substituted by one or two fluorine atoms, which is further substituted by one of said carbocyclic or heterocyclic groups), wherein said carbocyclic or heterocyclic group may be further substituted by one or more halogen, $C_1$-$C_4$alkyl, $C_1$-$C_4$haloalkyl, $C_1$-$C_3$alkoxy, $C_1$-$C_3$haloalkoxy, phenyl or oxo, while the others of $R^1$ to $R^4$ are independently 2,2-dimethylpropyl or 2-methylpropyl substituted by one or more fluorine.

In yet another embodiment, two of $R^1$ to $R^4$ is independently methylene (—$CH_2$—) or methylene substituted by one or two fluorine atoms (—CHF— or —$CF_2$—) which are independently substituted by a carbocyclic or heterocyclic group selected from the group consisting of cyclopropyl, cyclobutyl, cyclopentyl, cyclopentenyl, phenyl, oxetane, pyrrole, tetrahydrofuran and dihydrofuran (in other words methyl or methyl substituted by one or two fluorine atoms, each of which is independently further substituted by one of said carbocyclic or heterocyclic groups), wherein said carbocyclic or heterocyclic groups may be further independently substituted by one or more halogen, $C_1$-$C_4$alkyl, $C_1$-$C_4$haloalkyl, $C_1$-$C_3$alkoxy, $C_1$-$C_3$haloalkoxy, phenyl or oxo, while the others of $R^1$ to $R^4$ are independently 2,2-dimethylpropyl or 2-methylpropyl substituted by one or more fluorine.

In yet another embodiment, $R^2$ and $R^4$ are independently methylene (—$CH_2$—) or methylene substituted by one or two fluorine atoms (—CHF— or —$CF_2$—) which are independently substituted by a carbocyclic or heterocyclic group selected from the group consisting of cyclopropyl, cyclobutyl, cyclopentyl, cyclopentenyl, phenyl, oxetane, pyrrole, tetrahydrofuran and dihydrofuran (in other words methyl or methyl substituted by one or two fluorine atoms, each of which is independently further substituted by one of said carbocyclic or heterocyclic groups), wherein said carbocyclic or heterocyclic groups may be further independently substituted by one or more halogen, $C_1$-$C_4$alkyl, $C_1$-$C_4$haloalkyl, $C_1$-$C_3$alkoxy, $C_1$-$C_3$haloalkoxy, phenyl or oxo; and $R^1$ and $R^3$ are independently 2,2-dimethylpropyl or 2-methylpropyl substituted by one or more fluorine.

In yet another embodiment, $R^1$ and $R^3$ are independently methylene (—$CH_2$—) or methylene substituted by one or two fluorine atoms (—CHF— or —$CF_2$—) which are independently substituted by a carbocyclic or heterocyclic group selected from the group consisting of cyclopropyl, cyclobutyl, cyclopentyl, cyclopentenyl, phenyl, oxetane, pyrrole, tetrahydrofuran and dihydrofuran (in other words methyl or methyl substituted by one or two fluorine atoms, each of which is independently further substituted by one of said carbocyclic or heterocyclic groups), wherein said carbocyclic or heterocyclic groups may be further independently substituted by one or more halogen, $C_1$-$C_4$alkyl, $C_1$-$C_4$haloalkyl, $C_1$-$C_3$alkoxy, $C_1$-$C_3$haloalkoxy, phenyl or oxo; and $R^2$ and $R^4$ are independently 2,2-dimethylpropyl or 2-methylpropyl substituted by one or more fluorine.

In yet another embodiment, three of $R^1$ to $R^4$ are independently methylene (—$CH_2$—) or methylene substituted by one or two fluorine atoms (—CHF— or —$CF_2$—) which are independently substituted by a carbocyclic or heterocyclic group selected from the group consisting of cyclopropyl, cyclobutyl, cyclopentyl, cyclopentenyl, phenyl, oxetane, pyrrole, tetrahydrofuran and dihydrofuran (in other words methyl or methyl substituted by one or two fluorine atoms, each of which is independently further substituted by one of said carbocyclic or heterocyclic groups), wherein said carbocyclic or heterocyclic groups may be further independently substituted by one or more halogen, $C_1$-$C_4$alkyl, $C_1$-$C_4$haloalkyl, $C_1$-$C_3$alkoxy, $C_1$-$C_3$haloalkoxy, phenyl or oxo, while the other of $R^1$ to $R^4$ is 2,2-dimethylpropyl or 2-methylpropyl substituted by one or more fluorine.

In another embodiment of the invention, one of $R^1$ to $R^4$ together with the corresponding $R^{1'}$ to $R^{4'}$ form a 2- or 3-membered carbon chain to form a cyclopropyl or cyclobutyl ring which is optionally substituted by one or more fluoro, methyl or trifluoromethyl; and the others of $R^1$ to $R^4$ and $R^{1'}$ to $R^{4'}$ are independently hydrogen, 2-methylpropyl substituted by one or more fluorine or 2,2-dimethylpropyl.

In another embodiment of the invention, two of $R^1$ to $R^4$ together with the corresponding $R^{1'}$ to $R^{4'}$ independently form a 2- or 3-membered carbon chain to form a cyclopropyl or cyclobutyl ring, each of which is optionally independently substituted by one or more fluoro, methyl or trifluoromethyl; and the others of $R^1$ to $R^4$ and $R^{1'}$ to $R^{4'}$ are independently hydrogen, 2-methylpropyl substituted by one or more fluorine or 2,2-dimethylpropyl.

In another embodiment of the invention, three of $R^1$ to $R^4$ together with the corresponding $R^{1'}$ to $R^{4'}$ independently form a 2- or 3-membered carbon chain to form a cyclopropyl or cyclobutyl ring, each of which is optionally independently substituted by one or more fluoro, methyl or trifluoromethyl; and the other of $R^1$ to $R^4$ and the corresponding $R^{1'}$ to $R^{4'}$ are independently hydrogen, 2-methylpropyl substituted by one or more fluorine or 2,2-dimethylpropyl.

In one embodiment, the invention provides an anthelmintic cyclic depsipeptide of formula (I) wherein one or both of $R^1$ and $R^3$ are independently selected from $C_1$-$C_8$ alkyl, optionally independently substituted by one or more of: halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

In another embodiment, the invention provides an anthelmintic cyclic depsipeptide of formula (I) above, wherein one or both, preferably both of $R^1$ and $R^3$ are independently selected from $C_2$-$C_6$ alkyl, optionally independently substituted by one or more of halogen, preferably fluoro, chloro or iodo, more preferably fluoro or chloro and most preferably fluoro.

In yet another embodiment, the invention provides an anthelmintic cyclic depsipeptide of formula (I), wherein $R^1$ and $R^3$ are both independently selected from $C_3$-$C_5$ alkyl independently substituted by one or more of halogen, preferably fluoro, chloro or iodo, more preferably fluoro or chloro and most preferably fluoro.

In another embodiment, the invention provides an anthelmintic cyclic depsipeptide of formula (I), wherein $R^1$ and $R^3$ are both independently selected from $C_3$-$C_5$ alkyl substituted with one or more fluoro, and preferably wherein $R^1$ and $R^3$ are both independently selected from —$CH_2$—$CF(CH_3)_2$.

In another embodiment, the invention provides anthelmintic cyclic depsipeptide of formula (I) above, wherein $R^1$ and $R^3$ are the same.

In another embodiment, the invention provides anthelmintic cyclic depsipeptide of formula (I), wherein one or both $R^{1'}$ and $R^{3'}$ are H or alkyl, preferably H.

In yet another embodiment, the invention provides an anthelmintic cyclic depsipeptide of formula (I), wherein $R^{1'}$ and $R^{3'}$ are the same, and preferably both are H.

In yet another embodiment, the invention provides an anthelmintic cyclic depsipeptide of formula (I), wherein one or both of $R^2$ and $R^4$ is a 3- to 6-membered carbocyclic or 3- to 6-membered heterocyclic ring, or $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 6-membered carbocyclic or heterocyclic ring or 3- to 8-membered carbocyclic or heterocyclic ring may be further substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, alkylsulfinyl, haloalkylsulfinyl, halothio, alkylsulfonyl, haloalkylsulfonyl, alkoxyalkoxy, oxo, cyano, amino, alkylamino and dialkylamino.

In still another embodiment, the invention provides an anthelmintic cyclic depsipeptide of formula (I), wherein one or both of $R^2$ and $R^4$ is $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 8-membered carbocyclic or heterocyclic ring may be further substituted by one or more substituents selected from the group consisting of halogen, hydroxy, alkyl, haloalkyl, cycloalkyl, heterocyclyl, aryl, heteroaryl, alkoxy, haloalkoxy, alkylthio, haloalkylthio, alkylsulfinyl, haloalkylsulfinyl, halothio, alkylsulfonyl, haloalkylsulfonyl, alkoxyalkoxy, oxo, cyano, amino, alkylamino and dialkylamino.

In another embodiment, the invention provides an anthelmintic cyclic depsipeptide of formula (I), wherein one or both of $R^2$ and $R^4$ is $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic or 3- to 8-membered heterocyclic ring; wherein said 3- to 8-membered carbocyclic or heterocyclic ring may be further substituted by one or more substituents selected from the group consisting of halogen, hydroxy, alkyl, haloalkyl, alkoxy, haloalkoxy, alkylthio, haloalkylthio, alkylsulfinyl, haloalkylsulfinyl, halothio, alkylsulfonyl, haloalkylsulfonyl, oxo, cyano.

In another embodiment, the invention provides an anthelmintic cyclic depsipeptide of formula (I), wherein one or both of $R^2$ and $R^4$ is $C_1$-$C_3$ alkyl or $C_1$-$C_3$ haloalkyl, wherein the $C_1$-$C_3$ alkyl or $C_1$-$C_3$ haloalkyl is substituted by a 3- to 8-membered carbocyclic ring; wherein said 3- to 8-membered carbocyclic ring may be further substituted by one or more substituents selected from the group consisting of halogen, hydroxy, alkyl, haloalkyl, alkoxy and haloalkoxy.

In still another embodiment, the invention provides an anthelmintic cyclic depsipeptide of formula (I), wherein one or both of $R^2$ and $R^4$ is $C_1$-$C_3$ alkyl or $C_1$-$C_3$ haloalkyl, wherein the $C_1$-$C_3$ alkyl or $C_1$-$C_3$ haloalkyl is substituted by a 3- to 6-membered carbocyclic ring; wherein said 3- to 6-membered carbocyclic ring may be further substituted by one or more substituents selected from the group consisting of halogen, hydroxy, alkyl, haloalkyl, alkoxy and haloalkoxy.

In another embodiment, the invention provides an anthelmintic cyclic depsipeptide of formula (I), wherein $R^2$ and $R^4$ are each independently $C_1$-$C_3$ alkyl or $C_1$-$C_3$ haloalkyl, each of which are substituted by a carbocyclic or heterocyclic group selected from the group consisting of cyclopropyl, cyclobutyl, cyclopentyl, cyclopentenyl, phenyl, oxetane, pyrrole, tetrahydrofuran and dihydrofuran, wherein said carbocyclic or heterocyclic groups may be further substituted by one or more halogen, $C_1$-$C_4$alkyl, $C_1$-$C_4$haloalkyl, $C_1$-$C_3$alkoxy, $C_1$-$C_3$haloalkoxy, phenyl or oxo.

In another embodiment, provides is an anthelmintic cyclic depsipeptide of formula (I), wherein $R^2$ and $R^4$ are each independently methyl, mono-fluoro substituted methyl or di-fluoro substituted methyl, each of which are substituted by a carbocyclic or heterocyclic group selected from the group consisting of cyclopropyl, cyclobutyl, cyclopentyl, cyclopentenyl, phenyl, oxetane, pyrrole, tetrahydrofuran and dihydrofuran, wherein said carbocyclic or heterocyclic groups may be further substituted by one or more halogen, $C_1$-$C_4$alkyl, $C_1$-$C_4$haloalkyl, $C_1$-$C_3$alkoxy, $C_1$-$C_3$haloalkoxy, phenyl or oxo.

In another embodiment, the invention provides an anthelmintic cyclic depsipeptide of formula (I), wherein $R^2$ and $R^4$ are each independently methyl, mono-fluoro substituted methyl or di-fluoro substituted methyl, each of which are substituted by a carbocyclic group selected from the group consisting of cyclopropyl, cyclobutyl, cyclopentyl, cyclopentenyl and phenyl.

In yet another embodiment, the invention provides an anthelmintic cyclic depsipeptide of formula (I), wherein $R^2$ and $R^4$ are each independently methyl, mono-fluoro substituted methyl or di-fluoro substituted methyl, each of which are substituted by a carbocyclic group selected from the group consisting of cyclopropyl, cyclobutyl or cyclopentyl.

In another embodiment, provided is an anthelmintic cyclic depsipeptide of formula (I), wherein $R^2$ and $R^4$ are each independently methyl, mono-fluoro substituted methyl or di-fluoro substituted methyl, each of which is substituted by cyclopropyl.

In another embodiment, an anthelmintic cyclic depsipeptide of formula (I) is provided, wherein $R^2$ and $R^4$ are each methyl which is substituted by a 3-5 membered carbocyclic ring, preferably cyclopropyl, and preferably wherein $R^2$ and $R^4$ are each —$CH_2$-cyclopropyl.

In another embodiment, the invention provides an anthelmintic cyclic depsipeptide of formula (I), wherein $R^2$ and $R^4$ are the same.

In another embodiment, the invention provides an anthelmintic cyclic depsipeptide of any of formula (I), wherein one or both $R^1$ and $R^{3'}$ are H or alkyl, preferably H.

In another embodiment, provided is an anthelmintic cyclic depsipeptide of formula (I), wherein $R^1$ and $R^{3'}$ are the same, and preferably both are H.

In another embodiment, the invention provides an anthelmintic cyclic depsipeptide of formula (I), wherein R', R", R'" and R"" are each independently $C_1$-$C_3$alkyl, preferably methyl.

In another embodiment, the invention provides anthelmintic cyclic depsipeptide of formula (I), wherein $Cy^1$ and $Cy^2$ are each independently selected from the group consisting of: phenyl substituted with heterocyclyl, preferably wherein the heterocyclyl is selected from the group consisting of: pyrrolidinyl, furyl, tetrahydrofuryl, thienyl, piperidinyl, piperazinyl and morpholinyl and more preferably wherein the heterocyclyl is morpholinyl.

In another embodiment, the invention provides an anthelmintic cyclic depsipeptide of formula (I), wherein $Cy^1$ and $Cy^2$ are the same and are each phenyl substituted with morpholinyl, preferably N-morpholinyl, and more preferably para-N-morpholinylphenyl:

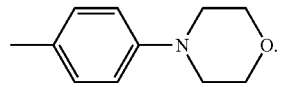

In another embodiment, the invention provides an anthelmintic cyclic depsipeptide of formula (I), wherein $Cy^1$ and $Cy^2$ are the same and are each phenyl substituted with tetrahydropyranyl, preferably para-tetrahydropyranyl, and more preferably para-tetrahydropyranylphenyl:

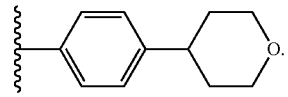

In another embodiment, the invention provides an anthelmintic cyclic depsipeptide of formula (I), wherein $R^a$ and $R^b$ are independently $C_1$-$C_3$alkyl or $C_1$-$C_3$haloalkyl, preferably $C_1$-$C_3$alkyl and more preferably methyl.

In another embodiment, the invention provides an anthelmintic cyclic depsipeptide of formula (I), wherein:

$R^1$ and $R^3$ are both independently selected from $C_3$-$C_5$ alkyl substituted with one or more fluoro, and preferably wherein $R^1$ and $R^3$ are both independently selected from —$CH_2$—$CF(CH_3)_2$;

$R^2$ and $R^4$ are each methyl which is substituted by a 3-5 membered carbocyclic ring, preferably cyclopropyl, and preferably wherein $R^2$ and $R^4$ are each —$CH_2$-cyclopropyl;

$R^{1'}$, $R^{2'}$, $R^{3'}$ and $R^{4'}$ are H;

R', R", R'" and R"" are each independently $C_1$-$C_3$alkyl;

$Cy^1$ and $Cy^2$ are each independently selected from the group consisting of: phenyl substituted with heterocyclyl, preferably wherein the heterocyclyl is selected from the group consisting of: pyrrolidinyl, furyl, tetrahydrofuryl, tetrahydropyranyl, thienyl, piperidinyl, piperazinyl and morpholinyl; and $R^a$ and $R^b$ are independently $C_1$-$C_3$alkyl.

In another embodiment, the invention provides anthelmintic cyclic depsipeptide of formula (I), wherein:

$R^1$ and $R^3$ are both independently selected from $C_3$-$C_5$ alkyl substituted with one or more fluoro, and preferably wherein $R^1$ and $R^3$ are both independently selected from —$CH_2$—$CF(CH_3)_2$;

R² and R⁴ are each methyl which is substituted by a 3-5 membered carbocyclic ring, preferably cyclopropyl, and preferably wherein R² and R⁴ are each —CH₂-cyclopropyl;

R¹', R²', R³' and R⁴' are H;

R', R'', R''' and R'''' are each independently $C_1$-$C_3$alkyl;

$Cy^1$ and $Cy^2$ are each independently selected from the group consisting of: phenyl substituted with heterocyclyl, preferably wherein the heterocyclyl is selected from the group consisting of: pyrrolidinyl, furyl, tetrahydrofuryl, thienyl, piperidinyl, piperazinyl and morpholinyl; and $R^a$ and $R^b$ are independently $C_1$-$C_3$alkyl.

In another embodiment of the invention, one, two or three of R¹ to R⁴ are cyclopropyl, cyclobutyl, phenyl or oxetane, or methylene (—CH₂—) or methylene substituted by one or two halogen atoms (—CHX— or —CX₂— where X is halogen) which are independently substituted by a 3- to 6-membered carbocyclic or 3- to 6-membered heterocyclic group (in other words methyl or methyl substituted by one or two halogen atoms, each of which is independently further substituted by a 3- to 6-membered carbocyclic or a 3- to 6-membered heterocyclic group), wherein said 3- to 6-membered carbocyclic or 3- to 6-membered heterocyclic group may be further independently substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, and the others of R¹ to R⁴ is the group G-1:

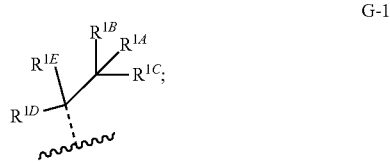

G-1 wherein $R^{1A}$, $R^{1B}$, $R^{1C}$, $R^{1D}$ and $R^{1E}$ are independently hydrogen, halogen, alkyl or haloalkyl.

In one embodiment, one, two or three of R¹ to R⁴ are independently cyclopropyl or phenyl or methylene (—CH₂—) or methylene substituted by one or two halogen atoms (—CHX— or —CX₂— where X is halogen) which are substituted by a carbocyclic or heterocyclic group selected from the group consisting of cyclopropyl, cyclobutyl, cyclopentyl, cyclopentenyl, phenyl, oxirane, oxetane, thiirane, thietane, aziridine, azetidine, pyrrolidine, pyrrole, thiophene, oxazole, isoxazole, isoxazoline, thiazole, isothiazole, 1,3,4-thiadazole, pyrazole, imidazole, triazole, tetrazole, furan, tetrahydrofuran and dihydrofuran, wherein said carbocyclic or heterocyclic groups may be further substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, and the others of R¹ to R⁴ are independently G-1 wherein $R^{1A}$, $R^{1B}$, $R^{1C}$, $R^{1D}$ and $R^{1E}$ are independently hydrogen, halogen, $C_1$-$C_3$-alkyl or $C_1$-$C_3$-haloalkyl.

In another embodiment, one, two or three of R¹ to R⁴ are independently cyclopropyl or methylene (—CH₂—) or methylene substituted by one or two halogen atoms (—CHX— or —CX₂— where X is halogen) which are substituted by a carbocyclic or heterocyclic group selected from the group consisting of cyclopropyl, cyclobutyl, cyclopentyl, cyclopentenyl, phenyl, oxetane, pyrrole, tetrahydrofuran and dihydrofuran, wherein said carbocyclic or heterocyclic groups may be further substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, and the others of R¹ to R⁴ are independently G-1 wherein $R^{1A}$, $R^{1B}$, $R^{1C}$, $R^{1D}$ and $R^{1E}$ are independently hydrogen, fluorine, $C_1$-$C_3$-alkyl or $C_1$-$C_3$-haloalkyl.

In yet another embodiment, one, two or three of R¹ to R⁴ are cyclopropyl or methylene (—CH₂—) or methylene substituted by one or two halogen atoms (—CHX— or —CX₂— where X is halogen) which are substituted by a carbocyclic or heterocyclic group selected from the group consisting of cyclopropyl, cyclobutyl, cyclopentyl, cyclopentenyl phenyl and oxetane, wherein said carbocyclic or heterocyclic groups may be further substituted by one or more substituents selected from the group consisting of halogen, hydroxy, alkyl, haloalkyl, $C_3$-$C_6$cycloalkyl, heterocyclyl, phenyl, heteroaryl, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino, and the others of R¹ to R⁴ are independently G-1 wherein $R^{1A}$, $R^{1B}$, $R^{1C}$, $R^{1D}$ and $R^{1E}$ are independently hydrogen, fluorine, $C_1$-$C_3$-alkyl or $C_1$-$C_3$-haloalkyl.

In yet another embodiment, one, two or three of R¹ to R⁴ are cyclopropyl or methylene (—CH₂—) or methylene substituted by one or two halogen atoms (—CHX— or —CX₂— where X is halogen) which are substituted by a cyclopropyl optionally substituted by halogen, and the others of R¹ to R⁴ are independently G-1 wherein $R^{1A}$, $R^{1B}$, $R^{1C}$, $R^{1D}$ and $R^{1E}$ are independently hydrogen, fluorine, methyl or trifluoromethyl.

In one embodiment, one, two or three of R¹ to R⁴ are cyclopropyl or methylene (—CH₂—) or methylene substituted by one or two halogen atoms (—CHX— or —CX₂— where X is halogen) which are substituted by a cyclopropyl optionally substituted by halogen, and the others of R¹ to R⁴ are independently G-1 wherein $R^{1A}$, $R^{1B}$, $R^{1C}$, $R^{1D}$ and $R^{1E}$ are independently hydrogen, fluoro, $C_1$-$C_3$ alkyl or $C_1$-$C_3$ haloalkyl.

In yet another embodiment, one, two or three of R¹ to R⁴ are cyclopropyl or methylene (—CH₂—) or methylene substituted by one or two halogen atoms (—CHX— or —CX₂— where X is halogen) which are substituted by a cyclopropyl optionally substituted by halogen, and the others of R¹ to R⁴ are independently G-1 wherein $R^{1D}$ and $R^{1E}$ are independently H or halogen. In another embodiment, $R^{1D}$ and $R^{1E}$ are independently $C_1$-$C_3$ alkyl or $C_1$-$C_3$ haloalkyl. In another embodiment, $R^{1A}$ is H or halogen. In another embodiment, $R^{1A}$ is $C_1$-$C_3$ alkyl or $C_1$-$C_3$ haloalkyl. In another embodiment, $R^{1A}$ is halogen, and $R^{1B}$ and $R^{1C}$ are independently $C_1$-$C_3$ alkyl or $C_1$-$C_3$ haloalkyl. In yet another embodiment, $R^{1D}$ and $R^{1E}$ are H, $R^{1A}$ is halogen, and $R^{1B}$ and $R^{1C}$ are independently $C_1$-$C_3$ alkyl or $C_1$-$C_3$ haloalkyl.

In yet another embodiment, one, two or three of R¹ to R⁴ are cyclopropyl or methylene (—CH₂—) or methylene substituted by one or two halogen atoms (—CHX— or —CX₂— where X is halogen) which are substituted by a cyclopropyl optionally substituted by halogen, and the others of R¹ to R⁴ are independently G-1 wherein $R^{1D}$ and $R^{1E}$ are independently H or F. In another embodiment, $R^{1D}$ and $R^{1E}$ are independently methyl or trifluoromethyl. In another embodiment, $R^{1A}$ is H or F. In another embodiment, $R^{1A}$ is methyl or trifluoromethyl. In another embodiment, $R^{1A}$ is F, and $R^{1B}$ and $R^{1C}$ are methyl or trifluoromethyl. In yet another embodiment, $R^{1D}$ and $R^{1E}$ are H, $R^{1A}$ is F, $R^{1B}$ and $R^{1C}$ are methyl or trifluoromethyl.

In another embodiment, one, two, three or all four of $R^1$ to $R^4$ are independently C1 to C28 shown below:

C1

C2
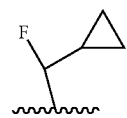

C3
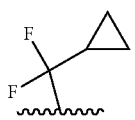

C4
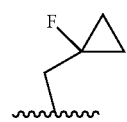

C5
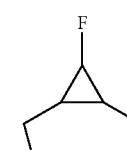

C6
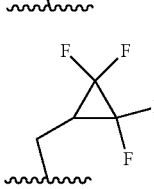

C7
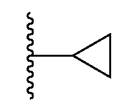

C8
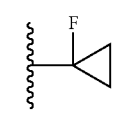

C9
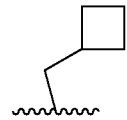

C10
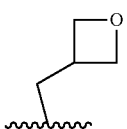

-continued

C11
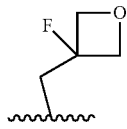

C12
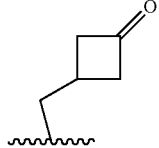

C13
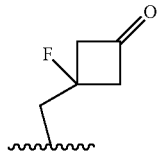

C14
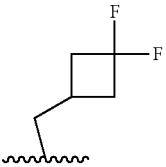

C15
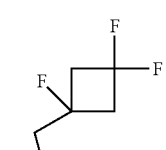

C16
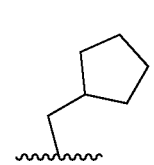

C17
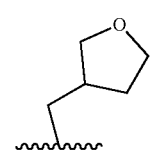

C18
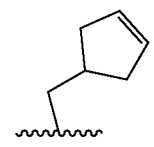

C19
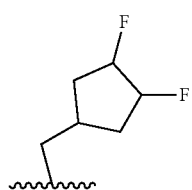

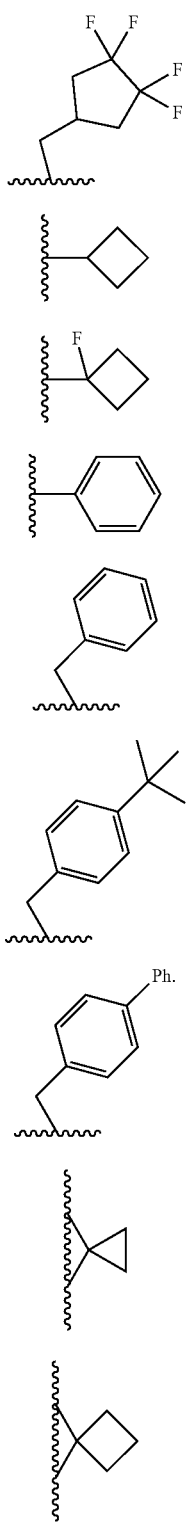

In another embodiment, one, two, three or all four of $R^1$ to $R^4$ are independently C1 to C8. In another embodiment, one, two, three or all four of $R^1$ to $R^4$ are independently C9 to C15. In yet another embodiment, one, two, three or all four of $R^1$ to $R^4$ are independently C16 to C20. In another embodiment, one, two, three or all four of $R^1$ to $R^4$ are independently C21 to C26. In another embodiment, one, two, three or all four of $R^1$ to $R^4$ together with the corresponding $R^{1'}$ to $R^{4'}$ are C27 or C28. In another embodiment, one, two, three or all four of $R^1$ to $R^4$, are independently C1 to C26 and the other of $R^1$ to $R^4$ are independently $C_1$-$C_6$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In yet another embodiment, one, two, three or all four of $R^1$ to $R^4$ are independently C1 to C26 and the other of $R^1$ to $R^4$ are independently $C_1$-$C_3$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino. In another embodiment, one, two, three or all four of $R^1$ to $R^4$ are independently C1 to C26 and the other of $R^1$ to $R^4$ are independently 2-methylpropyl or 2,2-dimethylpropyl.

In another embodiment, one, two, three or all four of $R^1$ to $R^4$ together with the corresponding $R^{1'}$ to $R^{4'}$ are C27 or C28 and the other of $R^1$ to $R^4$ and the corresponding $R^{1'}$ to $R^{4'}$ are independently hydrogen or $C_1$-$C_3$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino. In another embodiment, one, two, three or all four of $R^1$ to $R^4$ and the corresponding $R^{1'}$ to $R^{4'}$ are independently C27 or C28 and the other of $R^1$ to $R^4$ and the corresponding $R^{1'}$ to $R^{4'}$ are independently hydrogen, 2-methylpropyl or 2,2-dimethylpropyl.

In another embodiment, one, two, three or all four of $R^1$ to $R^4$ are independently C1 to C26 and the other of $R^1$ to $R^4$ are independently 2,2-dimethylpropyl or 2-methylpropyl substituted by one or more substituents selected from the group consisting of halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment, one, two, three or all four of $R^1$ to $R^4$ and the corresponding R to $R^{4'}$ are independently C27 or C28 and the other of $R^1$ to $R^4$ and the corresponding $R^{1'}$ to $R^{4'}$ are independently hydrogen or 2,2-dimethylpropyl or 2-methylpropyl substituted by one or more substituents selected from the group consisting of halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino.

In another embodiment, one, two, three or all four of $R^1$ to $R^4$ are independently C1 to C26 and the other of $R^1$ to $R^4$ are independently 2,2-dimethylpropyl or 2-methylpropyl substituted by one or more halogen.

In another embodiment, one, two, three or all four of $R^1$ to $R^4$ and the corresponding $R^{1'}$ to $R^{4'}$ are independently C27 or C28 and the other of $R^1$ to $R^4$ and the corresponding $R^{1'}$ to $R^{4'}$ are independently hydrogen or 2,2-dimethylpropyl or 2-methylpropyl substituted by one or more halogen.

In still another embodiment, one, two, three or all four of $R^1$ to $R^4$ are independently C1 to C26 and the other of $R^1$ to $R^4$ are independently 2,2-dimethylpropyl or 2-methylpropyl substituted by one or more fluorine.

In another embodiment, one, two, three or all four of $R^1$ to $R^4$ and the corresponding $R^{1'}$ to $R^{4'}$ are independently C27 or C28 and the other of $R^1$ to $R^4$ and the corresponding $R^{1'}$ to $R^{4'}$ are independently hydrogen or 2,2-dimethylpropyl or 2-methylpropyl, substituted by one or more fluorine.

In another embodiment, one, two, three or all four of $R^1$ to $R^4$ are independently C1 to C26 and the other of $R^1$ to $R^4$ are independently the group G-1 wherein $R^{1A}$, $R^{1B}$, $R^{1C}$, $R^{1D}$ and $R^{1E}$ are independently hydrogen, halogen, alkyl or haloalkyl.

In another embodiment, one, two, three or all four of $R^1$ to $R^4$ are independently C1 or C2 and the other of $R^1$ to $R^4$ are independently 2-methylpropyl substituted by one or more fluorine or 2,2-dimethylpropyl.

In another embodiment, one, two, three or all four of $R^1$ to $R^4$ are independently C3, C4 or C5 and the other of $R^1$ to $R^4$ are independently 2-methylpropyl substituted by one or more fluorine or 2,2-dimethylpropyl.

In still another embodiment, one, two, three or all four of $R^1$ to $R^4$ are independently C6, C7 or C8 and the other of $R^1$ to $R^4$ are independently 2-methylpropyl substituted by one or more fluorine or 2,2-dimethylpropyl.

In another embodiment, one, two, three or all four of $R^1$ to $R^4$ are independently C9, C10 or C11 and the other of $R^1$ to $R^4$ are independently 2-methylpropyl substituted by one or more fluorine or 2,2-dimethylpropyl.

In yet another embodiment, one, two, three or all four of $R^1$ to $R^4$ are independently C12, C13, C14 or C15 and the other of $R^1$ to $R^4$ are independently 2-methylpropyl substituted by one or more fluorine or 2,2-dimethylpropyl.

In another embodiment, one, two, three or all four of $R^1$ to $R^4$ are independently C16 to C20 and the other of $R^1$ to $R^4$ are independently 2-methylpropyl substituted by one or more fluorine or 2,2-dimethylpropyl. In yet another embodiment, $R^1$ and $R^3$ are independently C1 to C26 and $R^2$ and $R^4$ are independently 2-methylpropyl substituted by one or more fluorine or 2,2-dimethylpropyl.

In another embodiment, $R^1$ and $R^3$ are independently C1 or C2 and $R^2$ and $R^4$ are independently 2-methylpropyl substituted by one or more fluorine or 2,2-dimethylpropyl.

In another embodiment, $R^1$ and $R^3$ are independently C3, C4, C5 or C6 and $R^2$ and $R^4$ are independently 2-methylpropyl substituted by one or more fluorine or 2,2-dimethylpropyl.

In another embodiment, $R^1$ and $R^3$ are independently C7 or C8 and $R^2$ and $R^4$ are independently 2-methylpropyl substituted by one or more fluorine or 2,2-dimethylpropyl.

In another embodiment, $R^1$ and $R^3$ are independently C9, C10 or C11 and $R^2$ and $R^4$ are independently 2-methylpropyl substituted by one or more fluorine or 2,2-dimethylpropyl.

In another embodiment, $R^1$ and $R^3$ are independently C12, C13, C14 or C15 and $R^2$ and $R^4$ are independently 2-methylpropyl substituted by one or more fluorine or 2,2-dimethylpropyl.

In another embodiment, $R^1$ and $R^3$ are independently C16, C17, C18, C19 or C20 and $R^2$ and $R^4$ are independently 2-methylpropyl substituted by one or more fluorine or 2,2-dimethylpropyl.

In another embodiment, $R^1$ and $R^3$ are independently C21, C22, C23, C24, C25 or C26 and $R^2$ and $R^4$ are independently 2-methylpropyl substituted by one or more fluorine or 2,2-dimethylpropyl.

In another embodiment, $R^1$ together with $R^{1'}$ and/or $R^3$ together with $R^{3'}$ form a 2- to 3-membered carbon chain to form a cyclopropyl or cyclobutyl ring and $R^2$, $R^{2'}$, $R^4$ and $R^{4'}$ are independently hydrogen, 2-methylpropyl substituted by one or more fluorine or 2,2-dimethylpropyl.

In yet another embodiment, $R^2$ and $R^4$ are independently C1 to C26 and $R^1$ and $R^3$ are independently 2-methylpropyl substituted by one or more fluorine or 2,2-dimethylpropyl.

In another embodiment, $R^2$ and $R^4$ are independently C1 or C2 and $R^1$ and $R^3$ are independently 2-methylpropyl substituted by one or more fluorine or 2,2-dimethylpropyl.

In another embodiment, $R^2$ and $R^4$ are independently C3, C4, C5 or C6 and $R^1$ and $R^3$ are independently 2-methylpropyl substituted by one or more fluorine or 2,2-dimethylpropyl.

In another embodiment, $R^2$ and $R^4$ are independently C7 or C8 and $R^1$ and $R^3$ are independently 2-methylpropyl substituted by one or more fluorine or 2,2-dimethylpropyl.

In another embodiment, $R^2$ and $R^4$ are independently C9, C10 or C11 and $R^1$ and $R^3$ are independently 2-methylpropyl substituted by one or more fluorine or 2,2-dimethylpropyl.

In another embodiment, $R^2$ and $R^4$ are independently C12, C13, C14 or C15 and $R^1$ and $R^3$ are independently 2-methylpropyl substituted by one or more fluorine or 2,2-dimethylpropyl.

In another embodiment, $R^2$ and $R^4$ are independently C16, C17, C18, C19 or C20 and $R^1$ and $R^3$ are independently 2-methylpropyl substituted by one or more fluorine or 2,2-dimethylpropyl.

In another embodiment, $R^2$ and $R^4$ are independently C21, C22, C23, C24, C25 or C26 and $R^1$ and $R^3$ are independently 2-methylpropyl substituted by one or more fluorine or 2,2-dimethylpropyl.

In another embodiment, $R^2$ together with $R^{2'}$ and/or $R^4$ together with $R^{4'}$ form a 2- to 3-membered carbon chain to form a cyclopropyl or cyclobutyl ring and $R^1$, $R^{1'}$, $R^3$ and $R^{3'}$ are independently hydrogen, 2-methylpropyl substituted by one or more fluorine or 2,2-dimethylpropyl.

In one embodiment, the invention provides compounds of formula (I) wherein R', R'', R''' and R'''' are each independently hydrogen or $C_1$-$C_3$alkyl; and $Cy^1$, $Cy^2$, $R^a$, $R^b$, $R^1$, $R^2$, $R^3$ and $R^4$ are as described in Tables 2 to 38 below. In the compounds described in Tables 2 to 38, the variables $R^{1'}$, $R^{2'}$, $R^{3'}$ and $R^{4'}$ are hydrogen unless they form a carbon chain with the corresponding $R^1$ to $R^4$ to form a ring (e.g. when forming C27 or C28).

Compounds in Tables 2 to 38 where all of $R^a$, $R^b$, R', R'', R''' and R'''' are methyl are designated by the compound number X-YA, where X is the table number and Y is the sequential number in the table. Compounds in Tables 2 to 38 wherein $R^a$, $R^b$ are each hydrogen and R', R'', R''' and R'''' are methyl are designated by the compound number X-YB. Compounds in Tables 2 to 38 wherein $R^a$, $R^b$ are each methyl and R', R'', R''' and R'''' are hydrogen are designated by the compound numbers X-YC; and Compounds in Tables 2 to 38 wherein $R^a$, $R^b$ are each hydrogen and R', R'', R''' and R'''' are methyl are designated by the compound numbers X-YD.

TABLE 2

Compounds of formula (I), wherein Cy$^1$ and Cy$^2$ are unsubstituted phenyl, R', R", R'" and R"" are each independently hydrogen or methyl, and R$^a$, R$^b$ and R$^1$ to R$^4$ are as shown.

| Cmpd # | R$^a$/R$^b$ | R$^1$ | R$^2$ | R$^3$ | R$^4$ |
|---|---|---|---|---|---|
| 2-1 | CH$_3$ | Cl | Cl | Cl | Cl |
| 2-2 | CH$_3$ | Cl | —CH$_2$—iPr | —CH$_2$—iPr | —CH$_2$—iPr |
| 2-3 | CH$_3$ | —CH$_2$—iPr | Cl | —CH$_2$—iPr | —CH$_2$—iPr |
| 2-4 | CH$_3$ | —CH$_2$—iPr | —CH$_2$—iPr | Cl | —CH$_2$—iPr |
| 2-5 | CH$_3$ | —CH$_2$—iPr | —CH$_2$—iPr | —CH$_2$—iPr | Cl |
| 2-6 | CH$_3$ | —CH$_2$—iPr | Cl | —CH$_2$—iPr | Cl |
| 2-7 | CH$_3$ | Cl | —CH$_2$—iPr | Cl | —CH$_2$—iPr |
| 2-8 | CH$_3$ | —CH$_2$—iPr | Cl | Cl | —CH$_2$—iPr |
| 2-9 | CH$_3$ | Cl | Cl | —CH$_2$—iPr | —CH$_2$—iPr |
| 2-10 | CH$_3$ | —CH$_2$—iPr | —CH$_2$—iPr | Cl | Cl |
| 2-11 | CH$_3$ | Cl | —CH$_2$—iPr | —CH$_2$—iPr | Cl |
| 2-12 | CH$_3$ | —CH$_2$—iPr | Cl | Cl | Cl |
| 2-13 | CH$_3$ | Cl | —CH$_2$—iPr | Cl | Cl |
| 2-14 | CH$_3$ | Cl | Cl | —CH$_2$—iPr | Cl |
| 2-15 | CH$_3$ | Cl | Cl | Cl | —CH$_2$—iPr |
| 2-16 | CH$_3$ | Cl | —CH$_2$—C(CH$_3$)$_3$ | —CH$_2$—C(CH$_3$)$_3$ | —CH$_2$—C(CH$_3$)$_3$ |
| 2-17 | CH$_3$ | —CH$_2$—C(CH$_3$)$_3$ | Cl | —CH$_2$—C(CH$_3$)$_3$ | —CH$_2$—C(CH$_3$)$_3$ |
| 2-18 | CH$_3$ | —CH$_2$—C(CH$_3$)$_3$ | —CH$_2$—C(CH$_3$)$_3$ | Cl | —CH$_2$—C(CH$_3$)$_3$ |
| 2-19 | CH$_3$ | —CH$_2$—C(CH$_3$)$_3$ | —CH$_2$—C(CH$_3$)$_3$ | —CH$_2$—C(CH$_3$)$_3$ | Cl |
| 2-20 | CH$_3$ | —CH$_2$—C(CH$_3$)$_3$ | Cl | —CH$_2$—C(CH$_3$)$_3$ | Cl |
| 2-21 | CH$_3$ | Cl | —CH$_2$—C(CH$_3$)$_3$ | Cl | —CH$_2$—C(CH$_3$)$_3$ |
| 2-22 | CH$_3$ | —CH$_2$—C(CH$_3$)$_3$ | Cl | Cl | —CH$_2$—C(CH$_3$)$_3$ |
| 2-23 | CH$_3$ | Cl | —CH$_2$—C(CH$_3$)$_3$ | —CH$_2$—C(CH$_3$)$_3$ | Cl |
| 2-24 | CH$_3$ | Cl | Cl | —CH$_2$—C(CH$_3$)$_3$ | —CH$_2$—C(CH$_3$)$_3$ |
| 2-25 | CH$_3$ | —CH$_2$—C(CH$_3$)$_3$ | —CH$_2$—C(CH$_3$)$_3$ | Cl | Cl |
| 2-26 | CH$_3$ | —CH$_2$—C(CH$_3$)$_3$ | Cl | Cl | Cl |
| 2-27 | CH$_3$ | Cl | —CH$_2$—C(CH$_3$)$_3$ | Cl | Cl |
| 2-28 | CH$_3$ | Cl | Cl | —CH$_2$—C(CH$_3$)$_3$ | Cl |
| 2-29 | CH$_3$ | Cl | Cl | Cl | —CH$_2$—C(CH$_3$)$_3$ |
| 2-30 | CH$_3$ | Cl | —CH$_2$CF(CH$_3$)$_2$ | —CH$_2$CF(CH$_3$)$_2$ | —CHCF(CH$_3$)$_2$ |
| 2-31 | CH$_3$ | —CH$_2$CF(CH$_3$)$_2$ | Cl | —CH$_2$CF(CH$_3$)$_2$ | —CH$_2$CF(CH$_3$)$_2$ |
| 2-32 | CH$_3$ | —CH$_2$CF(CH$_3$)$_2$ | —CH$_2$CF(CH$_3$)$_2$ | Cl | —CH$_2$CF(CH$_3$)$_2$ |
| 2-33 | CH$_3$ | —CH$_2$CF(CH$_3$)$_2$ | —CH$_2$CF(CH$_3$)$_2$ | —CH$_2$CF(CH$_3$)$_2$ | Cl |
| 2-34 | CH$_3$ | —CH$_2$CF(CH$_3$)$_2$ | Cl | —CH$_2$CF(CH$_3$)$_2$ | Cl |
| 2-35 | CH$_3$ | Cl | —CH$_2$CF(CH$_3$)$_2$ | Cl | —CH$_2$CF(CH$_3$)$_2$ |
| 2-36 | CH$_3$ | —CH$_2$CF(CH$_3$)$_2$ | Cl | Cl | —CH$_2$CF(CH$_3$)$_2$ |
| 2-37 | CH$_3$ | Cl | —CH$_2$CF(CH$_3$)$_2$ | CH$_2$CF(CH$_3$)$_2$ | Cl |
| 2-38 | CH$_3$ | Cl | Cl | —CH$_2$CF(CH$_3$)$_2$ | —CH$_2$CF(CH$_3$)$_2$ |
| 2-39 | CH$_3$ | —CH$_2$CF(CH$_3$)$_2$ | —CH$_2$CF(CH$_3$)$_2$ | Cl | Cl |
| 2-40 | CH$_3$ | —CH$_2$CF(CH$_3$)$_2$ | Cl | Cl | Cl |
| 2-41 | CH$_3$ | Cl | —CH$_2$CF(CH$_3$)$_2$ | Cl | Cl |
| 2-42 | CH$_3$ | Cl | Cl | —CH$_2$CF(CH$_3$)$_2$ | Cl |
| 2-43 | CH$_3$ | Cl | Cl | Cl | —CH$_2$CF(CH$_3$)$_2$ |
| 2-44 | CH$_3$ | Cl | n-Propyl | n-Propyl | n-Propyl |
| 2-45 | CH$_3$ | n-Propyl | Cl | n-Propyl | n-Propyl |
| 2-46 | CH$_3$ | n-Propyl | n-Propyl | Cl | n-Propyl |
| 2-47 | CH$_3$ | n-Propyl | n-Propyl | n-Propyl | Cl |
| 2-48 | CH$_3$ | n-Propyl | Cl | n-Propyl | Cl |
| 2-49 | CH$_3$ | Cl | n-Propyl | Cl | n-Propyl |
| 2-50 | CH$_3$ | n-Propyl | Cl | Cl | n-Propyl |
| 2-51 | CH$_3$ | Cl | Cl | n-Propyl | n-Propyl |
| 2-52 | CH$_3$ | n-Propyl | n-Propyl | Cl | Cl |
| 2-53 | CH$_3$ | Cl | n-Propyl | n-Propyl | Cl |
| 2-54 | CH$_3$ | n-Propyl | Cl | Cl | Cl |
| 2-55 | CH$_3$ | Cl | n-Propyl | Cl | Cl |
| 2-56 | CH$_3$ | Cl | Cl | n-Propyl | Cl |
| 2-57 | CH$_3$ | Cl | Cl | Cl | n-Propyl |
| 2-58 | H | —CH$_2$CF(CH$_3$)$_2$ | Cl | —CH$_2$CF(CH$_3$)$_2$ | Cl |
| 2-59 | H | Cl | —CH$_2$CF(CH$_3$)$_2$ | Cl | —CH$_2$CF(CH$_3$)$_2$ |
| 2-60 | H | —CH$_2$CF(CH$_3$)$_2$ | Cl | Cl | —CH$_2$CF(CH$_3$)$_2$ |
| 2-61 | H | Cl | —CH$_2$CF(CH$_3$)$_2$ | —CH$_2$CF(CH$_3$)$_2$ | Cl |
| 2-62 | H | Cl | Cl | —CH$_2$CF(CH$_3$)$_2$ | —CH$_2$CF(CH$_3$)$_2$ |
| 2-63 | H | —CH$_2$CF(CH$_3$)$_2$ | —CH$_2$CF(CH$_3$)$_2$ | Cl | Cl |
| 2-64 | H | —CH$_2$—C(CH$_3$)$_3$ | Cl | —CH$_2$—C(CH$_3$)$_3$ | Cl |
| 2-65 | H | Cl | —CH$_2$—C(CH$_3$)$_3$ | Cl | —CH$_2$—C(CH$_3$)$_3$ |
| 2-66 | H | —CH$_2$—C(CH$_3$)$_3$ | Cl | Cl | —CH$_2$—C(CH$_3$)$_3$ |
| 2-67 | H | Cl | —CH$_2$—C(CH$_3$)$_3$ | —CH$_2$—C(CH$_3$)$_3$ | Cl |
| 2-68 | H | Cl | Cl | —CH$_2$—C(CH$_3$)$_3$ | —CH$_2$—C(CH$_3$)$_3$ |
| 2-69 | H | —CH$_2$—C(CH$_3$)$_3$ | —CH$_2$—C(CH$_3$)$_3$ | Cl | Cl |

TABLE 3

Compounds of formula (I), wherein $Cy^1$ and $Cy^2$ are p-fluorophenyl; R', R", R'"
and R"" are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 3-1 | CH₃ | Cl | Cl | Cl | Cl |
| 3-2 | CH₃ | Cl | —CH₂—iPr | —CH₂—iPr | —CH₂—iPr |
| 3-3 | CH₃ | —CH₂—iPr | Cl | —CH₂—iPr | —CH₂—iPr |
| 3-4 | CH₃ | —CH₂—iPr | —CH₂—iPr | Cl | —CH₂—iPr |
| 3-5 | CH₃ | —CH₂—iPr | —CH₂—iPr | —CH₂—iPr | Cl |
| 3-6 | CH₃ | —CH₂—iPr | Cl | —CH₂—iPr | Cl |
| 3-7 | CH₃ | Cl | —CH₂—iPr | Cl | —CH₂—iPr |
| 3-8 | CH₃ | —CH₂—iPr | Cl | Cl | —CH₂—iPr |
| 3-9 | CH₃ | Cl | Cl | —CH₂—iPr | —CH₂—iPr |
| 3-10 | CH₃ | —CH₂—iPr | —CH₂—iPr | Cl | Cl |
| 3-11 | CH₃ | Cl | —CH₂—iPr | —CH₂—iPr | Cl |
| 3-12 | CH₃ | —CH₂—iPr | Cl | Cl | Cl |
| 3-13 | CH₃ | Cl | —CH₂—iPr | Cl | Cl |
| 3-14 | CH₃ | Cl | Cl | —CH₂—iPr | Cl |
| 3-15 | CH₃ | Cl | Cl | Cl | —CH₂—iPr |
| 3-16 | CH₃ | Cl | —CH₂—C(CH₃)₃ | —CH₂—C(CH₃)₃ | —CH₂—C(CH₃)₃ |
| 3-17 | CH₃ | —CH₂—C(CH₃)₃ | Cl | —CH₂—C(CH₃)₃ | —CH₂—C(CH₃)₃ |
| 3-18 | CH₃ | —CH₂—C(CH₃)₃ | —CH₂—C(CH₃)₃ | Cl | —CH₂—C(CH₃)₃ |
| 3-19 | CH₃ | —CH₂—C(CH₃)₃ | —CH₂—C(CH₃)₃ | —CH₂—C(CH₃)₃ | Cl |
| 3-20 | CH₃ | —CH₂—C(CH₃)₃ | Cl | —CH₂—C(CH₃)₃ | Cl |
| 3-21 | CH₃ | Cl | —CH₂—C(CH₃)₃ | Cl | —CH₂—C(CH₃)₃ |
| 3-22 | CH₃ | —CH₂—C(CH₃)₃ | Cl | Cl | —CH₂—C(CH₃)₃ |
| 3-23 | CH₃ | Cl | —CH₂—C(CH₃)₃ | —CH₂—C(CH₃)₃ | Cl |
| 3-24 | CH₃ | Cl | Cl | —CH₂—C(CH₃)₃ | —CH₂—C(CH₃)₃ |
| 3-25 | CH₃ | —CH₂—C(CH₃)₃ | —CH₂—C(CH₃)₃ | Cl | Cl |
| 3-26 | CH₃ | —CH₂—C(CH₃)₃ | Cl | Cl | Cl |
| 3-27 | CH₃ | Cl | —CH₂—C(CH₃)₃ | Cl | Cl |
| 3-28 | CH₃ | Cl | Cl | —CH₂—C(CH₃)₃ | Cl |
| 3-29 | CH₃ | Cl | Cl | Cl | —CH₂—C(CH₃)₃ |
| 3-30 | CH₃ | Cl | —CH₂CF(CH₃)₂ | —CH₂CF(CH₃)₂ | —CHCF(CH₃)₂ |
| 3-31 | CH₃ | —CH₂CF(CH₃)₂ | Cl | —CH₂CF(CH₃)₂ | —CH₂CF(CH₃)₂ |
| 3-32 | CH₃ | —CH₂CF(CH₃)₂ | —CH₂CF(CH₃)₂ | Cl | —CH₂CF(CH₃)₂ |
| 3-33 | CH₃ | —CH₂CF(CH₃)₂ | —CH₂CF(CH₃)₂ | —CH₂CF(CH₃)₂ | Cl |
| 3-34 | CH₃ | —CH₂CF(CH₃)₂ | Cl | —CH₂CF(CH₃)₂ | Cl |
| 3-35 | CH₃ | Cl | —CH₂CF(CH₃)₂ | Cl | —CH₂CF(CH₃)₂ |
| 3-36 | CH₃ | —CH₂CF(CH₃)₂ | Cl | Cl | —CH₂CF(CH₃)₂ |
| 3-37 | CH₃ | Cl | —CH₂CF(CH₃)₂ | CH₂CF(CH₃)₂ | Cl |
| 3-38 | CH₃ | Cl | Cl | —CH₂CF(CH₃)₂ | —CH₂CF(CH₃)₂ |
| 3-39 | CH₃ | —CH₂CF(CH₃)₂ | —CH₂CF(CH₃)₂ | Cl | Cl |
| 3-40 | CH₃ | —CH₂CF(CH₃)₂ | Cl | Cl | Cl |
| 3-41 | CH₃ | Cl | —CH₂CF(CH₃)₂ | Cl | Cl |
| 3-42 | CH₃ | Cl | Cl | —CH₂CF(CH₃)₂ | Cl |
| 3-43 | CH₃ | Cl | Cl | Cl | —CH₂CF(CH₃)₂ |
| 3-44 | CH₃ | Cl | n-Propyl | n-Propyl | n-Propyl |
| 3-45 | CH₃ | n-Propyl | Cl | n-Propyl | n-Propyl |
| 3-46 | CH₃ | n-Propyl | n-Propyl | Cl | nPropyl |
| 3-47 | CH₃ | n-Propyl | n-Propyl | n-Propyl | Cl |
| 3-48 | CH₃ | n-Propyl | Cl | n-Propyl | Cl |
| 3-49 | CH₃ | Cl | n-Propyl | Cl | n-Propyl |
| 3-50 | CH₃ | n-Propyl | Cl | Cl | n-Propyl |
| 3-51 | CH₃ | Cl | Cl | n-Propyl | n-Propyl |
| 3-52 | CH₃ | n-Propyl | n-Propyl | Cl | Cl |
| 3-53 | CH₃ | Cl | n-Propyl | n-Propyl | Cl |
| 3-54 | CH₃ | n-Propyl | Cl | Cl | Cl |
| 3-55 | CH₃ | Cl | n-Propyl | Cl | Cl |
| 3-56 | CH₃ | Cl | Cl | n-Propyl | Cl |
| 3-57 | CH₃ | Cl | Cl | Cl | n-Propyl |
| 3-58 | H | —CH₂CF(CH₃)₂ | Cl | —CH₂CF(CH₃)₂ | Cl |
| 3-59 | H | Cl | —CH₂CF(CH₃)₂ | Cl | —CH₂CF(CH₃)₂ |
| 3-60 | H | —CH₂CF(CH₃)₂ | Cl | Cl | —CH₂CF(CH₃)₂ |
| 3-61 | H | Cl | —CH₂CF(CH₃)₂ | —CH₂CF(CH₃)₂ | Cl |
| 3-62 | H | Cl | Cl | —CH₂CF(CH₃)₂ | —CH₂CF(CH₃)₂ |
| 3-63 | H | —CH₂CF(CH₃)₂ | —CH₂CF(CH₃)₂ | Cl | Cl |
| 3-64 | H | —CH₂—C(CH₃)₃ | Cl | —CH₂—C(CH₃)₃ | Cl |
| 3-65 | H | Cl | —CH₂—C(CH₃)₃ | Cl | —CH₂—C(CH₃)₃ |
| 3-66 | H | —CH₂—C(CH₃)₃ | Cl | Cl | —CH₂—C(CH₃)₃ |
| 3-67 | H | Cl | —CH₂—C(CH₃)₃ | —CH₂—C(CH₃)₃ | Cl |
| 3-68 | H | Cl | Cl | —CH₂—C(CH₃)₃ | —CH₂—C(CH₃)₃ |
| 3-69 | H | —CH₂—C(CH₃)₃ | —CH₂—C(CH₃)₃ | Cl | Cl |

TABLE 4

Compounds of formula (I), wherein $Cy^1$ and $Cy^2$ are p-trifluoromethylphenyl; R', R'', R''' and R'''' are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 4-1 | CH₃ | Cl | Cl | Cl | Cl |
| 4-2 | CH₃ | Cl | —CH₂—iPr | —CH₂—iPr | —CH₂—iPr |
| 4-3 | CH₃ | —CH₂—iPr | Cl | —CH₂—iPr | —CH₂—iPr |
| 4-4 | CH₃ | —CH₂—iPr | —CH₂—iPr | Cl | —CH₂—iPr |
| 4-5 | CH₃ | —CH₂—iPr | —CH₂—iPr | —CH₂—iPr | Cl |
| 4-6 | CH₃ | —CH₂—iPr | Cl | —CH₂—iPr | Cl |
| 4-7 | CH₃ | Cl | —CH₂—iPr | Cl | —CH₂—iPr |
| 4-8 | CH₃ | —CH₂—iPr | Cl | Cl | —CH₂—iPr |
| 4-9 | CH₃ | Cl | Cl | —CH₂—iPr | —CH₂—iPr |
| 4-10 | CH₃ | —CH₂—iPr | —CH₂—iPr | Cl | Cl |
| 4-11 | CH₃ | Cl | —CH₂—iPr | —CH₂—iPr | Cl |
| 4-12 | CH₃ | —CH₂—iPr | Cl | Cl | Cl |
| 4-13 | CH₃ | Cl | —CH₂—iPr | Cl | Cl |
| 4-14 | CH₃ | Cl | Cl | —CH₂—iPr | Cl |
| 4-15 | CH₃ | Cl | Cl | Cl | —CH₂—iPr |
| 4-16 | CH₃ | Cl | —CH₂—C(CH₃)₃ | —CH₂—C(CH₃)₃ | —CH₂—C(CH₃)₃ |
| 4-17 | CH₃ | —CH₂—C(CH₃)₃ | Cl | —CH₂—C(CH₃)₃ | —CH₂—C(CH₃)₃ |
| 4-18 | CH₃ | —CH₂—C(CH₃)₃ | —CH₂—C(CH₃)₃ | Cl | —CH₂—C(CH₃)₃ |
| 4-19 | CH₃ | —CH₂—C(CH₃)₃ | —CH₂—C(CH₃)₃ | —CH₂—C(CH₃)₃ | Cl |
| 4-20 | CH₃ | —CH₂—C(CH₃)₃ | Cl | —CH₂—C(CH₃)₃ | Cl |
| 4-21 | CH₃ | Cl | —CH₂—C(CH₃)₃ | Cl | —CH₂—C(CH₃)₃ |
| 4-22 | CH₃ | —CH₂—C(CH₃)₃ | Cl | Cl | —CH₂—C(CH₃)₃ |
| 4-23 | CH₃ | Cl | —CH₂—C(CH₃)₃ | —CH₂—C(CH₃)₃ | Cl |
| 4-24 | CH₃ | Cl | Cl | —CH₂—C(CH₃)₃ | —CH₂—C(CH₃)₃ |
| 4-25 | CH₃ | —CH₂—C(CH₃)₃ | —CH₂—C(CH₃)₃ | Cl | Cl |
| 4-26 | CH₃ | —CH₂—C(CH₃)₃ | Cl | Cl | Cl |
| 4-27 | CH₃ | Cl | —CH₂—C(CH₃)₃ | Cl | Cl |
| 4-28 | CH₃ | Cl | Cl | —CH₂—C(CH₃)₃ | Cl |
| 4-29 | CH₃ | Cl | Cl | Cl | —CH₂—C(CH₃)₃ |
| 4-30 | CH₃ | Cl | —CH₂CF(CH₃)₂ | —CH₂CF(CH₃)₂ | —CHCF(CH₃)₂ |
| 4-31 | CH₃ | —CH₂CF(CH₃)₂ | Cl | —CH₂CF(CH₃)₂ | —CH₂CF(CH₃)₂ |
| 4-32 | CH₃ | —CH₂CF(CH₃)₂ | —CH₂CF(CH₃)₂ | Cl | —CH₂CF(CH₃)₂ |
| 4-33 | CH₃ | —CH₂CF(CH₃)₂ | —CH₂CF(CH₃)₂ | —CH₂CF(CH₃)₂ | Cl |
| 4-34 | CH₃ | —CH₂CF(CH₃)₂ | Cl | —CH₂CF(CH₃)₂ | Cl |
| 4-35 | CH₃ | Cl | —CH₂CF(CH₃)₂ | Cl | —CH₂CF(CH₃)₂ |
| 4-36 | CH₃ | —CH₂CF(CH₃)₂ | Cl | Cl | —CH₂CF(CH₃)₂ |
| 4-37 | CH₃ | Cl | —CH₂CF(CH₃)₂ | CH₂CF(CH₃)₂ | Cl |
| 4-38 | CH₃ | Cl | Cl | —CH₂CF(CH₃)₂ | —CH₂CF(CH₃)₂ |
| 4-39 | CH₃ | —CH₂CF(CH₃)₂ | —CH₂CF(CH₃)₂ | Cl | Cl |
| 4-40 | CH₃ | —CH₂CF(CH₃)₂ | Cl | Cl | Cl |
| 4-41 | CH₃ | Cl | —CH₂CF(CH₃)₂ | Cl | Cl |
| 4-42 | CH₃ | Cl | Cl | —CH₂CF(CH₃)₂ | Cl |
| 4-43 | CH₃ | Cl | Cl | Cl | —CH₂CF(CH₃)₂ |
| 4-44 | CH₃ | Cl | n-Propyl | n-Propyl | n-Propyl |
| 4-45 | CH₃ | n-Propyl | Cl | n-Propyl | n-Propyl |
| 4-46 | CH₃ | n-Propyl | n-Propyl | Cl | n-Propyl |
| 4-47 | CH₃ | n-Propyl | n-Propyl | n-Propyl | Cl |
| 4-48 | CH₃ | n-Propyl | Cl | n-Propyl | Cl |
| 4-49 | CH₃ | Cl | n-Propyl | Cl | n-Propyl |
| 4-50 | CH₃ | n-Propyl | Cl | Cl | n-Propyl |
| 4-51 | CH₃ | Cl | Cl | n-Propyl | n-Propyl |
| 4-52 | CH₃ | n-Propyl | n-Propyl | Cl | Cl |
| 4-53 | CH₃ | Cl | n-Propyl | n-Propyl | Cl |
| 4-54 | CH₃ | n-Propyl | Cl | Cl | Cl |
| 4-55 | CH₃ | Cl | n-Propyl | Cl | Cl |
| 4-56 | CH₃ | Cl | Cl | n-Propyl | Cl |
| 4-57 | CH₃ | Cl | Cl | Cl | n-Propyl |
| 4-58 | H | —CH₂CF(CH₃)₂ | Cl | —CH₂CF(CH₃)₂ | Cl |
| 4-59 | H | Cl | —CH₂CF(CH₃)₂ | —CH₂CF(CH₃)₂ | —CH₂CF(CH₃)₂ |
| 4-60 | H | —CH₂CF(CH₃)₂ | Cl | —CH₂CF(CH₃)₂ | —CH₂CF(CH₃)₂ |
| 4-61 | H | Cl | —CH₂CF(CH₃)₂ | —CH₂CF(CH₃)₂ | Cl |
| 4-62 | H | Cl | Cl | —CH₂CF(CH₃)₂ | —CH₂CF(CH₃)₂ |
| 4-63 | H | —CH₂CF(CH₃)₂ | —CH₂CF(CH₃)₂ | Cl | Cl |
| 4-64 | H | —CH₂—C(CH₃)₃ | Cl | —CH₂—C(CH₃)₃ | Cl |
| 4-65 | H | Cl | —CH₂—C(CH₃)₃ | Cl | —CH₂—C(CH₃)₃ |
| 4-66 | H | —CH₂—C(CH₃)₃ | Cl | Cl | —CH₂—C(CH₃)₃ |
| 4-67 | H | Cl | —CH₂—C(CH₃)₃ | —CH₂—C(CH₃)₃ | Cl |
| 4-68 | H | Cl | Cl | —CH₂—C(CH₃)₃ | —CH₂—C(CH₃)₃ |
| 4-69 | H | —CH₂—C(CH₃)₃ | —CH₂—C(CH₃)₃ | Cl | Cl |

TABLE 5

Compounds of formula (I), wherein $Cy^1$ and $Cy^2$ are p-trifluoromethoxyphenyl; R', R'', R''' and R'''' are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 5-1 | CH₃ | Cl | Cl | Cl | Cl |
| 5-2 | CH₃ | Cl | —CH₂—iPr | —CH₂—iPr | —CH₂—iPr |
| 5-3 | CH₃ | —CH₂—iPr | Cl | —CH₂—iPr | —CH₂—iPr |
| 5-4 | CH₃ | —CH₂—iPr | —CH₂—iPr | Cl | —CH₂—iPr |
| 5-5 | CH₃ | —CH₂—iPr | —CH₂—iPr | —CH₂—iPr | Cl |
| 5-6 | CH₃ | —CH₂—iPr | Cl | —CH₂—iPr | Cl |
| 5-7 | CH₃ | Cl | —CH₂—iPr | Cl | —CH₂—iPr |
| 5-8 | CH₃ | —CH₂—iPr | Cl | Cl | —CH₂—iPr |
| 5-9 | CH₃ | Cl | Cl | —CH₂—iPr | —CH₂—iPr |
| 5-10 | CH₃ | —CH₂—iPr | —CH₂—iPr | Cl | Cl |
| 5-11 | CH₃ | Cl | —CH₂—iPr | —CH₂—iPr | Cl |
| 5-12 | CH₃ | —CH₂—iPr | Cl | Cl | Cl |
| 5-13 | CH₃ | Cl | —CH₂—iPr | Cl | Cl |
| 5-14 | CH₃ | Cl | Cl | —CH₂—iPr | Cl |
| 5-15 | CH₃ | Cl | Cl | Cl | —CH₂—iPr |
| 5-16 | CH₃ | Cl | —CH₂—C(CH₃)₃ | —CH₂—C(CH₃)₃ | —CH₂—C(CH₃)₃ |
| 5-17 | CH₃ | —CH₂—C(CH₃)₃ | Cl | —CH₂—C(CH₃)₃ | —CH₂—C(CH₃)₃ |
| 5-18 | CH₃ | —CH₂—C(CH₃)₃ | —CH₂—C(CH₃)₃ | Cl | —CH₂—C(CH₃)₃ |
| 5-19 | CH₃ | —CH₂—C(CH₃)₃ | —CH₂—C(CH₃)₃ | —CH₂—C(CH₃)₃ | Cl |
| 5-20 | CH₃ | —CH₂—C(CH₃)₃ | Cl | —CH₂—C(CH₃)₃ | Cl |
| 5-21 | CH₃ | Cl | —CH₂—C(CH₃)₃ | Cl | —CH₂—C(CH₃)₃ |
| 5-22 | CH₃ | —CH₂—C(CH₃)₃ | Cl | Cl | —CH₂—C(CH₃)₃ |
| 5-23 | CH₃ | Cl | —CH₂—C(CH₃)₃ | —CH₂—C(CH₃)₃ | Cl |
| 5-24 | CH₃ | Cl | Cl | —CH₂—C(CH₃)₃ | —CH₂—C(CH₃)₃ |
| 5-25 | CH₃ | —CH₂—C(CH₃)₃ | —CH₂—C(CH₃)₃ | Cl | Cl |
| 5-26 | CH₃ | —CH₂—C(CH₃)₃ | Cl | Cl | Cl |
| 5-27 | CH₃ | Cl | —CH₂—C(CH₃)₃ | Cl | Cl |
| 5-28 | CH₃ | Cl | Cl | —CH₂—C(CH₃)₃ | Cl |
| 5-29 | CH₃ | Cl | Cl | Cl | —CH₂—C(CH₃)₃ |
| 5-30 | CH₃ | Cl | —CH₂CF(CH₃)₂ | —CH₂CF(CH₃)₂ | —CHCF(CH₃)₂ |
| 5-31 | CH₃ | —CH₂CF(CH₃)₂ | Cl | —CH₂CF(CH₃)₂ | —CH₂CF(CH₃)₂ |
| 5-32 | CH₃ | —CH₂CF(CH₃)₂ | —CH₂CF(CH₃)₂ | Cl | —CH₂CF(CH₃)₂ |
| 5-33 | CH₃ | —CH₂CF(CH₃)₂ | —CH₂CF(CH₃)₂ | —CH₂CF(CH₃)₂ | Cl |
| 5-34 | CH₃ | —CH₂CF(CH₃)₂ | Cl | —CH₂CF(CH₃)₂ | Cl |
| 5-35 | CH₃ | Cl | —CH₂CF(CH₃)₂ | Cl | —CH₂CF(CH₃)₂ |
| 5-36 | CH₃ | —CH₂CF(CH₃)₂ | Cl | Cl | —CH₂CF(CH₃)₂ |
| 5-37 | CH₃ | Cl | —CH₂CF(CH₃)₂ | CH₂CF(CH₃)₂ | Cl |
| 5-38 | CH₃ | Cl | Cl | —CH₂CF(CH₃)₂ | —CH₂CF(CH₃)₂ |
| 5-39 | CH₃ | —CH₂CF(CH₃)₂ | —CH₂CF(CH₃)₂ | Cl | Cl |
| 5-40 | CH₃ | —CH₂CF(CH₃)₂ | Cl | Cl | Cl |
| 5-41 | CH₃ | Cl | —CH₂CF(CH₃)₂ | Cl | Cl |
| 5-42 | CH₃ | Cl | Cl | —CH₂CF(CH₃)₂ | Cl |
| 5-43 | CH₃ | Cl | Cl | Cl | —CH₂CF(CH₃)₂ |
| 5-44 | CH₃ | Cl | n-Propyl | n-Propyl | n-Propyl |
| 5-45 | CH₃ | n-Propyl | Cl | n-Propyl | n-Propyl |
| 5-46 | CH₃ | n-Propyl | n-Propyl | Cl | n-Propyl |
| 5-47 | CH₃ | n-Propyl | n-Propyl | n-Propyl | Cl |
| 5-48 | CH₃ | n-Propyl | Cl | n-Propyl | Cl |
| 5-49 | CH₃ | Cl | n-Propyl | Cl | n-Propyl |
| 5-50 | CH₃ | n-Propyl | Cl | Cl | n-Propyl |
| 5-51 | CH₃ | Cl | Cl | n-Propyl | n-Propyl |
| 5-52 | CH₃ | n-Propyl | n-Propyl | Cl | Cl |
| 5-53 | CH₃ | Cl | n-Propyl | n-Propyl | Cl |
| 5-54 | CH₃ | n-Propyl | Cl | Cl | Cl |
| 5-55 | CH₃ | Cl | n-Propyl | Cl | Cl |
| 5-56 | CH₃ | Cl | Cl | n-Propyl | Cl |
| 5-57 | CH₃ | Cl | Cl | Cl | n-Propyl |
| 5-58 | H | —CH₂CF(CH₃)₂ | Cl | —CH₂CF(CH₃)₂ | Cl |
| 5-59 | H | Cl | —CH₂CF(CH₃)₂ | Cl | —CH₂CF(CH₃)₂ |
| 5-60 | H | —CH₂CF(CH₃)₂ | —CH₂CF(CH₃)₂ | Cl | —CH₂CF(CH₃)₂ |
| 5-61 | H | Cl | —CH₂CF(CH₃)₂ | —CH₂CF(CH₃)₂ | Cl |
| 5-62 | H | Cl | Cl | —CH₂CF(CH₃)₂ | —CH₂CF(CH₃)₂ |
| 5-63 | H | —CH₂CF(CH₃)₂ | —CH₂CF(CH₃)₂ | Cl | Cl |
| 5-64 | H | —CH₂—C(CH₃)₃ | Cl | —CH₂—C(CH₃)₃ | Cl |
| 5-65 | H | Cl | —CH₂—C(CH₃)₃ | Cl | —CH₂—C(CH₃)₃ |
| 5-66 | H | —CH₂—C(CH₃)₃ | Cl | Cl | —CH₂—C(CH₃)₃ |
| 5-67 | H | Cl | —CH₂—C(CH₃)₃ | —CH₂—C(CH₃)₃ | Cl |
| 5-68 | H | Cl | Cl | —CH₂—C(CH₃)₃ | —CH₂—C(CH₃)₃ |
| 5-69 | H | —CH₂—C(CH₃)₃ | —CH₂—C(CH₃)₃ | Cl | Cl |

TABLE 6

Compounds of formula (I), wherein Cy¹ and Cy² are

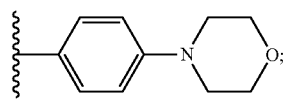 [SMILES: *c1ccc(C2CCOCC2)cc1]

R', R'', R''' and R'''' are each independently hydrogen or methyl;
and $R^a$, $R^b$ and $R^1$ to $R^4$ are as shown.

| Cmpd # | $R^a/R^b$ | R¹ | R² | R³ | R⁴ |
|---|---|---|---|---|---|
| 6-1 | CH₃ | Cl | Cl | Cl | Cl |
| 6-2 | CH₃ | Cl | —CH₂—iPr | —CH₂—iPr | —CH₂—iPr |
| 6-3 | CH₃ | —CH₂—iPr | Cl | —CH₂—iPr | —CH₂—iPr |
| 6-4 | CH₃ | —CH₂—iPr | —CH₂—iPr | Cl | —CH₂—iPr |
| 6-5 | CH₃ | —CH₂—iPr | —CH₂—iPr | —CH₂—iPr | Cl |
| 6-6 | CH₃ | —CH₂—iPr | Cl | —CH₂—iPr | Cl |
| 6-7 | CH₃ | Cl | —CH₂-iPr | Cl | —CH₂—iPr |
| 6-8 | CH₃ | —CH₂—iPr | Cl | Cl | —CH₂—iPr |
| 6-9 | CH₃ | Cl | Cl | —CH₂—iPr | —CH₂—iPr |
| 6-10 | CH₃ | —CH₂—iPr | —CH₂—iPr | Cl | Cl |
| 6-11 | CH₃ | Cl | —CH₂—iPr | —CH₂—iPr | Cl |
| 6-12 | CH₃ | —CH₂—iPr | Cl | Cl | Cl |
| 6-13 | CH₃ | Cl | —CH₂—iPr | Cl | Cl |
| 6-14 | CH₃ | Cl | Cl | —CH₂—iPr | Cl |
| 6-15 | CH₃ | Cl | Cl | Cl | —CH₂—iPr |
| 6-16 | CH₃ | Cl | —CH₂—C(CH₃)₃ | —CH₂—C(CH₃)₃ | —CH₂—C(CH₃)₃ |
| 6-17 | CH₃ | —CH₂—C(CH₃)₃ | Cl | —CH₂—C(CH₃)₃ | —CH₂—C(CH₃)₃ |
| 6-18 | CH₃ | —CH₂—C(CH₃)₃ | —CH₂—C(CH₃)₃ | Cl | —CH₂—C(CH₃)₃ |
| 6-19 | CH₃ | —CH₂—C(CH₃)₃ | —CH₂—C(CH₃)₃ | —CH₂—C(CH₃)₃ | Cl |
| 6-20 | CH₃ | —CH₂—C(CH₃)₃ | Cl | —CH₂—C(CH₃)₃ | Cl |
| 6-21 | CH₃ | Cl | —CH₂—C(CH₃)₃ | Cl | —CH₂—C(CH₃)₃ |
| 6-22 | CH₃ | —CH₂—C(CH₃)₃ | Cl | Cl | —CH₂—C(CH₃)₃ |
| 6-23 | CH₃ | Cl | —CH₂—C(CH₃)₃ | —CH₂—C(CH₃)₃ | Cl |
| 6-24 | CH₃ | Cl | Cl | —CH₂—C(CH₃)₃ | —CH₂—C(CH₃)₃ |
| 6-25 | CH₃ | —CH₂—C(CH₃)₃ | —CH₂—C(CH₃)₃ | Cl | Cl |
| 6-26 | CH₃ | —CH₂—C(CH₃)₃ | Cl | Cl | Cl |
| 6-27 | CH₃ | Cl | —CH₂—C(CH₃)₃ | Cl | Cl |
| 6-28 | CH₃ | Cl | Cl | —CH₂—C(CH₃)₃ | Cl |
| 6-29 | CH₃ | Cl | Cl | Cl | —CH₂—C(CH₃)₃ |
| 6-30 | CH₃ | Cl | —CH₂CF(CH₃)₂ | —CH₂CF(CH₃)₂ | —CHCF(CH₃)₂ |
| 6-31 | CH₃ | —CH₂CF(CH₃)₂ | Cl | —CH₂CF(CH₃)₂ | —CH₂CF(CH₃)₂ |
| 6-32 | CH₃ | —CH₂CF(CH₃)₂ | —CH₂CF(CH₃)₂ | Cl | —CH₂CF(CH₃)₂ |
| 6-33 | CH₃ | —CH₂CF(CH₃)₂ | —CH₂CF(CH₃)₂ | —CH₂CF(CH₃)₂ | Cl |
| 6-34 | CH₃ | —CH₂CF(CH₃)₂ | Cl | —CH₂CF(CH₃)₂ | Cl |
| 6-35 | CH₃ | Cl | —CH₂CF(CH₃)₂ | Cl | —CH₂CF(CH₃)₂ |
| 6-36 | CH₃ | —CH₂CF(CH₃)₂ | Cl | Cl | —CH₂CF(CH₃)₂ |
| 6-37 | CH₃ | Cl | —CH₂CF(CH₃)₂ | CH₂CF(CH₃)₂ | Cl |
| 6-38 | CH₃ | Cl | Cl | —CH₂CF(CH₃)₂ | —CH₂CF(CH₃)₂ |
| 6-39 | CH₃ | —CH₂CF(CH₃)₂ | —CH₂CF(CH₃)₂ | Cl | Cl |
| 6-40 | CH₃ | —CH₂CF(CH₃)₂ | Cl | Cl | Cl |
| 6-41 | CH₃ | Cl | —CH₂CF(CH₃)₂ | Cl | Cl |
| 6-42 | CH₃ | Cl | Cl | —CH₂CF(CH₃)₂ | Cl |
| 6-43 | CH₃ | Cl | Cl | Cl | —CH₂CF(CH₃)₂ |
| 6-44 | CH₃ | Cl | n-Propyl | n-Propyl | n-Propyl |
| 6-45 | CH₃ | n-Propyl | Cl | n-Propyl | n-Propyl |
| 6-46 | CH₃ | n-Propyl | n-Propyl | Cl | n-Propyl |
| 6-47 | CH₃ | n-Propyl | n-Propyl | n-Propyl | Cl |
| 6-48 | CH₃ | n-Propyl | Cl | n-Propyl | Cl |
| 6-49 | CH₃ | Cl | n-Propyl | Cl | n-Propyl |
| 6-50 | CH₃ | n-Propyl | Cl | Cl | n-Propyl |
| 6-51 | CH₃ | Cl | Cl | n-Propyl | n-Propyl |
| 6-52 | CH₃ | n-Propyl | n-Propyl | Cl | Cl |
| 6-53 | CH₃ | Cl | n-Propyl | n-Propyl | Cl |
| 6-54 | CH₃ | n-Propyl | Cl | Cl | Cl |
| 6-55 | CH₃ | Cl | n-Propyl | Cl | Cl |
| 6-56 | CH₃ | Cl | Cl | n-Propyl | Cl |
| 6-57 | CH₃ | Cl | Cl | Cl | n-Propyl |
| 6-58 | H | —CH₂CF(CH₃)₂ | Cl | —CH₂CF(CH₃)₂ | —CH₂CF(CH₃)₂ |
| 6-59 | H | Cl | —CH₂CF(CH₃)₂ | Cl | —CH₂CF(CH₃)₂ |
| 6-60 | H | —CH₂CF(CH₃)₂ | —CH₂CF(CH₃)₂ | Cl | —CH₂CF(CH₃)₂ |
| 6-61 | H | Cl | —CH₂CF(CH₃)₂ | —CH₂CF(CH₃)₂ | Cl |
| 6-62 | H | Cl | Cl | —CH₂CF(CH₃)₂ | —CH₂CF(CH₃)₂ |
| 6-63 | H | —CH₂CF(CH₃)₂ | —CH₂CF(CH₃)₂ | Cl | Cl |
| 6-64 | H | —CH₂—C(CH₃)₃ | Cl | —CH₂—C(CH₃)₃ | Cl |
| 6-65 | H | Cl | —CH₂—C(CH₃)₃ | Cl | —CH₂—C(CH₃)₃ |
| 6-66 | H | —CH₂—C(CH₃)₃ | Cl | Cl | —CH₂—C(CH₃)₃ |
| 6-67 | H | Cl | —CH₂—C(CH₃)₃ | —CH₂—C(CH₃)₃ | Cl |

TABLE 6-continued

Compounds of formula (I), wherein Cy¹ and Cy² are

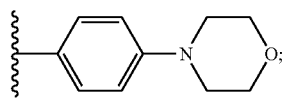

R', R'', R''' and R'''' are each independently hydrogen or methyl;
and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 6-68 | H | Cl | Cl | —CH₂—C(CH₃)₃ | —CH₂—C(CH₃)₃ |
| 6-69 | H | —CH₂—C(CH₃)₃ | —CH₂—C(CH₃)₃ | Cl | Cl |

TABLE 7

Compounds of formula (I), wherein Cy¹ and Cy² are

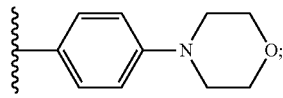

R', R'', R''' and R'''' are each independently hydrogen or
methyl; and $R^1$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 7-1 | CH₃ | Cl | Cl | Cl | Cl |
| 7-2 | CH₃ | Cl | —CH₂—iPr | —CH₂—iPr | —CH₂—iPr |
| 7-3 | CH₃ | —CH₂—iPr | Cl | —CH₂—iPr | —CH₂—iPr |
| 7-4 | CH₃ | —CH₂—Pr | —CH₂—iPr | Cl | —CH₂—iPr |
| 7-5 | CH₃ | —CH₂—iPr | —CH₂—iPr | —CH₂—Pr | Cl |
| 7-6 | CH₃ | —CH₂—iPr | Cl | —CH₂—iPr | Cl |
| 7-7 | CH₃ | Cl | —CH₂—iPr | Cl | —CH₂—iPr |
| 7-8 | CH₃ | —CH₂—iPr | Cl | Cl | —CH₂—iPr |
| 7-9 | CH₃ | Cl | Cl | —CH₂—iPr | —CH₂—iPr |
| 7-10 | CH₃ | —CH₂—iPr | —CH₂—iPr | Cl | Cl |
| 7-11 | CH₃ | Cl | —CH₂—iPr | —CH₂—iPr | Cl |
| 7-12 | CH₃ | —CH₂—Pr | Cl | Cl | Cl |
| 7-13 | CH₃ | Cl | —CH₂—iPr | Cl | Cl |
| 7-14 | CH₃ | Cl | Cl | —CH₂—iPr | Cl |
| 7-15 | CH₃ | Cl | Cl | Cl | —CH₂—iPr |
| 7-16 | CH₃ | Cl | —CH₂—C(CH₃)₃ | —CH₂—C(CH₃)₃ | —CH₂—C(CH₃)₃ |
| 7-17 | CH₃ | —CH₂—C(CH₃)₃ | Cl | —CH₂—C(CH₃)₃ | —CH₂—C(CH₃)₃ |
| 7-18 | CH₃ | —CH₂—C(CH₃)₃ | —CH₂—C(CH₃)₃ | Cl | —CH₂—C(CH₃)₃ |
| 7-19 | CH₃ | —CH₂—C(CH₃)₃ | —CH₂—C(CH₃)₃ | —CH₂—C(CH₃)₃ | Cl |
| 7-20 | CH₃ | —CH₂—C(CH₃)₃ | Cl | —CH₂—C(CH₃)₃ | Cl |
| 7-21 | CH₃ | Cl | —CH₂—C(CH₃)₃ | Cl | —CH₂—C(CH₃)₃ |
| 7-22 | CH₃ | —CH₂—C(CH₃)₃ | Cl | Cl | —CH₂—C(CH₃)₃ |
| 7-23 | CH₃ | Cl | —CH₂—C(CH₃)₃ | —CH₂—C(CH₃)₃ | Cl |
| 7-24 | CH₃ | Cl | Cl | —CH₂—C(CH₃)₃ | —CH₂—C(CH₃)₃ |
| 7-25 | CH₃ | —CH₂—C(CH₃)₃ | —CH₂—C(CH₃)₃ | Cl | Cl |
| 7-26 | CH₃ | —CH₂—C(CH₃)₃ | Cl | Cl | Cl |
| 7-27 | CH₃ | Cl | —CH₂—C(CH₃)₃ | Cl | Cl |
| 7-28 | CH₃ | Cl | Cl | —CH₂—C(CH₃)₃ | Cl |
| 7-29 | CH₃ | Cl | Cl | Cl | —CH₂—C(CH₃)₃ |
| 7-30 | CH₃ | Cl | —CH₂CF(CH₃)₂ | —CH₂CF(CH₃)₂ | —CHCF(CH₃)₂ |
| 7-31 | CH₃ | —CH₂CF(CH₃)₂ | Cl | —CH₂CF(CH₃)₂ | —CH₂CF(CH₃)₂ |
| 7-32 | CH₃ | —CH₂CF(CH₃)₂ | —CH₂CF(CH₃)₂ | Cl | —CH₂CF(CH₃)₂ |
| 7-33 | CH₃ | —CH₂CF(CH₃)₂ | —CH₂CF(CH₃)₂ | —CH₂CF(CH₃)₂ | Cl |
| 7-34 | CH₃ | —CH₂CF(CH₃)₂ | Cl | —CH₂CF(CH₃)₂ | Cl |
| 7-35 | CH₃ | Cl | —CH₂CF(CH₃)₂ | Cl | —CH₂CF(CH₃)₂ |
| 7-36 | CH₃ | —CH₂CF(CH₃)₂ | Cl | Cl | —CH₂CF(CH₃)₂ |
| 7-37 | CH₃ | Cl | —CH₂CF(CH₃)₂ | CH₂CF(CH₃)₂ | Cl |
| 7-38 | CH₃ | Cl | Cl | —CH₂CF(CH₃)₂ | —CH₂CF(CH₃)₂ |
| 7-39 | CH₃ | —CH₂CF(CH₃)₂ | —CH₂CF(CH₃)₂ | Cl | Cl |
| 7-40 | CH₃ | —CH₂CF(CH₃)₂ | Cl | Cl | Cl |
| 7-41 | CH₃ | Cl | —CH₂CF(CH₃)₂ | Cl | Cl |
| 7-42 | CH₃ | Cl | Cl | —CH₂CF(CH₃)₂ | Cl |
| 7-43 | CH₃ | Cl | Cl | Cl | —CH₂CF(CH₃)₂ |
| 7-44 | CH₃ | Cl | n-Propyl | n-Propyl | n-Propyl |
| 7-45 | CH₃ | n-Propyl | Cl | n-Propyl | n-Propyl |
| 7-46 | CH₃ | n-Propyl | n-Propyl | Cl | n-Propyl |

TABLE 7-continued

Compounds of formula (I), wherein Cy¹ and Cy² are

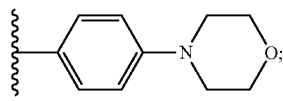

R', R'', R''' and R'''' are each independently hydrogen or methyl; and R$^a$, R$^b$ and R$^1$ to R$^4$ are as shown.

| Cmpd # | R$^a$/R$^b$ | R$^1$ | R$^2$ | R$^3$ | R$^4$ |
| --- | --- | --- | --- | --- | --- |
| 7-47 | CH$_3$ | n-Propyl | n-Propyl | n-Propyl | Cl |
| 7-48 | CH$_3$ | n-Propyl | Cl | n-Propyl | Cl |
| 7-49 | CH$_3$ | Cl | n-Propyl | Cl | n-Propyl |
| 7-50 | CH$_3$ | n-Propyl | Cl | Cl | n-Propyl |
| 7-51 | CH$_3$ | Cl | Cl | n-Propyl | n-Propyl |
| 7-52 | CH$_3$ | n-Propyl | n-Propyl | Cl | Cl |
| 7-53 | CH$_3$ | Cl | n-Propyl | n-Propyl | Cl |
| 7-54 | CH$_3$ | n-Propyl | Cl | Cl | Cl |
| 7-55 | CH$_3$ | Cl | n-Propyl | Cl | Cl |
| 7-56 | CH$_3$ | Cl | Cl | n-Propyl | Cl |
| 7-57 | CH$_3$ | Cl | Cl | Cl | n-Propyl |
| 7-58 | H | —CH$_2$CF(CH$_3$)$_2$ | Cl | —CH$_2$CF(CH$_3$)$_2$ | Cl |
| 7-59 | H | Cl | —CH$_2$CF(CH$_3$)$_2$ | Cl | —CH$_2$CF(CH$_3$)$_2$ |
| 7-60 | H | —CH$_2$CF(CH$_3$)$_2$ | Cl | Cl | —CH$_2$CF(CH$_3$)$_2$ |
| 7-61 | H | Cl | —CH$_2$CF(CH$_3$)$_2$ | —CH$_2$CF(CH$_3$)$_2$ | Cl |
| 7-62 | H | Cl | Cl | —CH$_2$CF(CH$_3$)$_2$ | —CH$_2$CF(CH$_3$)$_2$ |
| 7-63 | H | —CH$_2$CF(CH$_3$)$_2$ | —CH$_2$CF(CH$_3$)$_2$ | Cl | Cl |
| 7-64 | H | —CH$_2$—C(CH$_3$)$_3$ | Cl | —CH$_2$—C(CH$_3$)$_3$ | Cl |
| 7-65 | H | Cl | —CH$_2$—C(CH$_3$)$_3$ | Cl | —CH$_2$—C(CH$_3$)$_3$ |
| 7-66 | H | —CH$_2$—C(CH$_3$)$_3$ | Cl | Cl | —CH$_2$—C(CH$_3$)$_3$ |
| 7-67 | H | Cl | —CH$_2$—C(CH$_3$)$_3$ | —CH$_2$—C(CH$_3$)$_3$ | Cl |
| 7-68 | H | Cl | Cl | —CH$_2$—C(CH$_3$)$_3$ | —CH$_2$—C(CH$_3$)$_3$ |
| 7-69 | H | —CH$_2$—C(CH$_3$)$_3$ | —CH$_2$—C(CH$_3$)$_3$ | Cl | Cl |

TABLE 8

Compounds of formula (I), wherein Cy¹ and Cy² are

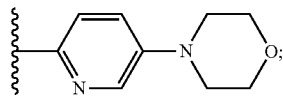

R', R'', R''' and R'''' are each independently hydrogen or methyl; and R$^a$, R$^b$ and R$^1$ to R$^4$ are as shown.

| Cmpd # | R$^a$/R$^b$ | R$^1$ | R$^2$ | R$^3$ | R$^4$ |
| --- | --- | --- | --- | --- | --- |
| 8-1 | CH$_3$ | Cl | Cl | Cl | Cl |
| 8-2 | CH$_3$ | Cl | —CH$_2$—iPr | —CH$_2$—iPr | —CH$_2$—iPr |
| 8-3 | CH$_3$ | —CH$_2$—iPr | Cl | —CH$_2$—iPr | —CH$_2$—iPr |
| 8-4 | CH$_3$ | —CH$_2$—iPr | —CH$_2$—iPr | Cl | —CH$_2$—iPr |
| 8-5 | CH$_3$ | —CH$_2$—iPr | —CH$_2$—iPr | —CH$_2$—iPr | Cl |
| 8-6 | CH$_3$ | —CH$_2$—iPr | Cl | —CH$_2$—iPr | Cl |
| 8-7 | CH$_3$ | Cl | —CH$_2$—iPr | Cl | —CH$_2$—iPr |
| 8-8 | CH$_3$ | —CH$_2$—iPr | Cl | Cl | —CH$_2$—iPr |
| 8-9 | CH$_3$ | Cl | Cl | —CH$_2$—iPr | —CH$_2$—iPr |
| 8-10 | CH$_3$ | —CH$_2$—iPr | —CH$_2$—iPr | Cl | Cl |
| 8-11 | CH$_3$ | Cl | —CH$_2$—iPr | —CH$_2$—iPr | Cl |
| 8-12 | CH$_3$ | —CH$_2$—iPr | Cl | Cl | Cl |
| 8-13 | CH$_3$ | Cl | —CH$_2$—iPr | Cl | Cl |
| 8-14 | CH$_3$ | Cl | Cl | —CH$_2$—iPr | Cl |
| 8-15 | CH$_3$ | Cl | Cl | Cl | —CH$_2$—iPr |
| 8-16 | CH$_3$ | Cl | —CH$_2$—C(CH$_3$)$_3$ | —CH$_2$—C(CH$_3$)$_3$ | —CH$_2$—C(CH$_3$)$_3$ |
| 8-17 | CH$_3$ | —CH$_2$—C(CH$_3$)$_3$ | Cl | —CH$_2$—C(CH$_3$)$_3$ | —CH$_2$—C(CH$_3$)$_3$ |
| 8-18 | CH$_3$ | —CH$_2$—C(CH$_3$)$_3$ | —CH$_2$—C(CH$_3$)$_3$ | Cl | —CH$_2$—C(CH$_3$)$_3$ |
| 8-19 | CH$_3$ | —CH$_2$—C(CH$_3$)$_3$ | —CH$_2$—C(CH$_3$)$_3$ | —CH$_2$—C(CH$_3$)$_3$ | Cl |
| 8-20 | CH$_3$ | —CH$_2$—C(CH$_3$)$_3$ | Cl | —CH$_2$—C(CH$_3$)$_3$ | Cl |
| 8-21 | CH$_3$ | Cl | —CH$_2$—C(CH$_3$)$_3$ | Cl | —CH$_2$—C(CH$_3$)$_3$ |
| 8-22 | CH$_3$ | —CH$_2$—C(CH$_3$)$_3$ | Cl | Cl | —CH$_2$—C(CH$_3$)$_3$ |
| 8-23 | CH$_3$ | Cl | —CH$_2$—C(CH$_3$)$_3$ | —CH$_2$—C(CH$_3$)$_3$ | Cl |
| 8-24 | CH$_3$ | Cl | Cl | —CH$_2$—C(CH$_3$)$_3$ | —CH$_2$—C(CH$_3$)$_3$ |
| 8-25 | CH$_3$ | —CH$_2$—C(CH$_3$)$_3$ | —CH$_2$—C(CH)$_3$ | Cl | Cl |

TABLE 8-continued

Compounds of formula (I), wherein $Cy^1$ and $Cy^2$ are

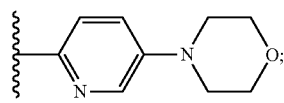 [SMILES: *c1ccc(N2CCOCC2)cn1]

R', R'', R''' and R'''' are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 8-26 | CH₃ | —CH₂—C(CH₃)₃ | Cl | Cl | Cl |
| 8-27 | CH₃ | Cl | —CH₂—C(CH₃)₃ | Cl | Cl |
| 8-28 | CH₃ | Cl | Cl | —CH₂—C(CH₃)₃ | Cl |
| 8-29 | CH₃ | Cl | Cl | Cl | —CH₂—C(CH₃)₃ |
| 8-30 | CH₃ | Cl | —CH₂CF(CH₃)₂ | —CH₂CF(CH₃)₂ | —CHCF(CH₃)₂ |
| 8-31 | CH₃ | —CH₂CF(CH₃)₂ | Cl | —CH₂CF(CH₃)₂ | —CH₂CF(CH₃)₂ |
| 8-32 | CH₃ | —CH₂CF(CH₃)₂ | —CH₂CF(CH₃)₂ | Cl | —CH₂CF(CH₃)₂ |
| 8-33 | CH₃ | —CH₂CF(CH₃)₂ | —CH₂CF(CH₃)₂ | —CH₂CF(CH₃)₂ | Cl |
| 8-34 | CH₃ | —CH₂CF(CH₃)₂ | —CH₂CF(CH₃)₂ | Cl | Cl |
| 8-35 | CH₃ | Cl | —CH₂CF(CH₃)₂ | Cl | —CH₂CF(CH₃)₂ |
| 8-36 | CH₃ | —CH₂CF(CH₃)₂ | Cl | Cl | —CH₂CF(CH₃)₂ |
| 8-37 | CH₃ | Cl | —CH₂CF(CH₃)₂ | CH₂CF(CH₃)₂ | Cl |
| 8-38 | CH₃ | Cl | Cl | —CH₂CF(CH₃)₂ | —CH₂CF(CH₃)₂ |
| 8-39 | CH₃ | —CH₂CF(CH₃)₂ | —CH₂CF(CH₃)₂ | Cl | Cl |
| 8-40 | CH₃ | —CH₂CF(CH₃)₂ | Cl | Cl | Cl |
| 8-41 | CH₃ | Cl | —CH₂CF(CH₃)₂ | Cl | Cl |
| 8-42 | CH₃ | Cl | Cl | —CH₂CF(CH₃)₂ | Cl |
| 8-43 | CH₃ | Cl | Cl | Cl | —CH₂CF(CH₃)₂ |
| 8-44 | CH₃ | Cl | n-Propyl | n-Propyl | n-Propyl |
| 8-45 | CH₃ | n-Propyl | Cl | n-Propyl | n-Propyl |
| 8-46 | CH₃ | n-Propyl | n-Propyl | Cl | n-Propyl |
| 8-47 | CH₃ | n-Propyl | n-Propyl | n-Propyl | Cl |
| 8-48 | CH₃ | n-Propyl | Cl | n-Propyl | Cl |
| 8-49 | CH₃ | Cl | n-Propyl | Cl | n-Propyl |
| 8-50 | CH₃ | n-Propyl | Cl | Cl | n-Propyl |
| 8-51 | CH₃ | Cl | Cl | n-Propyl | n-Propyl |
| 8-52 | CH₃ | n-Propyl | n-Propyl | Cl | Cl |
| 8-53 | CH₃ | Cl | n-Propyl | n-Propyl | Cl |
| 8-54 | CH₃ | n-Propyl | Cl | Cl | Cl |
| 8-55 | CH₃ | Cl | n-Propyl | Cl | Cl |
| 8-56 | CH₃ | Cl | Cl | n-Propyl | Cl |
| 8-57 | CH₃ | Cl | Cl | Cl | n-Propyl |
| 8-58 | H | —CH₂CF(CH₃)₂ | Cl | —CH₂CF(CH₃)₂ | Cl |
| 8-59 | H | Cl | —CH₂CF(CH₃)₂ | Cl | —CH₂CF(CH₃)₂ |
| 8-60 | H | —CH₂CF(CH₃)₂ | Cl | Cl | —CH₂CF(CH₃)₂ |
| 8-61 | H | Cl | —CH₂CF(CH₃)₂ | —CH₂CF(CH₃)₂ | Cl |
| 8-62 | H | Cl | Cl | —CH₂CF(CH₃)₂ | —CH₂CF(CH₃)₂ |
| 8-63 | H | —CH₂CF(CH₃)₂ | —CH₂CF(CH₃)₂ | Cl | Cl |
| 8-64 | H | —CH₂—C(CH₃)₃ | Cl | —CH₂—C(CH₃)₃ | Cl |
| 8-65 | H | Cl | —CH₂—C(CH₃)₃ | Cl | —CH₂—C(CH₃)₃ |
| 8-66 | H | —CH₂—C(CH₃)₃ | Cl | Cl | —CH₂—C(CH₃)₃ |
| 8-67 | H | Cl | —CH₂—C(CH₃)₃ | —CH₂—C(CH₃)₃ | Cl |
| 8-68 | H | Cl | Cl | —CH₂—C(CH₃)₃ | —CH₂—C(CH₃)₃ |
| 8-69 | H | —CH₂—C(CH₃)₃ | —CH₂—C(CH₃)₃ | Cl | Cl |

TABLE 9

Compounds of formula (I), wherein $Cy^1$ and $Cy^2$ are

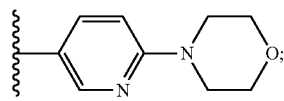

R', R'', R''' and R'''' are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 9-1 | CH₃ | Cl | Cl | Cl | Cl |
| 9-2 | CH₃ | Cl | —CH₂—iPr | —CH₂—iPr | —CH₂—iPr |
| 9-3 | CH₃ | —CH₂—iPr | Cl | —CH₂—iPr | —CH₂—iPr |
| 9-4 | CH₃ | —CH₂—iPr | —CH₂—iPr | Cl | —CH₂—iPr |

TABLE 9-continued

Compounds of formula (I), wherein Cy¹ and Cy² are

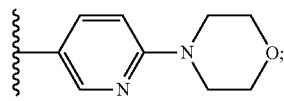 [SMILES: *c1ccc(N2CCOCC2)nc1]

R', R", R''' and R'''' are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 9-5 | CH₃ | —CH₂—iPr | —CH₂—iPr | —CH₂—iPr | Cl |
| 9-6 | CH₃ | —CH₂—iPr | Cl | —CH₂—iPr | Cl |
| 9-7 | CH | Cl | —CH₂—iPr | Cl | —CH₂—iPr |
| 9-8 | CH₃ | —CH₂—iPr | Cl | Cl | —CH₂—iPr |
| 9-9 | CH₃ | Cl | Cl | —CH₂—iPr | —CH₂—iPr |
| 9-10 | CH₃ | —CH₂—iPr | —CH₂—iPr | Cl | Cl |
| 9-11 | CH₃ | Cl | —CH₂—iPr | —CH₂—iPr | Cl |
| 9-12 | CH₃ | —CH₂—iPr | Cl | Cl | Cl |
| 9-13 | CH₃ | Cl | —CH₂—iPr | Cl | Cl |
| 9-14 | CH₃ | Cl | Cl | —CH₂—iPr | Cl |
| 9-15 | CH₃ | Cl | Cl | Cl | —CH₂—iPr |
| 9-16 | CH₃ | Cl | —CH₂—C(CH₃)₃ | —CH₂—C(CH₃)₃ | —CH₂—C(CH₃)₃ |
| 9-17 | CH₃ | —CH₂—C(CH₃)₃ | Cl | —CH₂—C(CH₃)₃ | —CH₂—C(CH₃)₃ |
| 9-18 | CH₃ | —CH₂—C(CH₃)₃ | —CH₂—C(CH₃)₃ | Cl | —CH₂—C(CH₃)₃ |
| 9-19 | CH₃ | —CH₂—C(CH₃)₃ | —CH₂—C(CH₃)₃ | —CH₂—C(CH₃)₃ | Cl |
| 9-20 | CH₃ | —CH₂—C(CH₃)₃ | Cl | —CH₂—C(CH₃)₃ | Cl |
| 9-21 | CH₃ | Cl | —CH₂—C(CH₃)₃ | Cl | —CH₂—C(CH₃)₃ |
| 9-22 | CH₃ | —CH₂—C(CH₃)₃ | Cl | Cl | —CH₂—C(CH₃)₃ |
| 9-23 | CH₃ | Cl | —CH₂—C(CH₃)₃ | —CH₂—C(CH₃)₃ | Cl |
| 9-24 | CH₃ | Cl | Cl | —CH₂—C(CH₃)₃ | —CH₂—C(CH₃)₃ |
| 9-25 | CH₃ | —CH₂—C(CH₃)₃ | —CH₂—C(CH₃)₃ | Cl | Cl |
| 9-26 | CH₃ | —CH₂—C(CH₃)₃ | Cl | Cl | Cl |
| 9-27 | CH₃ | Cl | —CH₂—C(CH₃)₃ | Cl | Cl |
| 9-28 | CH₃ | Cl | Cl | —CH₂—C(CH₃)₃ | Cl |
| 9-29 | CH₃ | Cl | Cl | Cl | —CH₂—C(CH₃)₃ |
| 9-30 | CH₃ | Cl | —CH₂CF(CH₃)₂ | —CH₂CF(CH₃)₂ | —CHCF(CH₃)₂ |
| 9-31 | CH₃ | —CH₂CF(CH₃)₂ | Cl | —CH₂CF(CH₃)₂ | —CH₂CF(CH₃)₂ |
| 9-32 | CH₃ | —CH₂CF(CH₃)₂ | —CH₂CF(CH₃)₂ | Cl | —CH₂CF(CH₃)₂ |
| 9-33 | CH₃ | —CH₂CF(CH₃)₂ | —CH₂CF(CH₃)₂ | —CH₂CF(CH₃)₂ | Cl |
| 9-34 | CH₃ | —CH₂CF(CH₃)₂ | Cl | —CH₂CF(CH₃)₂ | Cl |
| 9-35 | CH₃ | Cl | —CH₂CF(CH₃)₂ | Cl | —CH₂CF(CH₃)₂ |
| 9-36 | CH₃ | —CH₂CF(CH₃)₂ | Cl | Cl | —CH₂CF(CH₃)₂ |
| 9-37 | CH₃ | Cl | —CH₂CF(CH₃)₂ | CH₂CF(CH₃)₂ | Cl |
| 9-38 | CH₃ | Cl | Cl | —CH₂CF(CH₃)₂ | —CH₂CF(CH₃)₂ |
| 9-39 | CH₃ | —CH₂CF(CH₃)₂ | —CH₂CF(CH₃)₂ | Cl | Cl |
| 9-40 | CH₃ | —CH₂CF(CH₃)₂ | Cl | Cl | Cl |
| 9-41 | CH₃ | Cl | —CH₂CF(CH₃)₂ | Cl | Cl |
| 9-42 | CH₃ | Cl | Cl | —CH₂CF(CH₃)₂ | Cl |
| 9-43 | CH₃ | Cl | Cl | Cl | —CH₂CF(CH₃)₂ |
| 9-44 | CH₃ | Cl | n-Propyl | n-Propyl | n-Propyl |
| 9-45 | CH₃ | n-Propyl | Cl | n-Propyl | n-Propyl |
| 9-46 | CH₃ | n-Propyl | n-Propyl | Cl | n-Propyl |
| 9-47 | CH₃ | n-Propyl | n-Propyl | n-Propyl | Cl |
| 9-48 | CH₃ | n-Propyl | Cl | n-Propyl | Cl |
| 9-49 | CH₃ | Cl | n-Propyl | Cl | n-Propyl |
| 9-50 | CH₃ | n-Propyl | Cl | Cl | n-Propyl |
| 9-51 | CH₃ | Cl | Cl | n-Propyl | n-Propyl |
| 9-52 | CH₃ | n-Propyl | n-Propyl | Cl | Cl |
| 9-53 | CH₃ | Cl | n-Propyl | n-Propyl | Cl |
| 9-54 | CH₃ | n-Propyl | Cl | Cl | Cl |
| 9-55 | CH₃ | Cl | n-Propyl | Cl | Cl |
| 9-56 | CH₃ | Cl | Cl | n-Propyl | Cl |
| 9-57 | CH₃ | Cl | Cl | Cl | n-Propyl |
| 9-58 | H | —CH₂CF(CH₃)₂ | Cl | —CH₂CF(CH₃)₂ | Cl |
| 9-59 | H | Cl | —CH₂CF(CH₃)₂ | Cl | —CH₂CF(CH₃)₂ |
| 9-60 | H | —CH₂CF(CH₃)₂ | Cl | Cl | —CH₂CF(CH₃)₂ |
| 9-61 | H | Cl | —CH₂CF(CH₃)₂ | —CH₂CF(CH₃)₂ | Cl |
| 9-62 | H | Cl | Cl | —CH₂CF(CH₃)₂ | —CH₂CF(CH₃)₂ |
| 9-63 | H | —CH₂CF(CH₃)₂ | —CH₂CF(CH₃)₂ | Cl | Cl |
| 9-64 | H | —CH₂—C(CH₃)₃ | Cl | —CH₂—C(CH₃)₃ | Cl |
| 9-65 | H | Cl | —CH₂—C(CH₃)₃ | Cl | —CH₂—C(CH₃)₃ |
| 9-66 | H | —CH₂—C(CH₃)₃ | Cl | Cl | —CH₂—C(CH₃)₃ |
| 9-67 | H | Cl | —CH₂—C(CH₃)₃ | —CH₂—C(CH₃)₃ | Cl |
| 9-68 | H | Cl | Cl | —CH₂—C(CH₃)₃ | —CH₂—C(CH₃)₃ |
| 9-69 | H | —CH₂—C(CH₃)₃ | —CH₂—C(CH₃)₃ | Cl | Cl |

TABLE 10

Compounds of formula (I), wherein $Cy^1$ and $Cy^2$ are

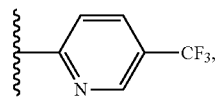

R', R'', R''' and R'''' are each independently hydrogen or methyl;
and $R^a$, $R^b$ and $R^1$ to $R^4$ are as shown.

| Cmpd # | $R^a/R^b$ | $R^1$ | $R^2$ | $R^3$ | $R^4$ |
| --- | --- | --- | --- | --- | --- |
| 10-1 | CH$_3$ | Cl | Cl | Cl | Cl |
| 10-2 | CH$_3$ | Cl | —CH$_2$—iPr | —CH$_2$—iPr | —CH$_2$—iPr |
| 10-3 | CH$_3$ | —CH$_2$—iPr | Cl | —CH$_2$—iPr | —CH$_2$—iPr |
| 10-4 | CH$_3$ | —CH$_2$—iPr | —CH$_2$—iPr | Cl | —CH$_2$—iPr |
| 10-5 | CH$_3$ | —CH$_2$—iPr | —CH$_2$—iPr | —CH$_2$—iPr | Cl |
| 10-6 | CH$_3$ | —CH$_2$—iPr | Cl | —CH$_2$—iPr | Cl |
| 10-7 | CH$_3$ | Cl | —CH$_2$—iPr | Cl | —CH$_2$—iPr |
| 10-8 | CH$_3$ | —CH$_2$—iPr | Cl | Cl | —CH$_2$—iPr |
| 10-9 | CH$_3$ | Cl | Cl | —CH$_2$—iPr | —CH$_2$—iPr |
| 10-10 | CH$_3$ | —CH$_2$—iPr | —CH$_2$—iPr | Cl | Cl |
| 10-11 | CH$_3$ | Cl | —CH$_2$—iPr | —CH$_2$—iPr | Cl |
| 10-12 | CH$_3$ | —CH$_2$—iPr | Cl | Cl | Cl |
| 10-13 | CH$_3$ | Cl | —CH$_2$—iPr | Cl | Cl |
| 10-14 | CH$_3$ | Cl | Cl | —CH$_2$—iPr | Cl |
| 10-15 | CH$_3$ | Cl | Cl | Cl | —CH$_2$—iPr |
| 10-16 | CH$_3$ | Cl | —CH$_2$—C(CH$_3$)$_3$ | —CH$_2$—C(CH$_3$)$_3$ | —CH$_2$—C(CH$_3$)$_3$ |
| 10-17 | CH$_3$ | —CH$_2$—C(CH$_3$)$_3$ | Cl | —CH$_2$—C(CH$_3$)$_3$ | —CH$_2$—C(CH$_3$)$_3$ |
| 10-18 | CH$_3$ | —CH$_2$—C(CH$_3$)$_3$ | —CH$_2$—C(CH$_3$)$_3$ | Cl | —CH$_2$—C(CH$_3$)$_3$ |
| 10-19 | CH$_3$ | —CH$_2$—C(CH$_3$)$_3$ | —CH$_2$—C(CH$_3$)$_3$ | —CH$_2$—C(CH$_3$)$_3$ | Cl |
| 10-20 | CH$_3$ | —CH$_2$—C(CH$_3$)$_3$ | Cl | —CH$_2$—C(CH$_3$)$_3$ | Cl |
| 10-21 | CH$_3$ | Cl | —CH$_2$—C(CH$_3$)$_3$ | Cl | —CH$_2$—C(CH$_3$)$_3$ |
| 10-22 | CH$_3$ | —CH$_2$—C(CH$_3$)$_3$ | Cl | Cl | —CH$_2$—C(CH$_3$)$_3$ |
| 10-23 | CH$_3$ | Cl | —CH$_2$—C(CH$_3$)$_3$ | —CH$_2$—C(CH$_3$)$_3$ | Cl |
| 10-24 | CH$_3$ | Cl | Cl | —CH$_2$—C(CH$_3$)$_3$ | —CH$_2$—C(CH$_3$)$_3$ |
| 10-25 | CH$_3$ | —CH$_2$—C(CH$_3$)$_3$ | —CH$_2$—C(CH$_3$)$_3$ | Cl | Cl |
| 10-26 | CH$_3$ | —CH$_2$—C(CH$_3$)$_3$ | Cl | Cl | Cl |
| 10-27 | CH$_3$ | Cl | —CH$_2$—C(CH$_3$)$_3$ | Cl | Cl |
| 10-28 | CH$_3$ | Cl | Cl | —CH$_2$—C(CH$_3$)$_3$ | Cl |
| 10-29 | CH$_3$ | Cl | Cl | Cl | —CH$_2$—C(CH$_3$)$_3$ |
| 10-30 | CH$_3$ | Cl | —CH$_2$CF(CH$_3$)$_2$ | —CH$_2$CF(CH$_3$)$_2$ | —CHCF(CH$_3$)$_2$ |
| 10-31 | CH$_3$ | —CH$_2$CF(CH$_3$)$_2$ | Cl | —CH$_2$CF(CH$_3$)$_2$ | —CH$_2$CF(CH$_3$)$_2$ |
| 10-32 | CH$_3$ | —CH$_2$CF(CH$_3$)$_2$ | —CH$_2$CF(CH$_3$)$_2$ | Cl | —CH$_2$CF(CH$_3$)$_2$ |
| 10-33 | CH$_3$ | —CH$_2$CF(CH$_3$)$_2$ | —CH$_2$CF(CH$_3$)$_2$ | —CH$_2$CF(CH$_3$)$_2$ | Cl |
| 10-34 | CH$_3$ | —CH$_2$CF(CH$_3$)$_2$ | Cl | —CH$_2$CF(CH$_3$)$_2$ | Cl |
| 10-35 | CH$_3$ | Cl | —CH$_2$CF(CH$_3$)$_2$ | Cl | —CH$_2$CF(CH$_3$)$_2$ |
| 10-36 | CH$_3$ | —CH$_2$CF(CH$_3$)$_2$ | Cl | Cl | —CH$_2$CF(CH$_3$)$_2$ |
| 10-37 | CH$_3$ | Cl | —CH$_2$CF(CH$_3$)$_2$ | CH$_2$CF(CH$_3$)$_2$ | Cl |
| 10-38 | CH$_3$ | Cl | Cl | —CH$_2$CF(CH$_3$)$_2$ | —CH$_2$CF(CH$_3$)$_2$ |
| 10-39 | CH$_3$ | —CH$_2$CF(CH$_3$)$_2$ | —CH$_2$CF(CH$_3$)$_2$ | Cl | Cl |
| 10-40 | CH$_3$ | —CH$_2$CF(CH$_3$)$_2$ | Cl | Cl | Cl |
| 10-41 | CH$_3$ | Cl | —CH$_2$CF(CH$_3$)$_2$ | Cl | Cl |
| 10-42 | CH$_3$ | Cl | Cl | —CH$_2$CF(CH$_3$)$_2$ | Cl |
| 10-43 | CH$_3$ | Cl | Cl | Cl | —CH$_2$CF(CH$_3$)$_2$ |
| 10-44 | CH$_3$ | Cl | n-Propyl | n-Propyl | n-Propyl |
| 10-45 | CH$_3$ | n-Propyl | Cl | n-Propyl | n-Propyl |
| 10-46 | CH$_3$ | n-Propyl | n-Propyl | Cl | n-Propyl |
| 10-47 | CH$_3$ | n-Propyl | n-Propyl | n-Propyl | Cl |
| 10-48 | CH$_3$ | n-Propyl | Cl | n-Propyl | Cl |
| 10-49 | CH$_3$ | Cl | n-Propyl | Cl | n-Propyl |
| 10-50 | CH$_3$ | n-Propyl | Cl | Cl | n-Propyl |
| 10-51 | CH$_3$ | Cl | Cl | n-Propyl | n-Propyl |
| 10-52 | CH$_3$ | n-Propyl | n-Propyl | Cl | Cl |
| 10-53 | CH$_3$ | Cl | n-Propyl | n-Propyl | Cl |
| 10-54 | CH$_3$ | n-Propyl | Cl | Cl | Cl |
| 10-55 | CH$_3$ | Cl | n-Propyl | Cl | Cl |
| 10-56 | CH$_3$ | Cl | Cl | n-Propyl | Cl |
| 10-57 | CH$_3$ | Cl | Cl | Cl | n-Propyl |
| 10-58 | H | —CH$_2$CF(CH$_3$)$_2$ | Cl | —CH$_2$CF(CH$_3$)$_2$ | —CH$_2$CF(CH$_3$)$_2$ |
| 10-59 | H | Cl | —CH$_2$CF(CH$_3$)$_2$ | Cl | —CH$_2$CF(CH$_3$)$_2$ |
| 10-60 | H | —CH$_2$CF(CH$_3$)$_2$ | Cl | Cl | —CH$_2$CF(CH$_3$)$_2$ |
| 10-61 | H | Cl | —CH$_2$CF(CH$_3$)$_2$ | —CH$_2$CF(CH$_3$)$_2$ | Cl |
| 10-62 | H | Cl | Cl | —CH$_2$CF(CH$_3$)$_2$ | —CH$_2$CF(CH$_3$)$_2$ |
| 10-63 | H | —CH$_2$CF(CH$_3$)$_2$ | —CH$_2$CF(CH$_3$)$_2$ | Cl | Cl |
| 10-64 | H | —CH$_2$—C(CH$_3$)$_3$ | Cl | —CH$_2$—C(CH$_3$)$_3$ | Cl |
| 10-65 | H | Cl | —CH$_2$—C(CH$_3$)$_3$ | Cl | —CH$_2$—C(CH$_3$)$_3$ |
| 10-66 | H | —CH$_2$—C(CH$_3$)$_3$ | Cl | Cl | —CH$_2$—C(CH$_3$)$_3$ |
| 10-67 | H | Cl | —CH$_2$—C(CH$_3$)$_3$ | —CH$_2$—C(CH$_3$)$_3$ | Cl |

TABLE 10-continued

Compounds of formula (I), wherein Cy¹ and Cy² are

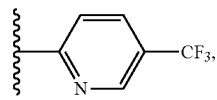

R', R'', R''' and R'''' are each independently hydrogen or methyl;
and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 10-68 | H | Cl | Cl | —CH₂—C(CH₃)₃ | —CH₂—C(CH₃)₃ |
| 10-69 | H | —CH₂—C(CH₃)₃ | —CH₂—C(CH₃)₃ | Cl | Cl |

TABLE 11

Compounds of formula (I), wherein Cy¹ and Cy² are

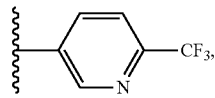

R', R'', R''' and R'''' are each independently hydrogen or methyl;
and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 11-1 | CH₃ | Cl | Cl | Cl | Cl |
| 11-2 | CH₃ | Cl | —CH₂—iPr | —CH₂—iPr | —CH₂—iPr |
| 11-3 | CH₃ | —CH₂—iPr | Cl | —CH₂—iPr | —CH₂—iPr |
| 11-4 | CH₃ | —CH₂—iPr | —CH₂—iPr | Cl | —CH₂—iPr |
| 11-5 | CH₃ | —CH₂—iPr | —CH₂—iPr | —CH₂—iPr | Cl |
| 11-6 | CH₃ | —CH₂—iPr | Cl | —CH₂—iPr | Cl |
| 11-7 | CH₃ | Cl | —CH₂—iPr | Cl | —CH₂—iPr |
| 11-8 | CH₃ | —CH₂—iPr | Cl | Cl | —CH₂—iPr |
| 11-9 | CH₃ | Cl | Cl | —CH₂—iPr | —CH₂—iPr |
| 11-10 | CH₃ | —CH₂—iPr | —CH₂—iPr | Cl | Cl |
| 11-11 | CH₃ | Cl | —CH₂—iPr | —CH₂—iPr | Cl |
| 11-12 | CH₃ | —CH₂—iPr | Cl | Cl | Cl |
| 11-13 | CH₃ | Cl | —CH₂—iPr | Cl | Cl |
| 11-14 | CH₃ | Cl | Cl | —CH₂—iPr | Cl |
| 11-15 | CH₃ | Cl | Cl | Cl | —CH₂—iPr |
| 11-16 | CH₃ | Cl | —CH₂—C(CH₃)₃ | —CH₂—C(CH₃)₃ | —CH₂—C(CH₃)₃ |
| 11-17 | CH₃ | —CH₂—C(CH₃)₃ | Cl | —CH₂—C(CH₃)₃ | —CH₂—C(CH₃)₃ |
| 11-18 | CH₃ | —CH₂—C(CH₃)₃ | —CH₂—C(CH₃)₃ | Cl | —CH₂—C(CH₃)₃ |
| 11-19 | CH₃ | —CH₂—C(CH₃)₃ | —CH₂—C(CH₃)₃ | —CH₂—C(CH₃)₃ | Cl |
| 11-20 | CH₃ | —CH₂—C(CH₃)₃ | Cl | —CH₂—C(CH₃)₃ | Cl |
| 11-21 | CH₃ | Cl | —CH₂—C(CH₃)₃ | Cl | —CH₂—C(CH₃)₃ |
| 11-22 | CH₃ | —CH₂—C(CH₃)₃ | Cl | Cl | —CH₂—C(CH₃)₃ |
| 11-23 | CH₃ | Cl | —CH₂—C(CH₃)₃ | —CH₂—C(CH₃)₃ | Cl |
| 11-24 | CH₃ | Cl | Cl | —CH₂—C(CH₃)₃ | —CH₂—C(CH₃)₃ |
| 11-25 | CH₃ | —CH₂—C(CH₃)₃ | —CH₂—C(CH₃)₃ | Cl | Cl |
| 11-26 | CH₃ | —CH₂—C(CH₃)₃ | Cl | Cl | Cl |
| 11-27 | CH₃ | Cl | —CH₂—C(CH₃)₃ | Cl | Cl |
| 11-28 | CH₃ | Cl | Cl | —CH₂—C(CH₃)₃ | Cl |
| 11-29 | CH₃ | Cl | Cl | Cl | —CH₂—C(CH₃)₃ |
| 11-30 | CH₃ | Cl | —CH₂CF(CH₃)₂ | —CH₂CF(CH₃)₂ | —CHCF(CH₃)₂ |
| 11-31 | CH₃ | —CH₂CF(CH₃)₂ | Cl | —CH₂CF(CH₃)₂ | —CH₂CF(CH₃)₂ |
| 11-32 | CH₃ | —CH₂CF(CH₃)₂ | —CH₂CF(CH₃)₂ | Cl | —CH₂CF(CH₃)₂ |
| 11-33 | CH₃ | —CH₂CF(CH₃)₂ | —CH₂CF(CH₃)₂ | —CH₂CF(CH₃)₂ | Cl |
| 11-34 | CH₃ | —CH₂CF(CH₃)₂ | Cl | —CH₂CF(CH₃)₂ | Cl |
| 11-35 | CH₃ | Cl | —CH₂CF(CH₃)₂ | Cl | —CH₂CF(CH₃)₂ |
| 11-36 | CH₃ | —CH₂CF(CH₃)₂ | Cl | Cl | —CH₂CF(CH₃)₂ |
| 11-37 | CH₃ | Cl | —CH₂CF(CH₃)₂ | CH₂CF(CH₃)₂ | Cl |
| 11-38 | CH₃ | Cl | Cl | —CH₂CF(CH₃)₂ | —CH₂CF(CH₃)₂ |
| 11-39 | CH₃ | —CH₂CF(CH₃)₂ | —CH₂CF(CH₃)₂ | Cl | Cl |
| 11-40 | CH₃ | —CH₂CF(CH₃)₂ | Cl | Cl | Cl |
| 11-41 | CH₃ | Cl | —CH₂CF(CH₃)₂ | Cl | Cl |
| 11-42 | CH₃ | Cl | Cl | —CH₂CF(CH₃)₂ | Cl |
| 11-43 | CH₃ | Cl | Cl | Cl | —CH₂CF(CH₃)₂ |
| 11-44 | CH₃ | Cl | n-Propyl | n-Propyl | n-Propyl |
| 11-45 | CH₃ | n-Propyl | Cl | n-Propyl | n-Propyl |
| 11-46 | CH₃ | n-Propyl | n-Propyl | Cl | n-Propyl |

TABLE 11-continued

Compounds of formula (I), wherein Cy¹ and Cy² are

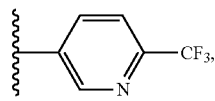

R', R", R''' and R'''' are each independently hydrogen or methyl;
and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 11-47 | CH₃ | n-Propyl | n-Propyl | n-Propyl | Cl |
| 11-48 | CH₃ | n-Propyl | Cl | n-Propyl | Cl |
| 11-49 | CH₃ | Cl | n-Propyl | Cl | n-Propyl |
| 11-50 | CH₃ | n-Propyl | Cl | Cl | n-Propyl |
| 11-51 | CH₃ | Cl | Cl | n-Propyl | n-Propyl |
| 11-52 | CH₃ | n-Propyl | n-Propyl | Cl | Cl |
| 11-53 | CH₃ | Cl | n-Propyl | n-Propyl | Cl |
| 11-54 | CH₃ | n-Propyl | Cl | Cl | Cl |
| 11-55 | CH₃ | Cl | n-Propyl | Cl | Cl |
| 11-56 | CH₃ | Cl | Cl | n-Propyl | Cl |
| 11-57 | CH₃ | Cl | Cl | Cl | n-Propyl |
| 11-58 | H | —CH₂CF(CH₃)₂ | Cl | —CH₂CF(CH₃)₂ | Cl |
| 11-59 | H | Cl | —CH₂CF(CH₃)₂ | Cl | —CH₂CF(CH₃)₂ |
| 11-60 | H | —CH₂CF(CH₃)₂ | Cl | Cl | —CH₂CF(CH₃)₂ |
| 11-61 | H | Cl | —CH₂CF(CH₃)₂ | —CH₂CF(CH₃)₂ | Cl |
| 11-62 | H | Cl | Cl | —CH₂CF(CH₃)₂ | —CH₂CF(CH₃)₂ |
| 11-63 | H | —CH₂CF(CH₃)₂ | —CH₂CF(CH₃)₂ | Cl | Cl |
| 11-64 | H | —CH₂—C(CH₃)₃ | Cl | —CH₂—C(CH₃)₃ | Cl |
| 11-65 | H | Cl | —CH₂—C(CH₃)₃ | Cl | —CH₂—C(CH₃)₃ |
| 11-66 | H | —CH₂—C(CH₃)₃ | Cl | Cl | —CH₂—C(CH₃)₃ |
| 11-67 | H | Cl | —CH₂—C(CH₃)₃ | —CH₂—C(CH₃)₃ | Cl |
| 11-68 | H | Cl | Cl | —CH₂—C(CH₃)₃ | —CH₂—C(CH₃)₃ |
| 11-69 | H | —CH₂—C(CH₃)₃ | —CH₂—C(CH₃)₃ | Cl | Cl |

TABLE 12

Compounds of formula (I), wherein Cy¹ and Cy² are

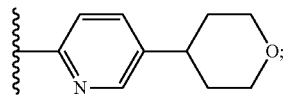

R', R", R''' and R'''' are each independently hydrogen or
methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 12-1 | CH₃ | Cl | Cl | Cl | Cl |
| 12-2 | CH₃ | Cl | —CH₂—iPr | —CH₂—iPr | —CH₂—iPr |
| 12-3 | CH₃ | —CH₂—iPr | Cl | —CH₂—iPr | —CH₂—iPr |
| 12-4 | CH₃ | —CH₂—iPr | —CH₂—iPr | Cl | —CH₂—iPr |
| 12-5 | CH₃ | —CH₂—iPr | —CH₂—iPr | —CH₂—iPr | Cl |
| 12-6 | CH₃ | —CH₂—iPr | Cl | —CH₂—iPr | Cl |
| 12-7 | CH₃ | Cl | —CH₂—iPr | Cl | —CH₂—iPr |
| 12-8 | CH₃ | —CH₂—iPr | Cl | Cl | —CH₂—iPr |
| 12-9 | CH₃ | Cl | Cl | —CH₂—iPr | —CH₂—iPr |
| 12-10 | CH₃ | —CH₂—iPr | —CH₂—iPr | Cl | Cl |
| 12-11 | CH₃ | Cl | —CH₂—iPr | —CH₂—iPr | Cl |
| 12-12 | CH₃ | —CH₂—iPr | Cl | Cl | Cl |
| 12-13 | CH₃ | Cl | —CH₂—iPr | Cl | Cl |
| 12-14 | CH₃ | Cl | Cl | —CH₂—iPr | Cl |
| 12-15 | CH₃ | Cl | Cl | Cl | —CH₂—iPr |
| 12-16 | CH₃ | Cl | —CH₂—C(CH₃)₃ | —CH₂—C(CH₃)₃ | —CH₂—C(CH₃)₃ |
| 12-17 | CH₃ | —CH₂—C(CH₃)₃ | Cl | —CH₂—C(CH₃)₃ | —CH₂—C(CH₃)₃ |
| 12-18 | CH₃ | —CH₂—C(CH₃)₃ | —CH₂—C(CH₃)₃ | Cl | —CH₂—C(CH₃)₃ |
| 12-19 | CH₃ | —CH₂—C(CH₃)₃ | —CH₂—C(CH₃)₃ | —CH₂—C(CH₃)₃ | Cl |
| 12-20 | CH₃ | —CH₂—C(CH₃)₃ | Cl | —CH₂—C(CH₃)₃ | Cl |
| 12-21 | CH₃ | Cl | —CH₂—C(CH₃)₃ | Cl | —CH₂—C(CH₃)₃ |
| 12-22 | CH₃ | —CH₂—C(CH₃)₃ | Cl | Cl | —CH₂—C(CH₃)₃ |
| 12-23 | CH₃ | Cl | —CH₂—C(CH₃)₃ | —CH₂—C(CH₃)₃ | Cl |
| 12-24 | CH₃ | Cl | Cl | —CH₂—C(CH₃)₃ | —CH₂—C(CH₃)₃ |
| 12-25 | CH₃ | —CH₂—C(CH₃)₃ | —CH₂—C(CH₃)₃ | Cl | Cl |
| 12-26 | CH₃ | —CH₂—C(CH₃)₃ | Cl | Cl | Cl |

TABLE 12-continued

Compounds of formula (I), wherein Cy¹ and Cy² are

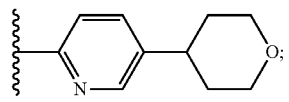

R', R'', R''' and R'''' are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 12-27 | CH₃ | Cl | —CH₂—C(CH₃)₃ | Cl | Cl |
| 12-28 | CH₃ | Cl | Cl | —CH₂—C(CH₃)₃ | Cl |
| 12-29 | CH₃ | Cl | Cl | Cl | —CH₂—C(CH₃)₃ |
| 12-30 | CH₃ | Cl | —CH₂CF(CH₃)₂ | —CH₂CF(CH₃)₂ | —CHCF(CH₃)₂ |
| 12-31 | CH₃ | —CH₂CF(CH₃)₂ | Cl | —CH₂CF(CH₃)₂ | —CH₂CF(CH₃)₂ |
| 12-32 | CH₃ | —CH₂CF(CH₃)₂ | —CH₂CF(CH₃)₂ | Cl | —CH₂CF(CH₃)₂ |
| 12-33 | CH₃ | —CH₂CF(CH₃)₂ | —CH₂CF(CH₃)₂ | —CH₂CF(CH₃)₂ | Cl |
| 12-34 | CH₃ | —CH₂CF(CH₃)₂ | Cl | —CH₂CF(CH₃)₂ | Cl |
| 12-35 | CH₃ | Cl | —CH₂CF(CH₃)₂ | Cl | —CH₂CF(CH₃)₂ |
| 12-36 | CH₃ | —CH₂CF(CH₃)₂ | Cl | Cl | —CH₂CF(CH₃)₂ |
| 12-37 | CH₃ | Cl | —CH₂CF(CH₃)₂ | CH₂CF(CH₃)₂ | Cl |
| 12-38 | CH₃ | Cl | Cl | —CH₂CF(CH₃)₂ | —CH₂CF(CH₃)₂ |
| 12-39 | CH₃ | —CH₂CF(CH₃)₂ | —CH₂CF(CH₃)₂ | Cl | Cl |
| 12-40 | CH₃ | —CH₂CF(CH₃)₂ | Cl | Cl | Cl |
| 12-41 | CH₃ | Cl | —CH₂CF(CH₃)₂ | Cl | Cl |
| 12-42 | CH₃ | Cl | Cl | —CH₂CF(CH₃)₂ | Cl |
| 12-43 | CH₃ | Cl | Cl | Cl | —CH₂CF(CH₃)₂ |
| 12-44 | CH₃ | Cl | n-Propyl | n-Propyl | n-Propyl |
| 12-45 | CH₃ | n-Propyl | Cl | n-Propyl | n-Propyl |
| 12-46 | CH₃ | n-Propyl | n-Propyl | Cl | n-Propyl |
| 12-47 | CH₃ | n-Propyl | n-Propyl | n-Propyl | Cl |
| 12-48 | CH₃ | n-Propyl | Cl | n-Propyl | Cl |
| 12-49 | CH₃ | Cl | n-Propyl | Cl | n-Propyl |
| 12-50 | CH₃ | n-Propyl | Cl | Cl | n-Propyl |
| 12-51 | CH₃ | Cl | Cl | n-Propyl | n-Propyl |
| 12-52 | CH₃ | n-Propyl | n-Propyl | Cl | Cl |
| 12-53 | CH₃ | Cl | n-Propyl | n-Propyl | Cl |
| 12-54 | CH₃ | n-Propyl | Cl | Cl | Cl |
| 12-55 | CH₃ | Cl | n-Propyl | Cl | Cl |
| 12-56 | CH₃ | Cl | Cl | n-Propyl | Cl |
| 12-57 | CH₃ | Cl | Cl | Cl | n-Propyl |
| 12-58 | H | —CH₂CF(CH₃)₂ | Cl | —CH₂CF(CH₃)₂ | Cl |
| 12-59 | H | Cl | —CH₂CF(CH₃)₂ | Cl | —CH₂CF(CH₃)₂ |
| 12-60 | H | —CH₂CF(CH₃)₂ | Cl | Cl | —CH₂CF(CH₃)₂ |
| 12-61 | H | Cl | —CH₂CF(CH₃)₂ | —CH₂CF(CH₃)₂ | Cl |
| 12-62 | H | Cl | Cl | —CH₂CF(CH₃)₂ | —CH₂CF(CH₃)₂ |
| 12-63 | H | —CH₂CF(CH₃)₂ | —CH₂CF(CH₃)₂ | Cl | Cl |
| 12-64 | H | —CH₂—C(CH₃)₃ | Cl | —CH₂—C(CH₃)₃ | Cl |
| 12-65 | H | Cl | —CH₂—C(CH₃)₃ | Cl | —CH₂—C(CH₃)₃ |
| 12-66 | H | —CH₂—C(CH₃)₃ | Cl | Cl | —CH₂—C(CH₃)₃ |
| 12-67 | H | Cl | —CH₂—C(CH₃)₃ | —CH₂—C(CH₃)₃ | Cl |
| 12-68 | H | Cl | Cl | —CH₂—C(CH₃)₃ | —CH₂—C(CH₃)₃ |
| 12-69 | H | —CH₂—C(CH₃)₃ | —CH₂—C(CH₃)₃ | Cl | Cl |

TABLE 13

Compounds of formula (I), wherein Cy¹ and Cy² are

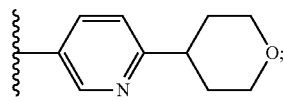

R', R'', R''' and R'''' are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 13-1 | CH₃ | Cl | Cl | Cl | Cl |
| 13-2 | CH₃ | Cl | —CH₂—iPr | —CH₂—iPr | —CH₂—iPr |
| 13-3 | CH₃ | —CH₂—iPr | Cl | —CH₂—iPr | —CH₂—iPr |
| 13-4 | CH₃ | —CH₂—iPr | —CH₂—iPr | Cl | —CH₂—iPr |
| 13-5 | CH₃ | —CH₂—iPr | —CH₂—iPr | —CH₂—iPr | Cl |
| 13-6 | CH₃ | —CH₂—iPr | Cl | —CH₂—iPr | Cl |

TABLE 13-continued

Compounds of formula (I), wherein Cy$^1$ and Cy$^2$ are

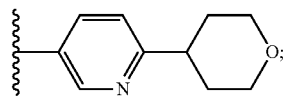

R', R", R''' and R'''' are each independently hydrogen or methyl; and R$^a$, R$^b$ and R$^1$ to R$^4$ are as shown.

| Cmpd # | R$^a$/R$^b$ | R$^1$ | R$^2$ | R$^3$ | R$^4$ |
|---|---|---|---|---|---|
| 13-7 | CH$_3$ | Cl | —CH$_2$—iPr | Cl | —CH$_2$—iPr |
| 13-8 | CH$_3$ | —CH$_2$—iPr | Cl | Cl | —CH$_2$—iPr |
| 13-9 | CH$_3$ | Cl | Cl | —CH$_2$—iPr | —CH$_2$—iPr |
| 13-10 | CH$_3$ | —CH$_2$—iPr | —CH$_2$—iPr | Cl | Cl |
| 13-11 | CH$_3$ | Cl | —CH$_2$—iPr | —CH$_2$—iPr | Cl |
| 13-12 | CH$_3$ | —CH$_2$—iPr | Cl | Cl | Cl |
| 13-13 | CH$_3$ | Cl | —CH$_2$—iPr | Cl | Cl |
| 13-14 | CH$_3$ | Cl | Cl | —CH$_2$—iPr | Cl |
| 13-15 | CH$_3$ | Cl | Cl | Cl | —CH$_2$—iPr |
| 13-16 | CH$_3$ | Cl | —CH$_2$—C(CH$_3$)$_3$ | —CH$_2$—C(CH$_3$)$_3$ | —CH$_2$—C(CH$_3$)$_3$ |
| 13-17 | CH$_3$ | —CH$_2$—C(CH$_3$)$_3$ | Cl | —CH$_2$—C(CH$_3$)$_3$ | —CH$_2$—C(CH$_3$)$_3$ |
| 13-18 | CH$_3$ | —CH$_2$—C(CH$_3$)$_3$ | —CH$_2$—C(CH$_3$)$_3$ | Cl | —CH$_2$—C(CH$_3$)$_3$ |
| 13-19 | CH$_3$ | —CH$_2$—C(CH$_3$)$_3$ | —CH$_2$—C(CH$_3$)$_3$ | —CH$_2$—C(CH$_3$)$_3$ | Cl |
| 13-20 | CH$_3$ | —CH$_2$—C(CH$_3$)$_3$ | Cl | —CH$_2$—C(CH$_3$)$_3$ | Cl |
| 13-21 | CH$_3$ | Cl | —CH$_2$—C(CH$_3$)$_3$ | Cl | —CH$_2$—C(CH$_3$)$_3$ |
| 13-22 | CH$_3$ | —CH$_2$—C(CH$_3$)$_3$ | Cl | Cl | —CH$_2$—C(CH$_3$)$_3$ |
| 13-23 | CH$_3$ | Cl | —CH$_2$—C(CH$_3$)$_3$ | —CH$_2$—C(CH$_3$)$_3$ | Cl |
| 13-24 | CH$_3$ | Cl | Cl | —CH$_2$—C(CH$_3$)$_3$ | —CH$_2$—C(CH$_3$)$_3$ |
| 13-25 | CH$_3$ | —CH$_2$—C(CH$_3$)$_3$ | —CH$_2$—C(CH$_3$)$_3$ | Cl | Cl |
| 13-26 | CH$_3$ | —CH$_2$—C(CH$_3$)$_3$ | Cl | Cl | Cl |
| 13-27 | CH$_3$ | Cl | —CH$_2$—C(CH$_3$)$_3$ | Cl | Cl |
| 13-28 | CH$_3$ | Cl | Cl | —CH$_2$—C(CH$_3$)$_3$ | Cl |
| 13-29 | CH$_3$ | Cl | Cl | Cl | —CH$_2$—C(CH$_3$)$_3$ |
| 13-30 | CH$_3$ | Cl | —CH$_2$CF(CH$_3$)$_2$ | —CH$_2$CF(CH$_3$)$_2$ | —CHCF(CH$_3$)$_2$ |
| 13-31 | CH$_3$ | —CH$_2$CF(CH$_3$)$_2$ | Cl | —CH$_2$CF(CH$_3$)$_2$ | —CH$_2$CF(CH$_3$)$_2$ |
| 13-32 | CH$_3$ | —CH$_2$CF(CH$_3$)$_2$ | —CH$_2$CF(CH$_3$)$_2$ | Cl | —CH$_2$CF(CH$_3$)$_2$ |
| 13-33 | CH$_3$ | —CH$_2$CF(CH$_3$)$_2$ | —CH$_2$CF(CH$_3$)$_2$ | —CH$_2$CF(CH$_3$)$_2$ | Cl |
| 13-34 | CH$_3$ | —CH$_2$CF(CH$_3$)$_2$ | Cl | —CH$_2$CF(CH$_3$)$_2$ | Cl |
| 13-35 | CH$_3$ | Cl | —CH$_2$CF(CH$_3$)$_2$ | Cl | —CH$_2$CF(CH$_3$)$_2$ |
| 13-36 | CH$_3$ | —CH$_2$CF(CH$_3$)$_2$ | Cl | Cl | —CH$_2$CF(CH$_3$)$_2$ |
| 13-37 | CH$_3$ | Cl | —CH$_2$CF(CH$_3$)$_2$ | CH$_2$CF(CH$_3$)$_2$ | Cl |
| 13-38 | CH$_3$ | Cl | Cl | —CH$_2$CF(CH$_3$)$_2$ | —CH$_2$CF(CH$_3$)$_2$ |
| 13-39 | CH$_3$ | —CH$_2$CF(CH$_3$)$_2$ | —CH$_2$CF(CH$_3$)$_2$ | Cl | Cl |
| 13-40 | CH$_3$ | —CH$_2$CF(CH$_3$)$_2$ | Cl | Cl | Cl |
| 13-41 | CH$_3$ | Cl | —CH$_2$CF(CH$_3$)$_2$ | Cl | Cl |
| 13-42 | CH$_3$ | Cl | Cl | —CH$_2$CF(CH$_3$)$_2$ | Cl |
| 13-43 | CH$_3$ | Cl | Cl | Cl | —CH$_2$CF(CH$_3$)$_2$ |
| 13-44 | CH$_3$ | Cl | n-Propyl | n-Propyl | n-Propyl |
| 13-45 | CH$_3$ | n-Propyl | Cl | n-Propyl | n-Propyl |
| 13-46 | CH$_3$ | n-Propyl | n-Propyl | Cl | n-Propyl |
| 13-47 | CH$_3$ | n-Propyl | n-Propyl | n-Propyl | Cl |
| 13-48 | CH$_3$ | n-Propyl | Cl | n-Propyl | Cl |
| 13-49 | CH$_3$ | Cl | n-Propyl | Cl | n-Propyl |
| 13-50 | CH$_3$ | n-Propyl | Cl | Cl | n-Propyl |
| 13-51 | CH$_3$ | Cl | Cl | n-Propyl | n-Propyl |
| 13-52 | CH$_3$ | n-Propyl | n-Propyl | Cl | Cl |
| 13-53 | CH$_3$ | Cl | n-Propyl | n-Propyl | Cl |
| 13-54 | CH$_3$ | n-Propyl | Cl | Cl | Cl |
| 13-55 | CH$_3$ | Cl | n-Propyl | Cl | Cl |
| 13-56 | CH$_3$ | Cl | Cl | n-Propyl | Cl |
| 13-57 | CH$_3$ | Cl | Cl | Cl | n-Propyl |
| 13-58 | H | —CH$_2$CF(CH$_3$)$_2$ | Cl | —CH$_2$CF(CH$_3$)$_2$ | Cl |
| 13-59 | H | Cl | —CH$_2$CF(CH$_3$)$_2$ | Cl | —CH$_2$CF(CH$_3$)$_2$ |
| 13-60 | H | —CH$_2$CF(CH$_3$)$_2$ | Cl | Cl | —CH$_2$CF(CH$_3$)$_2$ |
| 13-61 | H | Cl | —CH$_2$CF(CH$_3$)$_2$ | —CH$_2$CF(CH$_3$)$_2$ | Cl |
| 13-62 | H | Cl | Cl | —CH$_2$CF(CH$_3$)$_2$ | —CH$_2$CF(CH$_3$)$_2$ |
| 13-63 | H | —CH$_2$CF(CH$_3$)$_2$ | —CH$_2$CF(CH$_3$)$_2$ | Cl | Cl |
| 13-64 | H | —CH$_2$—C(CH$_3$)$_3$ | Cl | —CH$_2$—C(CH$_3$)$_3$ | Cl |
| 13-65 | H | Cl | —CH$_2$—C(CH$_3$)$_3$ | Cl | —CH$_2$—C(CH$_3$)$_3$ |
| 13-66 | H | —CH$_2$—C(CH$_3$)$_3$ | Cl | Cl | —CH$_2$—C(CH$_3$)$_3$ |
| 13-67 | H | Cl | —CH$_2$—C(CH$_3$)$_3$ | —CH$_2$—C(CH$_3$)$_3$ | Cl |
| 13-68 | H | Cl | Cl | —CH$_2$—C(CH$_3$)$_3$ | —CH$_2$—C(CH$_3$)$_3$ |
| 13-69 | H | —CH$_2$—C(CH$_3$)$_3$ | —CH$_2$—C(CH$_3$)$_3$ | Cl | Cl |

TABLE 14

Compounds of formula (I), wherein $Cy^1$ and $Cy^2$ are

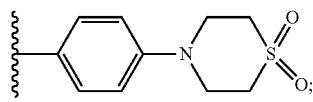

R', R", R''' and R'''' are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 14-1 | $CH_3$ | Cl | Cl | Cl | Cl |
| 14-2 | $CH_3$ | Cl | —$CH_2$—iPr | —$CH_2$—iPr | —$CH_2$—iPr |
| 14-3 | $CH_3$ | —$CH_2$—iPr | Cl | —$CH_2$—iPr | —$CH_2$—iPr |
| 14-4 | $CH_3$ | —$CH_2$—iPr | —$CH_2$—iPr | Cl | —$CH_2$—iPr |
| 14-5 | $CH_3$ | —$CH_2$—iPr | —$CH_2$—iPr | —$CH_2$—iPr | Cl |
| 14-6 | $CH_3$ | —$CH_2$—iPr | Cl | —$CH_2$—iPr | Cl |
| 14-7 | $CH_3$ | Cl | —$CH_2$—iPr | Cl | —$CH_2$—iPr |
| 14-8 | $CH_3$ | —$CH_2$—iPr | Cl | Cl | —$CH_2$—iPr |
| 14-9 | $CH_3$ | Cl | Cl | —$CH_2$—iPr | —$CH_2$—iPr |
| 14-10 | $CH_3$ | —$CH_2$—iPr | —$CH_2$—iPr | Cl | Cl |
| 14-11 | $CH_3$ | Cl | —$CH_2$—iPr | —$CH_2$—iPr | Cl |
| 14-12 | $CH_3$ | —$CH_2$—iPr | Cl | Cl | Cl |
| 14-13 | $CH_3$ | Cl | —$CH_2$—iPr | Cl | Cl |
| 14-14 | $CH_3$ | Cl | Cl | —$CH_2$—iPr | Cl |
| 14-15 | $CH_3$ | Cl | Cl | Cl | —$CH_2$—iPr |
| 14-16 | $CH_3$ | Cl | —$CH_2$—$C(CH_3)_3$ | —$CH_2$—$C(CH_3)_3$ | —$CH_2$—$C(CH_3)_3$ |
| 14-17 | $CH_3$ | —$CH_2$—$C(CH_3)_3$ | Cl | —$CH_2$—$C(CH_3)_3$ | —$CH_2$—$C(CH_3)_3$ |
| 14-18 | $CH_3$ | —$CH_2$—$C(CH_3)_3$ | —$CH_2$—$C(CH_3)_3$ | Cl | —$CH_2$—$C(CH_3)_3$ |
| 14-19 | $CH_3$ | —$CH_2$—$C(CH_3)_3$ | —$CH_2$—$C(CH_3)_3$ | —$CH_2$—$C(CH_3)_3$ | Cl |
| 14-20 | $CH_3$ | —$CH_2$—$C(CH_3)_3$ | Cl | —$CH_2$—$C(CH_3)_3$ | Cl |
| 14-21 | $CH_3$ | Cl | —$CH_2$—$C(CH_3)_3$ | Cl | —$CH_2$—$C(CH_3)_3$ |
| 14-22 | $CH_3$ | —$CH_2$—$C(CH_3)_3$ | Cl | Cl | —$CH_2$—$C(CH_3)_3$ |
| 14-23 | $CH_3$ | Cl | —$CH_2$—$C(CH_3)_3$ | —$CH_2$—$C(CH_3)_3$ | Cl |
| 14-24 | $CH_3$ | Cl | Cl | —$CH_2$—$C(CH_3)_3$ | —$CH_2$—$C(CH_3)_3$ |
| 14-25 | $CH_3$ | —$CH_2$—$C(CH_3)_3$ | —$CH_2$—$C(CH_3)_3$ | Cl | Cl |
| 14-26 | $CH_3$ | —$CH_2$—$C(CH_3)_3$ | Cl | Cl | Cl |
| 14-27 | $CH_3$ | Cl | —$CH_2$—$C(CH_3)_3$ | Cl | Cl |
| 14-28 | $CH_3$ | Cl | Cl | —$CH_2$—$C(CH_3)_3$ | Cl |
| 14-29 | $CH_3$ | Cl | Cl | Cl | —$CH_2$—$C(CH_3)_3$ |
| 14-30 | $CH_3$ | Cl | —$CH_2CF(CH_3)_2$ | —$CH_2CF(CH_3)_2$ | —$CHCF(CH_3)_2$ |
| 14-31 | $CH_3$ | —$CH_2CF(CH_3)_2$ | Cl | —$CH_2CF(CH_3)_2$ | —$CH_2CF(CH_3)_2$ |
| 14-32 | $CH_3$ | —$CH_2CF(CH_3)_2$ | —$CH_2CF(CH_3)_2$ | Cl | —$CH_2CF(CH_3)_2$ |
| 14-33 | $CH_3$ | —$CH_2CF(CH_3)_2$ | —$CH_2CF(CH_3)_2$ | —$CH_2CF(CH_3)_2$ | Cl |
| 14-34 | $CH_3$ | —$CH_2CF(CH_3)_2$ | Cl | —$CH_2CF(CH_3)_2$ | Cl |
| 14-35 | $CH_3$ | Cl | —$CH_2CF(CH_3)_2$ | Cl | —$CH_2CF(CH_3)_2$ |
| 14-36 | $CH_3$ | —$CH_2CF(CH_3)_2$ | Cl | Cl | —$CH_2CF(CH_3)_2$ |
| 14-37 | $CH_3$ | Cl | —$CH_2CF(CH_3)_2$ | $CH_2CF(CH_3)_2$ | Cl |
| 14-38 | $CH_3$ | Cl | Cl | —$CH_2CF(CH_3)_2$ | —$CH_2CF(CH_3)_2$ |
| 14-39 | $CH_3$ | —$CH_2CF(CH_3)_2$ | —$CH_2CF(CH_3)_2$ | Cl | Cl |
| 14-40 | $CH_3$ | —$CH_2CF(CH_3)_2$ | Cl | Cl | Cl |
| 14-41 | $CH_3$ | Cl | —$CH_2CF(CH_3)_2$ | Cl | Cl |
| 14-42 | $CH_3$ | Cl | Cl | —$CH_2CF(CH_3)_2$ | Cl |
| 14-43 | $CH_3$ | Cl | Cl | Cl | —$CH_2CF(CH_3)_2$ |
| 14-44 | $CH_3$ | Cl | n-Propyl | n-Propyl | n-Propyl |
| 14-45 | $CH_3$ | n-Propyl | Cl | n-Propyl | n-Propyl |
| 14-46 | $CH_3$ | n-Propyl | n-Propyl | Cl | n-Propyl |
| 14-47 | $CH_3$ | n-Propyl | n-Propyl | n-Propyl | Cl |
| 14-48 | $CH_3$ | n-Propyl | Cl | n-Propyl | Cl |
| 14-49 | $CH_3$ | Cl | n-Propyl | Cl | n-Propyl |
| 14-50 | $CH_3$ | n-Propyl | Cl | Cl | n-Propyl |
| 14-51 | $CH_3$ | Cl | Cl | n-Propyl | n-Propyl |
| 14-52 | $CH_3$ | n-Propyl | n-Propyl | Cl | Cl |
| 14-53 | $CH_3$ | Cl | n-Propyl | n-Propyl | Cl |
| 14-54 | $CH_3$ | n-Propyl | Cl | Cl | Cl |
| 14-55 | $CH_3$ | Cl | n-Propyl | Cl | Cl |
| 14-56 | $CH_3$ | Cl | Cl | n-Propyl | Cl |
| 14-57 | $CH_3$ | Cl | Cl | Cl | n-Propyl |
| 14-58 | H | —$CH_2CF(CH_3)_2$ | Cl | —$CH_2CF(CH_3)_2$ | Cl |
| 14-59 | H | Cl | —$CH_2CF(CH_3)_2$ | Cl | —$CH_2CF(CH_3)_2$ |
| 14-60 | H | —$CH_2CF(CH_3)_2$ | Cl | Cl | —$CH_2CF(CH_3)_2$ |
| 14-61 | H | Cl | —$CH_2CF(CH_3)_2$ | —$CH_2CF(CH_3)_2$ | Cl |
| 14-62 | H | Cl | —$CH_2CF(CH_3)_2$ | —$CH_2CF(CH_3)_2$ | —$CH_2CF(CH_3)_2$ |
| 14-63 | H | —$CH_2CF(CH_3)_2$ | —$CH_2CF(CH_3)_2$ | Cl | Cl |
| 14-64 | H | —$CH_2$—$C(CH_3)_3$ | Cl | —$CH_2$—$C(CH_3)_3$ | Cl |
| 14-65 | H | Cl | —$CH_2$—$C(CH_3)_3$ | Cl | —$CH_2$—$C(CH_3)_3$ |
| 14-66 | H | —$CH_2$—$C(CH_3)_3$ | Cl | Cl | —$CH_2$—$C(CH_3)_3$ |
| 14-67 | H | Cl | —$CH_2$—$C(CH_3)_3$ | —$CH_2$—$C(CH_3)_3$ | Cl |

TABLE 14-continued

Compounds of formula (I), wherein Cy¹ and Cy² are

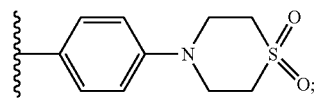 [SMILES: *c1ccc(N2CCS(=O)(=O)CC2)cc1]

R', R", R'" and R"" are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
| --- | --- | --- | --- | --- | --- |
| 14-68 | H | Cl | Cl | —CH₂—C(CH₃)₃ | —CH₂—C(CH₃)₃ |
| 14-69 | H | —CH₂—C(CH₃)₃ | —CH₂—C(CH₃)₃ | Cl | Cl |

TABLE 15

Compounds of formula (I), wherein Cy¹ and Cy² are

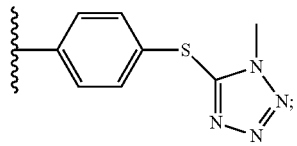 [SMILES: *c1ccc(Sc2nnnn2C)cc1]

R', R", R'" and R"" are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
| --- | --- | --- | --- | --- | --- |
| 15-1 | CH₃ | Cl | Cl | Cl | Cl |
| 15-2 | CH₃ | Cl | —CH₂—iPr | —CH₂—iPr | —CH₂—iPr |
| 15-3 | CH₃ | —CH₂—iPr | Cl | —CH₂—iPr | —CH₂—iPr |
| 15-4 | CH₃ | —CH₂—iPr | —CH₂—iPr | Cl | —CH₂—iPr |
| 15-5 | CH₃ | —CH₂—iPr | —CH₂—iPr | —CH₂—iPr | Cl |
| 15-6 | CH₃ | —CH₂—iPr | Cl | —CH₂—iPr | Cl |
| 15-7 | CH₃ | Cl | —CH₂—iPr | Cl | —CH₂—iPr |
| 15-8 | CH₃ | —CH₂—iPr | Cl | Cl | —CH₂—iPr |
| 15-9 | CH₃ | Cl | Cl | —CH₂—iPr | —CH₂—iPr |
| 15-10 | CH₃ | —CH₂—iPr | —CH₂—iPr | Cl | Cl |
| 15-11 | CH₃ | Cl | —CH₂—iPr | —CH₂—iPr | Cl |
| 15-12 | CH₃ | —CH₂—iPr | Cl | Cl | Cl |
| 15-13 | CH₃ | Cl | —CH₂—iPr | Cl | Cl |
| 15-14 | CH₃ | Cl | Cl | —CH₂—iPr | Cl |
| 15-15 | CH₃ | Cl | Cl | Cl | —CH₂—iPr |
| 15-16 | CH₃ | Cl | —CH₂—C(CH₃)₃ | —CH₂—C(CH₃)₃ | —CH₂—C(CH₃)₃ |
| 15-17 | CH₃ | —CH₂—C(CH₃)₃ | Cl | —CH₂—C(CH₃)₃ | —CH₂—C(CH₃)₃ |
| 15-18 | CH₃ | —CH₂—C(CH₃)₃ | —CH₂—C(CH₃)₃ | Cl | —CH₂—C(CH₃)₃ |
| 15-19 | CH₃ | —CH₂—C(CH₃)₃ | —CH₂—C(CH₃)₃ | —CH₂—C(CH₃)₃ | Cl |
| 15-20 | CH₃ | —CH₂—C(CH₃)₃ | Cl | —CH₂—C(CH₃)₃ | Cl |
| 15-21 | CH₃ | Cl | —CH₂—C(CH₃)₃ | Cl | —CH₂—C(CH₃)₃ |
| 15-22 | CH₃ | —CH₂—C(CH₃)₃ | Cl | Cl | —CH₂—C(CH₃)₃ |
| 15-23 | CH₃ | Cl | —CH₂—C(CH₃)₃ | —CH₂—C(CH₃)₃ | Cl |
| 15-24 | CH₃ | Cl | Cl | —CH₂—C(CH₃)₃ | —CH₂—C(CH₃)₃ |
| 15-25 | CH₃ | —CH₂—C(CH₃)₃ | —CH₂—C(CH₃)₃ | Cl | Cl |
| 15-26 | CH₃ | —CH₂—C(CH₃)₃ | Cl | Cl | Cl |
| 15-27 | CH₃ | Cl | —CH₂—C(CH₃)₃ | Cl | Cl |
| 15-28 | CH₃ | Cl | Cl | —CH₂—C(CH₃)₃ | Cl |
| 15-29 | CH₃ | Cl | Cl | Cl | —CH₂—C(CH₃)₃ |
| 15-30 | CH₃ | Cl | —CH₂CF(CH₃)₂ | —CH₂CF(CH₃)₂ | —CHCF(CH₃)₂ |
| 15-31 | CH₃ | —CH₂CF(CH₃)₂ | Cl | —CH₂CF(CH₃)₂ | —CH₂CF(CH₃)₂ |
| 15-32 | CH₃ | —CH₂CF(CH₃)₂ | —CH₂CF(CH₃)₂ | Cl | —CH₂CF(CH₃)₂ |
| 15-33 | CH₃ | —CH₂CF(CH₃)₂ | —CH₂CF(CH₃)₂ | —CH₂CF(CH₃)₂ | Cl |
| 15-34 | CH₃ | —CH₂CF(CH₃)₂ | Cl | —CH₂CF(CH₃)₂ | Cl |
| 15-35 | CH₃ | Cl | —CH₂CF(CH₃)₂ | Cl | —CH₂CF(CH₃)₂ |
| 15-36 | CH₃ | —CH₂CF(CH₃)₂ | Cl | Cl | —CH₂CF(CH₃)₂ |
| 15-37 | CH₃ | Cl | —CH₂CF(CH₃)₂ | CH₂CF(CH₃)₂ | Cl |
| 15-38 | CH₃ | Cl | Cl | —CH₂CF(CH₃)₂ | —CH₂CF(CH₃)₂ |
| 15-39 | CH₃ | —CH₂CF(CH₃)₂ | —CH₂CF(CH₃)₂ | Cl | Cl |
| 15-40 | CH₃ | —CH₂CF(CH₃)₂ | Cl | Cl | Cl |
| 15-41 | CH₃ | Cl | —CH₂CF(CH₃)₂ | Cl | Cl |
| 15-42 | CH₃ | Cl | Cl | —CH₂CF(CH₃)₂ | Cl |
| 15-43 | CH₃ | Cl | Cl | Cl | —CH₂CF(CH₃)₂ |
| 15-44 | CH₃ | Cl | n-Propyl | n-Propyl | n-Propyl |
| 15-45 | CH₃ | n-Propyl | Cl | n-Propyl | n-Propyl |

TABLE 15-continued

Compounds of formula (I), wherein Cy¹ and Cy² are

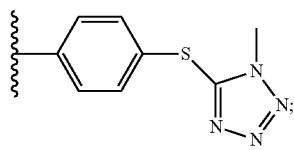

R', R", R'" and R"" are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 15-46 | CH₃ | n-Propyl | n-Propyl | Cl | n-Propyl |
| 15-47 | CH₃ | n-Propyl | n-Propyl | n-Propyl | Cl |
| 15-48 | CH₃ | n-Propyl | Cl | n-Propyl | Cl |
| 15-49 | CH₃ | Cl | n-Propyl | Cl | n-Propyl |
| 15-50 | CH₃ | n-Propyl | Cl | Cl | n-Propyl |
| 15-51 | CH₃ | Cl | Cl | n-Propyl | n-Propyl |
| 15-52 | CH₃ | n-Propyl | n-Propyl | Cl | Cl |
| 15-53 | CH₃ | Cl | n-Propyl | n-Propyl | Cl |
| 15-54 | CH₃ | n-Propyl | Cl | Cl | Cl |
| 15-55 | CH₃ | Cl | n-Propyl | Cl | Cl |
| 15-56 | CH₃ | Cl | Cl | n-Propyl | Cl |
| 15-57 | CH₃ | Cl | Cl | Cl | n-Propyl |
| 15-58 | H | —CH₂CF(CH₃)₂ | Cl | —CH₂CF(CH₃)₂ | Cl |
| 15-59 | H | Cl | —CH₂CF(CH₃)₂ | Cl | —CH₂CF(CH₃)₂ |
| 15-60 | H | —CH₂CF(CH₃)₂ | Cl | Cl | —CH₂CF(CH₃)₂ |
| 15-61 | H | Cl | —CH₂CF(CH₃)₂ | —CH₂CF(CH₃)₂ | Cl |
| 15-62 | H | Cl | Cl | —CH₂CF(CH₃)₂ | —CH₂CF(CH₃)₂ |
| 15-63 | H | —CH₂CF(CH₃)₂ | —CH₂CF(CH₃)₂ | Cl | Cl |
| 15-64 | H | —CH₂—C(CH₃)₃ | Cl | —CH₂—C(CH₃)₃ | Cl |
| 15-65 | H | Cl | —CH₂—C(CH₃)₃ | Cl | —CH₂—C(CH₃)₃ |
| 15-66 | H | —CH₂—C(CH₃)₃ | Cl | Cl | —CH₂—C(CH₃)₃ |
| 15-67 | H | Cl | —CH₂—C(CH₃)₃ | —CH₂—C(CH₃)₃ | Cl |
| 15-68 | H | Cl | Cl | —CH₂—C(CH₃)₃ | —CH₂—C(CH₃)₃ |
| 15-69 | H | —CH₂—C(CH₃)₃ | —CH₂—C(CH₃)₃ | Cl | Cl |

TABLE 16

Compounds of formula (I), wherein Cy¹ and Cy² are

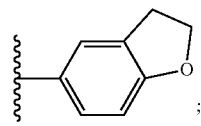

R', R", R'" and R"" are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 16-1 | CH₃ | Cl | Cl | Cl | Cl |
| 16-2 | CH₃ | Cl | —CH₂—iPr | —CH₂—iPr | —CH₂—iPr |
| 16-3 | CH₃ | —CH₂—iPr | Cl | —CH₂—iPr | —CH₂—iPr |
| 16-4 | CH₃ | —CH₂—iPr | —CH₂—iPr | Cl | —CH₂—iPr |
| 16-5 | CH₃ | —CH₂—iPr | —CH₂—iPr | —CH₂—iPr | Cl |
| 16-6 | CH₃ | —CH₂—iPr | Cl | —CH₂—iPr | Cl |
| 16-7 | CH₃ | Cl | —CH₂—iPr | Cl | —CH₂—iPr |
| 16-8 | CH₃ | —CH₂—iPr | Cl | Cl | —CH₂—iPr |
| 16-9 | CH₃ | Cl | Cl | —CH₂—iPr | —CH₂—iPr |
| 16-10 | CH₃ | —CH₂—iPr | —CH₂—iPr | Cl | Cl |
| 16-11 | CH₃ | Cl | —CH₂—iPr | —CH₂—iPr | Cl |
| 16-12 | CH₃ | —CH₂—iPr | Cl | Cl | Cl |
| 16-13 | CH₃ | Cl | —CH₂—iPr | Cl | Cl |
| 16-14 | CH₃ | Cl | Cl | —CH₂—iPr | Cl |
| 16-15 | CH₃ | Cl | Cl | Cl | —CH₂—iPr |
| 16-16 | CH₃ | Cl | —CH₂—C(CH₃)₃ | —CH₂—C(CH₃)₃ | —CH₂—C(CH₃)₃ |
| 16-17 | CH₃ | —CH₂—C(CH₃)₃ | Cl | —CH₂—C(CH₃)₃ | —CH₂—C(CH₃)₃ |
| 16-18 | CH₃ | —CH₂—C(CH₃)₃ | —CH₂—C(CH₃)₃ | Cl | —CH₂—C(CH₃)₃ |
| 16-19 | CH₃ | —CH₂—C(CH₃)₃ | —CH₂—C(CH₃)₃ | —CH₂—C(CH₃)₃ | Cl |

TABLE 16-continued

Compounds of formula (I), wherein $Cy^1$ and $Cy^2$ are

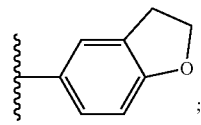 [SMILES: *c1ccc2c(c1)CCO2]
;

R', R'', R''' and R'''' are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 16-20 | CH₃ | —CH₂—C(CH₃)₃ | Cl | —CH₂—C(CH₃)₃ | Cl |
| 16-21 | CH₃ | Cl | —CH₂—C(CH₃)₃ | Cl | —CH₂—C(CH₃)₃ |
| 16-22 | CH₃ | —CH₂—C(CH₃)₃ | Cl | Cl | —CH₂—C(CH₃)₃ |
| 16-23 | CH₃ | Cl | —CH₂—C(CH₃)₃ | —CH₂—C(CH₃)₃ | Cl |
| 16-24 | CH₃ | Cl | Cl | —CH₂—C(CH₃)₃ | —CH₂—C(CH₃)₃ |
| 16-25 | CH₃ | —CH₂—C(CH₃)₃ | —CH₂—C(CH₃)₃ | Cl | Cl |
| 16-26 | CH₃ | —CH₂—C(CH₃)₃ | Cl | Cl | Cl |
| 16-27 | CH₃ | Cl | —CH₂—C(CH₃)₃ | Cl | Cl |
| 16-28 | CH₃ | Cl | Cl | —CH₂—C(CH₃)₃ | Cl |
| 16-29 | CH₃ | Cl | Cl | Cl | —CH₂—C(CH₃)₃ |
| 16-30 | CH₃ | Cl | —CH₂CF(CH₃)₂ | —CH₂CF(CH₃)₂ | —CHCF(CH₃)₂ |
| 16-31 | CH₃ | —CH₂CF(CH₃)₂ | Cl | —CH₂CF(CH₃)₂ | —CH₂CF(CH₃)₂ |
| 16-32 | CH₃ | —CH₂CF(CH₃)₂ | —CH₂CF(CH₃)₂ | Cl | —CH₂CF(CH₃)₂ |
| 16-33 | CH₃ | —CH₂CF(CH₃)₂ | —CH₂CF(CH₃)₂ | —CH₂CF(CH₃)₂ | Cl |
| 16-34 | CH₃ | —CH₂CF(CH₃)₂ | Cl | —CH₂CF(CH₃)₂ | Cl |
| 16-35 | CH₃ | Cl | —CH₂CF(CH₃)₂ | Cl | —CH₂CF(CH₃)₂ |
| 16-36 | CH₃ | —CH₂CF(CH₃)₂ | Cl | Cl | —CH₂CF(CH₃)₂ |
| 16-37 | CH₃ | Cl | —CH₂CF(CH₃)₂ | CH₂CF(CH₃)₂ | Cl |
| 16-38 | CH₃ | Cl | Cl | —CH₂CF(CH₃)₂ | —CH₂CF(CH₃)₂ |
| 16-39 | CH₃ | —CH₂CF(CH₃)₂ | —CH₂CF(CH₃)₂ | Cl | Cl |
| 16-40 | CH₃ | —CH₂CF(CH₃)₂ | Cl | Cl | Cl |
| 16-41 | CH₃ | Cl | —CH₂CF(CH₃)₂ | Cl | Cl |
| 16-42 | CH₃ | Cl | Cl | —CH₂CF(CH₃)₂ | Cl |
| 16-43 | CH₃ | Cl | Cl | Cl | —CH₂CF(CH₃)₂ |
| 16-44 | CH₃ | Cl | n-Propyl | n-Propyl | n-Propyl |
| 16-45 | CH₃ | n-Propyl | Cl | n-Propyl | n-Propyl |
| 16-46 | CH₃ | n-Propyl | n-Propyl | Cl | n-Propyl |
| 16-47 | CH₃ | n-Propyl | n-Propyl | n-Propyl | Cl |
| 16-48 | CH₃ | n-Propyl | Cl | n-Propyl | Cl |
| 16-49 | CH₃ | Cl | n-Propyl | Cl | n-Propyl |
| 16-50 | CH₃ | n-Propyl | Cl | Cl | n-Propyl |
| 16-51 | CH₃ | Cl | Cl | n-Propyl | n-Propyl |
| 16-52 | CH₃ | n-Propyl | n-Propyl | Cl | Cl |
| 16-53 | CH₃ | Cl | n-Propyl | n-Propyl | Cl |
| 16-54 | CH₃ | n-Propyl | Cl | Cl | Cl |
| 16-55 | CH₃ | Cl | n-Propyl | Cl | Cl |
| 16-56 | CH₃ | Cl | Cl | n-Propyl | Cl |
| 16-57 | CH₃ | Cl | Cl | Cl | n-Propyl |
| 16-58 | H | —CH₂CF(CH₃)₂ | Cl | —CH₂CF(CH₃)₂ | Cl |
| 16-59 | H | Cl | —CH₂CF(CH₃)₂ | Cl | —CH₂CF(CH₃)₂ |
| 16-60 | H | —CH₂CF(CH₃)₂ | Cl | Cl | —CH₂CF(CH₃)₂ |
| 16-61 | H | Cl | —CH₂CF(CH₃)₂ | —CH₂CF(CH₃)₂ | Cl |
| 16-62 | H | Cl | Cl | —CH₂CF(CH₃)₂ | —CH₂CF(CH₃)₂ |
| 16-63 | H | —CH₂CF(CH₃)₂ | —CH₂CF(CH₃)₂ | Cl | Cl |
| 16-64 | H | —CH₂—C(CH₃)₃ | Cl | —CH₂—C(CH₃)₃ | Cl |
| 16-65 | H | Cl | —CH₂—C(CH₃)₃ | Cl | —CH₂—C(CH₃)₃ |
| 16-66 | H | —CH₂—C(CH₃)₃ | Cl | Cl | —CH₂—C(CH₃)₃ |
| 16-67 | H | Cl | —CH₂—C(CH₃)₃ | —CH₂—C(CH₃)₃ | Cl |
| 16-68 | H | Cl | Cl | —CH₂—C(CH₃)₃ | —CH₂—C(CH₃)₃ |
| 16-69 | H | —CH₂—C(CH₃)₃ | —CH₂—C(CH₃)₃ | Cl | Cl |

TABLE 17

Compounds of formula (I), wherein Cy¹ and Cy² are

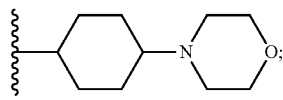

R', R'', R''' and R'''' are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 17-1 | CH₃ | Cl | Cl | Cl | Cl |
| 17-2 | CH₃ | Cl | —CH₂—iPr | —CH₂—iPr | —CH₂—iPr |
| 17-3 | CH₃ | —CH₂—iPr | Cl | —CH₂—iPr | —CH₂—iPr |
| 17-4 | CH₃ | —CH₂—iPr | —CH₂—iPr | Cl | —CH₂—iPr |
| 17-5 | CH₃ | —CH₂—iPr | —CH₂—iPr | —CH₂—iPr | Cl |
| 17-6 | CH₃ | —CH₂—iPr | Cl | —CH₂—iPr | Cl |
| 17-7 | CH₃ | Cl | —CH₂—iPr | Cl | —CH₂—iPr |
| 17-8 | CH₃ | —CH₂—iPr | Cl | Cl | —CH₂—iPr |
| 17-9 | CH₃ | Cl | Cl | —CH₂—iPr | —CH₂—iPr |
| 17-10 | CH₃ | —CH₂—iPr | —CH₂—iPr | Cl | Cl |
| 17-11 | CH₃ | Cl | —CH₂—iPr | —CH₂—iPr | Cl |
| 17-12 | CH₃ | —CH₂—iPr | Cl | Cl | Cl |
| 17-13 | CH₃ | Cl | —CH₂—iPr | Cl | Cl |
| 17-14 | CH₃ | Cl | Cl | —CH₂—iPr | Cl |
| 17-15 | CH₃ | Cl | Cl | Cl | —CH₂—iPr |
| 17-16 | CH₃ | Cl | —CH₂—C(CH₃)₃ | —CH₂—C(CH₃)₃ | —CH₂—C(CH₃)₃ |
| 17-17 | CH₃ | —CH₂—C(CH₃)₃ | Cl | —CH₂—C(CH₃)₃ | —CH₂—C(CH₃)₃ |
| 17-18 | CH₃ | —CH₂—C(CH₃)₃ | —CH₂—C(CH₃)₃ | Cl | —CH₂—C(CH₃)₃ |
| 17-19 | CH₃ | —CH₂—C(CH₃)₃ | —CH₂—C(CH₃)₃ | —CH₂—C(CH₃)₃ | Cl |
| 17-20 | CH₃ | —CH₂—C(CH₃)₃ | Cl | —CH₂—C(CH₃)₃ | Cl |
| 17-21 | CH₃ | Cl | —CH₂—C(CH₃)₃ | Cl | —CH₂—C(CH₃)₃ |
| 17-22 | CH₃ | —CH₂—C(CH₃)₃ | Cl | Cl | —CH₂—C(CH₃)₃ |
| 17-23 | CH₃ | Cl | —CH₂—C(CH₃)₃ | —CH₂—C(CH₃)₃ | Cl |
| 17-24 | CH₃ | Cl | Cl | —CH₂—C(CH₃)₃ | —CH₂—C(CH₃)₃ |
| 17-25 | CH₃ | —CH₂—C(CH₃)₃ | —CH₂—C(CH₃)₃ | Cl | Cl |
| 17-26 | CH₃ | —CH₂—C(CH₃)₃ | Cl | Cl | Cl |
| 17-27 | CH₃ | Cl | —CH₂—C(CH₃)₃ | Cl | Cl |
| 17-28 | CH₃ | Cl | Cl | —CH₂—C(CH₃)₃ | Cl |
| 17-29 | CH₃ | Cl | Cl | Cl | —CH₂—C(CH₃)₃ |
| 17-30 | CH₃ | Cl | —CH₂CF(CH₃)₂ | —CH₂CF(CH₃)₂ | —CH₂CF(CH₃)₂ |
| 17-31 | CH₃ | —CH₂CF(CH₃)₂ | Cl | —CH₂CF(CH₃)₂ | —CH₂CF(CH₃)₂ |
| 17-32 | CH₃ | —CH₂CF(CH₃)₂ | —CH₂CF(CH₃)₂ | Cl | —CH₂CF(CH₃)₂ |
| 17-33 | CH₃ | —CH₂CF(CH₃)₂ | —CH₂CF(CH₃)₂ | —CH₂CF(CH₃)₂ | Cl |
| 17-34 | CH₃ | —CH₂CF(CH₃)₂ | Cl | —CH₂CF(CH₃)₂ | Cl |
| 17-35 | CH₃ | Cl | —CH₂CF(CH₃)₂ | Cl | —CH₂CF(CH₃)₂ |
| 17-36 | CH₃ | —CH₂CF(CH₃)₂ | Cl | Cl | —CH₂CF(CH₃)₂ |
| 17-37 | CH₃ | Cl | —CH₂CF(CH₃)₂ | CH₂CF(CH₃)₂ | Cl |
| 17-38 | CH₃ | Cl | Cl | —CH₂CF(CH₃)₂ | —CH₂CF(CH₃)₂ |
| 17-39 | CH₃ | —CH₂CF(CH₃)₂ | —CH₂CF(CH₃)₂ | Cl | Cl |
| 17-40 | CH₃ | —CH₂CF(CH₃)₂ | Cl | Cl | Cl |
| 17-41 | CH₃ | Cl | —CH₂CF(CH₃)₂ | Cl | Cl |
| 17-42 | CH₃ | Cl | Cl | —CH₂CF(CH₃)₂ | Cl |
| 17-43 | CH₃ | Cl | Cl | Cl | —CH₂CF(CH₃)₂ |
| 17-44 | CH₃ | Cl | n-Propyl | n-Propyl | n-Propyl |
| 17-45 | CH₃ | n-Propyl | Cl | n-Propyl | n-Propyl |
| 17-46 | CH₃ | n-Propyl | n-Propyl | Cl | n-Propyl |
| 17-47 | CH₃ | n-Propyl | n-Propyl | n-Propyl | Cl |
| 17-48 | CH₃ | n-Propyl | Cl | n-Propyl | Cl |
| 17-49 | CH₃ | Cl | n-Propyl | Cl | n-Propyl |
| 17-50 | CH₃ | n-Propyl | Cl | Cl | n-Propyl |
| 17-51 | CH₃ | Cl | Cl | n-Propyl | n-Propyl |
| 17-52 | CH₃ | n-Propyl | n-Propyl | Cl | Cl |
| 17-53 | CH₃ | Cl | n-Propyl | n-Propyl | Cl |
| 17-54 | CH₃ | n-Propyl | Cl | Cl | Cl |
| 17-55 | CH₃ | Cl | n-Propyl | Cl | Cl |
| 17-56 | CH₃ | Cl | Cl | n-Propyl | Cl |
| 17-57 | CH₃ | Cl | Cl | Cl | n-Propyl |
| 17-58 | H | —CH₂CF(CH₃)₂ | Cl | —CH₂CF(CH₃)₂ | Cl |
| 17-59 | H | Cl | —CH₂CF(CH₃)₂ | Cl | —CH₂CF(CH₃)₂ |
| 17-60 | H | —CH₂CF(CH₃)₂ | Cl | Cl | —CH₂CF(CH₃)₂ |
| 17-61 | H | Cl | —CH₂CF(CH₃)₂ | —CH₂CF(CH₃)₂ | Cl |
| 17-62 | H | Cl | Cl | —CH₂CF(CH₃)₂ | —CH₂CF(CH₃)₂ |
| 17-63 | H | —CH₂CF(CH₃)₂ | —CH₂CF(CH₃)₂ | Cl | Cl |
| 17-64 | H | —CH₂—C(CH₃)₃ | Cl | —CH₂—C(CH₃)₃ | Cl |
| 17-65 | H | Cl | —CH₂—C(CH₃)₃ | Cl | —CH₂—C(CH₃)₃ |
| 17-66 | H | —CH₂—C(CH₃)₃ | Cl | Cl | —CH₂—C(CH₃)₃ |
| 17-67 | H | Cl | —CH₂—C(CH₃)₃ | —CH₂—C(CH₃)₃ | Cl |

TABLE 17-continued

Compounds of formula (I), wherein Cy¹ and Cy² are

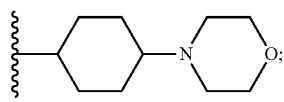

R', R", R'" and R"" are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 17-68 | H | Cl | Cl | —CH₂—C(CH₃)₃ | —CH₂—C(CH₃)₃ |
| 17-69 | H | —CH₂—C(CH₃)₃ | —CH₂—C(CH₃)₃ | Cl | Cl |

TABLE 18

Compounds of formula (I), wherein Cy¹ and Cy² are

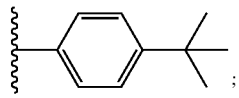

R', R", R'" and R"" are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 18-1 | CH₃ | Cl | Cl | Cl | Cl |
| 18-2 | CH₃ | Cl | —CH₂—iPr | —CH₂—iPr | —CH₂—iPr |
| 18-3 | CH₃ | —CH₂—iPr | Cl | —CH₂—iPr | —CH₂—iPr |
| 18-4 | CH₃ | —CH₂—iPr | —CH₂—iPr | Cl | —CH₂—iPr |
| 18-5 | CH₃ | —CH₂—iPr | —CH₂—iPr | —CH₂—iPr | Cl |
| 18-6 | CH₃ | —CH₂—iPr | Cl | —CH₂—iPr | Cl |
| 18-7 | CH₃ | Cl | —CH₂—iPr | Cl | —CH₂—iPr |
| 18-8 | CH₃ | —CH₂—iPr | Cl | Cl | —CH₂—iPr |
| 18-9 | CH₃ | Cl | Cl | —CH₂—iPr | —CH₂—iPr |
| 18-10 | CH₃ | —CH₂—iPr | —CH₂—iPr | Cl | Cl |
| 18-11 | CH₃ | Cl | —CH₂—iPr | —CH₂—iPr | Cl |
| 18-12 | CH₃ | —CH₂—iPr | Cl | Cl | Cl |
| 18-13 | CH₃ | Cl | —CH₂—iPr | Cl | Cl |
| 18-14 | CH₃ | Cl | Cl | —CH₂—iPr | Cl |
| 18-15 | CH₃ | Cl | Cl | Cl | —CH₂—iPr |
| 18-16 | CH₃ | Cl | —CH₂—C(CH₃)₃ | —CH₂—C(CH₃)₃ | —CH₂—C(CH₃)₃ |
| 18-17 | CH₃ | —CH₂—C(CH₃)₃ | Cl | —CH₂—C(CH₃)₃ | —CH₂—C(CH₃)₃ |
| 18-18 | CH₃ | —CH₂—C(CH₃)₃ | —CH₂—C(CH₃)₃ | Cl | —CH₂—C(CH₃)₃ |
| 18-19 | CH₃ | —CH₂—C(CH₃)₃ | —CH₂—C(CH₃)₃ | —CH₂—C(CH₃)₃ | Cl |
| 18-20 | CH₃ | —CH₂—C(CH₃)₃ | Cl | —CH₂—C(CH₃)₃ | Cl |
| 18-21 | CH₃ | Cl | —CH₂—C(CH₃)₃ | Cl | —CH₂—C(CH₃)₃ |
| 18-22 | CH₃ | —CH₂—C(CH₃)₃ | Cl | Cl | —CH₂—C(CH₃)₃ |
| 18-23 | CH₃ | Cl | Cl | —CH₂—C(CH₃)₃ | —CH₂—C(CH₃)₃ |
| 18-24 | CH₃ | Cl | Cl | —CH₂—C(CH₃)₃ | —CH₂—C(CH₃)₃ |
| 18-25 | CH₃ | —CH₂—C(CH₃)₃ | —CH₂—C(CH₃)₃ | Cl | Cl |
| 18-26 | CH₃ | —CH₂—C(CH₃)₃ | Cl | Cl | Cl |
| 18-27 | CH₃ | Cl | —CH₂—C(CH₃)₃ | Cl | Cl |
| 18-28 | CH₃ | Cl | Cl | —CH₂—C(CH₃)₃ | Cl |
| 18-29 | CH₃ | Cl | Cl | Cl | —CH₂—C(CH₃)₃ |
| 18-30 | CH₃ | Cl | —CH₂CF(CH₃)₂ | —CH₂CF(CH₃)₂ | —CHCF(CH₃)₂ |
| 18-31 | CH₃ | —CH₂CF(CH₃)₂ | Cl | —CH₂CF(CH₃)₂ | —CH₂CF(CH₃)₂ |
| 18-32 | CH₃ | —CH₂CF(CH₃)₂ | —CH₂CF(CH₃)₂ | Cl | —CH₂CF(CH₃)₂ |
| 18-33 | CH₃ | —CH₂CF(CH₃)₂ | —CH₂CF(CH₃)₂ | —CH₂CF(CH₃)₂ | Cl |
| 18-34 | CH₃ | —CH₂CF(CH₃)₂ | Cl | —CH₂CF(CH₃)₂ | Cl |
| 18-35 | CH₃ | Cl | —CH₂CF(CH₃)₂ | Cl | —CH₂CF(CH₃)₂ |
| 18-36 | CH₃ | —CH₂CF(CH₃)₂ | Cl | Cl | —CH₂CF(CH₃)₂ |
| 18-37 | CH₃ | Cl | —CH₂CF(CH₃)₂ | CH₂CF(CH₃)₂ | Cl |
| 18-38 | CH₃ | Cl | Cl | —CH₂CF(CH₃)₂ | —CH₂CF(CH₃)₂ |
| 18-39 | CH₃ | —CH₂CF(CH₃)₂ | —CH₂CF(CH₃)₂ | Cl | Cl |
| 18-40 | CH₃ | —CH₂CF(CH₃)₂ | Cl | Cl | Cl |
| 18-41 | CH₃ | Cl | —CH₂CF(CH₃)₂ | Cl | Cl |
| 18-42 | CH₃ | Cl | Cl | —CH₂CF(CH₃)₂ | Cl |
| 18-43 | CH₃ | Cl | Cl | Cl | —CH₂CF(CH₃)₂ |
| 18-44 | CH₃ | Cl | n-Propyl | n-Propyl | n-Propyl |
| 18-45 | CH₃ | n-Propyl | Cl | n-Propyl | n-Propyl |
| 18-46 | CH₃ | n-Propyl | n-Propyl | Cl | n-Propyl |
| 18-47 | CH₃ | n-Propyl | n-Propyl | n-Propyl | Cl |
| 18-48 | CH₃ | n-Propyl | Cl | n-Propyl | Cl |

TABLE 18-continued

Compounds of formula (I), wherein Cy¹ and Cy² are

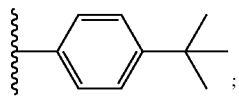 [SMILES: *c1ccc(C(C)(C)C)cc1]

R', R'', R''' and R'''' are each independently hydrogen or methyl; and R$^a$, R$^b$ and R$^1$ to R$^4$ are as shown.

| Cmpd # | R$^a$/R$^b$ | R$^1$ | R$^2$ | R$^3$ | R$^4$ |
| --- | --- | --- | --- | --- | --- |
| 18-49 | CH$_3$ | Cl | n-Propyl | Cl | n-Propyl |
| 18-50 | CH$_3$ | n-Propyl | Cl | Cl | n-Propyl |
| 18-51 | CH$_3$ | Cl | Cl | n-Propyl | n-Propyl |
| 18-52 | CH$_3$ | n-Propyl | n-Propyl | Cl | Cl |
| 18-53 | CH$_3$ | Cl | n-Propyl | n-Propyl | Cl |
| 18-54 | CH$_3$ | n-Propyl | Cl | Cl | Cl |
| 18-55 | CH$_3$ | Cl | n-Propyl | Cl | Cl |
| 18-56 | CH$_3$ | Cl | Cl | n-Propyl | Cl |
| 18-57 | CH$_3$ | Cl | Cl | Cl | n-Propyl |
| 18-58 | H | —CH$_2$CF(CH$_3$)$_2$ | Cl | —CH$_2$CF(CH$_3$)$_2$ | Cl |
| 18-59 | H | Cl | —CH$_2$CF(CH$_3$)$_2$ | Cl | —CH$_2$CF(CH$_3$)$_2$ |
| 18-60 | H | —CH$_2$CF(CH$_3$)$_2$ | Cl | Cl | —CH$_2$CF(CH$_3$)$_2$ |
| 18-61 | H | Cl | —CH$_2$CF(CH$_3$)$_2$ | —CH$_2$CF(CH$_3$)$_2$ | Cl |
| 18-62 | H | Cl | Cl | —CH$_2$CF(CH$_3$)$_2$ | —CH$_2$CF(CH$_3$)$_2$ |
| 18-63 | H | —CH$_2$CF(CH$_3$)$_2$ | —CH$_2$CF(CH$_3$)$_2$ | Cl | Cl |
| 18-64 | H | —CH$_2$—C(CH$_3$)$_3$ | Cl | —CH$_2$—C(CH$_3$)$_3$ | Cl |
| 18-65 | H | Cl | —CH$_2$—C(CH$_3$)$_3$ | Cl | —CH$_2$—C(CH$_3$)$_3$ |
| 18-66 | H | —CH$_2$—C(CH$_3$)$_3$ | Cl | Cl | —CH$_2$—C(CH$_3$)$_3$ |
| 18-67 | H | Cl | —CH$_2$—C(CH$_3$)$_3$ | —CH$_2$—C(CH$_3$)$_3$ | Cl |
| 18-68 | H | Cl | Cl | —CH$_2$—C(CH$_3$)$_3$ | —CH$_2$—C(CH$_3$)$_3$ |
| 18-69 | H | —CH$_2$—C(CH$_3$)$_3$ | —CH$_2$—C(CH$_3$)$_3$ | Cl | Cl |

TABLE 19

Compounds of formula (I), wherein Cy¹ and Cy² are

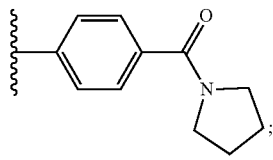

R', R'', R''' and R'''' are each independently hydrogen or methyl; and R$^a$, R$^b$ and R$^1$ to R$^4$ are as shown.

| Cmpd # | R$^a$/R$^b$ | R$^1$ | R$^2$ | R$^3$ | R$^4$ |
| --- | --- | --- | --- | --- | --- |
| 19-1 | CH$_3$ | Cl | Cl | Cl | Cl |
| 19-2 | CH$_3$ | Cl | —CH$_2$—iPr | —CH$_2$—iPr | —CH$_2$—iPr |
| 19-3 | CH$_3$ | —CH$_2$—iPr | Cl | —CH$_2$—iPr | —CH$_2$—iPr |
| 19-4 | CH$_3$ | —CH$_2$—iPr | —CH$_2$—iPr | Cl | —CH$_2$—iPr |
| 19-5 | CH$_3$ | —CH$_2$—iPr | —CH$_2$—iPr | —CH$_2$—iPr | Cl |
| 19-6 | CH$_3$ | —CH$_2$—iPr | Cl | —CH$_2$—iPr | Cl |
| 19-7 | CH$_3$ | Cl | —CH$_2$—iPr | Cl | —CH$_2$—iPr |
| 19-8 | CH$_3$ | —CH$_2$—iPr | Cl | Cl | —CH$_2$—iPr |
| 19-9 | CH$_3$ | Cl | Cl | —CH$_2$—iPr | —CH$_2$—iPr |
| 19-10 | CH$_3$ | —CH$_2$—iPr | —CH$_2$—iPr | Cl | Cl |
| 19-11 | CH$_3$ | Cl | —CH$_2$—iPr | —CH$_2$—iPr | Cl |
| 19-12 | CH$_3$ | —CH$_2$—iPr | Cl | Cl | Cl |
| 19-13 | CH$_3$ | Cl | —CH$_2$—iPr | Cl | Cl |
| 19-14 | CH$_3$ | Cl | Cl | —CH$_2$—iPr | Cl |
| 19-15 | CH$_3$ | Cl | Cl | Cl | —CH$_2$—iPr |
| 19-16 | CH$_3$ | Cl | —CH$_2$—C(CH$_3$)$_3$ | —CH$_2$—C(CH$_3$)$_3$ | —CH$_2$—C(CH$_3$)$_3$ |
| 19-17 | CH$_3$ | —CH$_2$—C(CH$_3$)$_3$ | Cl | —CH$_2$—C(CH$_3$)$_3$ | —CH$_2$—C(CH$_3$)$_3$ |
| 19-18 | CH$_3$ | —CH$_2$—C(CH$_3$)$_3$ | —CH$_2$—C(CH$_3$)$_3$ | Cl | —CH$_2$—C(CH$_3$)$_3$ |
| 19-19 | CH$_3$ | —CH$_2$—C(CH$_3$)$_3$ | —CH$_2$—C(CH$_3$)$_3$ | —CH$_2$—C(CH$_3$)$_3$ | Cl |
| 19-20 | CH$_3$ | —CH$_2$—C(CH$_3$)$_3$ | Cl | —CH$_2$—C(CH$_3$)$_3$ | Cl |
| 19-21 | CH$_3$ | Cl | —CH$_2$—C(CH$_3$)$_3$ | Cl | —CH$_2$—C(CH$_3$)$_3$ |
| 19-22 | CH$_3$ | —CH$_2$—C(CH$_3$)$_3$ | Cl | Cl | —CH$_2$—C(CH$_3$)$_3$ |
| 19-23 | CH$_3$ | Cl | —CH$_2$—C(CH$_3$)$_3$ | —CH$_2$—C(CH$_3$)$_3$ | Cl |
| 19-24 | CH$_3$ | Cl | Cl | —CH$_2$—C(CH$_3$)$_3$ | —CH$_2$—C(CH$_3$)$_3$ |
| 19-25 | CH$_3$ | —CH$_2$—C(CH$_3$)$_3$ | —CH$_2$—C(CH$_3$)$_3$ | Cl | Cl |
| 19-26 | CH$_3$ | —CH$_2$—C(CH$_3$)$_3$ | Cl | Cl | Cl |

TABLE 19-continued

Compounds of formula (I), wherein Cy$^1$ and Cy$^2$ are

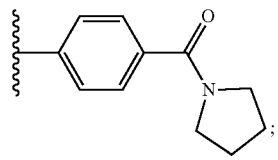 [SMILES: *c1ccc(C(=O)N2CCCC2)cc1]

R', R'', R''' and R'''' are each independently hydrogen or methyl; and R$^a$, R$^b$ and R$^1$ to R$^4$ are as shown.

| Cmpd # | R$^a$/R$^b$ | R$^1$ | R$^2$ | R$^3$ | R$^4$ |
|---|---|---|---|---|---|
| 19-27 | CH$_3$ | Cl | —CH$_2$—C(CH$_3$)$_3$ | Cl | Cl |
| 19-28 | CH$_3$ | Cl | Cl | —CH$_2$—C(CH$_3$)$_3$ | Cl |
| 19-29 | CH$_3$ | Cl | Cl | Cl | —CH$_2$—C(CH$_3$)$_3$ |
| 19-30 | CH$_3$ | Cl | —CH$_2$CF(CH$_3$)$_2$ | —CH$_2$CF(CH$_3$)$_2$ | —CHCF(CH$_3$)$_2$ |
| 19-31 | CH$_3$ | —CH$_2$CF(CH$_3$)$_2$ | Cl | —CH$_2$CF(CH$_3$)$_2$ | —CH$_2$CF(CH$_3$)$_2$ |
| 19-32 | CH$_3$ | —CH$_2$CF(CH$_3$)$_2$ | —CH$_2$CF(CH$_3$)$_2$ | Cl | —CH$_2$CF(CH$_3$)$_2$ |
| 19-33 | CH$_3$ | —CH$_2$CF(CH$_3$)$_2$ | —CH$_2$CF(CH$_3$)$_2$ | —CH$_2$CF(CH$_3$)$_2$ | Cl |
| 19-34 | CH$_3$ | —CH$_2$CF(CH$_3$)$_2$ | Cl | Cl | Cl |
| 19-35 | CH$_3$ | Cl | —CH$_2$CF(CH$_3$)$_2$ | Cl | —CH$_2$CF(CH$_3$)$_2$ |
| 19-36 | CH$_3$ | —CH$_2$CF(CH$_3$)$_2$ | Cl | Cl | —CH$_2$CF(CH$_3$)$_2$ |
| 19-37 | CH$_3$ | Cl | —CH$_2$CF(CH$_3$)$_2$ | CH$_2$CF(CH$_3$)$_2$ | Cl |
| 19-38 | CH$_3$ | Cl | Cl | —CH$_2$CF(CH$_3$)$_2$ | —CH$_2$CF(CH$_3$)$_2$ |
| 19-39 | CH$_3$ | —CH$_2$CF(CH$_3$)$_2$ | —CH$_2$CF(CH$_3$)$_2$ | Cl | Cl |
| 19-40 | CH$_3$ | —CH$_2$CF(CH$_3$)$_2$ | Cl | Cl | Cl |
| 19-41 | CH$_3$ | Cl | —CH$_2$CF(CH$_3$)$_2$ | Cl | Cl |
| 19-42 | CH$_3$ | Cl | Cl | —CH$_2$CF(CH$_3$)$_2$ | Cl |
| 19-43 | CH$_3$ | Cl | Cl | Cl | —CH$_2$CF(CH$_3$)$_2$ |
| 19-44 | CH$_3$ | Cl | n-Propyl | n-Propyl | n-Propyl |
| 19-45 | CH$_3$ | n-Propyl | Cl | n-Propyl | n-Propyl |
| 19-46 | CH$_3$ | n-Propyl | n-Propyl | Cl | n-Propyl |
| 19-47 | CH$_3$ | n-Propyl | n-Propyl | n-Propyl | Cl |
| 19-48 | CH$_3$ | n-Propyl | Cl | n-Propyl | Cl |
| 19-49 | CH$_3$ | Cl | n-Propyl | Cl | n-Propyl |
| 19-50 | CH$_3$ | n-Propyl | Cl | Cl | n-Propyl |
| 19-51 | CH$_3$ | Cl | Cl | n-Propyl | n-Propyl |
| 19-52 | CH$_3$ | n-Propyl | n-Propyl | Cl | Cl |
| 19-53 | CH$_3$ | Cl | n-Propyl | n-Propyl | Cl |
| 19-54 | CH$_3$ | n-Propyl | Cl | Cl | Cl |
| 19-55 | CH$_3$ | Cl | n-Propyl | Cl | Cl |
| 19-56 | CH$_3$ | Cl | Cl | n-Propyl | Cl |
| 19-57 | CH$_3$ | Cl | Cl | Cl | n-Propyl |
| 19-58 | H | —CH$_2$CF(CH$_3$)$_2$ | Cl | —CH$_2$CF(CH$_3$)$_2$ | Cl |
| 19-59 | H | Cl | —CH$_2$CF(CH$_3$)$_2$ | Cl | —CH$_2$CF(CH$_3$)$_2$ |
| 19-60 | H | —CH$_2$CF(CH$_3$)$_2$ | Cl | Cl | —CH$_2$CF(CH$_3$)$_2$ |
| 19-61 | H | Cl | —CH$_2$CF(CH$_3$)$_2$ | —CH$_2$CF(CH$_3$)$_2$ | Cl |
| 19-62 | H | Cl | Cl | —CH$_2$CF(CH$_3$)$_2$ | —CH$_2$CF(CH$_3$)$_2$ |
| 19-63 | H | —CH$_2$CF(CH$_3$)$_2$ | —CH$_2$CF(CH$_3$)$_2$ | Cl | Cl |
| 19-64 | H | —CH$_2$—C(CH$_3$)$_3$ | Cl | —CH$_2$—C(CH$_3$)$_3$ | Cl |
| 19-65 | H | Cl | —CH$_2$—C(CH$_3$)$_3$ | Cl | —CH$_2$—C(CH$_3$)$_3$ |
| 19-66 | H | —CH$_2$—C(CH$_3$)$_3$ | Cl | Cl | —CH$_2$—C(CH$_3$)$_3$ |
| 19-67 | H | Cl | —CH$_2$—C(CH$_3$)$_3$ | —CH$_2$—C(CH$_3$)$_3$ | Cl |
| 19-68 | H | Cl | Cl | —CH$_2$—C(CH$_3$)$_3$ | —CH$_2$—C(CH$_3$)$_3$ |
| 19-69 | H | —CH$_2$—C(CH$_3$)$_3$ | —CH$_2$—C(CH$_3$)$_3$ | Cl | Cl |

TABLE 20

Compounds of formula (I), wherein Cy$^1$ and Cy$^2$ are 3,4,5-trifluorophenyl; R', R'', R''' and R'''' are each independently hydrogen or methyl; and R$^a$, R$^b$ and R$^1$ to R$^4$ are as shown.

| Cmpd # | R$^a$/R$^b$ | R$^1$ | R$^2$ | R$^3$ | R$^4$ |
|---|---|---|---|---|---|
| 20-1 | CH$_3$ | Cl | Cl | Cl | Cl |
| 20-2 | CH$_3$ | Cl | —CH$_2$—iPr | —CH$_2$—iPr | —CH$_2$—iPr |
| 20-3 | CH$_3$ | —CH$_2$—iPr | Cl | —CH$_2$—iPr | —CH$_2$—iPr |
| 20-4 | CH$_3$ | —CH$_2$—iPr | —CH$_2$—iPr | Cl | —CH$_2$—iPr |
| 20-5 | CH$_3$ | —CH$_2$—iPr | —CH$_2$—iPr | —CH$_2$—iPr | Cl |
| 20-6 | CH$_3$ | —CH$_2$—iPr | Cl | —CH$_2$—iPr | Cl |
| 20-7 | CH$_3$ | Cl | —CH$_2$—iPr | Cl | —CH$_2$—iPr |
| 20-8 | CH$_3$ | —CH$_2$—iPr | Cl | Cl | —CH$_2$—iPr |
| 20-9 | CH$_3$ | Cl | Cl | —CH$_2$—iPr | —CH$_2$—iPr |
| 20-10 | CH$_3$ | —CH$_2$—iPr | —CH$_2$—iPr | Cl | Cl |

TABLE 20-continued

Compounds of formula (I), wherein $Cy^1$ and $Cy^2$ are 3,4,5-trifluorophenyl; $R'$, $R''$, $R'''$ and $R''''$ are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 20-11 | CH₃ | Cl | —CH₂—iPr | —CH₂—iPr | Cl |
| 20-12 | CH₃ | —CH₂—iPr | Cl | Cl | Cl |
| 20-13 | CH₃ | Cl | —CH₂—iPr | Cl | Cl |
| 20-14 | CH₃ | Cl | Cl | —CH₂—iPr | Cl |
| 20-15 | CH₃ | Cl | Cl | Cl | —CH₂—iPr |
| 20-16 | CH₃ | Cl | —CH₂—C(CH₃)₃ | —CH₂—C(CH₃)₃ | —CH₂—C(CH₃)₃ |
| 20-17 | CH₃ | —CH₂—C(CH₃)₃ | Cl | —CH₂—C(CH₃)₃ | —CH₂—C(CH₃)₃ |
| 20-18 | CH₃ | —CH₂—C(CH₃)₃ | —CH₂—C(CH₃)₃ | Cl | —CH₂—C(CH₃)₃ |
| 20-19 | CH₃ | —CH₂—C(CH₃)₃ | —CH₂—C(CH₃)₃ | —CH₂—C(CH₃)₃ | Cl |
| 20-20 | CH₃ | —CH₂—C(CH₃)₃ | Cl | —CH₂—C(CH₃)₃ | Cl |
| 20-21 | CH₃ | Cl | —CH₂—C(CH₃)₃ | Cl | —CH₂—C(CH₃)₃ |
| 20-22 | CH₃ | —CH₂—C(CH₃)₃ | Cl | Cl | —CH₂—C(CH₃)₃ |
| 20-23 | CH₃ | Cl | —CH₂—C(CH₃)₃ | —CH₂—C(CH₃)₃ | Cl |
| 20-24 | CH₃ | Cl | Cl | —CH₂—C(CH₃)₃ | —CH₂—C(CH₃)₃ |
| 20-25 | CH₃ | —CH₂—C(CH₃)₃ | —CH₂—C(CH₃)₃ | Cl | Cl |
| 20-26 | CH₃ | —CH₂—C(CH₃)₃ | Cl | Cl | Cl |
| 20-27 | CH₃ | Cl | —CH₂—C(CH₃)₃ | Cl | Cl |
| 20-28 | CH₃ | Cl | Cl | —CH₂—C(CH₃)₃ | Cl |
| 20-29 | CH₃ | Cl | Cl | Cl | —CH₂—C(CH₃)₃ |
| 20-30 | CH₃ | Cl | —CH₂CF(CH₃)₂ | —CH₂CF(CH₃)₂ | —CHCF(CH₃)₂ |
| 20-31 | CH₃ | —CH₂CF(CH₃)₂ | Cl | —CH₂CF(CH₃)₂ | —CH₂CF(CH₃)₂ |
| 20-32 | CH₃ | —CH₂CF(CH₃)₂ | —CH₂CF(CH₃)₂ | Cl | —CH₂CF(CH₃)₂ |
| 20-33 | CH₃ | —CH₂CF(CH₃)₂ | —CH₂CF(CH₃)₂ | —CH₂CF(CH₃)₂ | Cl |
| 20-34 | CH₃ | —CH₂CF(CH₃)₂ | Cl | —CH₂CF(CH₃)₂ | Cl |
| 20-35 | CH₃ | Cl | —CH₂CF(CH₃)₂ | Cl | —CH₂CF(CH₃)₂ |
| 20-36 | CH₃ | —CH₂CF(CH₃)₂ | Cl | Cl | —CH₂CF(CH₃)₂ |
| 20-37 | CH₃ | Cl | —CH₂CF(CH₃)₂ | CH₂CF(CH₃)₂ | Cl |
| 20-38 | CH₃ | Cl | Cl | —CH₂CF(CH₃)₂ | —CH₂CF(CH₃)₂ |
| 20-39 | CH₃ | —CH₂CF(CH₃)₂ | —CH₂CF(CH₃)₂ | Cl | Cl |
| 20-40 | CH₃ | —CH₂CF(CH₃)₂ | Cl | Cl | Cl |
| 20-41 | CH₃ | Cl | —CH₂CF(CH₃)₂ | Cl | Cl |
| 20-42 | CH₃ | Cl | Cl | —CH₂CF(CH₃)₂ | Cl |
| 20-43 | CH₃ | Cl | Cl | Cl | —CH₂CF(CH₃)₂ |
| 20-44 | CH₃ | Cl | n-Propyl | n-Propyl | n-Propyl |
| 20-45 | CH₃ | n-Propyl | Cl | n-Propyl | n-Propyl |
| 20-46 | CH₃ | n-Propyl | n-Propyl | Cl | n-Propyl |
| 20-47 | CH₃ | n-Propyl | n-Propyl | n-Propyl | Cl |
| 20-48 | CH₃ | n-Propyl | Cl | n-Propyl | Cl |
| 20-49 | CH₃ | Cl | n-Propyl | Cl | n-Propyl |
| 20-50 | CH₃ | n-Propyl | Cl | Cl | n-Propyl |
| 20-51 | CH₃ | Cl | Cl | n-Propyl | n-Propyl |
| 20-52 | CH₃ | n-Propyl | n-Propyl | Cl | Cl |
| 20-53 | CH₃ | Cl | n-Propyl | n-Propyl | Cl |
| 20-54 | CH₃ | n-Propyl | Cl | Cl | Cl |
| 20-55 | CH₃ | Cl | n-Propyl | Cl | Cl |
| 20-56 | CH₃ | Cl | Cl | n-Propyl | Cl |
| 20-57 | CH₃ | Cl | Cl | Cl | n-Propyl |
| 20-58 | H | —CH₂CF(CH₃)₂ | Cl | —CH₂CF(CH₃)₂ | Cl |
| 20-59 | H | Cl | —CH₂CF(CH₃)₂ | Cl | —CH₂CF(CH₃)₂ |
| 20-60 | H | —CH₂CF(CH₃)₂ | Cl | Cl | —CH₂CF(CH₃)₂ |
| 20-61 | H | Cl | —CH₂CF(CH₃)₂ | —CH₂CF(CH₃)₂ | Cl |
| 20-62 | H | Cl | Cl | —CH₂CF(CH₃)₂ | —CH₂CF(CH₃)₂ |
| 20-63 | H | —CH₂CF(CH₃)₂ | —CH₂CF(CH₃)₂ | Cl | Cl |
| 20-64 | H | —CH₂—C(CH₃)₃ | Cl | —CH₂—C(CH₃)₃ | Cl |
| 20-65 | H | Cl | —CH₂—C(CH₃)₃ | Cl | —CH₂—C(CH₃)₃ |
| 20-66 | H | —CH₂—C(CH₃)₃ | Cl | Cl | —CH₂—C(CH₃)₃ |
| 20-67 | H | Cl | —CH₂—C(CH₃)₃ | —CH₂—C(CH₃)₃ | Cl |
| 20-68 | H | Cl | Cl | —CH₂—C(CH₃)₃ | —CH₂—C(CH₃)₃ |
| 20-69 | H | —CH₂—C(CH₃)₃ | —CH₂—C(CH₃)₃ | Cl | Cl |

TABLE 21

Compounds of formula (I), wherein $Cy^1$ and $Cy^2$ are p-aminophenyl; $R'$, $R''$, $R'''$ and $R''''$ are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 21-1 | CH₃ | Cl | Cl | Cl | Cl |
| 21-2 | CH₃ | Cl | —CH₂—iPr | —CH₂—iPr | —CH₂—iPr |
| 21-3 | CH₃ | —CH₂—iPr | Cl | —CH₂—iPr | —CH₂—iPr |

TABLE 21-continued

Compounds of formula (I), wherein $Cy^1$ and $Cy^2$ are p-aminophenyl;
R', R'', R''' and R'''' are each independently hydrogen or methyl; and
$R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 21-4 | CH₃ | —CH₂—iPr | —CH₂—iPr | Cl | —CH₂—iPr |
| 21-5 | CH₃ | —CH₂—iPr | —CH₂—iPr | —CH₂—iPr | Cl |
| 21-6 | CH₃ | —CH₂—iPr | Cl | —CH₂—iPr | Cl |
| 21-7 | CH₃ | Cl | —CH₂—iPr | Cl | —CH₂—iPr |
| 21-8 | CH₃ | —CH₂—iPr | Cl | Cl | —CH₂—iPr |
| 21-9 | CH₃ | Cl | Cl | —CH₂—iPr | —CH₂—iPr |
| 21-10 | CH₃ | —CH₂—iPr | —CH₂—iPr | Cl | Cl |
| 21-11 | CH₃ | Cl | —CH₂—iPr | —CH₂—iPr | Cl |
| 21-12 | CH₃ | —CH₂—iPr | Cl | Cl | Cl |
| 21-13 | CH₃ | Cl | —CH₂—iPr | Cl | Cl |
| 21-14 | CH₃ | Cl | Cl | —CH₂—iPr | Cl |
| 21-15 | CH₃ | Cl | Cl | Cl | —CH₂—iPr |
| 21-16 | CH₃ | Cl | —CH₂—C(CH₃)₃ | —CH₂—C(CH₃)₃ | —CH₂—C(CH₃)₃ |
| 21-17 | CH₃ | —CH₂—C(CH₃)₃ | Cl | —CH₂—C(CH₃)₃ | —CH₂—C(CH₃)₃ |
| 21-18 | CH₃ | —CH₂—C(CH₃)₃ | —CH₂—C(CH₃)₃ | Cl | —CH₂—C(CH₃)₃ |
| 21-19 | CH₃ | —CH₂—C(CH₃)₃ | —CH₂—C(CH₃)₃ | —CH₂—C(CH₃)₃ | Cl |
| 21-20 | CH₃ | —CH₂—C(CH₃)₃ | Cl | —CH₂—C(CH₃)₃ | Cl |
| 21-21 | CH₃ | Cl | —CH₂—C(CH₃)₃ | Cl | —CH₂—C(CH₃)₃ |
| 21-22 | CH₃ | —CH₂—C(CH₃)₃ | Cl | Cl | —CH₂—C(CH₃)₃ |
| 21-23 | CH₃ | Cl | —CH₂—C(CH₃)₃ | —CH₂—C(CH₃)₃ | Cl |
| 21-24 | CH₃ | Cl | Cl | —CH₂—C(CH₃)₃ | —CH₂—C(CH₃)₃ |
| 21-25 | CH₃ | —CH₂—C(CH₃)₃ | —CH₂—C(CH₃)₃ | Cl | Cl |
| 21-26 | CH₃ | —CH₂—C(CH₃)₃ | Cl | Cl | Cl |
| 21-27 | CH₃ | Cl | —CH₂—C(CH₃)₃ | Cl | Cl |
| 21-28 | CH₃ | Cl | Cl | —CH₂—C(CH₃)₃ | Cl |
| 21-29 | CH₃ | Cl | Cl | Cl | —CH₂—C(CH₃)₃ |
| 21-30 | CH₃ | Cl | —CH₂CF(CH₃)₂ | —CH₂CF(CH₃)₂ | —CHCF(CH₃)₂ |
| 21-31 | CH₃ | —CH₂CF(CH₃)₂ | Cl | —CH₂CF(CH₃)₂ | —CH₂CF(CH₃)₂ |
| 21-32 | CH₃ | —CH₂CF(CH₃)₂ | —CH₂CF(CH₃)₂ | Cl | —CH₂CF(CH₃)₂ |
| 21-33 | CH₃ | —CH₂CF(CH₃)₂ | —CH₂CF(CH₃)₂ | —CH₂CF(CH₃)₂ | Cl |
| 21-34 | CH₃ | —CH₂CF(CH₃)₂ | Cl | —CH₂CF(CH₃)₂ | Cl |
| 21-35 | CH₃ | Cl | —CH₂CF(CH₃)₂ | Cl | —CH₂CF(CH₃)₂ |
| 21-36 | CH₃ | —CH₂CF(CH₃)₂ | Cl | Cl | —CH₂CF(CH₃)₂ |
| 21-37 | CH₃ | Cl | —CH₂CF(CH₃)₂ | CH₂CF(CH₃)₂ | Cl |
| 21-38 | CH₃ | Cl | Cl | —CH₂CF(CH₃)₂ | —CH₂CF(CH₃)₂ |
| 21-39 | CH₃ | —CH₂CF(CH₃)₂ | —CH₂CF(CH₃)₂ | Cl | Cl |
| 21-40 | CH₃ | —CH₂CF(CH₃)₂ | Cl | Cl | Cl |
| 21-41 | CH₃ | Cl | —CH₂CF(CH₃)₂ | Cl | Cl |
| 21-42 | CH₃ | Cl | Cl | —CH₂CF(CH₃)₂ | Cl |
| 21-43 | CH₃ | Cl | Cl | Cl | —CH₂CF(CH₃)₂ |
| 21-44 | CH₃ | Cl | n-Propyl | n-Propyl | n-Propyl |
| 21-45 | CH₃ | n-Propyl | Cl | n-Propyl | n-Propyl |
| 21-46 | CH₃ | n-Propyl | n-Propyl | Cl | n-Propyl |
| 21-47 | CH₃ | n-Propyl | n-Propyl | n-Propyl | Cl |
| 21-48 | CH₃ | n-Propyl | Cl | n-Propyl | Cl |
| 21-49 | CH₃ | Cl | n-Propyl | Cl | n-Propyl |
| 21-50 | CH₃ | n-Propyl | Cl | Cl | n-Propyl |
| 21-51 | CH₃ | Cl | Cl | n-Propyl | n-Propyl |
| 21-52 | CH₃ | n-Propyl | n-Propyl | Cl | Cl |
| 21-53 | CH₃ | Cl | n-Propyl | n-Propyl | Cl |
| 21-54 | CH₃ | n-Propyl | Cl | Cl | Cl |
| 21-55 | CH₃ | Cl | n-Propyl | Cl | Cl |
| 21-56 | CH₃ | Cl | Cl | n-Propyl | Cl |
| 21-57 | CH₃ | Cl | Cl | Cl | n-Propyl |
| 21-58 | H | —CH₂CF(CH₃)₂ | Cl | —CH₂CF(CH₃)₂ | Cl |
| 21-59 | H | Cl | —CH₂CF(CH₃)₂ | Cl | —CH₂CF(CH₃)₂ |
| 21-60 | H | —CH₂CF(CH₃)₂ | —CH₂CF(CH₃)₂ | Cl | —CH₂CF(CH₃)₂ |
| 21-61 | H | Cl | —CH₂CF(CH₃)₂ | —CH₂CF(CH₃)₂ | Cl |
| 21-62 | H | Cl | Cl | —CH₂CF(CH₃)₂ | —CH₂CF(CH₃)₂ |
| 21-63 | H | —CH₂CF(CH₃)₂ | —CH₂CF(CH₃)₂ | Cl | Cl |
| 21-64 | H | —CH₂—C(CH₃)₃ | Cl | —CH₂—C(CH₃)₃ | Cl |
| 21-65 | H | Cl | —CH₂—C(CH₃)₃ | Cl | —CH₂—C(CH₃)₃ |
| 21-66 | H | —CH₂—C(CH₃)₃ | Cl | Cl | —CH₂—C(CH₃)₃ |
| 21-67 | H | Cl | —CH₂—C(CH₃)₃ | —CH₂—C(CH₃)₃ | Cl |
| 21-68 | H | Cl | Cl | —CH₂—C(CH₃)₃ | —CH₂—C(CH₃)₃ |
| 21-69 | H | —CH₂—C(CH₃)₃ | —CH₂—C(CH₃)₃ | Cl | Cl |

TABLE 22

Compounds of formula (I), wherein $Cy^1$ and $Cy^2$ are p-iodophenyl;
R', R'', R''' and R'''' are each independently hydrogen or methyl;
and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 22-1 | CH₃ | Cl | Cl | Cl | Cl |
| 22-2 | CH₃ | Cl | —CH₂—iPr | —CH₂—iPr | —CH₂—iPr |
| 22-3 | CH₃ | —CH₂—iPr | Cl | —CH₂—iPr | —CH₂—iPr |
| 22-4 | CH₃ | —CH₂—iPr | —CH₂—iPr | Cl | —CH₂—iPr |
| 22-5 | CH₃ | —CH₂—iPr | —CH₂—iPr | —CH₂—iPr | Cl |
| 22-6 | CH₃ | —CH₂—iPr | Cl | —CH₂—iPr | Cl |
| 22-7 | CH₃ | Cl | —CH₂—iPr | Cl | —CH₂—iPr |
| 22-8 | CH₃ | —CH₂—iPr | Cl | Cl | —CH₂—iPr |
| 22-9 | CH₃ | Cl | Cl | —CH₂—iPr | —CH₂—iPr |
| 22-10 | CH₃ | —CH₂—iPr | —CH₂—iPr | Cl | Cl |
| 22-11 | CH₃ | Cl | —CH₂—iPr | —CH₂—iPr | Cl |
| 22-12 | CH₃ | —CH₂—iPr | Cl | Cl | Cl |
| 22-13 | CH₃ | Cl | —CH₂—iPr | Cl | Cl |
| 22-14 | CH₃ | Cl | Cl | —CH₂—iPr | Cl |
| 22-15 | CH₃ | Cl | Cl | Cl | —CH₂—iPr |
| 22-16 | CH₃ | Cl | —CH₂—C(CH₃)₃ | —CH₂—C(CH₃)₃ | —CH₂—C(CH₃)₃ |
| 22-17 | CH₃ | —CH₂—C(CH₃)₃ | Cl | —CH₂—C(CH₃)₃ | —CH₂—C(CH₃)₃ |
| 22-18 | CH₃ | —CH₂—C(CH₃)₃ | —CH₂—C(CH₃)₃ | Cl | —CH₂—C(CH₃)₃ |
| 22-19 | CH₃ | —CH₂—C(CH₃)₃ | —CH₂—C(CH₃)₃ | —CH₂—C(CH₃)₃ | Cl |
| 22-20 | CH₃ | —CH₂—C(CH₃)₃ | Cl | —CH₂—C(CH₃)₃ | Cl |
| 22-21 | CH₃ | Cl | —CH₂—C(CH₃)₃ | Cl | —CH₂—C(CH₃)₃ |
| 22-22 | CH₃ | —CH₂—C(CH₃)₃ | Cl | Cl | —CH₂—C(CH₃)₃ |
| 22-23 | CH₃ | Cl | —CH₂—C(CH₃)₃ | —CH₂—C(CH₃)₃ | Cl |
| 22-24 | CH₃ | Cl | Cl | —CH₂—C(CH₃)₃ | —CH₂—C(CH₃)₃ |
| 22-25 | CH₃ | —CH₂—C(CH₃)₃ | —CH₂—C(CH₃)₃ | Cl | Cl |
| 22-26 | CH₃ | —CH₂—C(CH₃)₃ | Cl | Cl | Cl |
| 22-27 | CH₃ | Cl | —CH₂—C(CH₃)₃ | Cl | Cl |
| 22-28 | CH₃ | Cl | Cl | —CH₂—C(CH₃)₃ | Cl |
| 22-29 | CH₃ | Cl | Cl | Cl | —CH₂—C(CH₃)₃ |
| 22-30 | CH₃ | Cl | —CH₂CF(CH₃)₂ | —CH₂CF(CH₃)₂ | —CHCF(CH₃)₂ |
| 22-31 | CH₃ | —CH₂CF(CH₃)₂ | Cl | —CH₂CF(CH₃)₂ | —CH₂CF(CH₃)₂ |
| 22-32 | CH₃ | —CH₂CF(CH₃)₂ | —CH₂CF(CH₃)₂ | Cl | —CH₂CF(CH₃)₂ |
| 22-33 | CH₃ | —CH₂CF(CH₃)₂ | —CH₂CF(CH₃)₂ | —CH₂CF(CH₃)₂ | Cl |
| 22-34 | CH₃ | —CH₂CF(CH₃)₂ | —CH₂CF(CH₃)₂ | Cl | Cl |
| 22-35 | CH₃ | Cl | —CH₂CF(CH₃)₂ | Cl | —CH₂CF(CH₃)₂ |
| 22-36 | CH₃ | —CH₂CF(CH₃)₂ | Cl | Cl | —CH₂CF(CH₃)₂ |
| 22-37 | CH₃ | Cl | —CH₂CF(CH₃)₂ | CH₂CF(CH₃)₂ | Cl |
| 22-38 | CH₃ | Cl | Cl | —CH₂CF(CH₃)₂ | —CH₂CF(CH₃)₂ |
| 22-39 | CH₃ | —CH₂CF(CH₃)₂ | —CH₂CF(CH₃)₂ | Cl | Cl |
| 22-40 | CH₃ | —CH₂CF(CH₃)₂ | Cl | Cl | Cl |
| 22-41 | CH₃ | Cl | —CH₂CF(CH₃)₂ | Cl | Cl |
| 22-42 | CH₃ | Cl | Cl | —CH₂CF(CH₃)₂ | Cl |
| 22-43 | CH₃ | Cl | Cl | Cl | —CH₂CF(CH₃)₂ |
| 22-44 | CH₃ | Cl | n-Propyl | n-Propyl | n-Propyl |
| 22-45 | CH₃ | n-Propyl | Cl | n-Propyl | n-Propyl |
| 22-46 | CH₃ | n-Propyl | n-Propyl | Cl | n-Propyl |
| 22-47 | CH₃ | n-Propyl | n-Propyl | n-Propyl | Cl |
| 22-48 | CH₃ | n-Propyl | Cl | n-Propyl | Cl |
| 22-49 | CH₃ | Cl | n-Propyl | Cl | n-Propyl |
| 22-50 | CH₃ | n-Propyl | Cl | Cl | n-Propyl |
| 22-51 | CH₃ | Cl | Cl | n-Propyl | n-Propyl |
| 22-52 | CH₃ | n-Propyl | n-Propyl | Cl | Cl |
| 22-53 | CH₃ | Cl | n-Propyl | n-Propyl | Cl |
| 22-54 | CH₃ | n-Propyl | Cl | Cl | Cl |
| 22-55 | CH₃ | Cl | n-Propyl | Cl | Cl |
| 22-56 | CH₃ | Cl | Cl | n-Propyl | Cl |
| 22-57 | CH₃ | Cl | Cl | Cl | n-Propyl |
| 22-58 | H | —CH₂CF(CH₃)₂ | Cl | —CH₂CF(CH₃)₂ | Cl |
| 22-59 | H | Cl | —CH₂CF(CH₃)₂ | —CH₂CF(CH₃)₂ | —CH₂CF(CH₃)₂ |
| 22-60 | H | —CH₂CF(CH₃)₂ | Cl | —CH₂CF(CH₃)₂ | —CH₂CF(CH₃)₂ |
| 22-61 | H | Cl | —CH₂CF(CH₃)₂ | —CH₂CF(CH₃)₂ | Cl |
| 22-62 | H | Cl | Cl | —CH₂CF(CH₃)₂ | —CH₂CF(CH₃)₂ |
| 22-63 | H | —CH₂CF(CH₃)₂ | —CH₂CF(CH₃)₂ | Cl | Cl |
| 22-64 | H | —CH₂—C(CH₃)₃ | Cl | —CH₂—C(CH₃)₃ | Cl |
| 22-65 | H | Cl | —CH₂—C(CH₃)₃ | Cl | —CH₂—C(CH₃)₃ |
| 22-66 | H | —CH₂—C(CH₃)₃ | Cl | Cl | —CH₂—C(CH₃)₃ |
| 22-67 | H | Cl | —CH₂—C(CH₃)₃ | —CH₂—C(CH₃)₃ | Cl |
| 22-68 | H | Cl | Cl | —CH₂—C(CH₃)₃ | —CH₂—C(CH₃)₃ |
| 22-69 | H | —CH₂—C(CH₃)₃ | —CH₂—C(CH₃)₃ | Cl | Cl |

TABLE 23

Compounds of formula (I), wherein Cy$^1$ and Cy$^2$ are p-bromophenyl;
R', R'', R''' and R'''' are each independently hydrogen or methyl;
and R$^a$, R$^b$ and R$^1$ to R$^4$ are as shown.

| Cmpd # | R$^a$/R$^b$ | R$^1$ | R$^2$ | R$^3$ | R$^4$ |
|---|---|---|---|---|---|
| 23-1 | CH$_3$ | Cl | Cl | Cl | Cl |
| 23-2 | CH$_3$ | Cl | —CH$_2$—iPr | —CH$_2$—iPr | —CH$_2$—iPr |
| 23-3 | CH$_3$ | —CH$_2$—iPr | Cl | —CH$_2$—iPr | —CH$_2$—iPr |
| 23-4 | CH$_3$ | —CH$_2$—iPr | —CH$_2$—iPr | Cl | —CH$_2$—iPr |
| 23-5 | CH$_3$ | —CH$_2$—iPr | —CH$_2$—iPr | —CH$_2$—iPr | Cl |
| 23-6 | CH$_3$ | —CH$_2$—iPr | Cl | —CH$_2$—iPr | Cl |
| 23-7 | CH$_3$ | Cl | —CH$_2$—iPr | Cl | —CH$_2$—iPr |
| 23-8 | CH$_3$ | —CH$_2$—iPr | Cl | Cl | —CH$_2$—iPr |
| 23-9 | CH$_3$ | Cl | Cl | —CH$_2$—iPr | —CH$_2$—iPr |
| 23-10 | CH$_3$ | —CH$_2$—iPr | —CH$_2$—iPr | Cl | Cl |
| 23-11 | CH$_3$ | Cl | —CH$_2$—iPr | —CH$_2$—iPr | Cl |
| 23-12 | CH$_3$ | —CH$_2$—iPr | Cl | Cl | Cl |
| 23-13 | CH$_3$ | Cl | —CH$_2$—iPr | Cl | Cl |
| 23-14 | CH$_3$ | Cl | Cl | —CH$_2$—iPr | Cl |
| 23-15 | CH$_3$ | Cl | Cl | Cl | —CH$_2$—iPr |
| 23-16 | CH$_3$ | Cl | —CH$_2$—C(CH$_3$)$_3$ | —CH$_2$—C(CH$_3$)$_3$ | —CH$_2$—C(CH$_3$)$_3$ |
| 23-17 | CH$_3$ | —CH$_2$—C(CH$_3$)$_3$ | Cl | —CH$_2$—C(CH$_3$)$_3$ | —CH$_2$—C(CH$_3$)$_3$ |
| 23-18 | CH$_3$ | —CH$_2$—C(CH$_3$)$_3$ | —CH$_2$—C(CH$_3$)$_3$ | Cl | —CH$_2$—C(CH$_3$)$_3$ |
| 23-19 | CH$_3$ | —CH$_2$—C(CH$_3$)$_3$ | —CH$_2$—C(CH$_3$)$_3$ | —CH$_2$—C(CH$_3$)$_3$ | Cl |
| 23-20 | CH$_3$ | —CH$_2$—C(CH$_3$)$_3$ | Cl | —CH$_2$—C(CH$_3$)$_3$ | Cl |
| 23-21 | CH$_3$ | Cl | —CH$_2$—C(CH$_3$)$_3$ | Cl | —CH$_2$—C(CH$_3$)$_3$ |
| 23-22 | CH$_3$ | —CH$_2$—C(CH$_3$)$_3$ | Cl | Cl | —CH$_2$—C(CH$_3$)$_3$ |
| 23-23 | CH$_3$ | Cl | —CH$_2$—C(CH$_3$)$_3$ | —CH$_2$—C(CH$_3$)$_3$ | Cl |
| 23-24 | CH$_3$ | Cl | Cl | —CH$_2$—C(CH$_3$)$_3$ | —CH$_2$—C(CH$_3$)$_3$ |
| 23-25 | CH$_3$ | —CH$_2$—C(CH$_3$)$_3$ | —CH$_2$—C(CH$_3$)$_3$ | Cl | Cl |
| 23-26 | CH$_3$ | —CH$_2$—C(CH$_3$)$_3$ | Cl | Cl | Cl |
| 23-27 | CH$_3$ | Cl | —CH$_2$—C(CH$_3$)$_3$ | Cl | Cl |
| 23-28 | CH$_3$ | Cl | Cl | —CH$_2$—C(CH$_3$)$_3$ | Cl |
| 23-29 | CH$_3$ | Cl | Cl | Cl | —CH$_2$—C(CH$_3$)$_3$ |
| 23-30 | CH$_3$ | Cl | —CH$_2$CF(CH$_3$)$_2$ | —CH$_2$CF(CH$_3$)$_2$ | —CHCF(CH$_3$)$_2$ |
| 23-31 | CH$_3$ | —CH$_2$CF(CH$_3$)$_2$ | Cl | —CH$_2$CF(CH$_3$)$_2$ | —CH$_2$CF(CH$_3$)$_2$ |
| 23-32 | CH$_3$ | —CH$_2$CF(CH$_3$)$_2$ | —CH$_2$CF(CH$_3$)$_2$ | Cl | —CH$_2$CF(CH$_3$)$_2$ |
| 23-33 | CH$_3$ | —CH$_2$CF(CH$_3$)$_2$ | —CH$_2$CF(CH$_3$)$_2$ | —CH$_2$CF(CH$_3$)$_2$ | Cl |
| 23-34 | CH$_3$ | —CH$_2$CF(CH$_3$)$_2$ | Cl | —CH$_2$CF(CH$_3$)$_2$ | Cl |
| 23-35 | CH$_3$ | Cl | —CH$_2$CF(CH$_3$)$_2$ | Cl | —CH$_2$CF(CH$_3$)$_2$ |
| 23-36 | CH$_3$ | —CH$_2$CF(CH$_3$)$_2$ | Cl | Cl | —CH$_2$CF(CH$_3$)$_2$ |
| 23-37 | CH$_3$ | Cl | —CH$_2$CF(CH$_3$)$_2$ | CH$_2$CF(CH$_3$)$_2$ | Cl |
| 23-38 | CH$_3$ | Cl | Cl | —CH$_2$CF(CH$_3$)$_2$ | —CH$_2$CF(CH$_3$)$_2$ |
| 23-39 | CH$_3$ | —CH$_2$CF(CH$_3$)$_2$ | —CH$_2$CF(CH$_3$)$_2$ | Cl | Cl |
| 23-40 | CH$_3$ | —CH$_2$CF(CH$_3$)$_2$ | Cl | Cl | Cl |
| 23-41 | CH$_3$ | Cl | —CH$_2$CF(CH$_3$)$_2$ | Cl | Cl |
| 23-42 | CH$_3$ | Cl | Cl | —CH$_2$CF(CH$_3$)$_2$ | Cl |
| 23-43 | CH$_3$ | Cl | Cl | Cl | —CH$_2$CF(CH$_3$)$_2$ |
| 23-44 | CH$_3$ | Cl | n-Propyl | n-Propyl | n-Propyl |
| 23-45 | CH$_3$ | n-Propyl | Cl | n-Propyl | n-Propyl |
| 23-46 | CH$_3$ | n-Propyl | n-Propyl | Cl | n-Propyl |
| 23-47 | CH$_3$ | n-Propyl | n-Propyl | n-Propyl | Cl |
| 23-48 | CH$_3$ | n-Propyl | Cl | n-Propyl | Cl |
| 23-49 | CH$_3$ | Cl | n-Propyl | Cl | n-Propyl |
| 23-50 | CH$_3$ | n-Propyl | Cl | Cl | n-Propyl |
| 23-51 | CH$_3$ | Cl | Cl | n-Propyl | n-Propyl |
| 23-52 | CH$_3$ | n-Propyl | n-Propyl | Cl | Cl |
| 23-53 | CH$_3$ | Cl | n-Propyl | n-Propyl | Cl |
| 23-54 | CH$_3$ | n-Propyl | Cl | Cl | Cl |
| 23-55 | CH$_3$ | Cl | n-Propyl | Cl | Cl |
| 23-56 | CH$_3$ | Cl | Cl | n-Propyl | Cl |
| 23-57 | CH$_3$ | Cl | Cl | Cl | n-Propyl |
| 23-58 | H | —CH$_2$CF(CH$_3$)$_2$ | Cl | —CH$_2$CF(CH$_3$)$_2$ | Cl |
| 23-59 | H | Cl | —CH$_2$CF(CH$_3$)$_2$ | —CH$_2$CF(CH$_3$)$_2$ | —CH$_2$CF(CH$_3$)$_2$ |
| 23-60 | H | —CH$_2$CF(CH$_3$)$_2$ | Cl | —CH$_2$CF(CH$_3$)$_2$ | —CH$_2$CF(CH$_3$)$_2$ |
| 23-61 | H | Cl | —CH$_2$CF(CH$_3$)$_2$ | —CH$_2$CF(CH$_3$)$_2$ | Cl |
| 23-62 | H | Cl | Cl | —CH$_2$CF(CH$_3$)$_2$ | —CH$_2$CF(CH$_3$)$_2$ |
| 23-63 | H | —CH$_2$CF(CH$_3$)$_2$ | —CH$_2$CF(CH$_3$)$_2$ | Cl | Cl |
| 23-64 | H | —CH$_2$—C(CH$_3$)$_3$ | Cl | —CH$_2$—C(CH$_3$)$_3$ | Cl |
| 23-65 | H | Cl | —CH$_2$—C(CH$_3$)$_3$ | Cl | —CH$_2$—C(CH$_3$)$_3$ |
| 23-66 | H | —CH$_2$—C(CH$_3$)$_3$ | Cl | Cl | —CH$_2$—C(CH$_3$)$_3$ |
| 23-67 | H | Cl | —CH$_2$—C(CH$_3$)$_3$ | —CH$_2$—C(CH$_3$)$_3$ | Cl |
| 23-68 | H | Cl | Cl | —CH$_2$—C(CH$_3$)$_3$ | —CH$_2$—C(CH$_3$)$_3$ |
| 23-69 | H | —CH$_2$—C(CH$_3$)$_3$ | —CH$_2$—C(CH$_3$)$_3$ | Cl | Cl |

TABLE 24

Compounds of formula (I), wherein Cy$^1$ and Cy$^2$ are p-cyanophenyl;
R', R", R''' and R'''' are each independently hydrogen or methyl;
and R$^a$, R$^b$ and R$^1$ to R$^4$ are as shown.

| Cmpd # | R$^a$/R$^b$ | R$^1$ | R$^2$ | R$^3$ | R$^4$ |
|---|---|---|---|---|---|
| 24-1 | CH$_3$ | Cl | Cl | Cl | Cl |
| 24-2 | CH$_3$ | Cl | —CH$_2$—iPr | —CH$_2$—iPr | —CH$_2$—iPr |
| 24-3 | CH$_3$ | —CH$_2$—iPr | Cl | —CH$_2$—iPr | —CH$_2$—iPr |
| 24-4 | CH$_3$ | —CH$_2$—iPr | —CH$_2$—iPr | Cl | —CH$_2$—iPr |
| 24-5 | CH$_3$ | —CH$_2$—iPr | —CH$_2$—iPr | —CH$_2$—iPr | Cl |
| 24-6 | CH$_3$ | —CH$_2$—iPr | Cl | —CH$_2$—iPr | Cl |
| 24-7 | CH$_3$ | Cl | —CH$_2$—iPr | Cl | —CH$_2$—iPr |
| 24-8 | CH$_3$ | —CH$_2$—iPr | Cl | Cl | —CH$_2$—iPr |
| 24-9 | CH$_3$ | Cl | Cl | —CH$_2$—iPr | —CH$_2$—iPr |
| 24-10 | CH$_3$ | —CH$_2$—iPr | —CH$_2$—iPr | Cl | Cl |
| 24-11 | CH$_3$ | Cl | —CH$_2$—iPr | —CH$_2$—iPr | Cl |
| 24-12 | CH$_3$ | —CH$_2$—iPr | Cl | Cl | Cl |
| 24-13 | CH$_3$ | Cl | —CH$_2$—iPr | Cl | Cl |
| 24-14 | CH$_3$ | Cl | Cl | —CH$_2$—iPr | Cl |
| 24-15 | CH$_3$ | Cl | Cl | Cl | —CH$_2$—iPr |
| 24-16 | CH$_3$ | Cl | —CH$_2$—C(CH$_3$)$_3$ | —CH$_2$—C(CH$_3$)$_3$ | —CH$_2$—C(CH$_3$)$_3$ |
| 24-17 | CH$_3$ | —CH$_2$—C(CH$_3$)$_3$ | Cl | —CH$_2$—C(CH$_3$)$_3$ | —CH$_2$—C(CH$_3$)$_3$ |
| 24-18 | CH$_3$ | —CH$_2$—C(CH$_3$)$_3$ | —CH$_2$—C(CH$_3$)$_3$ | Cl | —CH$_2$—C(CH$_3$)$_3$ |
| 24-19 | CH$_3$ | —CH$_2$—C(CH$_3$)$_3$ | —CH$_2$—C(CH$_3$)$_3$ | —CH$_2$—C(CH$_3$)$_3$ | Cl |
| 24-20 | CH$_3$ | —CH$_2$—C(CH$_3$)$_3$ | Cl | —CH$_2$—C(CH$_3$)$_3$ | Cl |
| 24-21 | CH$_3$ | Cl | —CH$_2$—C(CH$_3$)$_3$ | Cl | —CH$_2$—C(CH$_3$)$_3$ |
| 24-22 | CH$_3$ | —CH$_2$—C(CH$_3$)$_3$ | Cl | Cl | —CH$_2$—C(CH$_3$)$_3$ |
| 24-23 | CH$_3$ | Cl | —CH$_2$—C(CH$_3$)$_3$ | —CH$_2$—C(CH$_3$)$_3$ | Cl |
| 24-24 | CH$_3$ | Cl | Cl | —CH$_2$—C(CH$_3$)$_3$ | —CH$_2$—C(CH$_3$)$_3$ |
| 24-25 | CH$_3$ | —CH$_2$—C(CH$_3$)$_3$ | —CH$_2$—C(CH$_3$)$_3$ | Cl | Cl |
| 24-26 | CH$_3$ | —CH$_2$—C(CH$_3$)$_3$ | Cl | Cl | Cl |
| 24-27 | CH$_3$ | Cl | —CH$_2$—C(CH$_3$)$_3$ | Cl | Cl |
| 24-28 | CH$_3$ | Cl | Cl | —CH$_2$—C(CH$_3$)$_3$ | Cl |
| 24-29 | CH$_3$ | Cl | Cl | Cl | —CH$_2$—C(CH$_3$)$_3$ |
| 24-30 | CH$_3$ | Cl | —CH$_2$CF(CH$_3$)$_2$ | —CH$_2$CF(CH$_3$)$_2$ | —CHCF(CH$_3$)$_2$ |
| 24-31 | CH$_3$ | —CH$_2$CF(CH$_3$)$_2$ | Cl | —CH$_2$CF(CH$_3$)$_2$ | —CH$_2$CF(CH$_3$)$_2$ |
| 24-32 | CH$_3$ | —CH$_2$CF(CH$_3$)$_2$ | —CH$_2$CF(CH$_3$)$_2$ | Cl | —CH$_2$CF(CH$_3$)$_2$ |
| 24-33 | CH$_3$ | —CH$_2$CF(CH$_3$)$_2$ | —CH$_2$CF(CH$_3$)$_2$ | —CH$_2$CF(CH$_3$)$_2$ | Cl |
| 24-34 | CH$_3$ | —CH$_2$CF(CH$_3$)$_2$ | Cl | —CH$_2$CF(CH$_3$)$_2$ | Cl |
| 24-35 | CH$_3$ | Cl | —CH$_2$CF(CH$_3$)$_2$ | Cl | —CH$_2$CF(CH$_3$)$_2$ |
| 24-36 | CH$_3$ | —CH$_2$CF(CH$_3$)$_2$ | Cl | Cl | —CH$_2$CF(CH$_3$)$_2$ |
| 24-37 | CH$_3$ | Cl | —CH$_2$CF(CH$_3$)$_2$ | CH$_2$CF(CH$_3$)$_2$ | Cl |
| 24-38 | CH$_3$ | Cl | Cl | —CH$_2$CF(CH$_3$)$_2$ | —CH$_2$CF(CH$_3$)$_2$ |
| 24-39 | CH$_3$ | —CH$_2$CF(CH$_3$)$_2$ | —CH$_2$CF(CH$_3$)$_2$ | Cl | Cl |
| 24-40 | CH$_3$ | —CH$_2$CF(CH$_3$)$_2$ | Cl | Cl | Cl |
| 24-41 | CH$_3$ | Cl | —CH$_2$CF(CH$_3$)$_2$ | Cl | Cl |
| 24-42 | CH$_3$ | Cl | Cl | —CH$_2$CF(CH$_3$)$_2$ | Cl |
| 24-43 | CH$_3$ | Cl | Cl | Cl | —CH$_2$CF(CH$_3$)$_2$ |
| 24-44 | CH$_3$ | Cl | n-Propyl | n-Propyl | n-Propyl |
| 24-45 | CH$_3$ | n-Propyl | Cl | n-Propyl | n-Propyl |
| 24-46 | CH$_3$ | n-Propyl | n-Propyl | Cl | n-Propyl |
| 24-47 | CH$_3$ | n-Propyl | n-Propyl | n-Propyl | Cl |
| 24-48 | CH$_3$ | n-Propyl | Cl | n-Propyl | Cl |
| 24-49 | CH$_3$ | Cl | n-Propyl | Cl | n-Propyl |
| 24-50 | CH$_3$ | n-Propyl | Cl | Cl | n-Propyl |
| 24-51 | CH$_3$ | Cl | Cl | n-Propyl | n-Propyl |
| 24-52 | CH$_3$ | n-Propyl | n-Propyl | Cl | Cl |
| 24-53 | CH$_3$ | Cl | n-Propyl | n-Propyl | Cl |
| 24-54 | CH$_3$ | n-Propyl | Cl | Cl | Cl |
| 24-55 | CH$_3$ | Cl | n-Propyl | Cl | Cl |
| 24-56 | CH$_3$ | Cl | Cl | n-Propyl | Cl |
| 24-57 | CH$_3$ | Cl | Cl | Cl | n-Propyl |
| 24-58 | H | —CH$_2$CF(CH$_3$)$_2$ | Cl | —CH$_2$CF(CH$_3$)$_2$ | Cl |
| 24-59 | H | Cl | —CH$_2$CF(CH$_3$)$_2$ | Cl | —CH$_2$CF(CH$_3$)$_2$ |
| 24-60 | H | —CH$_2$CF(CH$_3$)$_2$ | Cl | Cl | —CH$_2$CF(CH$_3$)$_2$ |
| 24-61 | H | Cl | —CH$_2$CF(CH$_3$)$_2$ | —CH$_2$CF(CH$_3$)$_2$ | Cl |
| 24-62 | H | Cl | Cl | —CH$_2$CF(CH$_3$)$_2$ | —CH$_2$CF(CH$_3$)$_2$ |
| 24-63 | H | —CH$_2$CF(CH$_3$)$_2$ | —CH$_2$CF(CH$_3$)$_2$ | Cl | Cl |
| 24-64 | H | —CH$_2$—C(CH$_3$)$_3$ | Cl | —CH$_2$—C(CH$_3$)$_3$ | Cl |
| 24-65 | H | Cl | —CH$_2$—C(CH$_3$)$_3$ | Cl | —CH$_2$—C(CH$_3$)$_3$ |
| 24-66 | H | —CH$_2$—C(CH$_3$)$_3$ | Cl | Cl | —CH$_2$—C(CH$_3$)$_3$ |
| 24-67 | H | Cl | —CH$_2$—C(CH$_3$)$_3$ | —CH$_2$—C(CH$_3$)$_3$ | Cl |
| 24-68 | H | Cl | Cl | —CH$_2$—C(CH$_3$)$_3$ | —CH$_2$—C(CH$_3$)$_3$ |
| 24-69 | H | —CH$_2$—C(CH$_3$)$_3$ | —CH$_2$—C(CH$_3$)$_3$ | Cl | Cl |

TABLE 25

Compounds of formula (I), wherein $Cy^1$ and $Cy^2$ are

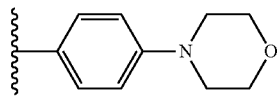

and unsubstituted phenyl, respectively; R', R'', R''' and R'''' are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 25-1 | CH₃ | Cl | Cl | Cl | Cl |
| 25-2 | CH₃ | Cl | —CH₂—iPr | —CH₂—iPr | —CH₂—iPr |
| 25-3 | CH₃ | —CH₂—iPr | Cl | —CH₂—iPr | —CH₂—iPr |
| 25-4 | CH₃ | —CH₂—iPr | —CH₂—iPr | Cl | —CH₂—iPr |
| 25-5 | CH₃ | —CH₂—iPr | —CH₂—iPr | —CH₂—iPr | Cl |
| 25-6 | CH₃ | —CH₂—iPr | Cl | —CH₂—iPr | Cl |
| 25-7 | CH₃ | Cl | —CH₂—iPr | Cl | —CH₂—iPr |
| 25-8 | CH₃ | —CH₂—iPr | Cl | Cl | —CH₂—iPr |
| 25-9 | CH₃ | Cl | Cl | —CH₂—iPr | —CH₂—iPr |
| 25-10 | CH₃ | —CH₂—iPr | —CH₂—iPr | Cl | Cl |
| 25-11 | CH₃ | Cl | —CH₂—iPr | —CH₂—iPr | Cl |
| 25-12 | CH₃ | —CH₂—iPr | Cl | Cl | Cl |
| 25-13 | CH₃ | Cl | —CH₂—iPr | Cl | Cl |
| 25-14 | CH₃ | Cl | Cl | —CH₂—iPr | Cl |
| 25-15 | CH₃ | Cl | Cl | Cl | —CH₂—iPr |
| 25-16 | CH₃ | Cl | —CH₂—C(CH₃)₃ | —CH₂—C(CH₃)₃ | —CH₂—C(CH₃)₃ |
| 25-17 | CH₃ | —CH₂—C(CH₃)₃ | Cl | —CH₂—C(CH₃)₃ | —CH₂—C(CH₃)₃ |
| 25-18 | CH₃ | —CH₂—C(CH₃)₃ | —CH₂—C(CH₃)₃ | Cl | —CH₂—C(CH₃)₃ |
| 25-19 | CH₃ | —CH₂—C(CH₃)₃ | —CH₂—C(CH₃)₃ | —CH₂—C(CH₃)₃ | Cl |
| 25-20 | CH₃ | —CH₂—C(CH₃)₃ | Cl | —CH₂—C(CH₃)₃ | Cl |
| 25-21 | CH₃ | Cl | —CH₂—C(CH₃)₃ | Cl | —CH₂—C(CH₃)₃ |
| 25-22 | CH₃ | —CH₂—C(CH₃)₃ | Cl | Cl | —CH₂—C(CH₃)₃ |
| 25-23 | CH₃ | Cl | —CH₂—C(CH₃)₃ | —CH₂—C(CH₃)₃ | Cl |
| 25-24 | CH₃ | Cl | Cl | —CH₂—C(CH₃)₃ | —CH₂—C(CH₃)₃ |
| 25-25 | CH₃ | —CH₂—C(CH₃)₃ | —CH₂—C(CH₃)₃ | Cl | Cl |
| 25-26 | CH₃ | —CH₂—C(CH₃)₃ | Cl | Cl | Cl |
| 25-27 | CH₃ | Cl | —CH₂—C(CH₃)₃ | Cl | Cl |
| 25-28 | CH₃ | Cl | Cl | —CH₂—C(CH₃)₃ | Cl |
| 25-29 | CH₃ | Cl | Cl | Cl | —CH₂—C(CH₃)₃ |
| 25-30 | CH₃ | Cl | —CH₂CF(CH₃)₂ | —CH₂CF(CH₃)₂ | —CHCF(CH₃)₂ |
| 25-31 | CH₃ | —CH₂CF(CH₃)₂ | Cl | —CH₂CF(CH₃)₂ | —CH₂CF(CH₃)₂ |
| 25-32 | CH₃ | —CH₂CF(CH₃)₂ | —CH₂CF(CH₃)₂ | Cl | —CH₂CF(CH₃)₂ |
| 25-33 | CH₃ | —CH₂CF(CH₃)₂ | —CH₂CF(CH₃)₂ | —CH₂CF(CH₃)₂ | Cl |
| 25-34 | CH₃ | —CH₂CF(CH₃)₂ | Cl | —CH₂CF(CH₃)₂ | Cl |
| 25-35 | CH₃ | Cl | —CH₂CF(CH₃)₂ | Cl | —CH₂CF(CH₃)₂ |
| 25-36 | CH₃ | —CH₂CF(CH₃)₂ | Cl | Cl | —CH₂CF(CH₃)₂ |
| 25-37 | CH₃ | Cl | —CH₂CF(CH₃)₂ | CH₂CF(CH₃)₂ | Cl |
| 25-38 | CH₃ | Cl | Cl | —CH₂CF(CH₃)₂ | —CH₂CF(CH₃)₂ |
| 25-39 | CH₃ | —CH₂CF(CH₃)₂ | —CH₂CF(CH₃)₂ | Cl | Cl |
| 25-40 | CH₃ | —CH₂CF(CH₃)₂ | Cl | Cl | Cl |
| 25-41 | CH₃ | Cl | —CH₂CF(CH₃)₂ | Cl | Cl |
| 25-42 | CH₃ | Cl | Cl | —CH₂CF(CH₃)₂ | Cl |
| 25-43 | CH₃ | Cl | Cl | Cl | —CH₂CF(CH₃)₂ |
| 25-44 | CH₃ | Cl | n-Propyl | n-Propyl | n-Propyl |
| 25-45 | CH₃ | n-Propyl | Cl | n-Propyl | n-Propyl |
| 25-46 | CH₃ | n-Propyl | n-Propyl | Cl | n-Propyl |
| 25-47 | CH₃ | n-Propyl | n-Propyl | n-Propyl | Cl |
| 25-48 | CH₃ | n-Propyl | Cl | n-Propyl | Cl |
| 25-49 | CH₃ | Cl | n-Propyl | Cl | n-Propyl |
| 25-50 | CH₃ | n-Propyl | Cl | Cl | n-Propyl |
| 25-51 | CH₃ | Cl | Cl | n-Propyl | n-Propyl |
| 25-52 | CH₃ | n-Propyl | n-Propyl | Cl | Cl |
| 25-53 | CH₃ | Cl | n-Propyl | n-Propyl | Cl |
| 25-54 | CH₃ | n-Propyl | Cl | Cl | Cl |
| 25-55 | CH₃ | Cl | n-Propyl | Cl | Cl |
| 25-56 | CH₃ | Cl | Cl | n-Propyl | Cl |
| 25-57 | CH₃ | Cl | Cl | Cl | n-Propyl |
| 25-58 | H | —CH₂CF(CH₃)₂ | Cl | —CH₂CF(CH₃)₂ | Cl |
| 25-59 | H | Cl | —CH₂CF(CH₃)₂ | Cl | —CH₂CF(CH₃)₂ |
| 25-60 | H | —CH₂CF(CH₃)₂ | Cl | Cl | —CH₂CF(CH₃)₂ |
| 25-61 | H | Cl | —CH₂CF(CH₃)₂ | —CH₂CF(CH₃)₂ | Cl |
| 25-62 | H | Cl | Cl | —CH₂CF(CH₃)₂ | —CH₂CF(CH₃)₂ |
| 25-63 | H | —CH₂CF(CH₃)₂ | —CH₂CF(CH₃)₂ | Cl | Cl |
| 25-64 | H | —CH₂—C(CH₃)₃ | Cl | —CH₂—C(CH₃)₃ | Cl |
| 25-65 | H | Cl | —CH₂—C(CH₃)₃ | Cl | —CH₂—C(CH₃)₃ |
| 25-66 | H | —CH₂—C(CH₃)₃ | Cl | Cl | —CH₂—C(CH₃)₃ |
| 25-67 | H | Cl | —CH₂—C(CH₃)₃ | —CH₂—C(CH₃)₃ | Cl |

TABLE 25-continued

Compounds of formula (I), wherein Cy$^1$ and Cy$^2$ are and unsubstituted phenyl, respectively; R', R'', R''' and R''''
are each independently hydrogen or methyl; and R$^a$, R$^b$ and R$^1$ to R$^4$ are as shown.

| Cmpd # | R$^a$/R$^b$ | R$^1$ | R$^2$ | R$^3$ | R$^4$ |
|---|---|---|---|---|---|
| 25-68 | H | Cl | Cl | —CH$_2$—C(CH$_3$)$_3$ | —CH$_2$—C(CH$_3$)$_3$ |
| 25-69 | H | —CH$_2$—C(CH$_3$)$_3$ | —CH$_2$—C(CH$_3$)$_3$ | Cl | Cl |

TABLE 26

Compounds of formula (I), wherein Cy$^1$ and Cy$^2$ are and p-iodophenyl, respectively; R', R'', R''' and R'''' are
each independently hydrogen or methyl; and R$^a$, R$^b$ and R$^1$ to R$^4$ are as shown.

| Cmpd # | R$^a$/R$^b$ | R$^1$ | R$^2$ | R$^3$ | R$^4$ |
|---|---|---|---|---|---|
| 26-1 | CH$_3$ | Cl | Cl | Cl | Cl |
| 26-2 | CH$_3$ | Cl | —CH$_2$—iPr | —CH$_2$—iPr | —CH$_2$—iPr |
| 26-3 | CH$_3$ | —CH$_2$—iPr | Cl | —CH$_2$—iPr | —CH$_2$—iPr |
| 26-4 | CH$_3$ | —CH$_2$—iPr | —CH$_2$—iPr | Cl | —CH$_2$—iPr |
| 26-5 | CH$_3$ | —CH$_2$—iPr | —CH$_2$—iPr | —CH$_2$—iPr | Cl |
| 26-6 | CH$_3$ | —CH$_2$—iPr | Cl | —CH$_2$—iPr | Cl |
| 26-7 | CH$_3$ | Cl | —CH$_2$—iPr | Cl | —CH$_2$—iPr |
| 26-8 | CH$_3$ | —CH$_2$—iPr | Cl | Cl | —CH$_2$—iPr |
| 26-9 | CH$_3$ | Cl | Cl | —CH$_2$—iPr | —CH$_2$—iPr |
| 26-10 | CH$_3$ | —CH$_2$—iPr | —CH$_2$—iPr | Cl | Cl |
| 26-11 | CH$_3$ | Cl | —CH$_2$—iPr | —CH$_2$—iPr | Cl |
| 26-12 | CH$_3$ | —CH$_2$—iPr | Cl | Cl | Cl |
| 26-13 | CH$_3$ | Cl | —CH$_2$—iPr | Cl | Cl |
| 26-14 | CH$_3$ | Cl | Cl | —CH$_2$—iPr | Cl |
| 26-15 | CH$_3$ | Cl | Cl | Cl | —CH$_2$—iPr |
| 26-16 | CH$_3$ | Cl | —CH$_2$—C(CH$_3$)$_3$ | —CH$_2$—C(CH$_3$)$_3$ | —CH$_2$—C(CH$_3$)$_3$ |
| 26-17 | CH$_3$ | —CH$_2$—C(CH$_3$)$_3$ | Cl | —CH$_2$—C(CH$_3$)$_3$ | —CH$_2$—C(CH$_3$)$_3$ |
| 26-18 | CH$_3$ | —CH$_2$—C(CH$_3$)$_3$ | —CH$_2$—C(CH$_3$)$_3$ | Cl | —CH$_2$—C(CH$_3$)$_3$ |
| 26-19 | CH$_3$ | —CH$_2$—C(CH$_3$)$_3$ | —CH$_2$—C(CH$_3$)$_3$ | —CH$_2$—C(CH$_3$)$_3$ | Cl |
| 26-20 | CH$_3$ | —CH$_2$—C(CH$_3$)$_3$ | Cl | —CH$_2$—C(CH$_3$)$_3$ | Cl |
| 26-21 | CH$_3$ | Cl | —CH$_2$—C(CH$_3$)$_3$ | Cl | —CH$_2$—C(CH$_3$)$_3$ |
| 26-22 | CH$_3$ | —CH$_2$—C(CH$_3$)$_3$ | Cl | Cl | —CH$_2$—C(CH$_3$)$_3$ |
| 26-23 | CH$_3$ | Cl | —CH$_2$—C(CH$_3$)$_3$ | —CH$_2$—C(CH$_3$)$_3$ | Cl |
| 26-24 | CH$_3$ | Cl | Cl | —CH$_2$—C(CH$_3$)$_3$ | —CH$_2$—C(CH$_3$)$_3$ |
| 26-25 | CH$_3$ | —CH$_2$—C(CH$_3$)$_3$ | —CH$_2$—C(CH$_3$)$_3$ | Cl | Cl |
| 26-26 | CH$_3$ | —CH$_2$—C(CH$_3$)$_3$ | Cl | Cl | Cl |
| 26-27 | CH$_3$ | Cl | —CH$_2$—C(CH$_3$)$_3$ | Cl | Cl |
| 26-28 | CH$_3$ | Cl | Cl | —CH$_2$—C(CH$_3$)$_3$ | Cl |
| 26-29 | CH$_3$ | Cl | Cl | Cl | —CH$_2$—C(CH$_3$)$_3$ |
| 26-30 | CH$_3$ | Cl | —CH$_2$CF(CH$_3$)$_2$ | —CH$_2$CF(CH$_3$)$_2$ | —CHCF(CH$_3$)$_2$ |
| 26-31 | CH$_3$ | —CH$_2$CF(CH$_3$)$_2$ | Cl | —CH$_2$CF(CH$_3$)$_2$ | —CH$_2$CF(CH$_3$)$_2$ |
| 26-32 | CH$_3$ | —CH$_2$CF(CH$_3$)$_2$ | —CH$_2$CF(CH$_3$)$_2$ | Cl | —CH$_2$CF(CH$_3$)$_2$ |
| 26-33 | CH$_3$ | —CH$_2$CF(CH$_3$)$_2$ | —CH$_2$CF(CH$_3$)$_2$ | —CH$_2$CF(CH$_3$)$_2$ | Cl |
| 26-34 | CH$_3$ | —CH$_2$CF(CH$_3$)$_2$ | Cl | —CH$_2$CF(CH$_3$)$_2$ | Cl |
| 26-35 | CH$_3$ | Cl | —CH$_2$CF(CH$_3$)$_2$ | Cl | —CH$_2$CF(CH$_3$)$_2$ |
| 26-36 | CH$_3$ | —CH$_2$CF(CH$_3$)$_2$ | Cl | Cl | —CH$_2$CF(CH$_3$)$_2$ |
| 26-37 | CH$_3$ | Cl | —CH$_2$CF(CH$_3$)$_2$ | CH$_2$CF(CH$_3$)$_2$ | Cl |
| 26-38 | CH$_3$ | Cl | Cl | —CH$_2$CF(CH$_3$)$_2$ | —CH$_2$CF(CH$_3$)$_2$ |
| 26-39 | CH$_3$ | —CH$_2$CF(CH$_3$)$_2$ | —CH$_2$CF(CH$_3$)$_2$ | Cl | Cl |
| 26-40 | CH$_3$ | —CH$_2$CF(CH$_3$)$_2$ | Cl | Cl | Cl |
| 26-41 | CH$_3$ | Cl | —CH$_2$CF(CH$_3$)$_2$ | Cl | Cl |
| 26-42 | CH$_3$ | Cl | Cl | —CH$_2$CF(CH$_3$)$_2$ | Cl |
| 26-43 | CH$_3$ | Cl | Cl | Cl | —CH$_2$CF(CH$_3$)$_2$ |
| 26-44 | CH$_3$ | Cl | n-Propyl | n-Propyl | n-Propyl |
| 26-45 | CH$_3$ | n-Propyl | Cl | n-Propyl | n-Propyl |

TABLE 26-continued

Compounds of formula (I), wherein $Cy^1$ and $Cy^2$ are

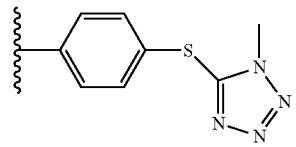

and p-iodophenyl, respectively; R', R'', R''' and R'''' are
each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 26-46 | CH₃ | n-Propyl | n-Propyl | Cl | n-Propyl |
| 26-47 | CH₃ | n-Propyl | n-Propyl | n-Propyl | Cl |
| 26-48 | CH₃ | n-Propyl | Cl | n-Propyl | Cl |
| 26-49 | CH₃ | Cl | n-Propyl | Cl | n-Propyl |
| 26-50 | CH₃ | n-Propyl | Cl | Cl | n-Propyl |
| 26-51 | CH₃ | Cl | Cl | n-Propyl | n-Propyl |
| 26-52 | CH₃ | n-Propyl | n-Propyl | Cl | Cl |
| 26-53 | CH₃ | Cl | n-Propyl | n-Propyl | Cl |
| 26-54 | CH₃ | n-Propyl | Cl | Cl | Cl |
| 26-55 | CH₃ | Cl | n-Propyl | Cl | Cl |
| 26-56 | CH₃ | Cl | Cl | n-Propyl | Cl |
| 26-57 | CH₃ | Cl | Cl | Cl | n-Propyl |
| 26-58 | H | —CH₂CF(CH₃)₂ | Cl | —CH₂CF(CH₃)₂ | Cl |
| 26-59 | H | Cl | —CH₂CF(CH₃)₂ | Cl | —CH₂CF(CH₃)₂ |
| 26-60 | H | —CH₂CF(CH₃)₂ | Cl | Cl | —CH₂CF(CH₃)₂ |
| 26-61 | H | Cl | —CH₂CF(CH₃)₂ | —CH₂CF(CH₃)₂ | Cl |
| 26-62 | H | Cl | Cl | —CH₂CF(CH₃)₂ | —CH₂CF(CH₃)₂ |
| 26-63 | H | —CH₂CF(CH₃)₂ | —CH₂CF(CH₃)₂ | Cl | Cl |
| 26-64 | H | —CH₂—C(CH₃)₃ | Cl | —CH₂—C(CH₃)₃ | Cl |
| 26-65 | H | Cl | —CH₂—C(CH₃)₃ | Cl | —CH₂—C(CH₃)₃ |
| 26-66 | H | —CH₂—C(CH₃)₃ | Cl | Cl | —CH₂—C(CH₃)₃ |
| 26-67 | H | Cl | —CH₂—C(CH₃)₃ | —CH₂—C(CH₃)₃ | Cl |
| 26-68 | H | Cl | Cl | —CH₂—C(CH₃)₃ | —CH₂—C(CH₃)₃ |
| 26-69 | H | —CH₂—C(CH₃)₃ | —CH₂—C(CH₃)₃ | Cl | Cl |

TABLE 27

Compounds of formula (I), wherein $Cy^1$ and $Cy^2$ are

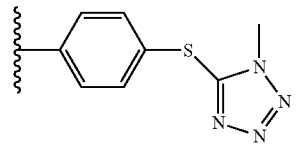 [SMILES: *c1ccc(Sc2nnnn2C)cc1]

and unsubstituted phenyl, respectively; R', R'', R''' and R''''
are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 27-1 | CH₃ | Cl | Cl | Cl | Cl |
| 27-2 | CH₃ | Cl | —CH₂—iPr | —CH₂—iPr | —CH₂—iPr |
| 27-3 | CH₃ | —CH₂—iPr | Cl | —CH₂—iPr | —CH₂—iPr |
| 27-4 | CH₃ | —CH₂—iPr | —CH₂—iPr | Cl | —CH₂—iPr |
| 27-5 | CH₃ | —CH₂—iPr | —CH₂—iPr | —CH₂—iPr | Cl |
| 27-6 | CH₃ | —CH₂—iPr | Cl | —CH₂—iPr | Cl |
| 27-7 | CH₃ | Cl | —CH₂—iPr | Cl | —CH₂—iPr |
| 27-8 | CH₃ | —CH₂—iPr | Cl | Cl | —CH₂—iPr |
| 27-9 | CH₃ | Cl | Cl | —CH₂—iPr | —CH₂—iPr |
| 27-10 | CH₃ | —CH₂—iPr | —CH₂—iPr | Cl | Cl |
| 27-11 | CH₃ | Cl | —CH₂—iPr | —CH₂—iPr | Cl |
| 27-12 | CH₃ | —CH₂—iPr | Cl | Cl | Cl |
| 27-13 | CH₃ | Cl | —CH₂—iPr | Cl | Cl |
| 27-14 | CH₃ | Cl | Cl | —CH₂—iPr | Cl |
| 27-15 | CH₃ | Cl | Cl | Cl | —CH₂—iPr |
| 27-16 | CH₃ | Cl | —CH₂—C(CH₃)₃ | —CH₂—C(CH₃)₃ | —CH₂—C(CH₃)₃ |
| 27-17 | CH₃ | —CH₂—C(CH₃)₃ | Cl | —CH₂—C(CH₃)₃ | —CH₂—C(CH₃)₃ |
| 27-18 | CH₃ | —CH₂—C(CH₃)₃ | —CH₂—C(CH₃)₃ | Cl | —CH₂—C(CH₃)₃ |
| 27-19 | CH₃ | —CH₂—C(CH₃)₃ | —CH₂—C(CH₃)₃ | —CH₂—C(CH₃)₃ | Cl |
| 27-20 | CH₃ | —CH₂—C(CH₃)₃ | Cl | —CH₂—C(CH₃)₃ | Cl |
| 27-21 | CH₃ | Cl | —CH₂—C(CH₃)₃ | Cl | —CH₂—C(CH₃)₃ |

TABLE 27-continued

Compounds of formula (I), wherein Cy¹ and Cy² are

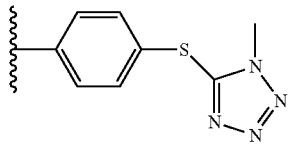 [SMILES: *c1ccc(Sc2nnnn2C)cc1]

and unsubstituted phenyl, respectively; R', R", R''' and R'''' are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 27-22 | CH₃ | —CH₂—C(CH₃)₃ | Cl | Cl | —CH₂—C(CH₃)₃ |
| 27-23 | CH₃ | Cl | —CH₂—C(CH₃)₃ | —CH₂—C(CH₃)₃ | Cl |
| 27-24 | CH₃ | Cl | Cl | —CH₂—C(CH₃)₃ | —CH₂—C(CH₃)₃ |
| 27-25 | CH₃ | —CH₂—C(CH₃)₃ | —CH₂—C(CH₃)₃ | Cl | Cl |
| 27-26 | CH₃ | —CH₂—C(CH₃)₃ | Cl | Cl | Cl |
| 27-27 | CH₃ | Cl | —CH₂—C(CH₃)₃ | Cl | Cl |
| 27-28 | CH₃ | Cl | Cl | —CH₂—C(CH₃)₃ | Cl |
| 27-29 | CH₃ | Cl | Cl | Cl | —CH₂—C(CH₃)₃ |
| 27-30 | CH₃ | Cl | —CH₂CF(CH₃)₂ | —CH₂CF(CH₃)₂ | —CHCF(CH₃)₂ |
| 27-31 | CH₃ | —CH₂CF(CH₃)₂ | Cl | —CH₂CF(CH₃)₂ | —CH₂CF(CH₃)₂ |
| 27-32 | CH₃ | —CH₂CF(CH₃)₂ | —CH₂CF(CH₃)₂ | Cl | —CH₂CF(CH₃)₂ |
| 27-33 | CH₃ | —CH₂CF(CH₃)₂ | —CH₂CF(CH₃)₂ | —CH₂CF(CH₃)₂ | Cl |
| 27-34 | CH₃ | —CH₂CF(CH₃)₂ | Cl | —CH₂CF(CH₃)₂ | Cl |
| 27-35 | CH₃ | Cl | —CH₂CF(CH₃)₂ | Cl | —CH₂CF(CH₃)₂ |
| 27-36 | CH₃ | —CH₂CF(CH₃)₂ | Cl | Cl | —CH₂CF(CH₃)₂ |
| 27-37 | CH₃ | Cl | —CH₂CF(CH₃)₂ | CH₂CF(CH₃)₂ | Cl |
| 27-38 | CH₃ | Cl | Cl | —CH₂CF(CH₃)₂ | —CH₂CF(CH₃)₂ |
| 27-39 | CH₃ | —CH₂CF(CH₃)₂ | —CH₂CF(CH₃)₂ | Cl | Cl |
| 27-40 | CH₃ | —CH₂CF(CH₃)₂ | Cl | Cl | Cl |
| 27-41 | CH₃ | Cl | —CH₂CF(CH₃)₂ | Cl | Cl |
| 27-42 | CH₃ | Cl | Cl | —CH₂CF(CH₃)₂ | Cl |
| 27-43 | CH₃ | Cl | Cl | Cl | —CH₂CF(CH₃)₂ |
| 27-44 | CH₃ | Cl | n-Propyl | n-Propyl | n-Propyl |
| 27-45 | CH₃ | n-Propyl | Cl | n-Propyl | n-Propyl |
| 27-46 | CH₃ | n-Propyl | n-Propyl | Cl | n-Propyl |
| 27-47 | CH₃ | n-Propyl | n-Propyl | n-Propyl | Cl |
| 27-48 | CH₃ | n-Propyl | Cl | n-Propyl | Cl |
| 27-49 | CH₃ | Cl | n-Propyl | Cl | n-Propyl |
| 27-50 | CH₃ | n-Propyl | Cl | Cl | n-Propyl |
| 27-51 | CH₃ | Cl | Cl | n-Propyl | n-Propyl |
| 27-52 | CH₃ | n-Propyl | n-Propyl | Cl | Cl |
| 27-53 | CH₃ | Cl | n-Propyl | n-Propyl | Cl |
| 27-54 | CH₃ | n-Propyl | Cl | Cl | Cl |
| 27-55 | CH₃ | Cl | n-Propyl | Cl | Cl |
| 27-56 | CH₃ | Cl | Cl | n-Propyl | Cl |
| 27-57 | CH₃ | Cl | Cl | Cl | n-Propyl |
| 27-58 | H | —CH₂CF(CH₃)₂ | Cl | —CH₂CF(CH₃)₂ | Cl |
| 27-59 | H | Cl | —CH₂CF(CH₃)₂ | Cl | —CH₂CF(CH₃)₂ |
| 27-60 | H | —CH₂CF(CH₃)₂ | Cl | Cl | —CH₂CF(CH₃)₂ |
| 27-61 | H | Cl | —CH₂CF(CH₃)₂ | —CH₂CF(CH₃)₂ | Cl |
| 27-62 | H | Cl | Cl | —CH₂CF(CH₃)₂ | —CH₂CF(CH₃)₂ |
| 27-63 | H | —CH₂CF(CH₃)₂ | —CH₂CF(CH₃)₂ | Cl | Cl |
| 27-64 | H | —CH₂—C(CH₃)₃ | Cl | —CH₂—C(CH₃)₃ | Cl |
| 27-65 | H | Cl | —CH₂—C(CH₃)₃ | Cl | —CH₂—C(CH₃)₃ |
| 27-66 | H | —CH₂—C(CH₃)₃ | Cl | Cl | —CH₂—C(CH₃)₃ |
| 27-67 | H | Cl | —CH₂—C(CH₃)₃ | —CH₂—C(CH₃)₃ | Cl |
| 27-68 | H | Cl | Cl | —CH₂—C(CH₃)₃ | —CH₂—C(CH₃)₃ |
| 27-69 | H | —CH₂—C(CH₃)₃ | —CH₂—C(CH₃)₃ | Cl | Cl |

TABLE 28

Compounds of formula (I), wherein Cy¹ and Cy² are p-nitrophenyl; R', R", R''' and R'''' are each independently hydrogen or methyl; and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 28-1 | CH₃ | Cl | Cl | Cl | Cl |
| 28-2 | CH₃ | Cl | —CH₂—iPr | —CH₂—iPr | —CH₂—iPr |
| 28-3 | CH₃ | —CH₂—iPr | Cl | —CH₂—iPr | —CH₂—iPr |
| 28-4 | CH₃ | —CH₂—iPr | —CH₂—iPr | Cl | —CH₂—iPr |
| 28-5 | CH₃ | —CH₂—iPr | —CH₂—iPr | —CH₂—iPr | Cl |
| 28-6 | CH₃ | —CH₂—iPr | Cl | —CH₂—iPr | Cl |

TABLE 28-continued

Compounds of formula (I), wherein $Cy^1$ and $Cy^2$ are p-nitrophenyl;
R', R'', R''' and R'''' are each independently hydrogen or methyl;
and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 28-7 | CH$_3$ | Cl | —CH$_2$—iPr | Cl | —CH$_2$—iPr |
| 28-8 | CH$_3$ | —CH$_2$—iPr | Cl | Cl | —CH$_2$—iPr |
| 28-9 | CH$_3$ | Cl | Cl | —CH$_2$—iPr | —CH$_2$—iPr |
| 28-10 | CH$_3$ | —CH$_2$—iPr | —CH$_2$—iPr | Cl | Cl |
| 28-11 | CH$_3$ | Cl | —CH$_2$—iPr | —CH$_2$—iPr | Cl |
| 28-12 | CH$_3$ | —CH$_2$—iPr | Cl | Cl | Cl |
| 28-13 | CH$_3$ | Cl | —CH$_2$—iPr | Cl | Cl |
| 28-14 | CH$_3$ | Cl | Cl | —CH$_2$—iPr | Cl |
| 28-15 | CH$_3$ | Cl | Cl | Cl | —CH$_2$—iPr |
| 28-16 | CH$_3$ | Cl | —CH$_2$—C(CH$_3$)$_3$ | —CH$_2$—C(CH$_3$)$_3$ | —CH$_2$—C(CH$_3$)$_3$ |
| 28-17 | CH$_3$ | —CH$_2$—C(CH$_3$)$_3$ | Cl | —CH$_2$—C(CH$_3$)$_3$ | —CH$_2$—C(CH$_3$)$_3$ |
| 28-18 | CH$_3$ | —CH$_2$—C(CH$_3$)$_3$ | —CH$_2$—C(CH$_3$)$_3$ | Cl | —CH$_2$—C(CH$_3$)$_3$ |
| 28-19 | CH$_3$ | —CH$_2$—C(CH$_3$)$_3$ | —CH$_2$—C(CH$_3$)$_3$ | —CH$_2$—C(CH$_3$)$_3$ | Cl |
| 28-20 | CH$_3$ | —CH$_2$—C(CH$_3$)$_3$ | Cl | —CH$_2$—C(CH$_3$)$_3$ | Cl |
| 28-21 | CH$_3$ | Cl | —CH$_2$—C(CH$_3$)$_3$ | Cl | —CH$_2$—C(CH$_3$)$_3$ |
| 28-22 | CH$_3$ | —CH$_2$—C(CH$_3$)$_3$ | Cl | Cl | —CH$_2$—C(CH$_3$)$_3$ |
| 28-23 | CH$_3$ | Cl | —CH$_2$—C(CH$_3$)$_3$ | —CH$_2$—C(CH$_3$)$_3$ | Cl |
| 28-24 | CH$_3$ | Cl | Cl | —CH$_2$—C(CH$_3$)$_3$ | —CH$_2$—C(CH$_3$)$_3$ |
| 28-25 | CH$_3$ | —CH$_2$—C(CH$_3$)$_3$ | —CH$_2$—C(CH$_3$)$_3$ | Cl | Cl |
| 28-26 | CH$_3$ | —CH$_2$—C(CH$_3$)$_3$ | Cl | Cl | Cl |
| 28-27 | CH$_3$ | Cl | —CH$_2$—C(CH$_3$)$_3$ | Cl | Cl |
| 28-28 | CH$_3$ | Cl | Cl | —CH$_2$—C(CH$_3$)$_3$ | Cl |
| 28-29 | CH$_3$ | Cl | Cl | Cl | —CH$_2$—C(CH$_3$)$_3$ |
| 28-30 | CH$_3$ | Cl | —CH$_2$CF(CH$_3$)$_2$ | —CH$_2$CF(CH$_3$)$_2$ | —CHCF(CH$_3$)$_2$ |
| 28-31 | CH$_3$ | —CH$_2$CF(CH$_3$)$_2$ | Cl | —CH$_2$CF(CH$_3$)$_2$ | —CH$_2$CF(CH$_3$)$_2$ |
| 28-32 | CH$_3$ | —CH$_2$CF(CH$_3$)$_2$ | —CH$_2$CF(CH$_3$)$_2$ | Cl | —CH$_2$CF(CH$_3$)$_2$ |
| 28-33 | CH$_3$ | —CH$_2$CF(CH$_3$)$_2$ | —CH$_2$CF(CH$_3$)$_2$ | —CH$_2$CF(CH$_3$)$_2$ | Cl |
| 28-34 | CH$_3$ | —CH$_2$CF(CH$_3$)$_2$ | Cl | —CH$_2$CF(CH$_3$)$_2$ | Cl |
| 28-35 | CH$_3$ | Cl | —CH$_2$CF(CH$_3$)$_2$ | Cl | —CH$_2$CF(CH$_3$)$_2$ |
| 28-36 | CH$_3$ | —CH$_2$CF(CH$_3$)$_2$ | Cl | Cl | —CH$_2$CF(CH$_3$)$_2$ |
| 28-37 | CH$_3$ | Cl | —CH$_2$CF(CH$_3$)$_2$ | CH$_2$CF(CH$_3$)$_2$ | Cl |
| 28-38 | CH$_3$ | Cl | Cl | —CH$_2$CF(CH$_3$)$_2$ | —CH$_2$CF(CH$_3$)$_2$ |
| 28-39 | CH$_3$ | —CH$_2$CF(CH$_3$)$_2$ | —CH$_2$CF(CH$_3$)$_2$ | Cl | Cl |
| 28-40 | CH$_3$ | —CH$_2$CF(CH$_3$)$_2$ | Cl | Cl | Cl |
| 28-41 | CH$_3$ | Cl | —CH$_2$CF(CH$_3$)$_2$ | Cl | Cl |
| 28-42 | CH$_3$ | Cl | Cl | —CH$_2$CF(CH$_3$)$_2$ | Cl |
| 28-43 | CH$_3$ | Cl | Cl | Cl | —CH$_2$CF(CH$_3$)$_2$ |
| 28-44 | CH$_3$ | Cl | n-Propyl | n-Propyl | n-Propyl |
| 28-45 | CH$_3$ | n-Propyl | Cl | n-Propyl | n-Propyl |
| 28-46 | CH$_3$ | n-Propyl | n-Propyl | Cl | n-Propyl |
| 28-47 | CH$_3$ | n-Propyl | n-Propyl | n-Propyl | Cl |
| 28-48 | CH$_3$ | n-Propyl | Cl | n-Propyl | Cl |
| 28-49 | CH$_3$ | Cl | n-Propyl | Cl | n-Propyl |
| 28-50 | CH$_3$ | n-Propyl | Cl | Cl | n-Propyl |
| 28-51 | CH$_3$ | Cl | Cl | n-Propyl | n-Propyl |
| 28-52 | CH$_3$ | n-Propyl | n-Propyl | Cl | Cl |
| 28-53 | CH$_3$ | Cl | n-Propyl | n-Propyl | Cl |
| 28-54 | CH$_3$ | n-Propyl | Cl | Cl | Cl |
| 28-55 | CH$_3$ | Cl | n-Propyl | Cl | Cl |
| 28-56 | CH$_3$ | Cl | Cl | n-Propyl | Cl |
| 28-57 | CH$_3$ | Cl | Cl | Cl | n-Propyl |
| 28-58 | H | —CH$_2$CF(CH$_3$)$_2$ | Cl | —CH$_2$CF(CH$_3$)$_2$ | Cl |
| 28-59 | H | Cl | —CH$_2$CF(CH$_3$)$_2$ | Cl | —CH$_2$CF(CH$_3$)$_2$ |
| 28-60 | H | —CH$_2$CF(CH$_3$)$_2$ | Cl | Cl | —CH$_2$CF(CH$_3$)$_2$ |
| 28-61 | H | Cl | —CH$_2$CF(CH$_3$)$_2$ | —CH$_2$CF(CH$_3$)$_2$ | Cl |
| 28-62 | H | Cl | Cl | —CH$_2$CF(CH$_3$)$_2$ | —CH$_2$CF(CH$_3$)$_2$ |
| 28-63 | H | —CH$_2$CF(CH$_3$)$_2$ | —CH$_2$CF(CH$_3$)$_2$ | Cl | Cl |
| 28-64 | H | —CH$_2$—C(CH$_3$)$_3$ | Cl | —CH$_2$—C(CH$_3$)$_3$ | Cl |
| 28-65 | H | Cl | —CH$_2$—C(CH$_3$)$_3$ | Cl | —CH$_2$—C(CH$_3$)$_3$ |
| 28-66 | H | —CH$_2$—C(CH$_3$)$_3$ | Cl | Cl | —CH$_2$—C(CH$_3$)$_3$ |
| 28-67 | H | Cl | —CH$_2$—C(CH$_3$)$_3$ | —CH$_2$—C(CH$_3$)$_3$ | Cl |
| 28-68 | H | Cl | Cl | —CH$_2$—C(CH$_3$)$_3$ | —CH$_2$—C(CH$_3$)$_3$ |
| 28-69 | H | —CH$_2$—C(CH$_3$)$_3$ | —CH$_2$—C(CH$_3$)$_3$ | Cl | Cl |

TABLE 29

Compounds of formula (I), wherein Cy$^1$ and Cy$^2$ are

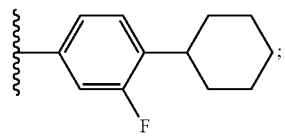 [SMILES: *c1ccc(C2CCCCC2)c(F)c1]

and R$^a$, R$^b$ and R$^1$ to R$^4$ are as shown.

| Cmpd # | R$^a$/R$^b$ | R$^1$ | R$^2$ | R$^3$ | R$^4$ |
|---|---|---|---|---|---|
| 29-1 | CH$_3$ | Cl | Cl | Cl | Cl |
| 29-2 | CH$_3$ | Cl | —CH$_2$—iPr | —CH$_2$—iPr | —CH$_2$—iPr |
| 29-3 | CH$_3$ | —CH$_2$—iPr | Cl | —CH$_2$—iPr | —CH$_2$—iPr |
| 29-4 | CH$_3$ | —CH$_2$—iPr | —CH$_2$—iPr | Cl | —CH$_2$—iPr |
| 29-5 | CH$_3$ | —CH$_2$—iPr | —CH$_2$—iPr | —CH$_2$—iPr | Cl |
| 29-6 | CH$_3$ | —CH$_2$—iPr | Cl | —CH$_2$—iPr | Cl |
| 29-7 | CH$_3$ | Cl | —CH$_2$—iPr | Cl | —CH$_2$—iPr |
| 29-8 | CH$_3$ | —CH$_2$—iPr | Cl | Cl | —CH$_2$—iPr |
| 29-9 | CH$_3$ | Cl | Cl | —CH$_2$—iPr | —CH$_2$—iPr |
| 29-10 | CH$_3$ | —CH$_2$—iPr | —CH$_2$—iPr | Cl | Cl |
| 29-11 | CH$_3$ | Cl | —CH$_2$—iPr | —CH$_2$—iPr | Cl |
| 29-12 | CH$_3$ | —CH$_2$—iPr | Cl | Cl | Cl |
| 29-13 | CH$_3$ | Cl | —CH$_2$—iPr | Cl | Cl |
| 29-14 | CH$_3$ | Cl | Cl | —CH$_2$—iPr | Cl |
| 29-15 | CH$_3$ | Cl | Cl | Cl | —CH$_2$—iPr |
| 29-16 | CH$_3$ | Cl | —CH$_2$—C(CH$_3$)$_3$ | —CH$_2$—C(CH$_3$)$_3$ | —CH$_2$—C(CH$_3$)$_3$ |
| 29-17 | CH$_3$ | —CH$_2$—C(CH$_3$)$_3$ | Cl | —CH$_2$—C(CH$_3$)$_3$ | —CH$_2$—C(CH$_3$)$_3$ |
| 29-18 | CH$_3$ | —CH$_2$—C(CH$_3$)$_3$ | —CH$_2$—C(CH$_3$)$_3$ | Cl | —CH$_2$—C(CH$_3$)$_3$ |
| 29-19 | CH$_3$ | —CH$_2$—C(CH$_3$)$_3$ | —CH$_2$—C(CH$_3$)$_3$ | —CH$_2$—C(CH$_3$)$_3$ | Cl |
| 29-20 | CH$_3$ | —CH$_2$—C(CH$_3$)$_3$ | Cl | —CH$_2$—C(CH$_3$)$_3$ | Cl |
| 29-21 | CH$_3$ | Cl | —CH$_2$—C(CH$_3$)$_3$ | Cl | —CH$_2$—C(CH$_3$)$_3$ |
| 29-22 | CH$_3$ | —CH$_2$—C(CH$_3$)$_3$ | Cl | Cl | —CH$_2$—C(CH$_3$)$_3$ |
| 29-23 | CH$_3$ | Cl | —CH$_2$—C(CH$_3$)$_3$ | —CH$_2$—C(CH$_3$)$_3$ | Cl |
| 29-24 | CH$_3$ | Cl | Cl | —CH$_2$—C(CH$_3$)$_3$ | —CH$_2$—C(CH$_3$)$_3$ |
| 29-25 | CH$_3$ | —CH$_2$—C(CH$_3$)$_3$ | —CH$_2$—C(CH$_3$)$_3$ | Cl | Cl |
| 29-26 | CH$_3$ | —CH$_2$—C(CH$_3$)$_3$ | Cl | Cl | Cl |
| 29-27 | CH$_3$ | Cl | —CH$_2$—C(CH$_3$)$_3$ | Cl | Cl |
| 29-28 | CH$_3$ | Cl | Cl | —CH$_2$—C(CH$_3$)$_3$ | Cl |
| 29-29 | CH$_3$ | Cl | Cl | Cl | —CH$_2$—C(CH$_3$)$_3$ |
| 29-30 | CH$_3$ | Cl | —CH$_2$CF(CH$_3$)$_2$ | —CH$_2$CF(CH$_3$)$_2$ | —CHCF(CH$_3$)$_2$ |
| 29-31 | CH$_3$ | —CH$_2$CF(CH$_3$)$_2$ | Cl | —CH$_2$CF(CH$_3$)$_2$ | —CH$_2$CF(CH$_3$)$_2$ |
| 29-32 | CH$_3$ | —CH$_2$CF(CH$_3$)$_2$ | —CH$_2$CF(CH$_3$)$_2$ | Cl | —CH$_2$CF(CH$_3$)$_2$ |
| 29-33 | CH$_3$ | —CH$_2$CF(CH$_3$)$_2$ | —CH$_2$CF(CH$_3$)$_2$ | —CH$_2$CF(CH$_3$)$_2$ | Cl |
| 29-34 | CH$_3$ | —CH$_2$CF(CH$_3$)$_2$ | Cl | —CH$_2$CF(CH$_3$)$_2$ | Cl |
| 29-35 | CH$_3$ | Cl | —CH$_2$CF(CH$_3$)$_2$ | Cl | —CH$_2$CF(CH$_3$)$_2$ |
| 29-36 | CH$_3$ | —CH$_2$CF(CH$_3$)$_2$ | Cl | Cl | —CH$_2$CF(CH$_3$)$_2$ |
| 29-37 | CH$_3$ | Cl | —CH$_2$CF(CH$_3$)$_2$ | CH$_2$CF(CH$_3$)$_2$ | Cl |
| 29-38 | CH$_3$ | Cl | Cl | —CH$_2$CF(CH$_3$)$_2$ | —CH$_2$CF(CH$_3$)$_2$ |
| 29-39 | CH$_3$ | —CH$_2$CF(CH$_3$)$_2$ | —CH$_2$CF(CH$_3$)$_2$ | Cl | Cl |
| 29-40 | CH$_3$ | —CH$_2$CF(CH$_3$)$_2$ | Cl | Cl | Cl |
| 29-41 | CH$_3$ | Cl | —CH$_2$CF(CH$_3$)$_2$ | Cl | Cl |
| 29-42 | CH$_3$ | Cl | Cl | —CH$_2$CF(CH$_3$)$_2$ | Cl |
| 29-43 | CH$_3$ | Cl | Cl | Cl | —CH$_2$CF(CH$_3$)$_2$ |
| 29-44 | CH$_3$ | Cl | n-Propyl | n-Propyl | n-Propyl |
| 29-45 | CH$_3$ | n-Propyl | Cl | n-Propyl | n-Propyl |
| 29-46 | CH$_3$ | n-Propyl | n-Propyl | Cl | n-Propyl |
| 29-47 | CH$_3$ | n-Propyl | n-Propyl | n-Propyl | Cl |
| 29-48 | CH$_3$ | n-Propyl | Cl | n-Propyl | Cl |
| 29-49 | CH$_3$ | Cl | n-Propyl | Cl | n-Propyl |
| 29-50 | CH$_3$ | n-Propyl | Cl | Cl | n-Propyl |
| 29-51 | CH$_3$ | Cl | Cl | n-Propyl | n-Propyl |
| 29-52 | CH$_3$ | n-Propyl | n-Propyl | Cl | Cl |
| 29-53 | CH$_3$ | Cl | n-Propyl | n-Propyl | Cl |
| 29-54 | CH$_3$ | n-Propyl | Cl | Cl | Cl |
| 29-55 | CH$_3$ | Cl | n-Propyl | Cl | Cl |
| 29-56 | CH$_3$ | Cl | Cl | n-Propyl | Cl |
| 29-57 | CH$_3$ | Cl | Cl | Cl | n-Propyl |
| 29-58 | H | —CH$_2$CF(CH$_3$)$_2$ | Cl | —CH$_2$CF(CH$_3$)$_2$ | —CH$_2$CF(CH$_3$)$_2$ |
| 29-59 | H | Cl | —CH$_2$CF(CH$_3$)$_2$ | Cl | —CH$_2$CF(CH$_3$)$_2$ |
| 29-60 | H | —CH$_2$CF(CH$_3$)$_2$ | —CH$_2$CF(CH$_3$)$_2$ | Cl | —CH$_2$CF(CH$_3$)$_2$ |
| 29-61 | H | Cl | —CH$_2$CF(CH$_3$)$_2$ | —CH$_2$CF(CH$_3$)$_2$ | Cl |
| 29-62 | H | Cl | Cl | —CH$_2$CF(CH$_3$)$_2$ | —CH$_2$CF(CH$_3$)$_2$ |
| 29-63 | H | —CH$_2$CF(CH$_3$)$_2$ | —CH$_2$CF(CH$_3$)$_2$ | Cl | Cl |
| 29-64 | H | —CH$_2$—C(CH$_3$)$_3$ | Cl | —CH$_2$—C(CH$_3$)$_3$ | Cl |
| 29-65 | H | Cl | —CH$_2$—C(CH$_3$)$_3$ | Cl | —CH$_2$—C(CH$_3$)$_3$ |
| 29-66 | H | —CH$_2$—C(CH$_3$)$_3$ | Cl | Cl | —CH$_2$—C(CH$_3$)$_3$ |
| 29-67 | H | Cl | —CH$_2$—C(CH$_3$)$_3$ | —CH$_2$—C(CH$_3$)$_3$ | Cl |

TABLE 29-continued

Compounds of formula (I), wherein Cy¹ and Cy² are

and R$^a$, R$^b$ and R$^1$ to R$^4$ are as shown.

| Cmpd # | R$^a$/R$^b$ | R$^1$ | R$^2$ | R$^3$ | R$^4$ |
|---|---|---|---|---|---|
| 29-68 | H | Cl | Cl | —CH$_2$—C(CH$_3$)$_3$ | —CH$_2$—C(CH$_3$)$_3$ |
| 29-69 | H | —CH$_2$—C(CH$_3$)$_3$ | —CH$_2$—C(CH$_3$)$_3$ | Cl | Cl |

TABLE 30

Compounds of formula (I), wherein Cy¹ and Cy² are

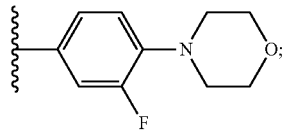

and R$^a$, R$^b$ and R$^1$ to R$^4$ are as shown.

| Cmpd # | R$^a$/R$^b$ | R$^1$ | R$^2$ | R$^3$ | R$^4$ |
|---|---|---|---|---|---|
| 30-1 | CH$_3$ | Cl | Cl | Cl | Cl |
| 30-2 | CH$_3$ | Cl | —CH$_2$—iPr | —CH$_2$—iPr | —CH$_2$—iPr |
| 30-3 | CH$_3$ | —CH$_2$—iPr | Cl | —CH$_2$—iPr | —CH$_2$—iPr |
| 30-4 | CH$_3$ | —CH$_2$—iPr | —CH$_2$—iPr | Cl | —CH$_2$—iPr |
| 30-5 | CH$_3$ | —CH$_2$—iPr | —CH$_2$—iPr | —CH$_2$—iPr | Cl |
| 30-6 | CH$_3$ | —CH$_2$—iPr | Cl | —CH$_2$—iPr | Cl |
| 30-7 | CH$_3$ | Cl | —CH$_2$—iPr | Cl | —CH$_2$—iPr |
| 30-8 | CH$_3$ | —CH$_2$—iPr | Cl | Cl | —CH$_2$—iPr |
| 30-9 | CH$_3$ | Cl | Cl | —CH$_2$—iPr | —CH$_2$—iPr |
| 30-10 | CH$_3$ | —CH$_2$—iPr | —CH$_2$—iPr | Cl | Cl |
| 30-11 | CH$_3$ | Cl | —CH$_2$—iPr | —CH$_2$—iPr | Cl |
| 30-12 | CH$_3$ | —CH$_2$—iPr | Cl | Cl | Cl |
| 30-13 | CH$_3$ | Cl | —CH$_2$—iPr | Cl | Cl |
| 30-14 | CH$_3$ | Cl | Cl | —CH$_2$—iPr | Cl |
| 30-15 | CH$_3$ | Cl | Cl | Cl | —CH$_2$—iPr |
| 30-16 | CH$_3$ | Cl | —CH$_2$—C(CH$_3$)$_3$ | —CH$_2$—C(CH$_3$)$_3$ | —CH$_2$—C(CH$_3$)$_3$ |
| 30-17 | CH$_3$ | —CH$_2$—C(CH$_3$)$_3$ | Cl | —CH$_2$—C(CH$_3$)$_3$ | —CH$_2$—C(CH$_3$)$_3$ |
| 30-18 | CH$_3$ | —CH$_2$—C(CH$_3$)$_3$ | —CH$_2$—C(CH$_3$)$_3$ | Cl | —CH$_2$—C(CH$_3$)$_3$ |
| 30-19 | CH$_3$ | —CH$_2$—C(CH$_3$)$_3$ | —CH$_2$—C(CH$_3$)$_3$ | —CH$_2$—C(CH$_3$)$_3$ | Cl |
| 30-20 | CH$_3$ | —CH$_2$—C(CH$_3$)$_3$ | Cl | —CH$_2$—C(CH$_3$)$_3$ | Cl |
| 30-21 | CH$_3$ | Cl | —CH$_2$—C(CH$_3$)$_3$ | Cl | —CH$_2$—C(CH$_3$)$_3$ |
| 30-22 | CH$_3$ | —CH$_2$—C(CH$_3$)$_3$ | Cl | Cl | —CH$_2$—C(CH$_3$)$_3$ |
| 30-23 | CH$_3$ | Cl | —CH$_2$—C(CH$_3$)$_3$ | —CH$_2$—C(CH$_3$)$_3$ | Cl |
| 30-24 | CH$_3$ | Cl | Cl | —CH$_2$—C(CH$_3$)$_3$ | —CH$_2$—C(CH$_3$)$_3$ |
| 30-25 | CH$_3$ | —CH$_2$—C(CH$_3$)$_3$ | —CH$_2$—C(CH$_3$)$_3$ | Cl | Cl |
| 30-26 | CH$_3$ | —CH$_2$—C(CH$_3$)$_3$ | Cl | Cl | Cl |
| 30-27 | CH$_3$ | Cl | —CH$_2$—C(CH$_3$)$_3$ | Cl | Cl |
| 30-28 | CH$_3$ | Cl | Cl | —CH$_2$—C(CH$_3$)$_3$ | Cl |
| 30-29 | CH$_3$ | Cl | Cl | Cl | —CH$_2$—C(CH$_3$)$_3$ |
| 30-30 | CH$_3$ | Cl | —CH$_2$CF(CH$_3$)$_2$ | —CH$_2$CF(CH$_3$)$_2$ | —CHCF(CH$_3$)$_2$ |
| 30-31 | CH$_3$ | —CH$_2$CF(CH$_3$)$_2$ | Cl | —CH$_2$CF(CH$_3$)$_2$ | —CH$_2$CF(CH$_3$)$_2$ |
| 30-32 | CH$_3$ | —CH$_2$CF(CH$_3$)$_2$ | —CH$_2$CF(CH$_3$)$_2$ | Cl | —CH$_2$CF(CH$_3$)$_2$ |
| 30-33 | CH$_3$ | —CH$_2$CF(CH$_3$)$_2$ | —CH$_2$CF(CH$_3$)$_2$ | —CH$_2$CF(CH$_3$)$_2$ | Cl |
| 30-34 | CH$_3$ | —CH$_2$CF(CH$_3$)$_2$ | Cl | —CH$_2$CF(CH$_3$)$_2$ | Cl |
| 30-35 | CH$_3$ | Cl | —CH$_2$CF(CH$_3$)$_2$ | Cl | —CH$_2$CF(CH$_3$)$_2$ |
| 30-36 | CH$_3$ | —CH$_2$CF(CH$_3$)$_2$ | Cl | Cl | —CH$_2$CF(CH$_3$)$_2$ |
| 30-37 | CH$_3$ | Cl | —CH$_2$CF(CH$_3$)$_2$ | CH$_2$CF(CH$_3$)$_2$ | Cl |
| 30-38 | CH$_3$ | Cl | Cl | —CH$_2$CF(CH$_3$)$_2$ | —CH$_2$CF(CH$_3$)$_2$ |
| 30-39 | CH$_3$ | —CH$_2$CF(CH$_3$)$_2$ | —CH$_2$CF(CH$_3$)$_2$ | Cl | Cl |
| 30-40 | CH$_3$ | —CH$_2$CF(CH$_3$)$_2$ | Cl | Cl | Cl |
| 30-41 | CH$_3$ | Cl | —CH$_2$CF(CH$_3$)$_2$ | Cl | Cl |
| 30-42 | CH$_3$ | Cl | Cl | —CH$_2$CF(CH$_3$)$_2$ | Cl |
| 30-43 | CH$_3$ | Cl | Cl | Cl | —CH$_2$CF(CH$_3$)$_2$ |
| 30-44 | CH$_3$ | Cl | n-Propyl | n-Propyl | n-Propyl |
| 30-45 | CH$_3$ | n-Propyl | Cl | n-Propyl | n-Propyl |
| 30-46 | CH$_3$ | n-Propyl | n-Propyl | Cl | n-Propyl |

TABLE 30-continued

Compounds of formula (I), wherein $Cy^1$ and $Cy^2$ are

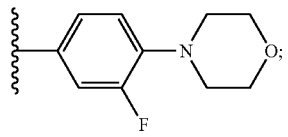 [SMILES: *c1ccc(N2CCOCC2)c(F)c1]

and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 30-47 | $CH_3$ | n-Propyl | n-Propyl | n-Propyl | Cl |
| 30-48 | $CH_3$ | n-Propyl | Cl | n-Propyl | Cl |
| 30-49 | $CH_3$ | Cl | n-Propyl | Cl | n-Propyl |
| 30-50 | $CH_3$ | n-Propyl | Cl | Cl | n-Propyl |
| 30-51 | $CH_3$ | Cl | Cl | n-Propyl | n-Propyl |
| 30-52 | $CH_3$ | n-Propyl | n-Propyl | Cl | Cl |
| 30-53 | $CH_3$ | Cl | n-Propyl | n-Propyl | Cl |
| 30-54 | $CH_3$ | n-Propyl | Cl | Cl | Cl |
| 30-55 | $CH_3$ | Cl | n-Propyl | Cl | Cl |
| 30-56 | $CH_3$ | Cl | Cl | n-Propyl | Cl |
| 30-57 | $CH_3$ | Cl | Cl | Cl | n-Propyl |
| 30-58 | H | —$CH_2CF(CH_3)_2$ | Cl | —$CH_2CF(CH_3)_2$ | Cl |
| 30-59 | H | Cl | —$CH_2CF(CH_3)_2$ | Cl | —$CH_2CF(CH_3)_2$ |
| 30-60 | H | —$CH_2CF(CH_3)_2$ | Cl | Cl | —$CH_2CF(CH_3)_2$ |
| 30-61 | H | Cl | —$CH_2CF(CH_3)_2$ | —$CH_2CF(CH_3)_2$ | Cl |
| 30-62 | H | Cl | Cl | —$CH_2CF(CH_3)_2$ | —$CH_2CF(CH_3)_2$ |
| 30-63 | H | —$CH_2CF(CH_3)_2$ | —$CH_2CF(CH_3)_2$ | Cl | Cl |
| 30-64 | H | —$CH_2$—$C(CH_3)_3$ | Cl | —$CH_2$—$C(CH_3)_3$ | Cl |
| 30-65 | H | Cl | —$CH_2$—$C(CH_3)_3$ | Cl | —$CH_2$—$C(CH_3)_3$ |
| 30-66 | H | —$CH_2$—$C(CH_3)_3$ | Cl | Cl | —$CH_2$—$C(CH_3)_3$ |
| 30-67 | H | Cl | —$CH_2$—$C(CH_3)_3$ | —$CH_2$—$C(CH_3)_3$ | Cl |
| 30-68 | H | Cl | Cl | —$CH_2$—$C(CH_3)_3$ | —$CH_2$—$C(CH_3)_3$ |
| 30-69 | H | —$CH_2$—$C(CH_3)_3$ | —$CH_2$—$C(CH_3)_3$ | Cl | Cl |

TABLE 31

Compounds of formula (I), wherein $Cy^1$ and $Cy^2$ are

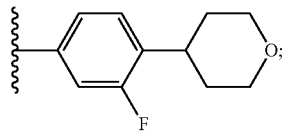 [SMILES: *c1ccc(C2CCOCC2)c(F)c1]

and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 31-1 | $CH_3$ | Cl | Cl | Cl | Cl |
| 31-2 | $CH_3$ | Cl | —$CH_2$—iPr | —$CH_2$—iPr | —$CH_2$—iPr |
| 31-3 | $CH_3$ | —$CH_2$—iPr | Cl | —$CH_2$—iPr | —$CH_2$—iPr |
| 31-4 | $CH_3$ | —$CH_2$—iPr | —$CH_2$—iPr | Cl | —$CH_2$—iPr |
| 31-5 | $CH_3$ | —$CH_2$—iPr | —$CH_2$—iPr | —$CH_2$—iPr | Cl |
| 31-6 | $CH_3$ | —$CH_2$—iPr | Cl | —$CH_2$—iPr | Cl |
| 31-7 | $CH_3$ | Cl | —$CH_2$—iPr | Cl | —$CH_2$—iPr |
| 31-8 | $CH_3$ | —$CH_2$—iPr | Cl | Cl | —$CH_2$—iPr |
| 31-9 | $CH_3$ | Cl | Cl | —$CH_2$—iPr | —$CH_2$—iPr |
| 31-10 | $CH_3$ | —$CH_2$—iPr | —$CH_2$—iPr | Cl | Cl |
| 31-11 | $CH_3$ | Cl | —$CH_2$—iPr | —$CH_2$—iPr | Cl |
| 31-12 | $CH_3$ | —$CH_2$—iPr | Cl | Cl | Cl |
| 31-13 | $CH_3$ | Cl | —$CH_2$—iPr | Cl | Cl |
| 31-14 | $CH_3$ | Cl | Cl | —$CH_2$—iPr | Cl |
| 31-15 | $CH_3$ | Cl | Cl | Cl | —$CH_2$—iPr |
| 31-16 | $CH_3$ | Cl | —$CH_2$—$C(CH_3)_3$ | —$CH_2$—$C(CH_3)_3$ | —$CH_2$—$C(CH_3)_3$ |
| 31-17 | $CH_3$ | —$CH_2$—$C(CH_3)_3$ | Cl | —$CH_2$—$C(CH_3)_3$ | —$CH_2$—$C(CH_3)_3$ |
| 31-18 | $CH_3$ | —$CH_2$—$C(CH_3)_3$ | —$CH_2$—$C(CH_3)_3$ | Cl | —$CH_2$—$C(CH_3)_3$ |
| 31-19 | $CH_3$ | —$CH_2$—$C(CH_3)_3$ | —$CH_2$—$C(CH_3)_3$ | —$CH_2$—$C(CH_3)_3$ | Cl |
| 31-20 | $CH_3$ | —$CH_2$—$C(CH_3)_3$ | Cl | —$CH_2$—$C(CH_3)_3$ | Cl |
| 31-21 | $CH_3$ | Cl | —$CH_2$—$C(CH_3)_3$ | Cl | —$CH_2$—$C(CH_3)_3$ |
| 31-22 | $CH_3$ | —$CH_2$—$C(CH_3)_3$ | Cl | Cl | —$CH_2$—$C(CH_3)_3$ |
| 31-23 | $CH_3$ | Cl | —$CH_2$—$C(CH_3)_3$ | —$CH_2$—$C(CH_3)_3$ | Cl |
| 31-24 | $CH_3$ | Cl | Cl | —$CH_2$—$C(CH_3)_3$ | —$CH_2$—$C(CH_3)_3$ |
| 31-25 | $CH_3$ | —$CH_2$—$C(CH_3)_3$ | —$CH_2$—$C(CH_3)_3$ | Cl | Cl |

TABLE 31-continued

Compounds of formula (I), wherein Cy$^1$ and Cy$^2$ are

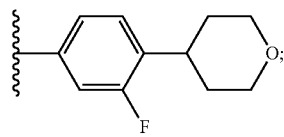

and R$^a$, R$^b$ and R$^1$ to R$^4$ are as shown.

| Cmpd # | R$^a$/R$^b$ | R$^1$ | R$^2$ | R$^3$ | R$^4$ |
|---|---|---|---|---|---|
| 31-26 | CH$_3$ | —CH$_2$—C(CH$_3$)$_3$ | Cl | Cl | Cl |
| 31-27 | CH$_3$ | Cl | —CH$_2$—C(CH$_3$)$_3$ | Cl | Cl |
| 31-28 | CH$_3$ | Cl | Cl | —CH$_2$—C(CH$_3$)$_3$ | Cl |
| 31-29 | CH$_3$ | Cl | Cl | Cl | —CH$_2$—C(CH$_3$)$_3$ |
| 31-30 | CH$_3$ | Cl | —CH$_2$CF(CH$_3$)$_2$ | —CH$_2$CF(CH$_3$)$_2$ | —CHCF(CH$_3$)$_2$ |
| 31-31 | CH$_3$ | —CH$_2$CF(CH$_3$)$_2$ | Cl | —CH$_2$CF(CH$_3$)$_2$ | —CH$_2$CF(CH$_3$)$_2$ |
| 31-32 | CH$_3$ | —CH$_2$CF(CH$_3$)$_2$ | —CH$_2$CF(CH$_3$)$_2$ | Cl | —CH$_2$CF(CH$_3$)$_2$ |
| 31-33 | CH$_3$ | —CH$_2$CF(CH$_3$)$_2$ | —CH$_2$CF(CH$_3$)$_2$ | —CH$_2$CF(CH$_3$)$_2$ | Cl |
| 31-34 | CH$_3$ | —CH$_2$CF(CH$_3$)$_2$ | Cl | —CH$_2$CF(CH$_3$)$_2$ | Cl |
| 31-35 | CH$_3$ | Cl | —CH$_2$CF(CH$_3$)$_2$ | Cl | —CH$_2$CF(CH$_3$)$_2$ |
| 31-36 | CH$_3$ | —CH$_2$CF(CH$_3$)$_2$ | Cl | Cl | —CH$_2$CF(CH$_3$)$_2$ |
| 31-37 | CH$_3$ | Cl | —CH$_2$CF(CH$_3$)$_2$ | CH$_2$CF(CH$_3$)$_2$ | Cl |
| 31-38 | CH$_3$ | Cl | Cl | —CH$_2$CF(CH$_3$)$_2$ | —CH$_2$CF(CH$_3$)$_2$ |
| 31-39 | CH$_3$ | —CH$_2$CF(CH$_3$)$_2$ | —CH$_2$CF(CH$_3$)$_2$ | Cl | Cl |
| 31-40 | CH$_3$ | —CH$_2$CF(CH$_3$)$_2$ | Cl | Cl | Cl |
| 31-41 | CH$_3$ | Cl | —CH$_2$CF(CH$_3$)$_2$ | Cl | Cl |
| 31-42 | CH$_3$ | Cl | Cl | —CH$_2$CF(CH$_3$)$_2$ | Cl |
| 31-43 | CH$_3$ | Cl | Cl | Cl | —CH$_2$CF(CH$_3$)$_2$ |
| 31-44 | CH$_3$ | Cl | n-Propyl | n-Propyl | n-Propyl |
| 31-45 | CH$_3$ | n-Propyl | Cl | n-Propyl | n-Propyl |
| 31-46 | CH$_3$ | n-Propyl | n-Propyl | Cl | n-Propyl |
| 31-47 | CH$_3$ | n-Propyl | n-Propyl | n-Propyl | Cl |
| 31-48 | CH$_3$ | n-Propyl | Cl | n-Propyl | Cl |
| 31-49 | CH$_3$ | Cl | n-Propyl | Cl | n-Propyl |
| 31-50 | CH$_3$ | n-Propyl | Cl | Cl | n-Propyl |
| 31-51 | CH$_3$ | Cl | Cl | n-Propyl | n-Propyl |
| 31-52 | CH$_3$ | n-Propyl | n-Propyl | Cl | Cl |
| 31-53 | CH$_3$ | Cl | n-Propyl | n-Propyl | Cl |
| 31-54 | CH$_3$ | n-Propyl | Cl | Cl | Cl |
| 31-55 | CH$_3$ | Cl | n-Propyl | Cl | Cl |
| 31-56 | CH$_3$ | Cl | Cl | n-Propyl | Cl |
| 31-57 | CH$_3$ | Cl | Cl | Cl | n-Propyl |
| 31-58 | H | —CH$_2$CF(CH$_3$)$_2$ | Cl | —CH$_2$CF(CH$_3$)$_2$ | Cl |
| 31-59 | H | Cl | —CH$_2$CF(CH$_3$)$_2$ | Cl | —CH$_2$CF(CH$_3$)$_2$ |
| 31-60 | H | —CH$_2$CF(CH$_3$)$_2$ | Cl | Cl | —CH$_2$CF(CH$_3$)$_2$ |
| 31-61 | H | Cl | —CH$_2$CF(CH$_3$)$_2$ | —CH$_2$CF(CH$_3$)$_2$ | Cl |
| 31-62 | H | Cl | Cl | —CH$_2$CF(CH$_3$)$_2$ | —CH$_2$CF(CH$_3$)$_2$ |
| 31-63 | H | —CH$_2$CF(CH$_3$)$_2$ | —CH$_2$CF(CH$_3$)$_2$ | Cl | Cl |
| 31-64 | H | —CH$_2$—C(CH$_3$)$_3$ | Cl | —CH$_2$—C(CH$_3$)$_3$ | Cl |
| 31-65 | H | Cl | —CH$_2$—C(CH$_3$)$_3$ | Cl | —CH$_2$—C(CH$_3$)$_3$ |
| 31-66 | H | —CH$_2$—C(CH$_3$)$_3$ | Cl | Cl | —CH$_2$—C(CH$_3$)$_3$ |
| 31-67 | H | Cl | —CH$_2$—C(CH$_3$)$_3$ | —CH$_2$—C(CH$_3$)$_3$ | Cl |
| 31-68 | H | Cl | Cl | —CH$_2$—C(CH$_3$)$_3$ | —CH$_2$—C(CH$_3$)$_3$ |
| 31-69 | H | —CH$_2$—C(CH$_3$)$_3$ | —CH$_2$—C(CH$_3$)$_3$ | Cl | Cl |

TABLE 32

Compounds of formula (I), wherein Cy$^1$ and Cy$^2$ are

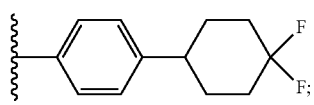

and R$^a$, R$^b$ and R$^1$ to R$^4$ are as shown.

| Cmpd # | R$^a$/R$^b$ | R$^1$ | R$^2$ | R$^3$ | R$^4$ |
|---|---|---|---|---|---|
| 32-1 | CH$_3$ | Cl | Cl | Cl | Cl |
| 32-2 | CH$_3$ | Cl | —CH$_2$—iPr | —CH$_2$—iPr | —CH$_2$—iPr |
| 32-3 | CH$_3$ | —CH$_2$—iPr | Cl | —CH$_2$—iPr | —CH$_2$—iPr |
| 32-4 | CH$_3$ | —CH$_2$—iPr | —CH$_2$—iPr | Cl | —CH$_2$—iPr |
| 32-5 | CH$_3$ | —CH$_2$—iPr | —CH$_2$—iPr | —CH$_2$—iPr | Cl |
| 32-6 | CH$_3$ | —CH$_2$—iPr | Cl | —CH$_2$—iPr | Cl |

TABLE 32-continued

Compounds of formula (I), wherein Cy¹ and Cy² are

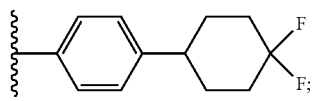

and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 32-7 | CH₃ | Cl | —CH₂—iPr | Cl | —CH₂—iPr |
| 32-8 | CH₃ | —CH₂—iPr | Cl | Cl | —CH₂—iPr |
| 32-9 | CH₃ | Cl | Cl | —CH₂—iPr | —CH₂—iPr |
| 32-10 | CH₃ | —CH₂—iPr | —CH₂—iPr | Cl | Cl |
| 32-11 | CH₃ | Cl | —CH₂—iPr | —CH₂—iPr | Cl |
| 32-12 | CH₃ | —CH₂—iPr | Cl | Cl | Cl |
| 32-13 | CH₃ | Cl | —CH₂—iPr | Cl | Cl |
| 32-14 | CH₃ | Cl | Cl | —CH₂—iPr | Cl |
| 32-15 | CH₃ | Cl | Cl | Cl | —CH₂—iPr |
| 32-16 | CH₃ | Cl | —CH₂—C(CH₃)₃ | —CH₂—C(CH₃)₃ | —CH₂—C(CH₃)₃ |
| 32-17 | CH₃ | —CH₂—C(CH₃)₃ | Cl | —CH₂—C(CH₃)₃ | —CH₂—C(CH₃)₃ |
| 32-18 | CH₃ | —CH₂—C(CH₃)₃ | —CH₂—C(CH₃)₃ | Cl | —CH₂—C(CH₃)₃ |
| 32-19 | CH₃ | —CH₂—C(CH₃)₃ | —CH₂—C(CH₃)₃ | —CH₂—C(CH₃)₃ | Cl |
| 32-20 | CH₃ | —CH₂—C(CH₃)₃ | Cl | —CH₂—C(CH₃)₃ | Cl |
| 32-21 | CH₃ | Cl | —CH₂—C(CH₃)₃ | Cl | —CH₂—C(CH₃)₃ |
| 32-22 | CH₃ | —CH₂—C(CH₃)₃ | Cl | Cl | —CH₂—C(CH₃)₃ |
| 32-23 | CH₃ | Cl | —CH₂—C(CH₃)₃ | —CH₂—C(CH₃)₃ | Cl |
| 32-24 | CH₃ | Cl | Cl | —CH₂—C(CH₃)₃ | —CH₂—C(CH₃)₃ |
| 32-25 | CH₃ | —CH₂—C(CH₃)₃ | —CH₂—C(CH₃)₃ | Cl | Cl |
| 32-26 | CH₃ | —CH₂—C(CH₃)₃ | Cl | Cl | Cl |
| 32-27 | CH₃ | Cl | —CH₂—C(CH₃)₃ | Cl | Cl |
| 32-28 | CH₃ | Cl | Cl | —CH₂—C(CH₃)₃ | Cl |
| 32-29 | CH₃ | Cl | Cl | Cl | —CH₂—C(CH₃)₃ |
| 32-30 | CH₃ | Cl | —CH₂CF(CH₃)₂ | —CH₂CF(CH₃)₂ | —CHCF(CH₃)₂ |
| 32-31 | CH₃ | —CH₂CF(CH₃)₂ | Cl | —CH₂CF(CH₃)₂ | —CH₂CF(CH₃)₂ |
| 32-32 | CH₃ | —CH₂CF(CH₃)₂ | —CH₂CF(CH₃)₂ | Cl | —CH₂CF(CH₃)₂ |
| 32-33 | CH₃ | —CH₂CF(CH₃)₂ | —CH₂CF(CH₃)₂ | —CH₂CF(CH₃)₂ | Cl |
| 32-34 | CH₃ | —CH₂CF(CH₃)₂ | Cl | —CH₂CF(CH₃)₂ | Cl |
| 32-35 | CH₃ | Cl | —CH₂CF(CH₃)₂ | —CH₂CF(CH₃)₂ | —CH₂CF(CH₃)₂ |
| 32-36 | CH₃ | —CH₂CF(CH₃)₂ | Cl | Cl | —CH₂CF(CH₃)₂ |
| 32-37 | CH₃ | Cl | —CH₂CF(CH₃)₂ | CH₂CF(CH₃)₂ | Cl |
| 32-38 | CH₃ | Cl | Cl | —CH₂CF(CH₃)₂ | —CH₂CF(CH₃)₂ |
| 32-39 | CH₃ | —CH₂CF(CH₃)₂ | —CH₂CF(CH₃)₂ | Cl | Cl |
| 32-40 | CH₃ | —CH₂CF(CH₃)₂ | Cl | Cl | Cl |
| 32-41 | CH₃ | Cl | —CH₂CF(CH₃)₂ | Cl | Cl |
| 32-42 | CH₃ | Cl | Cl | —CH₂CF(CH₃)₂ | Cl |
| 32-43 | CH₃ | Cl | Cl | Cl | —CH₂CF(CH₃)₂ |
| 32-44 | CH₃ | Cl | n-Propyl | n-Propyl | n-Propyl |
| 32-45 | CH₃ | n-Propyl | Cl | n-Propyl | n-Propyl |
| 32-46 | CH₃ | n-Propyl | n-Propyl | Cl | n-Propyl |
| 32-47 | CH₃ | n-Propyl | n-Propyl | n-Propyl | Cl |
| 32-48 | CH₃ | n-Propyl | Cl | n-Propyl | Cl |
| 32-49 | CH₃ | Cl | n-Propyl | Cl | n-Propyl |
| 32-50 | CH₃ | n-Propyl | Cl | Cl | n-Propyl |
| 32-51 | CH₃ | Cl | Cl | n-Propyl | n-Propyl |
| 32-52 | CH₃ | n-Propyl | n-Propyl | Cl | Cl |
| 32-53 | CH₃ | Cl | n-Propyl | n-Propyl | Cl |
| 32-54 | CH₃ | n-Propyl | Cl | Cl | Cl |
| 32-55 | CH₃ | Cl | n-Propyl | Cl | Cl |
| 32-56 | CH₃ | Cl | Cl | n-Propyl | Cl |
| 32-57 | CH₃ | Cl | Cl | Cl | n-Propyl |
| 32-58 | H | —CH₂CF(CH₃)₂ | Cl | —CH₂CF(CH₃)₂ | Cl |
| 32-59 | H | Cl | —CH₂CF(CH₃)₂ | Cl | —CH₂CF(CH₃)₂ |
| 32-60 | H | —CH₂CF(CH₃)₂ | —CH₂CF(CH₃)₂ | Cl | —CH₂CF(CH₃)₂ |
| 32-61 | H | Cl | —CH₂CF(CH₃)₂ | —CH₂CF(CH₃)₂ | Cl |
| 32-62 | H | Cl | Cl | —CH₂CF(CH₃)₂ | —CH₂CF(CH₃)₂ |
| 32-63 | H | —CH₂CF(CH₃)₂ | —CH₂CF(CH₃)₂ | Cl | Cl |
| 32-64 | H | —CH₂—C(CH₃)₃ | Cl | —CH₂—C(CH₃)₃ | —CH₂—C(CH₃)₃ |
| 32-65 | H | Cl | —CH₂—C(CH₃)₃ | Cl | —CH₂—C(CH₃)₃ |
| 32-66 | H | —CH₂—C(CH₃)₃ | —CH₂—C(CH₃)₃ | Cl | —CH₂—C(CH₃)₃ |
| 32-67 | H | Cl | —CH₂—C(CH₃)₃ | —CH₂—C(CH₃)₃ | Cl |
| 32-68 | H | Cl | Cl | —CH₂—C(CH₃)₃ | —CH₂—C(CH₃)₃ |
| 32-69 | H | —CH₂—C(CH₃)₃ | —CH₂—C(CH₃)₃ | Cl | Cl |

TABLE 33

Compounds of formula (I), wherein Cy¹ and Cy² are

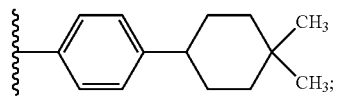 [SMILES: *c1ccc(C2CCC(C)(C)CC2)cc1]

and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 33-1 | CH₃ | Cl | Cl | Cl | Cl |
| 33-2 | CH₃ | Cl | —CH₂—iPr | —CH₂—iPr | —CH₂—iPr |
| 33-3 | CH₃ | —CH₂—iPr | Cl | —CH₂—iPr | —CH₂—iPr |
| 33-4 | CH₃ | —CH₂—iPr | —CH₂—iPr | Cl | —CH₂—iPr |
| 33-5 | CH₃ | —CH₂—iPr | —CH₂—iPr | —CH₂—iPr | Cl |
| 33-6 | CH₃ | —CH₂—iPr | Cl | —CH₂—iPr | Cl |
| 33-7 | CH₃ | Cl | —CH₂—iPr | Cl | —CH₂—iPr |
| 33-8 | CH₃ | —CH₂—iPr | Cl | Cl | —CH₂—iPr |
| 33-9 | CH₃ | Cl | Cl | —CH₂—iPr | —CH₂—iPr |
| 33-10 | CH₃ | —CH₂—iPr | —CH₂—iPr | Cl | Cl |
| 33-11 | CH₃ | Cl | —CH₂—iPr | —CH₂—iPr | Cl |
| 33-12 | CH₃ | —CH₂—iPr | Cl | Cl | Cl |
| 33-13 | CH₃ | Cl | —CH₂—iPr | Cl | Cl |
| 33-14 | CH₃ | Cl | Cl | —CH₂—iPr | Cl |
| 33-15 | CH₃ | Cl | Cl | Cl | —CH₂—iPr |
| 33-16 | CH₃ | Cl | —CH₂—C(CH₃)₃ | —CH₂—C(CH₃)₃ | —CH₂—C(CH₃)₃ |
| 33-17 | CH₃ | —CH₂—C(CH₃)₃ | Cl | —CH₂—C(CH₃)₃ | —CH₂—C(CH₃)₃ |
| 33-18 | CH₃ | —CH₂—C(CH₃)₃ | —CH₂—C(CH₃)₃ | Cl | —CH₂—C(CH₃)₃ |
| 33-19 | CH₃ | —CH₂—C(CH₃)₃ | —CH₂—C(CH₃)₃ | —CH₂—C(CH₃)₃ | Cl |
| 33-20 | CH₃ | —CH₂—C(CH₃)₃ | Cl | —CH₂—C(CH₃)₃ | Cl |
| 33-21 | CH₃ | Cl | —CH₂—C(CH₃)₃ | Cl | —CH₂—C(CH₃)₃ |
| 33-22 | CH₃ | —CH₂—C(CH₃)₃ | Cl | Cl | —CH₂—C(CH₃)₃ |
| 33-23 | CH₃ | Cl | —CH₂—C(CH₃)₃ | —CH₂—C(CH₃)₃ | Cl |
| 33-24 | CH₃ | Cl | Cl | —CH₂—C(CH₃)₃ | —CH₂—C(CH₃)₃ |
| 33-25 | CH₃ | —CH₂—C(CH₃)₃ | —CH₂—C(CH₃)₃ | Cl | Cl |
| 33-26 | CH₃ | —CH₂—C(CH₃)₃ | Cl | Cl | Cl |
| 33-27 | CH₃ | Cl | —CH₂—C(CH₃)₃ | Cl | Cl |
| 33-28 | CH₃ | Cl | Cl | —CH₂—C(CH₃)₃ | Cl |
| 33-29 | CH₃ | Cl | Cl | Cl | —CH₂—C(CH₃)₃ |
| 33-30 | CH₃ | Cl | —CH₂CF(CH₃)₂ | —CH₂CF(CH₃)₂ | —CHCF(CH₃)₂ |
| 33-31 | CH₃ | —CH₂CF(CH₃)₂ | Cl | —CH₂CF(CH₃)₂ | —CH₂CF(CH₃)₂ |
| 33-32 | CH₃ | —CH₂CF(CH₃)₂ | —CH₂CF(CH₃)₂ | Cl | —CH₂CF(CH₃)₂ |
| 33-33 | CH₃ | —CH₂CF(CH₃)₂ | —CH₂CF(CH₃)₂ | —CH₂CF(CH₃)₂ | Cl |
| 33-34 | CH₃ | —CH₂CF(CH₃)₂ | Cl | —CH₂CF(CH₃)₂ | Cl |
| 33-35 | CH₃ | Cl | —CH₂CF(CH₃)₂ | Cl | —CH₂CF(CH₃)₂ |
| 33-36 | CH₃ | —CH₂CF(CH₃)₂ | Cl | Cl | —CH₂CF(CH₃)₂ |
| 33-37 | CH₃ | Cl | —CH₂CF(CH₃)₂ | CH₂CF(CH₃)₂ | Cl |
| 33-38 | CH₃ | Cl | Cl | —CH₂CF(CH₃)₂ | —CH₂CF(CH₃)₂ |
| 33-39 | CH₃ | —CH₂CF(CH₃)₂ | —CH₂CF(CH₃)₂ | Cl | Cl |
| 33-40 | CH₃ | —CH₂CF(CH₃)₂ | Cl | Cl | Cl |
| 33-41 | CH₃ | Cl | —CH₂CF(CH₃)₂ | Cl | Cl |
| 33-42 | CH₃ | Cl | Cl | —CH₂CF(CH₃)₂ | Cl |
| 33-43 | CH₃ | Cl | Cl | Cl | —CH₂CF(CH₃)₂ |
| 33-44 | CH₃ | Cl | n-Propyl | n-Propyl | n-Propyl |
| 33-45 | CH₃ | n-Propyl | Cl | n-Propyl | n-Propyl |
| 33-46 | CH₃ | n-Propyl | n-Propyl | Cl | n-Propyl |
| 33-47 | CH₃ | n-Propyl | n-Propyl | n-Propyl | Cl |
| 33-48 | CH₃ | n-Propyl | Cl | n-Propyl | Cl |
| 33-49 | CH₃ | Cl | n-Propyl | Cl | n-Propyl |
| 33-50 | CH₃ | n-Propyl | Cl | Cl | n-Propyl |
| 33-51 | CH₃ | Cl | Cl | n-Propyl | n-Propyl |
| 33-52 | CH₃ | n-Propyl | n-Propyl | Cl | Cl |
| 33-53 | CH₃ | Cl | n-Propyl | n-Propyl | Cl |
| 33-54 | CH₃ | n-Propyl | Cl | Cl | Cl |
| 33-55 | CH₃ | Cl | n-Propyl | Cl | Cl |
| 33-56 | CH₃ | Cl | Cl | n-Propyl | Cl |
| 33-57 | CH₃ | Cl | Cl | Cl | n-Propyl |
| 33-58 | H | —CH₂CF(CH₃)₂ | Cl | —CH₂CF(CH₃)₂ | Cl |
| 33-59 | H | Cl | —CH₂CF(CH₃)₂ | Cl | —CH₂CF(CH₃)₂ |
| 33-60 | H | —CH₂CF(CH₃)₂ | Cl | Cl | —CH₂CF(CH₃)₂ |
| 33-61 | H | Cl | —CH₂CF(CH₃)₂ | —CH₂CF(CH₃)₂ | Cl |
| 33-62 | H | Cl | Cl | —CH₂CF(CH₃)₂ | —CH₂CF(CH₃)₂ |
| 33-63 | H | —CH₂CF(CH₃)₂ | —CH₂CF(CH₃)₂ | Cl | Cl |
| 33-64 | H | —CH₂—C(CH₃)₃ | Cl | —CH₂—C(CH₃)₃ | Cl |
| 33-65 | H | Cl | —CH₂—C(CH₃)₃ | Cl | —CH₂—C(CH₃)₃ |
| 33-66 | H | —CH₂—C(CH₃)₃ | Cl | Cl | —CH₂—C(CH₃)₃ |
| 33-67 | H | Cl | —CH₂—C(CH₃)₃ | —CH₂—C(CH₃)₃ | Cl |

TABLE 33-continued

Compounds of formula (I), wherein Cy¹ and Cy² are

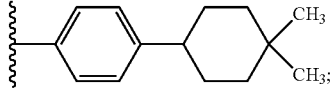

and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 33-68 | H | Cl | Cl | —CH$_2$—C(CH$_3$)$_3$ | —CH$_2$—C(CH$_3$)$_3$ |
| 33-69 | H | —CH$_2$—C(CH$_3$)$_3$ | —CH$_2$—C(CH$_3$)$_3$ | Cl | Cl |

TABLE 34

Compounds of formula (I), wherein Cy¹ and Cy² are

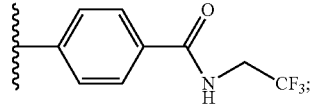

and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 34-1 | CH$_3$ | Cl | Cl | Cl | Cl |
| 34-2 | CH$_3$ | Cl | —CH$_2$—iPr | —CH$_2$—iPr | —CH$_2$—iPr |
| 34-3 | CH$_3$ | —CH$_2$—iPr | Cl | —CH$_2$—iPr | —CH$_2$—iPr |
| 34-4 | CH$_3$ | —CH$_2$—iPr | —CH$_2$—iPr | Cl | —CH$_2$—iPr |
| 34-5 | CH$_3$ | —CH$_2$—iPr | —CH$_2$—iPr | —CH$_2$—iPr | Cl |
| 34-6 | CH$_3$ | —CH$_2$—iPr | Cl | —CH$_2$—iPr | Cl |
| 34-7 | CH$_3$ | Cl | —CH$_2$—iPr | Cl | —CH$_2$—iPr |
| 34-8 | CH$_3$ | —CH$_2$—iPr | Cl | Cl | —CH$_2$—iPr |
| 34-9 | CH$_3$ | Cl | Cl | —CH$_2$—iPr | —CH$_2$—iPr |
| 34-10 | CH$_3$ | —CH$_2$—iPr | —CH$_2$—iPr | Cl | Cl |
| 34-11 | CH$_3$ | Cl | —CH$_2$—iPr | —CH$_2$—iPr | Cl |
| 34-12 | CH$_3$ | —CH$_2$—iPr | Cl | Cl | Cl |
| 34-13 | CH$_3$ | Cl | —CH$_2$—iPr | Cl | Cl |
| 34-14 | CH$_3$ | Cl | Cl | —CH$_2$—iPr | Cl |
| 34-15 | CH$_3$ | Cl | Cl | Cl | —CH$_2$—iPr |
| 34-16 | CH$_3$ | Cl | —CH$_2$—C(CH$_3$)$_3$ | —CH$_2$—C(CH$_3$)$_3$ | —CH$_2$—C(CH$_3$)$_3$ |
| 34-17 | CH$_3$ | —CH$_2$—C(CH$_3$)$_3$ | Cl | —CH$_2$—C(CH$_3$)$_3$ | —CH$_2$—C(CH$_3$)$_3$ |
| 34-18 | CH$_3$ | —CH$_2$—C(CH$_3$)$_3$ | —CH$_2$—C(CH$_3$)$_3$ | Cl | —CH$_2$—C(CH$_3$)$_3$ |
| 34-19 | CH$_3$ | —CH$_2$—C(CH$_3$)$_3$ | —CH$_2$—C(CH$_3$)$_3$ | —CH$_2$—C(CH$_3$)$_3$ | Cl |
| 34-20 | CH$_3$ | —CH$_2$—C(CH$_3$)$_3$ | Cl | —CH$_2$—C(CH$_3$)$_3$ | Cl |
| 34-21 | CH$_3$ | Cl | —CH$_2$—C(CH$_3$)$_3$ | Cl | —CH$_2$—C(CH$_3$)$_3$ |
| 34-22 | CH$_3$ | —CH$_2$—C(CH$_3$)$_3$ | Cl | Cl | —CH$_2$—C(CH$_3$)$_3$ |
| 34-23 | CH$_3$ | Cl | —CH$_2$—C(CH$_3$)$_3$ | —CH$_2$—C(CH$_3$)$_3$ | Cl |
| 34-24 | CH$_3$ | Cl | Cl | —CH$_2$—C(CH$_3$)$_3$ | —CH$_2$—C(CH$_3$)$_3$ |
| 34-25 | CH$_3$ | —CH$_2$—C(CH$_3$)$_3$ | —CH$_2$—C(CH$_3$)$_3$ | Cl | Cl |
| 34-26 | CH$_3$ | —CH$_2$—C(CH$_3$)$_3$ | Cl | Cl | Cl |
| 34-27 | CH$_3$ | Cl | —CH$_2$—C(CH$_3$)$_3$ | Cl | Cl |
| 34-28 | CH$_3$ | Cl | Cl | —CH$_2$—C(CH$_3$)$_3$ | Cl |
| 34-29 | CH$_3$ | Cl | Cl | Cl | —CH$_2$—C(CH$_3$)$_3$ |
| 34-30 | CH$_3$ | Cl | —CH$_2$CF(CH$_3$)$_2$ | —CH$_2$CF(CH$_3$)$_2$ | —CHCF(CH$_3$)$_2$ |
| 34-31 | CH$_3$ | —CH$_2$CF(CH$_3$)$_2$ | Cl | —CH$_2$CF(CH$_3$)$_2$ | —CH$_2$CF(CH$_3$)$_2$ |
| 34-32 | CH$_3$ | —CH$_2$CF(CH$_3$)$_2$ | —CH$_2$CF(CH$_3$)$_2$ | Cl | —CH$_2$CF(CH$_3$)$_2$ |
| 34-33 | CH$_3$ | —CH$_2$CF(CH$_3$)$_2$ | —CH$_2$CF(CH$_3$)$_2$ | —CH$_2$CF(CH$_3$)$_2$ | Cl |
| 34-34 | CH$_3$ | —CH$_2$CF(CH$_3$)$_2$ | Cl | —CH$_2$CF(CH$_3$)$_2$ | Cl |
| 34-35 | CH$_3$ | Cl | —CH$_2$CF(CH$_3$)$_2$ | Cl | —CH$_2$CF(CH$_3$)$_2$ |
| 34-36 | CH$_3$ | —CH$_2$CF(CH$_3$)$_2$ | Cl | Cl | —CH$_2$CF(CH$_3$)$_2$ |
| 34-37 | CH$_3$ | Cl | —CH$_2$CF(CH$_3$)$_2$ | CH$_2$CF(CH$_3$)$_2$ | Cl |
| 34-38 | CH$_3$ | Cl | Cl | —CH$_2$CF(CH$_3$)$_2$ | —CH$_2$CF(CH$_3$)$_2$ |
| 34-39 | CH$_3$ | —CH$_2$CF(CH$_3$)$_2$ | —CH$_2$CF(CH$_3$)$_2$ | Cl | Cl |
| 34-40 | CH$_3$ | —CH$_2$CF(CH$_3$)$_2$ | Cl | Cl | Cl |
| 34-41 | CH$_3$ | Cl | —CH$_2$CF(CH$_3$)$_2$ | Cl | Cl |
| 34-42 | CH$_3$ | Cl | Cl | —CH$_2$CF(CH$_3$)$_2$ | Cl |
| 34-43 | CH$_3$ | Cl | Cl | Cl | —CH$_2$CF(CH$_3$)$_2$ |
| 34-44 | CH$_3$ | Cl | n-Propyl | n-Propyl | n-Propyl |
| 34-45 | CH$_3$ | n-Propyl | Cl | n-Propyl | n-Propyl |
| 34-46 | CH$_3$ | n-Propyl | n-Propyl | Cl | n-Propyl |
| 34-47 | CH$_3$ | n-Propyl | n-Propyl | n-Propyl | Cl |
| 34-48 | CH$_3$ | n-Propyl | Cl | n-Propyl | Cl |
| 34-49 | CH$_3$ | Cl | n-Propyl | Cl | n-Propyl |

TABLE 34-continued

Compounds of formula (I), wherein Cy¹ and Cy² are

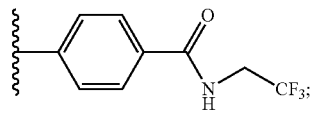 [SMILES: *c1ccc(C(=O)NCC(F)(F)F)cc1]

and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 34-50 | CH₃ | n-Propyl | Cl | Cl | n-Propyl |
| 34-51 | CH₃ | Cl | Cl | n-Propyl | n-Propyl |
| 34-52 | CH₃ | n-Propyl | n-Propyl | Cl | Cl |
| 34-53 | CH₃ | Cl | n-Propyl | n-Propyl | Cl |
| 34-54 | CH₃ | n-Propyl | Cl | Cl | Cl |
| 34-55 | CH₃ | Cl | n-Propyl | Cl | Cl |
| 34-56 | CH₃ | Cl | Cl | n-Propyl | Cl |
| 34-57 | CH₃ | Cl | Cl | Cl | n-Propyl |
| 34-58 | H | —CH₂CF(CH₃)₂ | Cl | —CH₂CF(CH₃)₂ | Cl |
| 34-59 | H | Cl | —CH₂CF(CH₃)₂ | Cl | —CH₂CF(CH₃)₂ |
| 34-60 | H | —CH₂CF(CH₃)₂ | Cl | Cl | —CH₂CF(CH₃)₂ |
| 34-61 | H | Cl | —CH₂CF(CH₃)₂ | —CH₂CF(CH₃)₂ | Cl |
| 34-62 | H | Cl | Cl | —CH₂CF(CH₃)₂ | —CH₂CF(CH₃)₂ |
| 34-63 | H | —CH₂CF(CH₃)₂ | —CH₂CF(CH₃)₂ | Cl | Cl |
| 34-64 | H | —CH₂—C(CH₃)₃ | Cl | —CH₂—C(CH₃)₃ | Cl |
| 34-65 | H | Cl | —CH₂—C(CH₃)₃ | Cl | —CH₂—C(CH₃)₃ |
| 34-66 | H | —CH₂—C(CH₃)₃ | Cl | Cl | —CH₂—C(CH₃)₃ |
| 34-67 | H | Cl | —CH₂—C(CH₃)₃ | —CH₂—C(CH₃)₃ | Cl |
| 34-68 | H | Cl | Cl | —CH₂—C(CH₃)₃ | —CH₂—C(CH₃)₃ |
| 34-69 | H | —CH₂—C(CH₃)₃ | —CH₂—C(CH₃)₃ | Cl | Cl |

TABLE 35

Compounds of formula (I), wherein Cy¹ and Cy² are

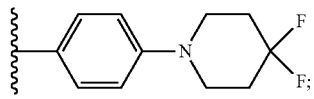

and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 35-1 | CH₃ | Cl | Cl | Cl | Cl |
| 35-2 | CH₃ | Cl | —CH₂—iPr | —CH₂—iPr | —CH₂—iPr |
| 35-3 | CH₃ | —CH₂—iPr | Cl | —CH₂—iPr | —CH₂—iPr |
| 35-4 | CH₃ | —CH₂—iPr | —CH₂—iPr | Cl | —CH₂—iPr |
| 35-5 | CH₃ | —CH₂—iPr | —CH₂—iPr | —CH₂—iPr | Cl |
| 35-6 | CH₃ | —CH₂—iPr | Cl | —CH₂—iPr | Cl |
| 35-7 | CH₃ | Cl | —CH₂—iPr | Cl | —CH₂—iPr |
| 35-8 | CH₃ | —CH₂—iPr | Cl | Cl | —CH₂—iPr |
| 35-9 | CH₃ | Cl | Cl | —CH₂—iPr | —CH₂—iPr |
| 35-10 | CH₃ | —CH₂—iPr | —CH₂—iPr | Cl | Cl |
| 35-11 | CH₃ | Cl | —CH₂—iPr | —CH₂—iPr | Cl |
| 35-12 | CH₃ | —CH₂—iPr | Cl | Cl | Cl |
| 35-13 | CH₃ | Cl | —CH₂—iPr | Cl | Cl |
| 35-14 | CH₃ | Cl | Cl | —CH₂—iPr | Cl |
| 35-15 | CH₃ | Cl | Cl | Cl | —CH₂—iPr |
| 35-16 | CH₃ | Cl | —CH₂—C(CH₃)₃ | —CH₂—C(CH₃)₃ | —CH₂—C(CH₃)₃ |
| 35-17 | CH₃ | —CH₂—C(CH₃)₃ | Cl | —CH₂—C(CH₃)₃ | —CH₂—C(CH₃)₃ |
| 35-18 | CH₃ | —CH₂—C(CH₃)₃ | —CH₂—C(CH₃)₃ | Cl | —CH₂—C(CH₃)₃ |
| 35-19 | CH₃ | —CH₂—C(CH₃)₃ | —CH₂—C(CH₃)₃ | —CH₂—C(CH₃)₃ | Cl |
| 35-20 | CH₃ | —CH₂—C(CH₃)₃ | Cl | —CH₂—C(CH₃)₃ | Cl |
| 35-21 | CH₃ | Cl | —CH₂—C(CH₃)₃ | Cl | —CH₂—C(CH₃)₃ |
| 35-22 | CH₃ | —CH₂—C(CH₃)₃ | Cl | Cl | —CH₂—C(CH₃)₃ |
| 35-23 | CH₃ | Cl | —CH₂—C(CH₃)₃ | —CH₂—C(CH₃)₃ | Cl |
| 35-24 | CH₃ | Cl | Cl | —CH₂—C(CH₃)₃ | —CH₂—C(CH₃)₃ |
| 35-25 | CH₃ | —CH₂—C(CH₃)₃ | —CH₂—C(CH₃)₃ | Cl | Cl |
| 35-26 | CH₃ | —CH₂—C(CH₃)₃ | Cl | Cl | Cl |
| 35-27 | CH₃ | Cl | —CH₂—C(CH₃)₃ | Cl | Cl |
| 35-28 | CH₃ | Cl | Cl | —CH₂—C(CH₃)₃ | Cl |
| 35-29 | CH₃ | Cl | Cl | Cl | —CH₂—C(CH₃)₃ |
| 35-30 | CH₃ | Cl | —CH₂CF(CH₃)₂ | —CH₂CF(CH₃)₂ | —CHCF(CH₃)₂ |
| 35-31 | CH₃ | —CH₂CF(CH₃)₂ | Cl | —CH₂CF(CH₃)₂ | —CH₂CF(CH₃)₂ |

TABLE 35-continued

Compounds of formula (I), wherein Cy¹ and Cy² are

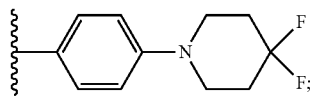 [SMILES: *c1ccc(N2CCC(F)(F)CC2)cc1]

and R$^a$, R$^b$ and R$^1$ to R$^4$ are as shown.

| Cmpd # | R$^a$/R$^b$ | R$^1$ | R$^2$ | R$^3$ | R$^4$ |
|---|---|---|---|---|---|
| 35-32 | CH$_3$ | —CH$_2$CF(CH$_3$)$_2$ | —CH$_2$CF(CH$_3$)$_2$ | Cl | —CH$_2$CF(CH$_3$)$_2$ |
| 35-33 | CH$_3$ | —CH$_2$CF(CH$_3$)$_2$ | —CH$_2$CF(CH$_3$)$_2$ | —CH$_2$CF(CH$_3$)$_2$ | Cl |
| 35-34 | CH$_3$ | —CH$_2$CF(CH$_3$)$_2$ | Cl | —CH$_2$CF(CH$_3$)$_2$ | Cl |
| 35-35 | CH$_3$ | Cl | —CH$_2$CF(CH$_3$)$_2$ | Cl | —CH$_2$CF(CH$_3$)$_2$ |
| 35-36 | CH$_3$ | —CH$_2$CF(CH$_3$)$_2$ | Cl | Cl | —CH$_2$CF(CH$_3$)$_2$ |
| 35-37 | CH$_3$ | Cl | —CH$_2$CF(CH$_3$)$_2$ | CH$_2$CF(CH$_3$)$_2$ | Cl |
| 35-38 | CH$_3$ | Cl | Cl | —CH$_2$CF(CH$_3$)$_2$ | —CH$_2$CF(CH$_3$)$_2$ |
| 35-39 | CH$_3$ | —CH$_2$CF(CH$_3$)$_2$ | —CH$_2$CF(CH$_3$)$_2$ | Cl | Cl |
| 35-40 | CH$_3$ | —CH$_2$CF(CH$_3$)$_2$ | Cl | Cl | Cl |
| 35-41 | CH$_3$ | Cl | —CH$_2$CF(CH$_3$)$_2$ | Cl | Cl |
| 35-42 | CH$_3$ | Cl | Cl | —CH$_2$CF(CH$_3$)$_2$ | Cl |
| 35-43 | CH$_3$ | Cl | Cl | Cl | —CH$_2$CF(CH$_3$)$_2$ |
| 35-44 | CH$_3$ | Cl | n-Propyl | n-Propyl | n-Propyl |
| 35-45 | CH$_3$ | n-Propyl | Cl | n-Propyl | n-Propyl |
| 35-46 | CH$_3$ | n-Propyl | n-Propyl | Cl | n-Propyl |
| 35-47 | CH$_3$ | n-Propyl | n-Propyl | n-Propyl | Cl |
| 35-48 | CH$_3$ | n-Propyl | Cl | n-Propyl | Cl |
| 35-49 | CH$_3$ | Cl | n-Propyl | Cl | n-Propyl |
| 35-50 | CH$_3$ | n-Propyl | Cl | Cl | n-Propyl |
| 35-51 | CH$_3$ | Cl | Cl | n-Propyl | n-Propyl |
| 35-52 | CH$_3$ | n-Propyl | n-Propyl | Cl | Cl |
| 35-53 | CH$_3$ | Cl | n-Propyl | n-Propyl | Cl |
| 35-54 | CH$_3$ | n-Propyl | Cl | Cl | Cl |
| 35-55 | CH$_3$ | Cl | n-Propyl | Cl | Cl |
| 35-56 | CH$_3$ | Cl | Cl | n-Propyl | Cl |
| 35-57 | CH$_3$ | Cl | Cl | Cl | n-Propyl |
| 35-58 | H | —CH$_2$CF(CH$_3$)$_2$ | Cl | —CH$_2$CF(CH$_3$)$_2$ | Cl |
| 35-59 | H | Cl | —CH$_2$CF(CH$_3$)$_2$ | Cl | —CH$_2$CF(CH$_3$)$_2$ |
| 35-60 | H | —CH$_2$CF(CH$_3$)$_2$ | Cl | Cl | —CH$_2$CF(CH$_3$)$_2$ |
| 35-61 | H | Cl | —CH$_2$CF(CH$_3$)$_2$ | —CH$_2$CF(CH$_3$)$_2$ | Cl |
| 35-62 | H | Cl | Cl | —CH$_2$CF(CH$_3$)$_2$ | —CH$_2$CF(CH$_3$)$_2$ |
| 35-63 | H | —CH$_2$CF(CH$_3$)$_2$ | —CH$_2$CF(CH$_3$)$_2$ | Cl | Cl |
| 35-64 | H | —CH$_2$—C(CH$_3$)$_3$ | Cl | —CH$_2$—C(CH$_3$)$_3$ | Cl |
| 35-65 | H | Cl | —CH$_2$—C(CH$_3$)$_3$ | Cl | —CH$_2$—C(CH$_3$)$_3$ |
| 35-66 | H | —CH$_2$—C(CH$_3$)$_3$ | Cl | Cl | —CH$_2$—C(CH$_3$)$_3$ |
| 35-67 | H | Cl | —CH$_2$—C(CH$_3$)$_3$ | —CH$_2$—C(CH$_3$)$_3$ | Cl |
| 35-68 | H | Cl | Cl | —CH$_2$—C(CH$_3$)$_3$ | —CH$_2$—C(CH$_3$)$_3$ |
| 35-69 | H | —CH$_2$—C(CH$_3$)$_3$ | —CH$_2$—C(CH$_3$)$_3$ | Cl | Cl |

TABLE 36

Compounds of formula (I), wherein Cy¹ and Cy² are

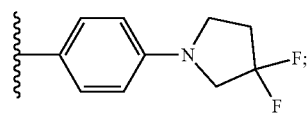 [SMILES: *c1ccc(N2CCC(F)(F)C2)cc1]

and R$^a$, R$^b$ and R$^1$ to R$^4$ are as shown.

| Cmpd # | R$^a$/R$^b$ | R$^1$ | R$^2$ | R$^3$ | R$^4$ |
|---|---|---|---|---|---|
| 36-1 | CH$_3$ | Cl | Cl | Cl | Cl |
| 36-2 | CH$_3$ | Cl | —CH$_2$—iPr | —CH$_2$—iPr | —CH$_2$—iPr |
| 36-3 | CH$_3$ | —CH$_2$—iPr | Cl | —CH$_2$—iPr | —CH$_2$—iPr |
| 36-4 | CH$_3$ | —CH$_2$—iPr | —CH$_2$—iPr | Cl | —CH$_2$—iPr |
| 36-5 | CH$_3$ | —CH$_2$—iPr | —CH$_2$—iPr | —CH$_2$—iPr | Cl |
| 36-6 | CH$_3$ | —CH$_2$—iPr | Cl | —CH$_2$—iPr | Cl |
| 36-7 | CH$_3$ | Cl | —CH$_2$—iPr | Cl | —CH$_2$—iPr |
| 36-8 | CH$_3$ | —CH$_2$—iPr | Cl | Cl | —CH$_2$—iPr |
| 36-9 | CH$_3$ | Cl | Cl | —CH$_2$—iPr | —CH$_2$—iPr |
| 36-10 | CH$_3$ | —CH$_2$—iPr | —CH$_2$—iPr | Cl | Cl |
| 36-11 | CH$_3$ | Cl | —CH$_2$—iPr | —CH$_2$—iPr | Cl |
| 36-12 | CH$_3$ | —CH$_2$—iPr | Cl | Cl | Cl |
| 36-13 | CH$_3$ | Cl | —CH$_2$—iPr | Cl | Cl |

TABLE 36-continued

Compounds of formula (I), wherein Cy¹ and Cy² are

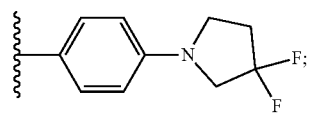

and R$^a$, R$^b$ and R$^1$ to R$^4$ are as shown.

| Cmpd # | R$^a$/R$^b$ | R$^1$ | R$^2$ | R$^3$ | R$^4$ |
|---|---|---|---|---|---|
| 36-14 | CH$_3$ | Cl | Cl | —CH$_2$—iPr | Cl |
| 36-15 | CH$_3$ | Cl | Cl | Cl | —CH$_2$—iPr |
| 36-16 | CH$_3$ | Cl | —CH$_2$—C(CH$_3$)$_3$ | —CH$_2$—C(CH$_3$)$_3$ | —CH$_2$—C(CH$_3$)$_3$ |
| 36-17 | CH$_3$ | —CH$_2$—C(CH$_3$)$_3$ | Cl | —CH$_2$—C(CH$_3$)$_3$ | —CH$_2$—C(CH$_3$)$_3$ |
| 36-18 | CH$_3$ | —CH$_2$—C(CH$_3$)$_3$ | —CH$_2$—C(CH$_3$)$_3$ | Cl | —CH$_2$—C(CH$_3$)$_3$ |
| 36-19 | CH$_3$ | —CH$_2$—C(CH$_3$)$_3$ | —CH$_2$—C(CH$_3$)$_3$ | —CH$_2$—C(CH$_3$)$_3$ | Cl |
| 36-20 | CH$_3$ | —CH$_2$—C(CH$_3$)$_3$ | Cl | —CH$_2$—C(CH$_3$)$_3$ | Cl |
| 36-21 | CH$_3$ | Cl | —CH$_2$—C(CH$_3$)$_3$ | Cl | —CH$_2$—C(CH$_3$)$_3$ |
| 36-22 | CH$_3$ | —CH$_2$—C(CH$_3$)$_3$ | Cl | Cl | —CH$_2$—C(CH$_3$)$_3$ |
| 36-23 | CH$_3$ | Cl | —CH$_2$—C(CH$_3$)$_3$ | —CH$_2$—C(CH$_3$)$_3$ | Cl |
| 36-24 | CH$_3$ | Cl | Cl | —CH$_2$—C(CH$_3$)$_3$ | —CH$_2$—C(CH$_3$)$_3$ |
| 36-25 | CH$_3$ | —CH$_2$—C(CH$_3$)$_3$ | —CH$_2$—C(CH$_3$)$_3$ | Cl | Cl |
| 36-26 | CH$_3$ | —CH$_2$—C(CH$_3$)$_3$ | Cl | Cl | Cl |
| 36-27 | CH$_3$ | Cl | —CH$_2$—C(CH$_3$)$_3$ | Cl | Cl |
| 36-28 | CH$_3$ | Cl | Cl | —CH$_2$—C(CH$_3$)$_3$ | Cl |
| 36-29 | CH$_3$ | Cl | Cl | Cl | —CH$_2$—C(CH$_3$)$_3$ |
| 36-30 | CH$_3$ | Cl | —CH$_2$CF(CH$_3$)$_2$ | —CH$_2$CF(CH$_3$)$_2$ | —CHCF(CH$_3$)$_2$ |
| 36-31 | CH$_3$ | —CH$_2$CF(CH$_3$)$_2$ | Cl | —CH$_2$CF(CH$_3$)$_2$ | —CH$_2$CF(CH$_3$)$_2$ |
| 36-32 | CH$_3$ | —CH$_2$CF(CH$_3$)$_2$ | —CH$_2$CF(CH$_3$)$_2$ | Cl | —CH$_2$CF(CH$_3$)$_2$ |
| 36-33 | CH$_3$ | —CH$_2$CF(CH$_3$)$_2$ | —CH$_2$CF(CH$_3$)$_2$ | —CH$_2$CF(CH$_3$)$_2$ | Cl |
| 36-34 | CH$_3$ | —CH$_2$CF(CH$_3$)$_2$ | Cl | —CH$_2$CF(CH$_3$)$_2$ | Cl |
| 36-35 | CH$_3$ | Cl | —CH$_2$CF(CH$_3$)$_2$ | Cl | —CH$_2$CF(CH$_3$)$_2$ |
| 36-36 | CH$_3$ | —CH$_2$CF(CH$_3$)$_2$ | Cl | Cl | —CH$_2$CF(CH$_3$)$_2$ |
| 36-37 | CH$_3$ | Cl | —CH$_2$CF(CH$_3$)$_2$ | CH$_2$CF(CH$_3$)$_2$ | Cl |
| 36-38 | CH$_3$ | Cl | Cl | —CH$_2$CF(CH$_3$)$_2$ | —CH$_2$CF(CH$_3$)$_2$ |
| 36-39 | CH$_3$ | —CH$_2$CF(CH$_3$)$_2$ | —CH$_2$CF(CH$_3$)$_2$ | Cl | Cl |
| 36-40 | CH$_3$ | —CH$_2$CF(CH$_3$)$_2$ | Cl | Cl | Cl |
| 36-41 | CH$_3$ | Cl | —CH$_2$CF(CH$_3$)$_2$ | Cl | Cl |
| 36-42 | CH$_3$ | Cl | Cl | —CH$_2$CF(CH$_3$)$_2$ | Cl |
| 36-43 | CH$_3$ | Cl | Cl | Cl | —CH$_2$CF(CH$_3$)$_2$ |
| 36-44 | CH$_3$ | Cl | n-Propyl | n-Propyl | n-Propyl |
| 36-45 | CH$_3$ | n-Propyl | Cl | n-Propyl | n-Propyl |
| 36-46 | CH$_3$ | n-Propyl | n-Propyl | Cl | n-Propyl |
| 36-47 | CH$_3$ | n-Propyl | n-Propyl | n-Propyl | Cl |
| 36-48 | CH$_3$ | n-Propyl | Cl | n-Propyl | Cl |
| 36-49 | CH$_3$ | Cl | n-Propyl | Cl | n-Propyl |
| 36-50 | CH$_3$ | n-Propyl | Cl | Cl | n-Propyl |
| 36-51 | CH$_3$ | Cl | Cl | n-Propyl | n-Propyl |
| 36-52 | CH$_3$ | n-Propyl | n-Propyl | Cl | Cl |
| 36-53 | CH$_3$ | Cl | n-Propyl | n-Propyl | Cl |
| 36-54 | CH$_3$ | n-Propyl | Cl | Cl | Cl |
| 36-55 | CH$_3$ | Cl | n-Propyl | Cl | Cl |
| 36-56 | CH$_3$ | Cl | Cl | n-Propyl | Cl |
| 36-57 | CH$_3$ | Cl | Cl | Cl | n-Propyl |
| 36-58 | H | —CH$_2$CF(CH$_3$)$_2$ | Cl | —CH$_2$CF(CH$_3$)$_2$ | Cl |
| 36-59 | H | Cl | —CH$_2$CF(CH$_3$)$_2$ | Cl | —CH$_2$CF(CH$_3$)$_2$ |
| 36-60 | H | —CH$_2$CF(CH$_3$)$_2$ | Cl | Cl | —CH$_2$CF(CH$_3$)$_2$ |
| 36-61 | H | Cl | —CH$_2$CF(CH$_3$)$_2$ | —CH$_2$CF(CH$_3$)$_2$ | Cl |
| 36-62 | H | Cl | Cl | —CH$_2$CF(CH$_3$)$_2$ | —CH$_2$CF(CH$_3$)$_2$ |
| 36-63 | H | —CH$_2$CF(CH$_3$)$_2$ | —CH$_2$CF(CH$_3$)$_2$ | Cl | Cl |
| 36-64 | H | —CH$_2$—C(CH$_3$)$_3$ | Cl | —CH$_2$—C(CH$_3$)$_3$ | Cl |
| 36-65 | H | Cl | —CH$_2$—C(CH$_3$)$_3$ | Cl | —CH$_2$—C(CH$_3$)$_3$ |
| 36-66 | H | —CH$_2$—C(CH$_3$)$_3$ | Cl | Cl | —CH$_2$—C(CH$_3$)$_3$ |
| 36-67 | H | Cl | —CH$_2$—C(CH$_3$)$_3$ | —CH$_2$—C(CH$_3$)$_3$ | Cl |
| 36-68 | H | Cl | Cl | —CH$_2$—C(CH$_3$)$_3$ | —CH$_2$—C(CH$_3$)$_3$ |
| 36-69 | H | —CH$_2$—C(CH$_3$)$_3$ | —CH$_2$—C(CH$_3$)$_3$ | Cl | Cl |

TABLE 37

Compounds of formula (I), wherein Cy¹ and Cy² are

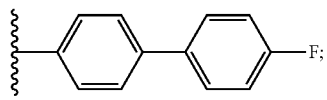 [SMILES: *c1ccc(-c2ccc(F)cc2)cc1]

—F;

and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 37-1 | CH₃ | Cl | Cl | Cl | Cl |
| 37-2 | CH₃ | Cl | —CH₂—iPr | —CH₂—iPr | —CH₂—iPr |
| 37-3 | CH₃ | —CH₂—iPr | Cl | —CH₂—iPr | —CH₂—iPr |
| 37-4 | CH₃ | —CH₂—iPr | —CH₂—iPr | Cl | —CH₂—iPr |
| 37-5 | CH₃ | —CH₂—iPr | —CH₂—iPr | —CH₂—iPr | Cl |
| 37-6 | CH₃ | —CH₂—iPr | Cl | —CH₂—iPr | Cl |
| 37-7 | CH₃ | Cl | —CH₂—iPr | Cl | —CH₂—iPr |
| 37-8 | CH₃ | —CH₂—iPr | Cl | Cl | —CH₂—iPr |
| 37-9 | CH₃ | Cl | Cl | —CH₂—iPr | —CH₂—iPr |
| 37-10 | CH₃ | —CH₂—iPr | —CH₂—iPr | Cl | Cl |
| 37-11 | CH₃ | Cl | —CH₂—iPr | —CH₂—iPr | Cl |
| 37-12 | CH₃ | —CH₂—iPr | Cl | Cl | Cl |
| 37-13 | CH₃ | Cl | —CH₂—iPr | Cl | Cl |
| 37-14 | CH₃ | Cl | Cl | —CH₂—iPr | Cl |
| 37-15 | CH₃ | Cl | Cl | Cl | —CH₂—iPr |
| 37-16 | CH₃ | Cl | —CH₂—C(CH₃)₃ | —CH₂—C(CH₃)₃ | —CH₂—C(CH₃)₃ |
| 37-17 | CH₃ | —CH₂—C(CH₃)₃ | Cl | —CH₂—C(CH₃)₃ | —CH₂—C(CH₃)₃ |
| 37-18 | CH₃ | —CH₂—C(CH₃)₃ | —CH₂—C(CH₃)₃ | Cl | —CH₂—C(CH₃)₃ |
| 37-19 | CH₃ | —CH₂—C(CH₃)₃ | —CH₂—C(CH₃)₃ | —CH₂—C(CH₃)₃ | Cl |
| 37-20 | CH₃ | —CH₂—C(CH₃)₃ | Cl | —CH₂—C(CH₃)₃ | Cl |
| 37-21 | CH₃ | Cl | —CH₂—C(CH₃)₃ | Cl | —CH₂—C(CH₃)₃ |
| 37-22 | CH₃ | —CH₂—C(CH₃)₃ | Cl | Cl | —CH₂—C(CH₃)₃ |
| 37-23 | CH₃ | Cl | —CH₂—C(CH₃)₃ | —CH₂—C(CH₃)₃ | Cl |
| 37-24 | CH₃ | Cl | Cl | —CH₂—C(CH₃)₃ | —CH₂—C(CH₃)₃ |
| 37-25 | CH₃ | —CH₂—C(CH₃)₃ | —CH₂—C(CH₃)₃ | Cl | Cl |
| 37-26 | CH₃ | —CH₂—C(CH₃)₃ | Cl | Cl | Cl |
| 37-27 | CH₃ | Cl | —CH₂—C(CH₃)₃ | Cl | Cl |
| 37-28 | CH₃ | Cl | Cl | —CH₂—C(CH₃)₃ | Cl |
| 37-29 | CH₃ | Cl | Cl | Cl | —CH₂—C(CH₃)₃ |
| 37-30 | CH₃ | Cl | —CH₂CF(CH₃)₂ | —CH₂CF(CH₃)₂ | —CHCF(CH₃)₂ |
| 37-31 | CH₃ | —CH₂CF(CH₃)₂ | Cl | —CH₂CF(CH₃)₂ | —CH₂CF(CH₃)₂ |
| 37-32 | CH₃ | —CH₂CF(CH₃)₂ | —CH₂CF(CH₃)₂ | Cl | —CH₂CF(CH₃)₂ |
| 37-33 | CH₃ | —CH₂CF(CH₃)₂ | —CH₂CF(CH₃)₂ | —CH₂CF(CH₃)₂ | Cl |
| 37-34 | CH₃ | —CH₂CF(CH₃)₂ | Cl | —CH₂CF(CH₃)₂ | Cl |
| 37-35 | CH₃ | Cl | —CH₂CF(CH₃)₂ | Cl | —CH₂CF(CH₃)₂ |
| 37-36 | CH₃ | —CH₂CF(CH₃)₂ | Cl | Cl | —CH₂CF(CH₃)₂ |
| 37-37 | CH₃ | Cl | —CH₂CF(CH₃)₂ | CH₂CF(CH₃)₂ | Cl |
| 37-38 | CH₃ | Cl | Cl | —CH₂CF(CH₃)₂ | —CH₂CF(CH₃)₂ |
| 37-39 | CH₃ | —CH₂CF(CH₃)₂ | —CH₂CF(CH₃)₂ | Cl | Cl |
| 37-40 | CH₃ | —CH₂CF(CH₃)₂ | Cl | Cl | Cl |
| 37-41 | CH₃ | Cl | —CH₂CF(CH₃)₂ | Cl | Cl |
| 37-42 | CH₃ | Cl | Cl | —CH₂CF(CH₃)₂ | Cl |
| 37-43 | CH₃ | Cl | Cl | Cl | —CH₂CF(CH₃)₂ |
| 37-44 | CH₃ | Cl | n-Propyl | n-Propyl | n-Propyl |
| 37-45 | CH₃ | n-Propyl | Cl | n-Propyl | n-Propyl |
| 37-46 | CH₃ | n-Propyl | n-Propyl | Cl | n-Propyl |
| 37-47 | CH₃ | n-Propyl | n-Propyl | n-Propyl | Cl |
| 37-48 | CH₃ | n-Propyl | Cl | n-Propyl | Cl |
| 37-49 | CH₃ | Cl | n-Propyl | Cl | n-Propyl |
| 37-50 | CH₃ | n-Propyl | Cl | Cl | n-Propyl |
| 37-51 | CH₃ | Cl | Cl | n-Propyl | n-Propyl |
| 37-52 | CH₃ | n-Propyl | n-Propyl | Cl | Cl |
| 37-53 | CH₃ | Cl | n-Propyl | n-Propyl | Cl |
| 37-54 | CH₃ | n-Propyl | Cl | Cl | Cl |
| 37-55 | CH₃ | Cl | n-Propyl | Cl | Cl |
| 37-56 | CH₃ | Cl | Cl | n-Propyl | Cl |
| 37-57 | CH₃ | Cl | Cl | Cl | n-Propyl |
| 37-58 | H | —CH₂CF(CH₃)₂ | Cl | —CH₂CF(CH₃)₂ | Cl |
| 37-59 | H | Cl | —CH₂CF(CH₃)₂ | Cl | —CH₂CF(CH₃)₂ |
| 37-60 | H | —CH₂CF(CH₃)₂ | Cl | Cl | —CH₂CF(CH₃)₂ |
| 37-61 | H | Cl | —CH₂CF(CH₃)₂ | —CH₂CF(CH₃)₂ | Cl |
| 37-62 | H | Cl | Cl | —CH₂CF(CH₃)₂ | —CH₂CF(CH₃)₂ |
| 37-63 | H | —CH₂CF(CH₃)₂ | —CH₂CF(CH₃)₂ | Cl | Cl |
| 37-64 | H | —CH₂—C(CH₃)₃ | Cl | —CH₂—C(CH₃)₃ | Cl |
| 37-65 | H | Cl | —CH₂—C(CH₃)₃ | Cl | —CH₂—C(CH₃)₃ |
| 37-66 | H | —CH₂—C(CH₃)₃ | Cl | Cl | —CH₂—C(CH₃)₃ |
| 37-67 | H | Cl | —CH₂—C(CH₃)₃ | —CH₂—C(CH₃)₃ | Cl |

TABLE 37-continued

Compounds of formula (I), wherein $Cy^1$ and $Cy^2$ are

[structure: biphenyl with F substituent]

and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 37-68 | H | Cl | Cl | —CH₂—C(CH₃)₃ | —CH₂—C(CH₃)₃ |
| 37-69 | H | —CH₂—C(CH₃)₃ | —CH₂—C(CH₃)₃ | Cl | Cl |

TABLE 38

Compounds of formula (I), wherein $Cy^1$ and $Cy^2$ are

[structure: naphthalene with morpholine substituent]

and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 38-1 | CH₃ | Cl | Cl | Cl | Cl |
| 38-2 | CH₃ | Cl | —CH₂—iPr | —CH₂—iPr | —CH₂—iPr |
| 38-3 | CH₃ | —CH₂—iPr | Cl | —CH₂—iPr | —CH₂—iPr |
| 38-4 | CH₃ | —CH₂—iPr | —CH₂—iPr | Cl | —CH₂—iPr |
| 38-5 | CH₃ | —CH₂—iPr | —CH₂—iPr | —CH₂—iPr | Cl |
| 38-6 | CH₃ | —CH₂—iPr | Cl | —CH₂—iPr | Cl |
| 38-7 | CH₃ | Cl | —CH₂—iPr | Cl | —CH₂—iPr |
| 38-8 | CH₃ | —CH₂—iPr | Cl | Cl | —CH₂—iPr |
| 38-9 | CH₃ | Cl | Cl | —CH₂—iPr | —CH₂—iPr |
| 38-10 | CH₃ | —CH₂—iPr | —CH₂—iPr | Cl | Cl |
| 38-11 | CH₃ | Cl | —CH₂—iPr | —CH₂—iPr | Cl |
| 38-12 | CH₃ | —CH₂—iPr | Cl | Cl | Cl |
| 38-13 | CH₃ | Cl | —CH₂—iPr | Cl | Cl |
| 38-14 | CH₃ | Cl | Cl | —CH₂—iPr | Cl |
| 38-15 | CH₃ | Cl | Cl | Cl | —CH₂—iPr |
| 38-16 | CH₃ | Cl | —CH₂—C(CH₃)₃ | —CH₂—C(CH₃)₃ | —CH₂—C(CH₃)₃ |
| 38-17 | CH₃ | —CH₂—C(CH₃)₃ | Cl | —CH₂—C(CH₃)₃ | —CH₂—C(CH₃)₃ |
| 38-18 | CH₃ | —CH₂—C(CH₃)₃ | —CH₂—C(CH₃)₃ | Cl | —CH₂—C(CH₃)₃ |
| 38-19 | CH₃ | —CH₂—C(CH₃)₃ | —CH₂—C(CH₃)₃ | —CH₂—C(CH₃)₃ | Cl |
| 38-20 | CH₃ | —CH₂—C(CH₃)₃ | Cl | —CH₂—C(CH₃)₃ | Cl |
| 38-21 | CH₃ | Cl | —CH₂—C(CH₃)₃ | Cl | —CH₂—C(CH₃)₃ |
| 38-22 | CH₃ | —CH₂—C(CH₃)₃ | Cl | Cl | —CH₂—C(CH₃)₃ |
| 38-23 | CH₃ | Cl | —CH₂—C(CH₃)₃ | —CH₂—C(CH₃)₃ | Cl |
| 38-24 | CH₃ | Cl | Cl | —CH₂—C(CH₃)₃ | —CH₂—C(CH₃)₃ |
| 38-25 | CH₃ | —CH₂—C(CH₃)₃ | —CH₂—C(CH₃)₃ | Cl | Cl |
| 38-26 | CH₃ | —CH₂—C(CH₃)₃ | Cl | Cl | Cl |
| 38-27 | CH₃ | Cl | —CH₂—C(CH₃)₃ | Cl | Cl |
| 38-28 | CH₃ | Cl | Cl | —CH₂—C(CH₃)₃ | Cl |
| 38-29 | CH₃ | Cl | Cl | Cl | —CH₂—C(CH₃)₃ |
| 38-30 | CH₃ | Cl | —CH₂CF(CH₃)₂ | —CH₂CF(CH₃)₂ | —CHCF(CH₃)₂ |
| 38-31 | CH₃ | —CH₂CF(CH₃)₂ | Cl | —CH₂CF(CH₃)₂ | —CH₂CF(CH₃)₂ |
| 38-32 | CH₃ | —CH₂CF(CH₃)₂ | —CH₂CF(CH₃)₂ | Cl | —CH₂CF(CH₃)₂ |
| 38-33 | CH₃ | —CH₂CF(CH₃)₂ | —CH₂CF(CH₃)₂ | —CH₂CF(CH₃)₂ | Cl |
| 38-34 | CH₃ | —CH₂CF(CH₃)₂ | Cl | —CH₂CF(CH₃)₂ | Cl |
| 38-35 | CH₃ | Cl | —CH₂CF(CH₃)₂ | Cl | —CH₂CF(CH₃)₂ |
| 38-36 | CH₃ | —CH₂CF(CH₃)₂ | Cl | Cl | —CH₂CF(CH₃)₂ |
| 38-37 | CH₃ | Cl | —CH₂CF(CH₃)₂ | CH₂CF(CH₃)₂ | Cl |
| 38-38 | CH₃ | Cl | Cl | —CH₂CF(CH₃)₂ | —CH₂CF(CH₃)₂ |
| 38-39 | CH₃ | —CH₂CF(CH₃)₂ | —CH₂CF(CH₃)₂ | Cl | Cl |
| 38-40 | CH₃ | —CH₂CF(CH₃)₂ | Cl | Cl | Cl |
| 38-41 | CH₃ | Cl | —CH₂CF(CH₃)₂ | Cl | Cl |
| 38-42 | CH₃ | Cl | Cl | —CH₂CF(CH₃)₂ | Cl |
| 38-43 | CH₃ | Cl | Cl | Cl | —CH₂CF(CH₃)₂ |
| 38-44 | CH₃ | Cl | n-Propyl | n-Propyl | n-Propyl |
| 38-45 | CH₃ | n-Propyl | Cl | n-Propyl | n-Propyl |
| 38-46 | CH₃ | n-Propyl | n-Propyl | Cl | n-Propyl |

TABLE 38-continued

Compounds of formula (I), wherein $Cy^1$ and $Cy^2$ are

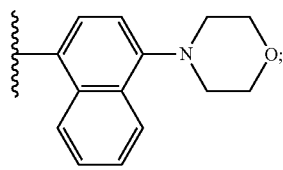 [SMILES: *c1ccc(N2CCOCC2)c2ccccc12]

and $R^a$, $R^b$ and $R^1$ to $R^4$ are as shown.

| Cmpd # | $R^a/R^b$ | $R^1$ | $R^2$ | $R^3$ | $R^4$ |
|---|---|---|---|---|---|
| 38-47 | $CH_3$ | n-Propyl | n-Propyl | n-Propyl | Cl |
| 38-48 | $CH_3$ | n-Propyl | Cl | n-Propyl | Cl |
| 38-49 | $CH_3$ | Cl | n-Propyl | Cl | n-Propyl |
| 38-50 | $CH_3$ | n-Propyl | Cl | Cl | n-Propyl |
| 38-51 | $CH_3$ | Cl | Cl | n-Propyl | n-Propyl |
| 38-52 | $CH_3$ | n-Propyl | n-Propyl | Cl | Cl |
| 38-53 | $CH_3$ | Cl | n-Propyl | n-Propyl | Cl |
| 38-54 | $CH_3$ | n-Propyl | Cl | Cl | Cl |
| 38-55 | $CH_3$ | Cl | n-Propyl | Cl | Cl |
| 38-56 | $CH_3$ | Cl | Cl | n-Propyl | Cl |
| 38-57 | $CH_3$ | Cl | Cl | Cl | n-Propyl |
| 38-58 | H | —$CH_2CF(CH_3)_2$ | Cl | —$CH_2CF(CH_3)_2$ | Cl |
| 38-59 | H | Cl | —$CH_2CF(CH_3)_2$ | Cl | —$CH_2CF(CH_3)_2$ |
| 38-60 | H | —$CH_2CF(CH_3)_2$ | Cl | Cl | —$CH_2CF(CH_3)_2$ |
| 38-61 | H | Cl | —$CH_2CF(CH_3)_2$ | —$CH_2CF(CH_3)_2$ | Cl |
| 38-62 | H | Cl | Cl | —$CH_2CF(CH_3)_2$ | —$CH_2CF(CH_3)_2$ |
| 38-63 | H | —$CH_2CF(CH_3)_2$ | —$CH_2CF(CH_3)_2$ | Cl | Cl |
| 38-64 | H | —$CH_2$—$C(CH_3)_3$ | Cl | —$CH_2$—$C(CH_3)_3$ | Cl |
| 38-65 | H | Cl | —$CH_2$—$C(CH_3)_3$ | Cl | —$CH_2$—$C(CH_3)_3$ |
| 38-66 | H | —$CH_2$—$C(CH_3)_3$ | Cl | Cl | —$CH_2$—$C(CH_3)_3$ |
| 38-67 | H | Cl | —$CH_2$—$C(CH_3)_3$ | —$CH_2$—$C(CH_3)_3$ | Cl |
| 38-68 | H | Cl | Cl | —$CH_2$—$C(CH_3)_3$ | —$CH_2$—$C(CH_3)_3$ |
| 38-69 | H | —$CH_2$—$C(CH_3)_3$ | —$CH_2$—$C(CH_3)_3$ | Cl | Cl |

Particular embodiments of the compounds of the invention are further described in Tables 39-1037 wherein the meaning of the variables $Cy^1$, $Cy^2$, $R^a$, $R^b$ and $R^1$ to $R^4$ are as described in Tables 2-38, with the exception that group C1 in Tables 2-38 is replaced with the groups C2 to C28.

Table 39: Compounds of formula (I), wherein $Cy^1$ and $Cy^2$ and $R^1$ to $R^4$ are as shown in Table 2, with the exception that C1 is replaced by C2.

Table 40: Compounds of formula (I), wherein $Cy^1$ and $Cy^2$ and $R^1$ to $R^4$ are as shown in Table 3, with the exception that C1 is replaced by C2.

Table 41: Compounds of formula (I), wherein $Cy^1$ and $Cy^2$ and $R^1$ to $R^4$ are as shown in Table 4, with the exception that C1 is replaced by C2.

Table 42: Compounds of formula (I), wherein $Cy^1$ and $Cy^2$ and $R^1$ to $R^4$ are as shown in Table 5, with the exception that C1 is replaced by C2.

Table 43: Compounds of formula (I), wherein $Cy^1$ and $Cy^2$ and $R^1$ to $R^4$ are as shown in Table 6, with the exception that C1 is replaced by C2.

Table 44: Compounds of formula (I), wherein $Cy^1$ and $Cy^2$ and $R^1$ to $R^4$ are as shown in Table 7, with the exception that C1 is replaced by C2.

Table 45: Compounds of formula (I), wherein $Cy^1$ and $Cy^2$ and $R^1$ to $R^4$ are as shown in Table 8, with the exception that C1 is replaced by C2.

Table 46: Compounds of formula (I), wherein $Cy^1$ and $Cy^2$ and $R^1$ to $R^4$ are as shown in Table 9, with the exception that C1 is replaced by C2.

Table 47: Compounds of formula (I), wherein $Cy^1$ and $Cy^2$ and $R^1$ to $R^4$ are as shown in Table 10, with the exception that C1 is replaced by C2.

Table 48: Compounds of formula (I), wherein $Cy^1$ and $Cy^2$ and $R^1$ to $R^4$ are as shown in Table 11, with the exception that C1 is replaced by C2.

Table 49: Compounds of formula (I), wherein $Cy^1$ and $Cy^2$ and $R^1$ to $R^4$ are as shown in Table 12, with the exception that C1 is replaced by C2.

Table 50: Compounds of formula (I), wherein $Cy^1$ and $Cy^2$ and $R^1$ to $R^4$ are as shown in Table 13, with the exception that C1 is replaced by C2.

Table 51: Compounds of formula (I), wherein $Cy^1$ and $Cy^2$ and $R^1$ to $R^4$ are as shown in Table 14, with the exception that C1 is replaced by C2.

Table 52: Compounds of formula (I), wherein $Cy^1$ and $Cy^2$ and $R^1$ to $R^4$ are as shown in Table 15, with the exception that C1 is replaced by C2.

Table 53: Compounds of formula (I), wherein $Cy^1$ and $Cy^2$ and $R^1$ to $R^4$ are as shown in Table 16, with the exception that C1 is replaced by C2.

Table 54: Compounds of formula (I), wherein $Cy^1$ and $Cy^2$ and $R^1$ to $R^4$ are as shown in Table 17, with the exception that C1 is replaced by C2.

Table 55: Compounds of formula (I), wherein $Cy^1$ and $Cy^2$ and $R^1$ to $R^4$ are as shown in Table 18, with the exception that C1 is replaced by C2.

Table 56: Compounds of formula (I), wherein $Cy^1$ and $Cy^2$ and $R^1$ to $R^4$ are as shown in Table 19, with the exception that C1 is replaced by C2.

Table 57: Compounds of formula (I), wherein $Cy^1$ and $Cy^2$ and $R^1$ to $R^4$ are as shown in Table 20, with the exception that C1 is replaced by C2.

Table 58: Compounds of formula (I), wherein $Cy^1$ and $Cy^2$ and $R^1$ to $R^4$ are as shown in Table 21, with the exception that C1 is replaced by C2.

Table 59: Compounds of formula (I), wherein $Cy^1$ and $Cy^2$ and $R^1$ to $R^4$ are as shown in Table 22, with the exception that C1 is replaced by C2.

Table 60: Compounds of formula (I), wherein $Cy^1$ and $Cy^2$ and $R^1$ to $R^4$ are as shown in Table 23, with the exception that C1 is replaced by C2.

Table 61: Compounds of formula (I), wherein $Cy^1$ and $Cy^2$ and $R^1$ to $R^4$ are as shown in Table 24, with the exception that C1 is replaced by C2.

Table 62: Compounds of formula (I), wherein $Cy^1$ and $Cy^2$ and $R^1$ to $R^4$ are as shown in Table 25, with the exception that C1 is replaced by C2.

Table 63: Compounds of formula (I), wherein $Cy^1$ and $Cy^2$ and $R^1$ to $R^4$ are as shown in Table 26, with the exception that C1 is replaced by C2.

Table 64: Compounds of formula (I), wherein $Cy^1$ and $Cy^2$ and $R^1$ to $R^4$ are as shown in Table 27, with the exception that C1 is replaced by C2.

Table 65: Compounds of formula (I), wherein $Cy^1$ and $Cy^2$ and $R^1$ to $R^4$ are as shown in Table 28, with the exception that C1 is replaced by C2.

Table 66: Compounds of formula (I), wherein $Cy^1$ and $Cy^2$ and $R^1$ to $R^4$ are as shown in Table 29, with the exception that C1 is replaced by C2.

Table 67: Compounds of formula (I), wherein $Cy^1$ and $Cy^2$ and $R^1$ to $R^4$ are as shown in Table 30, with the exception that C1 is replaced by C2.

Table 68: Compounds of formula (I), wherein $Cy^1$ and $Cy^2$ and $R^1$ to $R^4$ are as shown in Table 31, with the exception that C1 is replaced by C2.

Table 69: Compounds of formula (I), wherein $Cy^1$ and $Cy^2$ and $R^1$ to $R^4$ are as shown in Table 32, with the exception that C1 is replaced by C2.

Table 70: Compounds of formula (I), wherein $Cy^1$ and $Cy^2$ and $R^1$ to $R^4$ are as shown in Table 33, with the exception that C1 is replaced by C2.

Table 71: Compounds of formula (I), wherein $Cy^1$ and $Cy^2$ and $R^1$ to $R^4$ are as shown in Table 34, with the exception that C1 is replaced by C2.

Table 72: Compounds of formula (I), wherein $Cy^1$ and $Cy^2$ and $R^1$ to $R^4$ are as shown in Table 35, with the exception that C1 is replaced by C2.

Table 73: Compounds of formula (I), wherein $Cy^1$ and $Cy^2$ and $R^1$ to $R^4$ are as shown in Table 36, with the exception that C1 is replaced by C2.

Table 74: Compounds of formula (I), wherein $Cy^1$ and $Cy^2$ and $R^1$ to $R^4$ are as shown in Table 37, with the exception that C1 is replaced by C2.

Table 75: Compounds of formula (I), wherein $Cy^1$ and $Cy^2$ and $R^1$ to $R^4$ are as shown in Table 38, with the exception that C1 is replaced by C2.

Table 76: Compounds of formula (I), wherein Cy1 and Cy2 and R1 to R4 are as shown in Table 2, with the exception that C1 is replaced by C3.

Table 77: Compounds of formula (I), wherein Cy1 and Cy2 and R1 to R4 are as shown in Table 3, with the exception that C1 is replaced by C3.

Table 78: Compounds of formula (I), wherein Cy1 and Cy2 and R1 to R4 are as shown in Table 4, with the exception that C1 is replaced by C3.

Table 79: Compounds of formula (I), wherein Cy1 and Cy2 and R1 to R4 are as shown in Table 5, with the exception that C1 is replaced by C3.

Table 80: Compounds of formula (I), wherein Cy1 and Cy2 and R1 to R4 are as shown in Table 6, with the exception that C1 is replaced by C3.

Table 81: Compounds of formula (I), wherein Cy1 and Cy2 and R1 to R4 are as shown in Table 7, with the exception that C1 is replaced by C3.

Table 82: Compounds of formula (I), wherein Cy1 and Cy2 and R1 to R4 are as shown in Table 8, with the exception that C1 is replaced by C3.

Table 83: Compounds of formula (I), wherein Cy1 and Cy2 and R1 to R4 are as shown in Table 9, with the exception that C1 is replaced by C3.

Table 84: Compounds of formula (I), wherein Cy1 and Cy2 and R1 to R4 are as shown in Table 10, with the exception that C1 is replaced by C3.

Table 85: Compounds of formula (I), wherein Cy1 and Cy2 and R1 to R4 are as shown in Table 11, with the exception that C1 is replaced by C3.

Table 86: Compounds of formula (I), wherein Cy1 and Cy2 and R1 to R4 are as shown in Table 12, with the exception that C1 is replaced by C3.

Table 87: Compounds of formula (I), wherein Cy1 and Cy2 and R1 to R4 are as shown in Table 13, with the exception that C1 is replaced by C3.

Table 88: Compounds of formula (I), wherein Cy1 and Cy2 and R1 to R4 are as shown in Table 14, with the exception that C1 is replaced by C3.

Table 89: Compounds of formula (I), wherein Cy1 and Cy2 and R1 to R4 are as shown in Table 15, with the exception that C1 is replaced by C3.

Table 90: Compounds of formula (I), wherein Cy1 and Cy2 and R1 to R4 are as shown in Table 16, with the exception that C1 is replaced by C3.

Table 91: Compounds of formula (I), wherein Cy1 and Cy2 and R1 to R4 are as shown in Table 17, with the exception that C1 is replaced by C3.

Table 92: Compounds of formula (I), wherein Cy1 and Cy2 and R1 to R4 are as shown in Table 18, with the exception that C1 is replaced by C3.

Table 93: Compounds of formula (I), wherein Cy1 and Cy2 and R1 to R4 are as shown in Table 19, with the exception that C1 is replaced by C3.

Table 94: Compounds of formula (I), wherein Cy1 and Cy2 and R1 to R4 are as shown in Table 20, with the exception that C1 is replaced by C3.

Table 95: Compounds of formula (I), wherein Cy1 and Cy2 and R1 to R4 are as shown in Table 21, with the exception that C1 is replaced by C3.

Table 96: Compounds of formula (I), wherein Cy1 and Cy2 and R1 to R4 are as shown in Table 22, with the exception that C1 is replaced by C3.

Table 97: Compounds of formula (I), wherein Cy1 and Cy2 and R1 to R4 are as shown in Table 23, with the exception that C1 is replaced by C3.

Table 98: Compounds of formula (I), wherein Cy1 and Cy2 and R1 to R4 are as shown in Table 24, with the exception that C1 is replaced by C3.

Table 99: Compounds of formula (I), wherein Cy1 and Cy2 and R1 to R4 are as shown in Table 25, with the exception that C1 is replaced by C3.

Table 100: Compounds of formula (I), wherein Cy1 and Cy2 and R1 to R4 are as shown in Table 26, with the exception that C1 is replaced by C3.

Table 101: Compounds of formula (I), wherein Cy1 and Cy2 and R1 to R4 are as shown in Table 27, with the exception that C1 is replaced by C3.

Table 102: Compounds of formula (I), wherein Cy1 and Cy2 and R1 to R4 are as shown in Table 28, with the exception that C1 is replaced by C3.

Table 103: Compounds of formula (I), wherein Cy1 and Cy2 and R1 to R4 are as shown in Table 29, with the exception that C1 is replaced by C3.

Table 104: Compounds of formula (I), wherein Cy1 and Cy2 and R1 to R4 are as shown in Table 30, with the exception that C1 is replaced by C3.

Table 105: Compounds of formula (I), wherein Cy1 and Cy2 and R1 to R4 are as shown in Table 31, with the exception that C1 is replaced by C3.

Table 106: Compounds of formula (I), wherein Cy1 and Cy2 and R1 to R4 are as shown in Table 32, with the exception that C1 is replaced by C3.

Table 107: Compounds of formula (I), wherein Cy1 and Cy2 and R1 to R4 are as shown in Table 33, with the exception that C1 is replaced by C3.

Table 108: Compounds of formula (I), wherein Cy1 and Cy2 and R1 to R4 are as shown in Table 34, with the exception that C1 is replaced by C3.

Table 109: Compounds of formula (I), wherein Cy1 and Cy2 and R1 to R4 are as shown in Table 35, with the exception that C1 is replaced by C3.

Table 110: Compounds of formula (I), wherein Cy1 and Cy2 and R1 to R4 are as shown in Table 36, with the exception that C1 is replaced by C3.

Table 111: Compounds of formula (I), wherein Cy1 and Cy2 and R1 to R4 are as shown in Table 37, with the exception that C1 is replaced by C3.

Table 112: Compounds of formula (I), wherein Cy1 and Cy2 and R1 to R4 are as shown in Table 38, with the exception that C1 is replaced by C3.

Table 113: Compounds of formula (I), wherein Cy1 and Cy2 and R1 to R4 are as shown in Table 2, with the exception that C1 is replaced by C4.

Table 114: Compounds of formula (I), wherein Cy1 and Cy2 and R1 to R4 are as shown in Table 3, with the exception that C1 is replaced by C4.

Table 115: Compounds of formula (I), wherein Cy1 and Cy2 and R1 to R4 are as shown in Table 4, with the exception that C1 is replaced by C4.

Table 116: Compounds of formula (I), wherein Cy1 and Cy2 and R1 to R4 are as shown in Table 5, with the exception that C1 is replaced by C4.

Table 117: Compounds of formula (I), wherein Cy1 and Cy2 and R1 to R4 are as shown in Table 6, with the exception that C1 is replaced by C4.

Table 118: Compounds of formula (I), wherein Cy1 and Cy2 and R1 to R4 are as shown in Table 7, with the exception that C1 is replaced by C4.

Table 119: Compounds of formula (I), wherein Cy1 and Cy2 and R1 to R4 are as shown in Table 8, with the exception that C1 is replaced by C4.

Table 120: Compounds of formula (I), wherein Cy1 and Cy2 and R1 to R4 are as shown in Table 9, with the exception that C1 is replaced by C4.

Table 121: Compounds of formula (I), wherein Cy1 and Cy2 and R1 to R4 are as shown in Table 10, with the exception that C1 is replaced by C4.

Table 122: Compounds of formula (I), wherein Cy1 and Cy2 and R1 to R4 are as shown in Table 11, with the exception that C1 is replaced by C4.

Table 123: Compounds of formula (I), wherein Cy1 and Cy2 and R1 to R4 are as shown in Table 12, with the exception that C1 is replaced by C4.

Table 124: Compounds of formula (I), wherein Cy1 and Cy2 and R1 to R4 are as shown in Table 13, with the exception that C1 is replaced by C4.

Table 125: Compounds of formula (I), wherein Cy1 and Cy2 and R1 to R4 are as shown in Table 14, with the exception that C1 is replaced by C4.

Table 126: Compounds of formula (I), wherein Cy1 and Cy2 and R1 to R4 are as shown in Table 15, with the exception that C1 is replaced by C4.

Table 127: Compounds of formula (I), wherein Cy1 and Cy2 and R1 to R4 are as shown in Table 16, with the exception that C1 is replaced by C4.

Table 128: Compounds of formula (I), wherein Cy1 and Cy2 and R1 to R4 are as shown in Table 17, with the exception that C1 is replaced by C4.

Table 129: Compounds of formula (I), wherein Cy1 and Cy2 and R1 to R4 are as shown in Table 18, with the exception that C1 is replaced by C4.

Table 130: Compounds of formula (I), wherein Cy1 and Cy2 and R1 to R4 are as shown in Table 19, with the exception that C1 is replaced by C4.

Table 131: Compounds of formula (I), wherein Cy1 and Cy2 and R1 to R4 are as shown in Table 20, with the exception that C1 is replaced by C4.

Table 132: Compounds of formula (I), wherein Cy1 and Cy2 and R1 to R4 are as shown in Table 21, with the exception that C1 is replaced by C4.

Table 133: Compounds of formula (I), wherein Cy1 and Cy2 and R1 to R4 are as shown in Table 22, with the exception that C1 is replaced by C4.

Table 134: Compounds of formula (I), wherein Cy1 and Cy2 and R1 to R4 are as shown in Table 23, with the exception that C1 is replaced by C4.

Table 135: Compounds of formula (I), wherein Cy1 and Cy2 and R1 to R4 are as shown in Table 24, with the exception that C1 is replaced by C4.

Table 136: Compounds of formula (I), wherein Cy1 and Cy2 and R1 to R4 are as shown in Table 25, with the exception that C1 is replaced by C4.

Table 137: Compounds of formula (I), wherein Cy1 and Cy2 and R1 to R4 are as shown in Table 26, with the exception that C1 is replaced by C4.

Table 138: Compounds of formula (I), wherein Cy1 and Cy2 and R1 to R4 are as shown in Table 27, with the exception that C1 is replaced by C4.

Table 139: Compounds of formula (I), wherein Cy1 and Cy2 and R1 to R4 are as shown in Table 28, with the exception that C1 is replaced by C4.

Table 140: Compounds of formula (I), wherein Cy1 and Cy2 and R1 to R4 are as shown in Table 29, with the exception that C1 is replaced by C4.

Table 141: Compounds of formula (I), wherein Cy1 and Cy2 and R1 to R4 are as shown in Table 30, with the exception that C1 is replaced by C4.

Table 142: Compounds of formula (I), wherein Cy1 and Cy2 and R1 to R4 are as shown in Table 31, with the exception that C1 is replaced by C4.

Table 143: Compounds of formula (I), wherein Cy1 and Cy2 and R1 to R4 are as shown in Table 32, with the exception that C1 is replaced by C4.

Table 144: Compounds of formula (I), wherein Cy1 and Cy2 and R1 to R4 are as shown in Table 33, with the exception that C1 is replaced by C4.

Table 145: Compounds of formula (I), wherein Cy1 and Cy2 and R1 to R4 are as shown in Table 34, with the exception that C1 is replaced by C4.

Table 146: Compounds of formula (I), wherein Cy1 and Cy2 and R1 to R4 are as shown in Table 35, with the exception that C1 is replaced by C4.

Table 147: Compounds of formula (I), wherein Cy1 and Cy2 and R1 to R4 are as shown in Table 36, with the exception that C1 is replaced by C4.

Table 148: Compounds of formula (I), wherein Cy1 and Cy2 and R1 to R4 are as shown in Table 37, with the exception that C1 is replaced by C4.

Table 149: Compounds of formula (I), wherein Cy1 and Cy2 and R1 to R4 are as shown in Table 38, with the exception that C1 is replaced by C4.

Table 150: Compounds of formula (I), wherein Cy1 and Cy2 and R1 to R4 are as shown in Table 2, with the exception that C1 is replaced by C5.

Table 151: Compounds of formula (I), wherein Cy1 and Cy2 and R1 to R4 are as shown in Table 3, with the exception that C1 is replaced by C5.

Table 152: Compounds of formula (I), wherein Cy1 and Cy2 and R1 to R4 are as shown in Table 4, with the exception that C1 is replaced by C5.

Table 153: Compounds of formula (I), wherein Cy1 and Cy2 and R1 to R4 are as shown in Table 5, with the exception that C1 is replaced by C5.

Table 154: Compounds of formula (I), wherein Cy1 and Cy2 and R1 to R4 are as shown in Table 6, with the exception that C1 is replaced by C5.

Table 155: Compounds of formula (I), wherein Cy1 and Cy2 and R1 to R4 are as shown in Table 7, with the exception that C1 is replaced by C5.

Table 156: Compounds of formula (I), wherein Cy1 and Cy2 and R1 to R4 are as shown in Table 8, with the exception that C1 is replaced by C5.

Table 157: Compounds of formula (I), wherein Cy1 and Cy2 and R1 to R4 are as shown in Table 9, with the exception that C1 is replaced by C5.

Table 158: Compounds of formula (I), wherein Cy1 and Cy2 and R1 to R4 are as shown in Table 10, with the exception that C1 is replaced by C5.

Table 159: Compounds of formula (I), wherein Cy1 and Cy2 and R1 to R4 are as shown in Table 11, with the exception that C1 is replaced by C5.

Table 160: Compounds of formula (I), wherein Cy1 and Cy2 and R1 to R4 are as shown in Table 12, with the exception that C1 is replaced by C5.

Table 161: Compounds of formula (I), wherein Cy1 and Cy2 and R1 to R4 are as shown in Table 13, with the exception that C1 is replaced by C5.

Table 162: Compounds of formula (I), wherein Cy1 and Cy2 and R1 to R4 are as shown in Table 14, with the exception that C1 is replaced by C5.

Table 163: Compounds of formula (I), wherein Cy1 and Cy2 and R1 to R4 are as shown in Table 15, with the exception that C1 is replaced by C5.

Table 164: Compounds of formula (I), wherein Cy1 and Cy2 and R1 to R4 are as shown in Table 16, with the exception that C1 is replaced by C5.

Table 165: Compounds of formula (I), wherein Cy1 and Cy2 and R1 to R4 are as shown in Table 17, with the exception that C1 is replaced by C5.

Table 166: Compounds of formula (I), wherein Cy1 and Cy2 and R1 to R4 are as shown in Table 18, with the exception that C1 is replaced by C5.

Table 167: Compounds of formula (I), wherein Cy1 and Cy2 and R1 to R4 are as shown in Table 19, with the exception that C1 is replaced by C5.

Table 168: Compounds of formula (I), wherein Cy1 and Cy2 and R1 to R4 are as shown in Table 20, with the exception that C1 is replaced by C5.

Table 169: Compounds of formula (I), wherein Cy1 and Cy2 and R1 to R4 are as shown in Table 21, with the exception that C1 is replaced by C5.

Table 170: Compounds of formula (I), wherein Cy1 and Cy2 and R1 to R4 are as shown in Table 22, with the exception that C1 is replaced by C5.

Table 171: Compounds of formula (I), wherein Cy1 and Cy2 and R1 to R4 are as shown in Table 23, with the exception that C1 is replaced by C5.

Table 172: Compounds of formula (I), wherein Cy1 and Cy2 and R1 to R4 are as shown in Table 24, with the exception that C1 is replaced by C5.

Table 173: Compounds of formula (I), wherein Cy1 and Cy2 and R1 to R4 are as shown in Table 25, with the exception that C1 is replaced by C5.

Table 174: Compounds of formula (I), wherein Cy1 and Cy2 and R1 to R4 are as shown in Table 26, with the exception that C1 is replaced by C5.

Table 175: Compounds of formula (I), wherein Cy1 and Cy2 and R1 to R4 are as shown in Table 27, with the exception that C1 is replaced by C5.

Table 176: Compounds of formula (I), wherein Cy1 and Cy2 and R1 to R4 are as shown in Table 28, with the exception that C1 is replaced by C5.

Table 177: Compounds of formula (I), wherein Cy1 and Cy2 and R1 to R4 are as shown in Table 29, with the exception that C1 is replaced by C5.

Table 178: Compounds of formula (I), wherein Cy1 and Cy2 and R1 to R4 are as shown in Table 30, with the exception that C1 is replaced by C5.

Table 179: Compounds of formula (I), wherein Cy1 and Cy2 and R1 to R4 are as shown in Table 31, with the exception that C1 is replaced by C5.

Table 180: Compounds of formula (I), wherein Cy1 and Cy2 and R1 to R4 are as shown in Table 32, with the exception that C1 is replaced by C5.

Table 181: Compounds of formula (I), wherein Cy1 and Cy2 and R1 to R4 are as shown in Table 33, with the exception that C1 is replaced by C5.

Table 182: Compounds of formula (I), wherein Cy1 and Cy2 and R1 to R4 are as shown in Table 34, with the exception that C1 is replaced by C5.

Table 183: Compounds of formula (I), wherein Cy1 and Cy2 and R1 to R4 are as shown in Table 35, with the exception that C1 is replaced by C5.

Table 184: Compounds of formula (I), wherein Cy1 and Cy2 and R1 to R4 are as shown in Table 36, with the exception that C1 is replaced by C5.

Table 185: Compounds of formula (I), wherein Cy1 and Cy2 and R1 to R4 are as shown in Table 37, with the exception that C1 is replaced by C5.

Table 186: Compounds of formula (I), wherein Cy1 and Cy2 and R1 to R4 are as shown in Table 38, with the exception that C1 is replaced by C5.

Table 187: Compounds of formula (I), wherein Cy1 and Cy2 and R1 to R4 are as shown in Table 2, with the exception that C1 is replaced by C6.

Table 188: Compounds of formula (I), wherein Cy1 and Cy2 and R1 to R4 are as shown in Table 3, with the exception that C1 is replaced by C6.

Table 189: Compounds of formula (I), wherein Cy1 and Cy2 and R1 to R4 are as shown in Table 4, with the exception that C1 is replaced by C6.

Table 190: Compounds of formula (I), wherein Cy1 and Cy2 and R1 to R4 are as shown in Table 5, with the exception that C1 is replaced by C6.

Table 191: Compounds of formula (I), wherein Cy1 and Cy2 and R1 to R4 are as shown in Table 6, with the exception that C1 is replaced by C6.

Table 192: Compounds of formula (I), wherein Cy1 and Cy2 and R1 to R4 are as shown in Table 7, with the exception that C1 is replaced by C6.

Table 193: Compounds of formula (I), wherein Cy1 and Cy2 and R1 to R4 are as shown in Table 8, with the exception that C1 is replaced by C6.

Table 194: Compounds of formula (I), wherein Cy1 and Cy2 and R1 to R4 are as shown in Table 9, with the exception that C1 is replaced by C6.

Table 195: Compounds of formula (I), wherein Cy1 and Cy2 and R1 to R4 are as shown in Table 10, with the exception that C1 is replaced by C6.

Table 196: Compounds of formula (I), wherein Cy1 and Cy2 and R1 to R4 are as shown in Table 11, with the exception that C1 is replaced by C6.

Table 197: Compounds of formula (I), wherein Cy1 and Cy2 and R1 to R4 are as shown in Table 12, with the exception that C1 is replaced by C6.

Table 198: Compounds of formula (I), wherein Cy1 and Cy2 and R1 to R4 are as shown in Table 13, with the exception that C1 is replaced by C6.

Table 199: Compounds of formula (I), wherein Cy1 and Cy2 and R1 to R4 are as shown in Table 14, with the exception that C1 is replaced by C6.

Table 200: Compounds of formula (I), wherein Cy1 and Cy2 and R1 to R4 are as shown in Table 15, with the exception that C1 is replaced by C6.

Table 201: Compounds of formula (I), wherein Cy1 and Cy2 and R1 to R4 are as shown in Table 16, with the exception that C1 is replaced by C6.

Table 202: Compounds of formula (I), wherein Cy1 and Cy2 and R1 to R4 are as shown in Table 17, with the exception that C1 is replaced by C6.

Table 203: Compounds of formula (I), wherein Cy1 and Cy2 and R1 to R4 are as shown in Table 18, with the exception that C1 is replaced by C6.

Table 204: Compounds of formula (I), wherein Cy1 and Cy2 and R1 to R4 are as shown in Table 19, with the exception that C1 is replaced by C6.

Table 205: Compounds of formula (I), wherein Cy1 and Cy2 and R1 to R4 are as shown in Table 20, with the exception that C1 is replaced by C6.

Table 206: Compounds of formula (I), wherein Cy1 and Cy2 and R1 to R4 are as shown in Table 21, with the exception that C1 is replaced by C6.

Table 207: Compounds of formula (I), wherein Cy1 and Cy2 and R1 to R4 are as shown in Table 22, with the exception that C1 is replaced by C6.

Table 208: Compounds of formula (I), wherein Cy1 and Cy2 and R1 to R4 are as shown in Table 23, with the exception that C1 is replaced by C6.

Table 209: Compounds of formula (I), wherein Cy1 and Cy2 and R1 to R4 are as shown in Table 24, with the exception that C1 is replaced by C6.

Table 210: Compounds of formula (I), wherein Cy1 and Cy2 and R1 to R4 are as shown in Table 25, with the exception that C1 is replaced by C6.

Table 211: Compounds of formula (I), wherein Cy1 and Cy2 and R1 to R4 are as shown in Table 26, with the exception that C1 is replaced by C6.

Table 212: Compounds of formula (I), wherein Cy1 and Cy2 and R1 to R4 are as shown in Table 27, with the exception that C1 is replaced by C6.

Table 213: Compounds of formula (I), wherein Cy1 and Cy2 and R1 to R4 are as shown in Table 28, with the exception that C1 is replaced by C6.

Table 214: Compounds of formula (I), wherein Cy1 and Cy2 and R1 to R4 are as shown in Table 29, with the exception that C1 is replaced by C6.

Table 215: Compounds of formula (I), wherein Cy1 and Cy2 and R1 to R4 are as shown in Table 30, with the exception that C1 is replaced by C6.

Table 216: Compounds of formula (I), wherein Cy1 and Cy2 and R1 to R4 are as shown in Table 31, with the exception that C1 is replaced by C6.

Table 217: Compounds of formula (I), wherein Cy1 and Cy2 and R1 to R4 are as shown in Table 32, with the exception that C1 is replaced by C6.

Table 218: Compounds of formula (I), wherein Cy1 and Cy2 and R1 to R4 are as shown in Table 33, with the exception that C1 is replaced by C6.

Table 219: Compounds of formula (I), wherein Cy1 and Cy2 and R1 to R4 are as shown in Table 34, with the exception that C1 is replaced by C6.

Table 220: Compounds of formula (I), wherein Cy1 and Cy2 and R1 to R4 are as shown in Table 35, with the exception that C1 is replaced by C6.

Table 221: Compounds of formula (I), wherein Cy1 and Cy2 and R1 to R4 are as shown in Table 36, with the exception that C1 is replaced by C6.

Table 222: Compounds of formula (I), wherein Cy1 and Cy2 and R1 to R4 are as shown in Table 37, with the exception that C1 is replaced by C6.

Table 223: Compounds of formula (I), wherein Cy1 and Cy2 and R1 to R4 are as shown in Table 38, with the exception that C1 is replaced by C6.

Table 224: Compounds of formula (I), wherein Cy1 and Cy2 and R1 to R4 are as shown in Table 2, with the exception that C1 is replaced by C7.

Table 225: Compounds of formula (I), wherein Cy1 and Cy2 and R1 to R4 are as shown in Table 3, with the exception that C1 is replaced by C7.

Table 226: Compounds of formula (I), wherein Cy1 and Cy2 and R1 to R4 are as shown in Table 4, with the exception that C1 is replaced by C7.

Table 227: Compounds of formula (I), wherein Cy1 and Cy2 and R1 to R4 are as shown in Table 5, with the exception that C1 is replaced by C7.

Table 228: Compounds of formula (I), wherein Cy1 and Cy2 and R1 to R4 are as shown in Table 6, with the exception that C1 is replaced by C7.

Table 229: Compounds of formula (I), wherein Cy1 and Cy2 and R1 to R4 are as shown in Table 7, with the exception that C1 is replaced by C7.

Table 230: Compounds of formula (I), wherein Cy1 and Cy2 and R1 to R4 are as shown in Table 8, with the exception that C1 is replaced by C7.

Table 231: Compounds of formula (I), wherein Cy1 and Cy2 and R1 to R4 are as shown in Table 9, with the exception that C1 is replaced by C7.

Table 232: Compounds of formula (I), wherein Cy1 and Cy2 and R1 to R4 are as shown in Table 10, with the exception that C1 is replaced by C7.

Table 233: Compounds of formula (I), wherein Cy1 and Cy2 and R1 to R4 are as shown in Table 11, with the exception that C1 is replaced by C7.

Table 234: Compounds of formula (I), wherein Cy1 and Cy2 and R1 to R4 are as shown in Table 12, with the exception that C1 is replaced by C7.

Table 235: Compounds of formula (I), wherein Cy1 and Cy2 and R1 to R4 are as shown in Table 13, with the exception that C1 is replaced by C7.

Table 236: Compounds of formula (I), wherein Cy1 and Cy2 and R1 to R4 are as shown in Table 14, with the exception that C1 is replaced by C7.

Table 237: Compounds of formula (I), wherein Cy1 and Cy2 and R1 to R4 are as shown in Table 15, with the exception that C1 is replaced by C7.

Table 238: Compounds of formula (I), wherein Cy1 and Cy2 and R1 to R4 are as shown in Table 16, with the exception that C1 is replaced by C7.

Table 239: Compounds of formula (I), wherein Cy1 and Cy2 and R1 to R4 are as shown in Table 17, with the exception that C1 is replaced by C7.

Table 240: Compounds of formula (I), wherein Cy1 and Cy2 and R1 to R4 are as shown in Table 18, with the exception that C1 is replaced by C7.

Table 241: Compounds of formula (I), wherein Cy1 and Cy2 and R1 to R4 are as shown in Table 19, with the exception that C1 is replaced by C7.

Table 242: Compounds of formula (I), wherein Cy1 and Cy2 and R1 to R4 are as shown in Table 20, with the exception that C1 is replaced by C7.

Table 243: Compounds of formula (I), wherein Cy1 and Cy2 and R1 to R4 are as shown in Table 21, with the exception that C1 is replaced by C7.

Table 244: Compounds of formula (I), wherein Cy1 and Cy2 and R1 to R4 are as shown in Table 22, with the exception that C1 is replaced by C7.

Table 245: Compounds of formula (I), wherein Cy1 and Cy2 and R1 to R4 are as shown in Table 23, with the exception that C1 is replaced by C7.

Table 246: Compounds of formula (I), wherein Cy1 and Cy2 and R1 to R4 are as shown in Table 24, with the exception that C1 is replaced by C7.

Table 247: Compounds of formula (I), wherein Cy1 and Cy2 and R1 to R4 are as shown in Table 25, with the exception that C1 is replaced by C7.

Table 248: Compounds of formula (I), wherein Cy1 and Cy2 and R1 to R4 are as shown in Table 26, with the exception that C1 is replaced by C7.

Table 249: Compounds of formula (I), wherein Cy1 and Cy2 and R1 to R4 are as shown in Table 27, with the exception that C1 is replaced by C7.

Table 250: Compounds of formula (I), wherein Cy1 and Cy2 and R1 to R4 are as shown in Table 28, with the exception that C1 is replaced by C7.

Table 251: Compounds of formula (I), wherein Cy1 and Cy2 and R1 to R4 are as shown in Table 29, with the exception that C1 is replaced by C7.

Table 252: Compounds of formula (I), wherein Cy1 and Cy2 and R1 to R4 are as shown in Table 30, with the exception that C1 is replaced by C7.

Table 253: Compounds of formula (I), wherein Cy1 and Cy2 and R1 to R4 are as shown in Table 31, with the exception that C1 is replaced by C7.

Table 254: Compounds of formula (I), wherein Cy1 and Cy2 and R1 to R4 are as shown in Table 32, with the exception that C1 is replaced by C7.

Table 255: Compounds of formula (I), wherein Cy1 and Cy2 and R1 to R4 are as shown in Table 33, with the exception that C1 is replaced by C7.

Table 256: Compounds of formula (I), wherein Cy1 and Cy2 and R1 to R4 are as shown in Table 34, with the exception that C1 is replaced by C7.

Table 257: Compounds of formula (I), wherein Cy1 and Cy2 and R1 to R4 are as shown in Table 35, with the exception that C1 is replaced by C7.

Table 258: Compounds of formula (I), wherein Cy1 and Cy2 and R1 to R4 are as shown in Table 36, with the exception that C1 is replaced by C7.

Table 259: Compounds of formula (I), wherein Cy1 and Cy2 and R1 to R4 are as shown in Table 37, with the exception that C1 is replaced by C7.

Table 260: Compounds of formula (I), wherein Cy1 and Cy2 and R1 to R4 are as shown in Table 38, with the exception that C1 is replaced by C7.

Table 261: Compounds of formula (I), wherein Cy1 and Cy2 and R1 to R4 are as shown in Table 2, with the exception that C1 is replaced by C8.

Table 262: Compounds of formula (I), wherein Cy1 and Cy2 and R1 to R4 are as shown in Table 3, with the exception that C1 is replaced by C8.

Table 263: Compounds of formula (I), wherein Cy1 and Cy2 and R1 to R4 are as shown in Table 4, with the exception that C1 is replaced by C8.

Table 264: Compounds of formula (I), wherein Cy1 and Cy2 and R1 to R4 are as shown in Table 5, with the exception that C1 is replaced by C8.

Table 265: Compounds of formula (I), wherein Cy1 and Cy2 and R1 to R4 are as shown in Table 6, with the exception that C1 is replaced by C8.

Table 266: Compounds of formula (I), wherein Cy1 and Cy2 and R1 to R4 are as shown in Table 7, with the exception that C1 is replaced by C8.

Table 267: Compounds of formula (I), wherein Cy1 and Cy2 and R1 to R4 are as shown in Table 8, with the exception that C1 is replaced by C8.

Table 268: Compounds of formula (I), wherein Cy1 and Cy2 and R1 to R4 are as shown in Table 9, with the exception that C1 is replaced by C8.

Table 269: Compounds of formula (I), wherein Cy1 and Cy2 and R1 to R4 are as shown in Table 10, with the exception that C1 is replaced by C8.

Table 270: Compounds of formula (I), wherein Cy1 and Cy2 and R1 to R4 are as shown in Table 11, with the exception that C1 is replaced by C8.

Table 271: Compounds of formula (I), wherein Cy1 and Cy2 and R1 to R4 are as shown in Table 12, with the exception that C1 is replaced by C8.

Table 272: Compounds of formula (I), wherein Cy1 and Cy2 and R1 to R4 are as shown in Table 13, with the exception that C1 is replaced by C8.

Table 273: Compounds of formula (I), wherein Cy1 and Cy2 and R1 to R4 are as shown in Table 14, with the exception that C1 is replaced by C8.

Table 274: Compounds of formula (I), wherein Cy1 and Cy2 and R1 to R4 are as shown in Table 15, with the exception that C1 is replaced by C8.

Table 275: Compounds of formula (I), wherein Cy1 and Cy2 and R1 to R4 are as shown in Table 16, with the exception that C1 is replaced by C8.

Table 276: Compounds of formula (I), wherein Cy1 and Cy2 and R1 to R4 are as shown in Table 17, with the exception that C1 is replaced by C8.

Table 277: Compounds of formula (I), wherein Cy1 and Cy2 and R1 to R4 are as shown in Table 18, with the exception that C1 is replaced by C8.

Table 278: Compounds of formula (I), wherein Cy1 and Cy2 and R1 to R4 are as shown in Table 19, with the exception that C1 is replaced by C8.

Table 279: Compounds of formula (I), wherein Cy1 and Cy2 and R1 to R4 are as shown in Table 20, with the exception that C1 is replaced by C8.

Table 280: Compounds of formula (I), wherein Cy1 and Cy2 and R1 to R4 are as shown in Table 21, with the exception that C1 is replaced by C8.

Table 281: Compounds of formula (I), wherein Cy1 and Cy2 and R1 to R4 are as shown in Table 22, with the exception that C1 is replaced by C8.

Table 282: Compounds of formula (I), wherein Cy1 and Cy2 and R1 to R4 are as shown in Table 23, with the exception that C1 is replaced by C8.

Table 283: Compounds of formula (I), wherein Cy1 and Cy2 and R1 to R4 are as shown in Table 24, with the exception that C1 is replaced by C8.

Table 284: Compounds of formula (I), wherein Cy1 and Cy2 and R1 to R4 are as shown in Table 25, with the exception that C1 is replaced by C8.

Table 285: Compounds of formula (I), wherein Cy1 and Cy2 and R1 to R4 are as shown in Table 26, with the exception that C1 is replaced by C8.

Table 286: Compounds of formula (I), wherein Cy1 and Cy2 and R1 to R4 are as shown in Table 27, with the exception that C1 is replaced by C8.

Table 287: Compounds of formula (I), wherein Cy1 and Cy2 and R1 to R4 are as shown in Table 28, with the exception that C1 is replaced by C8.

Table 288: Compounds of formula (I), wherein Cy1 and Cy2 and R1 to R4 are as shown in Table 29, with the exception that C1 is replaced by C8.

Table 289: Compounds of formula (I), wherein Cy1 and Cy2 and R1 to R4 are as shown in Table 30, with the exception that C1 is replaced by C8.

Table 290: Compounds of formula (I), wherein Cy1 and Cy2 and R1 to R4 are as shown in Table 31, with the exception that C1 is replaced by C8.

Table 291: Compounds of formula (I), wherein Cy1 and Cy2 and R1 to R4 are as shown in Table 32, with the exception that C1 is replaced by C8.

Table 292: Compounds of formula (I), wherein Cy1 and Cy2 and R1 to R4 are as shown in Table 33, with the exception that C1 is replaced by C8.

Table 293: Compounds of formula (I), wherein Cy1 and Cy2 and R1 to R4 are as shown in Table 34, with the exception that C1 is replaced by C8.

Table 294: Compounds of formula (I), wherein Cy1 and Cy2 and R1 to R4 are as shown in Table 35, with the exception that C1 is replaced by C8.

Table 295: Compounds of formula (I), wherein Cy1 and Cy2 and R1 to R4 are as shown in Table 36, with the exception that C1 is replaced by C8.

Table 296: Compounds of formula (I), wherein Cy1 and Cy2 and R1 to R4 are as shown in Table 37, with the exception that C1 is replaced by C8.

Table 297: Compounds of formula (I), wherein Cy1 and Cy2 and R1 to R4 are as shown in Table 38, with the exception that C1 is replaced by C8.

Table 298: Compounds of formula (I), wherein Cy1 and Cy2 and R1 to R4 are as shown in Table 2, with the exception that C1 is replaced by C9.

Table 299: Compounds of formula (I), wherein Cy1 and Cy2 and R1 to R4 are as shown in Table 3, with the exception that C1 is replaced by C9.

Table 300: Compounds of formula (I), wherein Cy1 and Cy2 and R1 to R4 are as shown in Table 4, with the exception that C1 is replaced by C9.

Table 301: Compounds of formula (I), wherein Cy1 and Cy2 and R1 to R4 are as shown in Table 5, with the exception that C1 is replaced by C9.

Table 302: Compounds of formula (I), wherein Cy1 and Cy2 and R1 to R4 are as shown in Table 6, with the exception that C1 is replaced by C9.

Table 303: Compounds of formula (I), wherein Cy1 and Cy2 and R1 to R4 are as shown in Table 7, with the exception that C1 is replaced by C9.

Table 304: Compounds of formula (I), wherein Cy1 and Cy2 and R1 to R4 are as shown in Table 8, with the exception that C1 is replaced by C9.

Table 305: Compounds of formula (I), wherein Cy1 and Cy2 and R1 to R4 are as shown in Table 9, with the exception that C1 is replaced by C9.

Table 306: Compounds of formula (I), wherein Cy1 and Cy2 and R1 to R4 are as shown in Table 10, with the exception that C1 is replaced by C9.

Table 307: Compounds of formula (I), wherein Cy1 and Cy2 and R1 to R4 are as shown in Table 11, with the exception that C1 is replaced by C9.

Table 308: Compounds of formula (I), wherein Cy1 and Cy2 and R1 to R4 are as shown in Table 12, with the exception that C1 is replaced by C9.

Table 309: Compounds of formula (I), wherein Cy1 and Cy2 and R1 to R4 are as shown in Table 13, with the exception that C1 is replaced by C9.

Table 310: Compounds of formula (I), wherein Cy1 and Cy2 and R1 to R4 are as shown in Table 14, with the exception that C1 is replaced by C9.

Table 311: Compounds of formula (I), wherein Cy1 and Cy2 and R1 to R4 are as shown in Table 15, with the exception that C1 is replaced by C9.

Table 312: Compounds of formula (I), wherein Cy1 and Cy2 and R1 to R4 are as shown in Table 16, with the exception that C1 is replaced by C9.

Table 313: Compounds of formula (I), wherein Cy1 and Cy2 and R1 to R4 are as shown in Table 17, with the exception that C1 is replaced by C9.

Table 314: Compounds of formula (I), wherein Cy1 and Cy2 and R1 to R4 are as shown in Table 18, with the exception that C1 is replaced by C9.

Table 315: Compounds of formula (I), wherein Cy1 and Cy2 and R1 to R4 are as shown in Table 19, with the exception that C1 is replaced by C9.

Table 316: Compounds of formula (I), wherein Cy1 and Cy2 and R1 to R4 are as shown in Table 20, with the exception that C1 is replaced by C9.

Table 317: Compounds of formula (I), wherein Cy1 and Cy2 and R1 to R4 are as shown in Table 21, with the exception that C1 is replaced by C9.

Table 318: Compounds of formula (I), wherein Cy1 and Cy2 and R1 to R4 are as shown in Table 22, with the exception that C1 is replaced by C9.

Table 319: Compounds of formula (I), wherein Cy1 and Cy2 and R1 to R4 are as shown in Table 23, with the exception that C1 is replaced by C9.

Table 320: Compounds of formula (I), wherein Cy1 and Cy2 and R1 to R4 are as shown in Table 24, with the exception that C1 is replaced by C9.

Table 321: Compounds of formula (I), wherein Cy1 and Cy2 and R1 to R4 are as shown in Table 25, with the exception that C1 is replaced by C9.

Table 322: Compounds of formula (I), wherein Cy1 and Cy2 and R1 to R4 are as shown in Table 26, with the exception that C1 is replaced by C9.

Table 323: Compounds of formula (I), wherein Cy1 and Cy2 and R1 to R4 are as shown in Table 27, with the exception that C1 is replaced by C9.

Table 324: Compounds of formula (I), wherein Cy1 and Cy2 and R1 to R4 are as shown in Table 28, with the exception that C1 is replaced by C9.

Table 325: Compounds of formula (I), wherein Cy1 and Cy2 and R1 to R4 are as shown in Table 29, with the exception that C1 is replaced by C9.

Table 326: Compounds of formula (I), wherein Cy1 and Cy2 and R1 to R4 are as shown in Table 30, with the exception that C1 is replaced by C9.

Table 327: Compounds of formula (I), wherein Cy1 and Cy2 and R1 to R4 are as shown in Table 31, with the exception that C1 is replaced by C9.

Table 328: Compounds of formula (I), wherein Cy1 and Cy2 and R1 to R4 are as shown in Table 32, with the exception that C1 is replaced by C9.

Table 329: Compounds of formula (I), wherein Cy1 and Cy2 and R1 to R4 are as shown in Table 33, with the exception that C1 is replaced by C9.

Table 330: Compounds of formula (I), wherein Cy1 and Cy2 and R1 to R4 are as shown in Table 34, with the exception that C1 is replaced by C9.

Table 331: Compounds of formula (I), wherein Cy1 and Cy2 and R1 to R4 are as shown in Table 35, with the exception that C1 is replaced by C9.

Table 332: Compounds of formula (I), wherein Cy1 and Cy2 and R1 to R4 are as shown in Table 36, with the exception that C1 is replaced by C9.

Table 333: Compounds of formula (I), wherein Cy1 and Cy2 and R1 to R4 are as shown in Table 37, with the exception that C1 is replaced by C9.

Table 334: Compounds of formula (I), wherein Cy1 and Cy2 and R1 to R4 are as shown in Table 38, with the exception that C1 is replaced by C9.

Table 335: Compounds of formula (I), wherein Cy1 and Cy2 and R1 to R4 are as shown in Table 2, with the exception that C1 is replaced by C10.

Table 336: Compounds of formula (I), wherein Cy1 and Cy2 and R1 to R4 are as shown in Table 3, with the exception that C1 is replaced by C10.

Table 337: Compounds of formula (I), wherein Cy1 and Cy2 and R1 to R4 are as shown in Table 4, with the exception that C1 is replaced by C10.

Table 338: Compounds of formula (I), wherein Cy1 and Cy2 and R1 to R4 are as shown in Table 5, with the exception that C1 is replaced by C10.

Table 339: Compounds of formula (I), wherein Cy1 and Cy2 and R1 to R4 are as shown in Table 6, with the exception that C1 is replaced by C10.

Table 340: Compounds of formula (I), wherein Cy1 and Cy2 and R1 to R4 are as shown in Table 7, with the exception that C1 is replaced by C10.

Table 341: Compounds of formula (I), wherein Cy1 and Cy2 and R1 to R4 are as shown in Table 8, with the exception that C1 is replaced by C10.

Table 342: Compounds of formula (I), wherein Cy1 and Cy2 and R1 to R4 are as shown in Table 9, with the exception that C1 is replaced by C10.

Table 343: Compounds of formula (I), wherein Cy1 and Cy2 and R1 to R4 are as shown in Table 10, with the exception that C1 is replaced by C10.

Table 344: Compounds of formula (I), wherein Cy1 and Cy2 and R1 to R4 are as shown in Table 11, with the exception that C1 is replaced by C10.

Table 345: Compounds of formula (I), wherein Cy1 and Cy2 and R1 to R4 are as shown in Table 12, with the exception that C1 is replaced by C10.

Table 346: Compounds of formula (I), wherein Cy1 and Cy2 and R1 to R4 are as shown in Table 13, with the exception that C1 is replaced by C10.

Table 347: Compounds of formula (I), wherein Cy1 and Cy2 and R1 to R4 are as shown in Table 14, with the exception that C1 is replaced by C10.

Table 348: Compounds of formula (I), wherein Cy1 and Cy2 and R1 to R4 are as shown in Table 15, with the exception that C1 is replaced by C10.

Table 349: Compounds of formula (I), wherein Cy1 and Cy2 and R1 to R4 are as shown in Table 16, with the exception that C1 is replaced by C10.

Table 350: Compounds of formula (I), wherein Cy1 and Cy2 and R1 to R4 are as shown in Table 17, with the exception that C1 is replaced by C10.

Table 351: Compounds of formula (I), wherein Cy1 and Cy2 and R1 to R4 are as shown in Table 18, with the exception that C1 is replaced by C10.

Table 352: Compounds of formula (I), wherein Cy1 and Cy2 and R1 to R4 are as shown in Table 19, with the exception that C1 is replaced by C10.

Table 353: Compounds of formula (I), wherein Cy1 and Cy2 and R1 to R4 are as shown in Table 20, with the exception that C1 is replaced by C10.

Table 354: Compounds of formula (I), wherein Cy1 and Cy2 and R1 to R4 are as shown in Table 21, with the exception that C1 is replaced by C10.

Table 355: Compounds of formula (I), wherein Cy1 and Cy2 and R1 to R4 are as shown in Table 22, with the exception that C1 is replaced by C10.

Table 356: Compounds of formula (I), wherein Cy1 and Cy2 and R1 to R4 are as shown in Table 23, with the exception that C1 is replaced by C10.

Table 357: Compounds of formula (I), wherein Cy1 and Cy2 and R1 to R4 are as shown in Table 24, with the exception that C1 is replaced by C10.

Table 358: Compounds of formula (I), wherein Cy1 and Cy2 and R1 to R4 are as shown in Table 25, with the exception that C1 is replaced by C10.

Table 359: Compounds of formula (I), wherein Cy1 and Cy2 and R1 to R4 are as shown in Table 26, with the exception that C1 is replaced by C10.

Table 360: Compounds of formula (I), wherein Cy1 and Cy2 and R1 to R4 are as shown in Table 27, with the exception that C1 is replaced by C10.

Table 361: Compounds of formula (I), wherein Cy1 and Cy2 and R1 to R4 are as shown in Table 28, with the exception that C1 is replaced by C10.

Table 362: Compounds of formula (I), wherein Cy1 and Cy2 and R1 to R4 are as shown in Table 29, with the exception that C1 is replaced by C10.

Table 363: Compounds of formula (I), wherein Cy1 and Cy2 and R1 to R4 are as shown in Table 30, with the exception that C1 is replaced by C10.

Table 364: Compounds of formula (I), wherein Cy1 and Cy2 and R1 to R4 are as shown in Table 31, with the exception that C1 is replaced by C10.

Table 365: Compounds of formula (I), wherein Cy1 and Cy2 and R1 to R4 are as shown in Table 32, with the exception that C1 is replaced by C10.

Table 366: Compounds of formula (I), wherein Cy1 and Cy2 and R1 to R4 are as shown in Table 33, with the exception that C1 is replaced by C10.

Table 367: Compounds of formula (I), wherein Cy1 and Cy2 and R1 to R4 are as shown in Table 34, with the exception that C1 is replaced by C10.

Table 368: Compounds of formula (I), wherein Cy1 and Cy2 and R1 to R4 are as shown in Table 35, with the exception that C1 is replaced by C10.

Table 369: Compounds of formula (I), wherein Cy1 and Cy2 and R1 to R4 are as shown in Table 36, with the exception that C1 is replaced by C10.

Table 370: Compounds of formula (I), wherein Cy1 and Cy2 and R1 to R4 are as shown in Table 37, with the exception that C1 is replaced by C10.

Table 371: Compounds of formula (I), wherein Cy1 and Cy2 and R1 to R4 are as shown in Table 38, with the exception that C1 is replaced by C10.

Table 372: Compounds of formula (I), wherein Cy1 and Cy2 and R1 to R4 are as shown in Table 2, with the exception that C1 is replaced by C11.

Table 373: Compounds of formula (I), wherein Cy1 and Cy2 and R1 to R4 are as shown in Table 3, with the exception that C1 is replaced by C11.

Table 374: Compounds of formula (I), wherein Cy1 and Cy2 and R1 to R4 are as shown in Table 4, with the exception that C1 is replaced by C11.

Table 375: Compounds of formula (I), wherein Cy1 and Cy2 and R1 to R4 are as shown in Table 5, with the exception that C1 is replaced by C11.

Table 376: Compounds of formula (I), wherein Cy1 and Cy2 and R1 to R4 are as shown in Table 6, with the exception that C1 is replaced by C11.

Table 377: Compounds of formula (I), wherein Cy1 and Cy2 and R1 to R4 are as shown in Table 7, with the exception that C1 is replaced by C11.

Table 378: Compounds of formula (I), wherein Cy1 and Cy2 and R1 to R4 are as shown in Table 8, with the exception that C1 is replaced by C11.

Table 379: Compounds of formula (I), wherein Cy1 and Cy2 and R1 to R4 are as shown in Table 9, with the exception that C1 is replaced by C11.

Table 380: Compounds of formula (I), wherein Cy1 and Cy2 and R1 to R4 are as shown in Table 10, with the exception that C1 is replaced by C11.

Table 381: Compounds of formula (I), wherein Cy1 and Cy2 and R1 to R4 are as shown in Table 11, with the exception that C1 is replaced by C11.

Table 382: Compounds of formula (I), wherein Cy1 and Cy2 and R1 to R4 are as shown in Table 12, with the exception that C1 is replaced by C11.

Table 383: Compounds of formula (I), wherein Cy1 and Cy2 and R1 to R4 are as shown in Table 13, with the exception that C1 is replaced by C11.

Table 384: Compounds of formula (I), wherein Cy1 and Cy2 and R1 to R4 are as shown in Table 14, with the exception that C1 is replaced by C11.

Table 385: Compounds of formula (I), wherein Cy1 and Cy2 and R1 to R4 are as shown in Table 15, with the exception that C1 is replaced by C11.

Table 386: Compounds of formula (I), wherein Cy1 and Cy2 and R1 to R4 are as shown in Table 16, with the exception that C1 is replaced by C11.

Table 387: Compounds of formula (I), wherein Cy1 and Cy2 and R1 to R4 are as shown in Table 17, with the exception that C1 is replaced by C11.

Table 388: Compounds of formula (I), wherein Cy1 and Cy2 and R1 to R4 are as shown in Table 18, with the exception that C1 is replaced by C11.

Table 389: Compounds of formula (I), wherein Cy1 and Cy2 and R1 to R4 are as shown in Table 19, with the exception that C1 is replaced by C11.

Table 390: Compounds of formula (I), wherein Cy1 and Cy2 and R1 to R4 are as shown in Table 20, with the exception that C1 is replaced by C11.

Table 391: Compounds of formula (I), wherein Cy1 and Cy2 and R1 to R4 are as shown in Table 21, with the exception that C1 is replaced by C11.

Table 392: Compounds of formula (I), wherein Cy1 and Cy2 and R1 to R4 are as shown in Table 22, with the exception that C1 is replaced by C11.

Table 393: Compounds of formula (I), wherein Cy1 and Cy2 and R1 to R4 are as shown in Table 23, with the exception that C1 is replaced by C11.

Table 394: Compounds of formula (I), wherein Cy1 and Cy2 and R1 to R4 are as shown in Table 24, with the exception that C1 is replaced by C11.

Table 395: Compounds of formula (I), wherein Cy1 and Cy2 and R1 to R4 are as shown in Table 25, with the exception that C1 is replaced by C11.

Table 396: Compounds of formula (I), wherein Cy1 and Cy2 and R1 to R4 are as shown in Table 26, with the exception that C1 is replaced by C11.

Table 397: Compounds of formula (I), wherein Cy1 and Cy2 and R1 to R4 are as shown in Table 27, with the exception that C1 is replaced by C11.

Table 398: Compounds of formula (I), wherein Cy1 and Cy2 and R1 to R4 are as shown in Table 28, with the exception that C1 is replaced by C11.

Table 399: Compounds of formula (I), wherein Cy1 and Cy2 and R1 to R4 are as shown in Table 29, with the exception that C1 is replaced by C11.

Table 400: Compounds of formula (I), wherein Cy1 and Cy2 and R1 to R4 are as shown in Table 30, with the exception that C1 is replaced by C11.

Table 401: Compounds of formula (I), wherein Cy1 and Cy2 and R1 to R4 are as shown in Table 31, with the exception that C1 is replaced by C11.

Table 402: Compounds of formula (I), wherein Cy1 and Cy2 and R1 to R4 are as shown in Table 32, with the exception that C1 is replaced by C11.

Table 403: Compounds of formula (I), wherein Cy1 and Cy2 and R1 to R4 are as shown in Table 33, with the exception that C1 is replaced by C11.

Table 404: Compounds of formula (I), wherein Cy1 and Cy2 and R1 to R4 are as shown in Table 34, with the exception that C1 is replaced by C11.

Table 405: Compounds of formula (I), wherein Cy1 and Cy2 and R1 to R4 are as shown in Table 35, with the exception that C1 is replaced by C11.

Table 406: Compounds of formula (I), wherein Cy1 and Cy2 and R1 to R4 are as shown in Table 36, with the exception that C1 is replaced by C11.

Table 407: Compounds of formula (I), wherein Cy1 and Cy2 and R1 to R4 are as shown in Table 37, with the exception that C1 is replaced by C11.

Table 408: Compounds of formula (I), wherein Cy1 and Cy2 and R1 to R4 are as shown in Table 38, with the exception that C1 is replaced by C11.

Table 409: Compounds of formula (I), wherein Cy1 and Cy2 and R1 to R4 are as shown in Table 2, with the exception that C1 is replaced by C12.

Table 410: Compounds of formula (I), wherein Cy1 and Cy2 and R1 to R4 are as shown in Table 3, with the exception that C1 is replaced by C12.

Table 411: Compounds of formula (I), wherein Cy1 and Cy2 and R1 to R4 are as shown in Table 4, with the exception that C1 is replaced by C12.

Table 412: Compounds of formula (I), wherein Cy1 and Cy2 and R1 to R4 are as shown in Table 5, with the exception that C1 is replaced by C12.

Table 413: Compounds of formula (I), wherein Cy1 and Cy2 and R1 to R4 are as shown in Table 6, with the exception that C1 is replaced by C12.

Table 414: Compounds of formula (I), wherein Cy1 and Cy2 and R1 to R4 are as shown in Table 7, with the exception that C1 is replaced by C12.

Table 415: Compounds of formula (I), wherein Cy1 and Cy2 and R1 to R4 are as shown in Table 8, with the exception that C1 is replaced by C12.

Table 416: Compounds of formula (I), wherein Cy1 and Cy2 and R1 to R4 are as shown in Table 9, with the exception that C1 is replaced by C12.

Table 417: Compounds of formula (I), wherein Cy1 and Cy2 and R1 to R4 are as shown in Table 10, with the exception that C1 is replaced by C12.

Table 418: Compounds of formula (I), wherein Cy1 and Cy2 and R1 to R4 are as shown in Table 11, with the exception that C1 is replaced by C12.

Table 419: Compounds of formula (I), wherein Cy1 and Cy2 and R1 to R4 are as shown in Table 12, with the exception that C1 is replaced by C12.

Table 420: Compounds of formula (I), wherein Cy1 and Cy2 and R1 to R4 are as shown in Table 13, with the exception that C1 is replaced by C12.

Table 421: Compounds of formula (I), wherein Cy1 and Cy2 and R1 to R4 are as shown in Table 14, with the exception that C1 is replaced by C12.

Table 422: Compounds of formula (I), wherein Cy1 and Cy2 and R1 to R4 are as shown in Table 15, with the exception that C1 is replaced by C12.

Table 423: Compounds of formula (I), wherein Cy1 and Cy2 and R1 to R4 are as shown in Table 16, with the exception that C1 is replaced by C12.

Table 424: Compounds of formula (I), wherein Cy1 and Cy2 and R1 to R4 are as shown in Table 17, with the exception that C1 is replaced by C12.

Table 425: Compounds of formula (I), wherein Cy1 and Cy2 and R1 to R4 are as shown in Table 18, with the exception that C1 is replaced by C12.

Table 426: Compounds of formula (I), wherein Cy1 and Cy2 and R1 to R4 are as shown in Table 19, with the exception that C1 is replaced by C12.

Table 427: Compounds of formula (I), wherein Cy1 and Cy2 and R1 to R4 are as shown in Table 20, with the exception that C1 is replaced by C12.

Table 428: Compounds of formula (I), wherein Cy1 and Cy2 and R1 to R4 are as shown in Table 21, with the exception that C1 is replaced by C12.

Table 429: Compounds of formula (I), wherein Cy1 and Cy2 and R1 to R4 are as shown in Table 22, with the exception that C1 is replaced by C12.

Table 430: Compounds of formula (I), wherein Cy1 and Cy2 and R1 to R4 are as shown in Table 23, with the exception that C1 is replaced by C12.

Table 431: Compounds of formula (I), wherein Cy1 and Cy2 and R1 to R4 are as shown in Table 24, with the exception that C1 is replaced by C12.

Table 432: Compounds of formula (I), wherein Cy1 and Cy2 and R1 to R4 are as shown in Table 25, with the exception that C1 is replaced by C12.

Table 433: Compounds of formula (I), wherein Cy1 and Cy2 and R1 to R4 are as shown in Table 26, with the exception that C1 is replaced by C12.

Table 434: Compounds of formula (I), wherein Cy1 and Cy2 and R1 to R4 are as shown in Table 27, with the exception that C1 is replaced by C12.

Table 435: Compounds of formula (I), wherein Cy1 and Cy2 and R1 to R4 are as shown in Table 28, with the exception that C1 is replaced by C12.

Table 436: Compounds of formula (I), wherein Cy1 and Cy2 and R1 to R4 are as shown in Table 29, with the exception that C1 is replaced by C12.

Table 437: Compounds of formula (I), wherein Cy1 and Cy2 and R1 to R4 are as shown in Table 30, with the exception that C1 is replaced by C12.

Table 438: Compounds of formula (I), wherein Cy1 and Cy2 and R1 to R4 are as shown in Table 31, with the exception that C1 is replaced by C12.

Table 439: Compounds of formula (I), wherein Cy1 and Cy2 and R1 to R4 are as shown in Table 32, with the exception that C1 is replaced by C12.

Table 440: Compounds of formula (I), wherein Cy1 and Cy2 and R1 to R4 are as shown in Table 33, with the exception that C1 is replaced by C12.

Table 441: Compounds of formula (I), wherein Cy1 and Cy2 and R1 to R4 are as shown in Table 34, with the exception that C1 is replaced by C12.

Table 442: Compounds of formula (I), wherein Cy1 and Cy2 and R1 to R4 are as shown in Table 35, with the exception that C1 is replaced by C12.

Table 443: Compounds of formula (I), wherein Cy1 and Cy2 and R1 to R4 are as shown in Table 36, with the exception that C1 is replaced by C12.

Table 444: Compounds of formula (I), wherein Cy1 and Cy2 and R1 to R4 are as shown in Table 37, with the exception that C1 is replaced by C12.

Table 445: Compounds of formula (I), wherein Cy1 and Cy2 and R1 to R4 are as shown in Table 38, with the exception that C1 is replaced by C12.

Table 446: Compounds of formula (I), wherein Cy1 and Cy2 and R1 to R4 are as shown in Table 2, with the exception that C1 is replaced by C13.

Table 447: Compounds of formula (I), wherein Cy1 and Cy2 and R1 to R4 are as shown in Table 3, with the exception that C1 is replaced by C13.

Table 448: Compounds of formula (I), wherein Cy1 and Cy2 and R1 to R4 are as shown in Table 4, with the exception that C1 is replaced by C13.

Table 449: Compounds of formula (I), wherein Cy1 and Cy2 and R1 to R4 are as shown in Table 5, with the exception that C1 is replaced by C13.

Table 450: Compounds of formula (I), wherein Cy1 and Cy2 and R1 to R4 are as shown in Table 6, with the exception that C1 is replaced by C13.

Table 451: Compounds of formula (I), wherein Cy1 and Cy2 and R1 to R4 are as shown in Table 7, with the exception that C1 is replaced by C13.

Table 452: Compounds of formula (I), wherein Cy1 and Cy2 and R1 to R4 are as shown in Table 8, with the exception that C1 is replaced by C13.

Table 453: Compounds of formula (I), wherein Cy1 and Cy2 and R1 to R4 are as shown in Table 9, with the exception that C1 is replaced by C13.

Table 454: Compounds of formula (I), wherein Cy1 and Cy2 and R1 to R4 are as shown in Table 10, with the exception that C1 is replaced by C13.

Table 455: Compounds of formula (I), wherein Cy1 and Cy2 and R1 to R4 are as shown in Table 11, with the exception that C1 is replaced by C13.

Table 456: Compounds of formula (I), wherein Cy1 and Cy2 and R1 to R4 are as shown in Table 12, with the exception that C1 is replaced by C13.

Table 457: Compounds of formula (I), wherein Cy1 and Cy2 and R1 to R4 are as shown in Table 13, with the exception that C1 is replaced by C13.

Table 458: Compounds of formula (I), wherein Cy1 and Cy2 and R1 to R4 are as shown in Table 14, with the exception that C1 is replaced by C13.

Table 459: Compounds of formula (I), wherein Cy1 and Cy2 and R1 to R4 are as shown in Table 15, with the exception that C1 is replaced by C13.

Table 460: Compounds of formula (I), wherein Cy1 and Cy2 and R1 to R4 are as shown in Table 16, with the exception that C1 is replaced by C13.

Table 461: Compounds of formula (I), wherein Cy1 and Cy2 and R1 to R4 are as shown in Table 17, with the exception that C1 is replaced by C13.

Table 462: Compounds of formula (I), wherein Cy1 and Cy2 and R1 to R4 are as shown in Table 18, with the exception that C1 is replaced by C13.

Table 463: Compounds of formula (I), wherein Cy1 and Cy2 and R1 to R4 are as shown in Table 19, with the exception that C1 is replaced by C13.

Table 464: Compounds of formula (I), wherein Cy1 and Cy2 and R1 to R4 are as shown in Table 20, with the exception that C1 is replaced by C13.

Table 465: Compounds of formula (I), wherein Cy1 and Cy2 and R1 to R4 are as shown in Table 21, with the exception that C1 is replaced by C13.

Table 466: Compounds of formula (I), wherein Cy1 and Cy2 and R1 to R4 are as shown in Table 22, with the exception that C1 is replaced by C13.

Table 467: Compounds of formula (I), wherein Cy1 and Cy2 and R1 to R4 are as shown in Table 23, with the exception that C1 is replaced by C13.

Table 468: Compounds of formula (I), wherein Cy1 and Cy2 and R1 to R4 are as shown in Table 24, with the exception that C1 is replaced by C13.

Table 469: Compounds of formula (I), wherein Cy1 and Cy2 and R1 to R4 are as shown in Table 25, with the exception that C1 is replaced by C13.

Table 470: Compounds of formula (I), wherein Cy1 and Cy2 and R1 to R4 are as shown in Table 26, with the exception that C1 is replaced by C13.

Table 471: Compounds of formula (I), wherein Cy1 and Cy2 and R1 to R4 are as shown in Table 27, with the exception that C1 is replaced by C13.

Table 472: Compounds of formula (I), wherein Cy1 and Cy2 and R1 to R4 are as shown in Table 28, with the exception that C1 is replaced by C13.

Table 473: Compounds of formula (I), wherein Cy1 and Cy2 and R1 to R4 are as shown in Table 29, with the exception that C1 is replaced by C13.

Table 474: Compounds of formula (I), wherein Cy1 and Cy2 and R1 to R4 are as shown in Table 30, with the exception that C1 is replaced by C13.

Table 475: Compounds of formula (I), wherein Cy1 and Cy2 and R1 to R4 are as shown in Table 31, with the exception that C1 is replaced by C13.

Table 476: Compounds of formula (I), wherein Cy1 and Cy2 and R1 to R4 are as shown in Table 32, with the exception that C1 is replaced by C13.

Table 477: Compounds of formula (I), wherein Cy1 and Cy2 and R1 to R4 are as shown in Table 33, with the exception that C1 is replaced by C13.

Table 478: Compounds of formula (I), wherein Cy1 and Cy2 and R1 to R4 are as shown in Table 34, with the exception that C1 is replaced by C13.

Table 479: Compounds of formula (I), wherein Cy1 and Cy2 and R1 to R4 are as shown in Table 35, with the exception that C1 is replaced by C13.

Table 480: Compounds of formula (I), wherein Cy1 and Cy2 and R1 to R4 are as shown in Table 36, with the exception that C1 is replaced by C13.

Table 481: Compounds of formula (I), wherein Cy1 and Cy2 and R1 to R4 are as shown in Table 37, with the exception that C1 is replaced by C13.

Table 482: Compounds of formula (I), wherein Cy1 and Cy2 and R1 to R4 are as shown in Table 38, with the exception that C1 is replaced by C13.

Table 483: Compounds of formula (I), wherein Cy1 and Cy2 and R1 to R4 are as shown in Table 2, with the exception that C1 is replaced by C14.

Table 484: Compounds of formula (I), wherein Cy1 and Cy2 and R1 to R4 are as shown in Table 3, with the exception that C1 is replaced by C14.

Table 485: Compounds of formula (I), wherein Cy1 and Cy2 and R1 to R4 are as shown in Table 4, with the exception that C1 is replaced by C14.

Table 486: Compounds of formula (I), wherein Cy1 and Cy2 and R1 to R4 are as shown in Table 5, with the exception that C1 is replaced by C14.

Table 487: Compounds of formula (I), wherein Cy1 and Cy2 and R1 to R4 are as shown in Table 6, with the exception that C1 is replaced by C14.

Table 488: Compounds of formula (I), wherein Cy1 and Cy2 and R1 to R4 are as shown in Table 7, with the exception that C1 is replaced by C14.

Table 489: Compounds of formula (I), wherein Cy1 and Cy2 and R1 to R4 are as shown in Table 8, with the exception that C1 is replaced by C14.

Table 490: Compounds of formula (I), wherein Cy1 and Cy2 and R1 to R4 are as shown in Table 9, with the exception that C1 is replaced by C14.

Table 491: Compounds of formula (I), wherein Cy1 and Cy2 and R1 to R4 are as shown in Table 10, with the exception that C1 is replaced by C14.

Table 492: Compounds of formula (I), wherein Cy1 and Cy2 and R1 to R4 are as shown in Table 11, with the exception that C1 is replaced by C14.

Table 493: Compounds of formula (I), wherein Cy1 and Cy2 and R1 to R4 are as shown in Table 12, with the exception that C1 is replaced by C14.

Table 494: Compounds of formula (I), wherein Cy1 and Cy2 and R1 to R4 are as shown in Table 13, with the exception that C1 is replaced by C14.

Table 495: Compounds of formula (I), wherein Cy1 and Cy2 and R1 to R4 are as shown in Table 14, with the exception that C1 is replaced by C14.

Table 496: Compounds of formula (I), wherein Cy1 and Cy2 and R1 to R4 are as shown in Table 15, with the exception that C1 is replaced by C14.

Table 497: Compounds of formula (I), wherein Cy1 and Cy2 and R1 to R4 are as shown in Table 16, with the exception that C1 is replaced by C14.

Table 498: Compounds of formula (I), wherein Cy1 and Cy2 and R1 to R4 are as shown in Table 17, with the exception that C1 is replaced by C14.

Table 499: Compounds of formula (I), wherein Cy1 and Cy2 and R1 to R4 are as shown in Table 18, with the exception that C1 is replaced by C14.

Table 500: Compounds of formula (I), wherein Cy1 and Cy2 and R1 to R4 are as shown in Table 19, with the exception that C1 is replaced by C14.

Table 501: Compounds of formula (I), wherein Cy1 and Cy2 and R1 to R4 are as shown in Table 20, with the exception that C1 is replaced by C14.

Table 502: Compounds of formula (I), wherein Cy1 and Cy2 and R1 to R4 are as shown in Table 21, with the exception that C1 is replaced by C14.

Table 503: Compounds of formula (I), wherein Cy1 and Cy2 and R1 to R4 are as shown in Table 22, with the exception that C1 is replaced by C14.

Table 504: Compounds of formula (I), wherein Cy1 and Cy2 and R1 to R4 are as shown in Table 23, with the exception that C1 is replaced by C14.

Table 505: Compounds of formula (I), wherein Cy1 and Cy2 and R1 to R4 are as shown in Table 24, with the exception that C1 is replaced by C14.

Table 506: Compounds of formula (I), wherein Cy1 and Cy2 and R1 to R4 are as shown in Table 25, with the exception that C1 is replaced by C14.

Table 507: Compounds of formula (I), wherein Cy1 and Cy2 and R1 to R4 are as shown in Table 26, with the exception that C1 is replaced by C14.

Table 508: Compounds of formula (I), wherein Cy1 and Cy2 and R1 to R4 are as shown in Table 27, with the exception that C1 is replaced by C14.

Table 509: Compounds of formula (I), wherein Cy1 and Cy2 and R1 to R4 are as shown in Table 28, with the exception that C1 is replaced by C14.

Table 510: Compounds of formula (I), wherein Cy1 and Cy2 and R1 to R4 are as shown in Table 29, with the exception that C1 is replaced by C14.

Table 511: Compounds of formula (I), wherein Cy1 and Cy2 and R1 to R4 are as shown in Table 30, with the exception that C1 is replaced by C14.

Table 512: Compounds of formula (I), wherein Cy1 and Cy2 and R1 to R4 are as shown in Table 31, with the exception that C1 is replaced by C14.

Table 513: Compounds of formula (I), wherein Cy1 and Cy2 and R1 to R4 are as shown in Table 32, with the exception that C1 is replaced by C14.

Table 514: Compounds of formula (I), wherein Cy1 and Cy2 and R1 to R4 are as shown in Table 33, with the exception that C1 is replaced by C14.

Table 515: Compounds of formula (I), wherein Cy1 and Cy2 and R1 to R4 are as shown in Table 34, with the exception that C1 is replaced by C14.

Table 516: Compounds of formula (I), wherein Cy1 and Cy2 and R1 to R4 are as shown in Table 35, with the exception that C1 is replaced by C14.

Table 517: Compounds of formula (I), wherein Cy1 and Cy2 and R1 to R4 are as shown in Table 36, with the exception that C1 is replaced by C14.

Table 518: Compounds of formula (I), wherein Cy1 and Cy2 and R1 to R4 are as shown in Table 37, with the exception that C1 is replaced by C14.

Table 519: Compounds of formula (I), wherein Cy1 and Cy2 and R1 to R4 are as shown in Table 38, with the exception that C1 is replaced by C14.

Table 520: Compounds of formula (I), wherein Cy1 and Cy2 and R1 to R4 are as shown in Table 2, with the exception that C1 is replaced by C15.

Table 521: Compounds of formula (I), wherein Cy1 and Cy2 and R1 to R4 are as shown in Table 3, with the exception that C1 is replaced by C15.

Table 522: Compounds of formula (I), wherein Cy1 and Cy2 and R1 to R4 are as shown in Table 4, with the exception that C1 is replaced by C15.

Table 523: Compounds of formula (I), wherein Cy1 and Cy2 and R1 to R4 are as shown in Table 5, with the exception that C1 is replaced by C15.

Table 524: Compounds of formula (I), wherein Cy1 and Cy2 and R1 to R4 are as shown in Table 6, with the exception that C1 is replaced by C15.

Table 525: Compounds of formula (I), wherein Cy1 and Cy2 and R1 to R4 are as shown in Table 7, with the exception that C1 is replaced by C15.

Table 526: Compounds of formula (I), wherein Cy1 and Cy2 and R1 to R4 are as shown in Table 8, with the exception that C1 is replaced by C15.

Table 527: Compounds of formula (I), wherein Cy1 and Cy2 and R1 to R4 are as shown in Table 9, with the exception that C1 is replaced by C15.

Table 528: Compounds of formula (I), wherein Cy1 and Cy2 and R1 to R4 are as shown in Table 10, with the exception that C1 is replaced by C15.

Table 529: Compounds of formula (I), wherein Cy1 and Cy2 and R1 to R4 are as shown in Table 11, with the exception that C1 is replaced by C15.

Table 530: Compounds of formula (I), wherein Cy1 and Cy2 and R1 to R4 are as shown in Table 12, with the exception that C1 is replaced by C15.

Table 531: Compounds of formula (I), wherein Cy1 and Cy2 and R1 to R4 are as shown in Table 13, with the exception that C1 is replaced by C15.

Table 532: Compounds of formula (I), wherein Cy1 and Cy2 and R1 to R4 are as shown in Table 14, with the exception that C1 is replaced by C15.

Table 533: Compounds of formula (I), wherein Cy1 and Cy2 and R1 to R4 are as shown in Table 15, with the exception that C1 is replaced by C15.

Table 534: Compounds of formula (I), wherein Cy1 and Cy2 and R1 to R4 are as shown in Table 16, with the exception that C1 is replaced by C15.

Table 535: Compounds of formula (I), wherein Cy1 and Cy2 and R1 to R4 are as shown in Table 17, with the exception that C1 is replaced by C15.

Table 536: Compounds of formula (I), wherein Cy1 and Cy2 and R1 to R4 are as shown in Table 18, with the exception that C1 is replaced by C15.

Table 537: Compounds of formula (I), wherein Cy1 and Cy2 and R1 to R4 are as shown in Table 19, with the exception that C1 is replaced by C15.

Table 538: Compounds of formula (I), wherein Cy1 and Cy2 and R1 to R4 are as shown in Table 20, with the exception that C1 is replaced by C15.

Table 539: Compounds of formula (I), wherein Cy1 and Cy2 and R1 to R4 are as shown in Table 21, with the exception that C1 is replaced by C15.

Table 540: Compounds of formula (I), wherein Cy1 and Cy2 and R1 to R4 are as shown in Table 22, with the exception that C1 is replaced by C15.

Table 541: Compounds of formula (I), wherein Cy1 and Cy2 and R1 to R4 are as shown in Table 23, with the exception that C1 is replaced by C15.

Table 542: Compounds of formula (I), wherein Cy1 and Cy2 and R1 to R4 are as shown in Table 24, with the exception that C1 is replaced by C15.

Table 543: Compounds of formula (I), wherein Cy1 and Cy2 and R1 to R4 are as shown in Table 25, with the exception that C1 is replaced by C15.

Table 544: Compounds of formula (I), wherein Cy1 and Cy2 and R1 to R4 are as shown in Table 26, with the exception that C1 is replaced by C15.

Table 545: Compounds of formula (I), wherein Cy1 and Cy2 and R1 to R4 are as shown in Table 27, with the exception that C1 is replaced by C15.

Table 546: Compounds of formula (I), wherein Cy1 and Cy2 and R1 to R4 are as shown in Table 28, with the exception that C1 is replaced by C15.

Table 547: Compounds of formula (I), wherein Cy1 and Cy2 and R1 to R4 are as shown in Table 29, with the exception that C1 is replaced by C15.

Table 548: Compounds of formula (I), wherein Cy1 and Cy2 and R1 to R4 are as shown in Table 30, with the exception that C1 is replaced by C15.

Table 549: Compounds of formula (I), wherein Cy1 and Cy2 and R1 to R4 are as shown in Table 31, with the exception that C1 is replaced by C15.

Table 550: Compounds of formula (I), wherein Cy1 and Cy2 and R1 to R4 are as shown in Table 32, with the exception that C1 is replaced by C15.

Table 551: Compounds of formula (I), wherein Cy1 and Cy2 and R1 to R4 are as shown in Table 33, with the exception that C1 is replaced by C15.

Table 552: Compounds of formula (I), wherein Cy1 and Cy2 and R1 to R4 are as shown in Table 34, with the exception that C1 is replaced by C15.

Table 553: Compounds of formula (I), wherein Cy1 and Cy2 and R1 to R4 are as shown in Table 35, with the exception that C1 is replaced by C15.

Table 554: Compounds of formula (I), wherein Cy1 and Cy2 and R1 to R4 are as shown in Table 36, with the exception that C1 is replaced by C15.

Table 555: Compounds of formula (I), wherein Cy1 and Cy2 and R1 to R4 are as shown in Table 37, with the exception that C1 is replaced by C15.

Table 556: Compounds of formula (I), wherein Cy1 and Cy2 and R1 to R4 are as shown in Table 38, with the exception that C1 is replaced by C15.

Table 557: Compounds of formula (I), wherein Cy1 and Cy2 and R1 to R4 are as shown in Table 2, with the exception that C1 is replaced by C16.

Table 558: Compounds of formula (I), wherein Cy1 and Cy2 and R1 to R4 are as shown in Table 3, with the exception that C1 is replaced by C16.

Table 559: Compounds of formula (I), wherein Cy1 and Cy2 and R1 to R4 are as shown in Table 4, with the exception that C1 is replaced by C16.

Table 560: Compounds of formula (I), wherein Cy1 and Cy2 and R1 to R4 are as shown in Table 5, with the exception that C1 is replaced by C16.

Table 561: Compounds of formula (I), wherein Cy1 and Cy2 and R1 to R4 are as shown in Table 6, with the exception that C1 is replaced by C16.

Table 562: Compounds of formula (I), wherein Cy1 and Cy2 and R1 to R4 are as shown in Table 7, with the exception that C1 is replaced by C16.

Table 563: Compounds of formula (I), wherein Cy1 and Cy2 and R1 to R4 are as shown in Table 8, with the exception that C1 is replaced by C16.

Table 564: Compounds of formula (I), wherein Cy1 and Cy2 and R1 to R4 are as shown in Table 9, with the exception that C1 is replaced by C16.

Table 565: Compounds of formula (I), wherein Cy1 and Cy2 and R1 to R4 are as shown in Table 10, with the exception that C1 is replaced by C16.

Table 566: Compounds of formula (I), wherein Cy1 and Cy2 and R1 to R4 are as shown in Table 11, with the exception that C1 is replaced by C16.

Table 567: Compounds of formula (I), wherein Cy1 and Cy2 and R1 to R4 are as shown in Table 12, with the exception that C1 is replaced by C16.

Table 568: Compounds of formula (I), wherein Cy1 and Cy2 and R1 to R4 are as shown in Table 13, with the exception that C1 is replaced by C16.

Table 569: Compounds of formula (I), wherein Cy1 and Cy2 and R1 to R4 are as shown in Table 14, with the exception that C1 is replaced by C16.

Table 570: Compounds of formula (I), wherein Cy1 and Cy2 and R1 to R4 are as shown in Table 15, with the exception that C1 is replaced by C16.

Table 571: Compounds of formula (I), wherein Cy1 and Cy2 and R1 to R4 are as shown in Table 16, with the exception that C1 is replaced by C16.

Table 572: Compounds of formula (I), wherein Cy1 and Cy2 and R1 to R4 are as shown in Table 17, with the exception that C1 is replaced by C16.

Table 573: Compounds of formula (I), wherein Cy1 and Cy2 and R1 to R4 are as shown in Table 18, with the exception that C1 is replaced by C16.

Table 574: Compounds of formula (I), wherein Cy1 and Cy2 and R1 to R4 are as shown in Table 19, with the exception that C1 is replaced by C16.

Table 575: Compounds of formula (I), wherein Cy1 and Cy2 and R1 to R4 are as shown in Table 20, with the exception that C1 is replaced by C16.

Table 576: Compounds of formula (I), wherein Cy1 and Cy2 and R1 to R4 are as shown in Table 21, with the exception that C1 is replaced by C16.

Table 577: Compounds of formula (I), wherein Cy1 and Cy2 and R1 to R4 are as shown in Table 22, with the exception that C1 is replaced by C16.

Table 578: Compounds of formula (I), wherein Cy1 and Cy2 and R1 to R4 are as shown in Table 23, with the exception that C1 is replaced by C16.

Table 579: Compounds of formula (I), wherein Cy1 and Cy2 and R1 to R4 are as shown in Table 24, with the exception that C1 is replaced by C16.

Table 580: Compounds of formula (I), wherein Cy1 and Cy2 and R1 to R4 are as shown in Table 25, with the exception that C1 is replaced by C16.

Table 581: Compounds of formula (I), wherein Cy1 and Cy2 and R1 to R4 are as shown in Table 26, with the exception that C1 is replaced by C16.

Table 582: Compounds of formula (I), wherein Cy1 and Cy2 and R1 to R4 are as shown in Table 27, with the exception that C1 is replaced by C16.

Table 583: Compounds of formula (I), wherein Cy1 and Cy2 and R1 to R4 are as shown in Table 28, with the exception that C1 is replaced by C16.

Table 584: Compounds of formula (I), wherein Cy1 and Cy2 and R1 to R4 are as shown in Table 29, with the exception that C1 is replaced by C16.

Table 585: Compounds of formula (I), wherein Cy1 and Cy2 and R1 to R4 are as shown in Table 30, with the exception that C1 is replaced by C16.

Table 586: Compounds of formula (I), wherein Cy1 and Cy2 and R1 to R4 are as shown in Table 31, with the exception that C1 is replaced by C16.

Table 587: Compounds of formula (I), wherein Cy1 and Cy2 and R1 to R4 are as shown in Table 32, with the exception that C1 is replaced by C16.

Table 588: Compounds of formula (I), wherein Cy1 and Cy2 and R1 to R4 are as shown in Table 33, with the exception that C1 is replaced by C16.

Table 589: Compounds of formula (I), wherein Cy1 and Cy2 and R1 to R4 are as shown in Table 34, with the exception that C1 is replaced by C16.

Table 590: Compounds of formula (I), wherein Cy1 and Cy2 and R1 to R4 are as shown in Table 35, with the exception that C1 is replaced by C16.

Table 591: Compounds of formula (I), wherein Cy1 and Cy2 and R1 to R4 are as shown in Table 36, with the exception that C1 is replaced by C16.

Table 592: Compounds of formula (I), wherein Cy1 and Cy2 and R1 to R4 are as shown in Table 37, with the exception that C1 is replaced by C16.

Table 593: Compounds of formula (I), wherein Cy1 and Cy2 and R1 to R4 are as shown in Table 38, with the exception that C1 is replaced by C16.

Table 594: Compounds of formula (I), wherein Cy1 and Cy2 and R1 to R4 are as shown in Table 2, with the exception that C1 is replaced by C17.

Table 595: Compounds of formula (I), wherein Cy1 and Cy2 and R1 to R4 are as shown in Table 3, with the exception that C1 is replaced by C17.

Table 596: Compounds of formula (I), wherein Cy1 and Cy2 and R1 to R4 are as shown in Table 4, with the exception that C1 is replaced by C17.

Table 597: Compounds of formula (I), wherein Cy1 and Cy2 and R1 to R4 are as shown in Table 5, with the exception that C1 is replaced by C17.

Table 598: Compounds of formula (I), wherein Cy1 and Cy2 and R1 to R4 are as shown in Table 6, with the exception that C1 is replaced by C17.

Table 599: Compounds of formula (I), wherein Cy1 and Cy2 and R1 to R4 are as shown in Table 7, with the exception that C1 is replaced by C17.

Table 600: Compounds of formula (I), wherein Cy1 and Cy2 and R1 to R4 are as shown in Table 8, with the exception that C1 is replaced by C17.

Table 601: Compounds of formula (I), wherein Cy1 and Cy2 and R1 to R4 are as shown in Table 9, with the exception that C1 is replaced by C17.

Table 602: Compounds of formula (I), wherein Cy1 and Cy2 and R1 to R4 are as shown in Table 10, with the exception that C1 is replaced by C17.

Table 603: Compounds of formula (I), wherein Cy1 and Cy2 and R1 to R4 are as shown in Table 11, with the exception that C1 is replaced by C17.

Table 604: Compounds of formula (I), wherein Cy1 and Cy2 and R1 to R4 are as shown in Table 12, with the exception that C1 is replaced by C17.

Table 605: Compounds of formula (I), wherein Cy1 and Cy2 and R1 to R4 are as shown in Table 13, with the exception that C1 is replaced by C17.

Table 606: Compounds of formula (I), wherein Cy1 and Cy2 and R1 to R4 are as shown in Table 14, with the exception that C1 is replaced by C17.

Table 607: Compounds of formula (I), wherein Cy1 and Cy2 and R1 to R4 are as shown in Table 15, with the exception that C1 is replaced by C17.

Table 608: Compounds of formula (I), wherein Cy1 and Cy2 and R1 to R4 are as shown in Table 16, with the exception that C1 is replaced by C17.

Table 609: Compounds of formula (I), wherein Cy1 and Cy2 and R1 to R4 are as shown in Table 17, with the exception that C1 is replaced by C17.

Table 610: Compounds of formula (I), wherein Cy1 and Cy2 and R1 to R4 are as shown in Table 18, with the exception that C1 is replaced by C17.

Table 611: Compounds of formula (I), wherein Cy1 and Cy2 and R1 to R4 are as shown in Table 19, with the exception that C1 is replaced by C17.

Table 612: Compounds of formula (I), wherein Cy1 and Cy2 and R1 to R4 are as shown in Table 20, with the exception that C1 is replaced by C17.

Table 613: Compounds of formula (I), wherein Cy1 and Cy2 and R1 to R4 are as shown in Table 21, with the exception that C1 is replaced by C17.

Table 614: Compounds of formula (I), wherein Cy1 and Cy2 and R1 to R4 are as shown in Table 22, with the exception that C1 is replaced by C17.

Table 615: Compounds of formula (I), wherein Cy1 and Cy2 and R1 to R4 are as shown in Table 23, with the exception that C1 is replaced by C17.

Table 616: Compounds of formula (I), wherein Cy1 and Cy2 and R1 to R4 are as shown in Table 24, with the exception that C1 is replaced by C17.

Table 617: Compounds of formula (I), wherein Cy1 and Cy2 and R1 to R4 are as shown in Table 25, with the exception that C1 is replaced by C17.

Table 618: Compounds of formula (I), wherein Cy1 and Cy2 and R1 to R4 are as shown in Table 26, with the exception that C1 is replaced by C17.

Table 619: Compounds of formula (I), wherein Cy1 and Cy2 and R1 to R4 are as shown in Table 27, with the exception that C1 is replaced by C17.

Table 620: Compounds of formula (I), wherein Cy1 and Cy2 and R1 to R4 are as shown in Table 28, with the exception that C1 is replaced by C17.

Table 621: Compounds of formula (I), wherein Cy1 and Cy2 and R1 to R4 are as shown in Table 29, with the exception that C1 is replaced by C17.

Table 622: Compounds of formula (I), wherein Cy1 and Cy2 and R1 to R4 are as shown in Table 30, with the exception that C1 is replaced by C17.

Table 623: Compounds of formula (I), wherein Cy1 and Cy2 and R1 to R4 are as shown in Table 31, with the exception that C1 is replaced by C17.

Table 624: Compounds of formula (I), wherein Cy1 and Cy2 and R1 to R4 are as shown in Table 32, with the exception that C1 is replaced by C17.

Table 625: Compounds of formula (I), wherein Cy1 and Cy2 and R1 to R4 are as shown in Table 33, with the exception that C1 is replaced by C17.

Table 626: Compounds of formula (I), wherein Cy1 and Cy2 and R1 to R4 are as shown in Table 34, with the exception that C1 is replaced by C17.

Table 627: Compounds of formula (I), wherein Cy1 and Cy2 and R1 to R4 are as shown in Table 35, with the exception that C1 is replaced by C17.

Table 628: Compounds of formula (I), wherein Cy1 and Cy2 and R1 to R4 are as shown in Table 36, with the exception that C1 is replaced by C17.

Table 629: Compounds of formula (I), wherein Cy1 and Cy2 and R1 to R4 are as shown in Table 37, with the exception that C1 is replaced by C17.

Table 630: Compounds of formula (I), wherein Cy1 and Cy2 and R1 to R4 are as shown in Table 38, with the exception that C1 is replaced by C17.

Table 631: Compounds of formula (I), wherein Cy1 and Cy2 and R1 to R4 are as shown in Table 2, with the exception that C1 is replaced by C18.

Table 632: Compounds of formula (I), wherein Cy1 and Cy2 and R1 to R4 are as shown in Table 3, with the exception that C1 is replaced by C18.

Table 633: Compounds of formula (I), wherein Cy1 and Cy2 and R1 to R4 are as shown in Table 4, with the exception that C1 is replaced by C18.

Table 634: Compounds of formula (I), wherein Cy1 and Cy2 and R1 to R4 are as shown in Table 5, with the exception that C1 is replaced by C18.

Table 635: Compounds of formula (I), wherein Cy1 and Cy2 and R1 to R4 are as shown in Table 6, with the exception that C1 is replaced by C18.

Table 636: Compounds of formula (I), wherein Cy1 and Cy2 and R1 to R4 are as shown in Table 7, with the exception that C1 is replaced by C18.

Table 637: Compounds of formula (I), wherein Cy1 and Cy2 and R1 to R4 are as shown in Table 8, with the exception that C1 is replaced by C18.

Table 638: Compounds of formula (I), wherein Cy1 and Cy2 and R1 to R4 are as shown in Table 9, with the exception that C1 is replaced by C18.

Table 639: Compounds of formula (I), wherein Cy1 and Cy2 and R1 to R4 are as shown in Table 10, with the exception that C1 is replaced by C18.

Table 640: Compounds of formula (I), wherein Cy1 and Cy2 and R1 to R4 are as shown in Table 11, with the exception that C1 is replaced by C18.

Table 641: Compounds of formula (I), wherein Cy1 and Cy2 and R1 to R4 are as shown in Table 12, with the exception that C1 is replaced by C18.

Table 642: Compounds of formula (I), wherein Cy1 and Cy2 and R1 to R4 are as shown in Table 13, with the exception that C1 is replaced by C18.

Table 643: Compounds of formula (I), wherein Cy1 and Cy2 and R1 to R4 are as shown in Table 14, with the exception that C1 is replaced by C18.

Table 644: Compounds of formula (I), wherein Cy1 and Cy2 and R1 to R4 are as shown in Table 15, with the exception that C1 is replaced by C18.

Table 645: Compounds of formula (I), wherein Cy1 and Cy2 and R1 to R4 are as shown in Table 16, with the exception that C1 is replaced by C18.

Table 646: Compounds of formula (I), wherein Cy1 and Cy2 and R1 to R4 are as shown in Table 17, with the exception that C1 is replaced by C18.

Table 647: Compounds of formula (I), wherein Cy1 and Cy2 and R1 to R4 are as shown in Table 18, with the exception that C1 is replaced by C18.

Table 648: Compounds of formula (I), wherein Cy1 and Cy2 and R1 to R4 are as shown in Table 19, with the exception that C1 is replaced by C18.

Table 649: Compounds of formula (I), wherein Cy1 and Cy2 and R1 to R4 are as shown in Table 20, with the exception that C1 is replaced by C18.

Table 650: Compounds of formula (I), wherein Cy1 and Cy2 and R1 to R4 are as shown in Table 21, with the exception that C1 is replaced by C18.

Table 651: Compounds of formula (I), wherein Cy1 and Cy2 and R1 to R4 are as shown in Table 22, with the exception that C1 is replaced by C18.

Table 652: Compounds of formula (I), wherein Cy1 and Cy2 and R1 to R4 are as shown in Table 23, with the exception that C1 is replaced by C18.

Table 653: Compounds of formula (I), wherein Cy1 and Cy2 and R1 to R4 are as shown in Table 24, with the exception that C1 is replaced by C18.

Table 654: Compounds of formula (I), wherein Cy1 and Cy2 and R1 to R4 are as shown in Table 25, with the exception that C1 is replaced by C18.

Table 655: Compounds of formula (I), wherein Cy1 and Cy2 and R1 to R4 are as shown in Table 26, with the exception that C1 is replaced by C18.

Table 656: Compounds of formula (I), wherein Cy1 and Cy2 and R1 to R4 are as shown in Table 27, with the exception that C1 is replaced by C18.

Table 657: Compounds of formula (I), wherein Cy1 and Cy2 and R1 to R4 are as shown in Table 28, with the exception that C1 is replaced by C18.

Table 658: Compounds of formula (I), wherein Cy1 and Cy2 and R1 to R4 are as shown in Table 29, with the exception that C1 is replaced by C18.

Table 659: Compounds of formula (I), wherein Cy1 and Cy2 and R1 to R4 are as shown in Table 30, with the exception that C1 is replaced by C18.

Table 660: Compounds of formula (I), wherein Cy1 and Cy2 and R1 to R4 are as shown in Table 31, with the exception that C1 is replaced by C18.

Table 661: Compounds of formula (I), wherein Cy1 and Cy2 and R1 to R4 are as shown in Table 32, with the exception that C1 is replaced by C18.

Table 662: Compounds of formula (I), wherein Cy1 and Cy2 and R1 to R4 are as shown in Table 33, with the exception that C1 is replaced by C18.

Table 663: Compounds of formula (I), wherein Cy1 and Cy2 and R1 to R4 are as shown in Table 34, with the exception that C1 is replaced by C18.

Table 664: Compounds of formula (I), wherein Cy1 and Cy2 and R1 to R4 are as shown in Table 35, with the exception that C1 is replaced by C18.

Table 665: Compounds of formula (I), wherein Cy1 and Cy2 and R1 to R4 are as shown in Table 36, with the exception that C1 is replaced by C18.

Table 666: Compounds of formula (I), wherein Cy1 and Cy2 and R1 to R4 are as shown in Table 37, with the exception that C1 is replaced by C18.

Table 667: Compounds of formula (I), wherein Cy1 and Cy2 and R1 to R4 are as shown in Table 38, with the exception that C1 is replaced by C18.

Table 668: Compounds of formula (I), wherein Cy1 and Cy2 and R1 to R4 are as shown in Table 2, with the exception that C1 is replaced by C19.

Table 669: Compounds of formula (I), wherein Cy1 and Cy2 and R1 to R4 are as shown in Table 3, with the exception that C1 is replaced by C19.

Table 670: Compounds of formula (I), wherein Cy1 and Cy2 and R1 to R4 are as shown in Table 4, with the exception that C1 is replaced by C19.

Table 671: Compounds of formula (I), wherein Cy1 and Cy2 and R1 to R4 are as shown in Table 5, with the exception that C1 is replaced by C19.

Table 672: Compounds of formula (I), wherein Cy1 and Cy2 and R1 to R4 are as shown in Table 6, with the exception that C1 is replaced by C19.

Table 673: Compounds of formula (I), wherein Cy1 and Cy2 and R1 to R4 are as shown in Table 7, with the exception that C1 is replaced by C19.

Table 674: Compounds of formula (I), wherein Cy1 and Cy2 and R1 to R4 are as shown in Table 8, with the exception that C1 is replaced by C19.

Table 675: Compounds of formula (I), wherein Cy1 and Cy2 and R1 to R4 are as shown in Table 9, with the exception that C1 is replaced by C19.

Table 676: Compounds of formula (I), wherein Cy1 and Cy2 and R1 to R4 are as shown in Table 10, with the exception that C1 is replaced by C19.

Table 677: Compounds of formula (I), wherein Cy1 and Cy2 and R1 to R4 are as shown in Table 11, with the exception that C1 is replaced by C19.

Table 678: Compounds of formula (I), wherein Cy1 and Cy2 and R1 to R4 are as shown in Table 12, with the exception that C1 is replaced by C19.

Table 679: Compounds of formula (I), wherein Cy1 and Cy2 and R1 to R4 are as shown in Table 13, with the exception that C1 is replaced by C19.

Table 680: Compounds of formula (I), wherein Cy1 and Cy2 and R1 to R4 are as shown in Table 14, with the exception that C1 is replaced by C19.

Table 681: Compounds of formula (I), wherein Cy1 and Cy2 and R1 to R4 are as shown in Table 15, with the exception that C1 is replaced by C19.

Table 682: Compounds of formula (I), wherein Cy1 and Cy2 and R1 to R4 are as shown in Table 16, with the exception that C1 is replaced by C19.

Table 683: Compounds of formula (I), wherein Cy1 and Cy2 and R1 to R4 are as shown in Table 17, with the exception that C1 is replaced by C19.

Table 684: Compounds of formula (I), wherein Cy1 and Cy2 and R1 to R4 are as shown in Table 18, with the exception that C1 is replaced by C19.

Table 685: Compounds of formula (I), wherein Cy1 and Cy2 and R1 to R4 are as shown in Table 19, with the exception that C1 is replaced by C19.

Table 686: Compounds of formula (I), wherein Cy1 and Cy2 and R1 to R4 are as shown in Table 20, with the exception that C1 is replaced by C19.

Table 687: Compounds of formula (I), wherein Cy1 and Cy2 and R1 to R4 are as shown in Table 21, with the exception that C1 is replaced by C19.

Table 688: Compounds of formula (I), wherein Cy1 and Cy2 and R1 to R4 are as shown in Table 22, with the exception that C1 is replaced by C19.

Table 689: Compounds of formula (I), wherein Cy1 and Cy2 and R1 to R4 are as shown in Table 23, with the exception that C1 is replaced by C19.

Table 690: Compounds of formula (I), wherein Cy1 and Cy2 and R1 to R4 are as shown in Table 24, with the exception that C1 is replaced by C19.

Table 691: Compounds of formula (I), wherein Cy1 and Cy2 and R1 to R4 are as shown in Table 25, with the exception that C1 is replaced by C19.

Table 692: Compounds of formula (I), wherein Cy1 and Cy2 and R1 to R4 are as shown in Table 26, with the exception that C1 is replaced by C19.

Table 693: Compounds of formula (I), wherein Cy1 and Cy2 and R1 to R4 are as shown in Table 27, with the exception that C1 is replaced by C19.

Table 694: Compounds of formula (I), wherein Cy1 and Cy2 and R1 to R4 are as shown in Table 28, with the exception that C1 is replaced by C19.

Table 695: Compounds of formula (I), wherein Cy1 and Cy2 and R1 to R4 are as shown in Table 29, with the exception that C1 is replaced by C19.

Table 696: Compounds of formula (I), wherein Cy1 and Cy2 and R1 to R4 are as shown in Table 30, with the exception that C1 is replaced by C19.

Table 697: Compounds of formula (I), wherein Cy1 and Cy2 and R1 to R4 are as shown in Table 31, with the exception that C1 is replaced by C19.

Table 698: Compounds of formula (I), wherein Cy1 and Cy2 and R1 to R4 are as shown in Table 32, with the exception that C1 is replaced by C19.

Table 699: Compounds of formula (I), wherein Cy1 and Cy2 and R1 to R4 are as shown in Table 33, with the exception that C1 is replaced by C19.

Table 700: Compounds of formula (I), wherein Cy1 and Cy2 and R1 to R4 are as shown in Table 34, with the exception that C1 is replaced by C19.

Table 701: Compounds of formula (I), wherein Cy1 and Cy2 and R1 to R4 are as shown in Table 35, with the exception that C1 is replaced by C19.

Table 702: Compounds of formula (I), wherein Cy1 and Cy2 and R1 to R4 are as shown in Table 36, with the exception that C1 is replaced by C19.

Table 703: Compounds of formula (I), wherein Cy1 and Cy2 and R1 to R4 are as shown in Table 37, with the exception that C1 is replaced by C19.

Table 704: Compounds of formula (I), wherein Cy1 and Cy2 and R1 to R4 are as shown in Table 38, with the exception that C1 is replaced by C19.

Table 705: Compounds of formula (I), wherein Cy1 and Cy2 and R1 to R4 are as shown in Table 2, with the exception that C1 is replaced by C20.

Table 706: Compounds of formula (I), wherein Cy1 and Cy2 and R1 to R4 are as shown in Table 3, with the exception that C1 is replaced by C20.

Table 707: Compounds of formula (I), wherein Cy1 and Cy2 and R1 to R4 are as shown in Table 4, with the exception that C1 is replaced by C20.

Table 708: Compounds of formula (I), wherein Cy1 and Cy2 and R1 to R4 are as shown in Table 5, with the exception that C1 is replaced by C20.

Table 709: Compounds of formula (I), wherein Cy1 and Cy2 and R1 to R4 are as shown in Table 6, with the exception that C1 is replaced by C20.

Table 710: Compounds of formula (I), wherein Cy1 and Cy2 and R1 to R4 are as shown in Table 7, with the exception that C1 is replaced by C20.

Table 711: Compounds of formula (I), wherein Cy1 and Cy2 and R1 to R4 are as shown in Table 8, with the exception that C1 is replaced by C20.

Table 712: Compounds of formula (I), wherein Cy1 and Cy2 and R1 to R4 are as shown in Table 9, with the exception that C1 is replaced by C20.

Table 713: Compounds of formula (I), wherein Cy1 and Cy2 and R1 to R4 are as shown in Table 10, with the exception that C1 is replaced by C20.

Table 714: Compounds of formula (I), wherein Cy1 and Cy2 and R1 to R4 are as shown in Table 11, with the exception that C1 is replaced by C20.

Table 715: Compounds of formula (I), wherein Cy1 and Cy2 and R1 to R4 are as shown in Table 12, with the exception that C1 is replaced by C20.

Table 716: Compounds of formula (I), wherein Cy1 and Cy2 and R1 to R4 are as shown in Table 13, with the exception that C1 is replaced by C20.

Table 717: Compounds of formula (I), wherein Cy1 and Cy2 and R1 to R4 are as shown in Table 14, with the exception that C1 is replaced by C20.

Table 718: Compounds of formula (I), wherein Cy1 and Cy2 and R1 to R4 are as shown in Table 15, with the exception that C1 is replaced by C20.

Table 719: Compounds of formula (I), wherein Cy1 and Cy2 and R1 to R4 are as shown in Table 16, with the exception that C1 is replaced by C20.

Table 720: Compounds of formula (I), wherein Cy1 and Cy2 and R1 to R4 are as shown in Table 17, with the exception that C1 is replaced by C20.

Table 721: Compounds of formula (I), wherein Cy1 and Cy2 and R1 to R4 are as shown in Table 18, with the exception that C1 is replaced by C20.

Table 722: Compounds of formula (I), wherein Cy1 and Cy2 and R1 to R4 are as shown in Table 19, with the exception that C1 is replaced by C20.

Table 723: Compounds of formula (I), wherein Cy1 and Cy2 and R1 to R4 are as shown in Table 20, with the exception that C1 is replaced by C20.

Table 724: Compounds of formula (I), wherein Cy1 and Cy2 and R1 to R4 are as shown in Table 21, with the exception that C1 is replaced by C20.

Table 725: Compounds of formula (I), wherein Cy1 and Cy2 and R1 to R4 are as shown in Table 22, with the exception that C1 is replaced by C20.

Table 726: Compounds of formula (I), wherein Cy1 and Cy2 and R1 to R4 are as shown in Table 23, with the exception that C1 is replaced by C20.

Table 727: Compounds of formula (I), wherein Cy1 and Cy2 and R1 to R4 are as shown in Table 24, with the exception that C1 is replaced by C20.

Table 728: Compounds of formula (I), wherein Cy1 and Cy2 and R1 to R4 are as shown in Table 25, with the exception that C1 is replaced by C20.

Table 729: Compounds of formula (I), wherein Cy1 and Cy2 and R1 to R4 are as shown in Table 26, with the exception that C1 is replaced by C20.

Table 730: Compounds of formula (I), wherein Cy1 and Cy2 and R1 to R4 are as shown in Table 27, with the exception that C1 is replaced by C20.

Table 731: Compounds of formula (I), wherein Cy1 and Cy2 and R1 to R4 are as shown in Table 28, with the exception that C1 is replaced by C20.

Table 732: Compounds of formula (I), wherein Cy1 and Cy2 and R1 to R4 are as shown in Table 29, with the exception that C1 is replaced by C20.

Table 733: Compounds of formula (I), wherein Cy1 and Cy2 and R1 to R4 are as shown in Table 30, with the exception that C1 is replaced by C20.

Table 734: Compounds of formula (I), wherein Cy1 and Cy2 and R1 to R4 are as shown in Table 31, with the exception that C1 is replaced by C20.

Table 735: Compounds of formula (I), wherein Cy1 and Cy2 and R1 to R4 are as shown in Table 32, with the exception that C1 is replaced by C20.

Table 736: Compounds of formula (I), wherein Cy1 and Cy2 and R1 to R4 are as shown in Table 33, with the exception that C1 is replaced by C20.

Table 737: Compounds of formula (I), wherein Cy1 and Cy2 and R1 to R4 are as shown in Table 34, with the exception that C1 is replaced by C20.

Table 738: Compounds of formula (I), wherein Cy1 and Cy2 and R1 to R4 are as shown in Table 35, with the exception that C1 is replaced by C20.

Table 739: Compounds of formula (I), wherein Cy1 and Cy2 and R1 to R4 are as shown in Table 36, with the exception that C1 is replaced by C20.

Table 740: Compounds of formula (I), wherein Cy1 and Cy2 and R1 to R4 are as shown in Table 37, with the exception that C1 is replaced by C20.

Table 741: Compounds of formula (I), wherein Cy1 and Cy2 and R1 to R4 are as shown in Table 38, with the exception that C1 is replaced by C20.

Table 742: Compounds of formula (I), wherein Cy1 and Cy2 and R1 to R4 are as shown in Table 2, with the exception that C1 is replaced by C21.

Table 743: Compounds of formula (I), wherein Cy1 and Cy2 and R1 to R4 are as shown in Table 3, with the exception that C1 is replaced by C21.

Table 744: Compounds of formula (I), wherein Cy1 and Cy2 and R1 to R4 are as shown in Table 4, with the exception that C1 is replaced by C21.

Table 745: Compounds of formula (I), wherein Cy1 and Cy2 and R1 to R4 are as shown in Table 5, with the exception that C1 is replaced by C21.

Table 746: Compounds of formula (I), wherein Cy1 and Cy2 and R1 to R4 are as shown in Table 6, with the exception that C1 is replaced by C21.

Table 747: Compounds of formula (I), wherein Cy1 and Cy2 and R1 to R4 are as shown in Table 7, with the exception that C1 is replaced by C21.

Table 748: Compounds of formula (I), wherein Cy1 and Cy2 and R1 to R4 are as shown in Table 8, with the exception that C1 is replaced by C21.

Table 749: Compounds of formula (I), wherein Cy1 and Cy2 and R1 to R4 are as shown in Table 9, with the exception that C1 is replaced by C21.

Table 750: Compounds of formula (I), wherein Cy1 and Cy2 and R1 to R4 are as shown in Table 10, with the exception that C1 is replaced by C21.

Table 751: Compounds of formula (I), wherein Cy1 and Cy2 and R1 to R4 are as shown in Table 11, with the exception that C1 is replaced by C21.

Table 752: Compounds of formula (I), wherein Cy1 and Cy2 and R1 to R4 are as shown in Table 12, with the exception that C1 is replaced by C21.

Table 753: Compounds of formula (I), wherein Cy1 and Cy2 and R1 to R4 are as shown in Table 13, with the exception that C1 is replaced by C21.

Table 754: Compounds of formula (I), wherein Cy1 and Cy2 and R1 to R4 are as shown in Table 14, with the exception that C1 is replaced by C21.

Table 755: Compounds of formula (I), wherein Cy1 and Cy2 and R1 to R4 are as shown in Table 15, with the exception that C1 is replaced by C21.

Table 756: Compounds of formula (I), wherein Cy1 and Cy2 and R1 to R4 are as shown in Table 16, with the exception that C1 is replaced by C21.

Table 757: Compounds of formula (I), wherein Cy1 and Cy2 and R1 to R4 are as shown in Table 17, with the exception that C1 is replaced by C21.

Table 758: Compounds of formula (I), wherein Cy1 and Cy2 and R1 to R4 are as shown in Table 18, with the exception that C1 is replaced by C21.

Table 759: Compounds of formula (I), wherein Cy1 and Cy2 and R1 to R4 are as shown in Table 19, with the exception that C1 is replaced by C21.

Table 760: Compounds of formula (I), wherein Cy1 and Cy2 and R1 to R4 are as shown in Table 20, with the exception that C1 is replaced by C21.

Table 761: Compounds of formula (I), wherein Cy1 and Cy2 and R1 to R4 are as shown in Table 21, with the exception that C1 is replaced by C21.

Table 762: Compounds of formula (I), wherein Cy1 and Cy2 and R1 to R4 are as shown in Table 22, with the exception that C1 is replaced by C21.

Table 763: Compounds of formula (I), wherein Cy1 and Cy2 and R1 to R4 are as shown in Table 23, with the exception that C1 is replaced by C21.

Table 764: Compounds of formula (I), wherein Cy1 and Cy2 and R1 to R4 are as shown in Table 24, with the exception that C1 is replaced by C21.

Table 765: Compounds of formula (I), wherein Cy1 and Cy2 and R1 to R4 are as shown in Table 25, with the exception that C1 is replaced by C21.

Table 766: Compounds of formula (I), wherein Cy1 and Cy2 and R1 to R4 are as shown in Table 26, with the exception that C1 is replaced by C21.

Table 767: Compounds of formula (I), wherein Cy1 and Cy2 and R1 to R4 are as shown in Table 27, with the exception that C1 is replaced by C21.

Table 768: Compounds of formula (I), wherein Cy1 and Cy2 and R1 to R4 are as shown in Table 28, with the exception that C1 is replaced by C21.

Table 769: Compounds of formula (I), wherein Cy1 and Cy2 and R1 to R4 are as shown in Table 29, with the exception that C1 is replaced by C21.

Table 770: Compounds of formula (I), wherein Cy1 and Cy2 and R1 to R4 are as shown in Table 30, with the exception that C1 is replaced by C21.

Table 771: Compounds of formula (I), wherein Cy1 and Cy2 and R1 to R4 are as shown in Table 31, with the exception that C1 is replaced by C21.

Table 772: Compounds of formula (I), wherein Cy1 and Cy2 and R1 to R4 are as shown in Table 32, with the exception that C1 is replaced by C21.

Table 773: Compounds of formula (I), wherein Cy1 and Cy2 and R1 to R4 are as shown in Table 33, with the exception that C1 is replaced by C21.

Table 774: Compounds of formula (I), wherein Cy1 and Cy2 and R1 to R4 are as shown in Table 34, with the exception that C1 is replaced by C21.

Table 775: Compounds of formula (I), wherein Cy1 and Cy2 and R1 to R4 are as shown in Table 35, with the exception that C1 is replaced by C21.

Table 776: Compounds of formula (I), wherein Cy1 and Cy2 and R1 to R4 are as shown in Table 36, with the exception that C1 is replaced by C21.

Table 777: Compounds of formula (I), wherein Cy1 and Cy2 and R1 to R4 are as shown in Table 37, with the exception that C1 is replaced by C21.

Table 778: Compounds of formula (I), wherein Cy1 and Cy2 and R1 to R4 are as shown in Table 38, with the exception that C1 is replaced by C21.

Table 779: Compounds of formula (I), wherein Cy1 and Cy2 and R1 to R4 are as shown in Table 2, with the exception that C1 is replaced by C22.

Table 780: Compounds of formula (I), wherein Cy1 and Cy2 and R1 to R4 are as shown in Table 3, with the exception that C1 is replaced by C22.

Table 781: Compounds of formula (I), wherein Cy1 and Cy2 and R1 to R4 are as shown in Table 4, with the exception that C1 is replaced by C22.

Table 782: Compounds of formula (I), wherein Cy1 and Cy2 and R1 to R4 are as shown in Table 5, with the exception that C1 is replaced by C22.

Table 783: Compounds of formula (I), wherein Cy1 and Cy2 and R1 to R4 are as shown in Table 6, with the exception that C1 is replaced by C22.

Table 784: Compounds of formula (I), wherein Cy1 and Cy2 and R1 to R4 are as shown in Table 7, with the exception that C1 is replaced by C22.

Table 785: Compounds of formula (I), wherein Cy1 and Cy2 and R1 to R4 are as shown in Table 8, with the exception that C1 is replaced by C22.

Table 786: Compounds of formula (I), wherein Cy1 and Cy2 and R1 to R4 are as shown in Table 9, with the exception that C1 is replaced by C22.

Table 787: Compounds of formula (I), wherein Cy1 and Cy2 and R1 to R4 are as shown in Table 10, with the exception that C1 is replaced by C22.

Table 788: Compounds of formula (I), wherein Cy1 and Cy2 and R1 to R4 are as shown in Table 11, with the exception that C1 is replaced by C22.

Table 789: Compounds of formula (I), wherein Cy1 and Cy2 and R1 to R4 are as shown in Table 12, with the exception that C1 is replaced by C22.

Table 790: Compounds of formula (I), wherein Cy1 and Cy2 and R1 to R4 are as shown in Table 13, with the exception that C1 is replaced by C22.

Table 791: Compounds of formula (I), wherein Cy1 and Cy2 and R1 to R4 are as shown in Table 14, with the exception that C1 is replaced by C22.

Table 792: Compounds of formula (I), wherein Cy1 and Cy2 and R1 to R4 are as shown in Table 15, with the exception that C1 is replaced by C22.

Table 793: Compounds of formula (I), wherein Cy1 and Cy2 and R1 to R4 are as shown in Table 16, with the exception that C1 is replaced by C22.

Table 794: Compounds of formula (I), wherein Cy1 and Cy2 and R1 to R4 are as shown in Table 17, with the exception that C1 is replaced by C22.

Table 795: Compounds of formula (I), wherein Cy1 and Cy2 and R1 to R4 are as shown in Table 18, with the exception that C1 is replaced by C22.

Table 796: Compounds of formula (I), wherein Cy1 and Cy2 and R1 to R4 are as shown in Table 19, with the exception that C1 is replaced by C22.

Table 797: Compounds of formula (I), wherein Cy1 and Cy2 and R1 to R4 are as shown in Table 20, with the exception that C1 is replaced by C22.

Table 798: Compounds of formula (I), wherein Cy1 and Cy2 and R1 to R4 are as shown in Table 21, with the exception that C1 is replaced by C22.

Table 799: Compounds of formula (I), wherein Cy1 and Cy2 and R1 to R4 are as shown in Table 22, with the exception that C1 is replaced by C22.

Table 800: Compounds of formula (I), wherein Cy1 and Cy2 and R1 to R4 are as shown in Table 23, with the exception that C1 is replaced by C22.

Table 801: Compounds of formula (I), wherein Cy1 and Cy2 and R1 to R4 are as shown in Table 24, with the exception that C1 is replaced by C22.

Table 802: Compounds of formula (I), wherein Cy1 and Cy2 and R1 to R4 are as shown in Table 25, with the exception that C1 is replaced by C22.

Table 803: Compounds of formula (I), wherein Cy1 and Cy2 and R1 to R4 are as shown in Table 26, with the exception that C1 is replaced by C22.

Table 804: Compounds of formula (I), wherein Cy1 and Cy2 and R1 to R4 are as shown in Table 27, with the exception that C1 is replaced by C22.

Table 805: Compounds of formula (I), wherein Cy1 and Cy2 and R1 to R4 are as shown in Table 28, with the exception that C1 is replaced by C22.

Table 806: Compounds of formula (I), wherein Cy1 and Cy2 and R1 to R4 are as shown in Table 29, with the exception that C1 is replaced by C22.

Table 807: Compounds of formula (I), wherein Cy1 and Cy2 and R1 to R4 are as shown in Table 30, with the exception that C1 is replaced by C22.

Table 808: Compounds of formula (I), wherein Cy1 and Cy2 and R1 to R4 are as shown in Table 31, with the exception that C1 is replaced by C22.

Table 809: Compounds of formula (I), wherein Cy1 and Cy2 and R1 to R4 are as shown in Table 32, with the exception that C1 is replaced by C22.

Table 810: Compounds of formula (I), wherein Cy1 and Cy2 and R1 to R4 are as shown in Table 33, with the exception that C1 is replaced by C22.

Table 811: Compounds of formula (I), wherein Cy1 and Cy2 and R1 to R4 are as shown in Table 34, with the exception that C1 is replaced by C22.

Table 812: Compounds of formula (I), wherein Cy1 and Cy2 and R1 to R4 are as shown in Table 35, with the exception that C1 is replaced by C22.

Table 813: Compounds of formula (I), wherein Cy1 and Cy2 and R1 to R4 are as shown in Table 36, with the exception that C1 is replaced by C22.

Table 814: Compounds of formula (I), wherein Cy1 and Cy2 and R1 to R4 are as shown in Table 37, with the exception that C1 is replaced by C22.

Table 815: Compounds of formula (I), wherein Cy1 and Cy2 and R1 to R4 are as shown in Table 38, with the exception that C1 is replaced by C22.

Table 816: Compounds of formula (I), wherein Cy1 and Cy2 and R1 to R4 are as shown in Table 2, with the exception that C1 is replaced by C23.

Table 817: Compounds of formula (I), wherein Cy1 and Cy2 and R1 to R4 are as shown in Table 3, with the exception that C1 is replaced by C23.

Table 818: Compounds of formula (I), wherein Cy1 and Cy2 and R1 to R4 are as shown in Table 4, with the exception that C1 is replaced by C23.

Table 819: Compounds of formula (I), wherein Cy1 and Cy2 and R1 to R4 are as shown in Table 5, with the exception that C1 is replaced by C23.

Table 820: Compounds of formula (I), wherein Cy1 and Cy2 and R1 to R4 are as shown in Table 6, with the exception that C1 is replaced by C23.

Table 821: Compounds of formula (I), wherein Cy1 and Cy2 and R1 to R4 are as shown in Table 7, with the exception that C1 is replaced by C23.

Table 822: Compounds of formula (I), wherein Cy1 and Cy2 and R1 to R4 are as shown in Table 8, with the exception that C1 is replaced by C23.

Table 823: Compounds of formula (I), wherein Cy1 and Cy2 and R1 to R4 are as shown in Table 9, with the exception that C1 is replaced by C23.

Table 824: Compounds of formula (I), wherein Cy1 and Cy2 and R1 to R4 are as shown in Table 10, with the exception that C1 is replaced by C23.

Table 825: Compounds of formula (I), wherein Cy1 and Cy2 and R1 to R4 are as shown in Table 11, with the exception that C1 is replaced by C23.

Table 826: Compounds of formula (I), wherein Cy1 and Cy2 and R1 to R4 are as shown in Table 12, with the exception that C1 is replaced by C23.

Table 827: Compounds of formula (I), wherein Cy1 and Cy2 and R1 to R4 are as shown in Table 13, with the exception that C1 is replaced by C23.

Table 828: Compounds of formula (I), wherein Cy1 and Cy2 and R1 to R4 are as shown in Table 14, with the exception that C1 is replaced by C23.

Table 829: Compounds of formula (I), wherein Cy1 and Cy2 and R1 to R4 are as shown in Table 15, with the exception that C1 is replaced by C23.

Table 830: Compounds of formula (I), wherein Cy1 and Cy2 and R1 to R4 are as shown in Table 16, with the exception that C1 is replaced by C23.

Table 831: Compounds of formula (I), wherein Cy1 and Cy2 and R1 to R4 are as shown in Table 17, with the exception that C1 is replaced by C23.

Table 832: Compounds of formula (I), wherein Cy1 and Cy2 and R1 to R4 are as shown in Table 18, with the exception that C1 is replaced by C23.

Table 833: Compounds of formula (I), wherein Cy1 and Cy2 and R1 to R4 are as shown in Table 19, with the exception that C1 is replaced by C23.

Table 834: Compounds of formula (I), wherein Cy1 and Cy2 and R1 to R4 are as shown in Table 20, with the exception that C1 is replaced by C23.

Table 835: Compounds of formula (I), wherein Cy1 and Cy2 and R1 to R4 are as shown in Table 21, with the exception that C1 is replaced by C23.

Table 836: Compounds of formula (I), wherein Cy1 and Cy2 and R1 to R4 are as shown in Table 22, with the exception that C1 is replaced by C23.

Table 837: Compounds of formula (I), wherein Cy1 and Cy2 and R1 to R4 are as shown in Table 23, with the exception that C1 is replaced by C23.

Table 838: Compounds of formula (I), wherein Cy1 and Cy2 and R1 to R4 are as shown in Table 24, with the exception that C1 is replaced by C23.

Table 839: Compounds of formula (I), wherein Cy1 and Cy2 and R1 to R4 are as shown in Table 25, with the exception that C1 is replaced by C23.

Table 840: Compounds of formula (I), wherein Cy1 and Cy2 and R1 to R4 are as shown in Table 26, with the exception that C1 is replaced by C23.

Table 841: Compounds of formula (I), wherein Cy1 and Cy2 and R1 to R4 are as shown in Table 27, with the exception that C1 is replaced by C23.

Table 842: Compounds of formula (I), wherein Cy1 and Cy2 and R1 to R4 are as shown in Table 28, with the exception that C1 is replaced by C23.

Table 843: Compounds of formula (I), wherein Cy1 and Cy2 and R1 to R4 are as shown in Table 29, with the exception that C1 is replaced by C23.

Table 844: Compounds of formula (I), wherein Cy1 and Cy2 and R1 to R4 are as shown in Table 30, with the exception that C1 is replaced by C23.

Table 845: Compounds of formula (I), wherein Cy1 and Cy2 and R1 to R4 are as shown in Table 31, with the exception that C1 is replaced by C23.

Table 846: Compounds of formula (I), wherein Cy1 and Cy2 and R1 to R4 are as shown in Table 32, with the exception that C1 is replaced by C23.

Table 847: Compounds of formula (I), wherein Cy1 and Cy2 and R1 to R4 are as shown in Table 33, with the exception that C1 is replaced by C23.

Table 848: Compounds of formula (I), wherein Cy1 and Cy2 and R1 to R4 are as shown in Table 34, with the exception that C1 is replaced by C23.

Table 849: Compounds of formula (I), wherein Cy1 and Cy2 and R1 to R4 are as shown in Table 35, with the exception that C1 is replaced by C23.

Table 850: Compounds of formula (I), wherein Cy1 and Cy2 and R1 to R4 are as shown in Table 36, with the exception that C1 is replaced by C23.

Table 851: Compounds of formula (I), wherein Cy1 and Cy2 and R1 to R4 are as shown in Table 37, with the exception that C1 is replaced by C23.

Table 852: Compounds of formula (I), wherein Cy1 and Cy2 and R1 to R4 are as shown in Table 38, with the exception that C1 is replaced by C23.

Table 853: Compounds of formula (I), wherein Cy1 and Cy2 and R1 to R4 are as shown in Table 2, with the exception that C1 is replaced by C24.

Table 854: Compounds of formula (I), wherein Cy1 and Cy2 and R1 to R4 are as shown in Table 3, with the exception that C1 is replaced by C24.

Table 855: Compounds of formula (I), wherein Cy1 and Cy2 and R1 to R4 are as shown in Table 4, with the exception that C1 is replaced by C24.

Table 856: Compounds of formula (I), wherein Cy1 and Cy2 and R1 to R4 are as shown in Table 5, with the exception that C1 is replaced by C24.

Table 857: Compounds of formula (I), wherein Cy1 and Cy2 and R1 to R4 are as shown in Table 6, with the exception that C1 is replaced by C24.

Table 858: Compounds of formula (I), wherein Cy1 and Cy2 and R1 to R4 are as shown in Table 7, with the exception that C1 is replaced by C24.

Table 859: Compounds of formula (I), wherein Cy1 and Cy2 and R1 to R4 are as shown in Table 8, with the exception that C1 is replaced by C24.

Table 860: Compounds of formula (I), wherein Cy1 and Cy2 and R1 to R4 are as shown in Table 9, with the exception that C1 is replaced by C24.

Table 861: Compounds of formula (I), wherein Cy1 and Cy2 and R1 to R4 are as shown in Table 10, with the exception that C1 is replaced by C24.

Table 862: Compounds of formula (I), wherein Cy1 and Cy2 and R1 to R4 are as shown in Table 11, with the exception that C1 is replaced by C24.

Table 863: Compounds of formula (I), wherein Cy1 and Cy2 and R1 to R4 are as shown in Table 12, with the exception that C1 is replaced by C24.

Table 864: Compounds of formula (I), wherein Cy1 and Cy2 and R1 to R4 are as shown in Table 13, with the exception that C1 is replaced by C24.

Table 865: Compounds of formula (I), wherein Cy1 and Cy2 and R1 to R4 are as shown in Table 14, with the exception that C1 is replaced by C24.

Table 866: Compounds of formula (I), wherein Cy1 and Cy2 and R1 to R4 are as shown in Table 15, with the exception that C1 is replaced by C24.

Table 867: Compounds of formula (I), wherein Cy1 and Cy2 and R1 to R4 are as shown in Table 16, with the exception that C1 is replaced by C24.

Table 868: Compounds of formula (I), wherein Cy1 and Cy2 and R1 to R4 are as shown in Table 17, with the exception that C1 is replaced by C24.

Table 869: Compounds of formula (I), wherein Cy1 and Cy2 and R1 to R4 are as shown in Table 18, with the exception that C1 is replaced by C24.

Table 870: Compounds of formula (I), wherein Cy1 and Cy2 and R1 to R4 are as shown in Table 19, with the exception that C1 is replaced by C24.

Table 871: Compounds of formula (I), wherein Cy1 and Cy2 and R1 to R4 are as shown in Table 20, with the exception that C1 is replaced by C24.

Table 872: Compounds of formula (I), wherein Cy1 and Cy2 and R1 to R4 are as shown in Table 21, with the exception that C1 is replaced by C24.

Table 873: Compounds of formula (I), wherein Cy1 and Cy2 and R1 to R4 are as shown in Table 22, with the exception that C1 is replaced by C24.

Table 874: Compounds of formula (I), wherein Cy1 and Cy2 and R1 to R4 are as shown in Table 23, with the exception that C1 is replaced by C24.

Table 875: Compounds of formula (I), wherein Cy1 and Cy2 and R1 to R4 are as shown in Table 24, with the exception that C1 is replaced by C24.

Table 876: Compounds of formula (I), wherein Cy1 and Cy2 and R1 to R4 are as shown in Table 25, with the exception that C1 is replaced by C24.

Table 877: Compounds of formula (I), wherein Cy1 and Cy2 and R1 to R4 are as shown in Table 26, with the exception that C1 is replaced by C24.

Table 878: Compounds of formula (I), wherein Cy1 and Cy2 and R1 to R4 are as shown in Table 27, with the exception that C1 is replaced by C24.

Table 879: Compounds of formula (I), wherein Cy1 and Cy2 and R1 to R4 are as shown in Table 28, with the exception that C1 is replaced by C24.

Table 880: Compounds of formula (I), wherein Cy1 and Cy2 and R1 to R4 are as shown in Table 29, with the exception that C1 is replaced by C24.

Table 881: Compounds of formula (I), wherein Cy1 and Cy2 and R1 to R4 are as shown in Table 30, with the exception that C1 is replaced by C24.

Table 882: Compounds of formula (I), wherein Cy1 and Cy2 and R1 to R4 are as shown in Table 31, with the exception that C1 is replaced by C24.

Table 883: Compounds of formula (I), wherein Cy1 and Cy2 and R1 to R4 are as shown in Table 32, with the exception that C1 is replaced by C24.

Table 884: Compounds of formula (I), wherein Cy1 and Cy2 and R1 to R4 are as shown in Table 33, with the exception that C1 is replaced by C24.

Table 885: Compounds of formula (I), wherein Cy1 and Cy2 and R1 to R4 are as shown in Table 34, with the exception that C1 is replaced by C24.

Table 886: Compounds of formula (I), wherein Cy1 and Cy2 and R1 to R4 are as shown in Table 35, with the exception that C1 is replaced by C24.

Table 887: Compounds of formula (I), wherein Cy1 and Cy2 and R1 to R4 are as shown in Table 36, with the exception that C1 is replaced by C24.

Table 888: Compounds of formula (I), wherein Cy1 and Cy2 and R1 to R4 are as shown in Table 37, with the exception that C1 is replaced by C24.

Table 889: Compounds of formula (I), wherein Cy1 and Cy2 and R1 to R4 are as shown in Table 38, with the exception that C1 is replaced by C24.

Table 890: Compounds of formula (I), wherein Cy1 and Cy2 and R1 to R4 are as shown in Table 2, with the exception that C1 is replaced by C25.

Table 891: Compounds of formula (I), wherein Cy1 and Cy2 and R1 to R4 are as shown in Table 3, with the exception that C1 is replaced by C25.

Table 892: Compounds of formula (I), wherein Cy1 and Cy2 and R1 to R4 are as shown in Table 4, with the exception that C1 is replaced by C25.

Table 893: Compounds of formula (I), wherein Cy1 and Cy2 and R1 to R4 are as shown in Table 5, with the exception that C1 is replaced by C25.

Table 894: Compounds of formula (I), wherein Cy1 and Cy2 and R1 to R4 are as shown in Table 6, with the exception that C1 is replaced by C25.

Table 895: Compounds of formula (I), wherein Cy1 and Cy2 and R1 to R4 are as shown in Table 7, with the exception that C1 is replaced by C25.

Table 896: Compounds of formula (I), wherein Cy1 and Cy2 and R1 to R4 are as shown in Table 8, with the exception that C1 is replaced by C25.

Table 897: Compounds of formula (I), wherein Cy1 and Cy2 and R1 to R4 are as shown in Table 9, with the exception that C1 is replaced by C25.

Table 898: Compounds of formula (I), wherein Cy1 and Cy2 and R1 to R4 are as shown in Table 10, with the exception that C1 is replaced by C25.

Table 899: Compounds of formula (I), wherein Cy1 and Cy2 and R1 to R4 are as shown in Table 11, with the exception that C1 is replaced by C25.

Table 900: Compounds of formula (I), wherein Cy1 and Cy2 and R1 to R4 are as shown in Table 12, with the exception that C1 is replaced by C25.

Table 901: Compounds of formula (I), wherein Cy1 and Cy2 and R1 to R4 are as shown in Table 13, with the exception that C1 is replaced by C25.

Table 902: Compounds of formula (I), wherein Cy1 and Cy2 and R1 to R4 are as shown in Table 14, with the exception that C1 is replaced by C25.

Table 903: Compounds of formula (I), wherein Cy1 and Cy2 and R1 to R4 are as shown in Table 15, with the exception that C1 is replaced by C25.

Table 904: Compounds of formula (I), wherein Cy1 and Cy2 and R1 to R4 are as shown in Table 16, with the exception that C1 is replaced by C25.

Table 905: Compounds of formula (I), wherein Cy1 and Cy2 and R1 to R4 are as shown in Table 17, with the exception that C1 is replaced by C25.

Table 906: Compounds of formula (I), wherein Cy1 and Cy2 and R1 to R4 are as shown in Table 18, with the exception that C1 is replaced by C25.

Table 907: Compounds of formula (I), wherein Cy1 and Cy2 and R1 to R4 are as shown in Table 19, with the exception that C1 is replaced by C25.

Table 908: Compounds of formula (I), wherein Cy1 and Cy2 and R1 to R4 are as shown in Table 20, with the exception that C1 is replaced by C25.

Table 909: Compounds of formula (I), wherein Cy1 and Cy2 and R1 to R4 are as shown in Table 21, with the exception that C1 is replaced by C25.

Table 910: Compounds of formula (I), wherein Cy1 and Cy2 and R1 to R4 are as shown in Table 22, with the exception that C1 is replaced by C25.

Table 911: Compounds of formula (I), wherein Cy1 and Cy2 and R1 to R4 are as shown in Table 23, with the exception that C1 is replaced by C25.

Table 912: Compounds of formula (I), wherein Cy1 and Cy2 and R1 to R4 are as shown in Table 24, with the exception that C1 is replaced by C25.

Table 913: Compounds of formula (I), wherein Cy1 and Cy2 and R1 to R4 are as shown in Table 25, with the exception that C1 is replaced by C25.

Table 914: Compounds of formula (I), wherein Cy1 and Cy2 and R1 to R4 are as shown in Table 26, with the exception that C1 is replaced by C25.

Table 915: Compounds of formula (I), wherein Cy1 and Cy2 and R1 to R4 are as shown in Table 27, with the exception that C1 is replaced by C25.

Table 916: Compounds of formula (I), wherein Cy1 and Cy2 and R1 to R4 are as shown in Table 28, with the exception that C1 is replaced by C25.

Table 917: Compounds of formula (I), wherein Cy1 and Cy2 and R1 to R4 are as shown in Table 29, with the exception that C1 is replaced by C25.

Table 918: Compounds of formula (I), wherein Cy1 and Cy2 and R1 to R4 are as shown in Table 30, with the exception that C1 is replaced by C25.

Table 919: Compounds of formula (I), wherein Cy1 and Cy2 and R1 to R4 are as shown in Table 31, with the exception that C1 is replaced by C25.

Table 920: Compounds of formula (I), wherein Cy1 and Cy2 and R1 to R4 are as shown in Table 32, with the exception that C1 is replaced by C25.

Table 921: Compounds of formula (I), wherein Cy1 and Cy2 and R1 to R4 are as shown in Table 33, with the exception that C1 is replaced by C25.

Table 922: Compounds of formula (I), wherein Cy1 and Cy2 and R1 to R4 are as shown in Table 34, with the exception that C1 is replaced by C25.

Table 923: Compounds of formula (I), wherein Cy1 and Cy2 and R1 to R4 are as shown in Table 35, with the exception that C1 is replaced by C25.

Table 924: Compounds of formula (I), wherein Cy1 and Cy2 and R1 to R4 are as shown in Table 36, with the exception that C1 is replaced by C25.

Table 925: Compounds of formula (I), wherein Cy1 and Cy2 and R1 to R4 are as shown in Table 37, with the exception that C1 is replaced by C25.

Table 926: Compounds of formula (I), wherein Cy1 and Cy2 and R1 to R4 are as shown in Table 38, with the exception that C1 is replaced by C25.

Table 927: Compounds of formula (I), wherein Cy1 and Cy2 and R1 to R4 are as shown in Table 2, with the exception that C1 is replaced by C26.

Table 928: Compounds of formula (I), wherein Cy1 and Cy2 and R1 to R4 are as shown in Table 3, with the exception that C1 is replaced by C26.

Table 929: Compounds of formula (I), wherein Cy1 and Cy2 and R1 to R4 are as shown in Table 4, with the exception that C1 is replaced by C26.

Table 930: Compounds of formula (I), wherein Cy1 and Cy2 and R1 to R4 are as shown in Table 5, with the exception that C1 is replaced by C26.

Table 931: Compounds of formula (I), wherein Cy1 and Cy2 and R1 to R4 are as shown in Table 6, with the exception that C1 is replaced by C26.

Table 932: Compounds of formula (I), wherein Cy1 and Cy2 and R1 to R4 are as shown in Table 7, with the exception that C1 is replaced by C26.

Table 933: Compounds of formula (I), wherein Cy1 and Cy2 and R1 to R4 are as shown in Table 8, with the exception that C1 is replaced by C26.

Table 934: Compounds of formula (I), wherein Cy1 and Cy2 and R1 to R4 are as shown in Table 9, with the exception that C1 is replaced by C26.

Table 935: Compounds of formula (I), wherein Cy1 and Cy2 and R1 to R4 are as shown in Table 10, with the exception that C1 is replaced by C26.

Table 936: Compounds of formula (I), wherein Cy1 and Cy2 and R1 to R4 are as shown in Table 11, with the exception that C1 is replaced by C26.

Table 937: Compounds of formula (I), wherein Cy1 and Cy2 and R1 to R4 are as shown in Table 12, with the exception that C1 is replaced by C26.

Table 938: Compounds of formula (I), wherein Cy1 and Cy2 and R1 to R4 are as shown in Table 13, with the exception that C1 is replaced by C26.

Table 939: Compounds of formula (I), wherein Cy1 and Cy2 and R1 to R4 are as shown in Table 14, with the exception that C1 is replaced by C26.

Table 940: Compounds of formula (I), wherein Cy1 and Cy2 and R1 to R4 are as shown in Table 15, with the exception that C1 is replaced by C26.

Table 941: Compounds of formula (I), wherein Cy1 and Cy2 and R1 to R4 are as shown in Table 16, with the exception that C1 is replaced by C26.

Table 942: Compounds of formula (I), wherein Cy1 and Cy2 and R1 to R4 are as shown in Table 17, with the exception that C1 is replaced by C26.

Table 943: Compounds of formula (I), wherein Cy1 and Cy2 and R1 to R4 are as shown in Table 18, with the exception that C1 is replaced by C26.

Table 944: Compounds of formula (I), wherein Cy1 and Cy2 and R1 to R4 are as shown in Table 19, with the exception that C1 is replaced by C26.

Table 945: Compounds of formula (I), wherein Cy1 and Cy2 and R1 to R4 are as shown in Table 20, with the exception that C1 is replaced by C26.

Table 946: Compounds of formula (I), wherein Cy1 and Cy2 and R1 to R4 are as shown in Table 21, with the exception that C1 is replaced by C26.

Table 947: Compounds of formula (I), wherein Cy1 and Cy2 and R1 to R4 are as shown in Table 22, with the exception that C1 is replaced by C26.

Table 948: Compounds of formula (I), wherein Cy1 and Cy2 and R1 to R4 are as shown in Table 23, with the exception that C1 is replaced by C26.

Table 949: Compounds of formula (I), wherein Cy1 and Cy2 and R1 to R4 are as shown in Table 24, with the exception that C1 is replaced by C26.

Table 950: Compounds of formula (I), wherein Cy1 and Cy2 and R1 to R4 are as shown in Table 25, with the exception that C1 is replaced by C26.

Table 951: Compounds of formula (I), wherein Cy1 and Cy2 and R1 to R4 are as shown in Table 26, with the exception that C1 is replaced by C26.

Table 952: Compounds of formula (I), wherein Cy1 and Cy2 and R1 to R4 are as shown in Table 27, with the exception that C1 is replaced by C26.

Table 953: Compounds of formula (I), wherein Cy1 and Cy2 and R1 to R4 are as shown in Table 28, with the exception that C1 is replaced by C26.

Table 954: Compounds of formula (I), wherein Cy1 and Cy2 and R1 to R4 are as shown in Table 29, with the exception that C1 is replaced by C26.

Table 955: Compounds of formula (I), wherein Cy1 and Cy2 and R1 to R4 are as shown in Table 30, with the exception that C1 is replaced by C26.

Table 956: Compounds of formula (I), wherein Cy1 and Cy2 and R1 to R4 are as shown in Table 31, with the exception that C1 is replaced by C26.

Table 957: Compounds of formula (I), wherein Cy1 and Cy2 and R1 to R4 are as shown in Table 32, with the exception that C1 is replaced by C26.

Table 958: Compounds of formula (I), wherein Cy1 and Cy2 and R1 to R4 are as shown in Table 33, with the exception that C1 is replaced by C26.

Table 959: Compounds of formula (I), wherein Cy1 and Cy2 and R1 to R4 are as shown in Table 34, with the exception that C1 is replaced by C26.

Table 960: Compounds of formula (I), wherein Cy1 and Cy2 and R1 to R4 are as shown in Table 35, with the exception that C1 is replaced by C26.

Table 961: Compounds of formula (I), wherein Cy1 and Cy2 and R1 to R4 are as shown in Table 36, with the exception that C1 is replaced by C26.

Table 962: Compounds of formula (I), wherein Cy1 and Cy2 and R1 to R4 are as shown in Table 37, with the exception that C1 is replaced by C26.

Table 963: Compounds of formula (I), wherein Cy1 and Cy2 and R1 to R4 are as shown in Table 38, with the exception that C1 is replaced by C26.

Table 964: Compounds of formula (I), wherein Cy1 and Cy2 and R1 to R4 are as shown in Table 2, with the exception that C1 is replaced by C27.

Table 965: Compounds of formula (I), wherein Cy1 and Cy2 and R1 to R4 are as shown in Table 3, with the exception that C1 is replaced by C27.

Table 966: Compounds of formula (I), wherein Cy1 and Cy2 and R1 to R4 are as shown in Table 4, with the exception that C1 is replaced by C27.

Table 967: Compounds of formula (I), wherein Cy1 and Cy2 and R1 to R4 are as shown in Table 5, with the exception that C1 is replaced by C27.

Table 968: Compounds of formula (I), wherein Cy1 and Cy2 and R1 to R4 are as shown in Table 6, with the exception that C1 is replaced by C27.

Table 969: Compounds of formula (I), wherein Cy1 and Cy2 and R1 to R4 are as shown in Table 7, with the exception that C1 is replaced by C27.

Table 970: Compounds of formula (I), wherein Cy1 and Cy2 and R1 to R4 are as shown in Table 8, with the exception that C1 is replaced by C27.

Table 971: Compounds of formula (I), wherein Cy1 and Cy2 and R1 to R4 are as shown in Table 9, with the exception that C1 is replaced by C27.

Table 972: Compounds of formula (I), wherein Cy1 and Cy2 and R1 to R4 are as shown in Table 10, with the exception that C1 is replaced by C27.

Table 973: Compounds of formula (I), wherein Cy1 and Cy2 and R1 to R4 are as shown in Table 11, with the exception that C1 is replaced by C27.

Table 974: Compounds of formula (I), wherein Cy1 and Cy2 and R1 to R4 are as shown in Table 12, with the exception that C1 is replaced by C27.

Table 975: Compounds of formula (I), wherein Cy1 and Cy2 and R1 to R4 are as shown in Table 13, with the exception that C1 is replaced by C27.

Table 976: Compounds of formula (I), wherein Cy1 and Cy2 and R1 to R4 are as shown in Table 14, with the exception that C1 is replaced by C27.

Table 977: Compounds of formula (I), wherein Cy1 and Cy2 and R1 to R4 are as shown in Table 15, with the exception that C1 is replaced by C27.

Table 978: Compounds of formula (I), wherein Cy1 and Cy2 and R1 to R4 are as shown in Table 16, with the exception that C1 is replaced by C27.

Table 979: Compounds of formula (I), wherein Cy1 and Cy2 and R1 to R4 are as shown in Table 17, with the exception that C1 is replaced by C27.

Table 980: Compounds of formula (I), wherein Cy1 and Cy2 and R1 to R4 are as shown in Table 18, with the exception that C1 is replaced by C27.

Table 981: Compounds of formula (I), wherein Cy1 and Cy2 and R1 to R4 are as shown in Table 19, with the exception that C1 is replaced by C27.

Table 982: Compounds of formula (I), wherein Cy1 and Cy2 and R1 to R4 are as shown in Table 20, with the exception that C1 is replaced by C27.

Table 983: Compounds of formula (I), wherein Cy1 and Cy2 and R1 to R4 are as shown in Table 21, with the exception that C1 is replaced by C27.

Table 984: Compounds of formula (I), wherein Cy1 and Cy2 and R1 to R4 are as shown in Table 22, with the exception that C1 is replaced by C27.

Table 985: Compounds of formula (I), wherein Cy1 and Cy2 and R1 to R4 are as shown in Table 23, with the exception that C1 is replaced by C27.

Table 986: Compounds of formula (I), wherein Cy1 and Cy2 and R1 to R4 are as shown in Table 24, with the exception that C1 is replaced by C27.

Table 987: Compounds of formula (I), wherein Cy1 and Cy2 and R1 to R4 are as shown in Table 25, with the exception that C1 is replaced by C27.

Table 988: Compounds of formula (I), wherein Cy1 and Cy2 and R1 to R4 are as shown in Table 26, with the exception that C1 is replaced by C27.

Table 989: Compounds of formula (I), wherein Cy1 and Cy2 and R1 to R4 are as shown in Table 27, with the exception that C1 is replaced by C27.

Table 990: Compounds of formula (I), wherein Cy1 and Cy2 and R1 to R4 are as shown in Table 28, with the exception that C1 is replaced by C27.

Table 991: Compounds of formula (I), wherein Cy1 and Cy2 and R1 to R4 are as shown in Table 29, with the exception that C1 is replaced by C27.

Table 992: Compounds of formula (I), wherein Cy1 and Cy2 and R1 to R4 are as shown in Table 30, with the exception that C1 is replaced by C27.

Table 993: Compounds of formula (I), wherein Cy1 and Cy2 and R1 to R4 are as shown in Table 31, with the exception that C1 is replaced by C27.

Table 994: Compounds of formula (I), wherein Cy1 and Cy2 and R1 to R4 are as shown in Table 32, with the exception that C1 is replaced by C27.

Table 995: Compounds of formula (I), wherein Cy1 and Cy2 and R1 to R4 are as shown in Table 33, with the exception that C1 is replaced by C27.

Table 996: Compounds of formula (I), wherein Cy1 and Cy2 and R1 to R4 are as shown in Table 34, with the exception that C1 is replaced by C27.

Table 997: Compounds of formula (I), wherein Cy1 and Cy2 and R1 to R4 are as shown in Table 35, with the exception that C1 is replaced by C27.

Table 998: Compounds of formula (I), wherein Cy1 and Cy2 and R1 to R4 are as shown in Table 36, with the exception that C1 is replaced by C27.

Table 999: Compounds of formula (I), wherein Cy1 and Cy2 and R1 to R4 are as shown in Table 37, with the exception that C1 is replaced by C27.

Table 1000: Compounds of formula (I), wherein Cy1 and Cy2 and R1 to R4 are as shown in Table 38, with the exception that C1 is replaced by C27.

Table 1001: Compounds of formula (I), wherein Cy1 and Cy2 and R1 to R4 are as shown in Table 2, with the exception that C1 is replaced by C28.

Table 1002: Compounds of formula (I), wherein Cy1 and Cy2 and R1 to R4 are as shown in Table 3, with the exception that C1 is replaced by C28.

Table 1003: Compounds of formula (I), wherein Cy1 and Cy2 and R1 to R4 are as shown in Table 4, with the exception that C1 is replaced by C28.

Table 1004: Compounds of formula (I), wherein Cy1 and Cy2 and R1 to R4 are as shown in Table 5, with the exception that C1 is replaced by C28.

Table 1005: Compounds of formula (I), wherein Cy1 and Cy2 and R1 to R4 are as shown in Table 6, with the exception that C1 is replaced by C28.

Table 1006: Compounds of formula (I), wherein Cy1 and Cy2 and R1 to R4 are as shown in Table 7, with the exception that C1 is replaced by C28.

Table 1007: Compounds of formula (I), wherein Cy1 and Cy2 and R1 to R4 are as shown in Table 8, with the exception that C1 is replaced by C28.

Table 1008: Compounds of formula (I), wherein Cy1 and Cy2 and R1 to R4 are as shown in Table 9, with the exception that C1 is replaced by C28.

Table 1009: Compounds of formula (I), wherein Cy1 and Cy2 and R1 to R4 are as shown in Table 10, with the exception that C1 is replaced by C28.

Table 1010: Compounds of formula (I), wherein Cy1 and Cy2 and R1 to R4 are as shown in Table 11, with the exception that C1 is replaced by C28.

Table 1011: Compounds of formula (I), wherein Cy1 and Cy2 and R1 to R4 are as shown in Table 12, with the exception that C1 is replaced by C28.

Table 1012: Compounds of formula (I), wherein Cy1 and Cy2 and R1 to R4 are as shown in Table 13, with the exception that C1 is replaced by C28.

Table 1013: Compounds of formula (I), wherein Cy1 and Cy2 and R1 to R4 are as shown in Table 14, with the exception that C1 is replaced by C28.

Table 1014: Compounds of formula (I), wherein Cy1 and Cy2 and R1 to R4 are as shown in Table 15, with the exception that C1 is replaced by C28.

Table 1015: Compounds of formula (I), wherein Cy1 and Cy2 and R1 to R4 are as shown in Table 16, with the exception that C1 is replaced by C28.

Table 1016: Compounds of formula (I), wherein Cy1 and Cy2 and R1 to R4 are as shown in Table 17, with the exception that C1 is replaced by C28.

Table 1017: Compounds of formula (I), wherein Cy1 and Cy2 and R1 to R4 are as shown in Table 18, with the exception that C1 is replaced by C28.

Table 1018: Compounds of formula (I), wherein Cy1 and Cy2 and R1 to R4 are as shown in Table 19, with the exception that C1 is replaced by C28.

Table 1019: Compounds of formula (I), wherein Cy1 and Cy2 and R1 to R4 are as shown in Table 20, with the exception that C1 is replaced by C28.

Table 1020: Compounds of formula (I), wherein Cy1 and Cy2 and R1 to R4 are as shown in Table 21, with the exception that C1 is replaced by C28.

Table 1021: Compounds of formula (I), wherein Cy1 and Cy2 and R1 to R4 are as shown in Table 22, with the exception that C1 is replaced by C28.

Table 1022: Compounds of formula (I), wherein Cy1 and Cy2 and R1 to R4 are as shown in Table 23, with the exception that C1 is replaced by C28.

Table 1023: Compounds of formula (I), wherein Cy1 and Cy2 and R1 to R4 are as shown in Table 24, with the exception that C1 is replaced by C28.

Table 1024: Compounds of formula (I), wherein Cy1 and Cy2 and R1 to R4 are as shown in Table 25, with the exception that C1 is replaced by C28.

Table 1025: Compounds of formula (I), wherein Cy1 and Cy2 and R1 to R4 are as shown in Table 26, with the exception that C1 is replaced by C28.

Table 1026: Compounds of formula (I), wherein Cy1 and Cy2 and R1 to R4 are as shown in Table 27, with the exception that C1 is replaced by C28.

Table 1027: Compounds of formula (I), wherein Cy1 and Cy2 and R1 to R4 are as shown in Table 28, with the exception that C1 is replaced by C28.

Table 1028: Compounds of formula (I), wherein Cy1 and Cy2 and R1 to R4 are as shown in Table 29, with the exception that C1 is replaced by C28.

Table 1029: Compounds of formula (I), wherein Cy1 and Cy2 and R1 to R4 are as shown in Table 30, with the exception that C1 is replaced by C28.

Table 1030: Compounds of formula (I), wherein Cy1 and Cy2 and R1 to R4 are as shown in Table 31, with the exception that C1 is replaced by C28.

Table 1031: Compounds of formula (I), wherein Cy1 and Cy2 and R1 to R4 are as shown in Table 32, with the exception that C1 is replaced by C28.

Table 1032: Compounds of formula (I), wherein Cy1 and Cy2 and R1 to R4 are as shown in Table 33, with the exception that C1 is replaced by C28.

Table 1033: Compounds of formula (I), wherein Cy1 and Cy2 and R1 to R4 are as shown in Table 34, with the exception that C1 is replaced by C28.

Table 1034: Compounds of formula (I), wherein Cy1 and Cy2 and R1 to R4 are as shown in Table 35, with the exception that C1 is replaced by C28.

Table 1035: Compounds of formula (I), wherein Cy1 and Cy2 and R1 to R4 are as shown in Table 36, with the exception that C1 is replaced by C28.

Table 1036: Compounds of formula (I), wherein Cy1 and Cy2 and R1 to R4 are as shown in Table 37, with the exception that C1 is replaced by C28.

Table 1037: Compounds of formula (I), wherein Cy1 and Cy2 and R1 to R4 are as shown in Table 38, with the exception that C1 is replaced by C28.

Surprisingly, it has been found that substitution of the alkyl groups $R^1$, $R^2$, $R^3$ and $R^4$, which are 2-methylpropyl groups in the parent cyclic depsipeptide PF1022A and also in emodepside, with certain groups described herein improve the metabolic stability of the compounds and also improves the activity of the compounds against endoparasites and in some embodiments against ectoparasites. In some cases, the compounds of the invention may exhibit lower toxicity in mammals. Furthermore, it has been surprisingly found that substitution of the compounds of formula (I) with certain $Cy^1$ and/or $Cy^2$ groups described herein also significantly improves the metabolic stability of the compounds of the invention compared with PF1022A and emodepside. Thus, the compounds of the invention where the groups $Cy^1$ and/or $Cy^2$ and at least one of $R^1$, $R^2$, $R^3$ and $R^4$ are substituted with certain substituents described herein have been found to have significantly improved metabolic stability and equal or significantly improved efficacy against endoparasites including, but not limited to, *Dirofilaria immitis* microfilaria and/or L3 and L4 larvae and/or *Haemonchus contortus* larvae. The compounds of the invention are also active against hookworms, whipworms and roundworms of the digestive tract of animals. In some embodiments, the compounds of formula (I) with certain substituents will also exhibit improved activity against ectoparasites.

In some embodiments, certain compounds of the invention where at least one of $R^1$ to $R^4$ is an optionally substituted 3- to 6-membered carbocyclic or 3- to 6-membered heterocyclic ring or $C_1$-$C_3$ alkyl or $C_1$-$C_3$ haloalkyl, wherein the $C_1$-$C_3$ alkyl or $C_1$-$C_3$ haloalkyl is substituted by an optionally substituted 3- to 8-membered carbocyclic or 3- to 8-membered heterocyclic ring, or may exhibit improved toxicity profiles compared with compounds having acyclic alkyl groups at these positions. In other embodiments of the invention wherein one or more of $R^1$ to $R^4$ together with the corresponding $R^{1'}$ to $R^{4'}$ form a 2-6-membered carbon chain to form a ring the cyclic depsipeptides may exhibit improved toxicity profiles compared with compounds having acyclic alkyl groups at these positions.

It has also been surprisingly found that the spatial order of substitution of $R^1$ to $R^4$ also has a significant impact on the activity of the compounds. For example it has been found that when the naturally-occurring 2-methylpropyl groups at the positions identified as $R^1$ and $R^3$ in the compound of formula (I) are modified the activity of the compounds is significantly improved over compounds where the 2-methylpropyl groups at the positions $R^2$ and $R^4$ are substituted.

The influence of certain substituents on the naturally-occurring 2-methylpropyl group of the N-methyl leucine residues of PF1022A, corresponding to one or more of $R^1$, $R^2$, $R^3$ and $R^4$ in formula (I), is also surprising. Thus, substitution of one or more of the 2-methylpropyl at $R^1$, $R^2$, $R^3$ and $R^4$ with fluoro has been found to significantly improve the activity of the compounds of formula (I) on the motility of *Haemonchus contortus* larvae and *Dirofilaria immitis* microfilaria in vitro compared with unsubstituted compounds (e.g. PF1022A or analogs where $Cy^1$ and/or $Cy^2$ are substituted phenyl but $R^1$ to $R^4$ are 2-methylpropyl) or compounds in which the naturally-occurring 2-methylpropyl groups are substituted with a methyl group. In addition, the substitution of the 2-methylpropyl groups at $R^1$ and $R^3$ groups with fluoro has been found to result in significantly improved activity against *H. contortus* and *D. immitis* microfilaria larvae compared with compounds substituted with fluoro at $R^2$ and $R^4$ or other combinations. In addition, in some embodiments the inclusion in variables $R^1$ to $R^4$ of at least one optionally substituted 3- to 6-membered carbocyclic or 3- to 6-membered heterocyclic ring or a $C_1$-$C_3$ alkyl or $C_1$-$C_3$ haloalkyl, wherein the $C_1$-$C_3$ alkyl or $C_1$-$C_3$ haloalkyl is substituted by an optionally substituted 3- to 8-membered carbocyclic or 3- to 8-membered heterocyclic ring or wherein one or more of $R^1$ to $R^4$ together with the corresponding $R^{1'}$ to $R^{4'}$ form a 2-6-membered carbon chain to form a ring may improve the safety profile and/or the metabolic stability of the compounds thereby increasing the therapeutic window. It is apparent that the type of substitution in groups $R^1$, $R^2$, $R^3$ and $R^4$ as well as which of $R^1$, $R^2$, $R^3$ and $R^4$ are substituted have a significant influence on the activity, stability and safety of the compounds.

Scherkenbeck et al. (*Bioorg. Med. Chem. Lett.* 8 (1998), 1035-1040) described that the modification of the N-methyl leucine residues for a series of related N-methylated amino acids such as isoleucine, valine, norvaline, alanine and phenylalanine resulted in nearly complete loss of anthelmintic activity following oral administration in sheep. Furthermore, the publication reported that modification of half of the N-methyl leucine residues with either methyl or n-propyl side chains also surprisingly resulted in significantly reduced activity. It was concluded that the (L)-N-methyl leucine residues in the cyclic depsipeptide PF1022A were a critical part of the pharmacophore and essential for in vivo activity.

Thus, it is surprising and unexpected that modification of the groups $R^1$ to $R^4$ in the compound of formula (I), which correspond to the N-methyl leucine residues in PF1022A or emodepside, result in enhanced metabolic stability and/or lower toxicity and/or improved activity compared with the compounds containing unmodified N-methyl leucine residues. It is also very surprising and unexpected that the compounds of formula (I) in which the alkyl groups represented by $R^1$ and $R^3$ are substituted with certain groups described herein exhibit significantly improved efficacy against endoparasites compared to compounds that are substituted with the same groups at $R^2$ and $R^4$ or in other combinations. In addition, the inclusion of certain substituents described herein in groups $R^1$ to $R^4$ and $Cy^1$ and $Cy^2$ result in improved metabolic stability and lower toxicity compared with unsubstituted compounds. It follows that a combination of the substitution at $Cy^1$ and $Cy^2$ and $R^1$ to $R^4$ in the compounds of formula (I) results in significantly improved activity against endoparasites and improved metabolic stability.

Furthermore, the substitution of the naturally-occurring 2-methylpropyl groups with certain substituents, including fluoro and methyl, has been found to improve the in vitro permeability and the bioavailability of the compounds (see Method C in Examples). For example, compounds of formula (I) wherein $Cy^1$ and $Cy^2$ are either both unsubstituted phenyl or p-fluorophenyl groups and $R^2$ and $R^4$, respectively, are fluoro were found to have significantly improved permeability compared with the compounds where $R^2$ and $R^4$ are unsubstituted 2-methylpropyl. Further, compounds where $Cy^1$ and $Cy^2$ are p-morpholino phenyl and $R^2$ and $R^4$ are methyl were found to have significantly improved permeability compared with emodepside ($R^2$ and $R^4$=H).

The characteristics described above for the compounds of formula (I) are expected to result in compounds with superior antiparasitic efficacy against endoparasites and ectoparasites in or on animals.

Stereoisomers and Polymorphic Forms

It will be appreciated by those of skill in the art that the compounds of the invention may exist and be isolated as optically active and racemic forms. Compounds having one or more chiral centers, including that at a sulfur atom, may be present as single enantiomers or diastereomers or as mixtures of enantiomers and/or diastereomers. For example, it is well known in the art that sulfoxide compounds may be optically active and may exist as single enantiomers or racemic mixtures. In addition, compounds of the invention may include one or more chiral centers, which results in a theoretical number of optically active isomers. Where compounds of the invention include n chiral centers, the compounds may comprise up to $2^n$ optical isomers. The present invention encompasses the specific enantiomers or diastereomers of each compound as well as mixtures of different enantiomers and/or diastereomers of the compounds of the invention that possess the useful properties described herein. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compounds of present invention may also be present in different solid forms such as different crystalline forms or in the form of an amorphous solid. The present invention encompasses different crystalline forms as well as amorphous forms of the inventive compounds.

In addition, the compounds of the invention may exist as hydrates or solvates, in which a certain stoichiometric amount of water or a solvent is associated with the molecule in the crystalline form. The hydrates and solvates of the compounds of formula (I) are also the subject of the invention.

Salts

In addition to the neutral compounds of formula (I), salt forms of the compounds are also active against parasites. The terms "veterinarily acceptable salt" and "pharmaceutically acceptable salt" are used throughout the specification to describe any salts of the compounds that are acceptable for administration for veterinary applications, and which provides the active compound upon administration.

In cases where compounds are sufficiently basic or acidic to form stable non-toxic acid or base salts, the compounds may be in the form of a veterinarily, pharmaceutically or agriculturally acceptable salt. Veterinarily acceptable salts include those derived from veterinarily or agriculturally acceptable inorganic or organic bases and acids. Suitable salts include those comprising alkali metals such as lithium, sodium or potassium, alkaline earth metals such as calcium, magnesium and barium. Salts comprising transition metals including, but not limited to, manganese, copper, zinc and iron are also suitable. In addition, salts comprising ammonium cations ($NH_4^+$) as well as substituted ammonium cations, in which one or more of the hydrogen atoms are replaced by alkyl or aryl groups are encompassed by the invention.

Salts derived from inorganic acids including, but not limited to, hydrohalide acids (HCl, HBr, HF, HI), sulfuric acid, nitric acid, phosphoric acid, and the like are particularly suitable. Suitable inorganic salts also include, but not limited to, bicarbonate, and carbonate salts. In some embodiments, examples of veterinarily and agriculturally acceptable salts are organic acid addition salts formed with organic acids including, but not limited to, maleate, dimaleate, fumarate, tosylate, methanesulfonate, acetate, citrate, malonate, tartarate, succinate, benzoate, ascorbate, α-ketoglutarate, and α-glycerophosphate. Of course, other acceptable organic acids may be used.

Alkali metal (for example, sodium, potassium or lithium) or alkaline earth metal (for example calcium) salts of the compounds can also be made by reacting a sufficiently acidic residue on the compounds with a hydroxide of the alkali metal or alkaline earth metal.

Veterinarily acceptable salts may be obtained using standard procedures well known in the art, for example by reacting a sufficiently basic compound such as an amine with a suitably acid functional group present in the compound, or by reacting a suitable acid with a suitably basic functional group on the compound of the invention.

Processes for the Preparation of Compounds of Formula (I):

The compounds of formula (I) may be prepared by processes adapted from those described in U.S. Pat. Nos. 5,514,773; 5,747,448; 5,874,530; 5,856,436; 6,033,879; 5,763,221; 6,329,338, 5,116,815; 6,468,966; 6,369,028; 5,777,075; and 5,646,244, all which are hereby incorporated by reference in their entirety. In addition, various synthetic methods for cyclic depsipeptides have been reported in the chemical literature (see Luttenberg et al., *Tetrahedron* 68 (2012), 2068-2073; Byung H. Lee, *Tetrahedron Letters*, 1997, 38 (5), 757-760; Scherkenbeck et al., *Letters in Organic Chemistry*, 2016, 13, 441-445; *Eur. J. Org. Chem.*, 2012, 1546-1553; *Biosci. Biotech. Biochem.*, 1994, 58(6), 1193-1194; and Scherkenbeck et al., *Tetrahedron*, 1995, 51(31), 8459-8470) It will be understood by those skilled in the art that certain functional groups in the compounds and intermediates may be unprotected or protected by suitable protecting groups, as taught by Greene et al. *Protective Groups in Organic Synthesis*, John Wiley and Sons, Inc., 4$^{th}$ edition 2006. Further, it will be apparent to those skilled in the art that the compounds and intermediates may be isolated by standard aqueous work-up conditions and optionally purified. For example, the compounds or intermediates may be purified by chromatographic methods or crystallized to yield the desired product in suitable purity.

In one embodiment, the compounds of formula (I) where $R^1$, $R^{1'}$, $R^2$, $R^{2'}$, $R^3$, $R^{3'}$, $R^4$, $R^{4'}$, $R^a$, $R^b$, $Cy^1$ and $Cy^2$ are as defined above, R', R'', R''' and R'''' are methyl are prepared according to the general process described in Scheme 1 below:

unprotected amine with a second fragment having a free carboxylic acid group (see for example, Peptide Synthesis by Miklos Bodanszky and Miguel Ondetti, Interscience Publishers, 1966; Amino Acid and Peptide Synthesis, $2^{nd}$ Ed. By John Jones, Oxford University Press, 2002). The

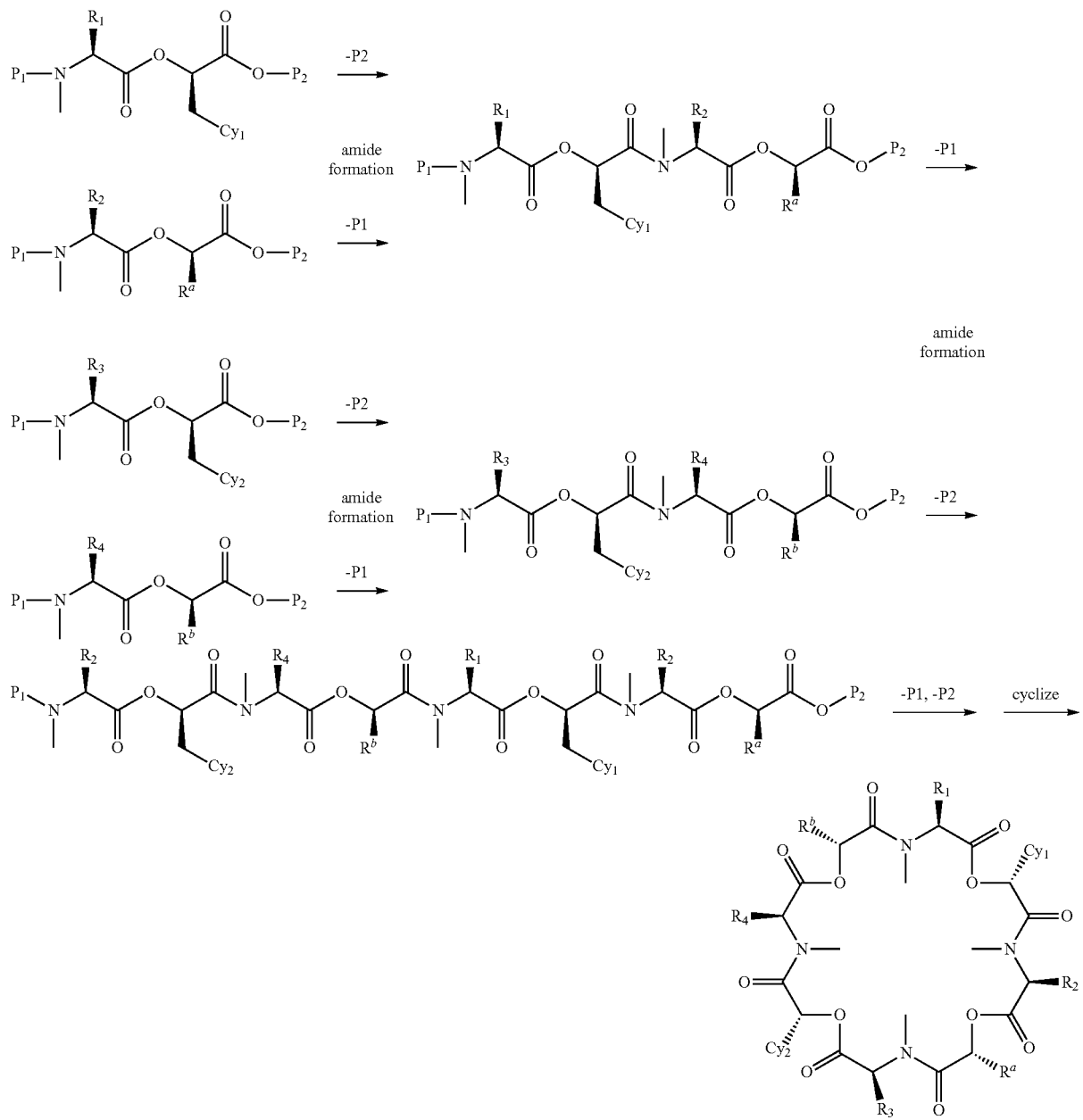

Scheme 1

In scheme 1, $P_1$ and $P_2$ are amine and carboxylic acid protecting groups, respectively, commonly used in the art (see, for example, Greene et al. *Protective Groups in Organic Synthesis*, John Wiley and Sons, Inc., 4th edition 2006) and $R^1$, $R^2$, $R^3$, $R^4$, $R^a$, $R^b$, $Cy^1$ and $Cy^2$ are as defined above.

Furthermore, the coupling of amines with carboxylic acids to form amides is well known in the art and standard reagents may be used in the coupling of a fragment with an compounds may be prepared by solution phase synthesis or using solid-phase synthesis with polymeric supports. For example, the formation of amide bonds may be mediated by activating reagents such as carbodiimide reagents (e.g. dicyclohexyldiimide, diisopropyldiimide and (N-(3-Dimethylaminopropyl)-N'-ethylcarbodiimide.HCl) in combination with additives such as N-hydroxybenzotriazole (HOBt) and the like. In addition, the formation of amide bonds in the synthesis may be accomplished by using phosphonium reagents such as BOP (Benzotriazol-1-yloxy-tris (dimethylamino)-phosphonium hexafluorophosphate), PyBOP (Benzotriazol-1-yloxy-tripyrrolidino-phosphonium hexafluorophosphate), PyBrOP (Bromo-tripyrrolidino-phosphonium hexa-fluorophosphate) and the like. Other useful reagents for forming the amide bonds of the compounds of the invention are the so called aminium/uronium-imonium reagents such as TBTU/HBTU (2-(1H-Benzotriazol-1-yl)-N,N,N',N'-tetramethylaminium tetrafluoroborate/hexafluorophosphate), HATU (2-(7-Aza-1H-benzotriazol-1-yl)-N,N,N',N'-tetramethylaminium hexafluorophosphate) and the like. These reagents and the methods employing these reagents for the preparation of amide bonds are well known in the art.

Veterinary Compositions:

The compounds of formula (I) and compositions comprising the compounds are useful for the prevention and treatment of parasitic infestations/infections in animals. The compositions of the invention comprise an effective amount of at least one cyclic depsipeptide compound of formula (I), or a veterinarily acceptable salt thereof, in combination with a veterinarily acceptable carrier or diluent and optionally other non-active excipients. The compositions may be in a variety of solid and liquid forms which are suitable for various forms of application or administration to an animal. For example, the veterinary compositions comprising the inventive compounds may be in formulations suitable for oral administration, injectable administration, including subcutaneous and parenteral administration, and topical administration (e.g. spot-on or pour-on), dermal or subdermal administration. The formulations are intended to be administered to an animal including, but not limited to, mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds. The use of the compounds of formula (I) to protect companion animals such as dogs and cats from endoparasites is particularly useful.

The compositions of the invention may be in a form suitable for oral use (see, e.g., U.S. Pat. No. 4,564,631, which is hereby incorporated by reference in its entirety), dietary supplements, troches, lozenges, chewables, tablets, hard or soft capsules, bolus, emulsions, aqueous or oily suspensions, aqueous or oily solutions, oral drench formulations, dispersible powders or granules, premixes, syrups or elixirs, enteric formulations or pastes. Compositions intended for oral use may be prepared according to any method known in the art for the manufacture of pharmaceutical compositions and such compositions may contain one or more sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 (all incorporated herein by reference in their entirety) to form osmotic therapeutic tablets for controlled release).

Oral formulations include hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example peanut oil, liquid paraffin, or olive oil.

In one embodiment, the compounds of formula (I) may be administered in chewable tablet compositions or soft chewable compositions such as those described in US 2013/0203692 A1, US 2010/0087492, US 2006/0222684, US 2004/0151759, U.S. Pat. No. 7,955,632, all incorporated herein by reference. The veterinary compositions may be in the form of a soft chewable formulation ("soft chew") which is palatable and acceptable to the animal. In addition to the active ingredient(s), the soft chews of the invention may include one or more of the following components: a solvent or mixture of solvents, one or more fillers, one or more binders, one or more surfactants, one or more humectants, one or more lubricants, one or more disintegrants, one or more colorants, one or more antimicrobial agents, one or more antioxidants, one or more pH modifiers and one or more flavoring agents.

Solvents that may be used in the compositions of the invention include, but are not limited to, various grades of liquid polyethylene glycol (PEG) including PEG 200, PEG 300, PEG 400 and PEG 540; propylene carbonate; alcohols including ethanol, isopropanol and benzyl alcohol; propylene glycol; triglycerides including, but not limited to caprylic/capric triglyceride, caprylic/capric/linoleic triglyceride (e.g. MIGLYOL® 810 and 812, caprylic/capric/succinic triglyceride, propylene glycol dicaprylate/dicaprate, and the like; water, sorbitol solution, glycerol caprylate/caprate and polyglycolized glycerides (GELUCIRE®), or a combination thereof.

Various fillers known in the art may be used in the soft chewable compositions of the invention. Fillers include, but are not limited to, corn starch, pre-gelatinized corn starch, soy protein fines, corn cob, and corn gluten meal, and the like. In some embodiments, a combination of two or more fillers may be used in the compositions.

Binders that may be used in the compositions of the invention include, but are not limited to, polyvinylpyrrolidone (e.g. Povidone), cross-linked polyvinylpyrrolidone (Crospovidone), polyethylene glycols of various grades including PEG 3350, PEG 4000, PEG 6000, PEG 8000 and even PEG 20,000, and the like; co-polymers of vinylpyrrolidone and vinyl acetate (e.g. Copovidone) such as the product sold by BASF by the tradename Kollidon® VA 64 and the like; starch such as potato starch, tapioca starch or corn starch; molasses, corn syrup, honey, maple syrup and sugars of various types; or a combination of two or more binders.

Humectants that may be used in the compositions include, but are not limited to, glycerol (also referred to herein as glycerin), propylene glycol, cetyl alcohol and glycerol monostearate, and the like. Polyethylene glycols of various grades may also be used as humectants.

Surfactants may be present in the composition to improve their solubility and absorption after ingestion. Surfactants are typically present in a concentration of about 1 to 10%

(w/w), more typically about 1 to about 5% (w/w). Examples of surfactants that may be used in the compositions include, but are not limited to, glyceryl monooleate, polyoxyethylene sorbitan fatty acid esters, sorbitan esters including sorbitan monooleate (Span® 20), polyvinyl alcohol, polysorbates including polysorbate 20 and polysorbate 80, d-α-tocopheryl polyethylene glycol 1000 succinate (TPGS), sodium lauryl sulfate, co-polymers of ethylene oxide and propylene oxide (e.g. poloxamers such as LUTROL® F87 and the like), polyethylene glycol castor oil derivatives including polyoxyl 35 castor oil (Cremophor® EL), polyoxyl 40 hydrogenated castor oil (Cremophor® RH 40), polyoxyl 60 hydrogenated castor oil (Cremophor® RH60); propylene glycol monolaurate (LAUROGLYCOL®); glyceride esters including glycerol caprylate/caprate (CAPMUL® MCM), polyglycolized glycerides (GELUCIRE®), PEG 300 caprylic/capric glycerides (Softigen® 767), PEG 400 caprylic/capric glycerides (Labrasol®), PEG 300 oleic glycerides (Labrafil® M-1944CS), PEG 300 linoleic glycerides (Labrafil® M-2125CS); polyethylene glycol stearates and polyethylene glycol hydroxy stearates including polyoxyl 8 stearate (PEG 400 monostearate), polyoxyl 40 stearate (PEG 1750 monostearate), and the like.

The inventive formulations may contain other inert ingredients such as antioxidants, preservatives, or pH stabilizers. These compounds are well known in the formulation art. Antioxidants may be added to the compositions of the invention to inhibit degradation of the active agents. Suitable antioxidants include, but are not limited to, alpha tocopherol, ascorbic acid, ascorbyl palmitate, fumaric acid, malic acid, sodium ascorbate, sodium metabisulfate, n-propyl gallate, BHA (butylated hydroxy anisole), BHT (butylated hydroxy toluene) monothioglycerol and the like.

The compositions of the invention may also include one or more lubricants and/or processing aids. In some cases, the lubricant/processing aid may also behave as a solvent, and accordingly, there some of the components of the inventive compositions may have dual functions. Lubricants/processing aids include, but are not limited to polyethylene glycols of various molecular weight ranges including PEG 3350 (Dow Chemical) and PEG 4000, corn oil, mineral oil, hydrogenated vegetable oils (STEROTEX or LUBRITAB), peanut oil and/or castor oil.

Many flavoring agents may be used in the compositions of the invention to improve the palatability of the oral veterinary formulations. Preferred flavoring agents are those that are not derived from animal sources. In various embodiments, flavoring components derived from fruit, meat (including, but not limited to pork, beef, chicken, fish, poultry, and the like), vegetable, cheese, bacon, cheese-bacon and/or artificial flavorings may be used. A flavoring component is typically chosen based upon consideration related to the organism that will be ingesting the soft chew. For example, a horse may prefer an apple flavoring component, while a dog may prefer a meat flavoring component. Although flavoring components derived from non-animal sources are preferred, in some embodiments, natural flavors containing beef or liver extracts, etc., may be used such as braised beef flavor artificial powdered beef flavor, roast beef flavor and corned beef flavor among others.

In another embodiment of the invention, the active composition may be administered via a drench, and may be administered either topically or orally. Drench formulations are those in which the liquid-containing compositions of the invention are administered to the mouth or throat of the animal, or poured onto the skin or coat of the animal.

The compositions of the invention may also be in the form of oil-in-water or water-in-oil emulsions. The oily phase maybe a vegetable oil, for example, olive oil or *arachis* oil, or a mineral oil, for example, liquid paraffin or mixtures of these. Suitable emulsifying agents include naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions may also contain sweetening agents, bittering agents, flavoring agents, and/or preservatives.

In one embodiment, the composition of the invention may be in the form of a microemulsion. Microemulsions are well suited as the liquid carrier vehicle. Microemulsions are quaternary systems comprising an aqueous phase, an oily phase, a surfactant and a co-surfactant. They are translucent and isotropic liquids.

Microemulsions are composed of stable dispersions of microdroplets of the aqueous phase in the oily phase or conversely of microdroplets of the oily phase in the aqueous phase. The size of these microdroplets may be less than 200 nm (1000 to 100,000 nm for emulsions). The interfacial film may be composed of an alternation of surface-active (SA) and co-surface-active (Co-SA) molecules which, by lowering the interfacial tension, allows the microemulsion to be formed spontaneously.

In one embodiment of the oily phase, the oily phase may be formed from mineral or vegetable oils, from unsaturated polyglycosylated glycerides or from triglycerides, or alternatively from mixtures of such compounds. In one embodiment of the oily phase, the oily phase may be comprised of triglycerides; in another embodiment of the oily phase, the triglycerides are medium-chain triglycerides, for example $C_8$-$C_{10}$ caprylic/capric triglyceride. In another embodiment of the oily phase may represent a % v/v range of about 2 to about 15%; about 7 to about 10%; and about 8 to about 9% v/v of the microemulsion.

The aqueous phase may include, for example water or glycol derivatives, such as propylene glycol, glycol ethers, polyethylene glycols or glycerol. In one embodiment, the glycol may be propylene glycol, diethylene glycol monoethyl ether, dipropylene glycol monoethyl ether or mixtures thereof. Generally, the aqueous phase will represent a proportion from about 1 to about 4% v/v in the microemulsion.

Surfactants for the microemulsion may include diethylene glycol monoethyl ether, dipropylene glycol monomethyl ether, polyglycolyzed $C_8$-$C_{10}$ glycerides or polyglyceryl-6 dioleate. In addition to these surfactants, the co-surfactants may include short-chain alcohols, such as ethanol and propanol.

Some compounds are common to the three components discussed above, i.e., aqueous phase, surfactant and co-surfactant. However, it is well within the skill level of the practitioner to use different compounds for each component of the same formulation. In one embodiment for the amount of surfactant/co-surfactant, the co-surfactant to surfactant ratio will be from about 1/7 to about 1/2. In another embodiment for the amount of co-surfactant, there will be from about 25 to about 75% v/v of surfactant and from about 10 to about 55% v/v of co-surfactant in the microemulsion.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an antioxidant such as ascorbic acid, or other known preservatives.

Aqueous suspensions may contain the active material in admixture with excipients suitable for the manufacture of aqueous suspensions. Such excipients include suspending agents, for example, sodium carboxymethylcellulose, methylcellulose, hydroxy-propylmethylcellulose, sodium alginate, polvinylpyrrolidone, gum tragacanth and gum acacia; dispersing or wetting agents include naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water may provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition may be in paste form. Examples of embodiments in a paste form include, but are not limited to, those described in U.S. Pat. Nos. 6,787,342 and 7,001,889 (each of which are incorporated herein by reference). In addition to the compounds of the invention, the paste may further contain fumed silica; a viscosity modifier; a carrier; optionally, an absorbent; and optionally, a colorant, stabilizer, surfactant, or preservative.

In one embodiment of the formulation, the formulation may be a paste containing the compounds of the invention, fumed silica, a viscosity modifier, an absorbent, a colorant; and a hydrophilic carrier which is triacetin, a monoglyceride, a diglyceride, or a triglyceride.

The paste may also include a viscosity modifier. Suitable viscosity modifiers include, but are not limited to, polyethylene glycols (PEG) including, but not limited to, PEG 200, PEG 300, PEG 400, PEG 600; monoethanolamine, triethanolamine, glycerol, propylene glycol, polyoxyethylene (20) sorbitan mono-oleate (polysorbate 80 or Tween 80), or poloxamers (e.g., Pluronic L 81); an absorbent such as magnesium carbonate, calcium carbonate, starch, and cellulose and its derivatives; and a colorant including, but not limited to, titanium dioxide iron oxide, or FD&C Blue #1 Aluminum Lake.

In some embodiments, the compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Co-solvents such as ethanol, propylene glycol, glycerol formal or polyethylene glycols may also be used. Preservatives, such as phenol or benzyl alcohol, may be used.

In addition, sterile, fixed oils may be conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal formulations may include, by way of non-limiting example, emulsions, creams, ointments, gels, pastes, powders, shampoos, pour-on formulations, ready-to-use formulations, spot-on solutions and suspensions, dips and sprays. Topical application of an inventive compound or of a composition including at least one inventive compound among active agent(s) therein, in the form of a spot-on, spray-on or pour-on composition, may allow for the inventive composition to be absorbed through the skin to achieve systemic levels, distributed through the sebaceous glands or on the surface of the skin achieving levels throughout the coat. When the compound is distributed through the sebaceous glands, they may act as a reservoir, whereby there may be a long-lasting effect (up to several months) effect. Spot-on formulations are typically applied in a localized region which refers to an area other than the entire animal. In one embodiment, the location may be between the shoulders. In another embodiment it may be a stripe, e.g. a stripe from head to tail of the animal.

Pour-on formulations are described in U.S. Pat. No. 6,010,710, also incorporated herein by reference. Pour-on formulations may be advantageously oily, and generally comprise a diluent or vehicle and also a solvent (e.g. an organic solvent) for the active ingredient if the latter is not soluble in the diluent.

Organic solvents that can be used in the invention include, but are not limited to, acetyltributyl citrate, fatty acid esters such as the dimethyl ester, diisobutyl adipate, acetone, acetonitrile, benzyl alcohol, ethyl alcohol, butyl diglycol, dimethylacetamide, dimethylformamide, dimethyl sulfoxide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), propylene carbonate, diethylene glycol monoethyl ether, ethylene glycol, triacetin, $C_1$-$C_{10}$ esters of carboxylic acids such as butyl or octyl acetate, and diethyl phthalate, or a mixture of at least two of these solvents.

The solvent will be used in proportion with the concentration of the active agent compound and its solubility in this solvent. It will be sought to have the lowest possible volume. The vehicle makes up the difference to 100%.

A vehicle or diluent for the formulations may include dimethyl sulfoxide (DMSO), glycol derivatives such as, for example, propylene glycol, glycol ethers, polyethylene glycols or glycerol. As vehicle or diluent, mention may also be made of plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$ to $C_{12}$) triglycerides.

In another embodiment of the invention, an emollient and/or spreading and/or film-forming agent may be added. In one embodiment, the emollient and/or spreading and/or film-forming agent may be:

(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulphates (e.g. sodium lauryl sulphate and sodium cetyl sulphate); sodium dodecylbenzenesulphonate, sodium dioctylsulphosuccinate; fatty acids (e.g. those derived from coconut oil), (c) cationic surfactants include water-soluble quaternary ammonium salts of formula $N^+R'R''R'''R''''$, $Y^-$ in which the radicals R are optionally hydroxylated hydrocarbon radicals and Y is an anion of a strong acid such as the halide, sulphate and sulphonate anions; cetyltrimethylammonium bromide is among the cationic surfactants which can be used, (d) amine salts of formula $N^+$ $HR'R''R'''$ in which the radicals R are optionally hydroxylated hydrocarbon radicals; octadecylamine hydrochloride is among the cationic surfactants which can be used, (e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine; or (g) a mixture of at least two of these agents.

In one embodiment of the amount of emollient, the emollient used may be in a proportion of from about 0.1 to 50% or 0.25 to 5%, by volume. In another embodiment, the emollient used may be in a proportion of from about 0.1% to about 30%, about 1% to about 30%, about 1% to about 20%, or about 5% to about 20% by volume.

In another embodiment of the invention, the composition may be in ready-to-use solution form as is described in U.S. Pat. No. 6,395,765, incorporated herein by reference. In addition to the compounds of the invention, the ready-to-use solution may contain a crystallization inhibitor and an organic solvent or a mixture of organic solvents. In some embodiments, water may be included with the organic solvent.

In various embodiments of the invention, the compositions may include a crystallization inhibitor in an amount of about 1 to about 50% (w/v) or about 5 to about 40% (w/v) based on the total weight of the formulation. In other embodiments, the amount of crystallization inhibitor in the inventive formulations may be about 1% to about 30%, about 5% to about 20%, about 1% to about 15%, or about 1% to about 10% (w/w). The type of crystallization inhibitor used in the inventive formulations is not limited as long as it functions to inhibit crystallization of the active or inactive agents from the formulation. For example, in certain embodiments of the invention, a solvent or co-solvent of the formulation may also function as a crystallization inhibitor if it sufficiently inhibits the formation of crystals from forming over time when the formulation is administered.

Crystallization inhibitors which are useful for the invention include, but are not limited to:

(a) polyvinylpyrrolidone, polyvinyl alcohols, copolymers of vinyl acetate and vinylpyrrolidone, polyethylene glycols, benzyl alcohol, dimethylformamide, dimethylacetamide, dimethylsulfoxide, 2-pyrrolidone, N-methylpyrrolidone, mannitol, glycerol, sorbitol or polyoxyethylenated esters of sorbitan; lecithin or sodium carboxymethylcellulose; or acrylic derivatives, such as acrylates or methacrylates or polymers or copolymers thereof, polyethyleneglycols (PEG) or polymers containing polyethyleneglycols, such as glycofurol and the like, and others;

(b) anionic surfactants, such as alkaline stearates (e.g. sodium, potassium or ammonium stearate); calcium stearate or triethanolamine stearate; sodium abietate; alkyl sulphates, which include but are not limited to sodium lauryl sulphate and sodium cetyl sulphate; sodium dodecylbenzenesulphonate or sodium dioctyl sulphosuccinate; or fatty acids (e.g. coconut oil);

(c) cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulphate and sulphonate anions; cetyltrimethylammonium bromide is one of the cationic surfactants which can be used;

(d) amine salts of formula $N^+HR'R''R'''$, in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine;

(g) a mixture of at least two of the compounds listed in (a)-(f) above; or (h) an organic solvent or mixture of solvents which inhibit the formation of crystals or amorphous solid after the formulation is administered.

In one embodiment of the crystallization inhibitor, a crystallization inhibitor pair will be used. Such pairs include, for example, the combination of a film-forming agent of polymeric type and of a surface-active agent. These agents will be selected from the compounds mentioned above as crystallization inhibitor.

In some embodiments, the organic solvent(s) may have a dielectric constant of between about 10 and about 35 or between about 20 and about 30. In other embodiments, the organic solvent may have a dielectric constant of between about 10 and about 40 or between about 20 and about 30. The content of this organic solvent or mixture of solvents in the overall composition is not limited and will be present in an amount sufficient to dissolve the desired components to a desired concentration. As discussed above, the organic solvent may also function as a crystallization inhibitor in the formulation.

In some embodiments, one or more of the organic solvent(s) may have a boiling point of below about 100° C., or below about 80° C. In other embodiments, the organic solvent(s) may have a boiling point of below about 300° C., below about 250° C., below about 230° C., below about 210° C. or below about 200° C.

In some embodiments where there is a mixture of solvents, i.e. a solvent and a co-solvent, the solvents may be present in the composition in a weight/weight (W/W) ratio of about 1/50 to about 1/1. Typically the solvents will be in a ratio of about 1/30 to about 1/1, about 1/20 to about 1/1, or about 1/15 to about 1/1 by weight. Preferably, the two solvents will be present in a weight/weight ratio of about 1/15 to about 1/2. In some embodiments, at least one of the solvents present may act as to improve solubility of the active agent or as a drying promoter. In particular embodiments, at least one of the solvents will be miscible with water.

The formulation may also comprise an antioxidizing agent intended to inhibit oxidation in air, this agent may be present in a proportion of about 0.005 to about 1% (w/v), about 0.01 to about 0.1%, or about 0.01 to about 0.05%.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of polysorbate, for example Polysorbate 80.

In another embodiment of the invention, the film-forming agent and the surface-active agent may be incorporated in similar or identical amounts within the limit of the total amounts of crystallization inhibitor mentioned elsewhere.

The crystallization inhibitor inhibits the formation of crystals on the coat, and improves the maintenance of the cosmetic appearance of the skin or fur; that is to say without a tendency towards sticking or towards a sticky appearance, despite the high concentration of active material. Substances other than those mentioned herein may be used as crystallization inhibitors in the present invention. In one embodiment, the effectiveness of the crystallization inhibitor may be demonstrated by a test according to which 0.3 mL of a solution comprising 10% (w/v) of the active agent in an appropriate solvent as defined above, and 10% (w/v) of the compound acting as a crystallization inhibitor are placed on a glass slide at 20° C. for 24 hours, after which fewer than 10 crystals, preferably 0 crystals, are seen with the naked eye on the glass slide.

In one embodiment of the antioxidizing agents, the agents are those conventional in the art and include but are not limited to butylated hydroxyanisole, butylated hydroxytoluene, ascorbic acid, sodium metabisulphite, propyl gallate, sodium thiosulphate or a mixture of at least two compounds with antioxidant properties.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume of the formulation applied will depend on the type of animal and the size of the animal as well as the strength of the formulation and the potency of the active agents. In one embodiment, an amount of about 0.1 to about 20 ml of the formulation may be applied to the animal. In other embodiment for the volume, the volume may be about 0.1 to about 10 ml, about 0.1 to about 5 ml, about 0.5 ml to about 10 ml, or about 0.3 to about 3 ml.

In another embodiment of the invention, application of a spot-on formulation according to the present invention may also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

For spot-on formulations, the carrier may be a liquid carrier vehicle as described in U.S. Pat. No. 6,426,333 (incorporated herein by reference), which in one embodiment of the spot-on formulation may comprise a solvent or mixture of solvents including, but not limited to, acetone, an aliphatic alcohol such as methanol, ethanol, propanol, butanol, isopropanol, pentanol, hexanol, heptanol, octanol, nonanol, cyclopentanol, cyclohexanol, ethylene glycol, propylene glycol and the like; an aromatic alcohol such as phenol, cresol, naphthol, benzyl alcohol and the like; acetonitrile, butyl diglycol, an organic amide such as dimethylacetamide, dimethylformamide, monomethylacetamide, 2-pyrrolidone, N-methylpyrrolidone, vinylpyrrolidone and the like; propylene or ethylene carbonate, dimethylsulfoxide (DMSO), a glycol polymer or an ether thereof, such as polyethylene glycol (PEG) of various grades, polypropylene glycols of various grades, dipropylene glycol n-butyl ether, ethylene glycol monoethyl ether, ethylene glycol monomethyl ether, dipropylene glycol monomethyl ether, diethylene glycol monoethyl ether, ethylene glycol, diethyl phthalate fatty acid esters, such as the diethyl ester or diisobutyl adipate, or a mixture of at least two of these solvents.

The liquid carrier vehicle may optionally contain a crystallization inhibitor including, but not limited to, those described in (a) to (h) above, or a compound that may act both as a solvent and a crystallization inhibitor (as defined above), or a mixture of these crystallization inhibitors.

Spot-on formulations may be prepared by dissolving the active ingredients into the pharmaceutically or veterinary acceptable vehicle. Alternatively, the spot-on formulation may be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Dosage forms may typically contain from about 0.1 mg to about 5 g. In other embodiments, the dosage form may contain about 0.5 mg to about 5 g of an active agent. In one embodiment of the dosage form, the dosage may contain from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

In one embodiment of the invention, the active agent may be present in the formulation at a concentration of about 0.05 to about 10% weight/volume. In another embodiment of the invention, the active agent may be present in the formulation as a concentration from about 0.1 to about 2% weight/volume. In yet another embodiment of the invention, the active agent may be present in the formulation as a concentration from about 0.25 to about 1.5% weight/volume. In still another embodiment of the invention, the active agent may be present in the formulation as a concentration about 1% weight/volume.

II. Methods of Treatment:

As discussed above, the compounds of formula (I) are effective against endoparasites and may be used to treat and prevent parasitic infections in or on animals. For avoidance of doubt, an animal includes mammals (including humans), birds or fish. In one embodiment, the present invention provides a method of treating or preventing an endoparasite infection in or on an animal comprising administering an endoparasiticidally effective amount of a compound of formula (I), or veterinarily or pharmaceutically acceptable salts thereof, or a composition of the invention, to the animal.

The compounds of formula (I) are also effective against ectoparasites and may be used to treat and prevent ectoparasitic infestations on animals. In another embodiment, the present invention provides a method of treating or preventing an ectoparasitic infestation on an animal comprising administering an ectoparasiticidally effective amount of a compound of formula (I), or pharmaceutically acceptable salts thereof, or a composition of the invention, to the animal.

In another embodiment, the invention provides a method for treating or preventing an endoparasitic infection and an ectoparasitic infestation in and on an animal, comprising administering a composition comprising an effective amount of a compound of formula (I) in combination with an effective amount of at least a second active agent, or pharmaceutically acceptable salts thereof, to the animal.

In still another embodiment of the invention, a method is provided for the treatment or prevention of a parasitic infestation at a locus, which comprises administering or applying a parasiticidally effective amount of a compound of formula (I), or pharmaceutically acceptable salts thereof, to the locus. With respect to animal health applications, "locus" is intended to mean a habitat, breeding ground, area, material or environment in which a parasite is growing or may grow, excluding in or on an animal.

In another embodiment, the invention provides methods and uses of the compounds of formula (I) for controlling pests in plants and crops or for protecting wood-containing structures.

Mammals which can be treated include but are not limited to humans, cats, dogs, cattle, chickens, bison, deer, goats, horses, llamas, camels, pigs, sheep and yaks. In one embodiment of the invention, the mammals treated are humans, cats or dogs.

In one embodiment of the invention, the compounds of formula (I) have been superior efficacy against endoparasites, and in particular against endoparasites that are resistant to active agents of the macrocyclic lactone class. In one embodiment, the compounds and compositions of the invention are effective for controlling *Haemonchus contortus, Ostertagia circumcincta* and *Trichostrongylus colubriformis* in mammals or birds.

In another embodiment, the invention provides a method for treating an parasitic infestation or infection in an animal, comprising administering an effective amount of an anthelmintic compound of the invention in combination with an effective amount of activators of invertebrate GABA receptors including an avermectin or milbemycin to the animal in need thereof. Avermectins that may be used in combination with the compounds of the invention include, but are not limited to abamectin, dimadectin, doramectin, emamectin, eprinomectin, ivermectin, latidectin, lepimectin and selamectin. Milbemycins compounds that may be used in combination with the compounds of the invention include, but are not limited to, milbemectin, milbemycin D, moxidectin and nemadectin. Also included are the 5-oxo and 5-oxime derivatives of said avermectins and milbemycins.

In one embodiment, the compounds and compositions of the invention may be used for treating or preventing an endoparasitic infection of the following parasite: Anaplocephala (*Anoplocephala*), *Ancylostoma, Necator, Ascaris, Brugia, Bunostomum, Capillaria, Chabertia, Cooperia, Cyathostomum, Cylicocyclus, Cylicodontophorus, Cylicostephanus, Craterostomum, Dictyocaulus, Dipetalonema, Dipylidium, Dirofilaria, Dracunculus, Echinococcus, Enterobius, Fasciola, Filaroides, Habronema, Haemonchus, Metastrongylus, Moniezia, Necator, Nematodirus, Nippostrongylus, Oesophagostomum, Onchocerca, Ostertagia, Oxyuris, Parascaris, Schistosoma, Strongylus, Taenia, Toxocara, Strongyloides, Toxascaris, Trichinella, Trichuris, Trichostrongylus, Triodontophorus, Uncinaria, Wuchereria,* and combinations thereof.

In a particularly preferred embodiment of the invention, the compounds and compositions of the invention are used to treat or prevent an infection by *Dirofilaria immitis*. The compounds of formula (I) have been found to be highly effective against *D. immitis* microfilaria and L4 larvae in vitro and have also been found to be effective for protecting animals from infection by *Dirofilaria immitis* in vivo. Thus, the compounds of formula (I) may be used to protect animals from developing heartworm disease by killing the immature stages of *D. immitis* before they can develop into adult worms. In one embodiment, the compounds of formula (I) and compositions comprising the compounds may be used to prevent the development of heartworm disease by killing immature stages of *D. immitis* that are resistant to macrocyclic lactones. In another embodiment the compounds and compositions of the invention are used to treat or prevent an infection by *Dirofilaria repens* or *Dirofilaria hongkongensis*.

In another embodiment of the invention, the parasite is *Haemonchus contortus, Ostertagia circumcincta, Trichostrongylus axei, Trichostrongylus colubriformis, Cooperia curticei, Nematodirus battus* and combinations thereof.

In another embodiment for treatment against endoparasites, and ectoparasites when combined with ectoparasiticidal agents, the ectoparasite is one or more insect or arachnid including those of the genera *Ctenocephalides, Rhipicephalus, Dermacentor, Ixodes, Boophilus, Amblyomma, Haemaphysalis, Hyalomma, Sarcoptes, Psoroptes, Otodectes, Chorioptes, Hypoderma, Damalinia, Linognathus, Haematopinus, Solenoptes, Trichodectes,* and *Felicola*.

In another embodiment for the treatment against ectoparasites, the ectoparasite is from the genera *Ctenocephalides, Rhipicephalus, Dermacentor, Ixodes* and/or *Boophilus*. The ectoparasites treated include but are not limited to fleas, ticks, mites, mosquitoes, flies, lice, blowfly and combinations thereof. Specific examples include but are not limited to cat and dog fleas (*Ctenocephalides felis, Ctenocephalides* spp. and the like), ticks (*Rhipicephalus* spp., *Ixodes* spp., *Dermacentor* spp., *Amblyomma* spp. and the like), and mites (*Demodex* spp., *Sarcoptes* spp., *Otodectes* spp. and the like), lice (*Trichodectes* spp., *Cheyletiella* spp., *Linognathus* spp., and the like), mosquitoes (*Aedes* spp., *Culex* spp., *Anopheles* spp., and the like) and flies (*Haematobia* spp., *Musca* spp., *Stomoxys* spp., *Dermatobia* spp., *Cochliomyia* spp., and the like). In yet another embodiment for the treatment against ectoparasites, the ectoparasite is a flea and/or tick.

Additional examples of ectoparasites include but are not limited to the tick genus *Boophilus*, especially those of the species *microplus* (cattle tick), *decoloratus* and *annulatus*; myiasis such as *Dermatobia hominis* (known as Berne in Brazil) and *Cochliomyia hominivorax* (greenbottle); sheep myiasis such as *Lucilia sericata, Lucilia cuprina* (known as blowfly strike in Australia, New Zealand and South Africa). Flies proper, namely those whose adult constitutes the parasite, such as *Haematobia irritans* (horn fly); lice such as *Linognathus vitulorum*, etc.; and mites such as *Sarcoptes scabiei* and *Psoroptes ovis*. The above list is not exhaustive and other ectoparasites are well known in the art to be harmful to animals and humans. These include, for example migrating dipterous larvae.

In another embodiment of the invention, the compounds and compositions of the invention are suitable for controlling pests such as insects selected from the group consisting of *Blatella germanica, Heliothis virescens, Leptinotarsa decemlineata, Tetramorium caespitum* and combinations thereof.

The phytoparasitic nematodes include, for example, *Anguina* spp., *Aphelenchoides* spp., *Belonolaimus* spp., *Bursaphelenchus* spp., *Ditylenchus dipsaci, Globodera* spp., *Helicotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans*, and *Xiphinema* spp.

In addition, with or without the other pesticidal agents added to the composition, the invention can also be used to treat other pests which include but are not limited to pests:

(1) from the order of Isopoda, for example *Oniscus asellus, Armadillidium vulgare* and *Porcellio scaber;*

(2) from the order of Diplopoda, for example *Blaniulus guttulatus;*

(3) from the order of Chilopoda, for example *Geophilus sarcophagus* and *Scutigera* spp.;

(4) from the order of Symphyla, for example *Scutigerella immaculata;*

(5) from the order of Thysanura, for example *Lepisma saccharina;*

(6) from the order of Collembola, for example *Onychiurus armatus;*

(7) from the order of Blattaria, for example *Blatta orientalis, Periplaneta americana, Leucophaea maderae* and *Blattella germanica;*

(8) from the order of Hymenoptera, for example *Diprion* spp., *Hoplocampa* spp., *Lasius* spp., *Monomorium pharaonis* and *Vespa* spp.;

(9) from the order of Siphonaptera, for example *Xenopsylla cheopis* and *Ceratophyllus* spp.;

(10) from the order of Anoplura (Phthiraptera), for example, *Damalinia* spp., *Haematopinus* spp., *Linognathus* spp., *Pediculus* spp., *Trichodectes* spp.;

(11) from the class of Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici;*

(12) from the class of Bivalva, for example *Dreissena* spp.;

(13) from the order of Coleoptera, for example *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.;

(14) from the order of Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyamni, Phorbia* spp., *Stomoxys* spp., *Tabanus* spp., *Tannia* spp., *Tipulapaludosa, Wohlfahrtia* spp.;

(15) from the class of Gastropoda, for example, *Arion* spp., *Biomphalaria* spp., *Bulinus* spp., *Deroceras* spp., *Galba* spp., *Lymnaea* spp., *Oncomelania* spp., *Succinea* spp.;

(16) from the class of helminths, for example, *Ancylostoma duodenale, Ancylostoma ceylanicum, Ancylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Strongyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti;*

(17) from the order of Heteroptera, for example, *Anasa tristis, Antestiopsis* spp., *Blissus* spp., *Calocoris* spp., *Camnpylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.;

(18) from the order of Homoptera, for example, *Acyrthosipon* spp., *Aeneolanmia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii;*

(19) from the order of Isoptera, for example, *Reticulitermes* spp., *Odontotermes* spp.;

(20) from the order of Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Cheimatobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.;

(21) from the order of Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria;*

(22) from the order of Thysanoptera, for example, *Baliothrips biformis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni*, *Thrips* spp.;

(23) from the class of Protozoa, for example, *Eimeria* spp.

In each aspect of the invention, the compounds and compositions of the invention can be applied against a single pest or combinations thereof.

III. Mixtures with Other Active Agents

In another embodiment, the compositions comprising the cyclic depsipeptides of formula (I) may also include other veterinary therapeutic agents. Veterinary pharmaceutical agents that may be included in the compositions of the invention are well-known in the art (see e.g. *Plumb' Veterinary Drug Handbook*, $5^{th}$ Edition, ed. Donald C. Plumb, Blackwell Publishing, (2005) or *The Merck Veterinary Manual*, $9^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdate, amoxicillin, clavulanate potassium, amphotericin B deoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, auranofin, aurothioglucose, azaperone, azathioprine, azithromycin, baclofen, barbiturates, benazepril, betamethasone, bethanechol chloride, bisacodyl, bismuth subsalicylate, bleomycin sulfate, boldenone undecylenate, bromides, bromocriptine mesylate, budesonide, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftriaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, *Propionibacterium acnes* injection, propofol, propranolol, protamine sulfate, pseudoephedrine, *psyllium* hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/1-deprenyl, sertraline, sevelamer, sevoflurane, silymarin/milk thistle, sodium bicarbonate, sodium polystyrene sulfonate, sodium stiboglusonate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds such as phenylpyrazoles may be included in the veterinary compositions of the invention. Arylpyrazoles are known in the art and are suitable for combination with the cyclic depsipeptides of formula (I) in the compositions of the invention. Examples of such arylpyrazole compounds include but are not limited to those described in U.S. Pat. Nos. 6,001,384; 6,010,710; 6,083,519; 6,096,329; 6,174,540; 6,685,954, 6,998,131 and 7,759,381 (all of which are incorporated herein by reference). A particularly preferred arylpyrazole active agent is fipronil.

In another embodiment of the invention, one or more macrocyclic lactones, which act as an acaricide, an anthelmintic agent and/or an insecticide, can be included in the compositions of the invention in combination with the compounds of formula (I). For the avoidance of doubt, the term "macrocyclic lactone" as used herein includes both naturally occurring and synthetic or semi-synthetic avermectin and milbemycin compounds.

The macrocyclic lactones that may be used in the compositions of the invention include, but are not limited to, the naturally produced avermectins (e.g. including the components designated as $A_1a$, $A_1b$, $A_2a$, $A_2b$, $B_1a$, $B_1b$, $B_2a$ and $B_2b$) and milbemycin compounds, semisynthetic avermectins and milbemycins, avermectin monosaccharide compounds and avermectin aglycone compounds. Examples of macrocyclic lactone compounds that may be used in the compositions include, but are not limited to, abamectin, dimadectin, doramectin, emamectin, eprinomectin, ivermectin, latidectin, lepimectin, selamectin, ML-1,694,554 and milbemycins including, but not limited to, milbemectin, milbemycin D, milbemycin $A_3$, milbemycin $A_4$, milbemycin oxime, moxidectin and nemadectin. Also included are the 5-oxo and 5-oxime derivatives of said avermectins and milbemycins.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schonberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054, both incorporated herein by reference.

The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia. Naturally occurring milbemycins are described in U.S. Pat. No. 3,950,360 as well as in the various references cited in "The Merck Index" 12$^{th}$ ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871, 719, 4,874,749, 4,427,663, 4,310,519, 4,199,569, 5,055,596, 4,973,711, 4,978,677, 4,920,148 and EP 0 667 054, all incorporated herein by reference.

In one embodiment, the veterinary compositions of the invention comprise an effective amount of at least one of abamectin, dimadectin, doramectin, emamectin, eprinomectin, ivermectin, latidectin, lepimectin, selamectin, milbemectin, milbemycin D, milbemycin $A_3$, milbemycin $A_4$, milbemycin oxime, moxidectin or nemadectin, or a combination thereof. In another embodiment, the invention provides a veterinary composition comprising an effective amount of at least one of abamectin, emamectin, eprinomectin, ivermectin, doramectin or selamectin, or a combination thereof. In still another embodiment, which is particularly preferred, the veterinary compositions of the invention comprise an effective amount of at least one of ivermectin, eprinomectin, milbemycin oxime or moxidectin, or a combination thereof.

In another embodiment of the invention, a composition comprising a compound of formula (I) in combination with a class of acaricide or insecticides known as insect growth regulators (IGRs) are provided. Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225, 598, 4,798,837, 4,751,225, EP 0 179 022 or U.K. 2 140 010 as well as U.S. Pat. Nos. 6,096,329 and 6,685,954 (all incorporated herein by reference).

In one embodiment the compositions of the invention may include an IGR compound that mimics juvenile hormone or that modulates levels of juvenile hormones in insects. Examples of juvenile hormone mimics include azadirachtin, diofenolan, fenoxycarb, hydroprene, kinoprene, methoprene, pyriproxyfen, tetrahydroazadirachtin and 4-chloro-2 (2-chloro-2-methyl-propyl)-5-(6-iodo-3-pyridylmethoxy) pyridazine-3(2H)-one. In another embodiment, the compositions of the invention comprise a compound of formula (I) in combination with methoprene or pyriproxyfen and a pharmaceutically acceptable carrier.

In another embodiment, the compositions of the invention include an IGR compound that is a chitin synthesis inhibitor. Chitin synthesis inhibitors include chlorofluazuron, cyromazine, diflubenzuron, fluazuron, flucycloxuron, flufenoxuron, hexaflumoron, lufenuron, tebufenozide, teflubenzuron, triflumuron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoroethoxy)-phenylurea and 1-(2,6-difluorobenzoyl)-3-(2-fluoro-4-trifluoromethyl)phenylurea.

In some embodiments, the compositions of the invention may include one or more antinematodal agents including, but not limited to, active agents in the benzimidazoles, imidazothiazoles, tetrahydropyrimidines and the organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the compositions of the invention may include an imidazothiazole compounds including, but not limited to, tetramisole, levamisole and butamisole.

In still other embodiments, the compositions of the invention may include tetrahydropyrimidine active agents including, but not limited to, pyrantel, oxantel, and morantel.

Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the compositions may include the antinematodal compounds phenothiazine, piperazine as the neutral compound and in various salt forms, diethylcarbamazine, phenols such as disophenol, arsenicals such as arsenide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the compositions of the invention may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, nitroxynil, brotianide, bromoxanide and closantel; triclabendazole, diamfenetide, clorsulon, hetolin and emetine.

Anticestodal compounds may also be advantageously used in the compositions of the invention including, but not limited to, arecoline in various salt forms, bunamidine, niclosamide, nitroscanate, paromomycin, paromomycin II, praziquantel and epsiprantel. In a particularly preferred embodiment, the compositions of the invention may comprise praziquantel.

In yet other embodiments, the compositions of the invention may include other active agents that are effective against arthropod parasites. Suitable active agents include, but are not limited to, bromocyclen, chlordane, DDT, endosulfan, lindane, methoxychlor, toxaphene, bromophos, bromophosethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, benzyl benzoate, carbon disulfide, crotamiton, diflubenzuron, diphenylamine, disulfiram, isobornyl thiocyanato acetate, monosulfiram, pirenonylbutoxide, rotenone, triphenyltin acetate, triphenyltin hydroxide, deet, dimethyl phthalate, and the compounds 1,5a,6,9,9a,9b-hexahydro-4a(4H)-dibenzofurancarboxaldehyde (MGK-11), 2-(2-ethylhexyl)-3a,4,7,7a-tetrahydro-4,7- methano-1H-isoindole-1,3(2H)dione (MGK-264), dipropyl-2,5-pyridinedicarboxylate (MGK-326) and 2-(octylthio)ethanol (MGK-874).

In yet another embodiment of the invention, adulticide insecticides and acaricides can also be added to the composition of the invention. These include pyrethrins (which include cinerin I, cinerin II, jasmolin I, jasmolin II, pyrethrin I, pyrethrin II and mixtures thereof) and synthetic pyrethroids. Pyrethroids are synthetic analogs of the pyrethrins with increased potency and stability. Pyrethroids that may be used in the compositions of the invention include, but are not limited to, permethrin, alphacypermethrin, cyfluthrin, beta-cyfluthrin, cyhalothrin, cypermethrin, cyphenothrin, deltamethrin, fenvalerate, flucythrinate, flumethrin, tau-fluvalinate, allethrin, bioallethrin, phenothrin, resmethrin, tetramethrin, transfluthrin and etofenprox.

Carbamate insecticides that may be used in the compositions of the invention include, but are not limited to, benomyl, carbanolate, carbaryl, carbofuran, methiocarb, metolcarb, promacyl, propoxur, aldicarb, butocarboxim, oxamyl, thiocarboxime and thiofanox.

In another embodiment, an antiparasitic agent that can be included in the veterinary composition containing a compound of formula (I) can be a biologically active peptide or protein including, but not limited to, depsipeptides other than the compounds of formula (I). These include PF1022A or analogs thereof and emodepside. These compounds act at the neuromuscular junction by stimulating presynaptic receptors belonging to the secretin receptor family resulting in the paralysis and death of parasites. In one embodiment of the depsipeptide, the depsipeptide is emodepside (see Wilson et al., *Parasitology*, January 2003, 126(Pt 1):79-86).

In another embodiment, the compositions of the invention may comprise an active agent from the neonicotinoid class of parasiticides. The neonicotinoids bind and inhibit insect specific nicotinic acetylcholine receptors. In one embodiment, the neonicotinoid insecticidal agent that can be combined with a compound of formula (I) in a composition of the invention is imidacloprid. Agents of this class are described, for example, in U.S. Pat. No. 4,742,060 or in EP 0 892 060 (both incorporated herein by reference). In another embodiment, the compositions of the invention may comprise nitenpyram, another active agent of the neonicotinoid class of pesticides. The use of nitenpyram for controlling fleas is described in U.S. Pat. No. 5,750,548, which is incorporated herein by reference in its entirety.

In certain other embodiments of the invention, the cyclic depsipeptides of formula (I) can be combined with the compositions of the invention is a semicarbazone, such as metaflumizone.

In another embodiment, the compositions of the invention may advantageously include one or more other isoxazoline compounds known in the art, including, but not limited to, afoxolaner, sarolaner, lotilaner and fluralaner. This class of active agents are described in U.S. Pat. Nos. 7,964,204, 8,410,153, WO 2014/036056, US 2010/0254960 A1, US2011/0159107, US2012/0309620, US2012/0030841, US2010/0069247, WO 2007/125984, WO 2012/086462, U.S. Pat. Nos. 8,318,757, 8,466,115, 8,618,126, 8,822,466, 8,383,659, 8,853,186, US 2011/0144349, U.S. Pat. Nos. 8,053,452; 8,952,175, US 2010/0254959, US 2011/152081, WO 2007/075459 and US 2009/0133319, WO 2009/025983 and U.S. Pat. No. 8,513,431, WO 2009/003075 and US 2010/0173948, WO 2008/150393, WO 2008/154528 and U.S. Pat. No. 8,623,875, WO 2010/003877 and U.S. Pat. No. 8,597,688, WO 2010/003923 and U.S. Pat. No. 8,563,474, WO 2009/045999 and U.S. Pat. No. 8,367,584, WO 2009/126668 and U.S. Pat. No. 8,546,618, WO 2009/051956, WO 2012/089623, WO 2012/089622, U.S. Pat. Nos. 8,119,671; 7,947,715; WO 2102/120135, WO 2012/107533, WO 2011/157748, US 2011/0245274, US 2011/0245239, US 2012/0232026, US 2012/0077765, US 2012/0035122, US 2011/0251247, WO 2011/154433, WO 2011/154434, US 2012/0238517, US 2011/0166193, WO 2011/104088, WO 2011/104087, WO 2011/104089, US 2012/015946, US 2009/0143410, WO 2007/123855 A2, US 2011/0118212, U.S. Pat. Nos. 7,951,828 & 7,662,972, US 2010/0137372 A1, US 2010/0179194 A2, US 2011/0086886 A2, US 2011/0059988 A1, US 2010/0179195 A1, U.S. Pat. Nos. 7,897,630, and 7,951,828, all of which are incorporated herein by reference in their entirety.

In another embodiment of the invention, nodulisporic acid and its derivatives may be added to the compositions of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the invention. These compounds are described, for example, in U.S. Pat. No. 7,084,280 to Ducray et al. (incorporated herein by reference); Sager et al., Veterinary Parasitology, 2009, 159, 49-54; Kaminsky et al., Nature vol. 452, 13 Mar. 2008, 176-181.

The compositions of the invention may also include aryloazol-2-yl cyanoethylamino compounds such as those described in U.S. Pat. No. 8,088,801 to Soll et al., which is incorporated herein by reference, and thioamide derivatives of these compounds, as described in U.S. Pat. No. 7,964,621 to Le Hir de Fallois, which is also incorporated herein by reference.

The compositions of the invention may also include paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds is a known class of compounds that include a spirodioxepino indole core with activity against certain parasites (see *Tett. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432 and US 2010/0197624, U.S. Pat. Nos. 5,703,078 and 5,750,695, all of which are hereby incorporated by reference in their entirety.

In another embodiment of the invention, the compositions may include a spinosyn active agent produced by the soil actinomycete *Saccharopolyspora spinosa* (see, for example Salgado V. L. and Sparks T. C., "*The Spinosyns: Chemistry, Biochemistry, Mode of Action, and Resistance*," in Comprehensive Molecular Insect Science, vol. 6, pp. 137-173, 2005) or a semi-synthetic spinosoid active agent. The spinosyns are typically referred to as factors or components A, B, C, D, E, F, G, H, J, K, L, M, N, O, P, Q, R, S, T, U, V, W, or Y, and any of these components, or a combination thereof, may be used in the compositions of the invention. The spinosyn compound may be a 5,6,5-tricylic ring system, fused to a 12-membered macro cyclic lactone, a neutral sugar (rhamnose), and an amino sugar (forosamine). These and other natural spinosyn compounds, including 21-butenyl spinosyn produced by *Saccharopolyspora pagona*, which may be used in the compositions of the invention, may be produced via fermentation by conventional techniques known in the art. Other spinosyn compounds that may be used in the compositions of the invention are disclosed in U.S. Pat. Nos. 5,496,931; 5,670,364; 5,591,606; 5,571,901; 5,202,242; 5,767,253; 5,840,861; 5,670,486; 5,631,155 and 6,001,981, all incorporated by reference herein in their entirety. The spinosyn compounds may include, but are not limited to, spinosyn A, spinosyn D, spinosad, spinetoram, or combinations thereof. Spinosad is a combination of spinosyn A and spinosyn D, and spinetoram is a combination of 3'-ethoxy-5,6-dihydro spinosyn J and 3'-ethoxy spinosyn L.

In general, additional active agents (other than the compound of formula (I) described above) is included in the dosage units of the invention in an amount of between about 0.1 μg and about 1000 mg. Typically, the active agent may be included in an amount of about 10 μg to about 500 mg, about 10 μg to about 400 mg, about 1 mg to about 300 mg, about 10 mg to about 200 mg or about 10 mg to about 100 mg. More typically the additional active agent will be present in an amount of about 5 mg to about 50 mg in the compositions of the invention.

The concentration of the additional active agent in the compositions of the invention will typically be from about 0.01% to about 30% (w/w) depending on the potency of the active agent. In certain embodiments for very potent active agents including, but not limited to a macrocyclic lactone active agent, the concentration of the active agent will typically be from about 0.01% to about 10% (w/w), from about 0.01 to about 1% (w/w), from about 0.01% to about 0.5% (w/w), from about 0.1% to about 0.5% (w/w) or from about 0.01% to about 0.1% (w/w). In other embodiments, the concentration of the active agent will typically be from about 0.1% to about 2% (w/w) or about 0.1% to about 1% (w/w).

In other embodiments, the additional active agent will typically be present at higher concentrations to achieve the desired efficacy. In some embodiments, the active agent will be present in a concentration of about 1% to about 30% (w/w), about 1% to about 20% (w/w) or about 1% to about 15% (w/w). In still other embodiments, the active agent will be present in a concentration of about 5% to about 20% (w/w) or about 5% to about 15% (w/w) in the composition.

In various embodiments of the invention, an additional active agent may be included in the composition to deliver a dose of about 0.001 mg/kg to about 50 mg/kg or about 0.5 mg/kg to about 50 mg/kg of body weight of the animal. In other embodiments, the active agent will typically be present in an amount sufficient to deliver a dose of about 0.05 mg/kg to about 30 mg/kg, about 0.1 mg/kg to about 20 mg/kg. In other embodiments, the active agent will be present in an amount sufficient to deliver a dose of about 0.1 mg/kg to about 10 mg/kg, about 0.1 mg/kg to about 1 mg/kg or about 0.5 mg/kg to about 50 mg/kg per body weight of the animal.

In certain embodiments of the invention where the additional active agent is a very potent compound such as a macrocyclic lactone or other potent compounds, the active agent will be present in a concentration to provide a dose of about 0.001 mg/kg to about 5 mg/kg, about 0.001 mg/kg to about 0.1 mg/kg or about 0.001 mg/kg to about 0.01 mg/kg.

In still other embodiments, the active agent is present in an amount sufficient to deliver a dose of about 0.01 mg/kg to about 2 mg/kg or about 0.1 mg/kg to about 1 mg/kg per body weight of the animal. In still other embodiments, the additional active agent may be present in an amount to deliver a dose of about 1 μg/kg to about 200 μg/kg or about 0.1 mg/kg to about 1 mg/kg of weight of animal.

In addition to the other active agents mentioned above, combinations of two or more active agents may be used with the compounds of the invention in a composition to treat a desired spectrum of pests and parasites. It would be well within the skill level of the practitioner to decide which individual compound can be used in the inventive formulation to treat a particular infection of an insect.

The invention will now be further described by way of the following non-limiting examples.

EXAMPLES

Preparation Examples

The preparation examples below are non-limiting examples of methods used to prepare the compounds of the invention. The 4-fluoro-N-methyl leucine reagent protected with the tert-butyloxycarbonyl group (BOC) shown below is used in the preparation of compounds of the invention having a —$CH_2C(CH_3)_2F$ group in the positions corresponding to $R^1$, $R^2$, $R^3$ or $R^4$.

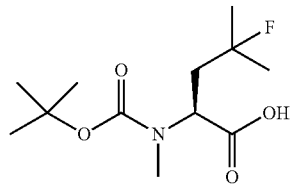 [SMILES: CN(C(=O)OC(C)(C)C)[C@@H](CC(C)(C)F)C(=O)O]

This compound is prepared according to standard procedures from commercially-available 4-fluoroleucine (Chemical Abstracts Registry Number 857026-04-1). It will be appreciated that other groups $R^1$ to $R^4$ may also be prepared with different leucine analogs in a similar manner. For example, 3-fluoroleucine (Chemical Abstracts Registry No. 171077-98-8, for example see Kaneko et al., *Chem. Pharm Bull.*, 1995, 43(5), 760-765) and 5-fluoroleucine (Chemical Abstracts Registry No. 159415-71-1, see Moody et al., *Tett. Lett.*, 1994, 35(30), 5485-8) are also known and could be used to prepare compounds where $R^1$ to $R^4$ are differently substituted fluoro leucine residues. In addition, it will be appreciated that alternative amino acids with different side chains may also used to prepare alternative compounds of the invention.

N-Boc-L-3-cyclopropylalanine shown below is also used in the preparation of certain compounds of the invention wherein $R^1$, $R^2$, $R^3$ or $R^4$ are C1. This compound is known (CAS 89483-06-7) and is commercially available as the dicyclohexylamine salt.

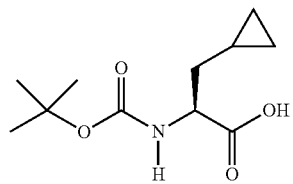 [SMILES: CC(C)(C)OC(=O)N[C@@H](CC1CC1)C(=O)O]

Benzyl (R)-2-hydroxy-3-(4-morpholinophenyl)propanoate, shown below, is also used in the preparation of certain compounds of the invention. This compound is known and its preparation is described, for example, Scherkenbeck et al., *Eur. J. Org. Chem.* 2012, 1546-1553.

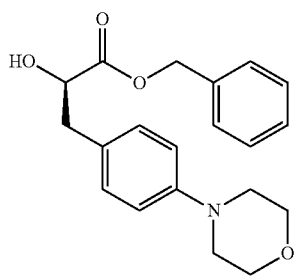 [SMILES: O=C(OCc1ccccc1)[C@H](O)Cc1ccc(N2CCOCC2)cc1]

Similarly, the compound shown below is used in the preparation of the compounds of the invention. This compound is known and is described, for example, in Dutton et al., *J. Antibiotics* 1994, 47(11), 1322-1327, among other places.

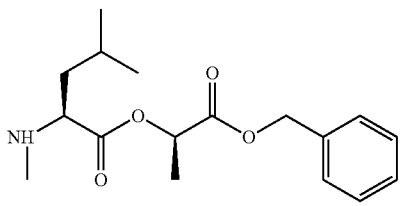 [SMILES: CN[C@@H](CC(C)C)C(=O)O[C@H](C)C(=O)OCc1ccccc1]

As shown in Scheme 1 above, the preparation of the compounds of the invention is conducted by cyclization of the precursor 1-7 after deprotection of the terminal amine and carboxylic acid groups. It will be appreciated by skilled persons in the art that using the general process outlined in Scheme 1 a wide variety of compounds of the invention may be prepared by selecting the appropriate monomer starting materials with the desired groups $R^1$, $R^2$, $R^3$, $R^4$, $Cy^1$ and $Cy^2$ in place and preparing the dimers of general formulae 1-1, 1-2, 1-3 and 1-4 by deprotection of the appropriate carboxylic acid and amino groups and amide formation.

Preparation Examples 1-16 shown below provide processes for the preparation of various monomer compounds M1 to M16 substituted with a wide variety of groups $R^1$, $R^2$, $R^3$, $R^4$, $Cy^1$ and $Cy^2$ that enable the preparation of a diverse set of dimer compounds used for the preparation of the compounds of the invention.

Preparation Example 1: Preparation of Monomer M1

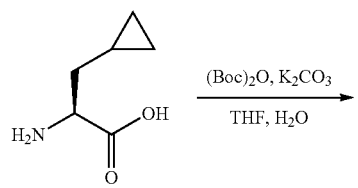

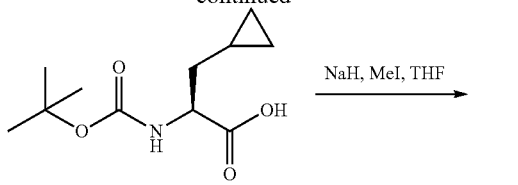

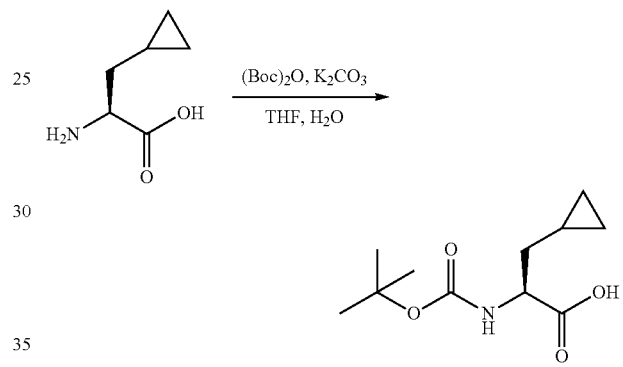

Experimental Details (2S)-2-[[(tert-butoxy)carbonyl]amino]-3-cyclopropylpropanoic Acid Into a 1000-mL 3-necked round-bottom flask, was placed (2S)-2-amino-3-cyclopropylpropanoic acid (10 g, 77.43 mmol, 1.00 equiv), tetrahydrofuran (120 mL), water (120 mL), potassium carbonate (36.7 g, 265.54 mmol, 3.40 equiv). This was followed by the addition of di-tert-butyl dicarbonate (21.9 g, 100.35 mmol, 0.80 equiv) dropwise with stirring at 0° C. The resulting solution was stirred for overnight at room temperature. The resulting solution was extracted with 2×60 mL of ether and the aqueous layers combined. and the organic layers combined. The pH value of the solution was adjusted to 3 with citric acid (2 mmol/L). The resulting solution was extracted with 3×100 mL of dichloromethane and the organic layers combined and dried over anhydrous sodium sulfate and concentrated under vacuum. This resulted in 17.2 g (97%) of (2S)-2-[[(tert-butoxy)carbonyl]amino]-3-cyclopropylpropanoic acid as colorless oil. MS (ES, m/z): 228 (M−H).

-continued

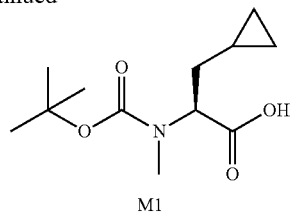

M1

(2S)-2-[[(tert-butoxy)carbonyl](methyl)amino]-3-cyclopropylpropanoic Acid (M1)

Into a 1000-mL 3-necked round-bottom flask, was placed (2S)-2-[[(tert-butoxy)carbonyl]amino]-3-cyclopropylpropanoic acid (8 g, 34.89 mmol, 1.00 equiv), tetrahydrofuran (450 mL). This was followed by the addition of sodium hydride (2.8 g, 83.33 mmol, 3.00 equiv) dropwise with stirring at 0° C. To this was added CH3I (40 g, 281.81 mmol, 8.00 equiv) dropwise with stirring at 0° C. The resulting solution was stirred for 1.5 h at room temperature. The resulting solution was allowed to react, with stirring, for an additional overnight at room temperature. The reaction was then quenched by the addition of 100 mL of water/ice. The resulting solution was extracted with 2×100 mL of MTBE and the aqueous layers combined. The pH value of the solution was adjusted to 4 with citric acid (2 mol/L). The resulting solution was extracted with 3×200 mL of ethyl acetate and the organic layers combined and dried over anhydrous sodium sulfate and concentrated under vacuum. This resulted in 6 g (71%) of (2S)-2-[[(tert-butoxy)carbonyl](methyl)amino]-3-cyclopropylpropanoic acid as yellow oil. MS (ES, m/z): 242 (M–H);

$^1$H NMR (DMSO, 300 MHz) δ: 12.59 (brs, 1H), 4.55-4.29 (m, 1H), 3.31 (s, 3H), 1.90-1.51 (m, 2H), 1.47-1.41 (m, 9H), 0.70-0.50 (m, 1H), 0.50-0.30 (m, 2H), 0.20-0.00 (m, 2H).

Preparation Example 2: Preparation of Monomer M2

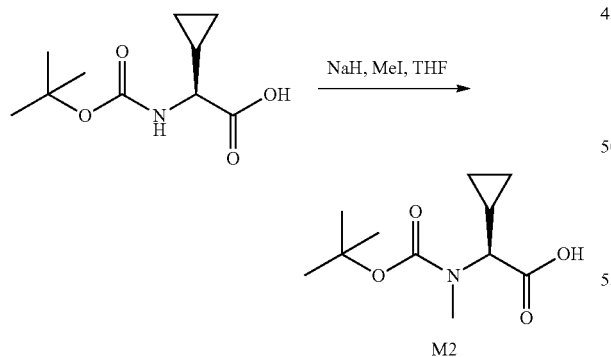

Experimental Details

(2S)-2-[[(tert-butoxy)carbonyl](methyl)amino]-2-cyclopropylacetic Acid (M2)

Into a 250-mL 3-necked round-bottom flask, was placed (2S)-2-[[(tert-butoxy)carbonyl]amino]-2-cyclopropylacetic acid (5 g, 23.23 mmol, 1.00 equiv), tetrahydrofuran (120 mL). This was followed by the addition of sodium hydride (1 g, 41.67 mmol, 3.00 equiv) in portion at 0° C. To this was added CH3I (16 g, 112.72 mmol, 8.00 equiv) dropwise with stirring at 0° C. The resulting solution was stirred for 1 h at room temperature. The reaction was then quenched by the addition of 20 mL of water/ice. The resulting solution was extracted with 2×30 mL of MTBE and the aqueous layers combined. The pH value of the aqueous phase was adjusted to 4 with citric acid. The resulting solution was extracted with 3×80 mL of ethyl acetate and the organic layers combined and dried over anhydrous sodium sulfate and concentrated under vacuum. This resulted in 3.4 g (64%) of (2S)-2-[[(tert-butoxy)carbonyl](methyl)amino]-2-cyclopropylacetic acid as yellow oil. MS (ES, m/z): 228 (M–H).

Preparation Example 3: Preparation of Monomer M3

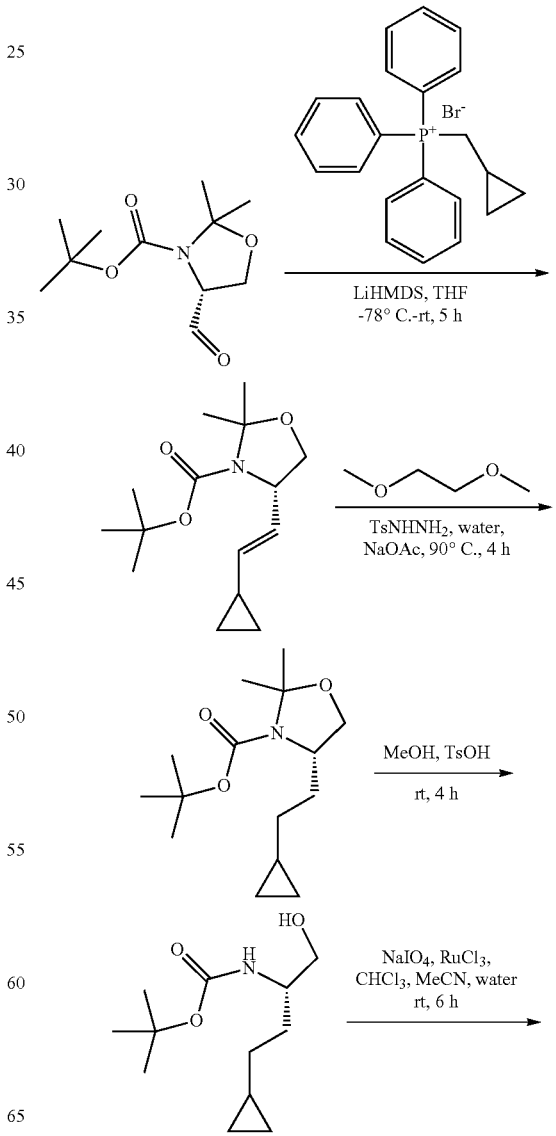

-continued

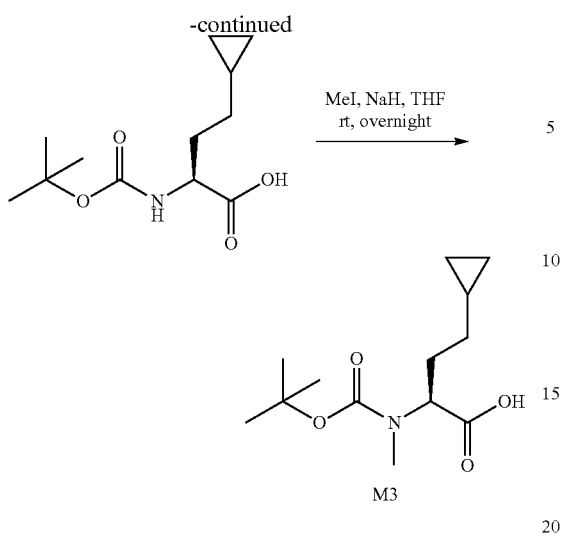

Experimental Details

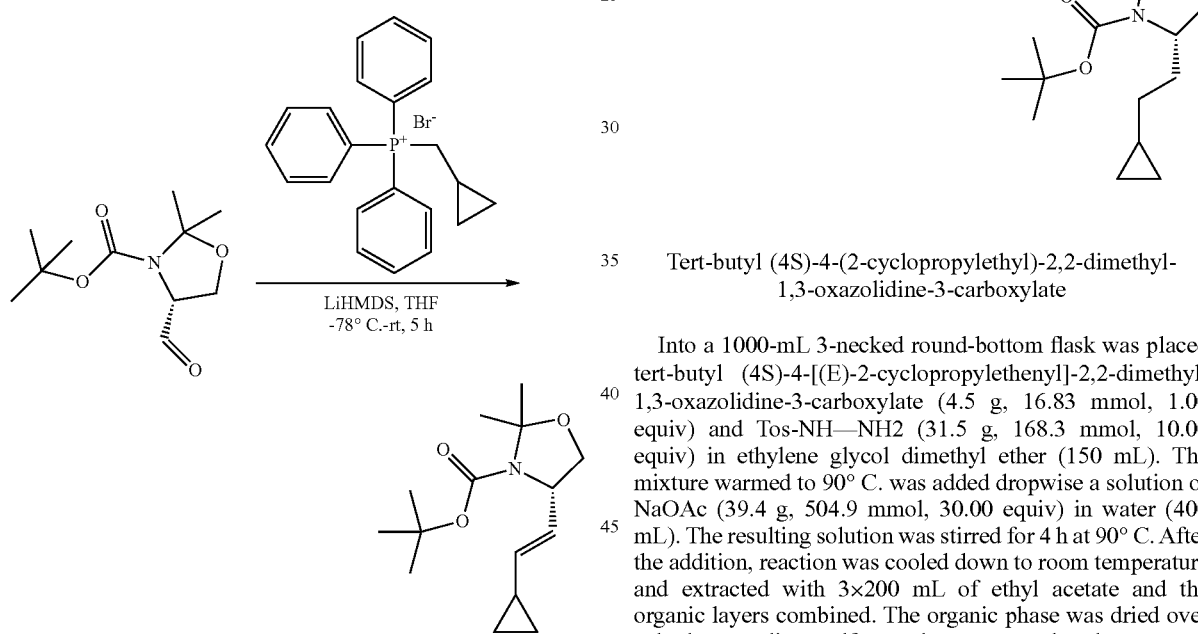

Tert-butyl (4S)-4-[(E)-2-cyclopropylethenyl]-2,2-dimethyl-1,3-oxazolidine-3-carboxylate Into a 500-mL 3-necked round-bottom flask was placed tetrahydrofuran (105 mL) under nitrogen atmosphere, (cyclopropylmethyl)triphenylphosphonium (9.1 g, 28.67 mmol, 1.50 equiv). This was followed by the addition of LiHMDS (1M) (23 mL, 23 mmol, 1.50 equiv) dropwise with stirring at −78° C. The resulting orange solution was warmed-up to room temperature for 1 h then cooled down to −78° C. To the above solution was added a solution of tert-butyl (4R)-4-formyl-2,2-dimethyl-1,3-oxazolidine-3-carboxylate (3.5 g, 15.27 mmol, 1.00 equiv) in THF (20 mL). The resulting solution was stirred for 5 h at room temperature. The resulting solution was quenched by the addition of 105 mL of methanol. The resulting solution was concentrated under vacuum. The residue was dissolved with 200 mL of ethyl acetate and 200 mL of water. The organic phase was collected. The aqueous solution was extracted with 2×200 mL of ethyl acetate and the organic layers combined and dried over sodium sulfate and concentrated under vacuum. The residue was applied onto a silica gel column with ethyl acetate/petroleum ether (1:10). This resulted in 2.3 g (56%) of tert-butyl (4S)-4-[(E)-2-cyclopropylethenyl]-2,2-dimethyl-1,3-oxazolidine-3-carboxylate as light yellow oil. MS (ES, m/z): 268 (M+H).

Tert-butyl (4S)-4-(2-cyclopropylethyl)-2,2-dimethyl-1,3-oxazolidine-3-carboxylate Into a 1000-mL 3-necked round-bottom flask was placed tert-butyl (4S)-4-[(E)-2-cyclopropylethenyl]-2,2-dimethyl-1,3-oxazolidine-3-carboxylate (4.5 g, 16.83 mmol, 1.00 equiv) and Tos-NH—NH2 (31.5 g, 168.3 mmol, 10.00 equiv) in ethylene glycol dimethyl ether (150 mL). The mixture warmed to 90° C. was added dropwise a solution of NaOAc (39.4 g, 504.9 mmol, 30.00 equiv) in water (400 mL). The resulting solution was stirred for 4 h at 90° C. After the addition, reaction was cooled down to room temperature and extracted with 3×200 mL of ethyl acetate and the organic layers combined. The organic phase was dried over anhydrous sodium sulfate and concentrated under vacuum. The residue was applied onto a silica gel column with ethyl acetate/petroleum ether (1:7). This resulted in 1.9 g (42%) of tert-butyl (4S)-4-(2-cyclopropylethyl)-2,2-dimethyl-1,3-oxazolidine-3-carboxylate as yellow oil. MS (ES, m/z): 270 (M+H).

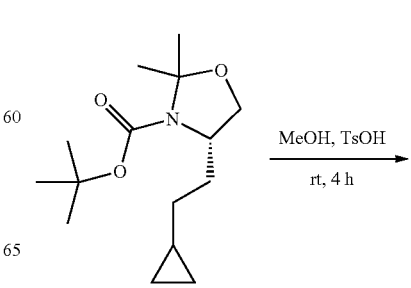

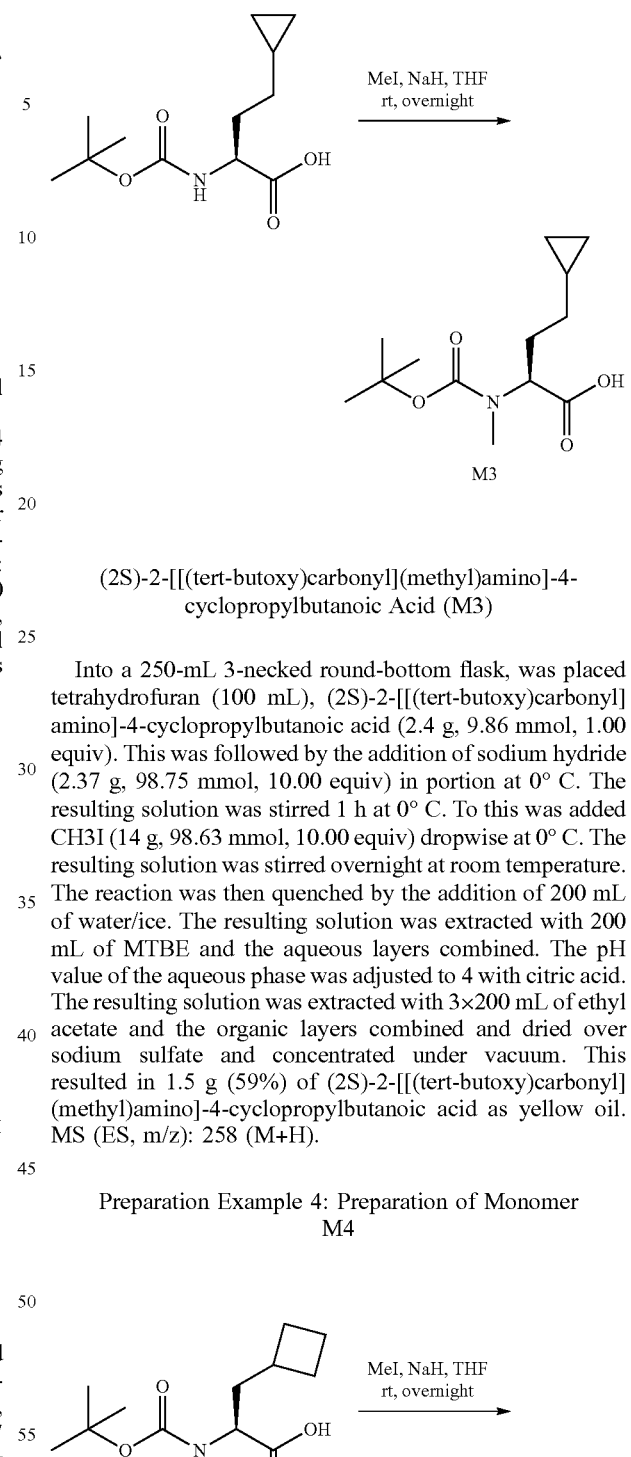

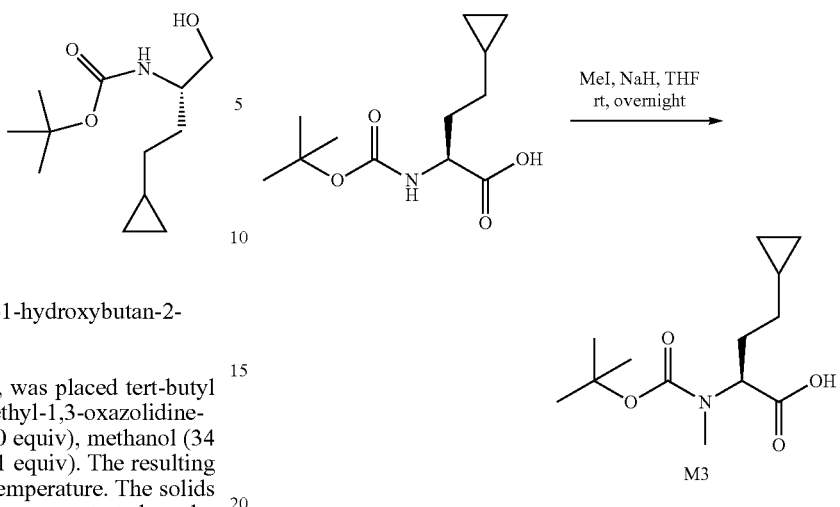

Tert-butyl N-[(2S)-4-cyclopropyl-1-hydroxybutan-2-yl]carbamate

Into a 100-mL round-bottom flask, was placed tert-butyl (4S)-4-(2-cyclopropylethyl)-2,2-dimethyl-1,3-oxazolidine-3-carboxylate (1.7 g, 6.31 mmol, 1.00 equiv), methanol (34 mL), TsOH (119 mg, 0.69 mmol, 0.11 equiv). The resulting solution was stirred for 4 h at room temperature. The solids were filtered out. The filtrate was concentrated under vacuum. The crude product (2.0 g) was purified by Flash-Prep-HPLC with the following conditions (CombiFlash-1): Column, C18 silica gel; mobile phase, CH3CN:H2O=30/70 increasing to CH3CN:H2O=100:0 within 40 min; Detector, UV 220 nm. This resulted in 1.4 g (97%) of tert-butyl N-[(2S)-4-cyclopropyl-1-hydroxybutan-2-yl]carbamate as yellow oil. MS (ES, m/z): 230 (M+H).

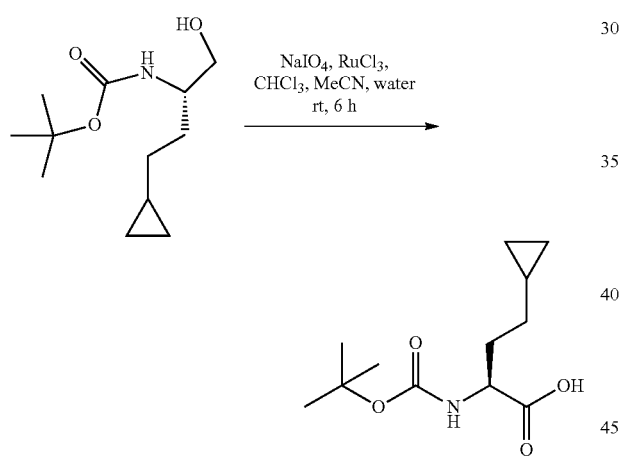

(2S)-2-[[(tert-butoxy)carbonyl]amino]-4-cyclopropylbutanoic Acid

Into a 500-mL 3-necked round-bottom flask, was placed tert-butyl N-[(2S)-4-cyclopropyl-1-hydroxybutan-2-yl]carbamate (1.2 g, 5.23 mmol, 1.00 equiv), chloroform (24 mL), water (36 mL), CH3CN (24 mL), RuCl3 (324 mg, 1.57 mmol, 0.30 equiv), NaIO4 (5.6 g, 5.00 equiv). The resulting solution was stirred for 6 h at room temperature. The reaction was then quenched by the addition of 500 mL of NaS2O3 (Sat.). The resulting solution was extracted with 300 mL of MTBE and the aqueous layers combined. The pH value of the aqueous phase was adjusted to 4 with citric acid. The resulting solution was extracted with 3×300 mL of ethyl acetate and the organic layers combined and dried over sodium sulfate and concentrated under vacuum. This resulted in 2.4 g (crude) of (2S)-2-[[(tert-butoxy)carbonyl]amino]-4-cyclopropylbutanoic acid as black oil. MS (ES, m/z): 244 (M+H).

(2S)-2-[[(tert-butoxy)carbonyl](methyl)amino]-4-cyclopropylbutanoic Acid (M3)

Into a 250-mL 3-necked round-bottom flask, was placed tetrahydrofuran (100 mL), (2S)-2-[[(tert-butoxy)carbonyl]amino]-4-cyclopropylbutanoic acid (2.4 g, 9.86 mmol, 1.00 equiv). This was followed by the addition of sodium hydride (2.37 g, 98.75 mmol, 10.00 equiv) in portion at 0° C. The resulting solution was stirred 1 h at 0° C. To this was added CH3I (14 g, 98.63 mmol, 10.00 equiv) dropwise at 0° C. The resulting solution was stirred overnight at room temperature. The reaction was then quenched by the addition of 200 mL of water/ice. The resulting solution was extracted with 200 mL of MTBE and the aqueous layers combined. The pH value of the aqueous phase was adjusted to 4 with citric acid. The resulting solution was extracted with 3×200 mL of ethyl acetate and the organic layers combined and dried over sodium sulfate and concentrated under vacuum. This resulted in 1.5 g (59%) of (2S)-2-[[(tert-butoxy)carbonyl](methyl)amino]-4-cyclopropylbutanoic acid as yellow oil. MS (ES, m/z): 258 (M+H).

Preparation Example 4: Preparation of Monomer M4

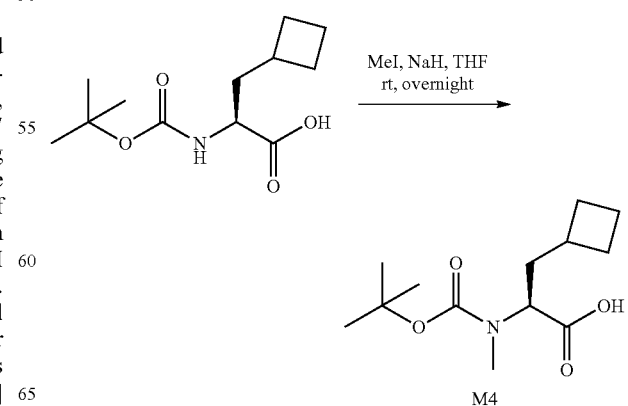

241

Experimental Details

(2S)-2-[[(tert-butoxy)carbonyl](methyl)amino]-3-cyclobutylpropanoic Acid (M4)

Into a 50-mL round-bottom flask, was placed tetrahydrofuran (200 mL), (2S)-2-[[(tert-butoxy)carbonyl]amino]-3-cyclobutylpropanoic acid (2 g, 8.22 mmol, 1.00 equiv), CH3I (24 g, 169.09 mmol, 20.57 equiv), sodium hydride (6.6 g, 275.00 mmol, 33.45 equiv). The resulting solution was stirred overnight at 38° C. The reaction was then quenched by the addition of water/ice. The pH value of the solution was adjusted to 4 with hydrogen chloride (2 mol/L). The resulting solution was extracted with 3×20 mL of ethyl acetate and the organic layers combined and dried over anhydrous sodium sulfate and concentrated under vacuum. This resulted in 1.8 g (85%) of (2S)-2-[[(tert-butoxy)carbonyl](methyl)amino]-3-cyclobutylpropanoic acid as colorless oil. MS (ES, m/z): 258 (M+H).

Preparation Example 5: Preparation of Monomer M5

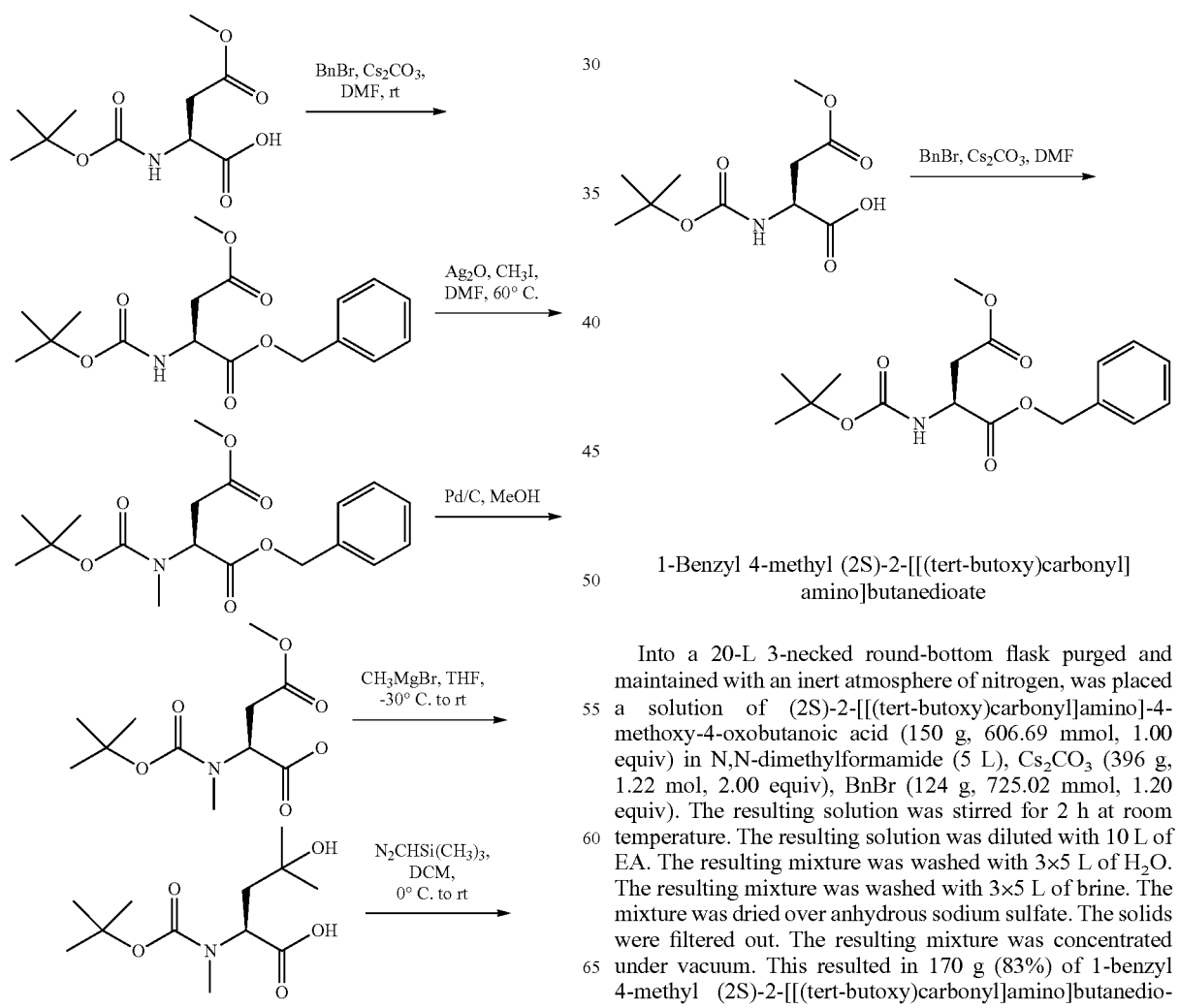

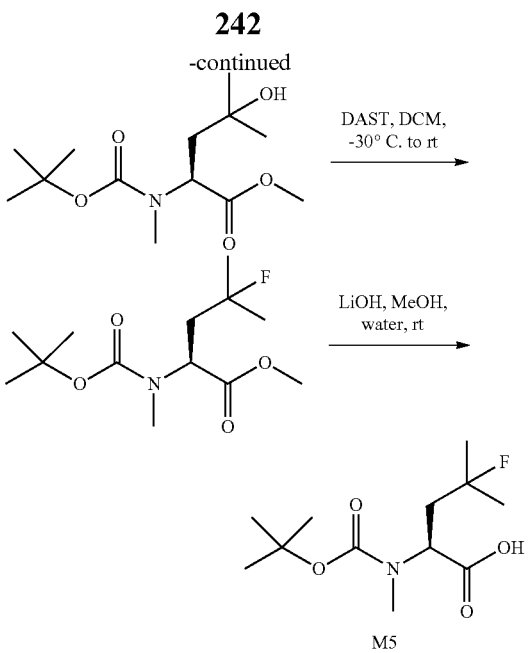

Experimental Details

1-Benzyl 4-methyl (2S)-2-[[(tert-butoxy)carbonyl]amino]butanedioate

Into a 20-L 3-necked round-bottom flask purged and maintained with an inert atmosphere of nitrogen, was placed a solution of (2S)-2-[[(tert-butoxy)carbonyl]amino]-4-methoxy-4-oxobutanoic acid (150 g, 606.69 mmol, 1.00 equiv) in N,N-dimethylformamide (5 L), Cs$_2$CO$_3$ (396 g, 1.22 mol, 2.00 equiv), BnBr (124 g, 725.02 mmol, 1.20 equiv). The resulting solution was stirred for 2 h at room temperature. The resulting solution was diluted with 10 L of EA. The resulting mixture was washed with 3×5 L of H$_2$O. The resulting mixture was washed with 3×5 L of brine. The mixture was dried over anhydrous sodium sulfate. The solids were filtered out. The resulting mixture was concentrated under vacuum. This resulted in 170 g (83%) of 1-benzyl 4-methyl (2S)-2-[[(tert-butoxy)carbonyl]amino]butanedioate as a white solid. MS (ES, m/z): 338 (M+H).

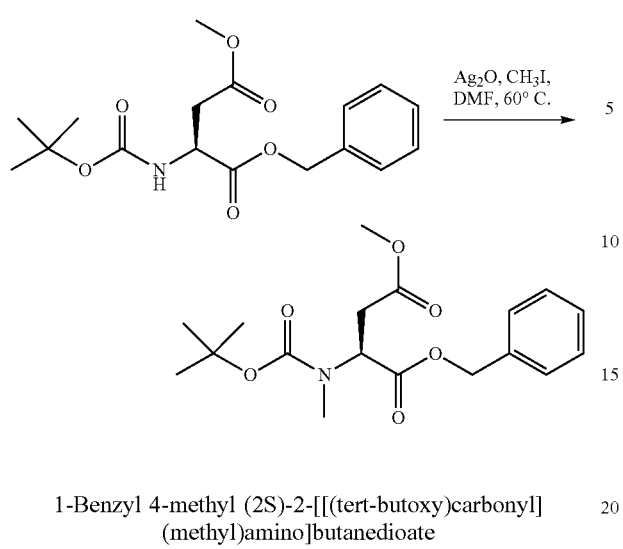

1-Benzyl 4-methyl (2S)-2-[[(tert-butoxy)carbonyl](methyl)amino]butanedioate

Into a 10 L 3-necked round-bottom flask purged and maintained with an inert atmosphere of nitrogen, was placed a solution of 1-benzyl 4-methyl (2S)-2-[[(tert-butoxy)carbonyl]amino]butanedioate (170 g, 503.90 mmol, 1.00 equiv) in N,N-dimethylformamide (5 mL), Ag₂O (348 g, 3.00 equiv), CH3I (1433 g, 10.10 mol, 20.00 equiv). The resulting solution was stirred for 1 h at 60° C. in an oil bath. The resulting solution was diluted with 10 L of EA. The resulting mixture was washed with 3×8 L of H₂O. The resulting mixture was washed with 3×8 L of brine. The organic phase was dried over anhydrous sodium sulfate. The solids were filtered out. The resulting mixture was concentrated under vacuum. This resulted in 159 g (90%) of 1-benzyl 4-methyl (2S)-2-[[(tert-butoxy)carbonyl](methyl)amino]butanedioate as yellow oil. MS (ES, m/z): 352 (M+H).

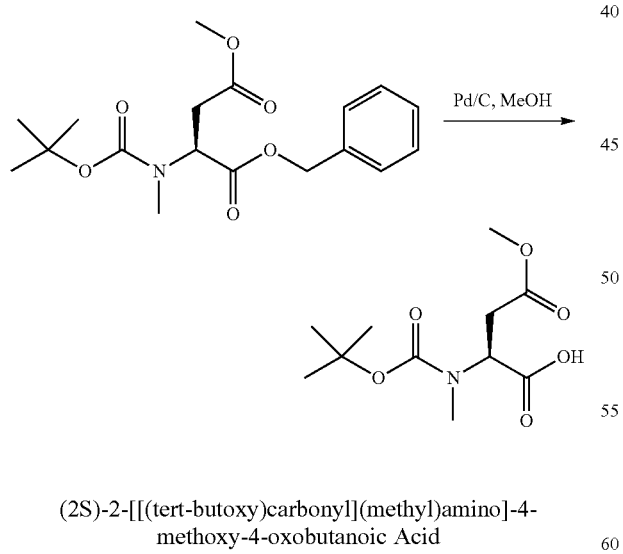

(2S)-2-[[(tert-butoxy)carbonyl](methyl)amino]-4-methoxy-4-oxobutanoic Acid

Into a 10-L 3-necked round-bottom flask, was placed a solution of 1-benzyl 4-methyl (2S)-2-[[(tert-butoxy)carbonyl](methyl)amino]butanedioate (159 g) in methanol (3 L), Palladium carbon (15.9 g, 0.10 equiv), H₂ (gas) (enough). The resulting solution was stirred for 2 h at room temperature.

The solids were filtered out. The resulting mixture was concentrated under vacuum. This resulted in 115 g (97%) of (2S)-2-[[(tert-butoxy)carbonyl](methyl)amino]-4-methoxy-4-oxobutanoic acid as yellow oil. MS (ES, m/z): 262 (M+H).

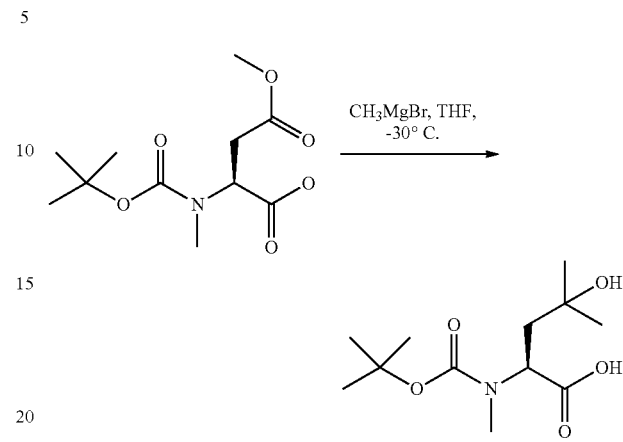

(2S)-2-[[(tert-butoxy)carbonyl](methyl)amino]-4-hydroxy-4-methylpentanoic Acid

Into a 3-L 3-necked round-bottom flask purged and maintained with an inert atmosphere of nitrogen, was placed a solution of (2S)-2-[[(tert-butoxy)carbonyl](methyl)amino]-4-methoxy-4-oxobutanoic acid (114 g) in tetrahydrofuran (4 L), CH₃MgBr (874 mL, 6.00 equiv). The resulting solution was stirred for 3 h at −30° C. in a cold bath. The reaction was then quenched by the addition of 1000 mL of NH₄Cl/H₂O. The pH value of the solution was adjusted to 3-4 with hydrogen chloride/H₂O. The resulting solution was diluted with 6 L of H₂O. The resulting solution was extracted with 3×4 L of ethyl acetate and the organic layers combined. The resulting mixture was washed with 2×5 L of brine. The organic phase was dried over anhydrous sodium sulfate. The solids were filtered out. The resulting mixture was concentrated under vacuum. This resulted in 90 g (crude) of (2S)-2-[[(tert-butoxy)carbonyl](methyl)amino]-4-hydroxy-4-methylpentanoic acid as yellow oil. MS (ES, m/z): 262 (M+H).

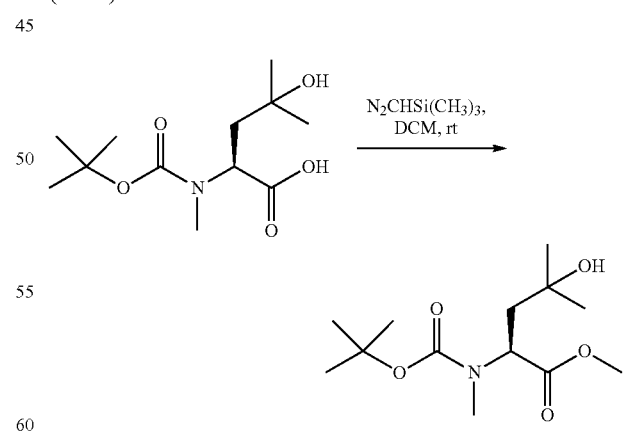

Methyl (2S)-2-[[(tert-butoxy)carbonyl](methyl)amino]-4-hydroxy-4-methylpentanoate Into a 3-L 3-necked round-bottom flask purged and maintained with an inert atmosphere of nitrogen, was placed a solution of (2S)-2-[[(tert-butoxy)carbonyl](methyl)amino]-4-hydroxy-4-methylpentanoic acid (90 g) in dichloromethane (4 L), (diazomethyl)trimethylsilane (340 mL, 2.00 equiv, 2M). The resulting solution was stirred for 2 h at room temperature in an ice/salt bath. The resulting mixture was washed with 2×3 L of H$_2$O. The resulting mixture was washed with 2×3 L of brine. The organic phase was dried over anhydrous sodium sulfate. The solids were filtered out. The resulting mixture was concentrated under vacuum. This resulted in 92 g (crude) of methyl (2S)-2-[[(tert-butoxy)carbonyl](methyl)amino]-4-hydroxy-4-methylpentanoate as yellow oil. MS (ES, m/z): 276 (M+H).

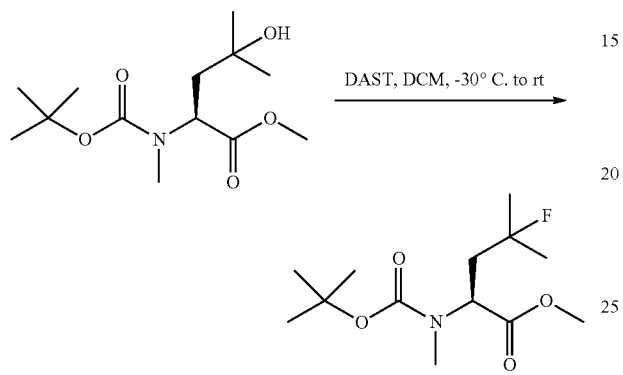

Methyl (2S)-2-[[(tert-butoxy)carbonyl](methyl)amino]-4-fluoro-4-methylpentanoate Into a 3-L 3-necked round-bottom flask purged and maintained with an inert atmosphere of nitrogen, was placed a solution of methyl (2S)-2-[[(tert-butoxy)carbonyl](methyl)amino]-4-hydroxy-4-methylpentanoate (90 g) in dichloromethane (3.0 L), DAST (106 g, 2.00 equiv). The resulting solution was stirred for 2 h at −30° C. in a cold bath. The reaction was then quenched by the addition of 1 L of NaHCO$_3$ at 0° C. The resulting mixture was washed with 2×1 L of H$_2$O. The resulting mixture was washed with 2×1 L of brine. The organic phase was dried over anhydrous sodium sulfate. The solids were filtered out. The resulting mixture was concentrated under vacuum. The residue was applied onto a silica gel column with ethyl acetate/petroleum ether (1:100-1:20). This resulted in 15 g (16%) of methyl (2S)-2-[[(tert-butoxy)carbonyl](methyl)amino]-4-fluoro-4-methylpentanoate as yellow oil. MS (ES, m/z): 278 (M+H).

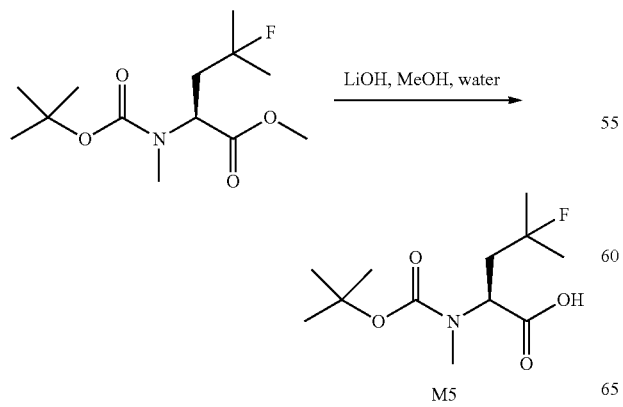

(S)-2-(tert-butoxycarbonyl(methyl)amino)-4-fluoro-4-methylpentanoic Acid (M5)

Into a 500 mL 3-necked round-bottom flask, was placed a solution of (S)-methyl 2-(tert-butoxycarbonyl(methyl)amino)-4-fluoro-4-methylpentanoate (15 g) in MeOH (80 mL), LiOH (11.4 g, 5.00 equiv) in H$_2$O (150 mL). The resulting solution was stirred for 2 h at room temperature. The resulting solution was extracted with 3×100 mL of ethyl acetate. The pH value of the water layers was adjusted to 3~4 with hydrogen chloride/H$_2$O. The resulting solution was extracted with 3×100 mL of ethyl acetate and the organic layers combined. The resulting mixture was washed with 2×5 L of brine. The organic phase was dried over anhydrous sodium sulfate. The solids were filtered out. The resulting mixture was concentrated under vacuum. This resulted in 12.6 g (89%) of (S)-2-(tert-butoxycarbonyl(methyl)amino)-4-fluoro-4-methylpentanoic acid as yellow oil. MS (ES, m/z): 264 (M+H).

Preparation Example 6: Preparation of Monomer M6

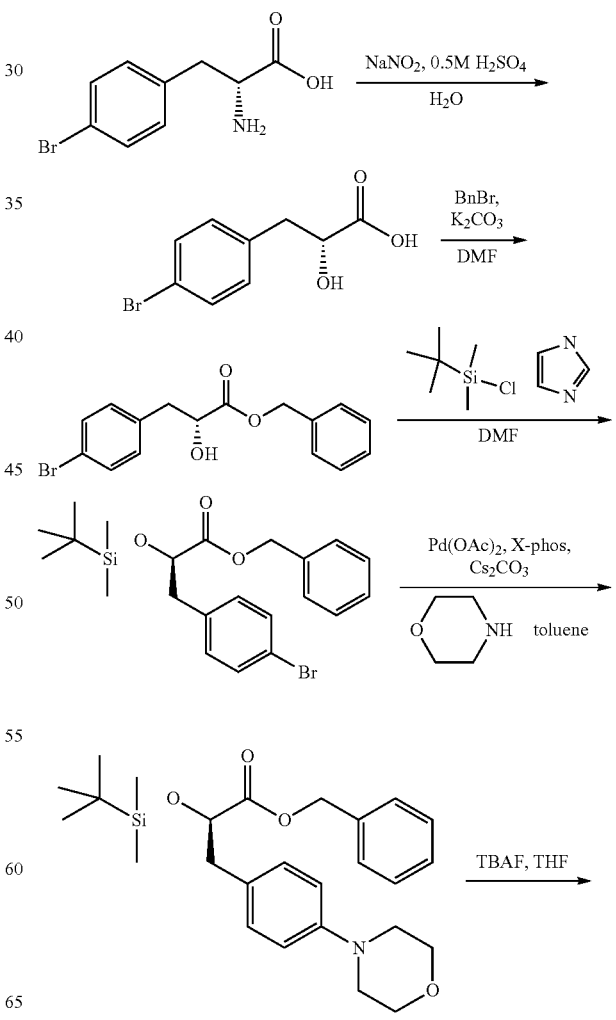

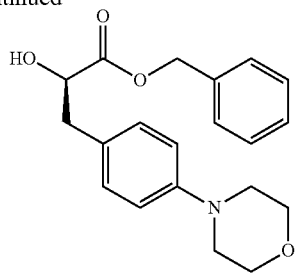

M6

Experimental Details

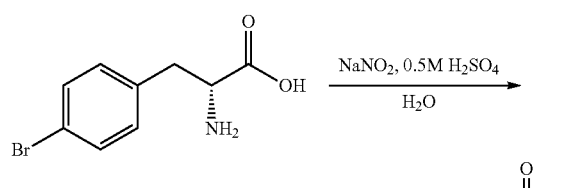

(2R)-3-(4-bromophenyl)-2-hydroxypropanoic Acid

Into a 2000-mL 4-necked round-bottom flask, was placed (2R)-2-amino-3-(4-bromophenyl)propanoic acid (150 g, 614.54 mmol, 1.00 equiv), sulfuric acid (0.5M/L) (2500 mL). This was followed by the addition of a solution of NaNO$_2$ (256 g, 3.71 mol, 6.00 equiv) in water (900 mL) dropwise with stirring. The resulting solution was stirred for 48 h at room temperature. The solids were collected by filtration. The solid was dried in an oven under reduced pressure. This resulted in 240 g (80%) of (2R)-3-(4-bromophenyl)-2-hydroxypropanoic acid as a white solid. MS (ES, m/z): 243 (M−H); $^1$H NMR (DMSO, 300 MHz) δ: 12.59 (brs, 1H), 7.51-7.44 (m, 2H), 7.27-7.14 (m, 2H), 5.34 (brs, 1H), 4.16-4.12 (m, 1H), 2.97-2.91 (m, 1H), 2.80-2.70 (m, 1H).

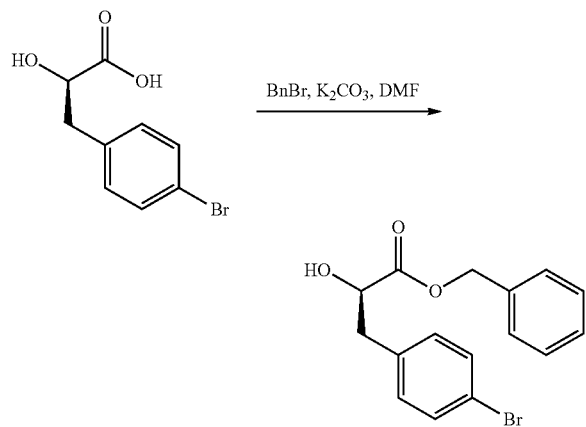

Benzyl (2R)-3-(4-bromophenyl)-2-hydroxypropanoate

Into a 2000-mL 4-necked round-bottom flask, was placed (2R)-3-(4-bromophenyl)-2-hydroxypropanoic acid (60 g, 244.83 mmol, 1.00 equiv), potassium carbonate (67.6 g, 489.11 mmol, 2.00 equiv), N,N-dimethylformamide (1000 mL). This was followed by the addition of BnBr (50.3 g, 294.10 mmol, 1.20 equiv) dropwise with stirring. The resulting solution was stirred for 1 overnight at room temperature. The resulting solution was diluted with 2000 mL of H$_2$O. The resulting solution was extracted with 3×500 mL of ethyl acetate and the organic layers combined. The organic layer was washed with 3×500 mL of water and 1×500 mL of brine. The organic layers was dried over anhydrous sodium sulfate and concentrated under vacuum. The residue was applied onto a silica gel column with ethyl acetate/petroleum ether (1:5). This resulted in 62 g (76%) of benzyl (2R)-3-(4-bromophenyl)-2-hydroxypropanoate as a white solid. $^1$H NMR (DMSO, 300 MHz) δ: 7.49 (d, J=3.9 Hz, 2H), 741-7.34 (m, 5H), 7.15 (d, J=4.4 Hz, 2H), 5.28-5.15 (m, 2H), 4.55-4.51 (m, 1H), 3.23-3.16 (m, 1H), 3.07-3.01 (m, 1H).

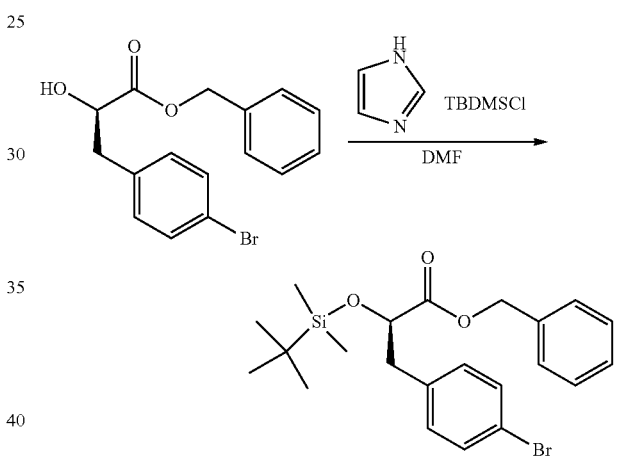

Benzyl (2R)-3-(4-bromophenyl)-2-[(tert-butyldimethylsilyl)oxy]propanoate

Into a 2-L 4-necked round-bottom flask, was placed benzyl (2R)-3-(4-bromophenyl)-2-hydroxypropanoate (60 g, 179.00 mmol, 1.00 equiv), N,N-dimethylformamide (1000 mL), 1H-imidazole (24.5 g, 359.89 mmol, 2.00 equiv). This was followed by the addition of TBDMSCl (32.4 g, 1.20 equiv) dropwise with stirring. The resulting solution was stirred for 16 h at room temperature. The resulting solution was diluted with 2 L of H$_2$O. The resulting solution was extracted with 3×500 mL of ethyl acetate and the organic layers combined. The organic layers was washed with 3×500 mL of brine. The organic layers was dried over anhydrous sodium sulfate and concentrated under vacuum. The residue was applied onto a silica gel column with ethyl acetate/petroleum ether (1:50). This resulted in 78 g (97%) of benzyl (2R)-3-(4-bromophenyl)-2-[(tert-butyldimethylsilyl)oxy]propanoate as yellow oil. MS (ES, m/z): 449 (M+H); $^1$H NMR (DMSO, 300 MHz) δ: 7.44 (d, J=4.2 Hz, 2H), 7.40-7.31 (m, 5H), 7.16 (d, J=4.0 Hz, 2H), 5.13 (s, 2H), 4.50-4.46 (m, 1H), 3.03-2.98 (m, 1H), 2.86-2.79 (m, 1H), 0.73 (s, 9H), −0.15 (s, 3H), −0.25 (s, 3H).

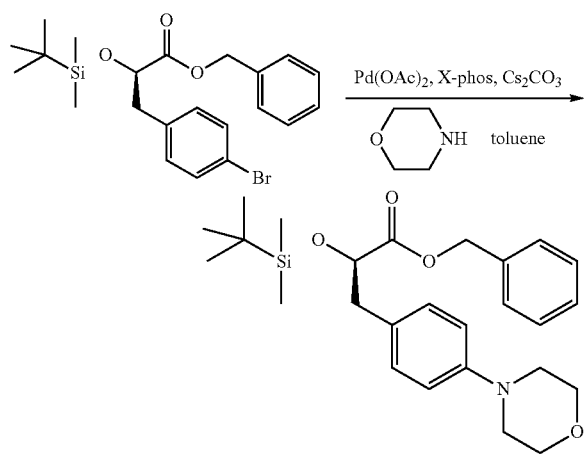

Benzyl (2R)-2-[(tert-butyldimethylsilyl)oxy]-3-[4-(morpholin-4-yl)phenyl]propanoate Into a 2-L 4-necked round-bottom flask purged and maintained with an inert atmosphere of nitrogen, was placed benzyl (2R)-3-(4-bromophenyl)-2-[(tert-butyldimethylsilyl) oxy]propanoate (78 g, 173.54 mmol, 1.00 equiv), X-phos (8.27 g, 0.10 equiv), Pd(OAc)$_2$ (1.95 g, 8.69 mmol, 0.05 equiv), toluene (1500 mL), morpholine (45.3 g, 519.97 mmol, 3.00 equiv), CsCO$_3$ (170 g, 3.00 equiv). The resulting solution was stirred for 16 h at 90° C. The solids were filtered out. The residue was applied onto a silica gel column with ethyl acetate/petroleum ether (1:5). This resulted in 64 g (81%) of benzyl (2R)-2-[(tert-butyldimethylsilyl)oxy]-3-[4-(morpholin-4-yl)phenyl]propanoate as yellow oil. MS (ES, m/z): 456 (M+H); $^1$H NMR (CDCl3, 300 MHz) δ: 7.34-7.31 (m, 5H), 7.12 (d, J=4.2 Hz, 2H), 6.90-6.80 (m, 2H), 5.20-5.10 (m, 2H), 4.36-4.32 (m, 1H), 3.90-3.80 (m, 4H), 3.13-3.05 (m, 4H), 3.04-2.95 (m, 1H), 2.89-2.82 (m, 1H), 0.79 (s, 9H), −0.15 (s, 3H), −0.20 (s, 3H).

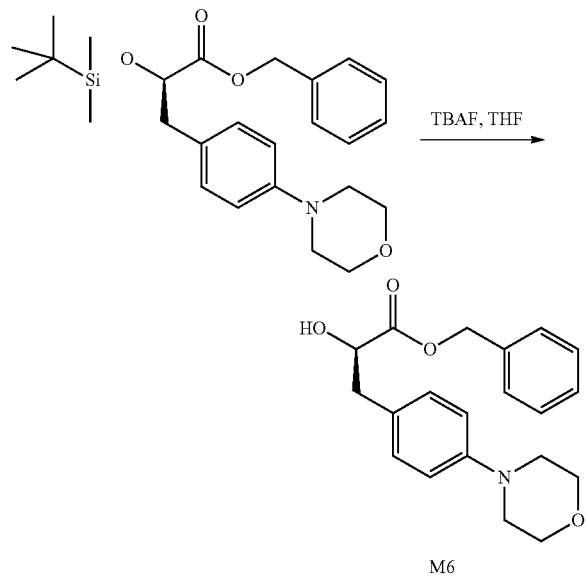

M6

Benzyl (2R)-2-hydroxy-3-[4-(morpholin-4-yl)phenyl]propanoate (M6)

Into a 2000-mL 4-necked round-bottom flask, was placed benzyl (2R)-2-[(tert-butyldimethylsilyl)oxy]-3-[4-(morpholin-4-yl)phenyl]propanoate (60 g, 131.68 mmol, 1.00 equiv), tetrahydrofuran (1200 mL). This was followed by the addition of TBAF (51.7 g, 197.74 mmol, 1.20 equiv), in portions at 0° C. The resulting solution was stirred for 20 min at room temperature. The resulting solution was diluted with 2000 mL of H$_2$O. The resulting solution was extracted with 3×500 mL of ethyl acetate and the organic layers combined. The organic layers was washed with 3×500 mL of water and 1×500 mL of brine. The organic layers was dried over anhydrous sodium sulfate and concentrated under vacuum. The residue was applied onto a silica gel column with ethyl acetate/petroleum ether (1:3). This resulted in 42 g (93%) of benzyl (2R)-2-hydroxy-3-[4-(morpholin-4-yl)phenyl]propanoate as a yellow solid. MS (ES, m/z): 342 (M+H); $^1$H NMR (DMSO, 300 MHz) δ: 7.40-7.27 (m, 5H), 7.06 (d, J=8.4 Hz, 2H), 6.82 (d, J=8.7 Hz, 2H), 5.57 (d, J=6.3 Hz, 1H), 5.08 (s, 2H), 4.27-4.21 (m, 1H), 3.75-3.71 (m, 4H), 3.06-3.03 (m, 4H), 2.91-2.74 (m, 2H).

Preparation Example 7: Preparation of Monomer M7

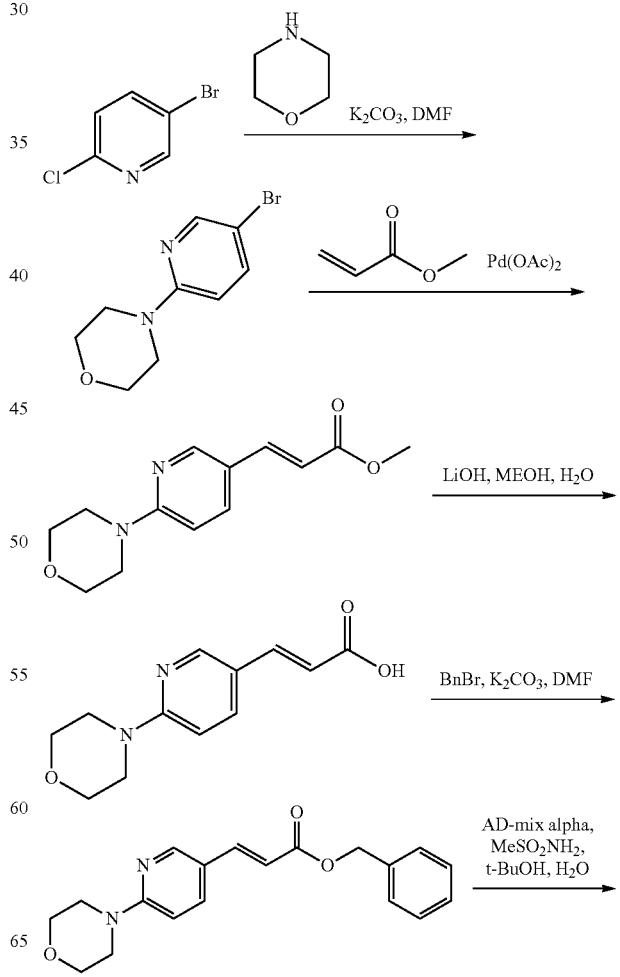

251

-continued

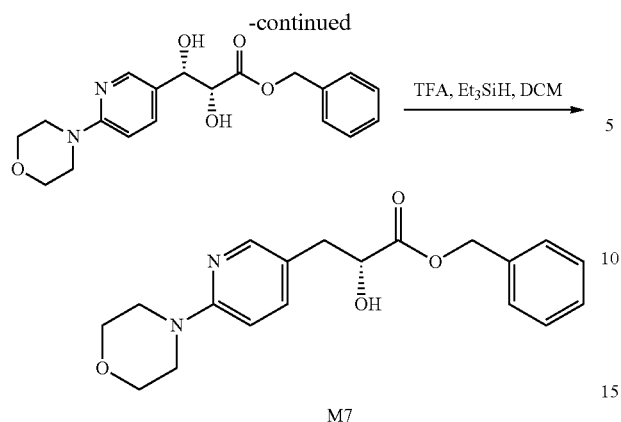

M7

Experimental Details

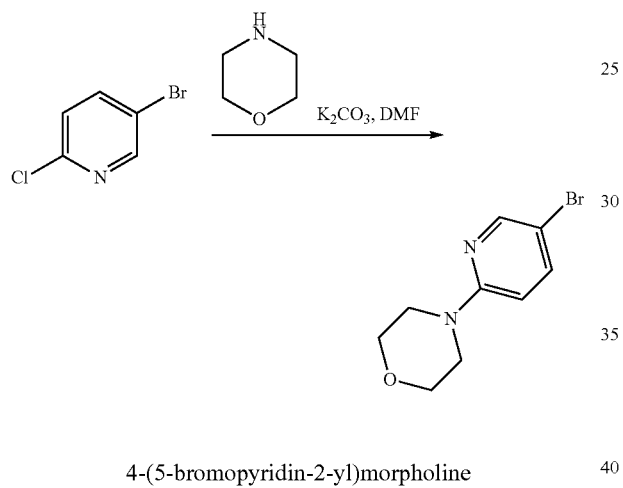

4-(5-bromopyridin-2-yl)morpholine

Into a 1-L round-bottom flask, was placed a solution of 5-bromo-2-chloropyridine (50 g, 259.82 mmol, 1.00 equiv) in N,N-dimethylformamide (300 mL), morpholine (91 g, 1.04 mol, 4.00 equiv), potassium carbonate (108 g, 781.42 mmol, 3.00 equiv). The resulting solution was stirred overnight at 120° C. The resulting solution was extracted with 5×150 mL of ethyl acetate and the organic layers combined. The resulting mixture was washed with 3×100 mL of brine. The mixture was dried over anhydrous sodium sulfate and concentrated under vacuum. The resulting mixture was washed with PE:EA=1:5. This resulted in 80 g (63%) of 4-(5-bromopyridin-2-yl)morpholine as a white solid. MS (ES, m/z): 243 (M+H); $^1$H NMR (CDCl3, 300 MHz) δ: 8.22 (s, 1H), 7.57 (d, J=4.5 Hz, 1H), 6.54 (d, J=2.4 Hz, 1H), 3.82 (t, J=5.1 Hz, 4H), 3.48 (t, J=5.1 Hz, 4H).

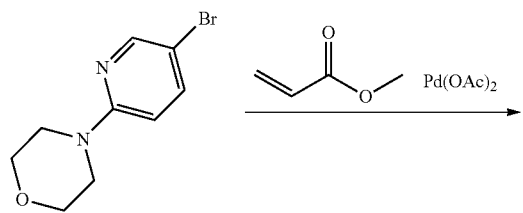

252

-continued

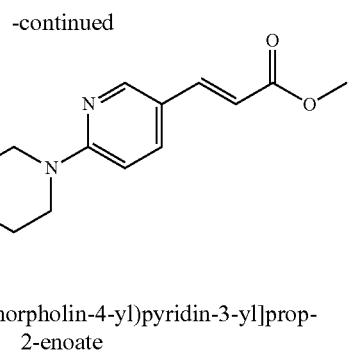

methyl (2E)-3-[6-(morpholin-4-yl)pyridin-3-yl]prop-2-enoate

Into a 250-mL round-bottom flask and maintained with an inert atmosphere of nitrogen, was placed a solution of 4-(5-bromopyridin-2-yl)morpholine (5 g, 20.57 mmol, 1.00 equiv) in N,N-dimethylformamide (120 mL), methyl prop-2-enoate (3.54 g, 41.12 mmol, 2.00 equiv), Pd(OAc)2 (92 mg, 0.41 mmol, 0.02 equiv), sodium bicarbonate (3.46 g, 41.19 mmol, 2.00 equiv), Bu4NCl (11.4 g, 41.02 mmol, 2.00 equiv). The resulting solution was stirred for 3 days at 100° C. The resulting solution was extracted with 5×150 mL of ethyl acetate and the organic layers combined. The resulting mixture was washed with 3×100 mL of brine. The mixture was dried over anhydrous sodium sulfate and concentrated under vacuum. The solids were filtered out. This resulted in 11.5 g (56%) of methyl (2E)-3-[6-(morpholin-4-yl)pyridin-3-yl]prop-2-enoate as a light brown solid. MS (ES, m/z): 249 (M+H); $^1$H NMR (CDCl3, 300 MHz) δ: 8.30 (s, 1H), 7.72-7.58 (m, 2H), 6.64 (d, J=4.5 Hz, 1H), 6.27 (d, J=8.0 Hz, 1H), 3.84-3.80 (m, 7H), 3.62 (t, J=4.8 Hz, 4H).

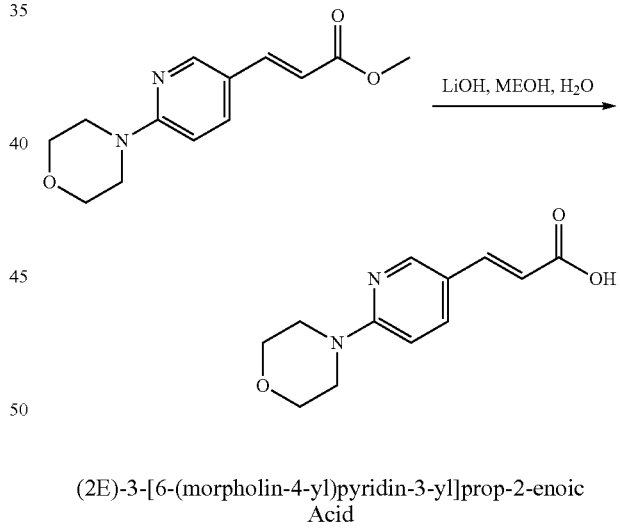

(2E)-3-[6-(morpholin-4-yl)pyridin-3-yl]prop-2-enoic Acid

Into a 500-mL round-bottom flask, was placed a solution of methyl (2E)-3-[6-(morpholin-4-yl)pyridin-3-yl]prop-2-enoate (11 g, 44.31 mmol, 1.00 equiv) in methanol/H2O (60:60 mL), LiOH (10.6 g, 442.59 mmol, 10.00 equiv). The resulting solution was stirred for 1 h at 80° C. The resulting solution was diluted with 150 ml of water. The pH value of the solution was adjusted to 6-7 with NaHCO3(Sat.). The resulting solution was extracted with 5×150 mL of ethyl acetate and the organic layers combined. The organic phase was washed with 3×150 mL of brine. The organic phase was dried over anhydrous sodium sulfate and concentrated under vacuum. This resulted in 10.4 g (crude) of (2E)-3-[6-(morpholin-4-yl)pyridin-3-yl]prop-2-enoic acid as a light brown solid. MS (ES, m/z): 245 (M+H).

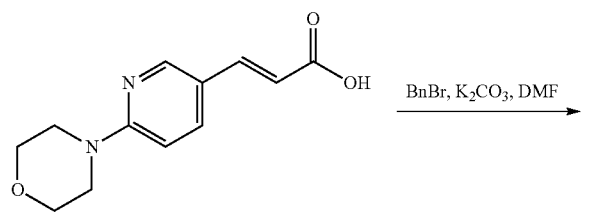

benzyl (2E)-3-[6-(morpholin-4-yl)pyridin-3-yl]prop-2-enoate

Into a 250-mL round-bottom flask, was placed a solution of (2E)-3-[6-(morpholin-4-yl)pyridin-3-yl]prop-2-enoic acid (4 g, 17.08 mmol, 1.00 equiv) in N,N-dimethylformamide (70 mL), potassium carbonate (7.1 g, 51.37 mmol, 3.00 equiv), (bromomethyl)benzene (4.4 g, 25.73 mmol, 1.50 equiv). The resulting solution was stirred overnight at room temperature. The resulting solution was extracted with 5×150 mL of ethyl acetate and the organic layers combined. The resulting mixture was washed with 3×150 mL of brine. The mixture was dried over anhydrous sodium sulfate and concentrated under vacuum. The resulting mixture was washed with 1×70 mL of PE. The solids were collected by filtration. This resulted in 10 g (72%) of benzyl (2E)-3-[6-(morpholin-4-yl)pyridin-3-yl]prop-2-enoate as a yellow solid. MS (ES, m/z): 325 (M+H); $^1$H NMR (CDCl3, 300 MHz) δ: 8.30 (s, 1H), 7.70-7.62 (m, 2H), 7.45-7.32 (m, 5H), 6.63 (d, J=4.5 Hz, 1H), 6.32 (d, J=8.0 Hz, 1H), 5.25 (s, 2H), 3.82 (t, J=4.5 Hz, 4H), 3.63-3.60 (m, 4H).

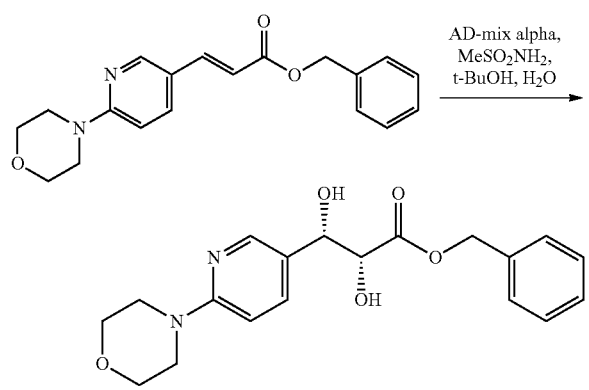

(2R,3S)-2,3-dihydroxy-3-[6-(morpholin-4-yl)pyridin-3-yl]propanoate

Into a 100-mL 3-necked round-bottom flask, was placed tert-Butanol:H2O (20:20 mL), AD-MIX (8.6 g), This was followed by addition of benzyl (2E)-3-[6-(morpholin-4-yl)pyridin-3-yl]prop-2-enoate (2 g, 6.17 mmol, 1.00 equiv) and MeSO2NH2 (586 g, 6.17 mol, 1.00 equiv) with stirring at 0° C. The resulting solution was stirred for 3 days at room temperature. The reaction was then quenched by the addition of Na2SO3. The resulting solution was extracted with 3×150 mL of ethyl acetate and the organic layers combined and dried over anhydrous sodium sulfate and concentrated under vacuum. The residue was applied onto a silica gel column with ethyl acetate/petroleum ether (1:1). This resulted in 5.4 g (49%) of benzyl (2R,3S)-2,3-dihydroxy-3-[6-(morpholin-4-yl)pyridin-3-yl]propanoate as a light yellow solid. MS (ES, m/z): 359 (M+H).

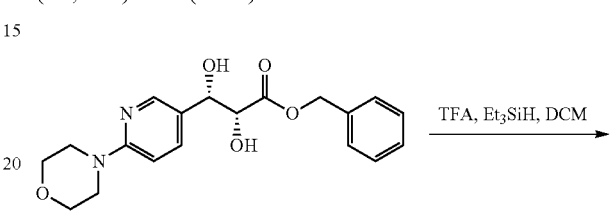

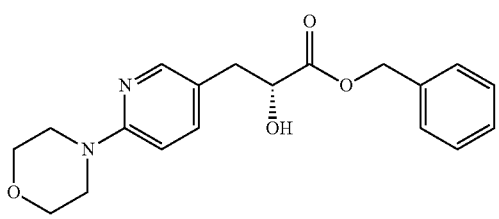

M7 benzyl (2R)-2-hydroxy-3-[6-(morpholin-4-yl)pyridin-3-yl]propanoate (M7)

Into a 100-mL round-bottom flask, was placed a solution of benzyl (2R,3S)-2,3-dihydroxy-3-[6-(morpholin-4-yl)pyridin-3-yl]propanoate (1.5 g, 4.19 mmol, 1.00 equiv) in dichloromethane (15 mL), trifluoroacetic acid (5 mL), Et3SiH (10 mL). The resulting solution was stirred for 3 days at 50° C. The resulting mixture was concentrated under vacuum. The reaction was then quenched by the addition of water/ice. The pH value of the solution was adjusted to 9 with sodium bicarbonate aq. The resulting solution was extracted with 3×40 mL of dichloromethane and the organic layers combined and dried over anhydrous sodium sulfate and concentrated under vacuum. The residue was applied onto a silica gel column with ethyl acetate/petroleum ether (1:2). This resulted in 2.3 g (27%) of benzyl (2R)-2-hydroxy-3-[6-(morpholin-4-yl)pyridin-3-yl]propanoate as yellow oil. MS (ES, m/z): 343 (M+H); $^1$H NMR (CDCl3, 300 MHz) δ: 8.02 (s, 1H), 7.43-7.32 (m, 6H), 6.54 (d, J=4.4 Hz, 1H), 5.21 (s, 2H), 4.52-4.46 (m, 1H), 3.84 (t, J=7.8 Hz, 4H), 3.48 (t, J=4.8 Hz, 4H) 3.05-3.01 (m, 1H), 2.91-2.85 (m, 1H).

Preparation Example 8: Preparation of Monomer M8

M8

Experimental Details

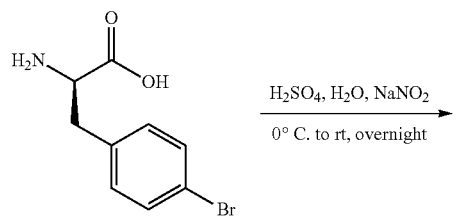

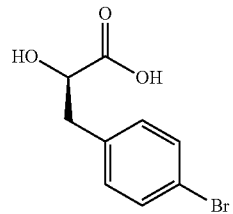

(2R)-3-(4-bromophenyl)-2-hydroxypropanoic Acid

Into a 5-L 4-necked round-bottom flask, was placed sulfuric acid/H2O (0.5 mol/L)(3.2 L), (2R)-2-amino-3-(4-bromophenyl)propanoic acid (100 g, 409.69 mmol, 1.00 equiv). This was followed by the addition of a solution of NaNO2 (350 g, 5.07 mol, 12.38 equiv) in H2O (500 mL) dropwise with stirring at 0° C. The resulting solution was stirred overnight at room temperature. The solids were collected by filtration. The solid was dried in an oven under reduced pressure. This resulted in 146 g (73%) of (2R)-3-(4-bromophenyl)-2-hydroxypropanoic acid as a white solid. MS (ES, m/z): 243 (M–H).

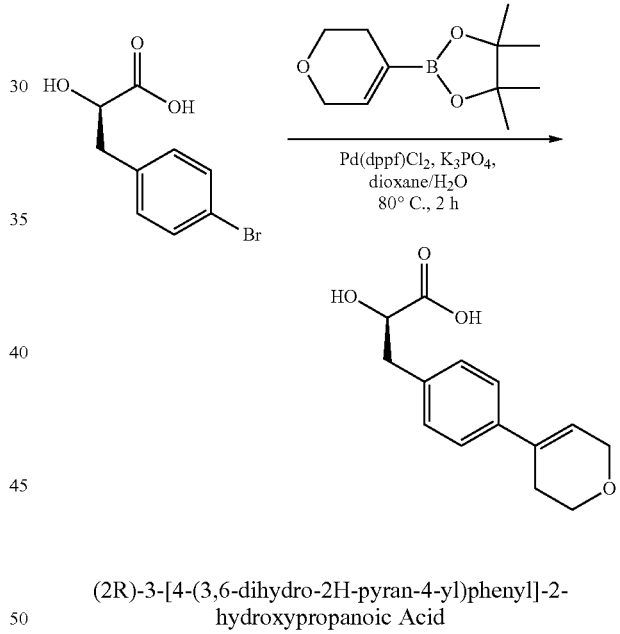

(2R)-3-[4-(3,6-dihydro-2H-pyran-4-yl)phenyl]-2-hydroxypropanoic Acid

Into a 1-L round-bottom flask purged and maintained with an inert atmosphere of nitrogen, was placed dioxane (500 mL), H2O (50 mL), (2R)-3-(4-bromophenyl)-2-hydroxypropanoic acid (30 g, 122.41 mmol, 1.00 equiv), 2-(3,6-dihydro-2H-pyran-4-yl)-4,4,5,5-tetramethyl-1,3,2-dioxaborolane (40 g, 190.41 mmol, 1.60 equiv), K3PO4 (65 g, 306.21 mmol, 2.50 equiv), Pd(dppf)Cl2 (4.5 g, 6.15 mmol, 0.05 equiv). The resulting solution was stirred for 2 h at 75° C. in an oil bath. The reaction mixture was cooled. The resulting mixture was concentrated under vacuum. The residue was dissolved in 100 mL of ether. The solids were filtered out. The solids were dissolved in 10 mL of H2O and 500 mL of THF. The pH value of the solution was adjusted to 4-5 with hydrogen chloride (12 mol/L). The solids were filtered out. The filtrate was dried over anhydrous sodium sulfate and concentrated under vacuum. This resulted in 28 g (92%) of (2R)-3-[4-(3,6-dihydro-2H-pyran-4-yl)phenyl]-2-hydroxypropanoic acid as a light brown solid. MS (ES, m/z): 249 (M+H).

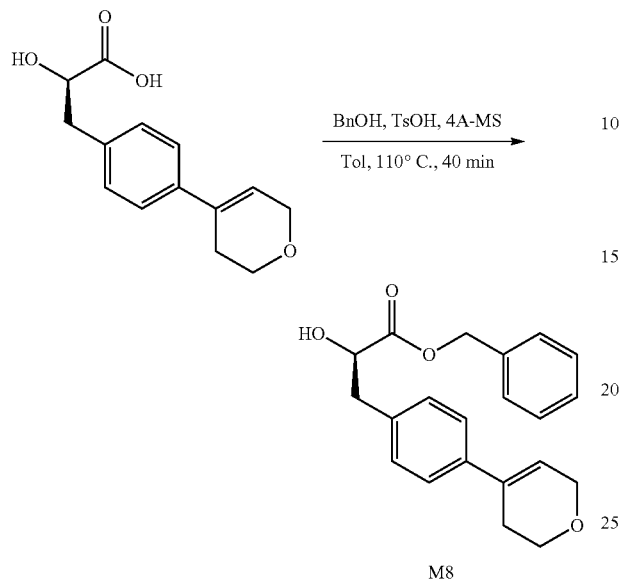

M8

Benzyl (2R)-3-[4-(3,6-dihydro-2H-pyran-4-yl)phenyl]-2-hydroxypropanoate (M8)

Into a 500-mL round-bottom flask, was placed toluene (300 mL), (2R)-3-[4-(3,6-dihydro-2H-pyran-4-yl)phenyl]-2-hydroxypropanoic acid (9 g, 36.25 mmol, 1.00 equiv), phenylmethanol (10.3 g, 95.25 mmol, 2.50 equiv), TsOH (2 g, 11.61 mmol, 0.30 equiv), 4A-MS (5.4 g). The resulting solution was stirred for 40 min at 110° C. in an oil bath. The reaction mixture was cooled. The solids were filtered out. The filtrate was concentrated under vacuum. The residue was applied onto a silica gel column with ethyl acetate/petroleum ether (1:10-1:3). This resulted in 24 g (98%) of benzyl (2R)-3-[4-(3,6-dihydro-2H-pyran-4-yl)phenyl]-2-hydroxypropanoate as a white solid. MS (ES, m/z): 339 (M+H); $^1$HNMR (300 MHz, CDCl$_3$, ppm): δ 7.62-7.30 (m, 7H), 7.13 (d, J=8.4 Hz, 2H), 6.12-6.10 (m, 1H), 5.24 (s, 2H), 4.52-4.48 (m, 1H), 4.35-4.32 (m, 2H), 3.96-3.92 (m, 2H), 3.16-2.95 (m, 2H), 2.67-2.49 (m, 2H).

Preparation Example 9: Preparation of Monomer M9

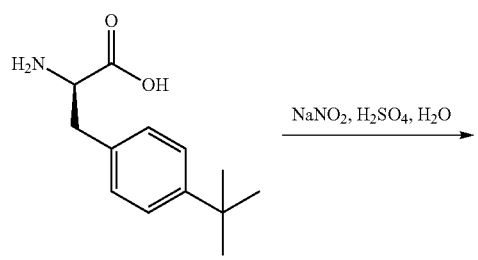

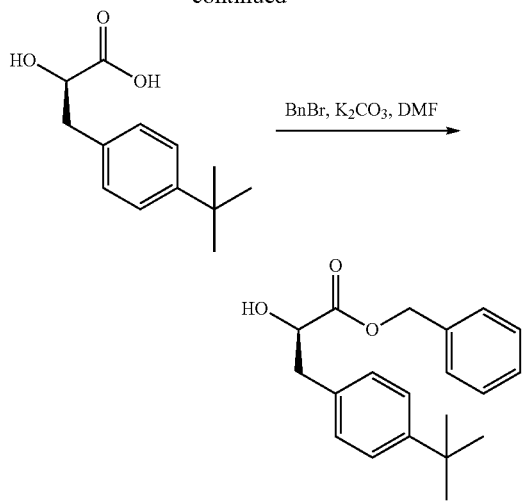

M9

Experimental Details

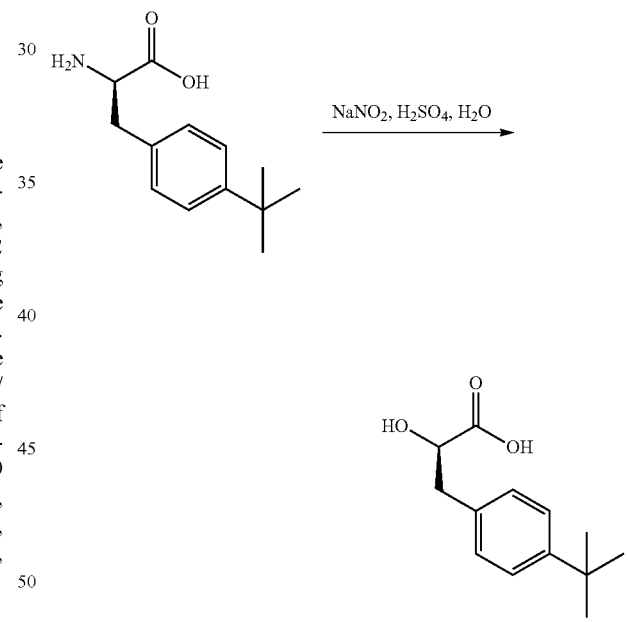

(2R)-3-(4-tert-butylphenyl)-2-hydroxypropanoic Acid

Into a 2000-mL 3-necked round-bottom flask, was placed a solution of (2R)-2-amino-3-(4-tert-butylphenyl)propanoic acid (30 g, 135.57 mmol, 1.00 equiv) in sulfuric acid (0.5M) (480 mL), a solution of NaN2 (94 g, 1.36 mol, 10.00 equiv) in water (180 mL). The resulting solution was stirred overnight at room temperature in an ice/salt bath. The solids were collected by filtration. This resulted in 20.0 g (66%) of (2R)-3-(4-tert-butylphenyl)-2-hydroxypropanoic acid as a white solid. MS (ES, m/z): 221 (M−H).

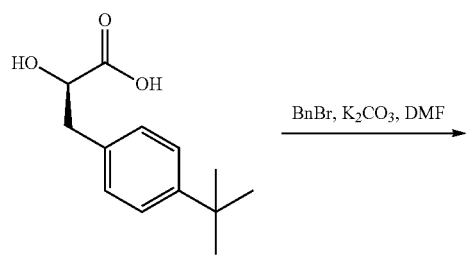

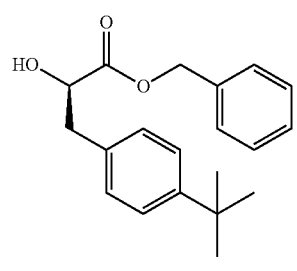

(2R)-3-(4-tert-butylphenyl)-2-hydroxypropanoate (M9)

Into a 2000-mL 3-necked round-bottom flask, was placed a solution of (2R)-3-(4-tert-butylphenyl)-2-hydroxypropanoic acid (40 g, 179.95 mmol, 1.00 equiv) in N,N-dimethylformamide (1000 mL), potassium carbonate (50 g, 361.77 mmol, 2.00 equiv), BnBr (61 g, 356.66 mmol, 2.00 equiv). The resulting solution was stirred for 2 h at room temperature. The resulting solution was diluted with 2000 mL of EA. The resulting mixture was washed with 3×2000 mL of H2O. The resulting mixture was washed with 2×2000 mL of Brine. The mixture was dried over anhydrous sodium sulfate. The solids were filtered out. The resulting mixture was concentrated under vacuum. The residue was applied onto a silica gel column with ethyl acetate/petroleum ether (1:50-1:10). This resulted in 42 g (75%) of benzyl (2R)-3-(4-tert-butylphenyl)-2-hydroxypropanoate as yellow oil. $^1$HNMR (300 MHz, CDCl$_3$, ppm): δ 7.40-7.27 (m, 7H), 7.10 (d, J=8.1 Hz, 2H), 5.20 (s, 2H), 4.49 (t, J=5.4 Hz, 1H), 3.14-2.93 (m, 2H), 1.31 (s, 9H).

Preparation Example 10: Preparation of Monomer M10

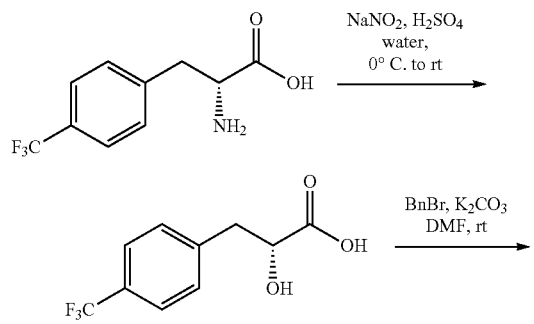

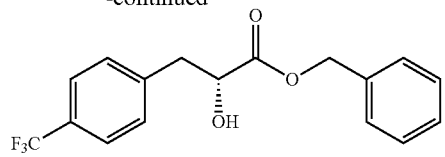

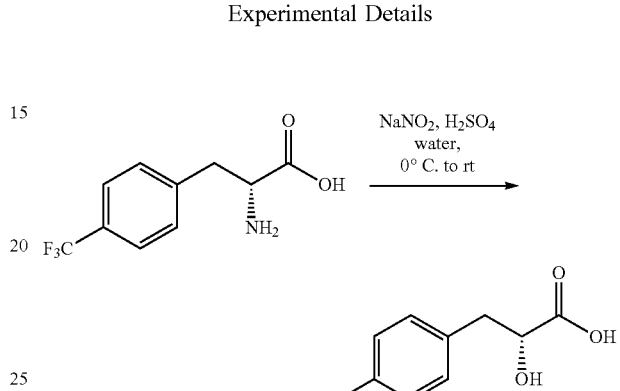

2-Hydroxy-3-[4-(trifluoromethyl)phenyl]propanoic Acid

Into a 500-mL 3-necked round-bottom flask, was placed 2-amino-3-[4-(trifluoromethyl)phenyl]propanoic acid (20 g, 85.77 mmol, 1.00 equiv), sulfuric acid (0.5 M) (340 mL). This was followed by the addition of a solution of NaNO$_2$ (35.5 g, 514.49 mmol, 6.00 equiv) in water (80 mL) dropwise with stirring at 0° C. The resulting solution was stirred for 1 h at 0° C. The resulting solution was allowed to react, with stirring, overnight at room temperature. The solids were collected by filtration. This resulted in 17.5 g (87%) of 2-hydroxy-3-[4-(trifluoromethyl)phenyl]propanoic acid as a white solid. MS (ES, m/z): 233 (M−H); $^1$H NMR (DMSO, 300 MHz) δ: 7.63 (d, J=3.9 Hz, 2H), 7.46 (d, J=4.0 Hz, 2H), 4.21-4.17 (m, 1H), 3.09-3.03 (m, 1H), 2.91-2.84 (m, 1H).

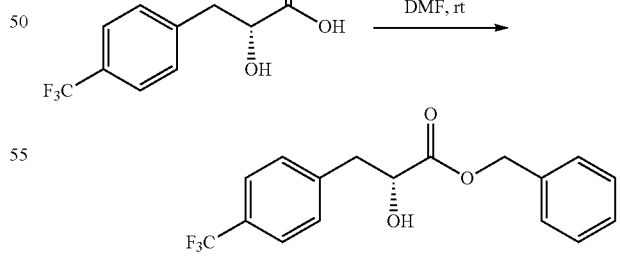

Benzyl (2R)-2-hydroxy-3-[4-(trifluoromethyl)phenyl]propanoate (M10)

Into a 500-mL 3-necked round-bottom flask, was placed (2R)-2-hydroxy-3-[4-(trifluoromethyl)phenyl]propanoic acid (17.5 g, 74.73 mmol, 1.00 equiv), (bromomethyl)benzene (15.3 g, 89.46 mmol, 1.20 equiv), potassium carbonate (31 g, 224.30 mmol, 3.00 equiv), N,N-dimethylformamide (100 mL). The resulting solution was stirred for 30 min at 0° C. and allowed to reach room temperature with stirring overnight. The reaction was then quenched by the addition of 250 mL of water. The resulting solution was extracted with 3×150 mL of ethyl acetate and the organic layers were combined. The resulting mixture was washed with 3×250 mL of brine. The organic phase was dried over anhydrous sodium sulfate and concentrated under vacuum. The residue was purified on a silica gel column with ethyl acetate/petroleum ether (1:6) to give 10.6 g (44%) of benzyl (2R)-2-hydroxy-3-[4-(trifluoromethyl)phenyl]propanoate as a white solid. $^1$H NMR (DMSO, 300 MHz) δ: 7.60 (d, J=4.0 Hz, 2H), 7.42 (d, J=4.0 Hz, 2H), 7.39-7.27 (m, 5H), 5.72 (d, J=3 Hz, 1H), 5.10 (s, 2H), 4.40-4.33 (m, 1H), 3.10-3.04 (m, 1H), 2.99-2.91 (m, 1H).

Preparation Example 11: Preparation of Monomer M11

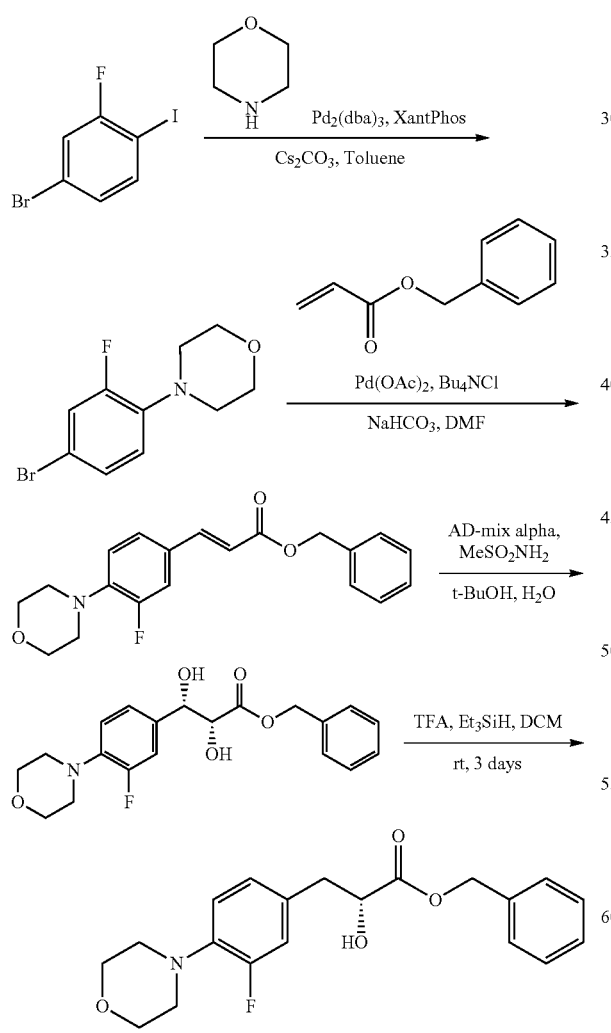

M11

Experimental Details

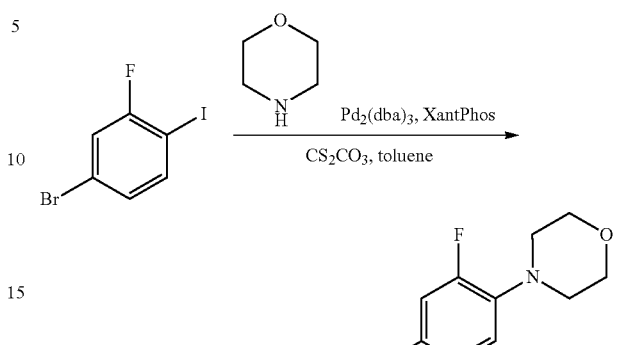

4-(4-Bromo-2-fluorophenyl)morpholine

Into a 1-L round-bottom flask purged and maintained with an inert atmosphere of nitrogen, was placed a solution of 4-bromo-2-fluoro-1-iodobenzene (15 g, 49.85 mmol, 1.00 equiv) in toluene (300 mL). Pd$_2$(dba)$_3$ (1.3 g, 1.42 mmol, 0.03 equiv). Cs2CO3 (41 g, 125.45 mmol, 2.50 equiv). XantPhos (2.9 g, 5.01 mmol, 0.10 equiv). morpholine (4.3 g, 49.36 mmol, 1.00 equiv). The resulting solution was stirred overnight at 100° C. The reaction was then quenched by the addition of 150 mL of water. The resulting solution was extracted with 3×100 mL of ethyl acetate and the organic layers combined and dried over anhydrous sodium sulfate and concentrated under vacuum. The residue was applied onto a silica gel column with ethyl acetate/petroleum ether (1:15). This resulted in 10.5 g (81%) of 4-(4-bromo-2-fluorophenyl)morpholine as a yellow solid. MS (ES, m/z): 260 (M+H).

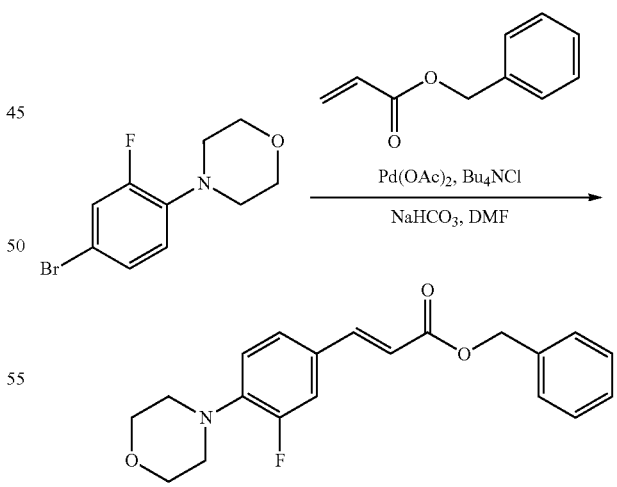

Benzyl (2E)-3-[3-fluoro-4-(morpholin-4-yl)phenyl]prop-2-enoate

Into a 100-mL round-bottom flask purged and maintained with an inert atmosphere of nitrogen, was placed 4-(4-bromo-2-fluorophenyl)morpholine (1.25 g, 4.81 mmol, 1.00 equiv). Pd(OAc)2 (50 mg, 0.22 mmol, 0.05 equiv). a solution of sodium bicarbonate (810 mg, 9.64 mmol, 2.00 equiv) in N,N-dimethylformamide (30 mL). Bu4NCl (2.7 g, 9.72 mmol, 2.00 equiv). benzyl prop-2-enoate (1.6 g, 9.87 mmol, 2.00 equiv). The resulting solution was stirred for 36 h at 100° C. The reaction was then quenched by the addition of water. The resulting solution was extracted with 4×100 mL of ethyl acetate and the organic layers combined. The organic phase was washed with 3×60 mL of brine. The organic phase was dried over anhydrous sodium sulfate and concentrated under vacuum. The residue was applied onto a silica gel column with ethyl acetate/petroleum ether (1:5). This resulted in 10.5 g (80%) of benzyl (2E)-3-[3-fluoro-4-(morpholin-4-yl)phenyl]prop-2-enoate as a yellow solid. MS (ES, m/z): 342 (M+H).

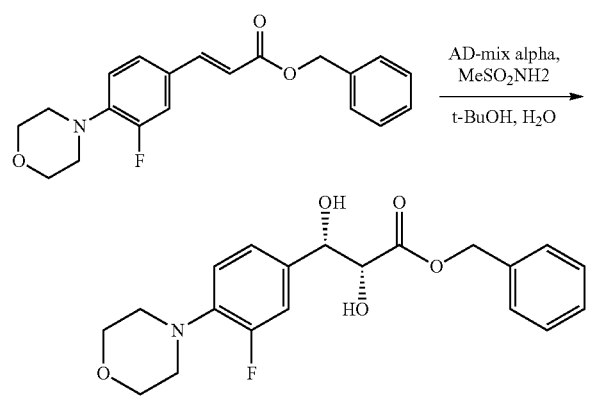

Benzyl (2R,3S)-3-[3-fluoro-4-(morpholin-4-yl)phenyl]-2,3-dihydroxypropanoate

Into a 250-mL 3-necked round-bottom flask, was placed a solution of AD-mix (12.3 g) in tert-Butanol/H2O (60:60 mL). This was followed by the addition of benzyl (2E)-3-[3-fluoro-4-(morpholin-4-yl)phenyl]prop-2-enoate (3 g, 8.79 mmol, 1.00 equiv), in portions at 0° C. To this was added MeSO2NH2 (1.23 g, 1.00 equiv), in portions at 0° C. The resulting solution was stirred for 3 days at room temperature. The reaction was then quenched by the addition of Na2SO3. The resulting solution was extracted with 3×100 mL of ethyl acetate and the organic layers combined. The organic phase was washed with 3×60 mL of brine. The organic phase was dried over anhydrous sodium sulfate and concentrated under vacuum. The residue was applied onto a silica gel column with ethyl acetate/petroleum ether (1:1). This resulted in 9.5 g (72%) of benzyl (2R,3S)-3-[3-fluoro-4-(morpholin-4-yl)phenyl]-2,3-dihydroxypropanoate as yellow oil. MS (ES, m/z): 376 (M+H).

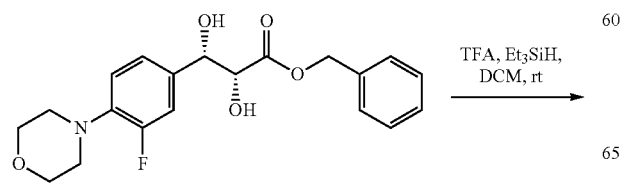

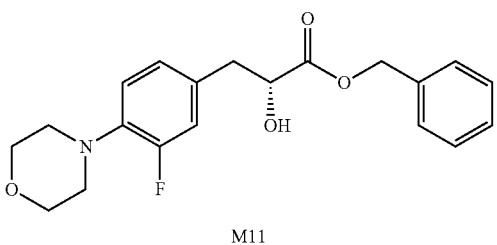

M11

Benzyl (2R)-3-[3-fluoro-4-(morpholin-4-yl)phenyl]-2-hydroxypropanoate (M11)

Into a 40-mL vial, was placed a solution of benzyl (2R,3S)-3-[3-fluoro-4-(morpholin-4-yl)phenyl]-2,3-dihydroxypropanoate (900 mg, 2.40 mmol, 1.00 equiv) in dichloromethane (2 mL), Et3SiH (4 mL)., trifluoroacetic acid (2 mL). The resulting solution was stirred for 3 days at room temperature. The reaction was then quenched by the addition of water/ice. The resulting solution was extracted with 3×80 mL of ethyl acetate and the organic layers combined. The organic phase was washed with 3×60 mL of brine. The organic phase was dried over anhydrous sodium sulfate and concentrated under vacuum. The residue was applied onto a silica gel column with ethyl acetate/petroleum ether (1:3). This resulted in 4.1 g (48%) of benzyl (2R)-3-[3-fluoro-4-(morpholin-4-yl)phenyl]-2-hydroxypropanoate as reddish oil. MS (ES, m/z): 360 (M+H).

Preparation Example 12: Preparation of Monomer M12

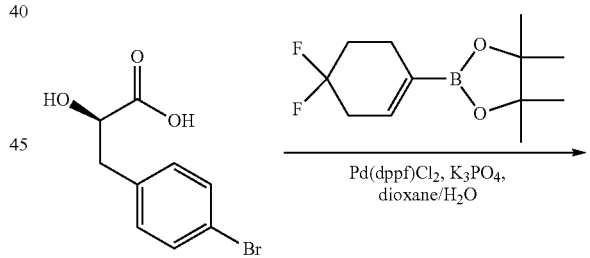

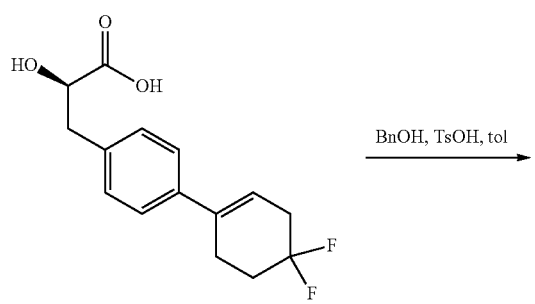

Experimental Details

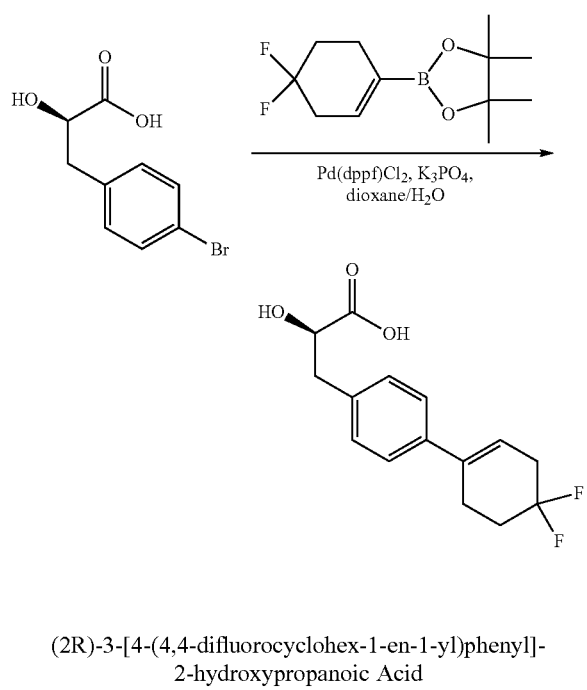

(2R)-3-[4-(4,4-difluorocyclohex-1-en-1-yl)phenyl]-2-hydroxypropanoic Acid

Into a 250-mL round-bottom flask purged and maintained with an inert atmosphere of nitrogen, was placed dioxane/H₂O (88 mL), (2R)-3-(4-bromophenyl)-2-hydroxypropanoic acid (4 g, 16.32 mmol, 1.00 equiv), 2-(4,4-difluorocyclohex-1-en-1-yl)-4,4,5,5-tetramethyl-1,3,2-dioxaborolane (4.0 g, 16.39 mmol, 1.00 equiv), Pd(dppf)Cl₂ (640 mg, 0.87 mmol, 0.05 equiv), K₃PO₄ (11 g, 51.82 mmol, 3.00 equiv). The resulting solution was stirred for 4 h at 80° C. in an oil bath. The reaction mixture was cooled. The resulting mixture was concentrated under vacuum. The residue was dissolved in 50 mL of ether. The solids were collected by filtration. The solids were dissolved in 50 mL of THF. The pH value of the solution was adjusted to 5 with hydrogen chloride (12 mol/L). The resulting solution was diluted with 200 mL of ethyl acetate. The solids were collected by filtration. The filtrate was dried over anhydrous sodium sulfate and concentrated under vacuum. This resulted in 4.5 g (98%) of (2R)-3-[4-(4,4-difluorocyclohex-1-en-1-yl)phenyl]-2-hydroxypropanoic acid as light yellow oil. MS (ES, m/z): 281 (M-H).

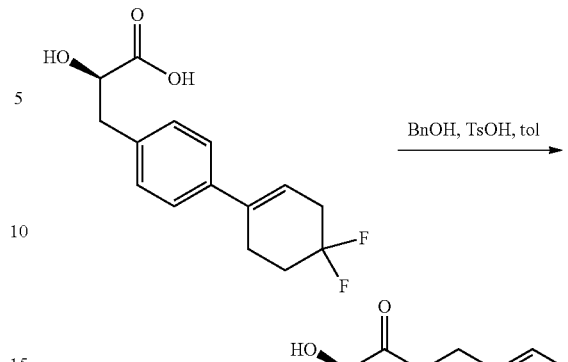

Benzyl (2R)-3-[4-(4,4-difluorocyclohex-1-en-1-yl)phenyl]-2-hydroxypropanoate (M12)

Into a 500-mL round-bottom flask, was placed toluene (200 mL), (2R)-3-[4-(4,4-difluorocyclohex-1-en-1-yl)phenyl]-2-hydroxypropanoic acid (4.5 g, 15.94 mmol, 1.00 equiv), BnOH (2.24 g, 1.30 equiv), TsOH (540 mg, 3.14 mmol, 0.20 equiv), 4A-MS (2 g). The resulting solution was stirred for 4 h at 110° C. in an oil bath. The reaction mixture was cooled. The solids were filtered out. The filtrate mixture was concentrated under vacuum. The residue was applied onto a silica gel column with ethyl acetate/petroleum ether (1:20-1:10). This resulted in 5 g (84%) of benzyl (2R)-3-[4-(4,4-difluorocyclohex-1-en-1-yl)phenyl]-2-hydroxypropanoate as a light yellow solid. ¹HNMR (300 MHz, CDCl3, ppm): δ 7.62-7.30 (m, 7H), 7.11 (d, J=8.4 Hz, 2H), 5.89 (br, 1H), 5.21 (s, 2H), 4.52-4.48 (m, 1H), 3.16-2.95 (m, 2H), 2.71-2.67 (m, 4H), 2.25-2.12 (m, 2H).

Preparation Example 13: Preparation of Monomer M13

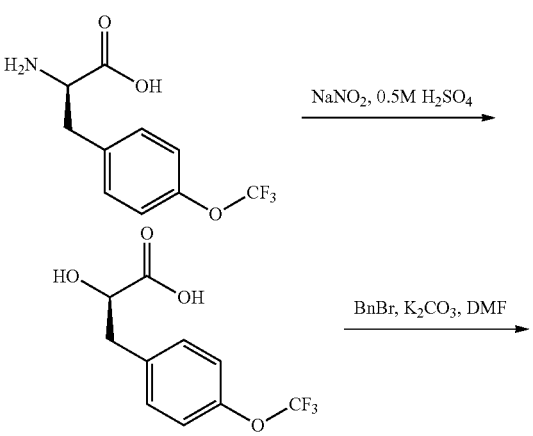

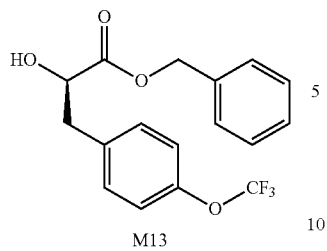

Experimental Details

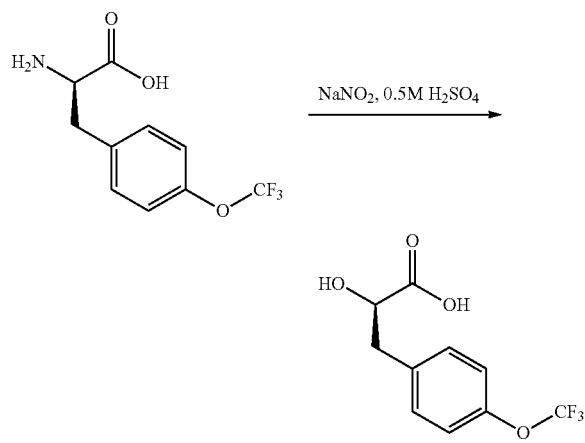

(2R)-2-hydroxy-3-[4-(trifluoromethoxy)phenyl]propanoic Acid

Into a 1 000-mL 3-necked round-bottom flask, was placed (2R)-2-amino-3-[4-(trifluoromethoxy)phenyl]propanoic acid hydrochloride (10 g, 35.01 mmol, 1.00 equiv). This was followed by the addition of a solution of NaNO2 (29 g, 420.29 mmol, 12.00 equiv) in water (150 mL) dropwise with stirring at 0° C. To this was added sulfuric acid (0.5M/L) (300 mL). The resulting solution was stirred overnight at room temperature. The resulting solution was extracted with 3×200 mL of ethyl acetate and the organic layers combined. The resulting mixture was washed with 3×200 mL of brine. The mixture was dried over anhydrous sodium sulfate and concentrated under vacuum. This resulted in 11 g (crude) of (2R)-2-hydroxy-3-[4-(trifluoromethoxy)phenyl]propanoic acid as yellow oil. MS (ES, m/z): 249 (M−H).

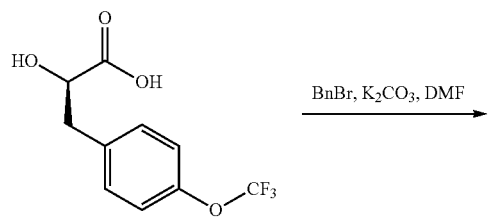

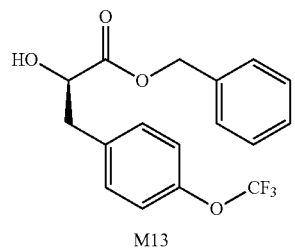

benzyl (2R)-2-hydroxy-3-[4-(trifluoromethoxy)phenyl]propanoate (M13)

Into a 1000-mL 3-necked round-bottom flask, was placed (2R)-2-hydroxy-3-[4-(trifluoromethoxy)phenyl]propanoic acid (11 g, 43.97 mmol, 1.00 equiv), N,N-dimethylformamide (300 mL), potassium carbonate (12 g, 86.82 mmol, 2.00 equiv). This was followed by the addition of (bromomethyl)benzene (9 g, 52.62 mmol, 1.20 equiv) dropwise with stirring at 0° C. The resulting solution was stirred overnight at room temperature. The reaction was then quenched by the addition of 100 mL of water. The resulting solution was extracted with 3×150 mL of ethyl acetate and the organic layers combined. The resulting mixture was washed with 3×200 mL of brine. The mixture was dried over anhydrous sodium sulfate and concentrated under vacuum. This resulted in 7.6 g (51%) of benzyl (2R)-2-hydroxy-3-[4-(trifluoromethoxy)phenyl]propanoate as yellow oil. $^1$H NMR (DMSO, 300 MHz) δ: 7.45-7.30 (m, 7H), 7.25-7.17 (m, 2H), 5.70 (d, J=2.7 Hz, 1H), 5.10 (s, 2H), 4.34-4.32 (m, 1H), 3.04-2.98 (m, 1H), 2.92-2.85 (m, 1H).

Preparation Example 14: Preparation of Monomer M14

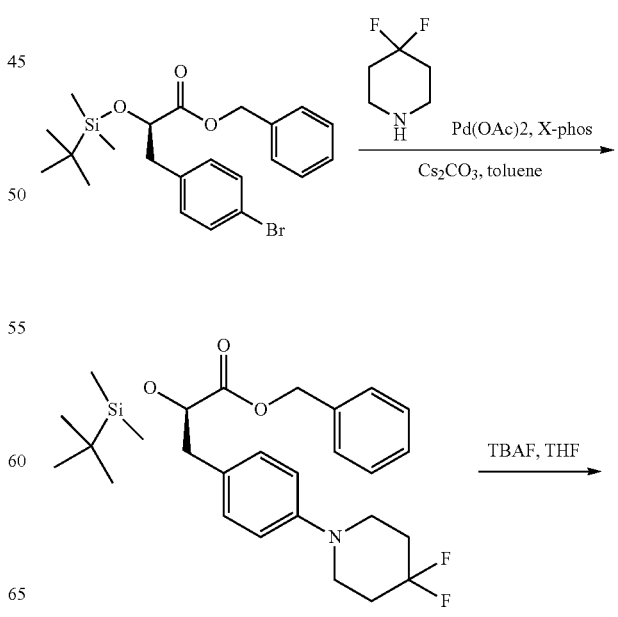

-continued

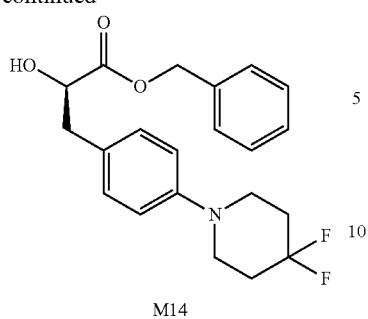

M14

Experimental Details

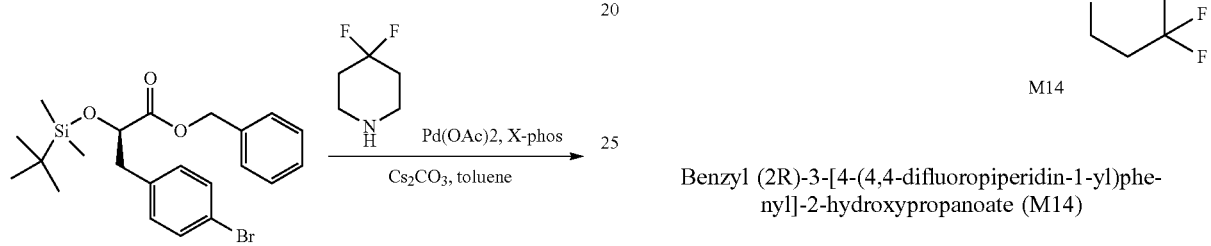

Benzyl (2R)-2-[(tert-butyldimethylsilyl)oxy]-3-[4-(4,4-difluoropiperidin-1-yl)phenyl]propanoate Into a 250-mL round-bottom flask purged and maintained with an inert atmosphere of nitrogen, was placed benzyl (2R)-3-(4-bromophenyl)-2-[(tert-butyldimethylsilyl)oxy]propanoate (14.53 g, 32.33 mmol, 1.00 equiv), 4,4-difluoropiperidine (6.2 g, 51.19 mmol, 1.20 equiv), CsCO3 (19 g, 3.00 equiv), X-PhOS (309 mg, 0.02 equiv), Tol (50 mL), Pd(OAc)2 (145 mg, 0.65 mmol, 0.02 equiv). The resulting solution was stirred for 16 h at 900° C. The resulting mixture was concentrated under vacuum. The residue was applied onto a silica gel column with ethyl acetate/petroleum ether (1:6). This resulted in 12.28 g (78%) of benzyl (2R)-2-[(tert-butyldimethylsilyl)oxy]-3-[4-(4,4-difluoropiperidin-1-yl)phenyl]propanoate as colorless oil.

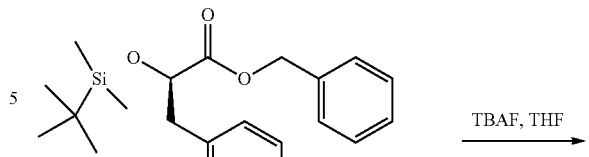

Benzyl (2R)-3-[4-(4,4-difluoropiperidin-1-yl)phenyl]-2-hydroxypropanoate (M14)

Into a 100-mL 3-necked round-bottom flask, was placed benzyl (2R)-2-[(tert-butyldimethylsilyl)oxy]-3-[4-(4,4-difluoropiperidin-1-yl)phenyl]propanoate (12.28 g, 25.08 mmol, 1.00 equiv), tetrahydrofuran (30 mL), TBAF (8.4 g, 32.13 mmol, 1.20 equiv). The resulting solution was stirred for 20 min at room temperature. The resulting mixture was concentrated under vacuum. The resulting solution was diluted with 100 mL of ethyl acetate. The residue was applied onto a silica gel column with ethyl acetate/petroleum ether (1:10). This resulted in 6.8 g (72%) of benzyl (2R)-3-[4-(4,4-difluoropiperidin-1-yl)phenyl]-2-hydroxypropanoate as a white solid. MS (ES, m/z): 376 (M+H).

Preparation Example 15: Preparation of Monomer M15

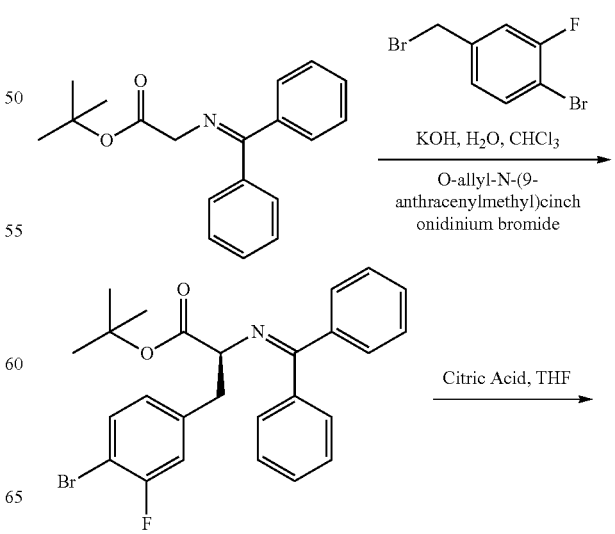

Experimental Details

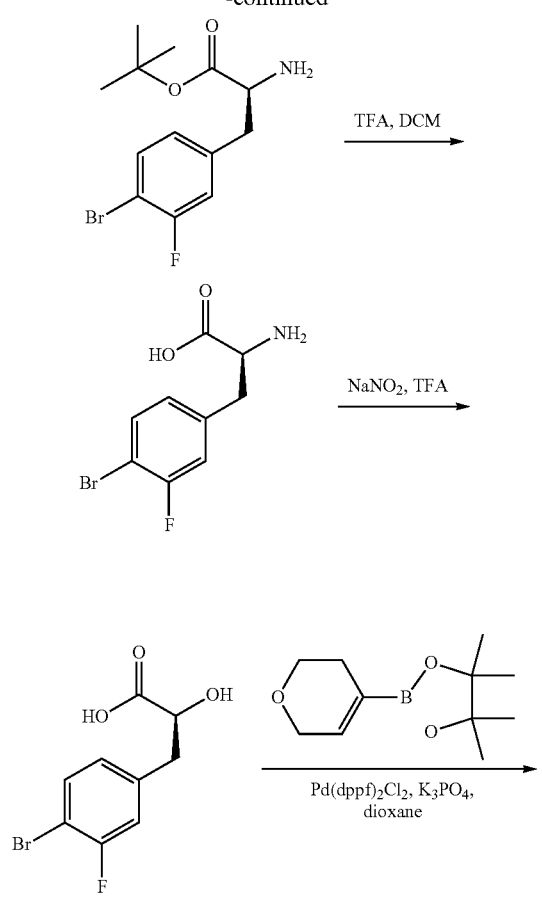

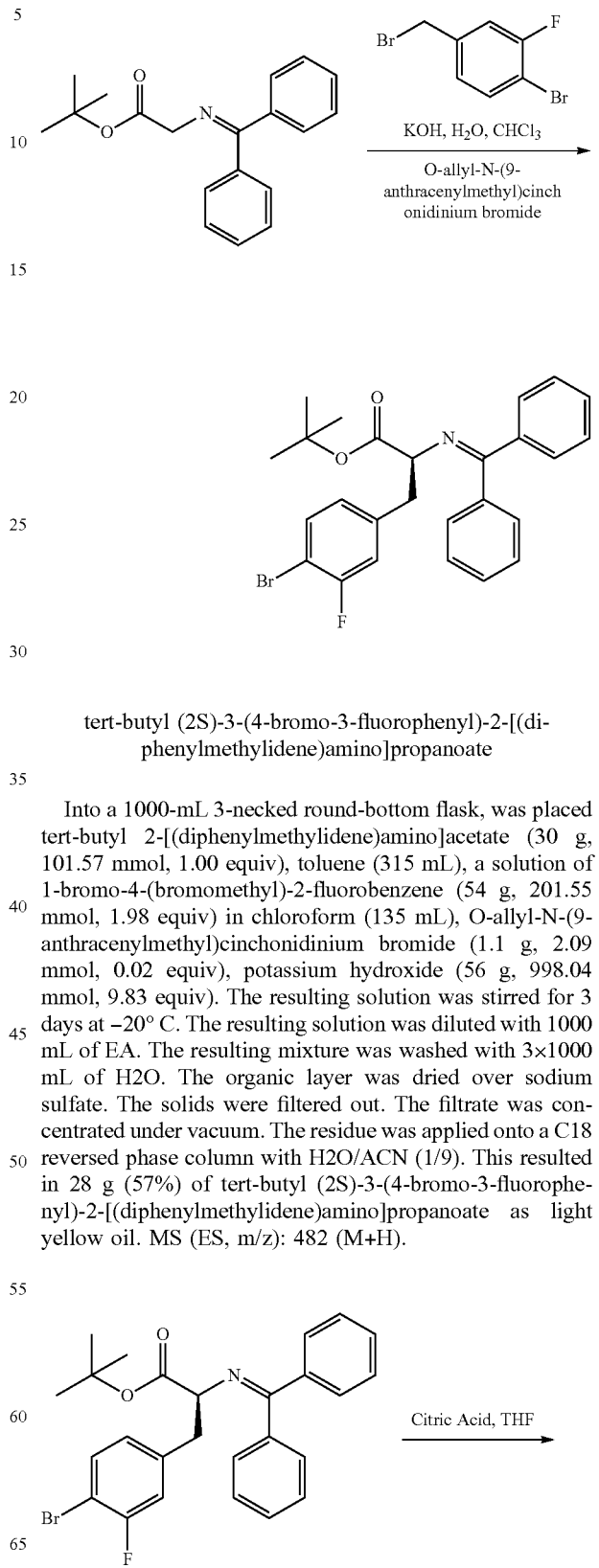

tert-butyl (2S)-3-(4-bromo-3-fluorophenyl)-2-[(diphenylmethylidene)amino]propanoate Into a 1000-mL 3-necked round-bottom flask, was placed tert-butyl 2-[(diphenylmethylidene)amino]acetate (30 g, 101.57 mmol, 1.00 equiv), toluene (315 mL), a solution of 1-bromo-4-(bromomethyl)-2-fluorobenzene (54 g, 201.55 mmol, 1.98 equiv) in chloroform (135 mL), O-allyl-N-(9-anthracenylmethyl)cinchonidinium bromide (1.1 g, 2.09 mmol, 0.02 equiv), potassium hydroxide (56 g, 998.04 mmol, 9.83 equiv). The resulting solution was stirred for 3 days at −20° C. The resulting solution was diluted with 1000 mL of EA. The resulting mixture was washed with 3×1000 mL of H2O. The organic layer was dried over sodium sulfate. The solids were filtered out. The filtrate was concentrated under vacuum. The residue was applied onto a C18 reversed phase column with H2O/ACN (1/9). This resulted in 28 g (57%) of tert-butyl (2S)-3-(4-bromo-3-fluorophenyl)-2-[(diphenylmethylidene)amino]propanoate as light yellow oil. MS (ES, m/z): 482 (M+H).

-continued

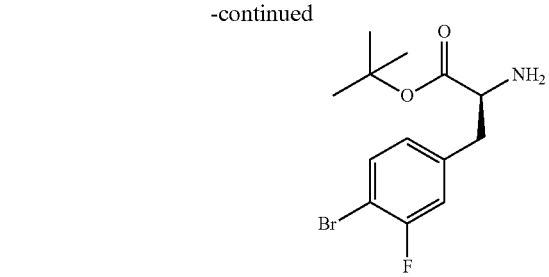

tert-butyl (2S)-2-amino-3-(4-bromo-3-fluorophenyl)propanoate

Into a 2-L 3-necked round-bottom flask, was placed tert-butyl (2S)-3-(4-bromo-3-fluorophenyl)-2-[(diphenylmethylidene)amino]propanoate (28 g, 58.04 mmol, 1.00 equiv), tetrahydrofuran (580 mL), Citric Acid (580 mL). The resulting solution was stirred for 4 h at room temperature. The resulting mixture was concentrated under vacuum. The resulting solution was diluted with 1000 mL of water. The resulting solution was extracted with 3×200 mL of ether and the aqueous layers combined. The pH value of the aqueous layer was adjusted to 8 with sodium bicarbonate and extracted with 3×300 mL of ethyl acetate. The organic layers combined and dried over sodium sulfate and concentrated under vacuum. This resulted in 14.8 g (80%) of tert-butyl (2S)-2-amino-3-(4-bromo-3-fluorophenyl)propanoate as light yellow oil. MS (ES, m/z): 318 (M+H).

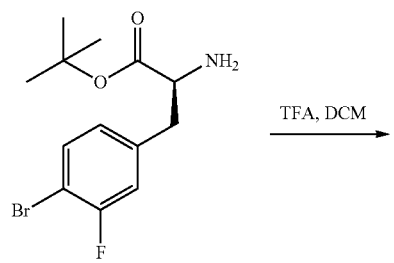

TFA, DCM →

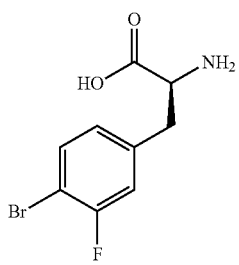

(2S)-2-amino-3-(4-bromo-3-fluorophenyl)propanoic Acid

Into a 500-mL round-bottom flask, was placed tert-butyl (2S)-2-amino-3-(4-bromo-3-fluorophenyl)propanoate (5.9 g, 18.54 mmol, 1.00 equiv), dichloromethane (200 mL), trifluoroacetic acid (21 g, 185.77 mmol, 10.02 equiv). The resulting solution was stirred for 3 days at room temperature. The resulting mixture was concentrated under vacuum. The residue was applied onto a C18 reversed phase column with H2O/ACN (1/3). This resulted in 5.4 g (crude) of (2S)-2-amino-3-(4-bromo-3-fluorophenyl)propanoic acid as a white solid. MS (ES, m/z): 262 (M+H).

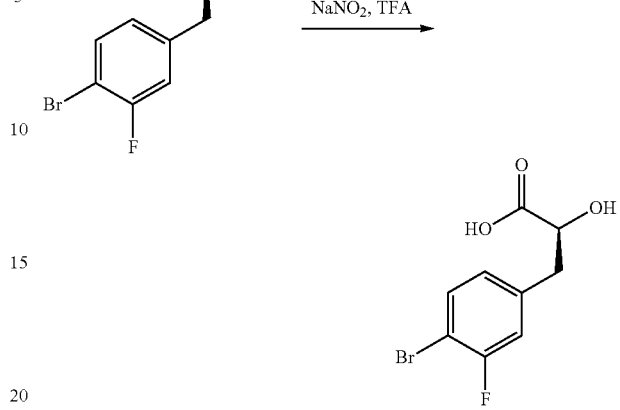

(2S)-3-(4-bromo-3-fluorophenyl)-2-hydroxypropanoic Acid

Into a 500-mL 3-necked round-bottom flask, was placed (2S)-2-amino-3-(4-bromo-3-fluorophenyl)propanoic acid (5.4 g, 20.60 mmol, 1.00 equiv), trifluoroacetic acid (28.3 g, 250.35 mmol, 12.15 equiv), water (180 mL), to the above was added a solution of NaNO2 (17.1 g, 247.83 mmol, 12.03 equiv) in water (180 mL) slowly. The resulting solution was stirred for 16 h at room temperature. The solids were collected by filtration. This resulted in 3.1 g (57%) of (2S)-3-(4-bromo-3-fluorophenyl)-2-hydroxypropanoic acid as a light yellow solid.

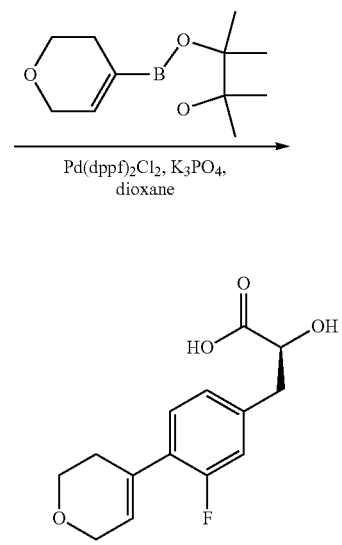

(2S)-3-[4-(3,6-dihydro-2H-pyran-4-yl)-3-fluorophenyl]-2-hydroxypropanoic Acid

Into a 500-mL 3-necked round-bottom flask purged and maintained with an inert atmosphere of nitrogen, was placed (2S)-3-(4-bromo-3-fluorophenyl)-2-hydroxypropanoic acid (3 g, 11.40 mmol, 1.00 equiv), 2-(3,6-dihydro-2H-pyran-4- yl)-4,4,5,5-tetramethyl-1,3,2-dioxaborolane (4.8 g, 22.85 mmol, 2.00 equiv), K3PO4 (7.28 g, 34.30 mmol, 3.01 equiv), dioxane (180 mL), water (18 mL), Pd(dppf)Cl2 (1.67 g, 2.28 mmol, 0.20 equiv). The resulting solution was stirred for 5 h at 80° C. The resulting mixture was concentrated under vacuum. The resulting mixture was diluted with 900 mL of ether. The solids were collected by filtration. The solids were dissolved in 200 mL of tetrahydrofuran. The pH value of the solution was adjusted to 3-4 with hydrogen chloride. The solid was filtered out. The filtrate was concentrated under vacuum. The residue was applied onto a silica gel column with ethyl acetate/petroleum ether (1/10). This resulted in 2.63 g (87%) of (2S)-3-[4-(3,6-dihydro-2H-pyran-4-yl)-3-fluorophenyl]-2-hydroxypropanoic acid as brown solid. MS (ES, m/z): 265 (M−H).

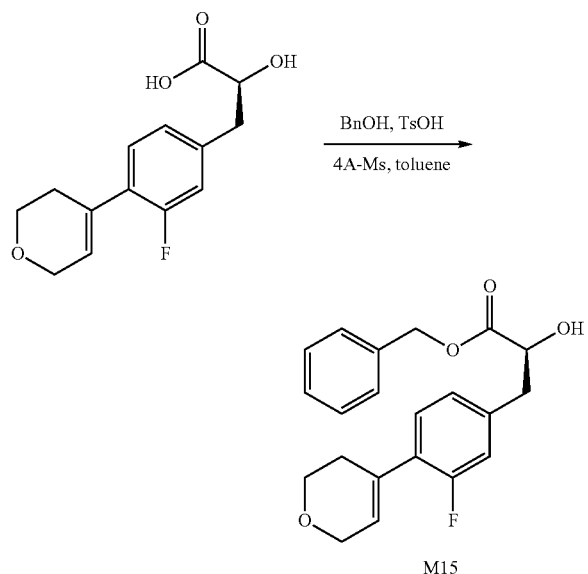

Benzyl (2S)-3-[4-(3,6-dihydro-2H-pyran-4-yl)-3-fluorophenyl]-2-hydroxypropanoate (M15)

Into a 100-mL round-bottom flask, was placed (2S)-3-[4-(3,6-dihydro-2H-pyran-4-yl)-3-fluorophenyl]-2-hydroxypropanoic acid (1 g, 3.76 mmol, 1.00 equiv), BnOH (1.1 g), TsOH (160 mg, 0.93 mmol, 0.25 equiv), 4A-Ms (1 g), toluene (20 mL). The resulting solution was stirred for 4 h at 110° C. The resulting mixture was concentrated under vacuum. The residue was applied onto a silica gel column with ethyl acetate/petroleum ether (1/4). This resulted in 350 mg (26%) of benzyl (2S)-3-[4-(3,6-dihydro-2H-pyran-4-yl)-3-fluorophenyl]-2-hydroxypropanoate as brown oil. $^1$HNMR (300 MHz, CD$_3$OD, ppm): δ 7.37-7.29 (m, 5H), 7.20-7.15 (m, 1H), 6.97-6.92 (m, 2H), 6.02 (br, 1H), 5.19 (s, 2H), 4.44-4.40 (m, 1H), 4.30-4.27 (m, 2H), 3.92-3.885 (m, 2H), 3.33-2.90 (m, 2H), 2.47-2.46 (m, 2H).

Preparation Example 16: Preparation of Monomer M16

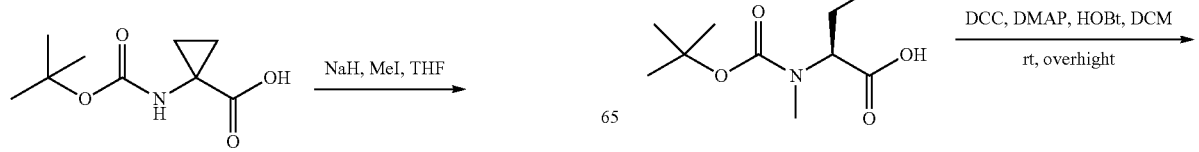

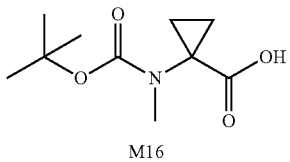

Experimental Details

1-[[(tert-butoxy)carbonyl](methyl)amino]cyclopropane-1-carboxylic Acid (M16)

Into a 100-mL round-bottom flask, was placed 1-[[(tert-butoxy)carbonyl]amino]cyclopropane-1-carboxylic acid (2 g, 9.94 mmol, 1.00 equiv), tetrahydrofuran (30 mL). This was followed by the addition of MeI (5 mL, 8.00 equiv) at 0° C. in 10 min. To this was added sodium hydride (1.32 g, 55.00 mmol, 5.50 equiv) in portions at 0° C. in 10 min. The resulting solution was stirred for 24 h at room temperature. The reaction was slowly poured into 150 mL of water at 0° C. The resulting solution was washed with 30 mL of ether. The aqueous solution was collected and the pH value was adjusted to 3 with citric acid (1 mol/L). The resulting solution was extracted with 3×40 mL of ethyl acetate and the organic layers combined and concentrated under vacuum. This resulted in 2.5 g (crude) of 1-[[(tert-butoxy)carbonyl](methyl)amino]cyclopropane-1-carboxylic acid as a yellow solid. MS (ES, m/z): 216 (M+H).

Preparation Examples 17-32 shown below provide processes for the preparation of various dimer compounds D1 to D16 substituted with a wide variety of groups $R^1$, $R^2$, $R^3$, $R^4$, $Cy^1$ and $Cy^2$ that enable the preparation of a diverse set of dimer compounds used for the preparation of the compounds of the invention.

Preparation Example 17: Preparation of Dimer D1

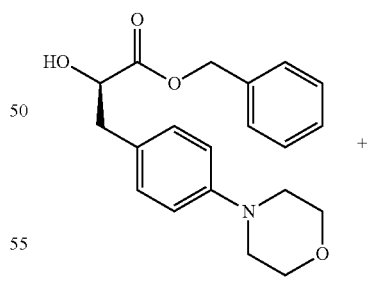

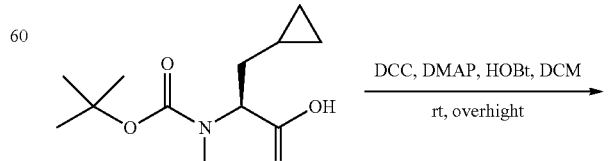

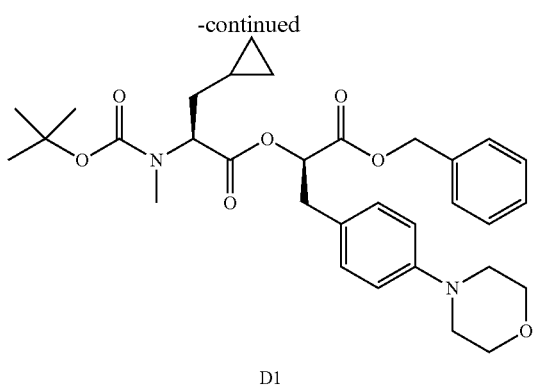

D1

(2R)-1-(benzyloxy)-3-[4-(morpholin-4-yl)phenyl]-1-oxopropan-2-yl (2S)-2-[[(tert-butoxy)carbonyl](methyl)amino]-3-cyclopropylpropanoate (D1)

Into a 250-mL 3-necked round-bottom flask, was placed benzyl (2R)-2-hydroxy-3-[4-(morpholin-4-yl)phenyl]propanoate (2.8 g, 8.20 mmol, 1.00 equiv), (2S)-2-[[(tert-butoxy)carbonyl]amino]-3-cyclopropylpropanoic acid (2 g, 8.72 mmol, 1.00 equiv), dichloromethane (80 mL). This was followed by the addition of DCC (1.9 g, 9.21 mmol, 1.10 equiv), 4-dimethylaminopyridine (1.1 g, 9.00 mmol, 1.10 equiv) and HOBt (1.2 g, 8.88 mmol, 1.10 equiv) in portions with stirring at 0° C. The resulting solution was stirred for 1 overnight at room temperature. The solids were filtered out. The filtrate was concentrated under vacuum. The residue was applied onto a silica gel column with ethyl acetate/petroleum ether (1:5). This resulted in 4.2 g (90%) of (2R)-1-(benzyloxy)-3-[4-(morpholin-4-yl)phenyl]-1-oxopropan-2-yl (2S)-2-[[(tert-butoxy)carbonyl](methyl)amino]-3-cyclopropylpropanoate as a yellow solid. MS (ES, m/z): 567 (M+H).

Preparation Example 18: Preparation of Dimer D2

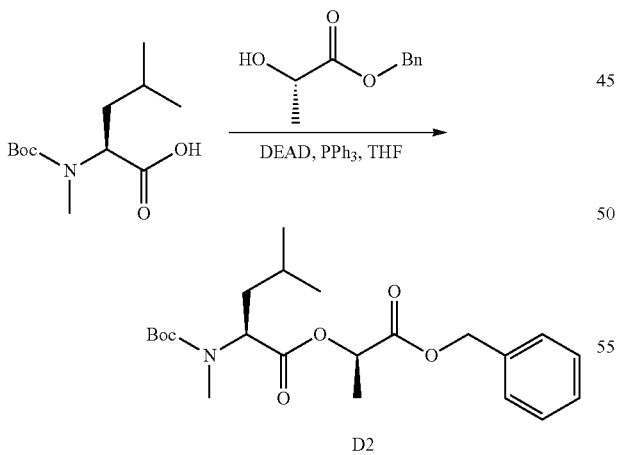

D2

(2R)-1-(benzyloxy)-1-oxopropan-2-yl (2S)-2-[[(tert-butoxy)carbonyl](methyl)amino]-4-methylpentanoate (D2)

Into a 2-L round-bottom flask purged and maintained with an inert atmosphere of nitrogen, was placed tetrahydrofuran (1.5 L), (2S)-2-[[(tert-butoxy)carbonyl](methyl)amino]-4-methylpentanoic acid (50 g, 203.82 mmol, 1.00 equiv), benzyl (2S)-2-hydroxypropanoate (36.7 g, 203.66 mmol, 1.00 equiv), triphenylphosphine (85 g, 324.07 mmol, 1.50 equiv). This was followed by the addition of DEAD (56.5 g, 324.43 mmol, 1.20 equiv) dropwise with stirring at 0° C. The resulting solution was stirred overnight at room temperature. The resulting mixture was concentrated under vacuum. The residue was applied onto a silica gel column with ethyl acetate/petroleum ether (1:50-1:10). This resulted in 82 g (99%) of (2R)-1-(benzyloxy)-1-oxopropan-2-yl (2S)-2-[[(tert-butoxy)carbonyl](methyl)amino]-4-methylpentanoate as pink oil. MS (ES, m/z): 408 (M+H); 1HNMR (300 MHz, CDCl3, ppm): δ7.41-7.31 (m, 5H), 5.31-5.10 (m, 3H), 5.01-4.73 (m, 1H), 2.77-2.74 (m, 3H), 1.72-1.65 (m, 2H), 1.60-1.58 (m, 1H), 1.52-1.50 (m, 3H), 1.47 (s, 9H), 0.96-0.94 (m, 6H).

Preparation Example 19: Preparation of Dimer D3

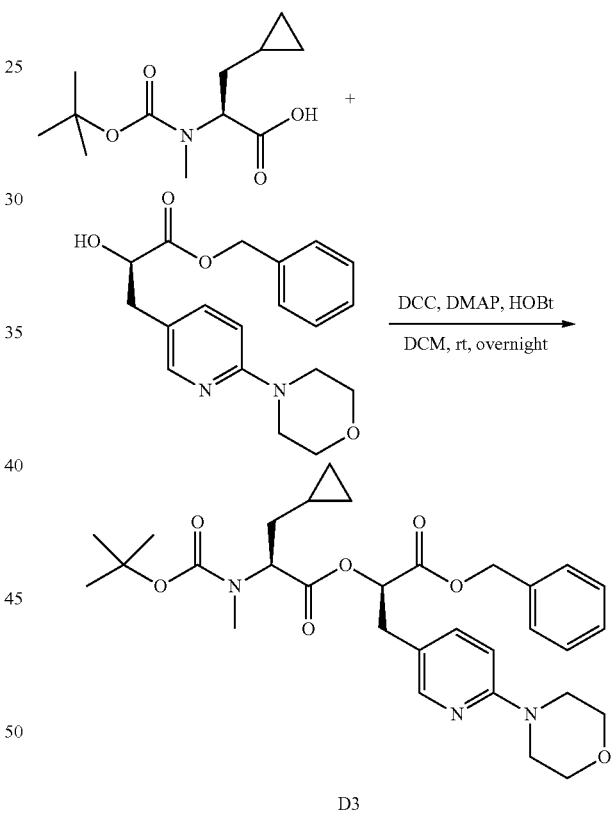

D3

(2R)-1-(benzyloxy)-3-[6-(morpholin-4-yl)pyridin-3-yl]-1-oxopropan-2-yl (2S)-2-[[(tert-butoxy)carbonyl](methyl)amino]-3-cyclopropylpropanoate (D3)

Into a 100-mL round-bottom flask, was placed a solution of (2S)-2-[[(tert-butoxy)carbonyl](methyl)amino]-3-cyclopropylpropanoic acid (700 mg, 2.88 mmol, 1.00 equiv) in dichloromethane (20 mL), benzyl (2R)-2-hydroxy-3-[6-(morpholin-4-yl)pyridin-3-yl]propanoate (1 g, 2.92 mmol, 1.00 equiv). This was followed by the addition of DCC (660 mg, 3.20 mmol, 1.10 equiv), in portions at 0° C. To this was added 4-dimethylaminopyridine (400 mg, 3.27 mmol, 1.10 equiv), in portions at 0° C. To the mixture was added HOBT (440 mg, 3.26 mmol, 1.10 equiv), in portions at 0° C. The resulting solution was stirred overnight at room temperature. The resulting mixture was concentrated under vacuum. The residue was applied onto a silica gel column with ethyl acetate/petroleum ether (1:3). This resulted in 1 g (61%) of (2R)-1-(benzyloxy)-3-[6-(morpholin-4-yl)pyridin-3-yl]-1-oxopropan-2-yl (2S)-2-[[(tert-butoxy)carbonyl](methyl)amino]-3-cyclopropylpropanoate as a white solid. MS (ESI, m/z): 568 [M+H]+.

Preparation Example 20: Preparation of Dimer D4

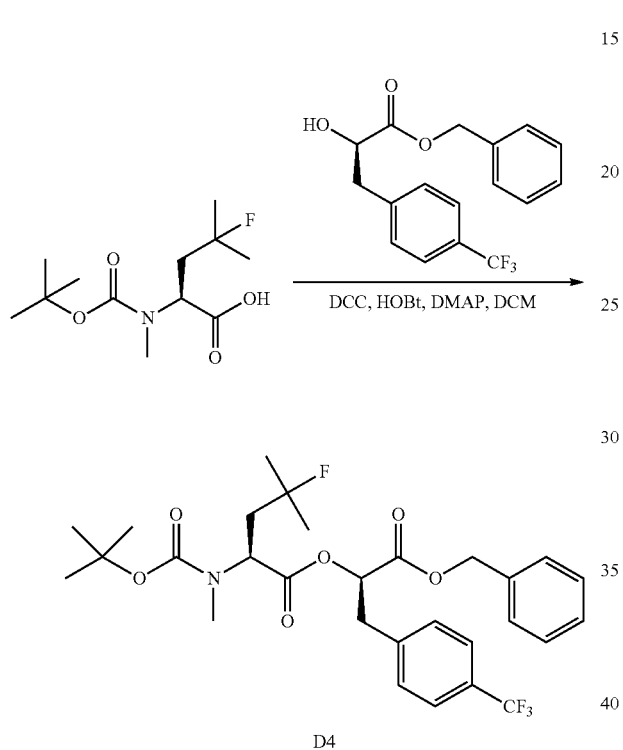

D4

(2R)-1-(benzyloxy)-1-oxo-3-[4-(trifluoromethyl)phenyl]propan-2-yl (2S)-2-[[(tert-butoxy)carbonyl](methyl)amino]-4-fluoro-4-methylpentanoate (D4)

Into a 1000-mL 3-necked round-bottom flask purged and maintained with an inert atmosphere of nitrogen, was placed a solution of (2S)-2-[[(tert-butoxy)carbonyl](methyl)amino]-4-fluoro-4-methylpentanoic acid (15 g, 56.97 mmol, 1.00 equiv) in dichloromethane (400 mL), benzyl (2R)-2-hydroxy-3-[4-(trifluoromethyl)phenyl]propanoate (12 g, 37.00 mmol, 1.00 equiv). This was followed by the addition of HOBT (7.5 g, 55.51 mmol, 1.20 equiv), DCC (11 g, 53.31 mmol, 1.20 equiv) and 4-dimethylaminopyridine (6.8 g, 55.66 mmol, 1.20 equiv) respectively in portions with stirring at 0° C. The resulting solution was stirred overnight at room temperature. The resulting mixture was concentrated under vacuum. The residue was applied onto a silica gel column with ethyl acetate/petroleum ether (1:10). This resulted in 21 g (65%) of (2R)-1-(benzyloxy)-1-oxo-3-[4-(trifluoromethyl)phenyl]propan-2-yl (2S)-2-[[(tert-butoxy)carbonyl](methyl)amino]-4-fluoro-4-methylpentanoate as red oil. MS (ES, m/z): 570 (M+H).

Preparation Example 21: Preparation of Dimer D5

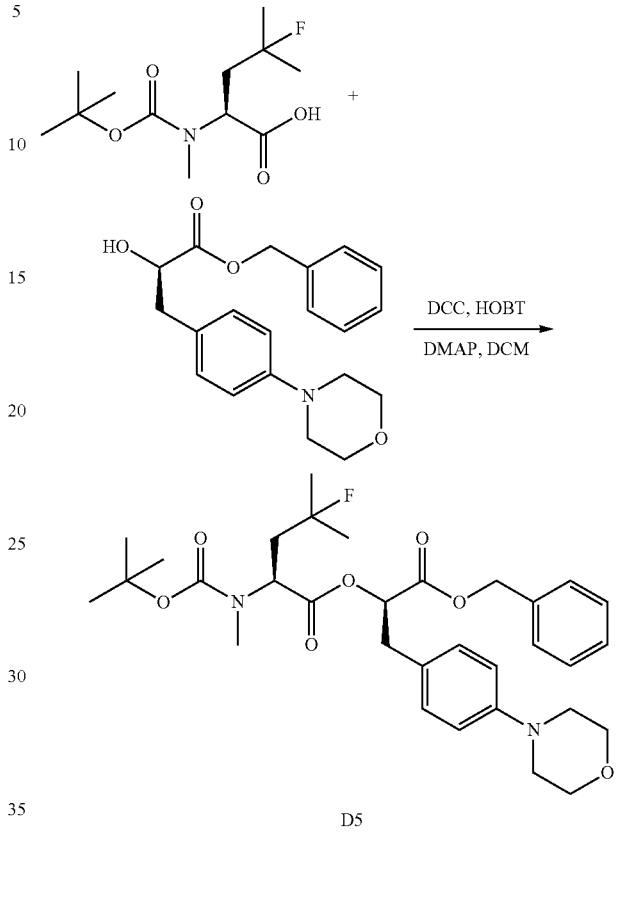

D5

(2R)-1-(benzyloxy)-3-[4-(morpholin-4-yl)phenyl]-1-oxopropan-2-yl (2S)-2-[[(tert-butoxy)carbonyl](methyl)amino]-4-fluoro-4-methylpentanoate (D5)

Into a 100-mL 3-necked round-bottom flask purged and maintained with an inert atmosphere of nitrogen, was placed dichloromethane (10 mL, 1.10 equiv), benzyl (2R)-2-hydroxy-3-[4-(morpholin-4-yl)phenyl]propanoate (130 mg, 0.38 mmol, 1.00 equiv), (2S)-2-[(tert-butoxy)carbonyl](methyl)amino-4-fluoro-4-methylpentanoic acid (100 mg, 0.38 mmol, 1.00 equiv). This was followed by the addition of HOBT (57 mg, 0.42 mmol, 1.10 equiv), DCC (86 mg, 0.42 mmol, 1.10 equiv) and 4-dimethylaminopyridine (51 mg, 0.42 mmol, 1.10 equiv) respectively in portions with stirring at 0° C. The resulting solution was stirred overnight at room temperature. The solids were filtered out. The filtrate was concentrated under vacuum. The residue was applied onto a silica gel column with ethyl acetate/petroleum ether (1:10). This resulted in 180 mg (80.5%) of (2R)-1-(benzyloxy)-3-[4-(morpholin-4-yl)phenyl]-1-oxopropan-2-yl (2S)-2-[[(tert-butoxy)carbonyl](methyl)amino]-4-fluoro-4-methylpentanoate as a light yellow solid. MS (ES, m/z): 587 (M+H); $^1$HNMR (300 MHz, CDCl$_3$, ppm): δ 7.38-7.36 (m, 4H), 7.29-7.25 (m, 1H), 7.20-6.99 (m, 4H), 5.27-5.18 (m, 1H), 5.18-5.09 (m, 2H), 5.08-4.83 (m, 1H), 4.01 (br, 4H), 3.23 (br, 4H), 3.15-3.05 (m, 2H), 2.68 (s, 3H), 2.28-1.91 (m, 2H), 1.51-1.28 (m, 15H).

Preparation Example 22: Preparation of Dimer D6

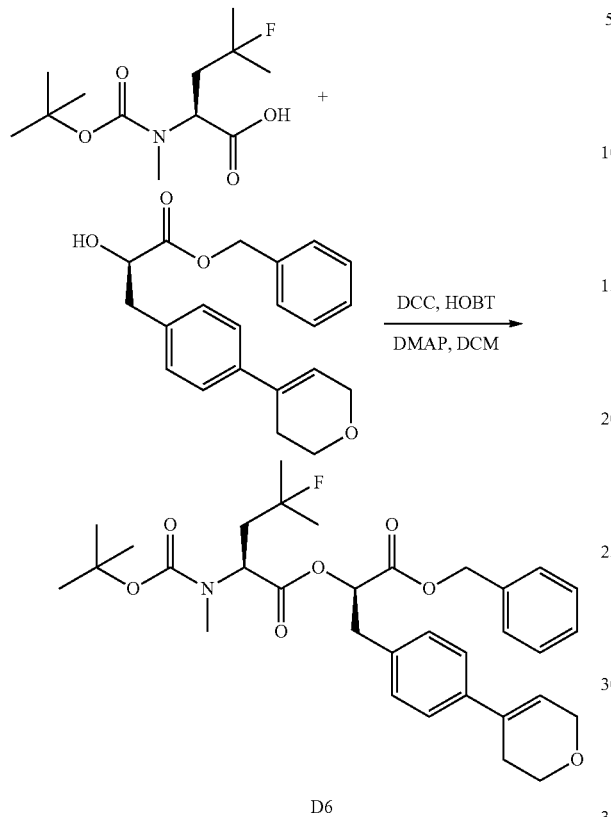

(2R)-1-(benzyloxy)-3-[4-(3,6-dihydro-2H-pyran-4-yl)phenyl]-1-oxopropan-2-yl (2S)-2-[[(tert-butoxy)carbonyl](methyl)amino]-4-fluoro-4-methylpentanoate (D6)

Into a 500-mL round-bottom flask, was placed dichloromethane (400 mL), (2S)-2-[[(tert-butoxy)carbonyl](methyl)amino]-4-fluoro-4-methylpentanoic acid (20 g, 75.96 mmol, 1.00 equiv), benzyl (2R)-3-[4-(3,6-dihydro-2H-pyran-4-yl)phenyl]-2-hydroxypropanoate (25.8 g, 76.24 mmol, 1.00 equiv). This was followed by the addition of HOBT (12 g, 88.81 mmol, 1.15 equiv), DCC (18 g, 87.24 mmol, 1.15 equiv) and 4-dimethylaminopyridine (10.7 g, 87.58 mmol, 1.15 equiv) respectively in portions with stirring at 0° C. The resulting solution was stirred for 4 h at room temperature. The solids were filtered out. The filtrate was concentrated under vacuum. The residue was applied onto a silica gel column with ethyl acetate/petroleum ether (1:10-1:5). This resulted in 80 g (90%) of (2R)-1-(benzyloxy)-3-[4-(3,6-dihydro-2H-pyran-4-yl)phenyl]-1-oxopropan-2-yl (2S)-2-[[(tert-butoxy)carbonyl](methyl)amino]-4-fluoro-4-methylpentanoate as colorless oil. MS (ES, m/z): 584 (M+H); $^1$HNMR (300 MHz, CDCl$_3$, ppm): δ 7.37-7.16 (m, 7H), 7.14 (d, J=8.4 Hz, 2H), 6.12 (s, 1H), 5.28-5.25 (m, 1H), 5.15-5.13 (m, 2H), 5.12-4.81 (m, 1H), 4.35-4.33 (m, 2H), 3.95 (t, J=8.7 Hz, 2H), 3.18-3.14 (m, 2H), 2.68 (d, J=12.9 Hz, 3H), 2.53-2.49 (m, 2H), 2.22-2.10 (m, 1H), 2.06-1.85 (m, 1H), 1.48 (d, J=16.8 Hz, 9H), 1.39 (s, 3H), 1.32 (s, 3H).

Preparation Example 23: Preparation of Dimer D7

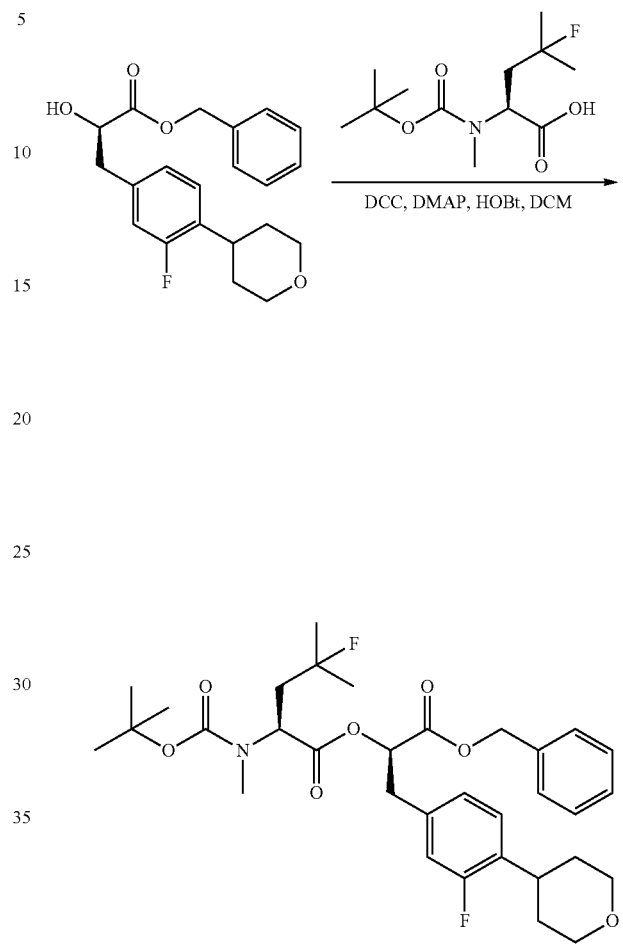

(2R)-1-(benzyloxy)-3-[3-fluoro-4-(oxan-4-yl)phenyl]-1-oxopropan-2-yl (2S)-2-[[(tert-butoxy)carbonyl](methyl)amino]-4-fluoro-4-methylpentanoate (D7)

Into a 100-mL round-bottom flask, was placed (2S)-2-[[(tert-butoxy)carbonyl](methyl)amino]-4-fluoro-4-methylpentanoic acid (700 mg, 2.66 mmol, 1.00 equiv), DCM (30 mL), benzyl (2S)-3-[3-fluoro-4-(oxan-4-yl)phenyl]-2-hydroxypropanoate (513 mg, 1.43 mmol, 1.00 equiv). This was followed by the addition of HOBT (262 mg, 1.94 mmol, 1.10 equiv), DCC (442 mg, 2.14 mmol, 1.10 equiv) and 4-dimethylaminopyridine (290 mg, 2.37 mmol, 1.10 equiv) respectively in portions with stirring at 0° C. The resulting solution was stirred overnight at room temperature. The solids were filtered out. The filtrate was concentrated under vacuum. The residue was applied onto a silica gel column with ethyl acetate/petroleum ether (1:5). This resulted in 850 mg (53%) of (2R)-1-(benzyloxy)-3-[3-fluoro-4-(oxan-4-yl)phenyl]-1-oxopropan-2-yl (2S)-2-[[(tert-butoxy)carbonyl](methyl)amino]-4-fluoro-4-methylpentanoate as colorless oil. MS (ES, m/z): 604 (M+H).

Preparation Example 24: Preparation of Dimer D8

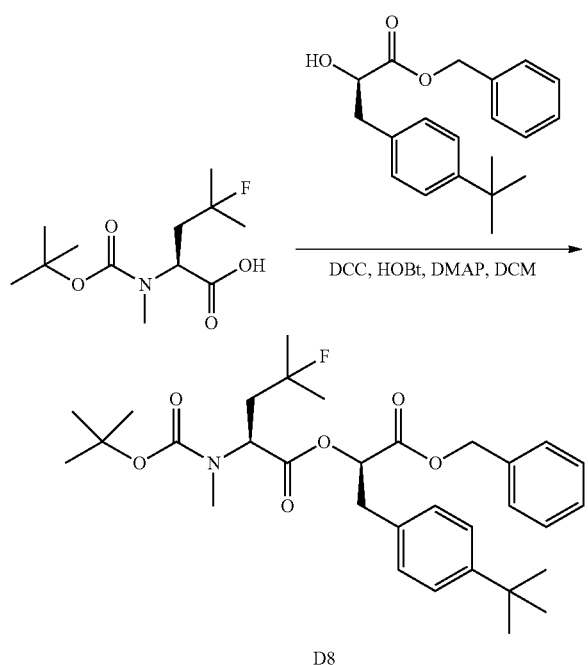

(2R)-1-(benzyloxy)-3-(4-tert-butylphenyl)-1-oxopropan-2-yl (2S)-2-[[(tert-butoxy)carbonyl](methyl)amino]-4-fluoro-4-methylpentanoate (D8)

Into a 1000-mL 3-necked round-bottom flask, was placed a solution of (2S)-2-[[(tert-butoxy)carbonyl](methyl)amino]-4-fluoro-4-methylpentanoic acid (25 g, 94.95 mmol, 1.00 equiv) in dichloromethane (1000 mL), benzyl (2R)-3-(4-tert-butylphenyl)-2-hydroxypropanoate (30 g, 96.03 mmol, 1.00 equiv), DCC (40 g, 193.86 mmol, 2.00 equiv), HOBT (26 g, 192.42 mmol, 2.00 equiv), 4-dimethylaminopyridine (23.5 g, 192.35 mmol, 2.00 equiv). The resulting solution was stirred for 2 h at room temperature in an ice/salt bath. The resulting mixture was concentrated under vacuum. The residue was applied onto a silica gel column with ethyl acetate/petroleum ether (1:50-1:10). This resulted in 50 g (94%) of (2R)-1-(benzyloxy)-3-(4-tert-butylphenyl)-1-oxopropan-2-yl (2S)-2-[[(tert-butoxy)carbonyl](methyl)amino]-4-fluoro-4-methylpentanoate as colorless oil. MS (ES, m/z): 558 (M+H); $^1$HNMR (300 MHz, CDCl$_3$, ppm): δ 7.35-7.27 (m, 7H), 7.12-7.09 (m, 2H), 5.27-4.62 (m, 4H), 3.15-3.09 (m, 2H), 2.69-2.61 (m, 3H), 2.20-1.82 (m, 2H), 1.61-1.31 (m, 24H).

Preparation Example 25: Preparation of Dimer D9

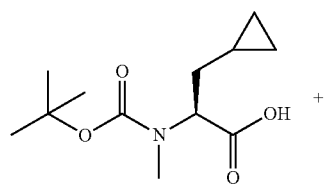

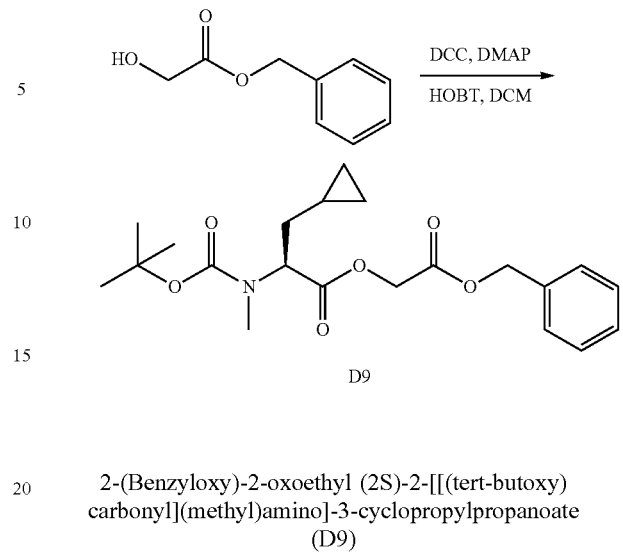

2-(Benzyloxy)-2-oxoethyl (2S)-2-[[(tert-butoxy)carbonyl](methyl)amino]-3-cyclopropylpropanoate (D9)

Into a 100-mL round-bottom flask, was placed (2S)-2-[[(tert-butoxy)carbonyl](methyl)amino]-3-cyclopropylpropanoic acid (1.5 g, 6.17 mmol, 1.00 equiv), benzyl 2-hydroxyacetate (1.02 g, 6.14 mmol, 1.00 equiv) in dichloromethane (30 mL). This was followed by the addition of DCC (1.52 g, 7.37 mmol, 1.20 equiv), 4-dimethylaminopyridine (900 mg, 7.37 mmol, 1.20 equiv) and HOBt (1.0 g, 7.40 mmol, 1.20 equiv) respectively in portions with stirring at 0° C. The resulting solution was stirred for 12 h at room temperature. The resulting mixture was concentrated under vacuum. The residue was applied onto a silica gel column with ethyl acetate/petroleum ether (3:1). This resulted in 2 g (83%) of 2-(benzyloxy)-2-oxoethyl (2S)-2-[[(tert-butoxy)carbonyl](methyl)amino]-3-cyclopropylpropanoate as yellow oil. MS (ES, m/z): 392 (M+H); $^1$HNMR (300 MHz, CDCl$_3$, ppm): δ 7.42-7.32 (m, 5H), 5.19 (s, 2H), 4.96-4.91 (m, 0.5H), 4.71-4.65 (m, 2H), 4.65-4.63 (m, 0.5H), 2.87 (d, J=14.1 Hz, 3H), 1.90-1.62 (m, 2H), 1.47 (d, J=6.0 Hz, 9H), 0.78-0.67 (m, 1H), 0.49-0.42 (m, 2H), 0.13-0.09 (m, 2H).

Preparation Example 26: Preparation of Monomer D10

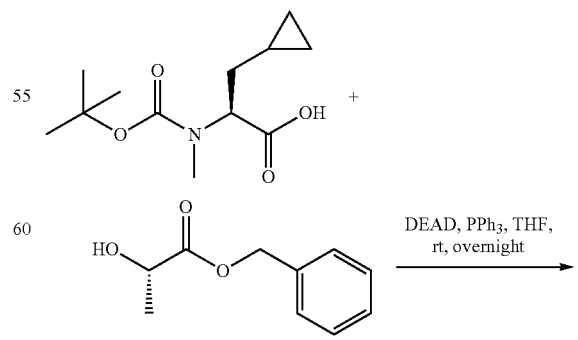

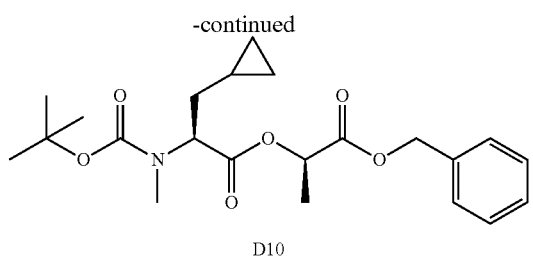

D10

(S)—((R)-1-(benzyloxy)-1-oxopropan-2-yl) 2-(tert-butoxycarbonyl(methyl)amino)-3-cyclopropylpropanoate (D10)

Into a 500-mL 3-necked round-bottom flask, was placed (2S)-2-[[(tert-butoxy)carbonyl](methyl)amino]-3-cyclopropylpropanoic acid (4 g, 16.44 mmol, 1.00 equiv), benzyl (2S)-2-hydroxypropanoate (3 g, 16.65 mmol, 1.00 equiv), PPh$_3$ (5.2 g, 19.83 mmol, 1.20 equiv), tetrahydrofuran (150 mL). This was followed by the addition of a solution of DEAD (3.5 g, 20.10 mmol, 1.20 equiv) in tetrahydrofuran (30 mL) dropwise with stirring at 0° C. The resulting solution was stirred for overnight at room temperature. The solids were filtered out. The filtrate was concentrated under vacuum. The residue was applied onto a silica gel column with ethyl acetate/petroleum ether (1:20). This resulted in 7 g (crude) of (2R)-1-(benzyloxy)-1-oxopropan-2-yl (2S)-2-[[(tert-butoxy)carbonyl](methyl)amino]-3-cyclopropylpropanoate as colorless oil. MS (ES, m/z): 406 (M+H).

Preparation Example 27: Preparation of Monomer D11

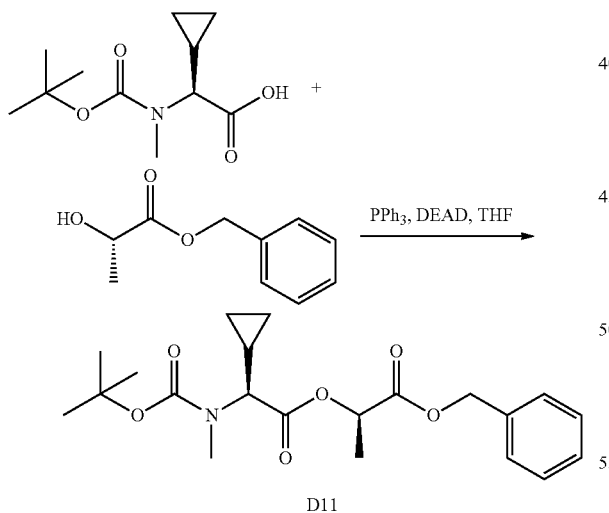

Benzyl (2R)-2-[[(2S)-2-[[(tert-butoxy)carbonyl](methyl)amino]-2-cyclopropylacetyl]oxy]propanoate (D11)

Into a 250-mL 3-necked round-bottom flask purged and maintained with an inert atmosphere of nitrogen, was placed (2S)-2-[[(tert-butoxy)carbonyl](methyl)amino]-2-cyclopropylacetic acid (3.4 g, 14.83 mmol, 1.00 equiv), benzyl (2S)-2-hydroxypropanoate (2.7 g, 14.98 mmol, 1.00 equiv), tetrahydrofuran (100 mL), PPh$_3$ (3.1 g, 11.82 mmol, 1.20 equiv). This was followed by the addition of DEAD (4.7 g, 26.99 mmol, 1.20 equiv) dropwise with stirring at 0° C. The resulting solution was stirred overnight at room temperature. The resulting mixture was concentrated under vacuum. The residue was applied onto a silica gel column with ethyl acetate/petroleum ether (1:15). This resulted in 4.2 g (72%) of benzyl (2R)-2-[[(2S)-2-[[(tert-butoxy)carbonyl](methyl)amino]-2-cyclopropylacetyl]oxy]propanoate as yellow oil. MS (ES, m/z): 392 (M+H); $^1$HNMR (300 MHz, CDCl$_3$, ppm): δ 7.41-7.34 (m, 5H), 5.24-5.15 (m, 3H), 4.08-3.66 (m, 1H), 2.97 (br, 3H), 1.53 (d, J=6.9 Hz, 3H), 1.46 (s, 9H), 1.25-1.14 (m, 1H), 0.78-0.72 (m, 1H), 0.60-0.55 (m, 2H), 0.39-0.34 (m, 1H).

Preparation Example 28: Preparation of Monomer D12

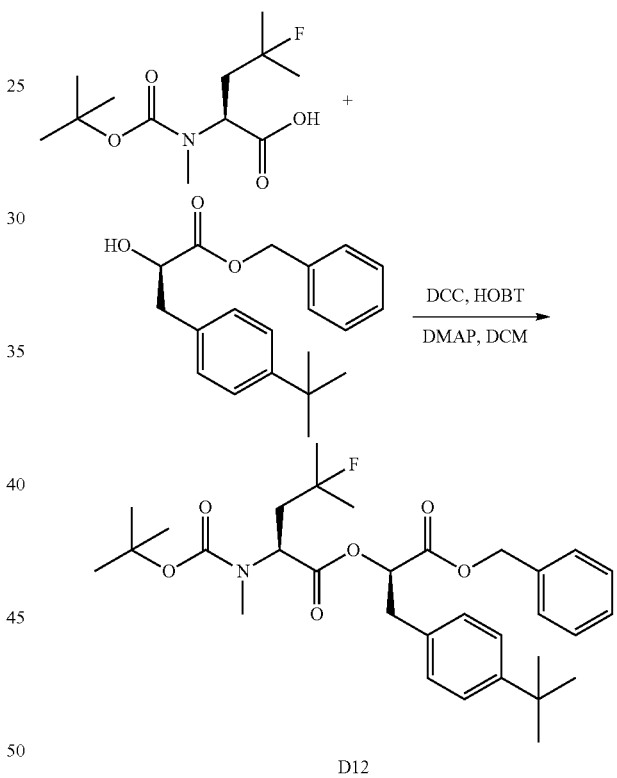

(2R)-1-(benzyloxy)-3-[4-(cyclohex-1-en-1-yl)-3-fluorophenyl]-1-oxopropan-2-yl (2S)-2-[[(tert-butoxy)carbonyl](methyl)amino]-4-fluoro-4-methylpentanoate (D12)

Into a 100-mL 3-necked round-bottom flask purged and maintained with an inert atmosphere of nitrogen, was placed tetrahydrofuran (25 mL), benzyl (2S)-3-[4-(cyclohex-1-en-1-yl)-3-fluorophenyl]-2-hydroxypropanoate (710 mg, 2.00 mmol, 1.00 equiv), (2S)-2-[(tert-butoxy)carbonyl](methyl)amino-4-fluoro-4-methylpentanoic acid (527 mg, 2.00 mmol, 1.00 equiv), PPh$_3$ (790 mg, 3.01 mmol, 1.50 equiv). This was followed by the addition of DEAD (517 mg, 2.97 mmol, 1.50 equiv) dropwise with stirring at 0° C. The resulting solution was stirred for 2 h at room temperature. The resulting mixture was concentrated under vacuum. The residue was purified by thin layer chromatography developed with ethyl acetate/PE (1/5). This resulted in 710 mg (59%) of (2R)-1-(benzyloxy)-3-[4-(cyclohex-1-en-1-yl)-3-fluorophenyl]-1-oxopropan-2-yl (2S)-2-[[(tert-butoxy)carbonyl](methyl)amino]-4-fluoro-4-methylpentanoate as colorless oil. MS (ES, m/z): 600 (M+H).

Preparation Example 29: Preparation of Monomer D13

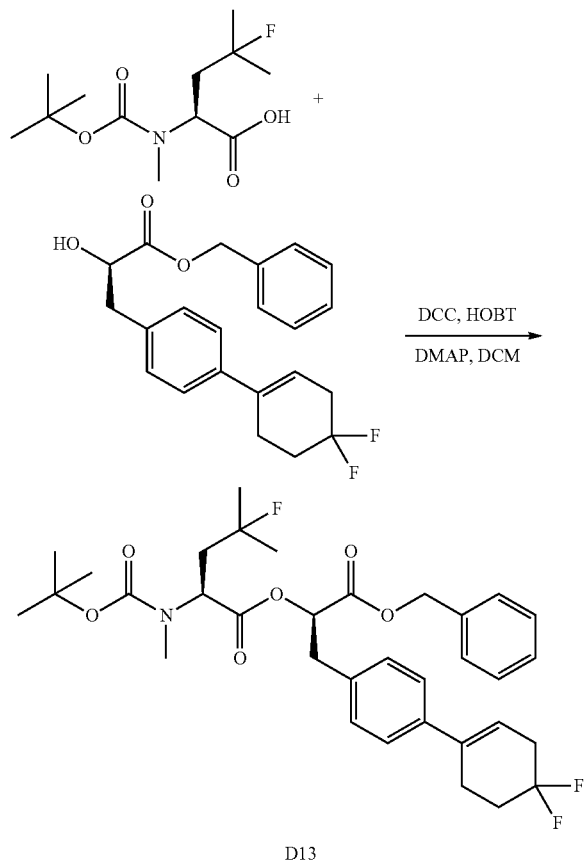

D13

(2R)-1-(benzyloxy)-3-[4-(4,4-difluorocyclohex-1-en-1-yl)phenyl]-1-oxopropan-2-yl (2S)-2-[[(tert-butoxy)carbonyl](methyl)amino]-4-fluoro-4-methylpentanoate (D13)

Into a 100-mL round-bottom flask, was placed dichloromethane (50 mL), benzyl (2R)-3-[4-(4,4-difluorocyclohex-1-en-1-yl)phenyl]-2-hydroxypropanoate (2 g, 5.37 mmol, 1.00 equiv), (2S)-2-[(tert-butoxy)carbonyl](methyl) amino-4-fluoro-4-methylpentanoic acid (1.42 g, 5.39 mmol, 1.10 equiv). This was followed by the addition of HOBT (870 mg, 6.44 mmol, 1.20 equiv), in portions. To this was added DCC (1.33 g, 6.45 mmol, 1.20 equiv), in portions. To the mixture was added 4-dimethylaminopyridine (780 mg, 6.38 mmol, 1.20 equiv), in portions. The resulting solution was stirred for 2 h at room temperature. The resulting mixture was concentrated under vacuum. The residue was applied onto a silica gel column with ethyl acetate/petroleum ether (1:20-1:15). This resulted in 3.2 g (96%) of (2R)-1-(benzyloxy)-3-[4-(4,4-difluorocyclohex-1-en-1-yl)phenyl]-1-oxopropan-2-yl (2S)-2-[[(tert-butoxy)carbonyl](methyl)amino]-4-fluoro-4-methylpentanoate as colorless oil. MS (ES, m/z): 618 (M+H); $^1$HNMR (300 MHz, CDCl3, ppm): δ 7.36-7.34 (m, 5H), 7.26-7.25 (m, 2H), 7.14-7.11 (m, 2H), 5.89 (br, 1H), 5.29-5.23 (m, 1H), 5.18-5.06 (m, 2H), 4.89-4.78 (m, 1H), 3.17-3.10 (m, 2H), 2.77-2.65 (m, 7H), 2.23-1.97 (m, 2H), 1.59-1.15 (m, 17H).

Preparation Example 30: Preparation of Monomer D14

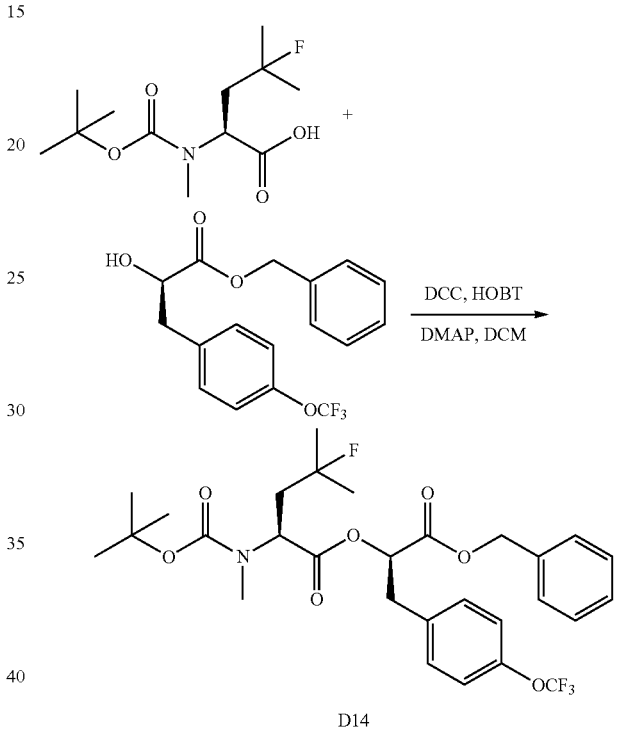

D14

(2R)-1-(benzyloxy)-1-oxo-3-[4-(trifluoromethoxy)phenyl]propan-2-yl (2S)-2-[[(tert-butoxy)carbonyl](methyl)amino]-4-fluoro-4-methylpentanoate (D14)

Into a 250-mL 3-necked round-bottom flask, was placed (2S)-2-[[(tert-butoxy)carbonyl](methyl)amino]-4-fluoro-4-methylpentanoic acid (3.1 g, 11.77 mmol, 1.00 equiv), benzyl (2R)-2-hydroxy-3-[4-(trifluoromethoxy)phenyl]propanoate (4 g, 11.75 mmol, 1.00 equiv), dichloromethane (120 mL). This was followed by the addition of DCC (2.7 g, 13.09 mmol, 1.10 equiv), 4-dimethylaminopyridine (1.6 g, 13.10 mmol, 1.10 equiv) and HOBt (1.7 g, 12.58 mmol, 1.10 equiv) respectively in portions with stirring at 0° C. The resulting solution was stirred overnight at room temperature. The resulting mixture was concentrated under vacuum. The residue was applied onto a silica gel column with ethyl acetate/petroleum ether (1:10). This resulted in 3.5 g (51%) of (2R)-1-(benzyloxy)-1-oxo-3-[4-(trifluoromethoxy)phenyl]propan-2-yl (2S)-2-[[(tert-butoxy)carbonyl](methyl)amino]-4-fluoro-4-methylpentanoate as yellow oil. MS (ES, m/z): 586 (M+H); $^1$HNMR (300 MHz, CDCl$_3$, ppm): δ 7.39-7.37 (m, 4H), 7.28-7.26 (m, 1H), 7.19-7.08 (m, 4H), 5.30-5.27 (m, 1H), 5.22-5.10 (m, 2H), 5.05-4.82 (m, 1H), 3.19-3.16 (m, 2H), 2.66 (d, J=22.5 Hz, 3H), 2.28-2.16 (m, 1H), 2.07-1.92 (m, 1H), 1.51-1.33 (m, 15H).

Preparation Example 31: Preparation of Monomer D15

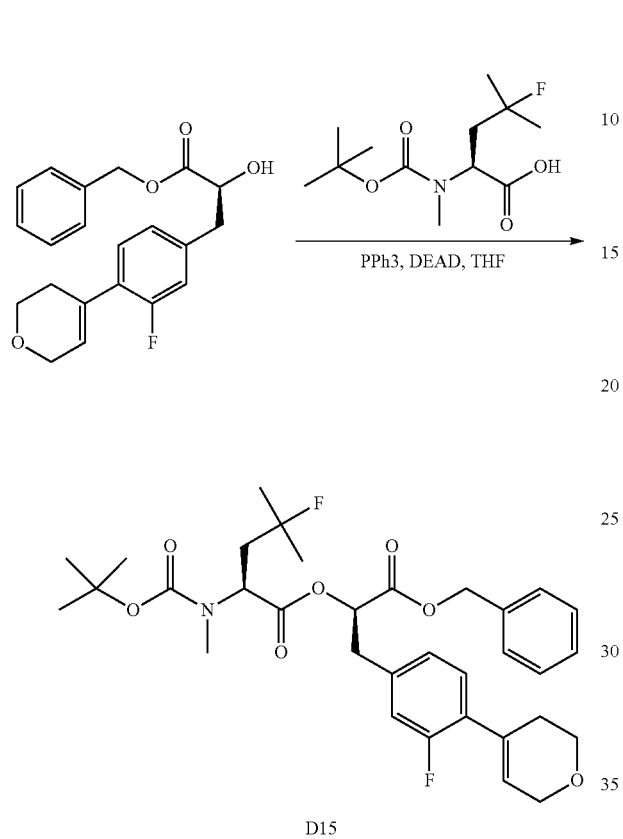

D15

(2R)-1-(benzyloxy)-3-[4-(3,6-dihydro-2H-pyran-4-yl)-3-fluorophenynyl]-oxopropan-2-yl (2S)-2-[[(tert-butoxy)carbonyl](methyl)amino]-4-fluoro-4-methyl-pentanoate (D15)

Into a 250-mL round-bottom flask purged and maintained with an inert atmosphere of nitrogen, was placed benzyl (2S)-3-[4-(3,6-dihydro-2H-pyran-4-yl)-3-fluorophenyl]-2-hydroxypropanoate (700 mg, 1.96 mmol, 1.00 equiv), (2S)-2-[[(tert-butoxy)carbonyl](methyl)amino]-4-fluoro-4-methylpentanoic acid (776 mg, 2.95 mmol, 1.50 equiv), PPh$_3$ (1.03 g, 3.93 mmol, 2.00 equiv), tetrahydrofuran (50 mL). This was followed by the addition of DEAD (684 mg, 3.93 mmol, 2.00 equiv) dropwise with stirring at 0° C. The resulting solution was stirred for 2 h at room temperature. The resulting mixture was concentrated under vacuum. The residue was applied onto a silica gel column with ethyl acetate/petroleum ether (1/4). This resulted in 950 mg (80%) of (2R)-1-(benzyloxy)-3-[4-(3,6-dihydro-2H-pyran-4-yl)-3-fluorophenyl]-1-oxopropan-2-yl (2S)-2-[[(tert-butoxy)carbonyl](methyl)amino]-4-fluoro-4-methylpentanoate as light yellow oil. MS (ES, m/z): 602 (M+H); $^1$HNMR (300 MHz, CD$_3$OD, ppm): δ 7.36-7.28 (m, 5H), 7.14-7.12 (m, 1H), 6.97-6.93 (m, 2H), 6.03 (br, 1H), 5.33-5.31 (m, 1H), 5.17-5.12 (m, 2H), 4.93-4.90 (m, 0.5H), 4.73-4.56 (m, 0.5H), 4.34-4.23 (m, 2H), 3.88-3.83 (m, 2H), 3.15-3.12 (m, 2H), 2.75-2.71 (m, 3H), 2.50 (br, 2H), 2.31-1.97 (m, 2H), 1.47-1.23 (m, 15H).

Preparation Example 32: Preparation of Monomer D16

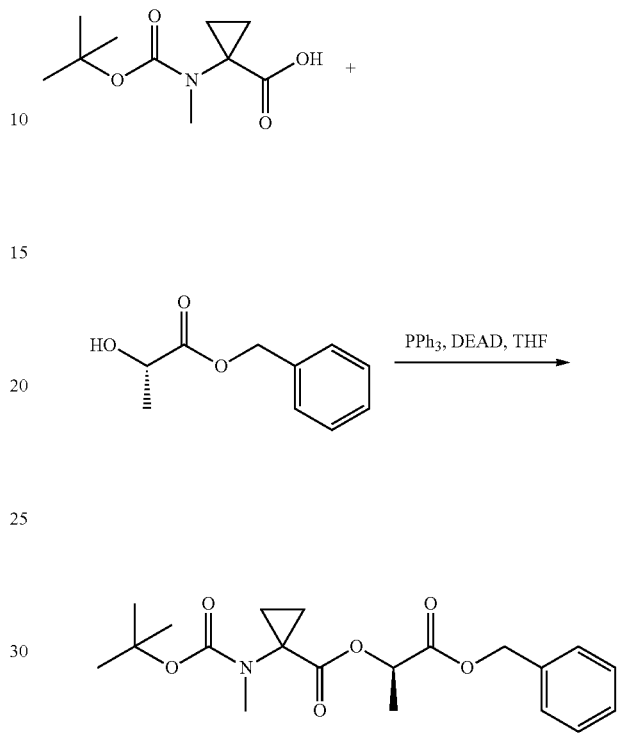

Benzyl (2R)-2-[(1-[[(tert-butoxy)carbonyl](methyl)amino]cyclopropyl)carbonyloxy]propanoate (D16)

Into a 100-mL 3-necked round-bottom flask purged and maintained with an inert atmosphere of nitrogen, was placed 1-[[(tert-butoxy)carbonyl](methyl)amino]cyclopropane-1-carboxylic acid (2 g, 9.29 mmol, 1.00 equiv), PPh$_3$ (7.3 g, 27.83 mmol, 3.00 equiv), tetrahydrofuran (35 mL), benzyl (2S)-2-hydroxypropanoate (2.02 g, 11.21 mmol, 1.20 equiv). This was followed by the addition of DEAD (4.86 g, 27.91 mmol, 3.00 equiv) dropwise with stirred at 0° C. in 10 min. The resulting solution was stirred for 2 h at room temperature. The reaction was then quenched by the addition of 100 mL of water. The resulting solution was extracted with 3×40 mL of ethyl acetate and the organic layers combined and washed with 1×30 mL of brine. The organic layers were collected and dried over anhydrous sodium sulfate and concentrated under vacuum. The residue was applied onto a silica gel column with ethyl acetate/petroleum ether (1:3). This resulted in 2.8 g (80%) of benzyl (2R)-2-[(1-[[(tert butoxy)carbonyl](methyl)amino]cyclopropyl)carbonyloxy]propanoate as orange oil. MS (ES, m/z): 378 (M+H).

Preparation Examples 33 to 40 below are non-limiting illustrations of the methods used to prepare the compounds of the invention. The skilled person will understand that these methods may be adapted to prepare other compounds of the invention.

Preparation Example 33: Preparation of Compound 6-7A in Table 6, Wherein R$^a$, R$^b$, R', R", R'" and R"" are Each Methyl
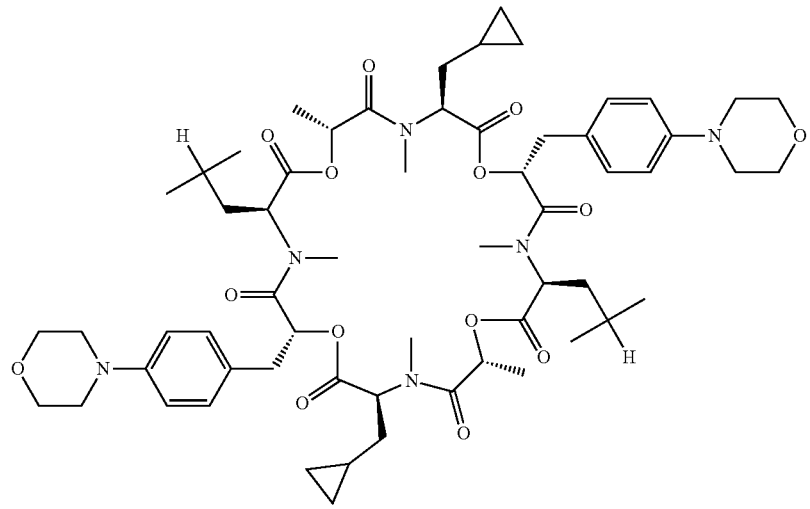
6-7A
Compound 6-7A was prepared according to Schemes 2 and 3 shown below.
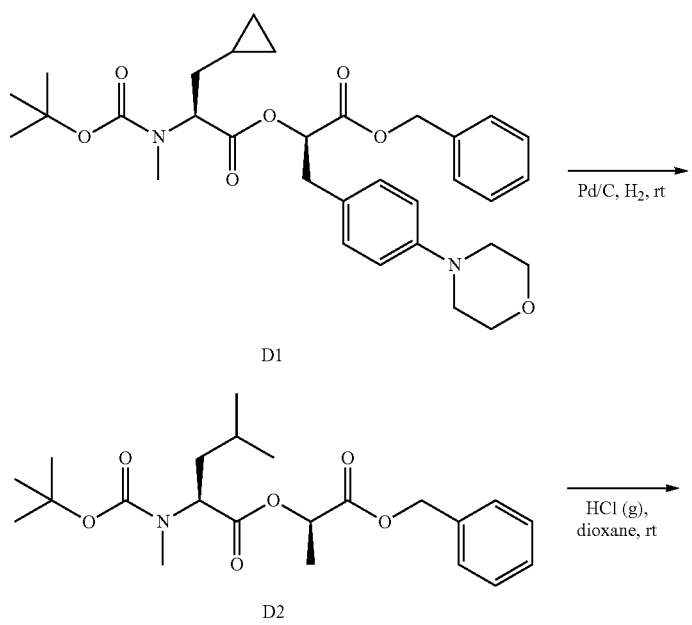

-continued
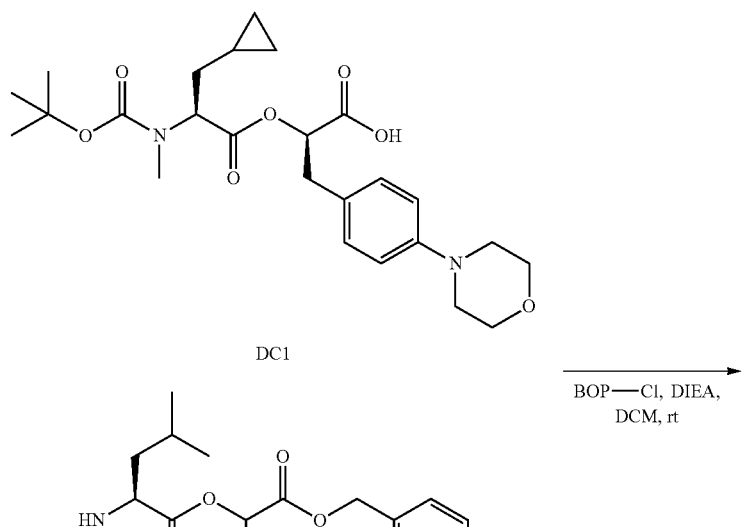
DC1
DA2
BOP—Cl, DIEA, DCM, rt
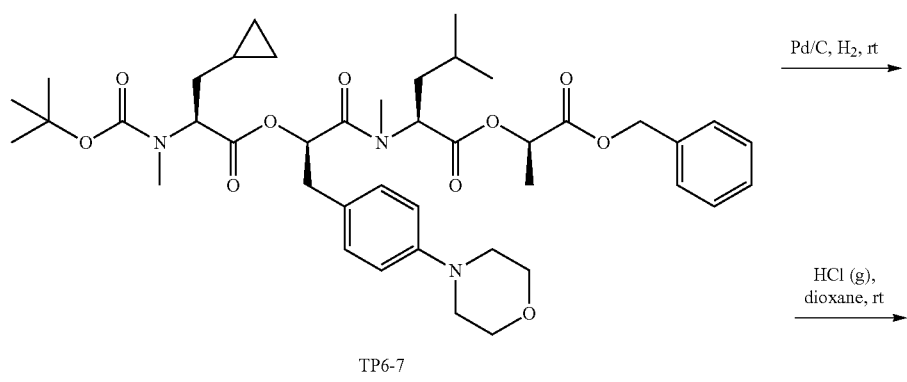
TP6-7
Pd/C, H₂, rt
HCl (g), dioxane, rt -continued
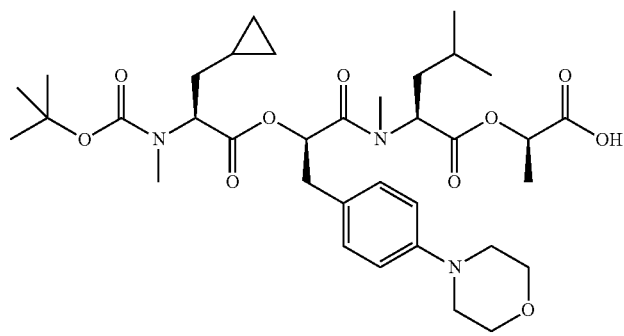
TC6-7
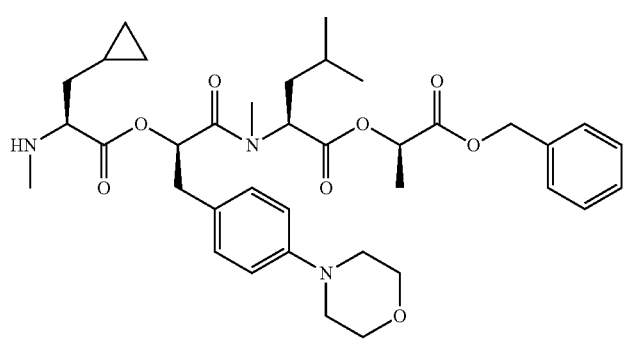
TA6-7
BOP—Cl, DIEA, DCM, rt
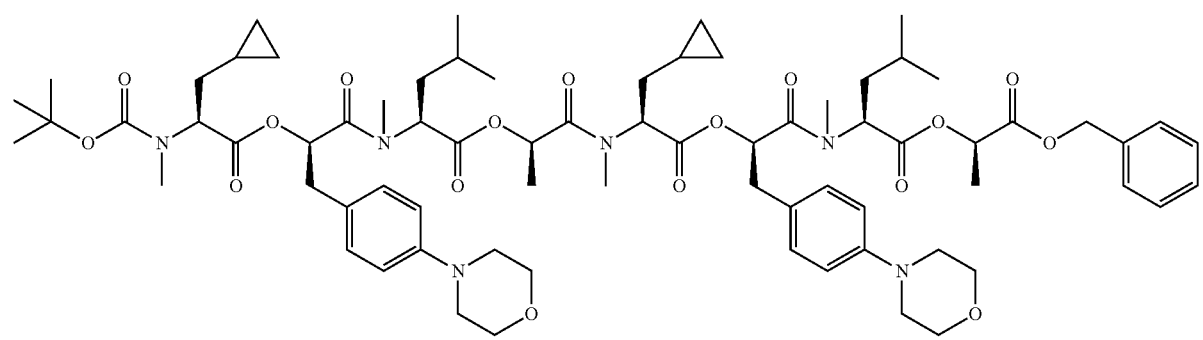
OP6-7

Scheme 3
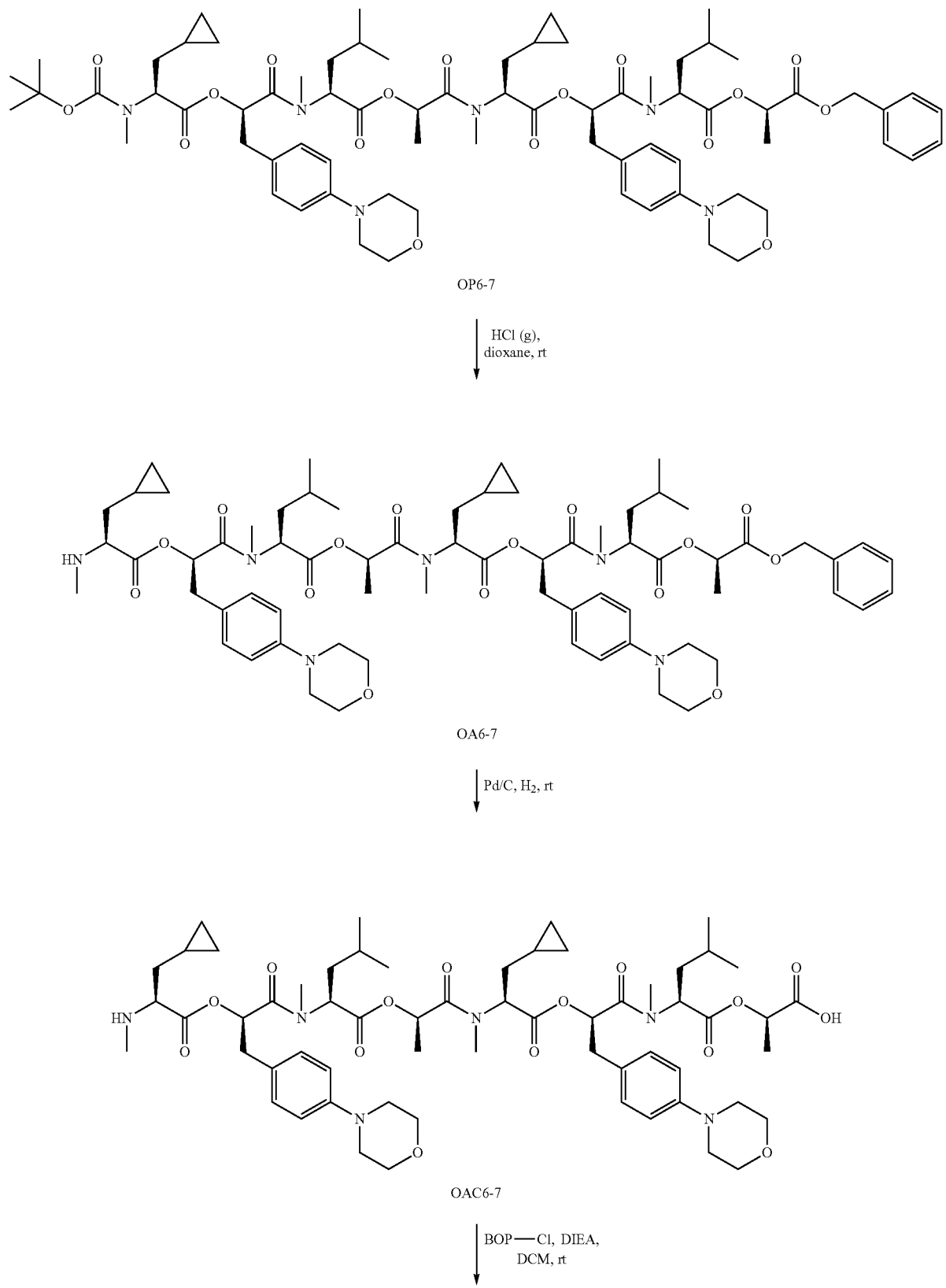
OP6-7
HCl (g), dioxane, rt
OA6-7
Pd/C, H₂, rt
OAC6-7
BOP—Cl, DIEA, DCM, rt

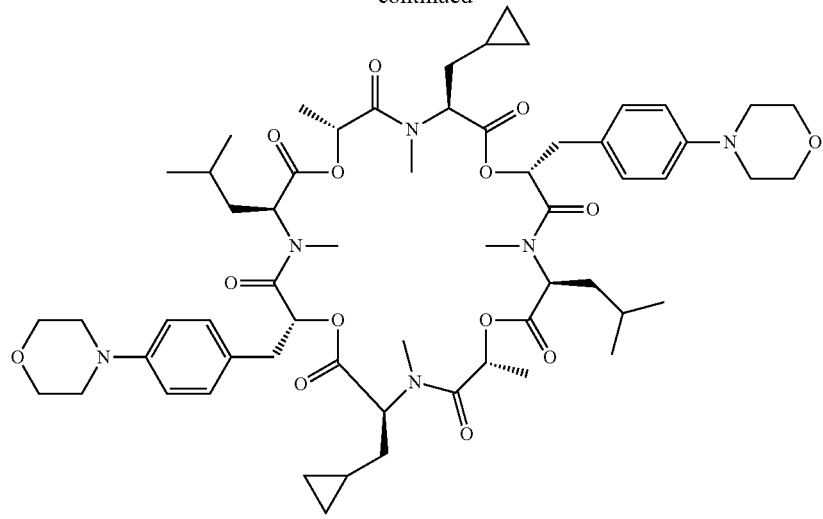

6-7

Experimental Details

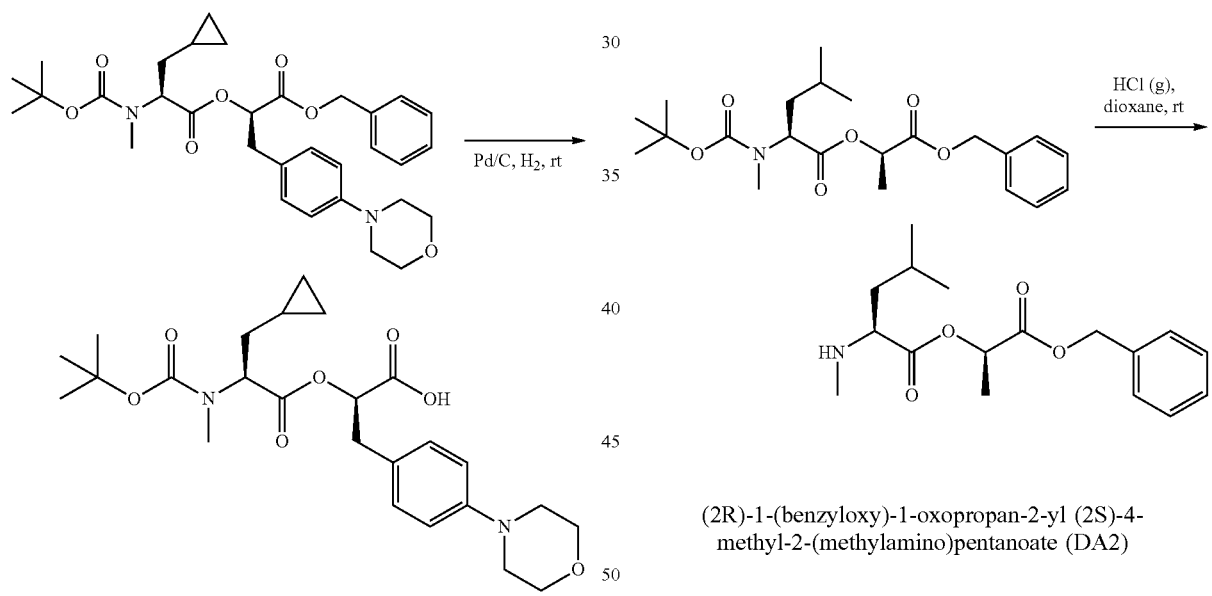

(2R)-2-[[(2S)-2-[[(tert-butoxy)carbonyl](methyl)amino]-3-cyclopropylpropanoyl]oxy]-3-[4-(morpholin-4-yl)phenyl]propanoic Acid (DC1)

Into a 250-mL round-bottom flask, was placed (2R)-1-(benzyloxy)-3-[4-(morpholin-4-yl)phenyl]-1-oxopropan-2-yl (2S)-2-[[(tert-butoxy)carbonyl](methyl)amino]-3-cyclopropylpropanoate (2.5 g, 4.41 mmol, 1.00 equiv), methanol (100 mL), Palladium carbon (500 mg). To the above mixture was introduced hydrogen. The resulting solution was stirred for 1 h at room temperature. The solids were filtered out. The filtrate was concentrated under vacuum. This resulted in 2 g (95%) of (2R)-2-[[(2S)-2-[[(tert-butoxy)carbonyl](methyl) amino]-3-cyclopropylpropanoyl]oxy]-3-[4-(morpholin-4-yl)phenyl]propanoic acid as a white solid. MS (ES, m/z): 477 (M+H).

(2R)-1-(benzyloxy)-1-oxopropan-2-yl (2S)-4-methyl-2-(methylamino)pentanoate (DA2)

Into a 100-mL 3-necked round-bottom flask, was placed (2R)-1-(benzyloxy)-1-oxopropan-2-yl (2S)-2-[[(tert-butoxy)carbonyl](methyl)amino]-4-methylpentanoate (3.50 g, 8.35 mmol, 1.00 equiv), dichloromethane (20 mL), HCl (gas)/dioxane (50 mL). The resulting solution was stirred for 1.0 h at room temperature. The resulting mixture was concentrated under vacuum. The pH value of the solution was adjusted to 8 with sodium bicarbonate (Sat.). The resulting solution was extracted with 3×100 mL of dichloromethane and the organic layers combined and washed with 3×100 mL of brine. The organic phase was collected and dried over anhydrous sodium sulfate and concentrated under vacuum. This resulted in 2.42 g (94%) of (2R)-1-(benzyloxy)-1-oxopropan-2-yl (2S)-4-methyl-2-(methylamino)pentanoate as colorless oil. MS (ES, m/z): 308 (M+H).

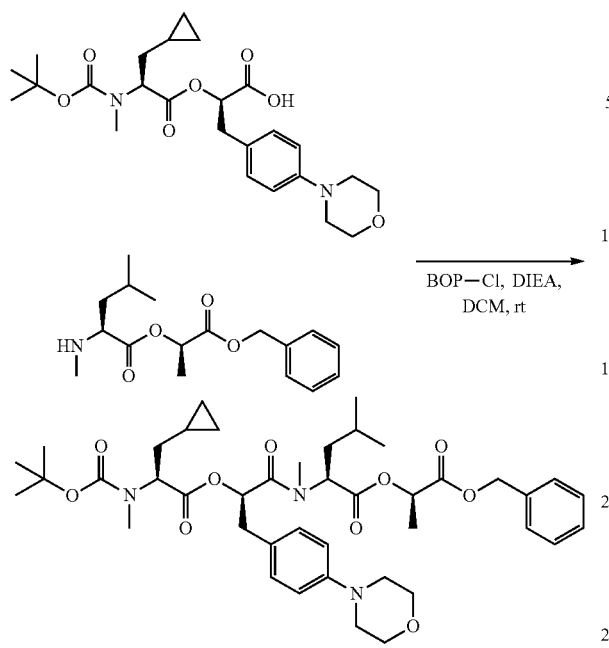

(2R)-1-(benzyloxy)-1-oxopropan-2-yl (2S)-2-[(2R)-2-[[(2S)-2-[[(tert-butoxy)carbonyl](methyl)amino]-3-cyclopropylpropanoyl]oxy]-N-methyl-3-[4-(morpholin-4-yl)phenyl]propanamido]-4-methylpentanoate (TP6-7)

Into a 250-mL 3-necked round-bottom flask, was placed (2R)-1-(benzyloxy)-1-oxopropan-2-yl (2S)-4-methyl-2-(methylamino) pentanoate (1.35 g, 4.39 mmol, 1.00 equiv), (2R)-2-[[(2S)-2-[[(tert-butoxy)carbonyl](methyl)amino]-3-cyclopropylpropanoyl]oxy]-3-[4-(morpholin-4-yl)phenyl] propanoic acid (2 g, 4.20 mmol, 1.00 equiv), dichloromethane (100 mL). This was followed by the addition of BOP—Cl (2.14 g, 8.41 mmol, 2.00 equiv) in portions at 0° C. To this was added DIEA (1.08 g, 8.36 mmol, 2.00 equiv) dropwise with stirring at 0° C. The resulting solution was stirred overnight at room temperature. The solids were filtered out. The filtrate was concentrated under vacuum. The residue was applied onto a silica gel column with ethyl acetate/petroleum ether (1:3). This resulted in 2 g (59%) of (2R)-1-(benzyloxy)-1-oxopropan-2-yl (2S)-2-[(2R)-2-[[(2S)-2-[[(tert-butoxy)carbonyl](methyl)amino]-3-cyclopropylpropanoyl]oxy]-N-methyl-3-[4-(morpholin-4-yl)phenyl]propanamido]-4-methylpentanoate as yellow oil. MS (ES, m/z): 766 (M+H).

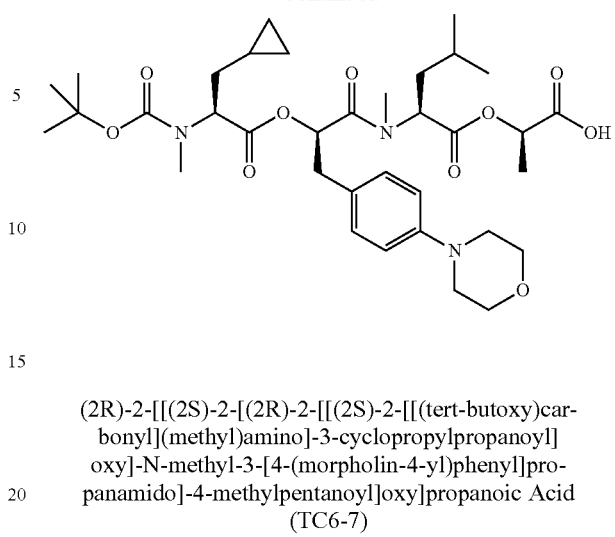

(2R)-2-[[(2S)-2-[(2R)-2-[[(2S)-2-[[(tert-butoxy)carbonyl](methyl)amino]-3-cyclopropylpropanoyl]oxy]-N-methyl-3-[4-(morpholin-4-yl)phenyl]propanamido]-4-methylpentanoyl]oxy]propanoic Acid (TC6-7)

Into a 250-mL round-bottom flask, was placed (2R)-1-(benzyloxy)-1-oxopropan-2-yl (2S)-2-[(2R)-2-[[(2S)-2-[[(tert-butoxy)carbonyl](methyl)amino]-3-cyclopropylpropanoyl]oxy]-N-methyl-3-[4-(morpholin-4-yl)phenyl]propanamido]-4-methylpentanoate (1 g, 1.31 mmol, 1.00 equiv), methanol (100 mL), Palladium carbon (300 mg). To the above mixture was introduced hydrogen. The resulting solution was stirred for 1 h at room temperature. The solids were filtered out. The filtrate was concentrated under vacuum. This resulted in 800 mg (91%) of (2R)-2-[[(2S)-2-[(2R)-2-[[(2S)-2-[[(tert-butoxy)carbonyl](methyl)amino]-3-cyclopropylpropanoyl]oxy]-N-methyl-3-[4-(morpholin-4-yl)phenyl]propanamido]-4-methylpentanoyl]oxy]propanoic acid as a white solid. MS (ES, m/z): 676 (M+H).

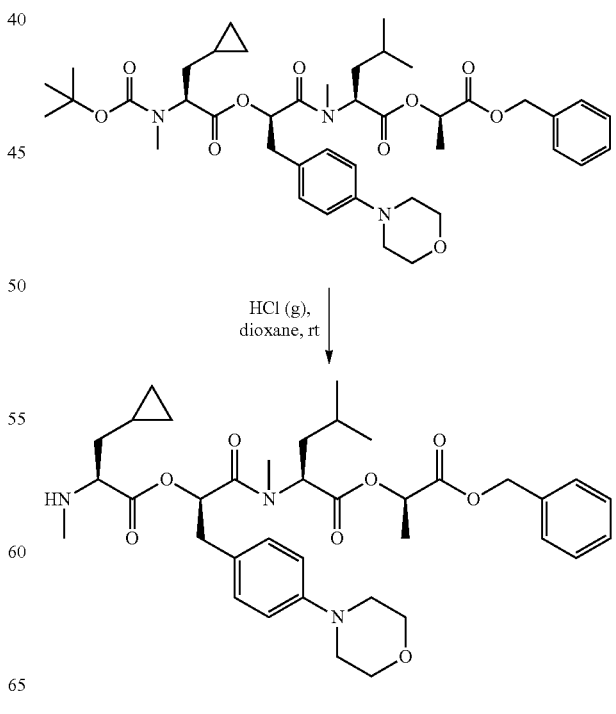

303

(2R)-1-(benzyloxy)-1-oxopropan-2-yl (2S)-2-[(2R)-2-[[(2S)-3-cyclopropyl-2-(methylamino)propanoyl]oxy]-N-methyl-3-[4-(morpholin-4-yl)phenyl]propanamido]-4-methylpentanoate (TA6-7)

Into a 250-mL round-bottom flask, was placed (2R)-1-(benzyloxy)-1-oxopropan-2-yl (2S)-2-[(2R)-2-[[(2S)-2-[[(tert-butoxy)carbonyl](methyl)amino]-3-cyclopropylpropanoyl]oxy]-N-methyl-3-[4-(morpholin-4-yl)phenyl]propanamido]-4-methylpentanoate (1 g, 1.31 mmol, 1.00 equiv), HCl(gas)/dioxane (50 mL). The resulting solution was stirred for 1 h at room temperature. The pH value of the solution was adjusted to 8 with sodium bicarbonate aq (Sat.). The resulting solution was extracted with 3×100 mL of dichloromethane and the organic layers combined and washed with 3×100 mL of brine. The organic phase was collected and dried over anhydrous sodium sulfate and concentrated under vacuum. This resulted in 820 mg (94%) of (2R)-1-(benzyloxy)-1-oxopropan-2-yl (2S)-2-[(2R)-2-[[(2S)-3-cyclopropyl-2-(methylamino)propanoyl]oxy]-N-methyl-3-[4-(morpholin-4-yl)phenyl]propanamido]-4-methylpentanoate as yellow oil. MS (ES, m/z): 666 (M+H).

304

[(1R)-2-[[(1S)-2-[(1R)-2-[[(1S)-1-[(1R)-2-benzyloxy-1-methyl-2-oxo-ethoxy]carbonyl-3-methyl-butyl]-methyl-amino]-1-[(4-morphoinophenyl)methyl]-2-oxo-ethoxy]-1-(cyclopropylmethyl)-2-oxo-ethyl]-methyl-amino]-1-methyl-2-oxo-ethyl] (2S)-2-[[(2R)-2-[(2S)-2-[tert-butoxycarbonyl(methyl)amino]-3-cyclopropyl-propanoyl]oxy-3-(4-morpholinophenyl)propanoyl]-methyl-amino]-4-methyl-pentanoate (OP6-7)

Into a 250-mL 3-necked round-bottom flask, was placed (2R)-2-[[(2S)-2-[(2R)-2-[[(2S)-2-[[(tert-butoxy)carbonyl](methyl)amino]-3-cyclopropylpropanoyl]oxy]-N-methyl-3-[4-(morpholin-4-yl)phenyl]propanamido]-4-methylpentanoyl]oxy]propanoic acid (800 mg, 1.18 mmol, 1.00 equiv), (2R)-1-(benzyloxy)-1-oxopropan-2-yl (2S)-2-[(2R)-2-[[(2S)-3-cyclopropyl-2-(methylamino)propanoyl]oxy]-N-methyl-3-[4-(morpholin-4-yl)phenyl]propanamido]-4-methylpentanoate (788 mg, 1.18 mmol, 1.00 equiv), dichloromethane (120 mL). This was followed by the addition of BOP—Cl (602 mg, 2.00 equiv) in portions at 0° C. To this was added DIEA (304 mg, 2.35 mmol, 2.00 equiv)

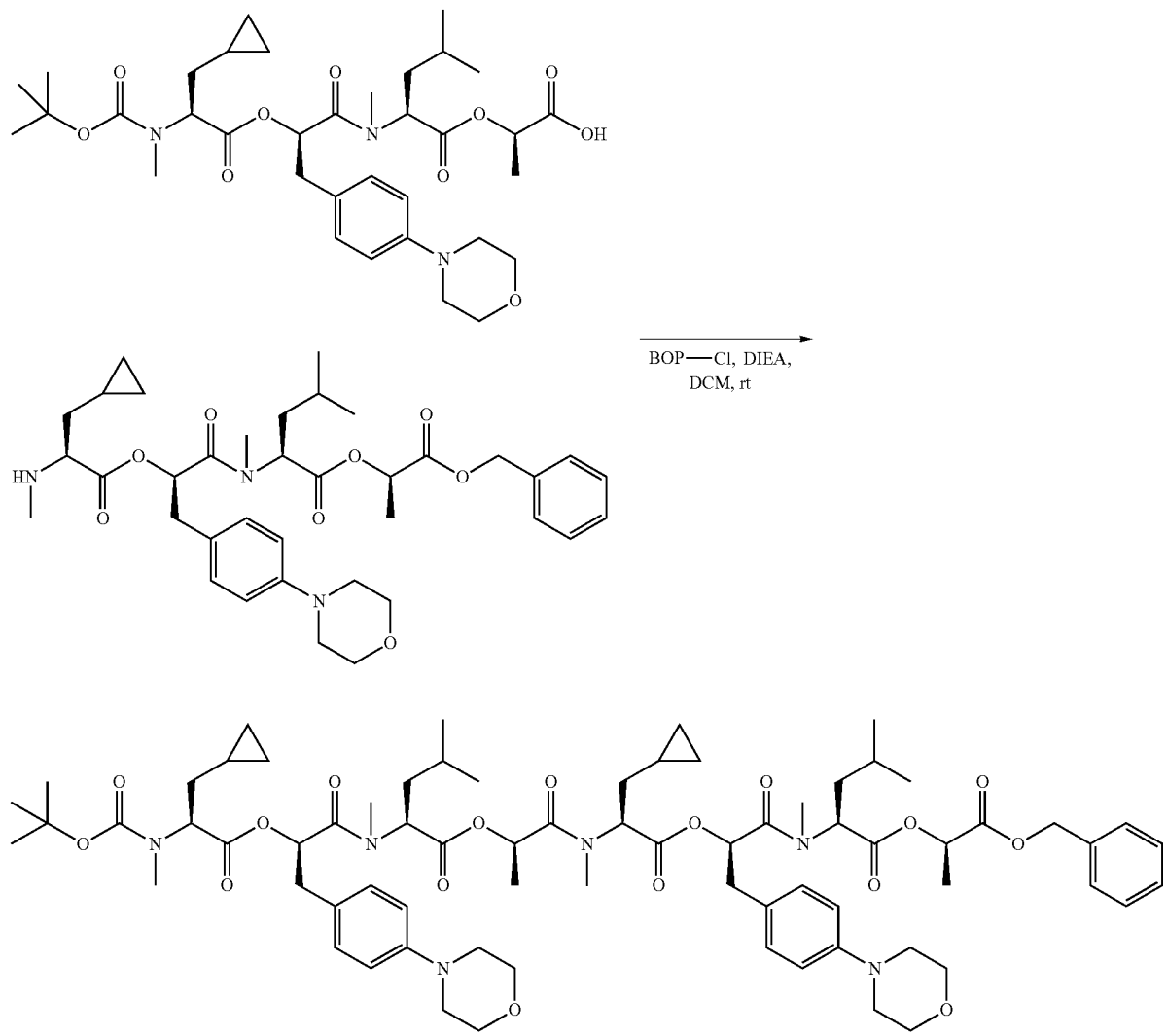

OP6-7A dropwise with stirring at 0° C. The resulting solution was stirred overnight at room temperature. The solids were filtered out. The filtrate was concentrated under vacuum. The residue was applied onto a silica gel column with ethyl acetate/petroleum ether (1:1). This resulted in 850 mg (54%) of OP6-7 as a yellow solid. MS (ES, m/z): 1324 (M+H).

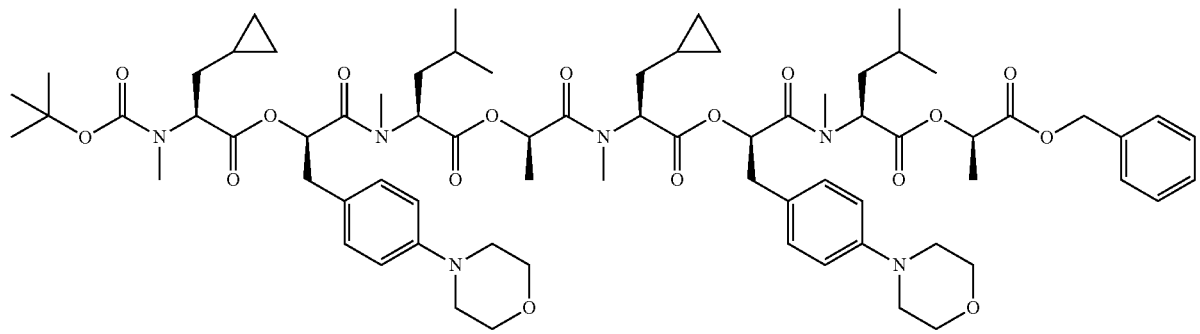

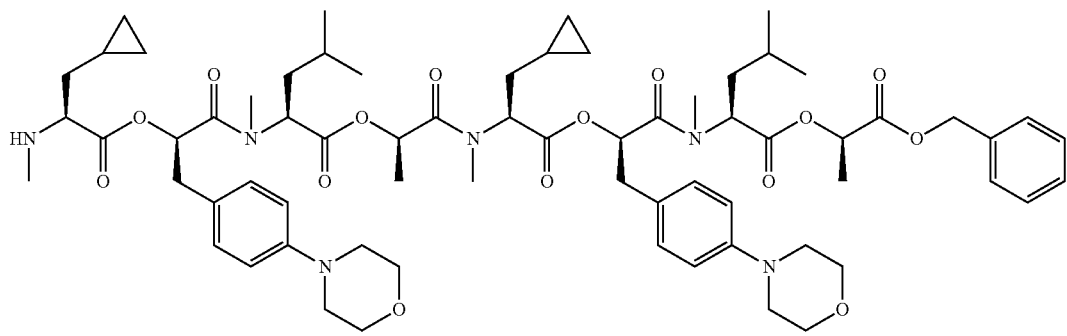

(1R)-1-[[(2S)-1-[(1R)-1-[[(2S)-1-[[(2R)-1-(benzyloxy)-1-oxopropan-2-yl]oxy]-4-methyl-1-oxopentan-2-yl](methyl)carbamoyl]-2-[4-(morpholin-4-yl)phenyl]ethoxy]-3-cyclopropyl-1-oxopropan-2-yl](methyl)carbamoyl]ethyl (2S)-2-[(2R)-2-[[(2S)-3-cyclopropyl-2-(methylamino)propanoyl]oxy]-N-methyl-3-[4-(morpholin-4-yl)phenyl]propanamido]-4-methylpentanoate (OA6-7)

Into a 100-mL round-bottom flask, was placed OP6-7 (850 mg, 0.64 mmol, 1.00 equiv), HCl(gas)/dioxane (20 mL). The resulting solution was stirred for 1 h at room temperature. The pH value of the solution was adjusted to 8 with sodium bicarbonate (aq.). The resulting solution was extracted with 3×60 mL of dichloromethane and the organic layers combined and washed with 3×100 mL of brine. The organic phase was collected and dried over anhydrous sodium sulfate and concentrated under vacuum. This resulted in 800 mg (crude) of (1R)-1-[[(2S)-1-[(1R)-1-[[(2S)-1-[[(2R)-1-(benzyloxy)-1-oxopropan-2-yl]oxy]-4-methyl-1-oxopentan-2-yl](methyl)carbamoyl]-2-[4-(morpholin-4-yl)phenyl]ethoxy]-3-cyclopropyl-1-oxopropan-2-yl](methyl)carbamoyl]ethyl (2S)-2-[(2R)-2-[[(2S)-3-cyclopropyl-2-(methylamino)propanoyl]oxy]-N-methyl-3-[4-(morpholin-4-yl)phenyl]propanamido]-4-methylpentanoate (OA6-7) as a yellow solid. MS (ES, m/z): 1224 (M+H).

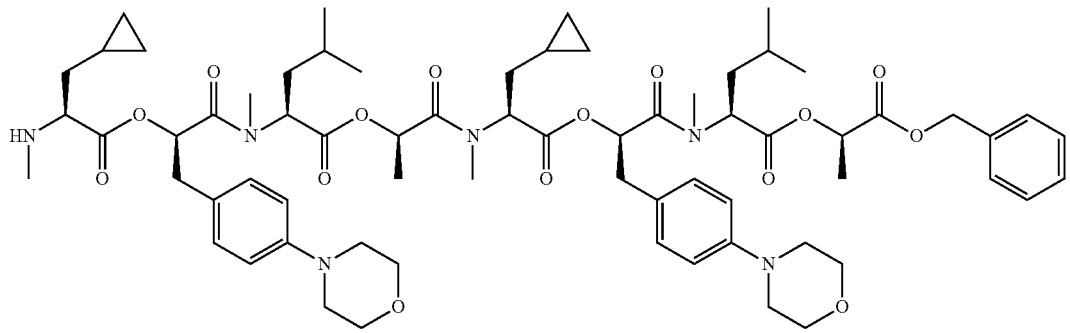

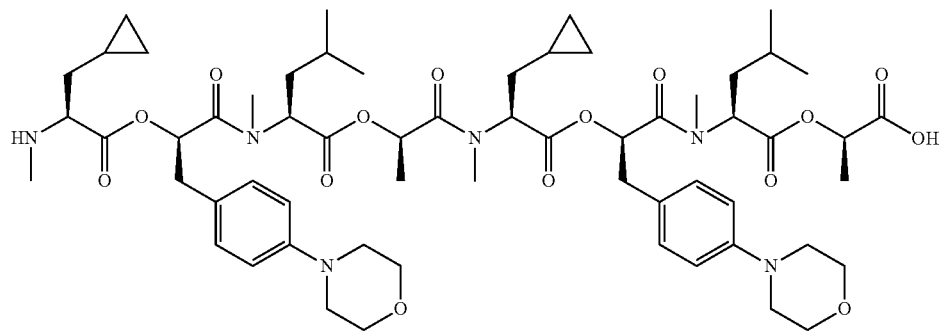

(2R)-2-[[(2S)-2-[(2R)-2-[[(2S)-3-cyclopropyl-2-[(2R)-2-[[(2S)-2-[(2R)-2-[[(2S)-3-cyclopropyl-2-(methylamino)propanoyl]oxy]-N-methyl-3-[4-(morpholin-4-yl)phenyl]propanamido]-4-methylpentanoyl]oxy]-N-methylpropanamido]propanoyl]oxy]-N-methyl-3-[4-(morpholin-4-yl)phenyl]propanamido]-4-methylpentanoyl]oxy] propanoic Acid (OAC6-7)

Into a 100-mL round-bottom flask, was placed OA6-7 (800 mg, 0.65 mmol, 1.00 equiv), methanol (50 mL), Palladium carbon (100 mg). To the above mixture was introduced hydrogen. The resulting solution was stirred for 1 h at room temperature. The solids were filtered out. The filtrate was concentrated under vacuum. This resulted in 720 mg (97%) of (2R)-2-[[(2S)-2-[(2R)-2-[[(2S)-3-cyclopropyl-2-[(2R)-2-[[(2S)-2-[(2R)-2-[[(2S)-3-cyclopropyl-2-(methylamino)propanoyl]oxy]-N-methyl-3-[4-(morpholin-4-yl)phenyl]propanamido]-4-methylpentanoyl]oxy]-N-methylpropanamido]propanoyl]oxy]-N-methyl-3-[4-(morpholin-4-yl)phenyl]propanamido]-4-methylpentanoyl]oxy]propanoic acid (OAC6-7) as a white solid. MS (ES, m/z): 1134 (M+H).

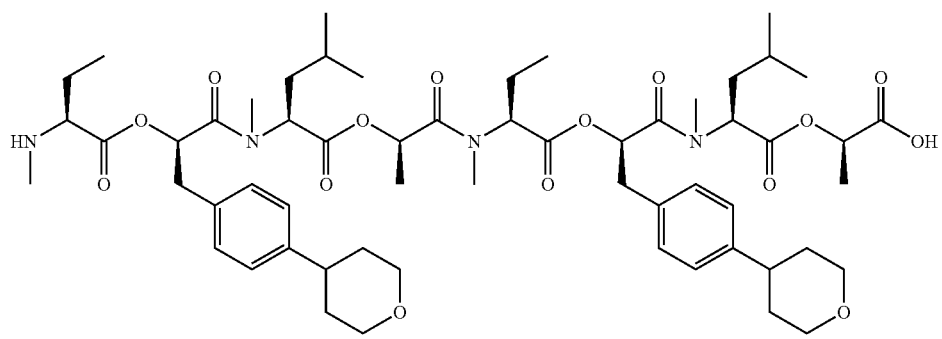

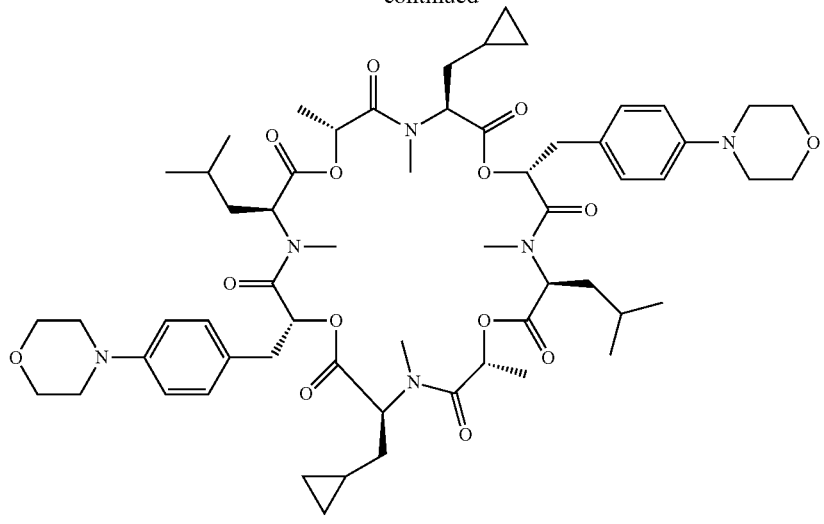

6-7A (3S,6R,9S,12R,15S,18R,21S,24R)-3,15-bis(cyclopropylmethyl)-4,6,10,16,18,22-hexamethyl-9,21-bis(2-methylpropyl)-12,24-bis([[4-(morpholin-4-yl)phenyl]methyl])-1,7,13,19-tetraoxa-4,10,16,22-tetraazacyclotetracosan-2,5,8,11,14,17,20,23-octone (6-7A)

Into a 250-mL 3-necked round-bottom flask, was placed OAC6-7 (720 mg, 0.64 mmol, 1.00 equiv), dichloromethane (200 mL). This was followed by the addition of BOP—Cl (324 mg, 1.27 mmol, 2.00 equiv) in portions at 0° C. To this was added DIEA (164 mg, 1.27 mmol, 2.00 equiv) dropwise with stirring at 0° C. The resulting solution was stirred overnight at room temperature. The solids were filtered out. The filtrate was concentrated under vacuum. The crude product was purified by Prep-HPLC with the following conditions (waters-2767): Column, SunFire Prep C18, m, 19*150 mm; mobile phase, Water and CH$_3$CN (70% CH$_3$CN up to 80% in 8 min); Detector, UV 220 nm. This resulted in 53.6 mg (8%) of (3S,6R,9S,12R,15S,18R,21S,24R)-3,15-bis(cyclopropylmethyl)-4,6,10,16,18,22-hexamethyl-9,21-bis(2-methylpropyl)-12,24-bis([[4-(morpholin-4-yl)phenyl]methyl])-1,7,13,19-tetraoxa-4,10,16,22-tetraazacyclotetracosan-2,5,8,11,14,17,20,23-octone (6-7A) as a white solid. $^1$H-NMR (CD$_3$OD, 300 MHz) δ: 7.22-7.15 (m, 4H), 6.94-6.85 (m, 4H), 5.73-5.62 (m, 2H), 5.55-5.15 (m, 5H), 4.82-4.72 (m, 1H), 3.85-3.75 (m, 8H), 3.15-2.98 (m, 18H), 2.98-2.86 (m, 6H), 2.22-1.35 (m, 12H), 1.01-0.98 (m, 3H), 0.94-0.69 (m, 14H), 0.69-0.05 (m, 9H); MS (ES, m/z): 1116.0 (M+H); [α]=−91.66°, T=27.2° C., C=0.90 g/100 mL in MeOH.

Preparation Example 34: Preparation of Compound 9-7A in Table 9, Wherein R$^a$, R$^b$, R', R'', R''' and R'''' are Each Methyl

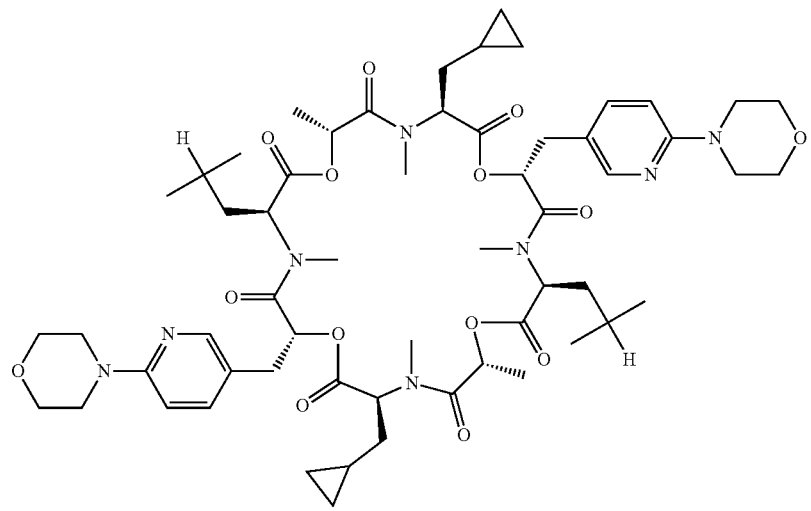

9-7A

Compound 9-7A was prepared in a similar way to compound 6-7A according to Schemes 4 and 5 shown below.
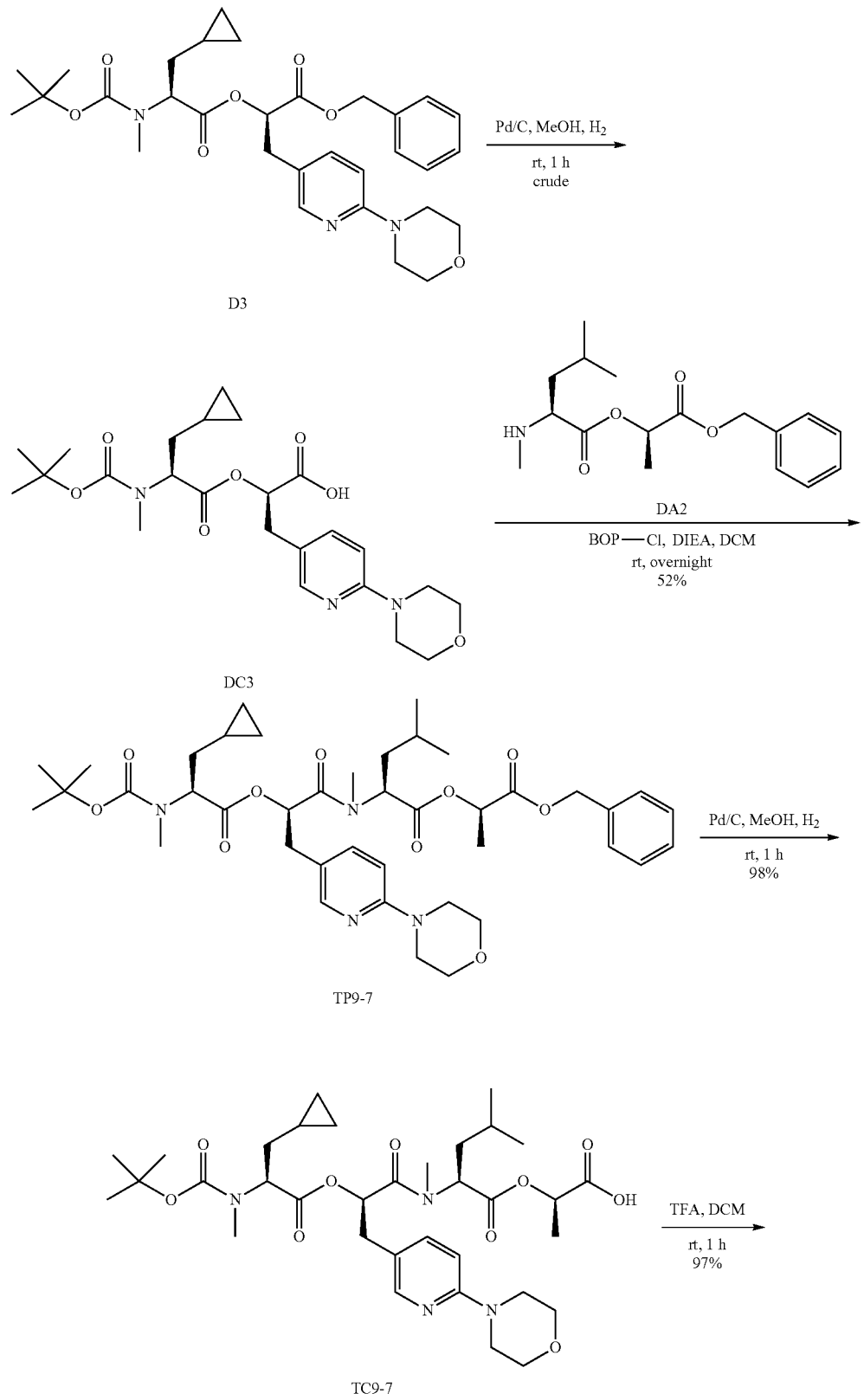

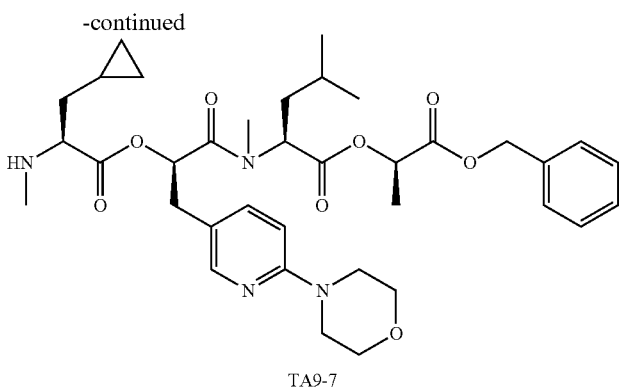
TA9-7
Scheme 5
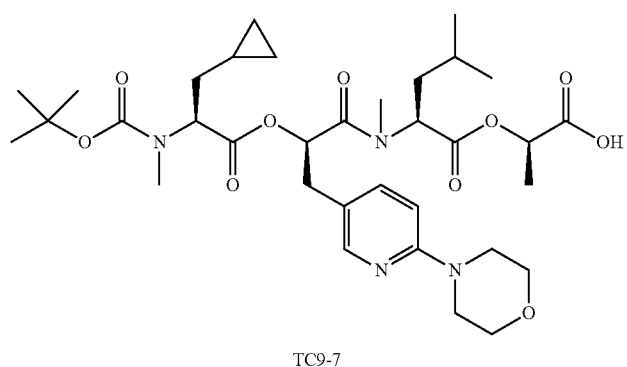
TC9-7 +
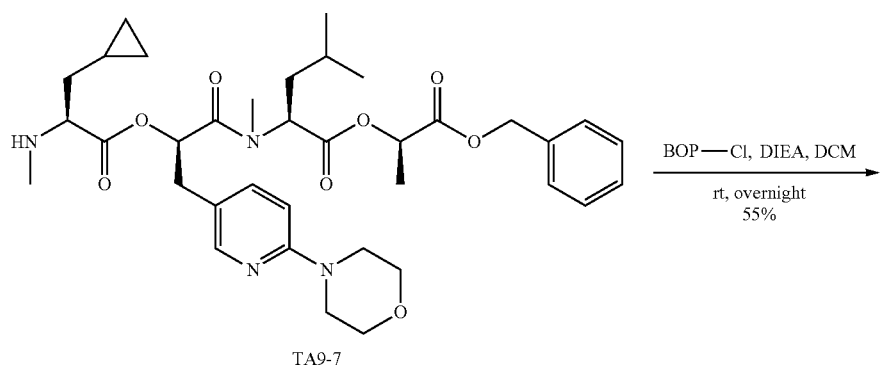
TA9-7
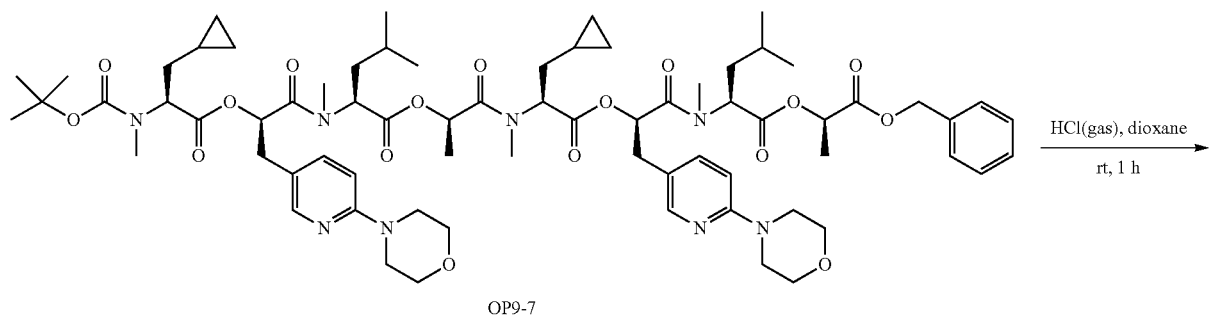
OP9-7

315
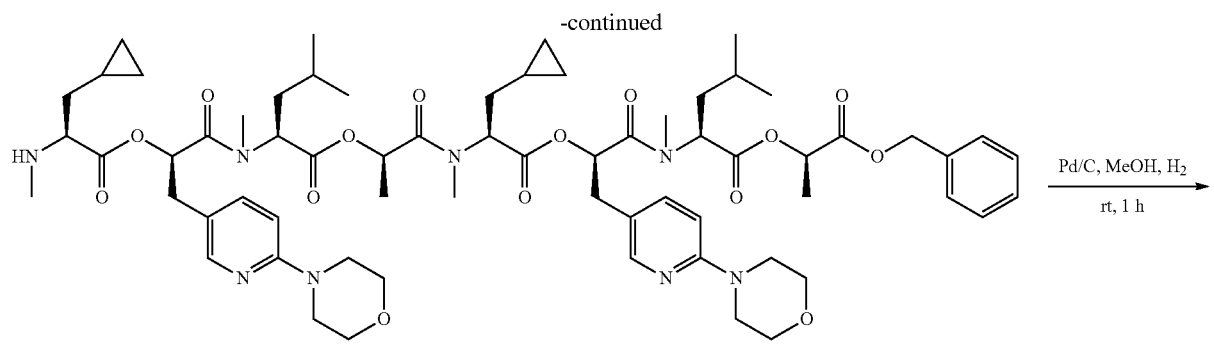
OA9-7
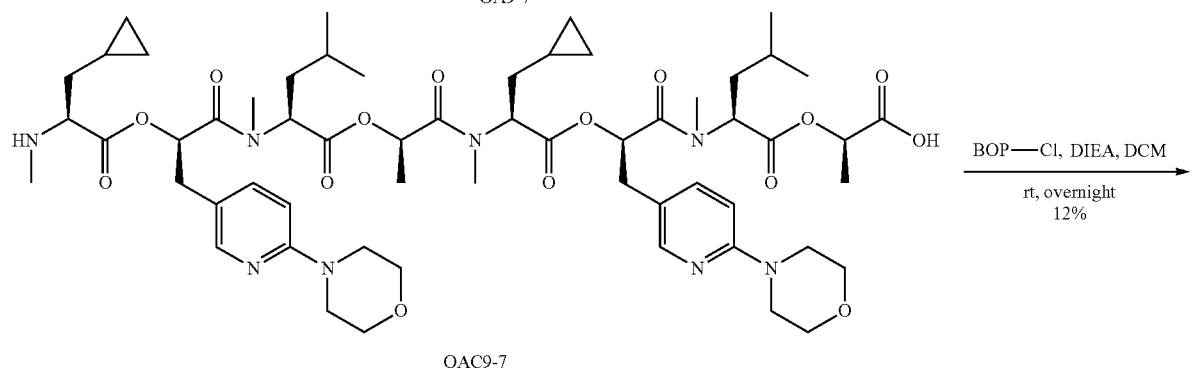
OAC9-7
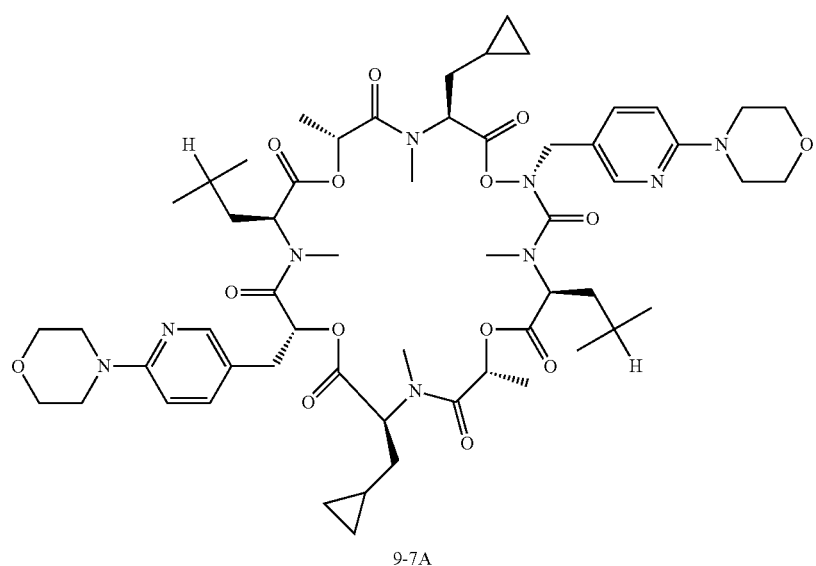
9-7A
Experimental Details
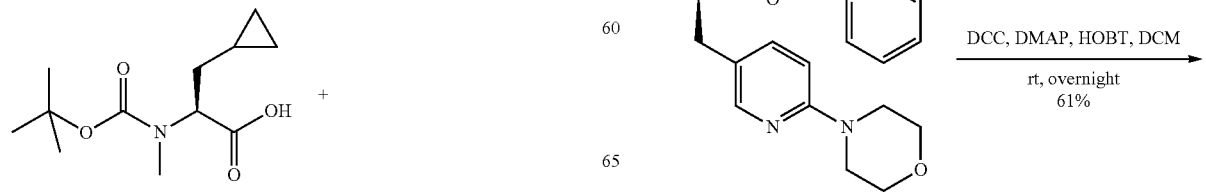

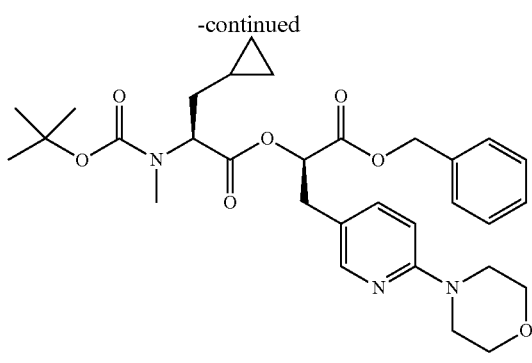

(2R)-1-(benzyloxy)-3-[6-(morpholin-4-yl)pyridin-3-yl]-1-oxopropan-2-yl (2S)-2-[[(tert-butoxy)carbonyl](methyl)amino]-3-cyclopropylpropanoate (D3)

Into a 100-mL round-bottom flask, was placed a solution of (2S)-2-[[(tert-butoxy)carbonyl](methyl)amino]-3-cyclopropylpropanoic acid (700 mg, 2.88 mmol, 1.00 equiv), dichloromethane (20 mL), benzyl (2R)-2-hydroxy-3-[6-(morpholin-4-yl)pyridin-3-yl]propanoate (1 g, 2.92 mmol, 1.00 equiv). This was followed by the addition of DCC (660 mg, 3.20 mmol, 1.10 equiv), 4-dimethylaminopyridine (400 mg, 3.27 mmol, 1.10 equiv) and HOBT (440 mg, 3.26 mmol, 1.10 equiv) in portions at 0° C. The resulting solution was stirred overnight at room temperature. The solids were filtered out. The filtrate was concentrated under vacuum. The residue was applied onto a silica gel column with ethyl acetate/petroleum ether (1:3). This resulted in 1 g (61%) of (2R)-1-(benzyloxy)-3-[6-(morpholin-4-yl)pyridin-3-yl]-1-oxopropan-2-yl (2S)-2-[[(tert-butoxy)carbonyl](methyl)amino]-3-cyclopropylpropanoate (D3) as a white solid. MS (ESI, m/z): 568 [M+H]⁺.

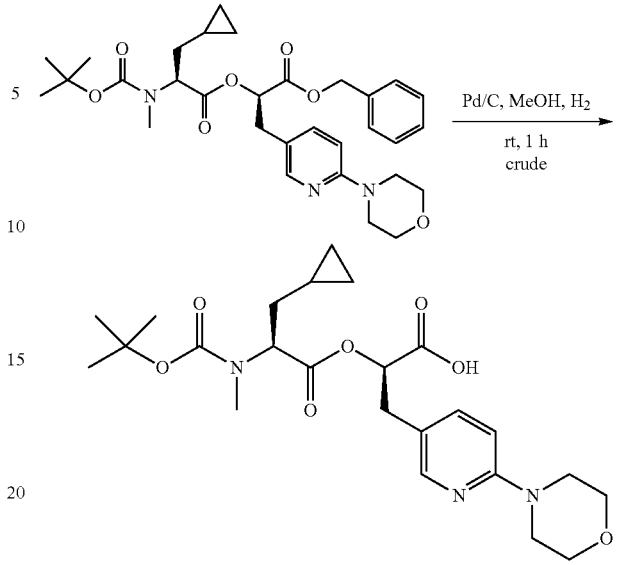

(2R)-2-[[(2S)-2-[[(tert-butoxy)carbonyl](methyl)amino]-3-cyclopropylpropanoyl]oxy]-3-[6-(morpholin-4-yl)pyridin-3-yl]propanoic Acid (DC3)

Into a 250-mL round-bottom flask, was placed a solution of (2R)-1-(benzyloxy)-3-[6-(morpholin-4-yl)pyridin-3-yl]-1-oxopropan-2-yl (2S)-2-[[(tert-butoxy)carbonyl](methyl)amino]-3-cyclopropylpropanoate (D3, 1.1 g, 1.94 mmol, 1.00 equiv), methanol (15 mL) and Palladium carbon (100 mg). To the above mixture was introduced hydrogen. The resulting solution was stirred for 1 h at room temperature. The solids were filtered out. The filtrate was concentrated under vacuum. This resulted in 1 g (crude) of (2R)-2-[[(2S)-2-[[(tert-butoxy)carbonyl](methyl)amino]-3-cyclopropylpropanoyl]oxy]-3-[6-(morpholin-4-yl)pyridin-3-yl]propanoic acid as a white solid. MS (ESI, m/z): 478 [M+H]⁺.

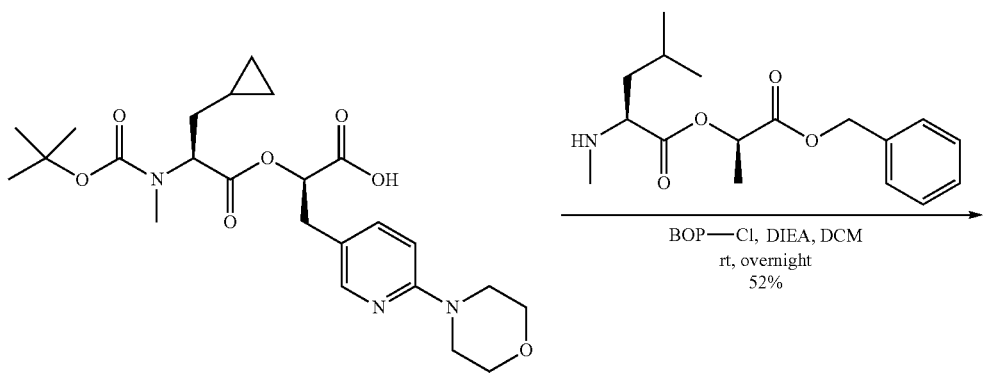

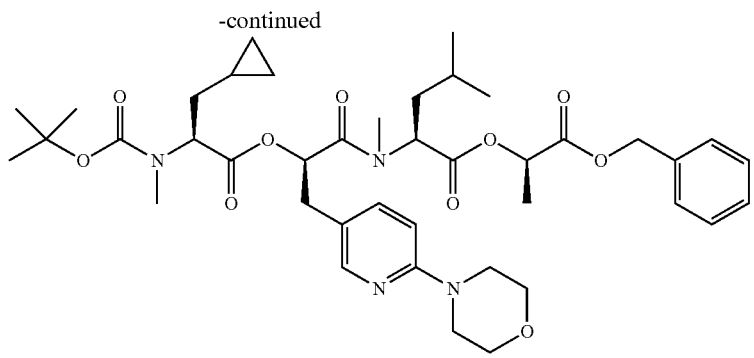

(2R)-1-(benzyloxy)-1-oxopropan-2-yl (2S)-2-[(2R)-2-[[(2S)-2-[[(tert-butoxy)carbonyl](methyl)amino]-3-cyclopropylpropanoyl]oxy]-N-methyl-3-[6-(morpholin-4-yl)pyridin-3-yl]propanamido]-4-methylpentanoate (TP9-7)

Into a 100-mL 3-necked round-bottom flask, was placed a solution of (2R)-1-(benzyloxy)-1-oxopropan-2-yl (2S)-4-methyl-2-(methylamino)pentanoate (1 g, 3.25 mmol, 1.00 equiv), dichloromethane (30 mL) and (2R)-2-[[(2S)-2-[[(tert-butoxy)carbonyl](methyl)amino]-3-cyclopropylpropanoyl]oxy]-3-[6-(morpholin-4-yl)pyridin-3-yl]propanoic acid (650 mg, 1.36 mmol, 1.00 equiv). This was followed by the addition of BOP—Cl (1.1 g, 2.00 equiv) in portions at 0° C. To this was added DIEA (540 mg, 4.18 mmol, 2.00 equiv) dropwise with stirring at 0° C. The resulting solution was stirred overnight at room temperature. The solids were filtered out. The filtrate was concentrated under vacuum. The residue was applied onto a silica gel column with ethyl acetate/petroleum ether (1:2). This resulted in 1.3 g (52%) of (2R)-1-(benzyloxy)-1-oxopropan-2-yl (2S)-2-[(2R)-2-[[(2S)-2-[[(tert-butoxy)carbonyl](methyl)amino]-3-cyclopropylpropanoyl]oxy]-N-methyl-3-[6-(morpholin-4-yl)pyridin-3-yl]propanamido]-4-methylpentanoate as a white solid. MS (ESI, m/z): 767 [M+H]+.

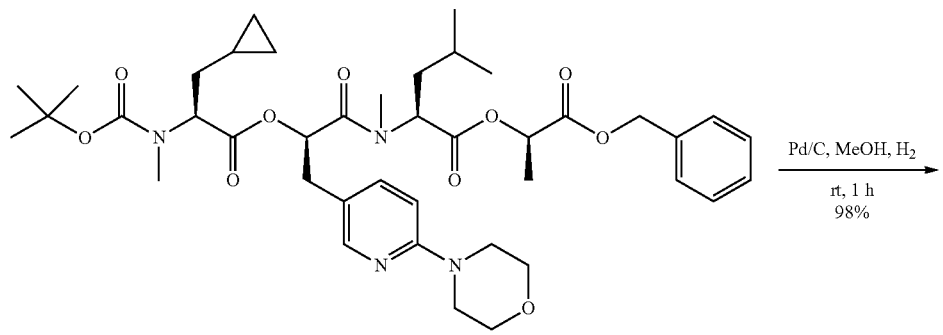

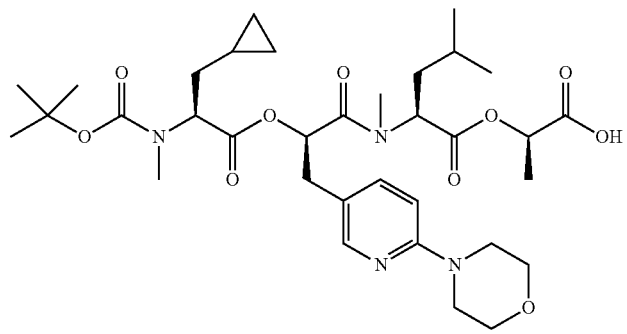

(2R)-2-[[(2S)-2-[(2R)-2-[[(2S)-2-[[(tert-butoxy)car-
bonyl](methyl)amino]-3-cyclopropylpropanoyl]
oxy]-N-methyl-3-[6-(morpholin-4-yl)pyridin-3-yl]
propanamido]-4-methylpentanoyl]oxy]propanoic
Acid (TC9-7)

Into a 100-mL round-bottom flask, was placed a solution of (2R)-1-(benzyloxy)-1-oxopropan-2-yl (2S)-2-[(2R)-2-[[(2S)-2-[[(tert-butoxy)carbonyl](methyl)amino]-3-cyclopropylpropanoyl]oxy]-N-methyl-3-[6-(morpholin-4-yl)pyridin-3-yl]propanamido]-4-methylpentanoate (650 mg, 0.85 mmol, 1.00 equiv), methanol (15 mL) and Palladium carbon (100 mg). To the above mixture was introduced hydrogen. The resulting solution was stirred for 1 h at room temperature. The solids were filtered out. The filtrate was concentrated under vacuum. This resulted in 560 mg (98%) of (2R)-2-[[(2S)-2-[(2R)-2-[[(2S)-2-[[(tert-butoxy)carbonyl](methyl)amino]-3-cyclopropylpropanoyl]oxy]-N-methyl-3-[6-(morpholin-4-yl)pyridin-3-yl]propanamido]-4-methylpentanoyl]oxy]propanoic acid as a white solid. MS (ESI, m/z): 677 [M+H]+.

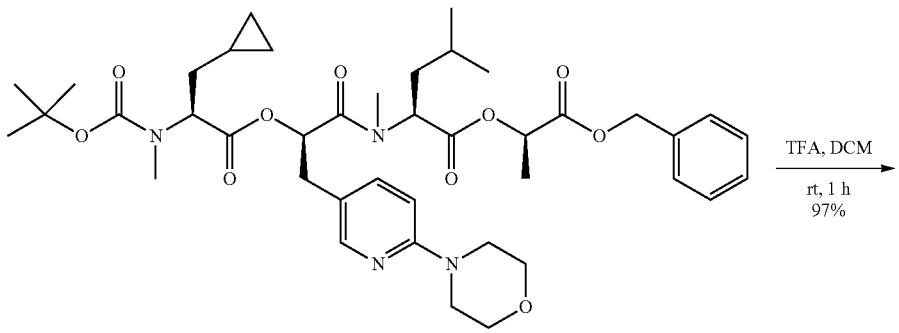

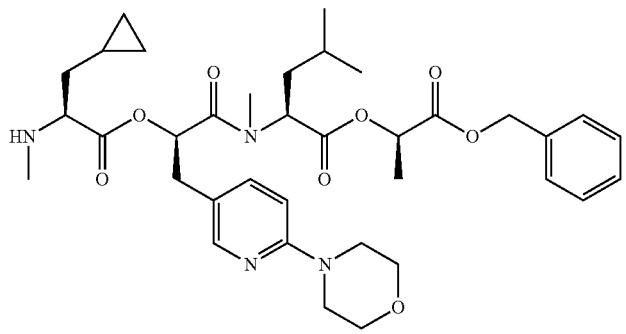

(2R)-1-(benzyloxy)-1-oxopropan-2-yl (2S)-2-[(2R)-
2-[[(2S)-3-cyclopropyl-2-(methylamino)propanoyl]
oxy]-N-methyl-3-[6-(morpholin-4-yl)pyridin-3-yl]
propanamido]-4-methylpentanoate (TA9-7)

Into a 100-mL round-bottom flask, was placed a solution of (2R)-1-(benzyloxy)-1-oxopropan-2-yl (2S)-2-[(2R)-2-[[(2S)-2-[[(tert-butoxy)carbonyl](methyl)amino]-3-cyclopropylpropanoyl]oxy]-N-methyl-3-[6-(morpholin-4-yl)pyridin-3-yl]propanamido]-4-methylpentanoate (650 mg, 0.85 mmol, 1.00 equiv), dichloromethane (10 mL). To this was added trifluoroacetic acid (1 mL) dropwise with stirring at 0° C. The resulting solution was stirred for 1 h at room temperature. The pH value of the solution was adjusted to 9 with sodium bicarbonate(aq.). The resulting solution was extracted with 3×20 mL of dichloromethane and the organic layers combined. The organic phase was dried over anhydrous sodium sulfate and concentrated under vacuum. This resulted in 550 mg (97%) of (2R)-1-(benzyloxy)-1-oxopropan-2-yl (2S)-2-[(2R)-2-[[(2S)-3-cyclopropyl-2-(methylamino)propanoyl]oxy]-N-methyl-3-[6-(morpholin-4-yl)pyridin-3-yl]propanamido]-4-methylpentanoate as a light yellow semi-solid. MS (ESI, m/z): 667 [M+H]+.

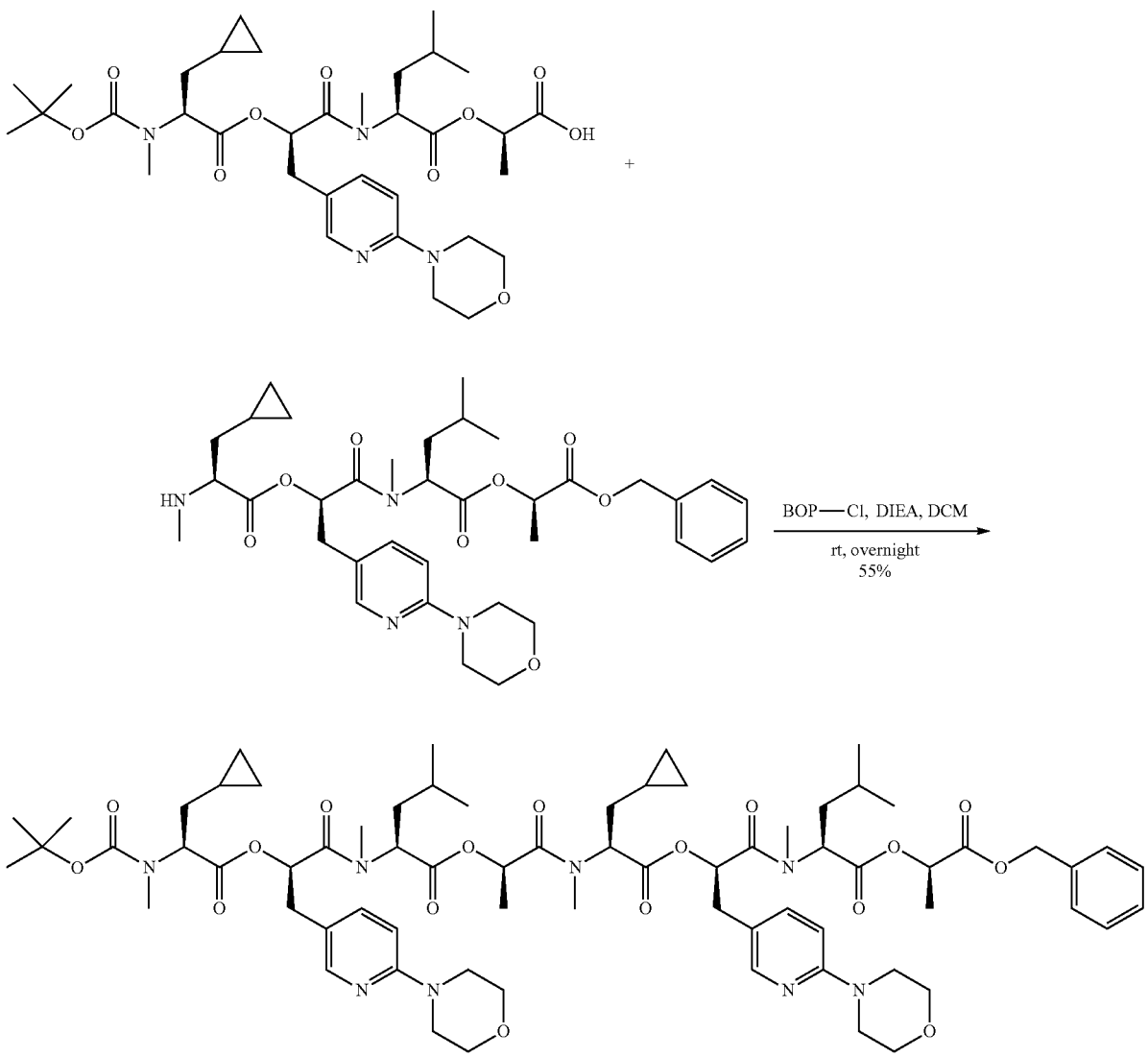

OP9-7:

Into a 250-mL 3-necked round-bottom flask, was placed a solution of TC9-7 (560 mg, 0.83 mmol, 1.00 equiv), dichloromethane (50 mL) and TA9-7 (550 mg, 0.82 mmol, 1.00 equiv). This was followed by the addition of BOP—Cl (421 mg, 2.00 equiv) in portions at 0° C. To this was added DIEA (210 mg, 1.62 mmol, 2.00 equiv) dropwise with stirring at 0° C. The resulting solution was stirred overnight at room temperature. The solids were filtered out. The filtrate was concentrated under vacuum. The residue was applied onto a silica gel column with ethyl acetate/petroleum ether (1:1). This resulted in 600 mg (55%) of 9-7-6 as colorless oil. MS (ESI, m/z): 1326 [M+H]$^+$.

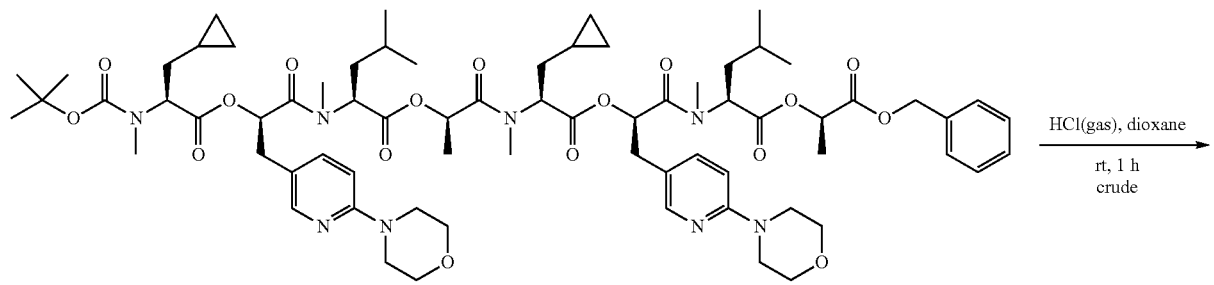

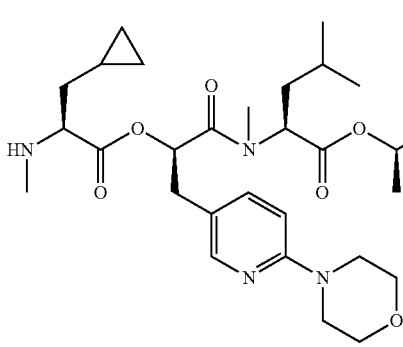
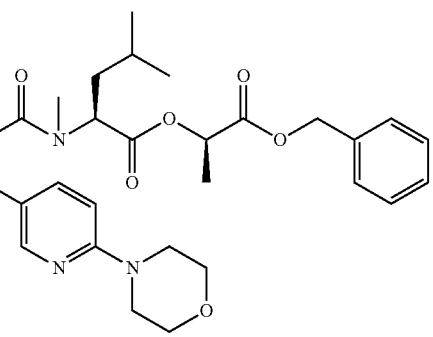

OA9-7:

Into a 100-mL 3-necked round-bottom flask, was placed a solution of OP9-7 (600 mg, 0.45 mmol, 1.00 equiv), dioxane (20 mL). To the above hydrogen chloride (gas) was introduced in. The resulting solution was stirred for 1 h at room temperature. The resulting solution was stirred for 1 h at room temperature. The pH value of the solution was adjusted to 9 with sodium bicarbonate (aq.). The resulting solution was extracted with 3×20 mL of dichloromethane and the organic layers combined. The organic phase was dried over anhydrous sodium sulfate and concentrated under vacuum. This resulted in 510 mg (crude) of OA9-7 as a yellow semi-solid. MS (ESI, m/z): 1226 [M+H]+.

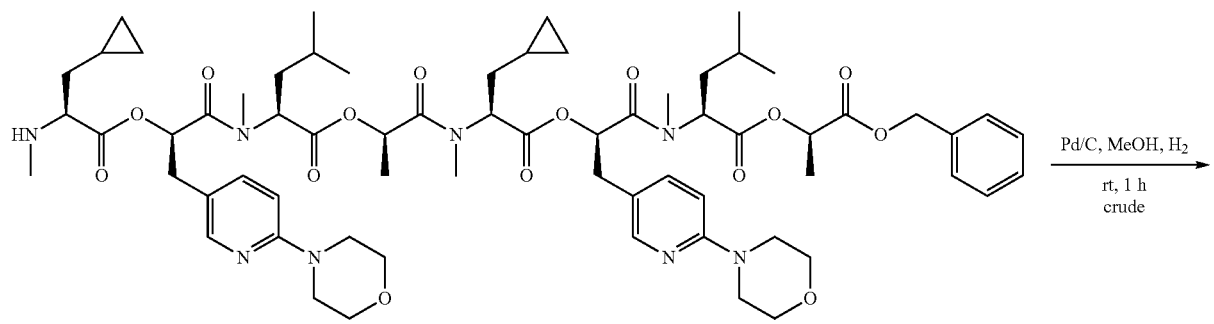

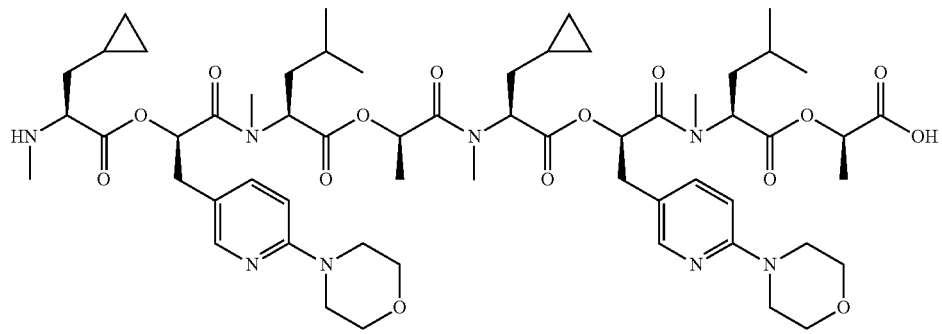

OAC9-7:

Into a 100-mL round-bottom flask, was placed a solution of OA9-7 (510 mg, 0.42 mmol, 1.00 equiv), methanol (10 mL) and Palladium carbon (50 mg). To the above mixture was introduced hydrogen. The resulting solution was stirred for 1 h at room temperature. The solids were filtered out. The filtrate was concentrated under vacuum. This resulted in 480 mg (crude) of OAC9-7 as a white solid. MS (ESI, m/z): 1136 [M+H]+.

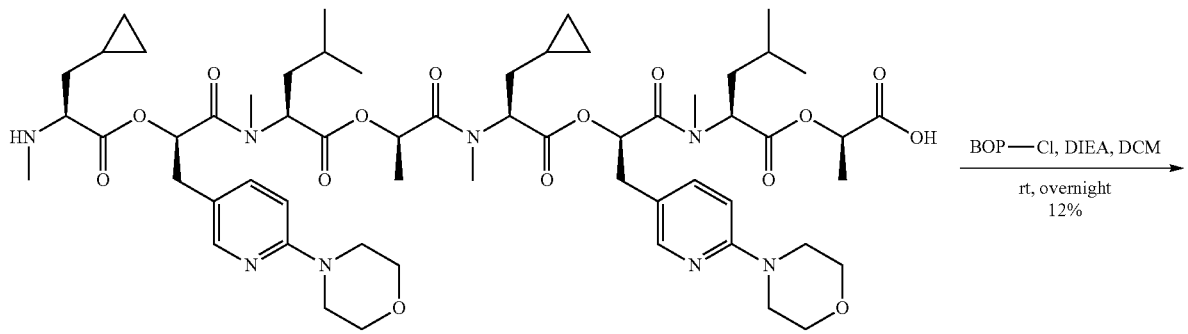

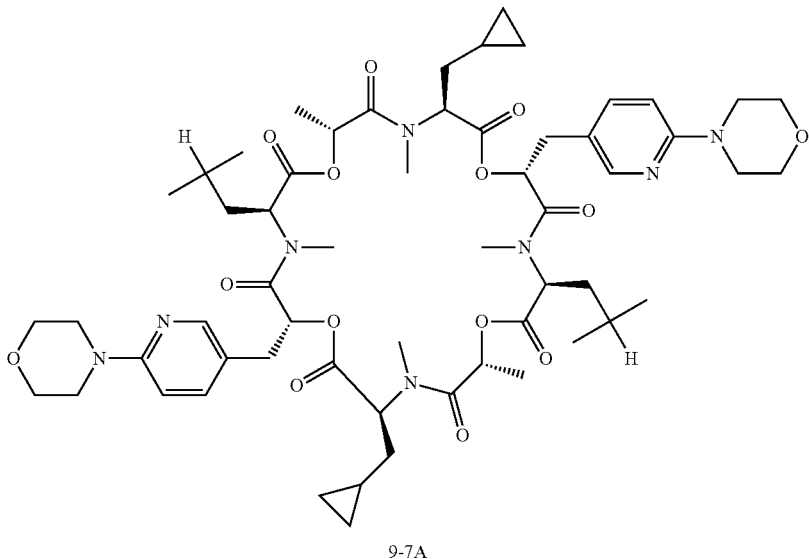

9-7A (3S,6R,9S,12R,15S,18R,21S,24R)-3,15-bis(cyclo-
propylmethyl)-4,6,10,16,18,22-hexamethyl-9,21-bis
(2-methylpropyl)-12,24-bis([[6-(morpholin-4-yl)
pyridin-3-yl]methyl])-1,7,13,19-tetraoxa-4,10,16,22-
tetraazacyclotetracosan-2,5,8,11,14,17,20,23-octone
(9-7A)

Into a 250-mL 3-necked round-bottom flask, was placed a solution of OAC9-7 (480 mg, 0.042 mmol, 1.00 equiv) and DCM (100 mL). This was followed by the addition of BOP—Cl (216 mg, 0.85 mmol, 2.00 equiv) in portions at 0° C. To this was added DIEA (110 mg, 0.85 mmol, 2.00 equiv) dropwise with stirring at 0° C. The resulting solution was stirred overnight at room temperature. The solids were filtered out. The filtrate was concentrated under vacuum. The crude product was purified by Prep-HPLC with the following conditions (waters-2767): Column, SunFire Prep C18, 5 um, 19*150 mm; mobile phase, 0.05% Trifluoroacetic acid in water and $CH_3CN$ (70% $CH_3CN$ up to 80% in 8 min); Detector, UV 254 nm. This resulted in 57.2 mg (12%) of (3S,6R,9S,12R,15S,18R,21S,24R)-3,15-bis(cyclopropylm-ethyl)-4,6,10,16,18,22-hexamethyl-9,21-bis(2-methylpropyl)-12,24-bis([[6-(morpholin-4-yl)pyridin-3-yl]methyl])-1,7,13,19-tetraoxa-4,10,16,22-tetraazacyclotetracosan-2,5,8,11,14,17,20,23-octone (9-7) as a white solid. $^1$H NMR ($CD_3OD$, 300 MHz) δ: 8.1-7.9 (m, 2H), 7.60-7.50 (m, 2H), 6.85-6.65 (m, 2H), 5.90-5.10 (m, 7H), 4.80-4.70 (m, 1H), 3.85-3.65 (m, 8H), 3.55-3.40 (m, 8H), 3.20-2.80 (m, 16H), 2.25-1.30 (m, 12H), 1.10-0.70 (m, 17H), 0.70-0.35 (m, 5H), 0.30-0.01 (m, 4H); MS (ESI, m/z): 1118 [M+H]+; [α]=−77.340, T=27.2° C., C=1.00 g/100 mL, MeOH.

Preparation Example 35: Synthesis of Compound 6-34A in Table 6, Wherein $R^a$, $R^b$, R', R'', R''' and R'''' are Each Methyl
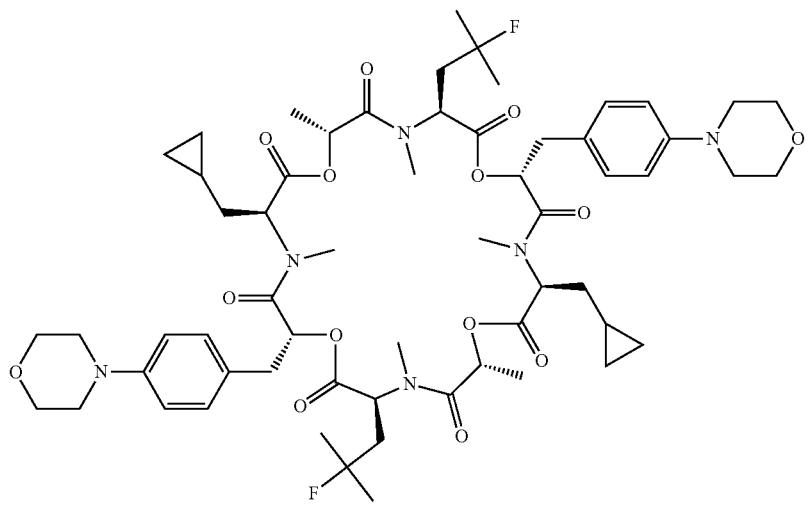
6-34A
Compound 6-30A was prepared in a similar way to compound 6-7A according to Schemes 6 and 7 shown below.
Scheme 6
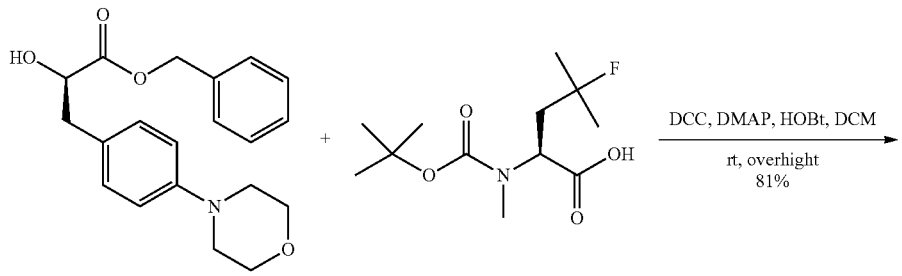
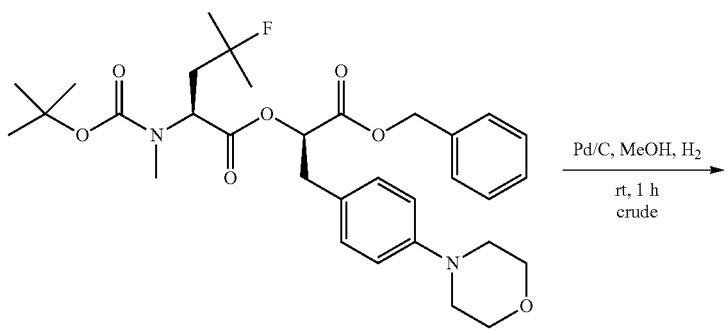
D5

-continued
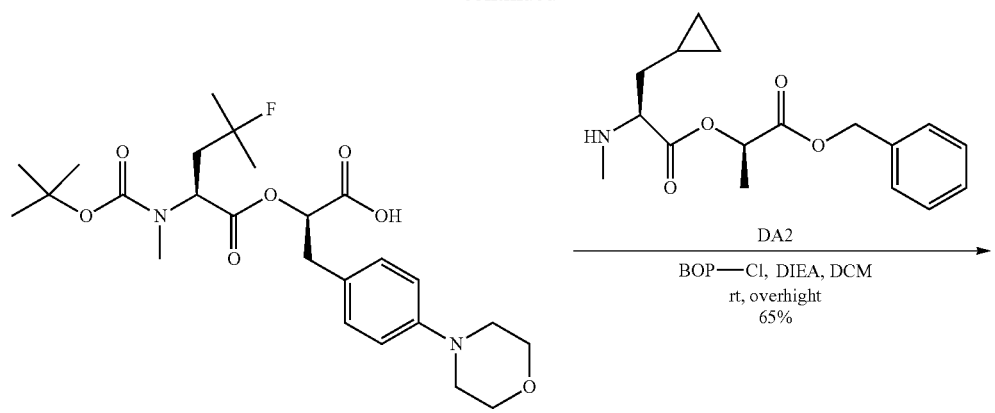
DC5
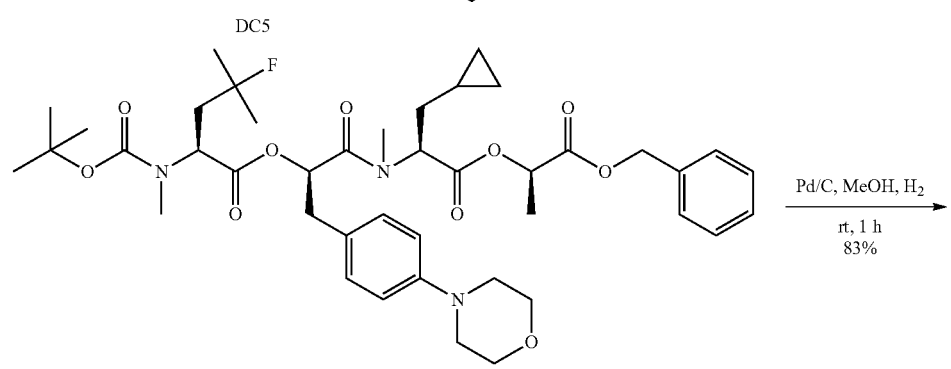
TP6-34
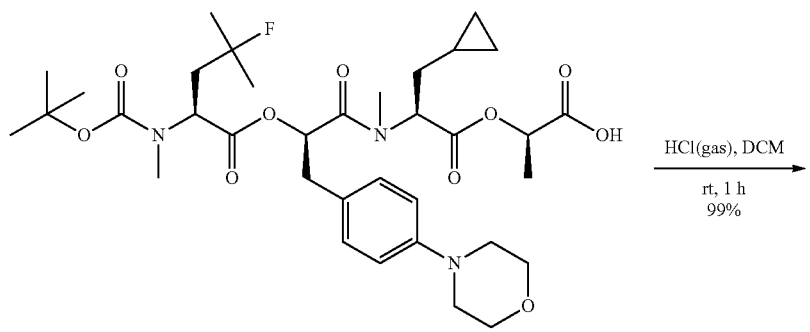
TC6-34
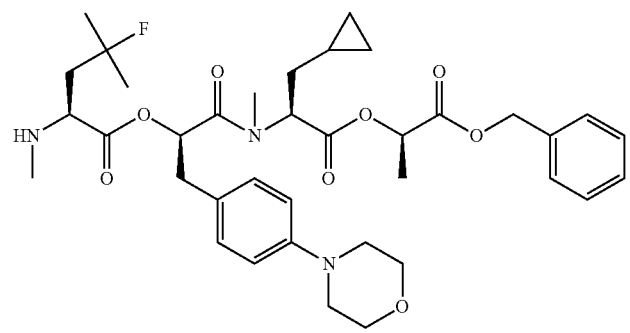
TA6-34

Scheme 7
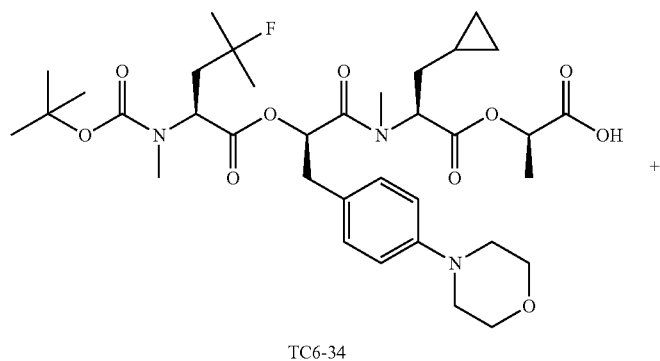
TC6-34 +
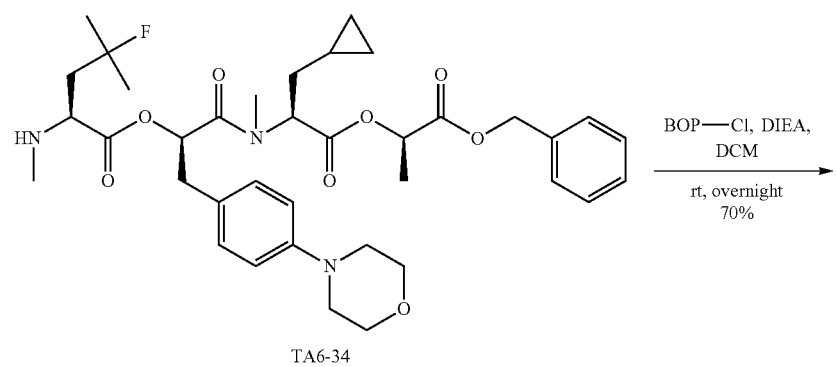
TA6-34
BOP—Cl, DIEA,
DCM
———————→
rt, overnight
70%
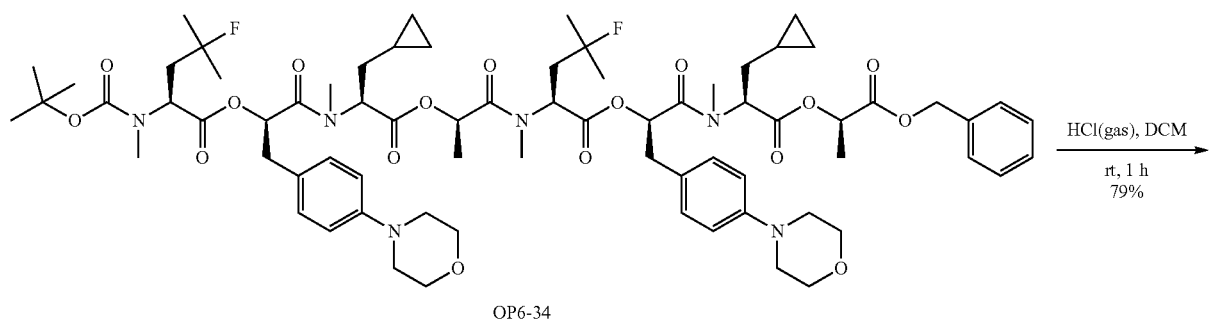
OP6-34
HCl(gas), DCM
———————→
rt, 1 h
79%

-continued
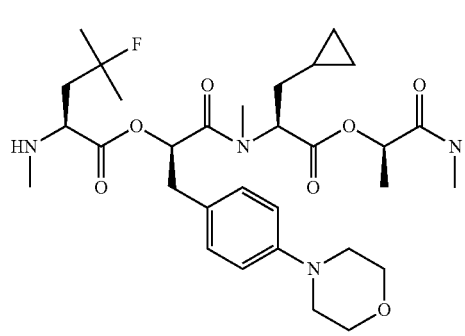 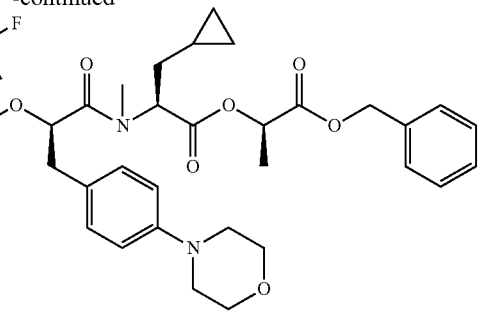
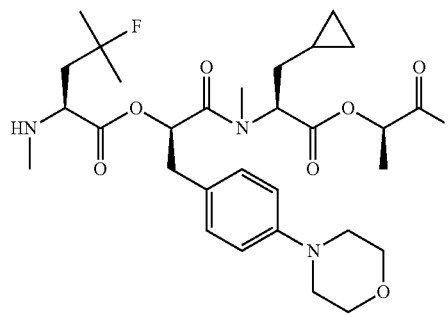
OAC6-34
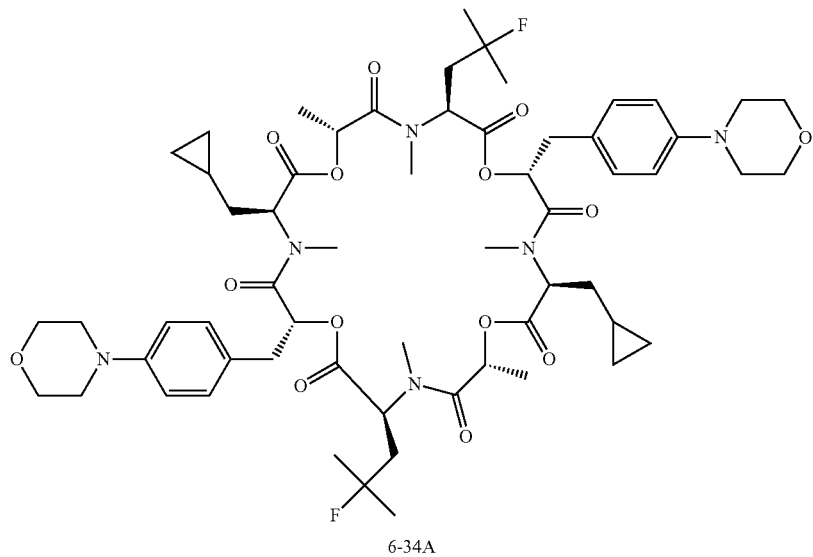
6-34A
Experimental Details
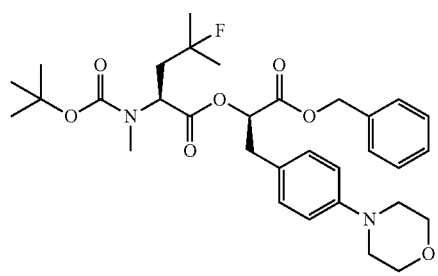
-continued
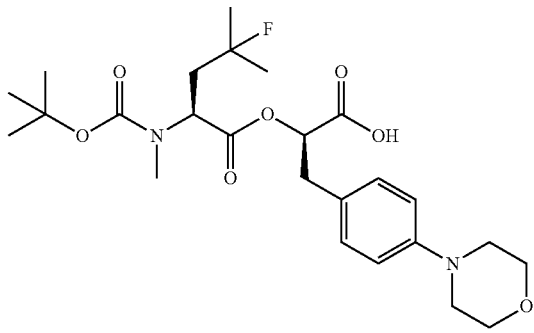

(R)-2-((S)-2-(tert-butoxycarbonyl(methyl)amino)-4-fluoro-4-methylpentanoyloxy)-3-(4-morpholinophenyl)propanoic Acid (DC5)

Into a 250-mL round-bottom flask, was placed (2R)-1-(benzyloxy)-3-[4-(morpholin-4-yl)phenyl]-1-oxopropan-2-yl (2S)-2-[[(tert-butoxy)carbonyl](methyl)amino]-4-fluoro-4-methylpentanoate (D5, 3.5 g, 5.97 mmol, 1.00 equiv), methanol (100 mL), Palladium carbon (1 g). To the above mixture was introduced hydrogen. The resulting solution was stirred for 1 h at room temperature. The solids were filtered out. The filtrate was concentrated under vacuum. This resulted in 3 g (crude) of (2R)-2-[[(2S)-2-[[(tert-butoxy)carbonyl](methyl)amino]-4-fluoro-4-methylpentanoyl]oxy]-3-[4-(morpholin-4-yl)phenyl]propanoic acid as a white solid. MS (ES, m/z): 497 (M+H).

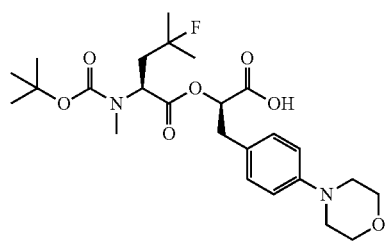

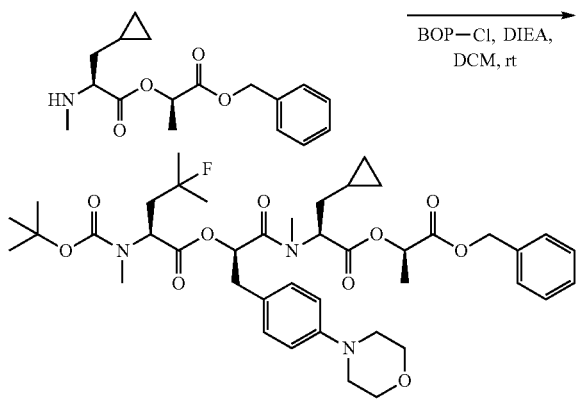

(S)—((R)-1-(((S)-1-((R)-1-(benzyloxy)-1-oxopropan-2-yloxy)-3-cyclopropyl-1-oxopropan-2-yl)(methyl)amino)-3-(4-morpholinophenyl)-1-oxopropan-2-yl) 2-(tert-butoxycarbonyl(methyl)amino)-4-fluoro-4-methylpentanoate (TP6-34)

Into a 250-mL 3-necked round-bottom flask, was placed (2R)-1-(benzyloxy)-1-oxopropan-2-yl (2S)-3-cyclopropyl-2-(methylamino)propanoate (DA2, 1.8 g, 5.89 mmol, 1.00 equiv), (2R)-2-[[(2S)-2-[[(tert-butoxy)carbonyl](methyl)amino]-4-fluoro-4-methylpentanoyl]oxy]-3-[4-(morpholin-4-yl)phenyl]propanoic acid (DC5, 3 g, 6.04 mmol, 1.00 equiv), dichloromethane (120 mL). This was followed by the addition of BOP—Cl (3.1 g, 12.18 mmol, 2.00 equiv) in portions at 0° C. To this was added DIEA (1.6 g, 12.38 mmol, 2.00 equiv) dropwise with stirring at 0° C. The resulting solution was stirred overnight at room temperature. The solids were filtered out. The filtrate was concentrated under vacuum. The residue was applied onto a silica gel column with ethyl acetate/petroleum ether (1:6). This resulted in 3 g (65%) of (1R)-1-[[(2S)-1-[[(2R)-1-(benzyloxy)-1-oxopropan-2-yl]oxy]-3-cyclopropyl-1-oxopropan-2-yl](methyl)carbamoyl]-2-[4-(morpholin-4-yl)phenyl]ethyl (2S)-2-[[(tert-butoxy)carbonyl](methyl)amino]-4-fluoro-4-methylpentanoate as yellow oil. MS (ES, m/z): 784 (M+H).

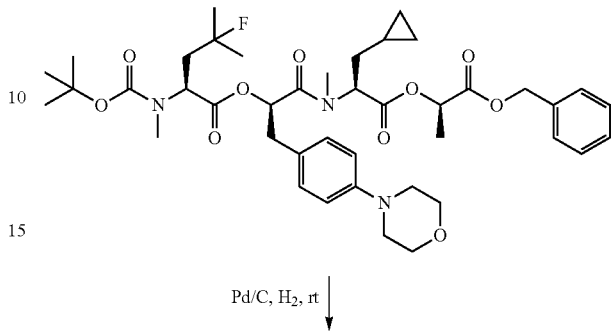

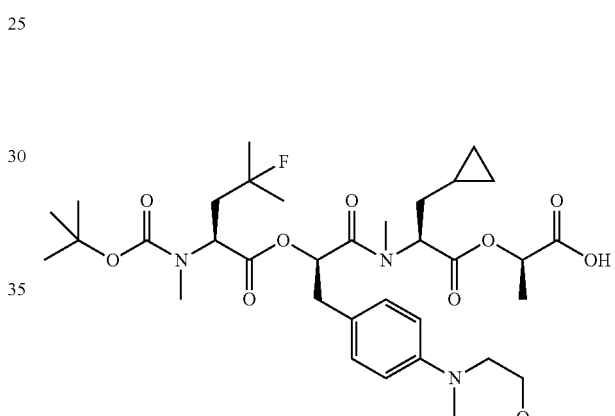

(2R)-2-[[(2S)-2-[(2R)-2-[[(2S)-2-[[(tert-butoxy)carbonyl](methyl)amino]-4-fluoro-4-methylpentanoyl]oxy]-N-methyl-3-[4-(morpholin-4-yl)phenyl]propanamido]-3-cyclopropylpropanoyl]oxy]propanoic Acid (TC6-34)

Into a 250-mL round-bottom flask, was placed (1R)-1-[[(2S)-1-[[(2R)-1-(benzyloxy)-1-oxopropan-2-yl]oxy]-3-cyclopropyl-1-oxopropan-2-yl](methyl)carbamoyl]-2-[4-(morpholin-4-yl)phenyl]ethyl (2S)-2-[[(tert-butoxy)carbonyl](methyl)amino]-4-fluoro-4-methylpentanoate (TP6-34, 1.5 g, 1.91 mmol, 1.00 equiv), methanol (100 mL), Palladium carbon (500 mg). To the above mixture was introduced hydrogen. The resulting solution was stirred for 1 h at room temperature. The solids were filtered out. The filtrate was concentrated under vacuum. This resulted in 1.1 g (83%) of (2R)-2-[[(2S)-2-[(2R)-2-[[(2S)-2-[[(tert-butoxy)carbonyl](methyl)amino]-4-fluoro-4-methylpentanoyl]oxy]-N-methyl-3-[4-(morpholin-4-yl)phenyl]propanamido]-3-cyclopropylpropanoyl]oxy]propanoic acid as a white solid. MS (ES, m/z): 694 (M+H).

339

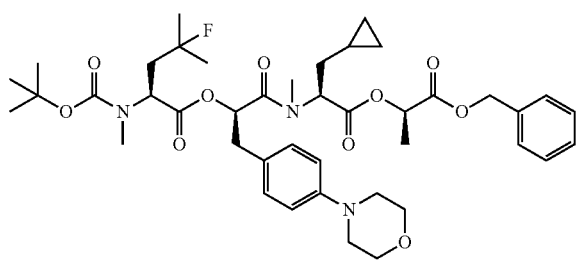

HCl (gas),
DCM, rt

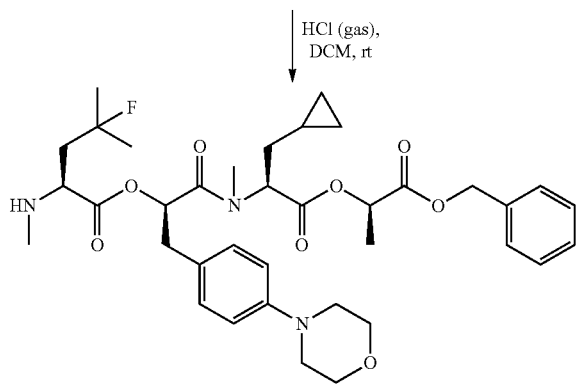

340

(1R)-1-[[(2S)-1-[[(2R)-1-(benzyloxy)-1-oxopropan-2-yl]oxy]-3-cyclopropyl-1-oxopropan-2-yl](methyl) carbamoyl]-2-[4-(morpholin-4-yl)phenyl]ethyl (2S)-4-fluoro-4-methyl-2-(methylamino)pentanoate (TA6-34)

Into a 250-mL 3-necked round-bottom flask, was placed (1R)-1-[[(2S)-1-[[(2R)-1-(benzyloxy)-1-oxopropan-2-yl]oxy]-3-cyclopropyl-1-oxopropan-2-yl](methyl)carbamoyl]-2-[4-(morpholin-4-yl)phenyl]ethyl (2S)-2-[[(tert-butoxy)carbonyl](methyl)amino]-4-fluoro-4-methylpentanoate (TP6-34, 1.5 g, 1.91 mmol, 1.00 equiv), dichloromethane (100 mL). To the above HCl (gas) was introduced in. The resulting solution was stirred for 1 h at room temperature. The pH value of the solution was adjusted to 8 with sodium bicarbonate (aq). The resulting solution was extracted with 3×80 mL of dichloromethane and the organic layers combined and washed with 3×100 mL of brine. The organic phase was collected and dried over anhydrous sodium sulfate and concentrated under vacuum. This resulted in 1.3 g (99%) of (1R)-1-[[(2S)-1-[[(2R)-1-(benzyloxy)-1-oxopropan-2-yl]oxy]-3-cyclopropyl-1-oxopropan-2-yl](methyl) carbamoyl]-2-[4-(morpholin-4-yl)phenyl]ethyl (2S)-4-fluoro-4-methyl-2-(methylamino)pentanoate as yellow oil. MS (ES, m/z): 684 (M+H).

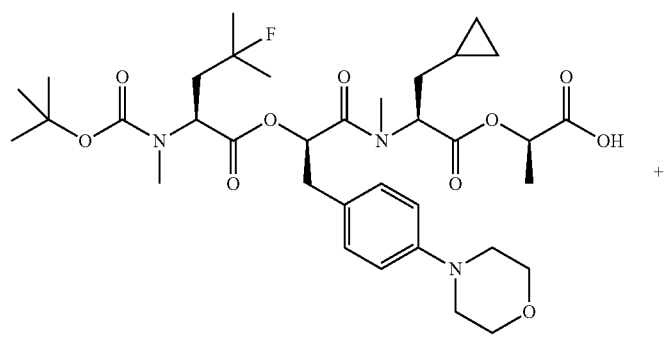

+

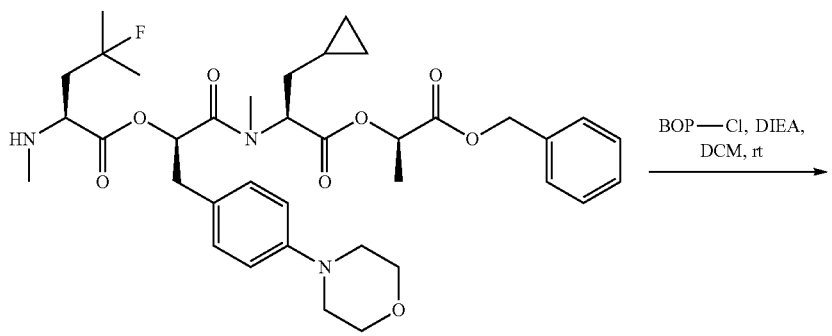

BOP—Cl, DIEA,
DCM, rt 341 342

-continued

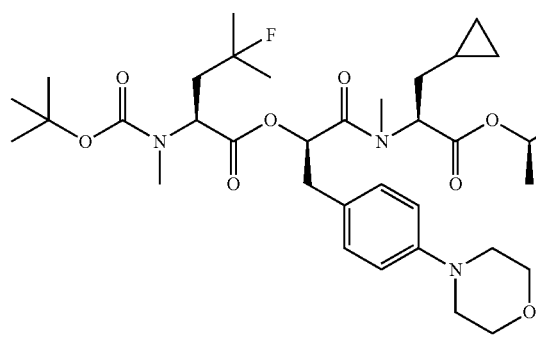 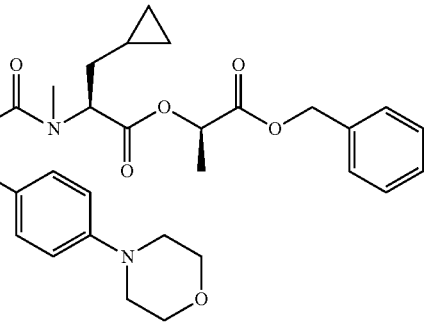

[(1R)-2-[[(1S)-2-[(1R)-2-benzyloxy-1-methyl-2-oxo-ethoxy]-1-(cyclopropylmethyl)-2-oxo-ethyl]-methyl-amino]-1-[(4-morpholinophenyl)methyl]-2-oxo-ethyl](2S)-2-[[(2R)-2-[(2S)-2-[[(2R)-2-[(2S)-2-[tert-butoxycarbonyl(methyl)amino]-4-fluoro-4-methyl-pentanoyl]oxy-3-(4-morpholinophenyl)propanoyl]-methyl-amino]-3-cyclopropyl-propanoyl]oxypropanoyl]-methyl-amino]-4-fluoro-4-methyl-pentanoate (OP6-34)

Into a 250-mL 3-necked round-bottom flask, was placed (2R)-2-[[(2S)-2-[(2R)-2-[[(2S)-2-[[(tert-butoxy)carbonyl](methyl)amino]-4-fluoro-4-methylpentanoyl]oxy]-N-methyl-3-[4-(morpholin-4-yl)phenyl]propanamido]-3-cyclopropylpropanoyl]oxy]propanoic acid (TC6-34, 1.1 g, 1.59 mmol, 1.00 equiv), (1R)-1-[[(2S)-1-[[(2R)-1-(benzyloxy)-1-oxopropan-2-yl]oxy]-3-cyclopropyl-1-oxopropan-2-yl](methyl)carbamoyl]-2-[4-(morpholin-4-yl)phenyl] ethyl (2S)-4-fluoro-4-methyl-2-(methylamino)pentanoate (TA6-34, 1.1 g, 1.61 mmol, 1.00 equiv), dichloromethane (120 mL). This was followed by the addition of BOP—Cl (808 mg, 3.17 mmol, 2.00 equiv) in portions at 0° C. To this was added DIEA (409 mg, 3.16 mmol, 2.00 equiv) dropwise with stirring at 0° C. The resulting solution was stirred overnight at room temperature. The solids were filtered out. The filtrate was concentrated under vacuum. The residue was applied onto a silica gel column with ethyl acetate/petroleum ether (1:1). This resulted in 1.5 g (70%) of OP6-34 as a yellow solid. MS (ES, m/z): 1360 (Ms+H).

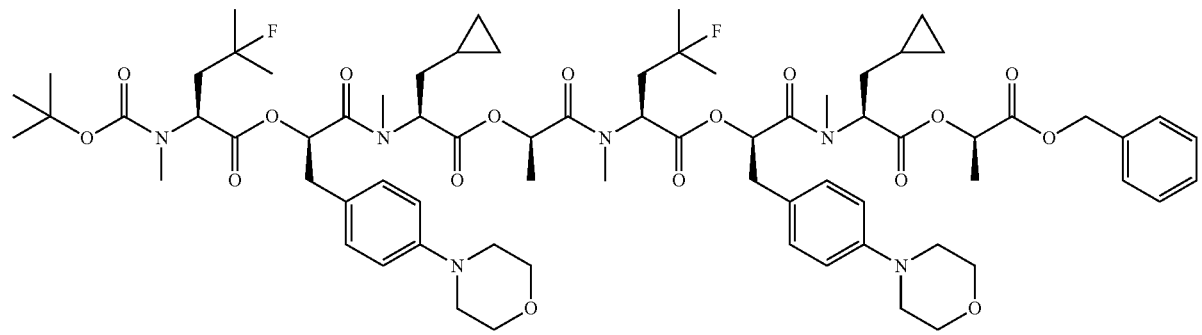

HCl (gas), DCM, rt

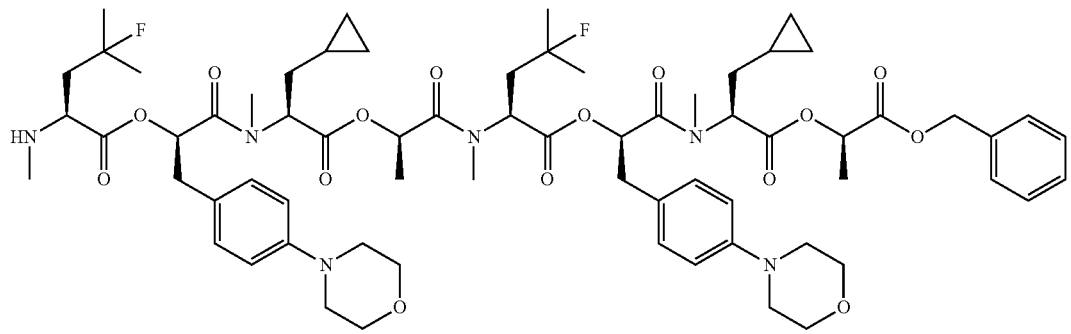

(1R)-1-[[(2S)-1-[(1R)-1-[[(2S)-1-[(1R)-1-[[(2S)-1-[[(2R)-1-(benzyloxy)-1-oxopropan-2-yl]oxy]-3-cyclopropyl-1-oxopropan-2-yl](methyl)carbamoyl]-2-[4-(morpholin-4-yl)phenyl]ethoxy]-4-fluoro-4-methyl-1l-oxopentan-2-yl](methyl)carbamoyl]ethoxy]-3-cyclopropyl-1-oxopropan-2-yl](methyl)carbamoyl]-2-[4-(morpholin-4-yl)phenyl]ethyl (2S)-4-fluoro-4-methyl-2-(methylamino)pentanoate (OA6-34)

Into a 250-mL 3-necked round-bottom flask, was placed OP6-34 (1.5 g, 1.10 mmol, 1.00 equiv), dichloromethane (100 mL). To the above HCl (gas) was introduced in. The resulting solution was stirred for 1 h at room temperature. The pH value of the solution was adjusted to 8 with sodium bicarbonate (aq). The resulting solution was extracted with 3×100 mL of dichloromethane and the organic layers combined and washed with 3×100 mL of brine. The organic phase was collected and dried over anhydrous sodium sulfate and concentrated under vacuum. This resulted in 1.1 g (79%) of (1R)-1-[[(2S)-1-[(1R)-1-[[(2S)-1-[(1R)-1-[[(2S)-1-[[(2R)-1-(benzyloxy)-1-oxopropan-2-yl]oxy]-3-cyclopropyl-1-oxopropan-2-yl](methyl)carbamoyl]-2-[4-(morpholin-4-yl)phenyl]ethoxy]-4-fluoro-4-methyl-1-oxopentan-2-yl](methyl)carbamoyl]ethoxy]-3-cyclopropyl-1-oxopropan-2-yl](methyl)carbamoyl]-2-[4-(morpholin-4-yl)phenyl]ethyl (2S)-4-fluoro-4-methyl-2-(methylamino)pentanoate as a yellow solid. MS (ES, m/z): 1260 (M+H).

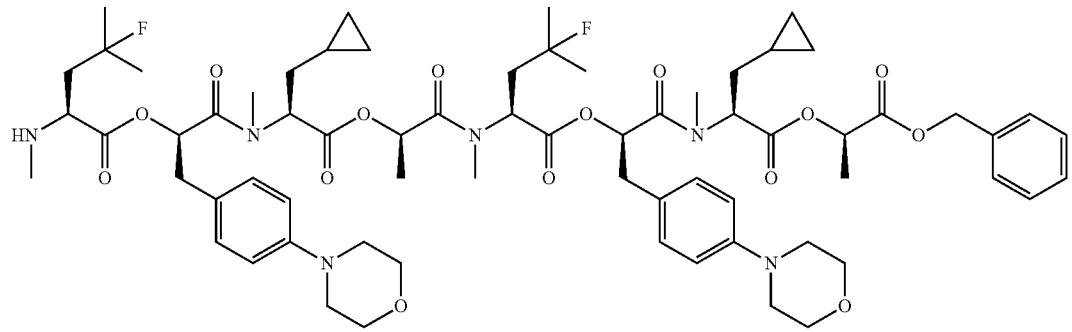

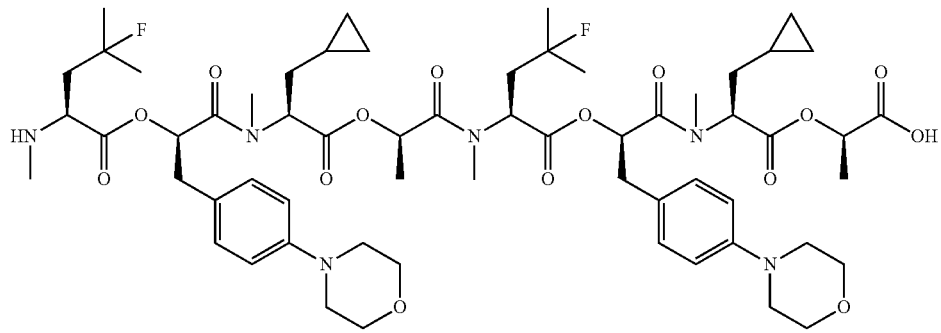

345

(2R)-2-[[(2S)-3-cyclopropyl-2-[(2R)-2-[[(2S)-2-[(2R)-2-[[(2S)-3-cyclopropyl-2-[(2R)-2-[[(2S)-4-fluoro-4-methyl-2-(methylamino)pentanoyl]oxy]-N-methyl-3-[4-(morpholin-4-yl)phenyl]propanamido]propanoyl]oxy]-N-methylpropanamido]-4-fluoro-4-methylpentanoyl]oxy]-N-methyl-3-[4-(morpholin-4-yl)phenyl]propanamido]propanoyl]oxy]propanoic Acid (OAC6-34)

Into a 250-mL round-bottom flask, was placed 1R)-1-[[(2S)-1-[(1R)-1-[[(2S)-1-[(1R)-1-[[(2S)-1-[[(2R)-1-2-(benzyloxy)-1-oxopropan-2-yl]oxy]-3-cyclopropyl-1-oxopropan-2-yl](methyl)carbamoyl]-2-[4-(morpholin-4-yl)phenyl]ethoxy]-4-fluoro-4-methyl-1-oxopentan-2-yl](methyl)carbamoyl]ethoxy]-3-cyclopropyl-1-oxopropan-2-yl]

346

(methyl)carbamoyl]-2-[4-(morpholin-4-yl)phenyl]ethyl (2S)-4-fluoro-4-methyl-2-(methylamino)pentanoate (OA6-34, 1.1 g, 0.87 mmol, 1.00 equiv), methanol (100 mL), Palladium carbon (300 mg). To the above mixture was introduced hydrogen. The resulting solution was stirred for 1 h at room temperature. The solids were filtered out. The filtrate mixture was concentrated under vacuum. This resulted in 1 g (98%) of (2R)-2-[[(2S)-3-cyclopropyl-2-[(2R)-2-[[(2S)-2-[(2R)-2-[[(2S)-3-cyclopropyl-2-[(2R)-2-[[(2S)-4-fluoro-4-methyl-2-(methylamino)pentanoyl]oxy]-N-methyl-3-[4-(morpholin-4-yl)phenyl]propanamido]propanoyl]oxy]-N-methylpropanamido]-4-fluoro-4-methylpentanoyl]oxy]-N-methyl-3-[4-(morpholin-4-yl)phenyl]propanamido]propanoyl]oxy]propanoic acid as a white solid. MS (ES, m/z): 1170 (M+H).

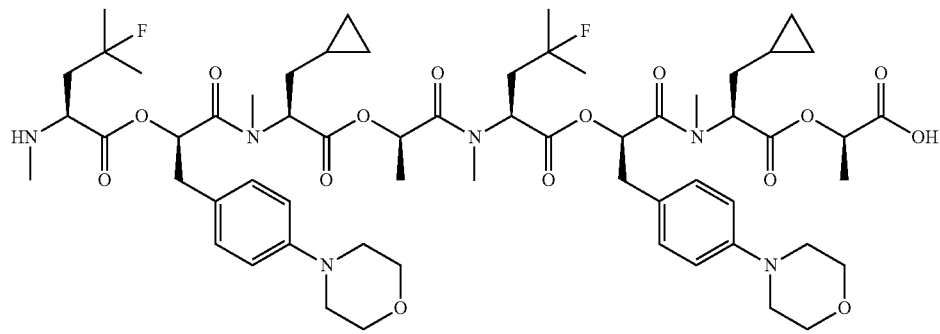

BOP—Cl, DIEA, DCM, rt

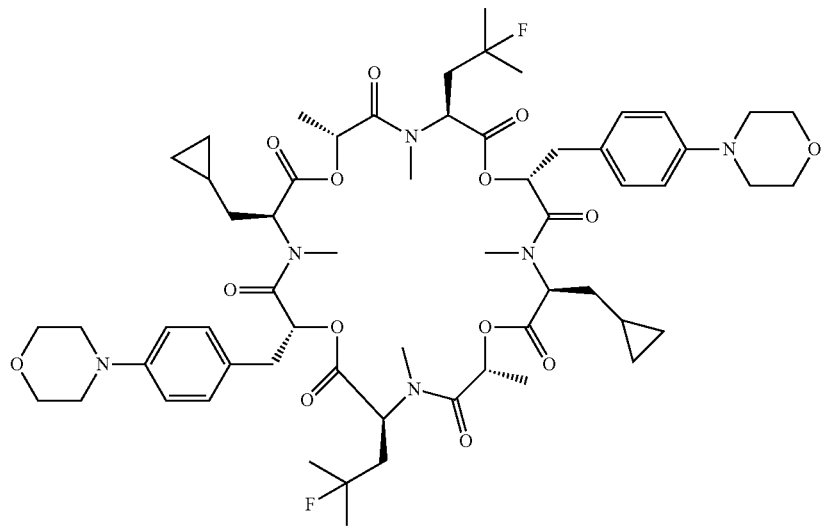

6-34A (3S,6R,9S,12R,15S,18R,21S,24R)-3,15-bis(cyclopropylmethyl)-9,21-bis(2-fluoro-2-methylpropyl)-4,10,12,16,22,24-hexamethyl-6,18-bis([[4-(morpholin-4-yl)phenyl]methyl])-1,7,13,19-tetraoxa-4,10,16,22-tetraazacyclotetracosan-2,5,8,11,14,17,20,23-octone (6-34A)

Into a 250-mL 3-necked round-bottom flask, was placed (2R)-2-[[(2S)-3-cyclopropyl-2-[(2R)-2-[[(2S)-2-[(2R)-2-[[(2S)-3-cyclopropyl-2-[(2R)-2-[[(2S)-4-fluoro-4-methyl-2-(methylamino)pentanoyl]oxy]-N-methyl-3-[4-(morpholin-4-yl)phenyl]propanamido]propanoyl]oxy]-N-methylpropanamido]-4-fluoro-4-methylpentanoyl]oxy]-N-methyl-3-[4-(morpholin-4-yl)phenyl]propanamido]propanoyl]oxy]propanoic acid (OAC6-34, 300 mg, 0.26 mmol, 1.00 equiv), dichloromethane (150 mL). This was followed by the addition of BOP—Cl (131 mg, 0.51 mmol, 2.00 equiv) in portions at 0° C. To this was added DIEA (66 mg, 0.51 mmol, 2.00 equiv) dropwise with stirring at 0° C. The resulting solution was stirred overnight at room temperature. The solids were filtered out. The filtrate was concentrated under vacuum. The crude product was purified by Prep-HPLC with the following conditions (waters-2767): Column, SunFire Prep C18, 5 um, 19*150 mm; mobile phase, Water and $CH_3CN$ (70% $CH_3CN$ up to 80% in 8 min); Detector, UV 220 nm. This resulted in 72.3 mg (24%) of (3S,6R,9S,12R,15S,18R,21S,24R)-3,15-bis(cyclopropylmethyl)-9,21-bis(2-fluoro-2-methylpropyl)-4,10,12,16,22,24-hexamethyl-6,18-bis([[4-(morpholin-4-yl)phenyl]methyl])-1,7,13,19-tetraoxa-4,10,16,22-tetraazacyclotetracosan-2,5,8,11,14,17,20,23-octone as a white solid. MS (ES, m/z): 1152 (M+H); $^1$H NMR: (300 MHz, $CD_3OD$, ppm): δ 7.19-7.12 (m, 4H), 6.98-6.81 (m, 4H), 5.88-5.55 (m, 2H), 5.55-5.16 (m, 5H), 5.01-4.88 (m, 1H), 3.92-3.78 (m, 8H), 3.19-2.82 (m, 24H), 2.35-2.00 (m, 4H), 1.92-1.55 (m, 3H), 1.55-1.20 (m, 18H), 1.02-0.91 (m, 1H), 0.55-0.11 (m, 10H); MS (ESI, m/z): 1152 [M+H]+; [α]=−71.7°, T=27.2° C., C=0.75 g/100 mL in MeOH.

Preparation Example 36: Synthesis of Compound 6-1A in Table 6, Wherein R', R", R'" and R"" are Each Methyl

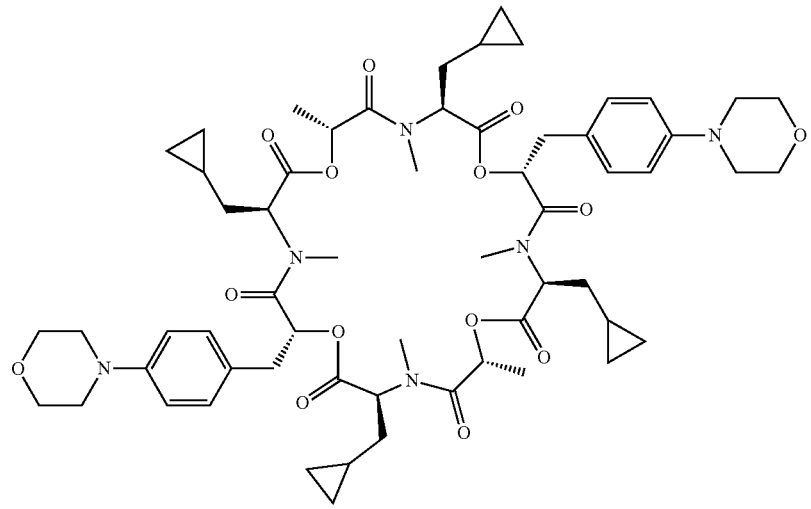

6-1A

Compound 6-1A was prepared in a similar way to compound 6-7A according to Schemes 8 and 9 shown below.

Scheme 8

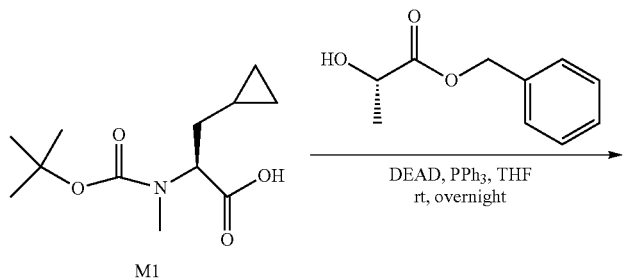

M1

-continued
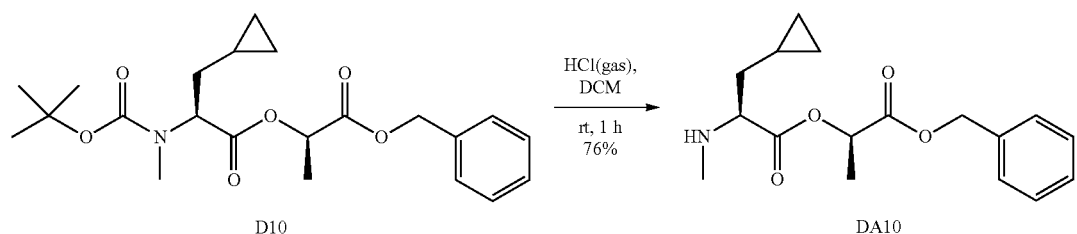
D10 → DA10
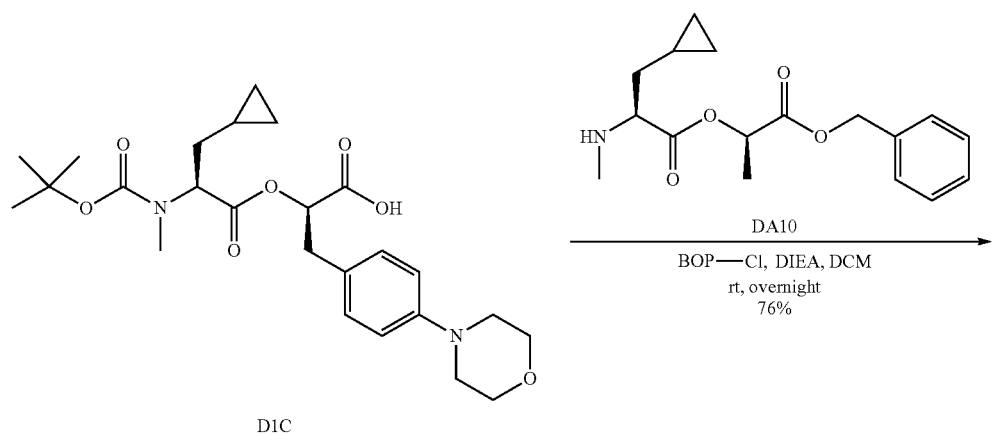
D1C + DA10 → (BOP—Cl, DIEA, DCM, rt, overnight, 76%)
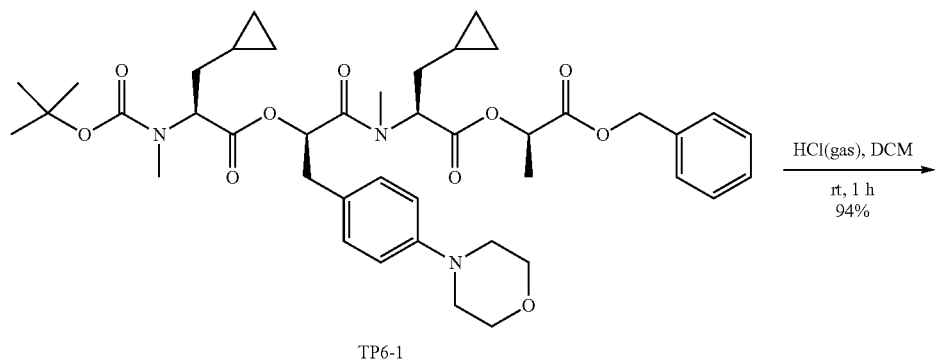
TP6-1
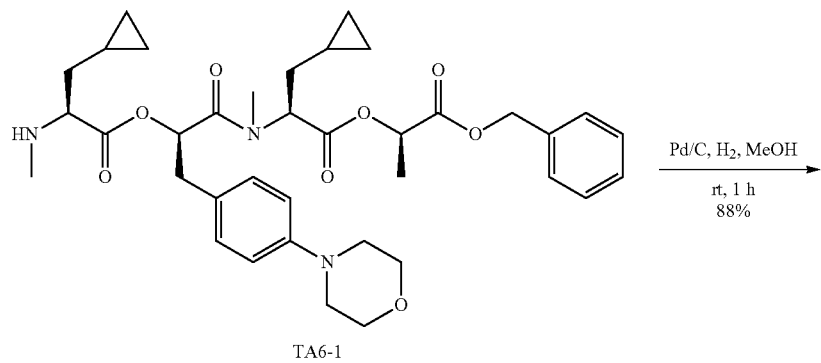
TA6-1

-continued
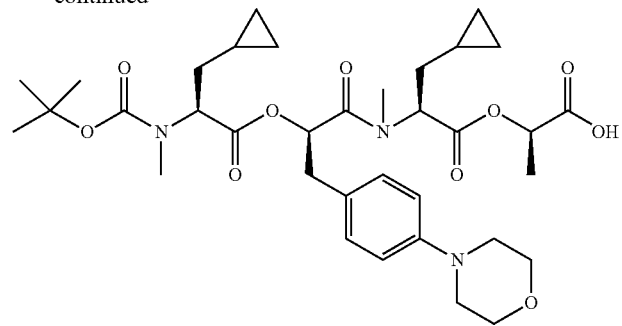
TC6-1
Scheme 9
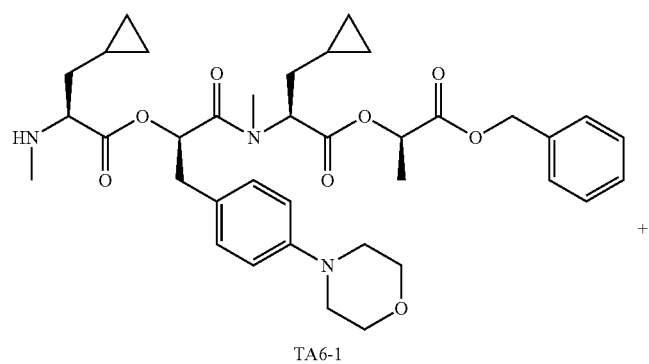
TA6-1
+
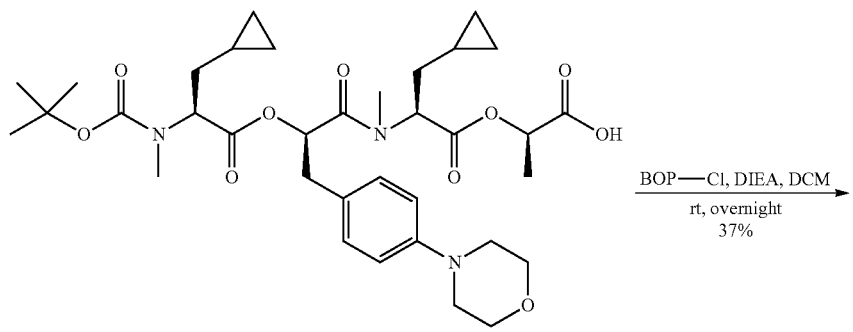
TC6-1
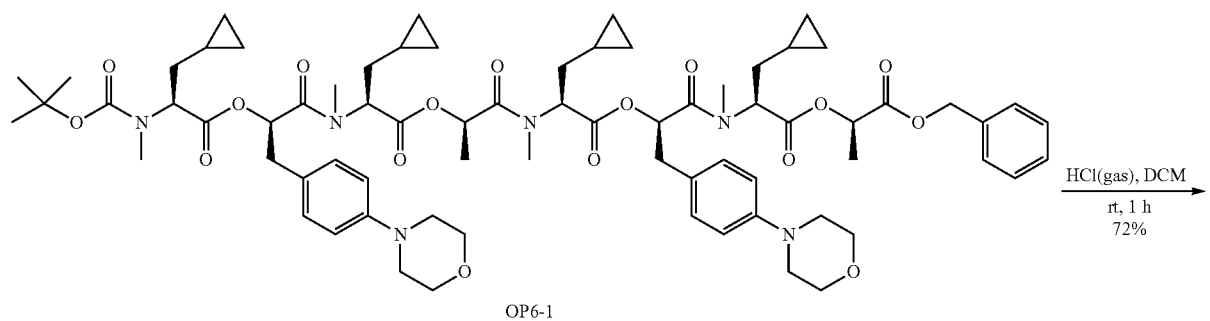
OP6-1

-continued
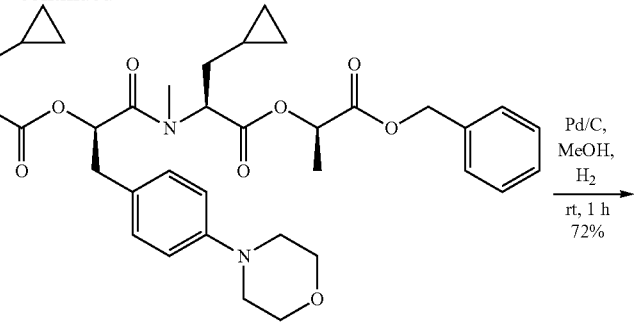
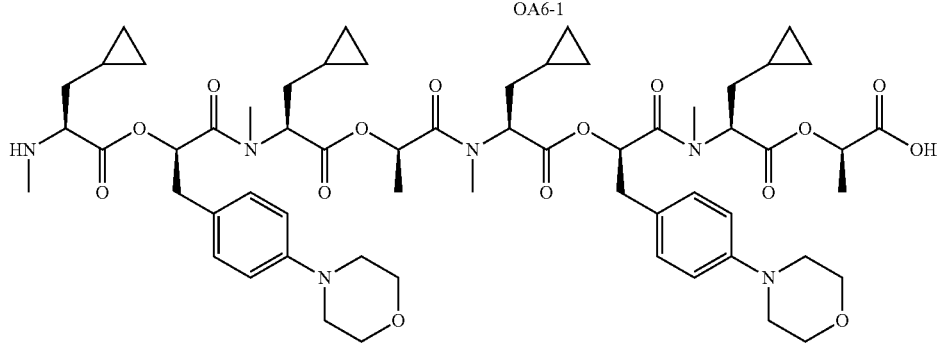
OA6-1
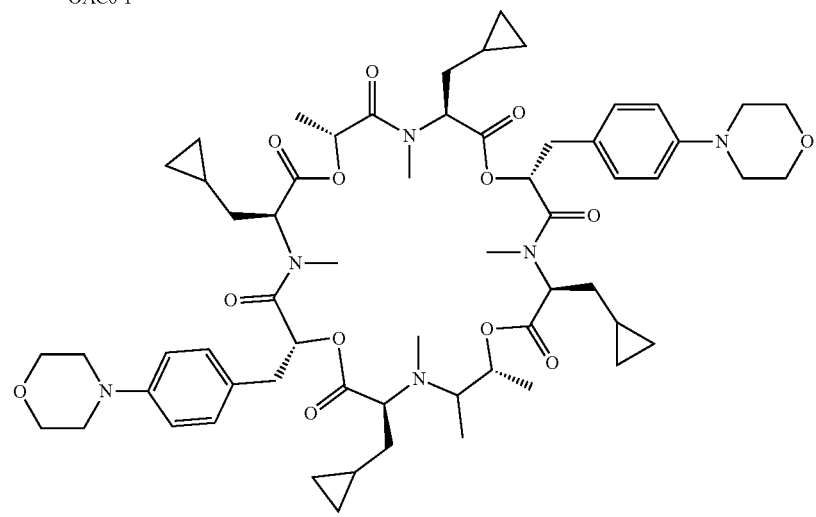
OAC6-1
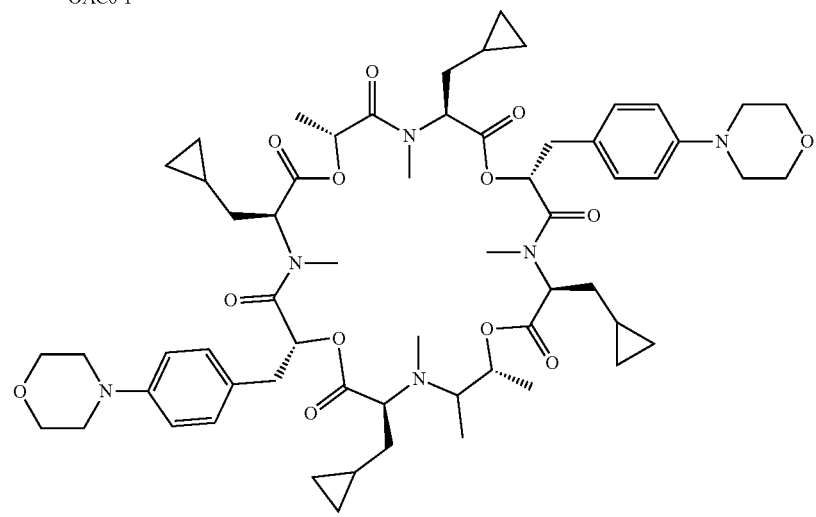
6-1A
Experimental Details
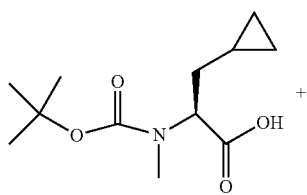
-continued
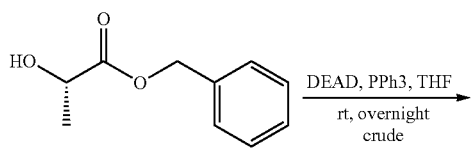
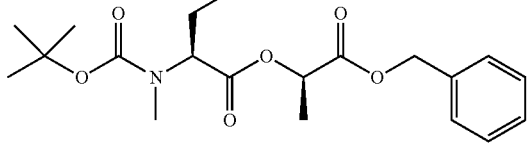

355

(S)—((R)-1-(benzyloxy)-1-oxopropan-2-yl) 2-(tert-butoxycarbonyl(methyl)amino)-3-cyclopropylpropanoate (D10)

Into a 500-mL 3-necked round-bottom flask, was placed (2S)-2-[[(tert-butoxy)carbonyl](methyl)amino]-3-cyclopropylpropanoic acid (4 g, 16.44 mmol, 1.00 equiv), benzyl (2S)-2-hydroxypropanoate (3 g, 16.65 mmol, 1.00 equiv), PPh$_3$ (5.2 g, 19.83 mmol, 1.20 equiv), tetrahydrofuran (150 mL). This was followed by the addition of a solution of DEAD (3.5 g, 20.10 mmol, 1.20 equiv) in tetrahydrofuran (30 mL) dropwise with stirring at 0° C. The resulting solution was stirred overnight at room temperature. The solids were filtered out. The filtrate was concentrated under vacuum. The residue was applied onto a silica gel column with ethyl acetate/petroleum ether (1:20). This resulted in 7 g (crude) of (2R)-1-(benzyloxy)-1-oxopropan-2-yl (2S)-2-[[(tert-butoxy)carbonyl](methyl)amino]-3-cyclopropylpropanoate as colorless oil. MS (ESI, m/z): 406 [M+H]$^+$.

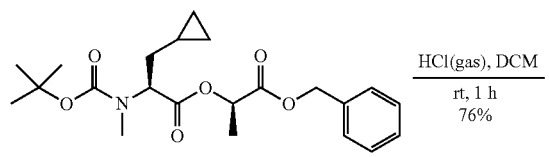

356

-continued

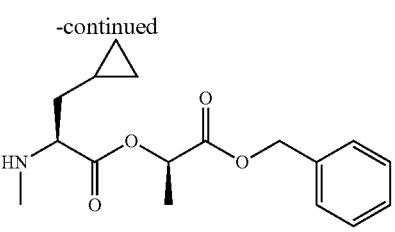

(S)—((R)-1-(benzyloxy)-1-oxopropan-2-yl) 3-cyclopropyl-2-(methylamino)propanoate (DA10)

Into a 500-mL round-bottom flask, was placed (2R)-1-(benzyloxy)-1-oxopropan-2-yl (2S)-2-[[(tert-butoxy)carbonyl](methyl)amino]-3-cyclopropylpropanoate (D10, 7 g, 17.26 mmol, 1.00 equiv), dichloromethane (200 mL). To the above HCl(gas) was introduced. The resulting solution was stirred for 1 h at room temperature. The pH value of the solution was adjusted to 8 with sodium bicarbonate (aq). The resulting solution was extracted with 3×200 mL of dichloromethane and the organic layers combined. The organic layers were washed with 3×200 mL of brine. The organic layers were dried over anhydrous sodium sulfate and concentrated under vacuum. This resulted in 4 g (76%) of (2R)-1-(benzyloxy)-1-oxopropan-2-yl (2S)-3-cyclopropyl-2-(methylamino)propanoate as yellow oil. MS (ESI, m/z): 306 [M+H]$^+$.

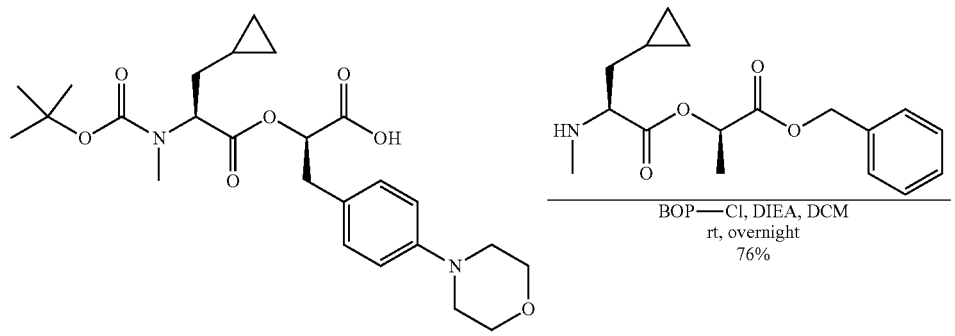

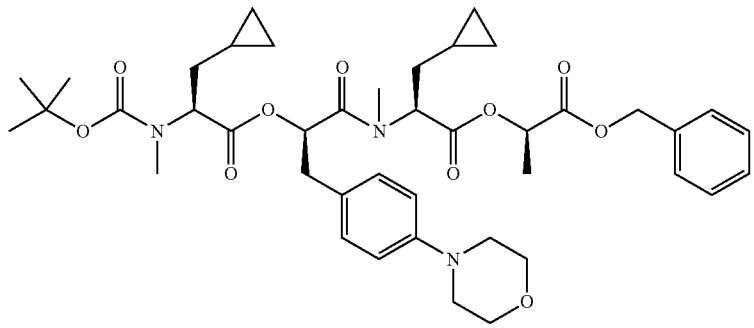

(S)—((R)-1-(((S)-1-((R)-1-(benzyloxy)-1-oxopropan-2-yloxy)-3-cyclopropyl-1-oxopropan-2-yl)(methyl)amino)-3-(4-morpholinophenyl)-1-oxopropan-2-yl) 2-(tert-butoxycarbonyl(methyl)amino)-3-cyclopropylpropanoate (TP6-1)

Into a 250-mL 3-necked round-bottom flask, was placed (2R)-1-(benzyloxy)-1-oxopropan-2-yl (2S)-3-cyclopropyl-2-(methylamino)propanoate (DA10, 900 mg, 2.95 mmol, 1.00 equiv), (2R)-2-[[(2S)-2-[[(tert-butoxy)carbonyl](methyl)amino]-3-cyclopropylpropanoyl]oxy]-3-[4-(morpholin-4-yl)phenyl]propanoic acid (DC1, 1.3 g, 2.73 mmol, 1.00 equiv), dichloromethane (80 mL). This was followed by the addition of BOP—Cl (1.5 g, 5.89 mmol, 2.00 equiv) in portions at 0° C. To this was added DIEA (770 mg, 5.96 mmol, 2.00 equiv) dropwise with stirring at 0° C. The resulting solution was stirred overnight at room temperature. The solids were filtered out. The filtrate was concentrated under vacuum. The residue was applied onto a silica gel column with ethyl acetate/petroleum ether (1:4). This resulted in 1.7 g (76%) of (1R)-1-[[(2S)-1-[[(2R)-1-(benzyloxy)-1-oxopropan-2-yl]oxy]-3-cyclopropyl-1-oxopropan-2-yl](methyl)carbamoyl]-2-[4-(morpholin-4-yl)phenyl]ethyl (2S)-2-[[(tert-butoxy)carbonyl](methyl)amino]-3-cyclopropylpropanoate as yellow oil. MS (ESI, m/z): 764 [M+H]⁺.

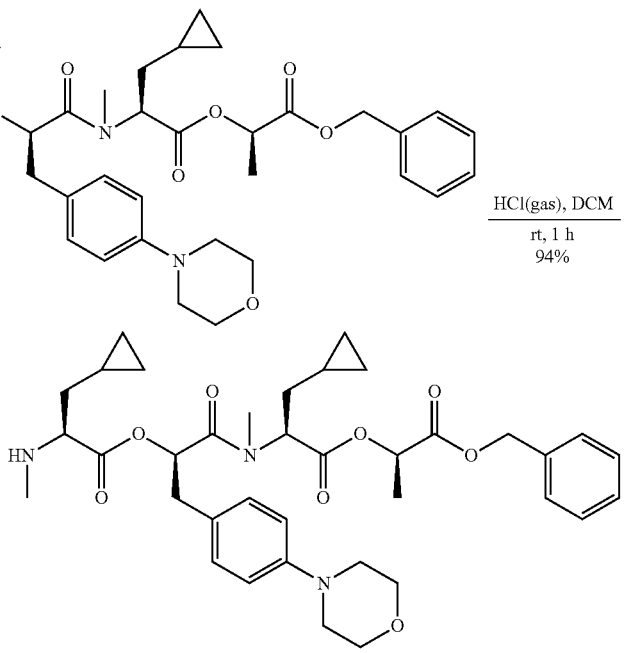

(S)—((R)-1-(benzyloxy)-1-oxopropan-2-yl) 3-cyclopropyl-2-((R)-2-((S)-3-cyclopropyl-2-(methylamino)propanoyloxy)-N-methyl-3-(4-morpholinophenyl)propanamido)propanoate (TA6-1)

Into a 100-mL round-bottom flask, was placed (1R)-1-[[(2S)-1-[[(2R)-1-(benzyloxy)-1-oxopropan-2-yl]oxy]-3-cyclopropyl-1-oxopropan-2-yl](methyl)carbamoyl]-2-[4-(morpholin-4-yl)phenyl]ethyl (2S)-2-[[(tert-butoxy)carbonyl](methyl)amino]-3-cyclopropylpropanoate (TP6-1) (800 mg, 1.05 mmol, 1.00 equiv), dichloromethane (60 mL). To the above HCl(gas) was introduced in. The resulting solution was stirred for 1 h at room temperature. The pH value of the solution was adjusted to 8 with sodium bicarbonate(aq). The resulting solution was extracted with 3×50 mL of dichloromethane and the organic layers combined. The organic layers were washed with 3×60 mL of brine. The organic layers were dried over anhydrous sodium sulfate and concentrated under vacuum. This resulted in 650 mg (94%) of (1R)-1-[[(2S)-1-[[(2R)-1-(benzyloxy)-1-oxopropan-2-yl]oxy]-3-cyclopropyl-1-oxopropan-2-yl](methyl)carbamoyl]-2-[4-(morpholin-4-yl)phenyl]ethyl (2S)-3-cyclopropyl-2-(methylamino)propanoate as yellow oil. MS (ESI, m/z): 664 [M+H]⁺.

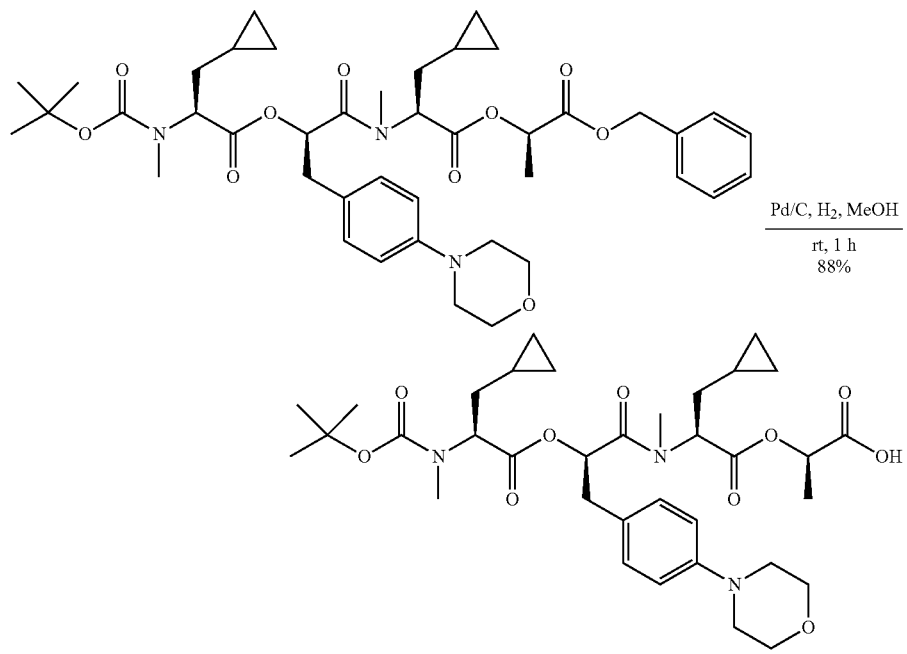

(2R)-2-[[(2S)-2-[(2R)-2-[[(2S)-2-[[(tert-butoxy)carbonyl](methyl)amino]-3-cyclopropylpropanoyl]oxy]-N-methyl-3-[4-(morpholin-4-yl)phenyl]propanamido]-3-cyclopropylpropanoyl]oxy]propanoic Acid (TC6-1)

Into a 250-mL round-bottom flask, was placed (1R)-1-[[(2S)-1-[[(2R)-1-(benzyloxy)-1-oxopropan-2-yl]oxy]-3-cyclopropyl-1-oxopropan-2-yl](methyl)carbamoyl]-2-[4-(morpholin-4-yl)phenyl]ethyl (2S)-2-[[(tert-butoxy)carbonyl](methyl)amino]-3-cyclopropylpropanoate (TP6-1, 800 mg, 1.05 mmol, 1.00 equiv), Palladium carbon (100 mg), methanol (80 mL). To the above hydrogen was introduced. The resulting solution was stirred for 1 h at room temperature. The solids were filtered out. The resulting mixture was concentrated under vacuum. This resulted in 620 mg (88%) of (2R)-2-[[(2S)-2-[(2R)-2-[[(2S)-2-[[(tert-butoxy)carbonyl](methyl)amino]-3-cyclopropylpropanoyl]oxy]-N-methyl-3-[4-(morpholin-4-yl)phenyl]propanamido]-3-cyclopropylpropanoyl]oxy]propanoic acid as a white solid. MS (ESI, m/z): 674 [M+H]+.

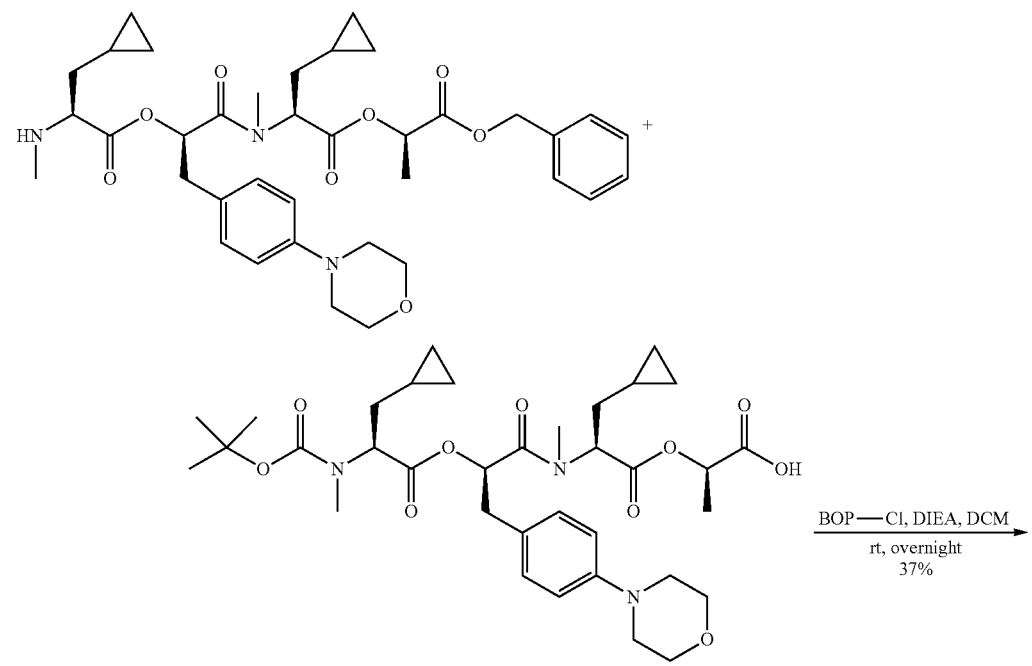

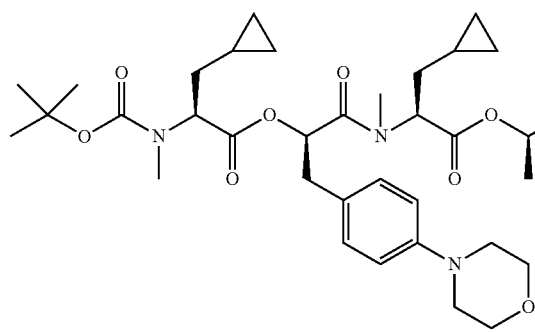
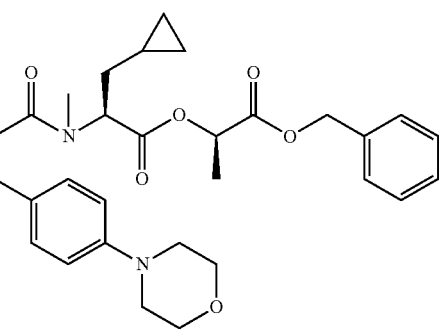

Compound OP6-1:

Into a 250-mL 3-necked round-bottom flask, was placed a solution of TC6-1 (620 mg, 0.92 mmol, 1.00 equiv), dichloromethane (100 mL), TA6-1 (611 mg, 0.92 mmol, 1.00 equiv). This was followed by the addition of BOP—Cl (469 mg, 2.00 equiv) in portions at 0° C. To this was added DIEA (237 mg, 1.83 mmol, 2.00 equiv) dropwise with stirring at 0° C. The resulting solution was stirred overnight at room temperature. The solids were filtered out. The filtrate was concentrated under vacuum. The residue was applied onto a silica gel column with ethyl acetate/petroleum ether (1/1). This resulted in 450 mg (37%) of OP6-1 as yellow oil. MS (ESI, m/z): 1320 [M+H]$^+$.

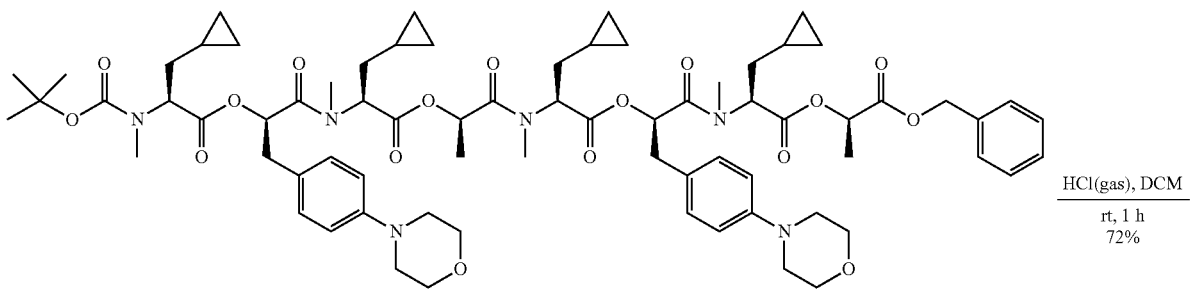

HCl(gas), DCM
rt, 1 h
72%

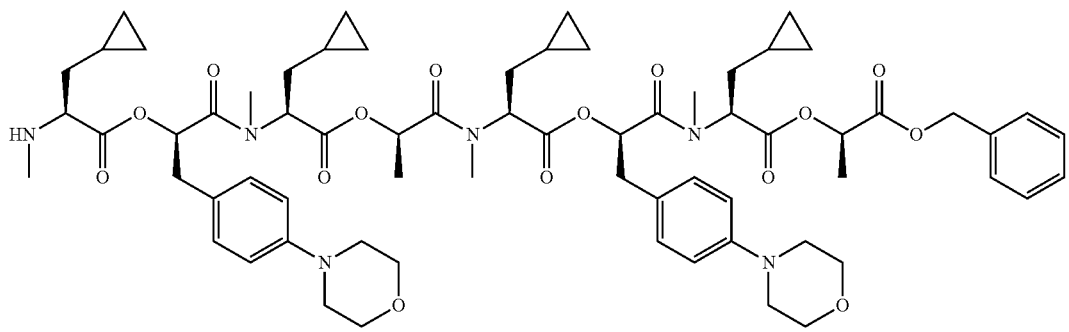

(1R)-1-[[(2S)-1-[(1R)-1-[[(2S)-1-[(1R)-1-[[(2S)-1-[[(2R)-1-(benzyloxy)-1-oxopropan-2-yl]oxy]-3-cyclopropyl-1-oxopropan-2-yl](methyl)carbamoyl]-2-[4-(morpholin-4-yl)phenyl]ethoxy]-3-cyclopropyl-1-oxopropan-2-yl](methyl)carbamoyl]ethoxy]-3-cyclopropyl-1-oxopropan-2-yl](methyl)carbamoyl]-2-[4-(morpholin-4-yl)phenyl]ethyl (2S)-3-cyclopropyl-2-(methylamino)propanoate (OA6-1)

Into a 100-mL round-bottom flask, was placed OP6-1 (450 mg, 0.34 mmol, 1.00 equiv), dichloromethane (50 mL). To the above HCl(g) was introduced in. The resulting solution was stirred for 1 h at room temperature. The pH value of the solution was adjusted to 8 with sodium bicarbonate (aq). The resulting solution was extracted with 3×50 mL of dichloromethane and the organic layers combined. The organic layer was washed with 3×70 mL of brine. The organic layer was dried over anhydrous sodium sulfate and concentrated under vacuum. This resulted in 300 mg (72%) of (1R)-1-[[(2S)-1-[(1R)-1-[[(2S)-1-[(1R)-1-[[(2S)-1-[[(2R)-1-(benzyloxy)-1-oxopropan-2-yl]oxy]-3-cyclopropyl-1-oxopropan-2-yl](methyl)carbamoyl]-2-[4-(morpholin-4-yl)phenyl]ethoxy]-3-cyclopropyl-1-oxopropan-2-yl](methyl)carbamoyl]ethoxy]-3-cyclopropyl-1-oxopropan-2-yl](methyl)carbamoyl]-2-[4-(morpholin-4-yl)phenyl]ethyl (2S)-3-cyclopropyl-2-(methylamino)propanoate as yellow oil. MS (ESI, m/z): 1220 [M+H]$^+$.

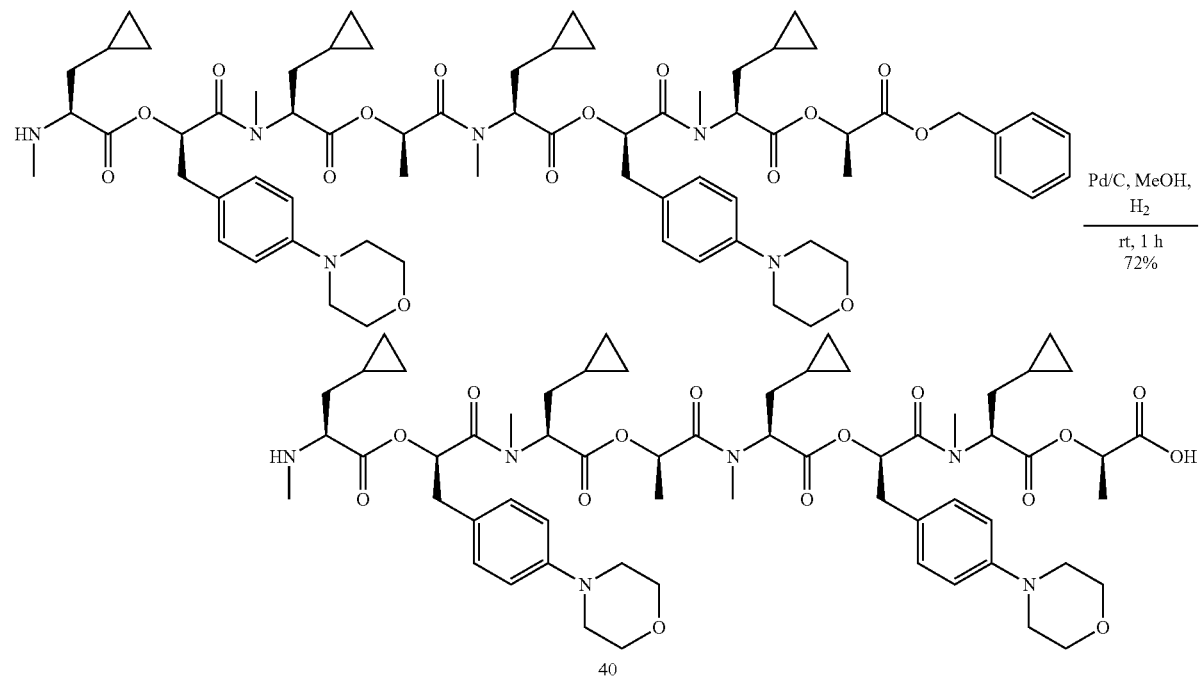

(2R)-2-[[(2S)-3-cyclopropyl-2-[(2R)-2-[[(2S)-3-cyclopropyl-2-[(2R)-2-[[(2S)-3-cyclopropyl-2-[(2R)-2-[[(2S)-3-cyclopropyl-2-(methylamino)propanoyl]oxy]-N-methyl-3-[4-(morpholin-4-yl)phenyl]propanamido]propanoyl]oxy]-N-methylpropanamido]propanoyl]oxy]-N-methyl-3-[4-(morpholin-4-yl)phenyl]propanamido]propanoyl]oxy]propanoic Acid (OAC6-1)

Into a 100-mL round-bottom flask, was placed (1R)-1-[[(2S)-1-[(1R)-1-[[(2S)-1-[(1R)-1-[[(2S)-1-[[(2R)-1-(benzyloxy)-1-oxopropan-2-yl]oxy]-3-cyclopropyl-1-oxopropan-2-yl](methyl)carbamoyl]-2-[4-(morpholin-4-yl)phenyl]ethoxy]-3-cyclopropyl-1-oxopropan-2-yl](methyl)carbamoyl]ethoxy]-3-cyclopropyl-1-oxopropan-2-yl](methyl)carbamoyl]-2-[4-(morpholin-4-yl)phenyl]ethyl (2S)-3-cyclopropyl-2-(methylamino)propanoate (OAC6-1) (300 mg, 0.25 mmol, 1.00 equiv), methanol (50 mL), Palladium carbon (100 mg). To the above mixture was introduced hydrogen. The resulting solution was stirred for 1 h at room temperature. The solids were filtered out. The filtrate was concentrated under vacuum. This resulted in 200 mg (72%) of (2R)-2-[[(2S)-3-cyclopropyl-2-[(2R)-2-[[(2S)-3-cyclopropyl-2-[(2R)-2-[[(2S)-3-cyclopropyl-2-(methylamino)propanoyl]oxy]-N-methyl-3-[4-(morpholin-4-yl)phenyl]propanamido]propanoyl]oxy]-N-methylpropanamido]propanoyl]oxy]-N-methyl-3-[4-(morpholin-4-yl)phenyl]propanamido]propanoyl]oxy]propanoic acid as a white solid. MS (ESI, m/z): 1130 [M+H]$^+$.

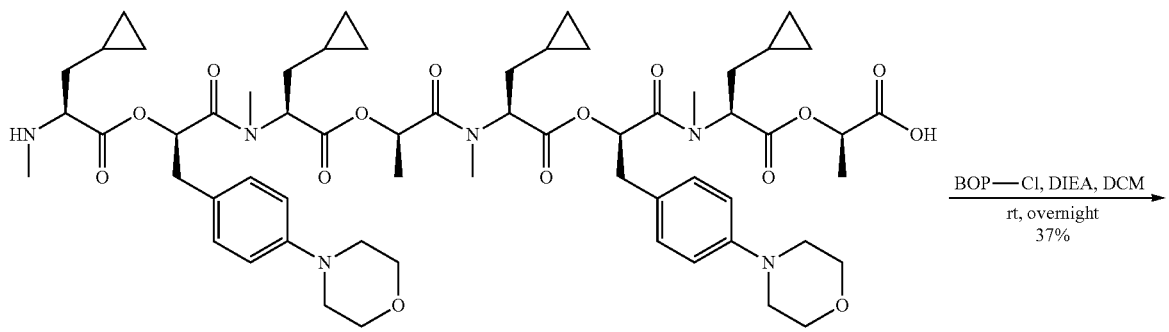

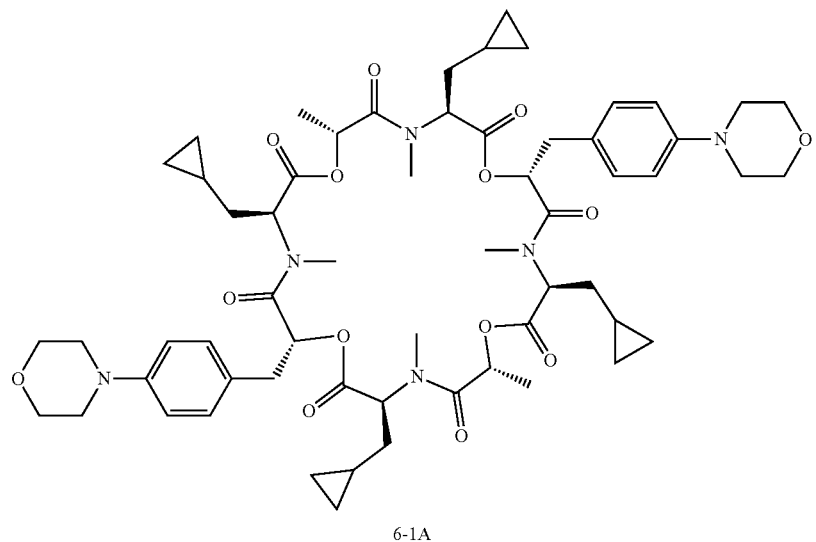

6-1A (3S,6R,9S,12R,15S,18R,21S,24R)-3,9,15,21-tetrakis(cyclopropylmethyl)-4,10,12,16,22,24-hexamethyl-6,18-bis([[4-(morpholin-4-yl)phenyl]methyl])-1,7,13,19-tetraoxa-4,10,16,22-tetraazacyclotetracosan-2,5,8,11,14,17,20,23-octone (6-1A)

Into a 250-mL 3-necked round-bottom flask, was placed OAC6-1 (200 mg, 0.18 mmol, 1.00 equiv), dichloromethane (120 mL). This was followed by the addition of BOP—Cl (90 mg, 0.35 mmol, 2.00 equiv) in portions at 0° C. To this was added DIEA (46 mg, 0.36 mmol, 2.00 equiv) dropwise with stirring at 0° C. The resulting solution was stirred overnight at room temperature. The solids were filtered out. The filtrate was concentrated under vacuum. The crude product was purified by Prep-HPLC with the following conditions (waters-2767): Column, SunFire Prep C18, 5 um, 19*150 mm; mobile phase, Water and $CH_3CN$ (70% $CH_3CN$ up to 80% in 8 min); Detector, UV 254 nm. This resulted in 24.7 mg (13%) of (3S,6R,9S,12R,15S,18R,21S,24R)-3,9,15,21-tetrakis(cyclopropylmethyl)-4,10,12,16,22,24-hexamethyl-6,18-bis([[4-(morpholin-4-yl)phenyl]methyl])-1,7,13,19-tetraoxa-4,10,16,22-tetraazacyclotetracosan-2,5,8,11,14,17,20,23-octone as a white solid. $^1$H NMR (CD$_3$OD, 300 MHz) δ: 7.31-7.08 (m, 4H), 6.98-6.81 (m, 4H), 5.08-5.02 (m, 7H), 4.82-4.68 (m, 1H), 3.92-3.76 (m, 8H), 3.25-2.82 (m, 24H), 2.51-1.18 (m, 13H), 1.08-0.95 (m, 2H), 0.78-0.03 (m, 19H); (ES, m/z): 1111 [M+H]$^+$. [c]$^=$−110.72°, T=27.2° C., C=0.23 g/100 mL in MeOH.

Preparation Example 37: Synthesis of Compound 7-34A in Table 7, wherein $R^a$, $R^b$, R', R'', R''' and R'''' are each methyl
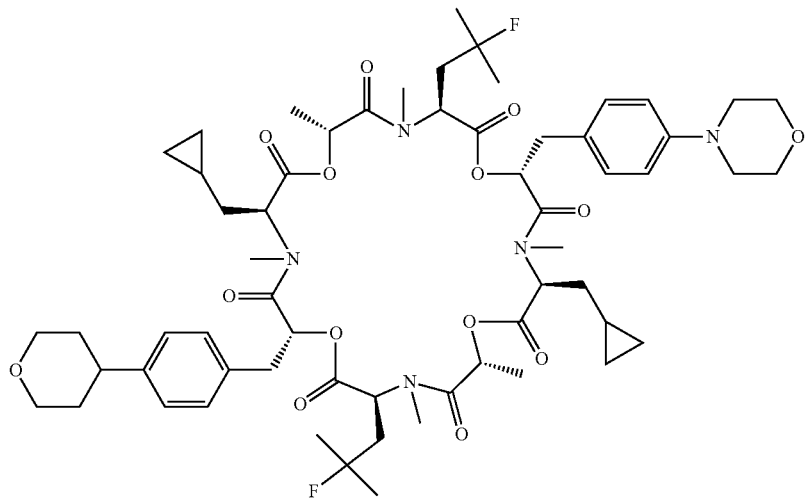
7-34A
Compound 7-34A was prepared in a similar way to compound 6-7A according to Schemes 10 to 12 shown below.
Scheme 10
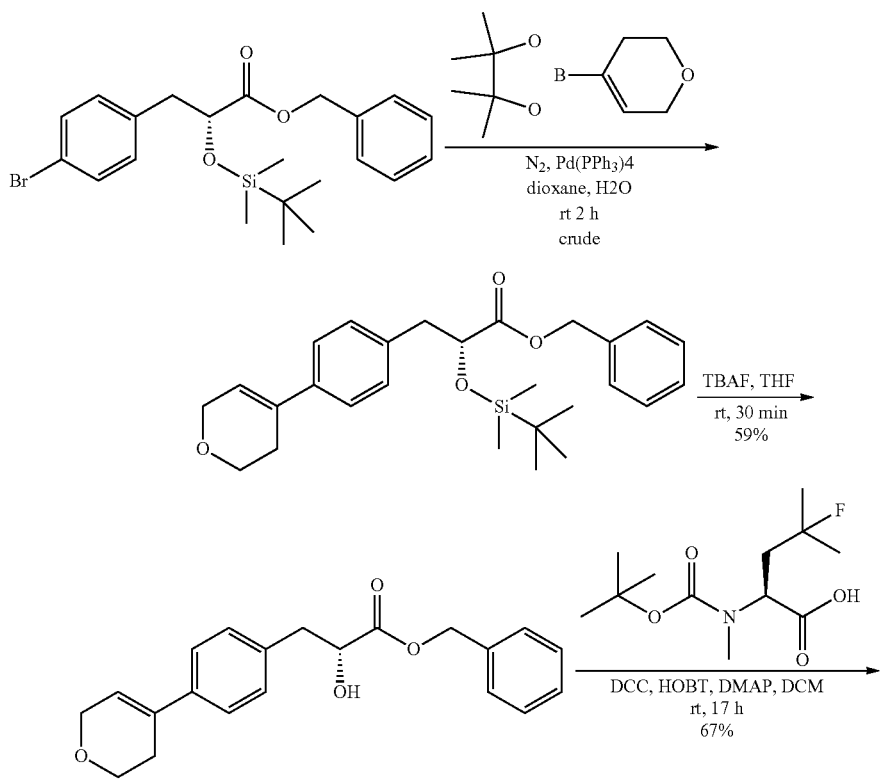

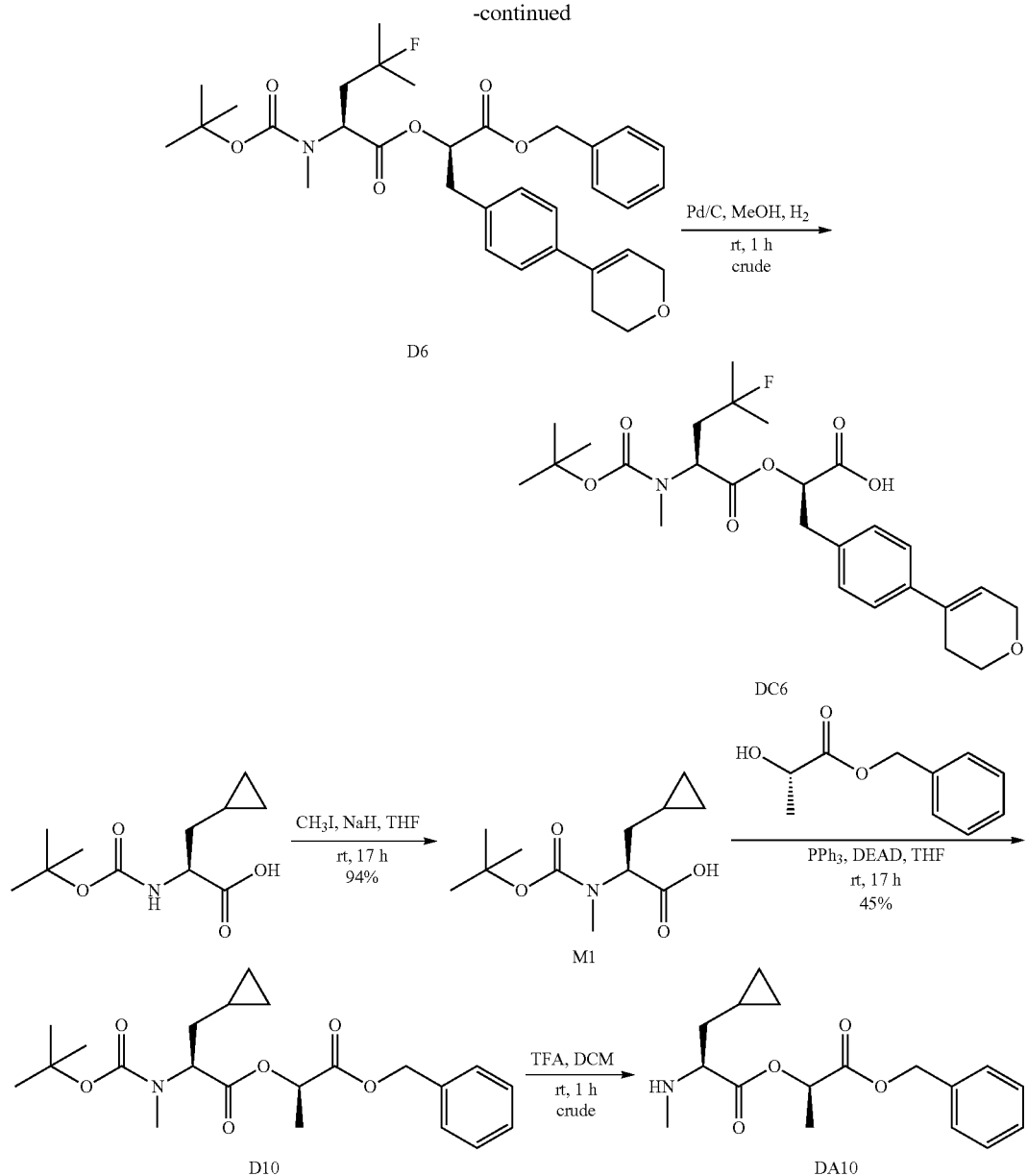
Scheme 11
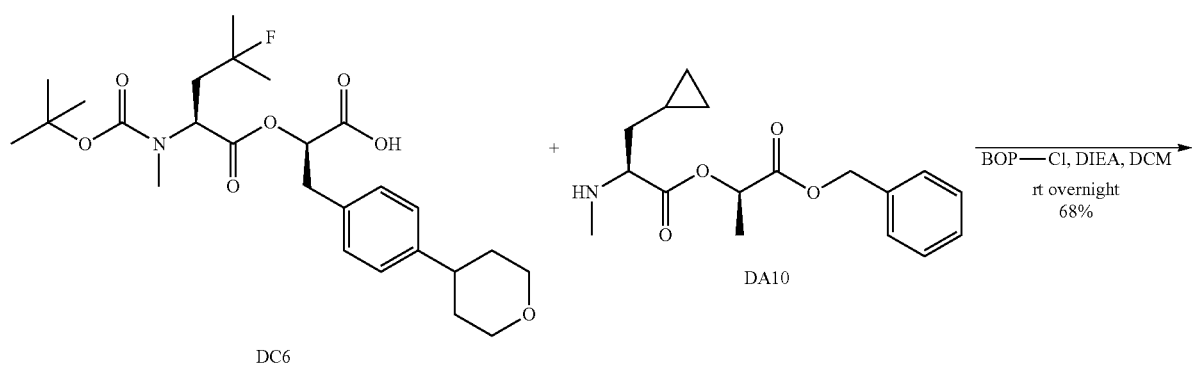

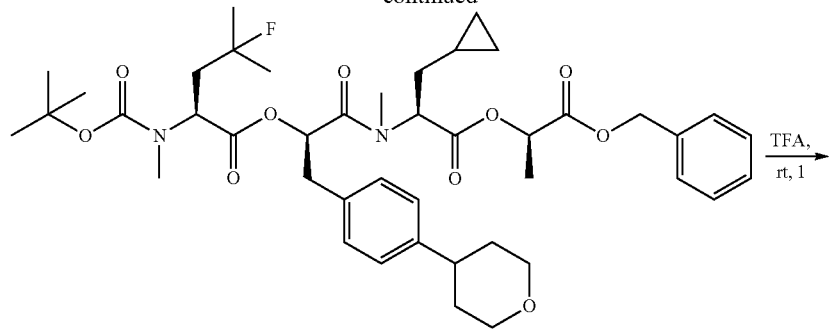
TP7-34
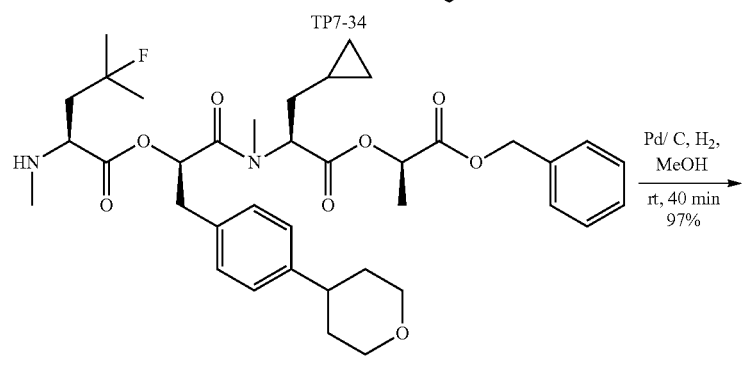
TA7-34
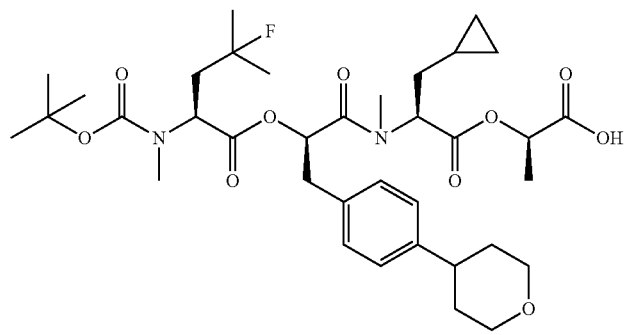
TC7-34
Scheme 12
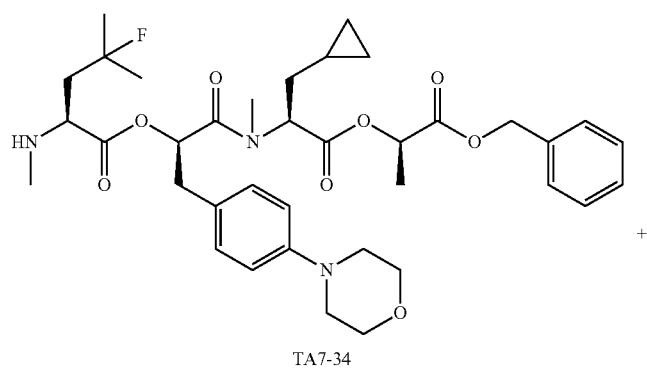
TA7-34
+

-continued
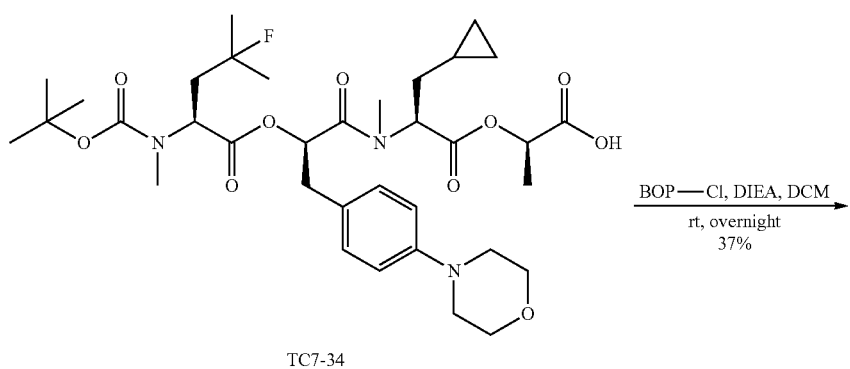
TC7-34
BOP—Cl, DIEA, DCM
rt, overnight
37%
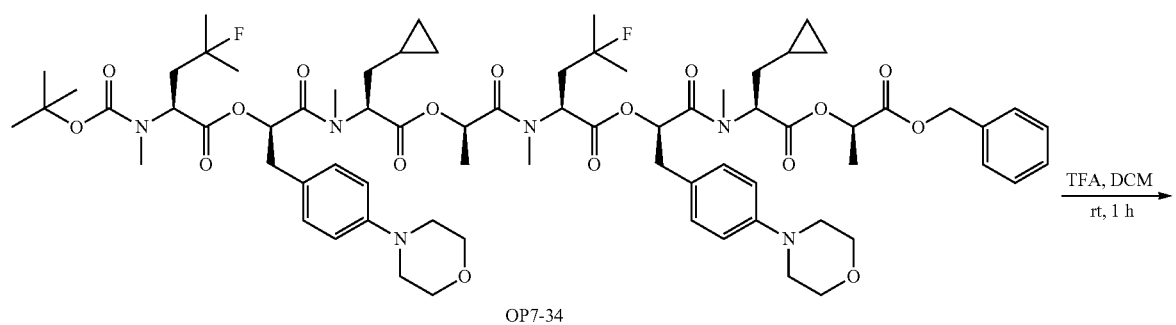
OP7-34
TFA, DCM
rt, 1 h
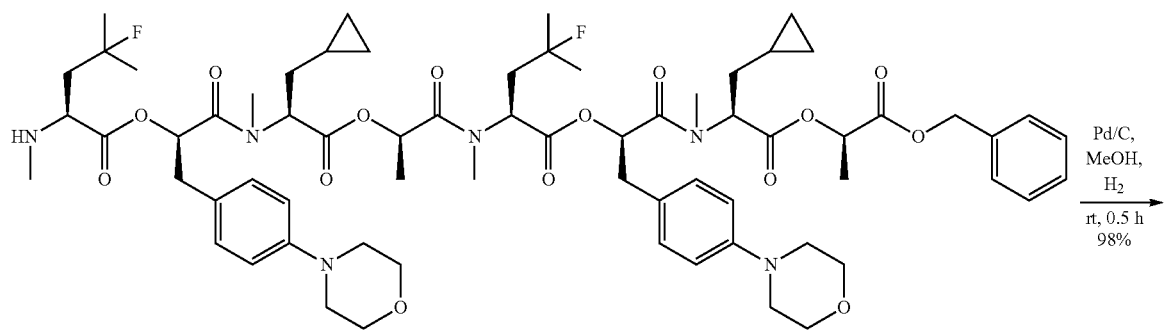
OA7-34
Pd/C, MeOH, H₂
rt, 0.5 h
98%
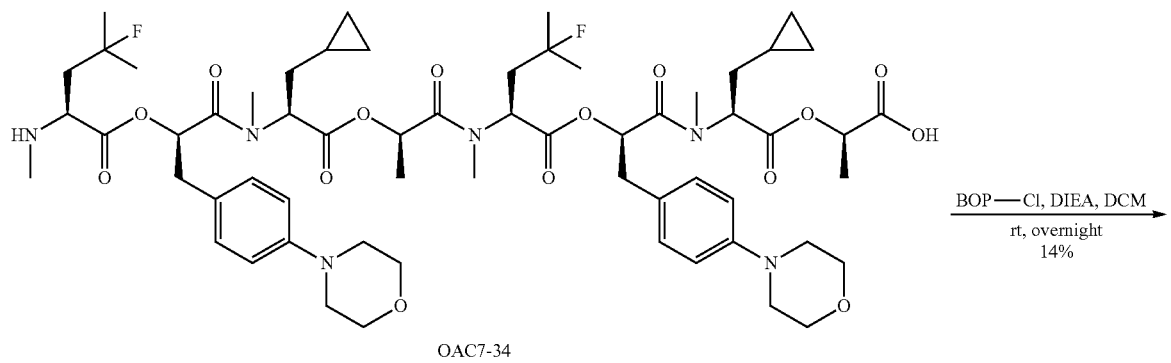
OAC7-34
BOP—Cl, DIEA, DCM
rt, overnight
14%

-continued

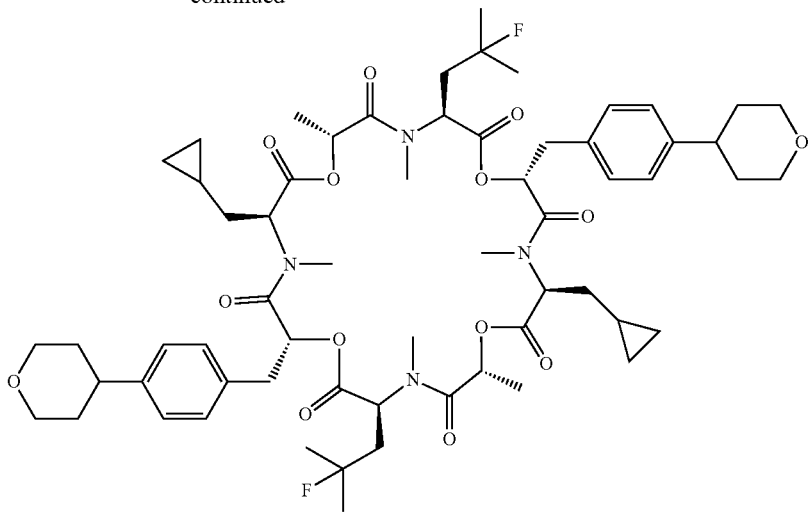

7-34A

Experimental Details

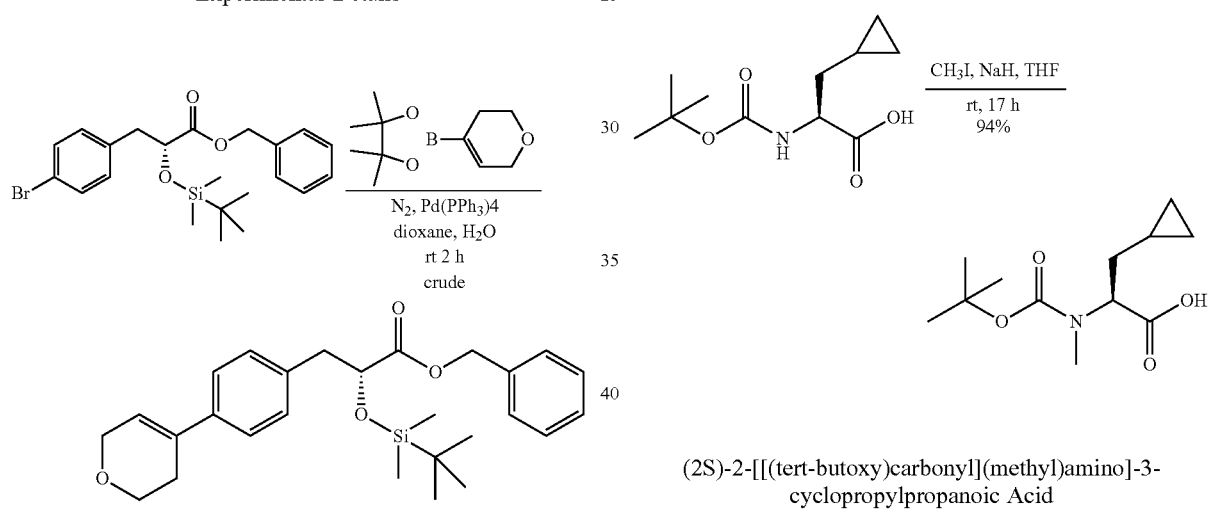

Benzyl (2R)-2-[(tert-butyldimethylsilyl)oxy]-3-[4-(3,6-dihydro-2H-pyran-4-yl)phenyl]propanoate Into a 250-mL round-bottom flask purged and maintained with an inert atmosphere of nitrogen, was placed benzyl (2R)-3-(4-bromophenyl)-2-[(tert-butyldimethylsilyl)oxy]propanoate (7 g, 15.57 mmol, 1.00 equiv), 2-(3,6-dihydro-2H-pyran-4-yl)-4,4,5,5-tetramethyl-1,3,2-dioxaborolane (3.3 g, 15.71 mmol, 1.00 equiv), sodium carbonate (5 g, 47.17 mmol, 3.00 equiv), dioxane (50 mL), water (10 mL), Pd(PPh$_3$)$_4$ (900 mg, 0.78 mmol, 0.05 equiv). The resulting solution was stirred for 2 h at 75° C. The solids were filtered out. The filtrate was concentrated under vacuum. The residue was applied onto a silica gel column with ethyl acetate/petroleum ether (1:10). This resulted in 8 g (crude) of benzyl (2R)-2-[(tert-butyldimethylsilyl)oxy]-3-[4-(3,6-dihydro-2H-pyran-4-yl)phenyl]propanoate as colorless oil. MS (ESI, m/z): 453 [M+H]$^+$.

(2S)-2-[[(tert-butoxy)carbonyl](methyl)amino]-3-cyclopropylpropanoic Acid

Into a 1000-mL 3-necked round-bottom flask, was placed (2S)-2-[[(tert-butoxy)carbonyl]amino]-3-cyclopropylpropanoic acid (9 g, 39.25 mmol, 1.00 equiv), tetrahydrofuran (500 mL), This was followed by the addition of sodium hydride (4.7 g, 117.50 mmol, 3.00 equiv, 60%) in portions at 0° C. To this was added CH$_3$I (45 g, 317.04 mmol, 8.00 equiv) dropwise with stirring at 0° C. The resulting solution was stirred for 17 h at room temperature. The reaction was then quenched by the addition of water (500 mL). The resulting solution was extracted with 3×500 mL of methyl tert-butyl ether and the aqueous layers combined. The pH value of the solution was adjusted to 4 with Citric acid. The resulting solution was extracted with 3×500 mL of ethyl acetate and the organic layers combined. The organic layer was washed with 1×500 mL of brine. The organic layer was dried over sodium sulfate and concentrated under vacuum. This resulted in 8.99 g (94%) of (2S)-2-[[(tert-butoxy)carbonyl](methyl)amino]-3-cyclopropylpropanoic acid as yellow oil. MS (ESI, m/z): 242 [M−H]$^−$.

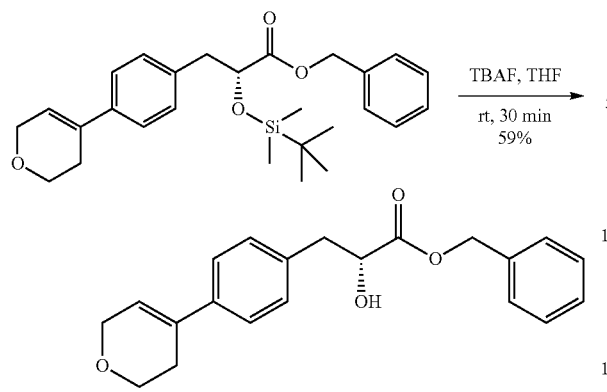
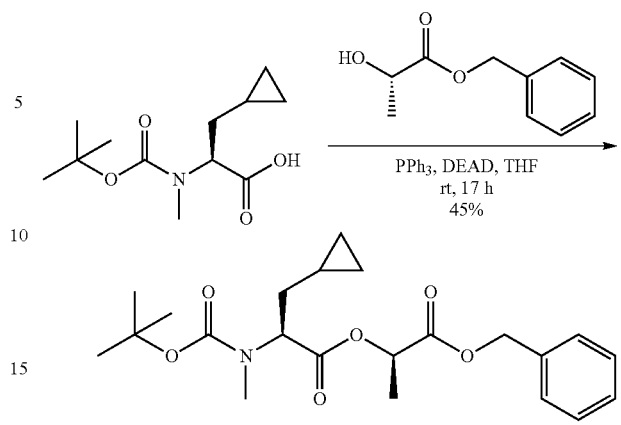

Benzyl (2R)-3-[4-(3,6-dihydro-2H-pyran-4-yl)phenyl]-2-hydroxypropanoate

Into a 250-mL 3-necked round-bottom flask, was placed benzyl (2R)-2-[(tert-butyldimethylsilyl)oxy]-3-[4-(3,6-dihydro-2H-pyran-4-yl)phenyl]propanoate (8 g, 17.67 mmol, 1.00 equiv), tetrahydrofuran (60 mL), This was followed by the additions of TBAF (6 g, 22.95 mmol, 1.20 equiv) in portions at 0° C. The resulting solution was stirred for 30 min at room temperature. The reaction was then quenched by the addition of water (200 mL). The resulting solution was extracted with 3×50 mL of ethyl acetate and the organic layers combined. The organic layer was washed with 3×50 mL of water and 1×50 mL of brine. The organic layer was dried over sodium sulfate and concentrated under vacuum. The residue was applied onto a silica gel column with ethyl acetate/petroleum ether (1:7). This resulted in 3.5 g (59%) of benzyl (2R)-3-[4-(3,6-dihydro-2H-pyran-4-yl)phenyl]-2-hydroxypropanoate as a white solid.

(2R)-1-(benzyloxy)-1-oxopropan-2-yl (2S)-2-[[(tert-butoxy)carbonyl](methyl)amino]-3-cyclopropylpropanoate Into a 100-mL 3-necked round-bottom flask purged and maintained with an inert atmosphere of nitrogen, was placed (2S)-2-[[(tert-butoxy)carbonyl](methyl)amino]-3-cyclopropylpropanoic acid (4 g, 16.44 mmol, 1.00 equiv), benzyl (2S)-2-hydroxypropanoate (3 g, 16.65 mmol, 1.00 equiv), tetrahydrofuran (30 mL), PPh$_3$ (5.2 g, 19.83 mmol, 1.20 equiv). To this was added the DEAD (3.5 g, 20.10 mmol, 1.20 equiv) in tetrahydrofuran (10 mL) dropwise with stirring at 0° C. The resulting solution was stirred for 17 h at room temperature. The solids were filtered out. The filtrate was concentrated under vacuum. The residue was applied onto a silica gel column with ethyl acetate/petroleum ether (1:20). This resulted in 3 g (45%) of (2R)-1-(benzyloxy)-1-oxopropan-2-yl (2S)-2-[[(tert-butoxy)carbonyl](methyl)amino]-3-cyclopropylpropanoate as white oil. MS (ESI, m/z): 406 [M+H]$^+$.

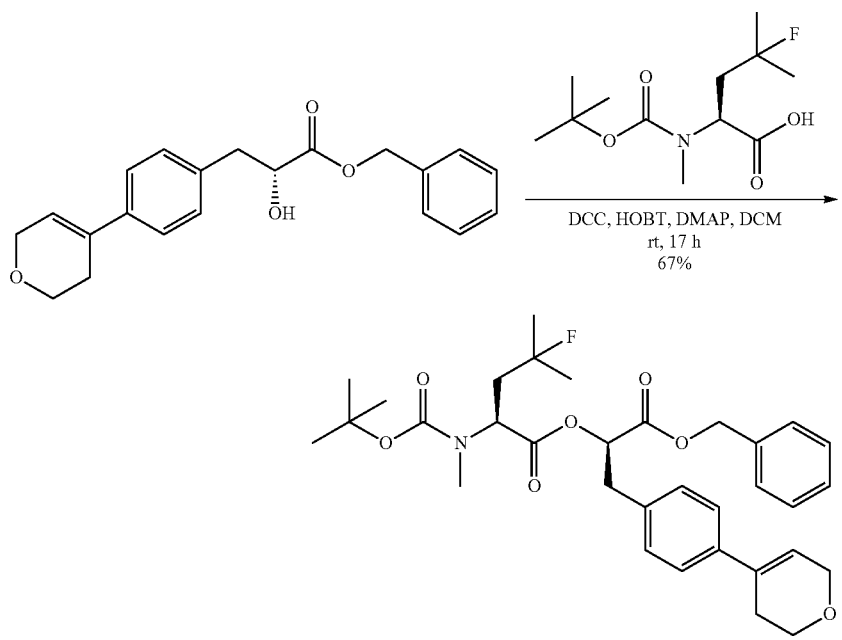

(2R)-1-(benzyloxy)-3-[4-(3,6-dihydro-2H-pyran-4-yl)phenyl]-1-oxopropan-2-yl (2S)-2-[[(tert-butoxy)carbonyl](methyl)amino]-4-fluoro-4-methylpentanoate (D6)

Into a 50-mL 3-necked round-bottom flask, was placed benzyl (2R)-3-[4-(3,6-dihydro-2H-pyran-4-yl)phenyl]-2-hydroxypropanoate (1.3 g, 3.84 mmol, 1.00 equiv), (2S)-2-[[(tert-butoxy)carbonyl](methyl)amino]-4-fluoro-4-methyl-pentanoic acid (1 g, 3.80 mmol, 1.00 equiv), dichloromethane (15 mL), This was followed by the addition of DCC (872 mg, 4.23 mmol, 1.10 equiv), 4-dimethylaminopyridine (516 mg, 4.22 mmol, 1.10 equiv) and HOBT (571 mg, 4.23 mmol, 1.10 equiv) in portion at 0° C. The resulting solution was stirred for 17 h at room temperature. The solids were filtered out. The filtrate was concentrated under vacuum. The residue was applied onto a silica gel column with ethyl acetate/petroleum ether (1:8). This resulted in 1.5 g (67%) of (2R)-1-(benzyloxy)-3-[4-(3,6-dihydro-2H-pyran-4-yl)phenyl]-1-oxopropan-2-yl (2S)-2-[[(tert-butoxy)-carbonyl](methyl)amino]-4-fluoro-4-methylpentanoate as a white solid. MS (ESI, m/z): 584 [M+H]$^+$.

value of the solution was adjusted to 8 with sodium bicarbonate (aq.). The resulting solution was extracted with 100 mL of dichloromethane and the organic layers combined and dried over sodium sulfate and concentrated under vacuum. This resulted in 1.4 g (crude) of (2R)-1-(benzyloxy)-1-oxopropan-2-yl (2S)-3-cyclopropyl-2-(methylamino)propanoate as a white solid. MS (ESI, m/z): 306 [M+H]$^+$.

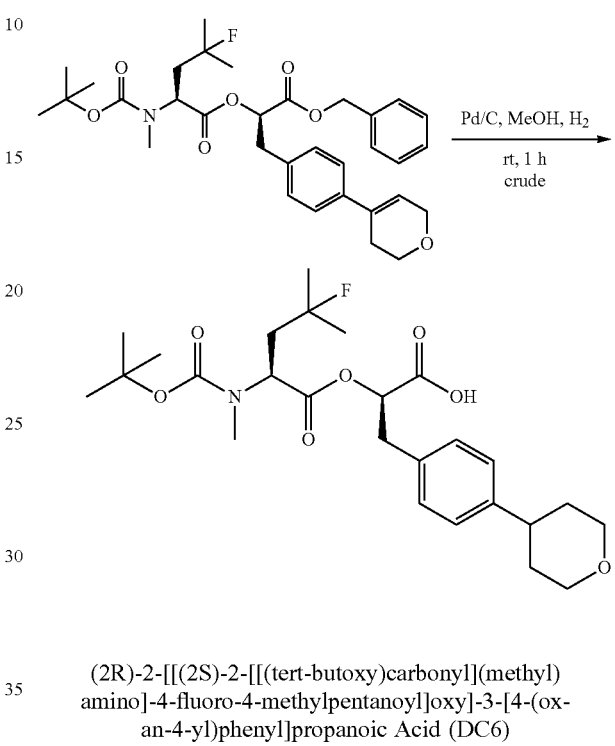

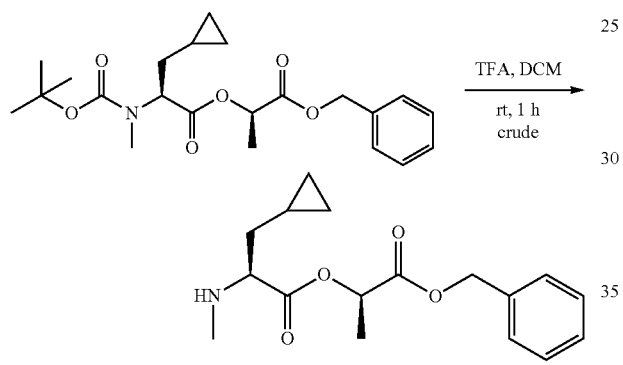

(2R)-1-(benzyloxy)-1-oxopropan-2-yl (2S)-3-cyclopropyl-2-(methylamino)propanoate (DA10)

Into a 100-mL 3-necked round-bottom flask, was placed (2R)-1-(benzyloxy)-1-oxopropan-2-yl (2S)-2-[[(tert-butoxy)carbonyl](methyl)amino]-3-cyclopropylpropanoate (D10, 1.5 g, 3.70 mmol, 1.00 equiv), dichloromethane (30 mL), This was followed by the addition of trifluoroacetic acid (7 mL) dropwise with stirring at 0° C. The resulting solution was stirred for 1 h at room temperature. The pH

(2R)-2-[[(2S)-2-[[(tert-butoxy)carbonyl](methyl)amino]-4-fluoro-4-methylpentanoyl]oxy]-3-[4-(oxan-4-yl)phenyl]propanoic Acid (DC6)

Into a 250-mL round-bottom flask, was placed (2R)-1-(benzyloxy)-3-[4-(3,6-dihydro-2H-pyran-4-yl)phenyl]-1-oxopropan-2-yl (2S)-2-[[(tert-butoxy)carbonyl](methyl)amino]-4-fluoro-4-methylpentanoate (D6, 1.5 g, 2.57 mmol, 1.00 equiv), MeOH (80 mL) and Palladium carbon (800 mg). To the above mixture was introduced hydrogen. The resulting solution was stirred for 1 h at room temperature. The solids were filtered out. The filtrate was concentrated under vacuum. This resulted in 1.3 g (crude) of (2R)-2-[[(2S)-2-[[(tert-butoxy)carbonyl](methyl)amino]-4-fluoro-4-methylpentanoyl]oxy]-3-[4-(oxan-4-yl)phenyl]propanoic acid as a white solid. MS (ESI, m/z): 496 [M+H]$^+$.

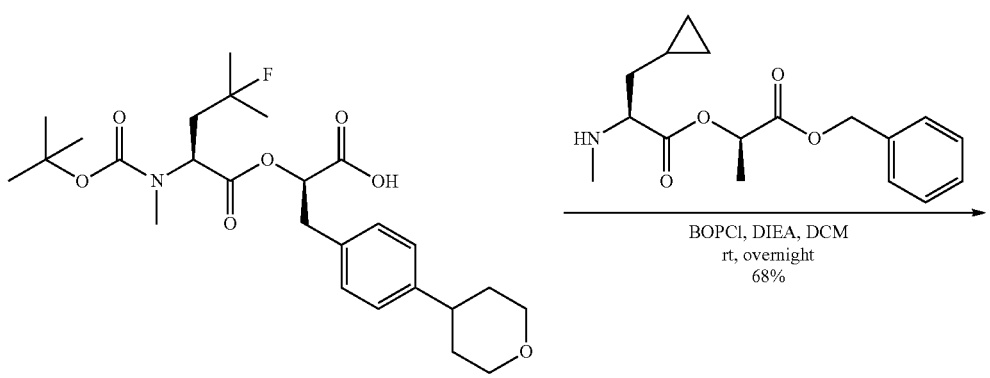

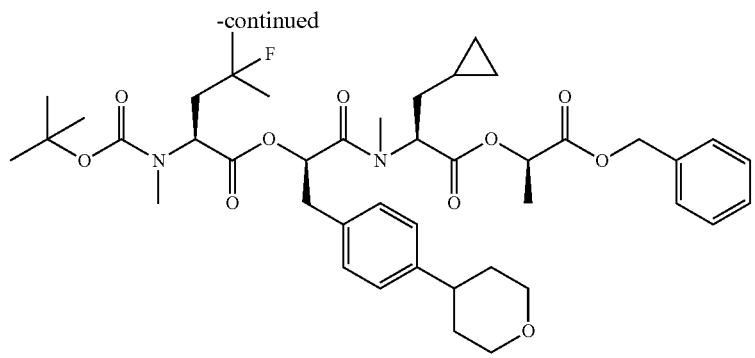

(1R)-1-[[(2S)-1-[[(2R)-1-(benzyloxy)-1-oxopropan-2-yl]oxy]-3-cyclopropyl-1-oxopropan-2-yl](methyl)carbamoyl]-2-[4-(oxan-4-yl)phenyl]ethyl (2S)-2-[[(tert-butoxy)carbonyl](methyl)amino]-4-fluoro-4-methylpentanoate (TP7-34)

Into a 100-mL 3-necked round-bottom flask, was placed DC6 (1.3 g, 2.62 mmol, 1.00 equiv), DA10 (801 mg, 2.62 mmol, 1.00 equiv), dichloromethane (20 mL), The was followed by the addition of BOP—Cl (1.3 g, 5.11 mmol, 2.00 equiv) in portions at 0° C. To this was added DIEA (678 mg, 5.25 mmol, 2.00 equiv) dropwise with stirring at 0° C. The resulting solution was stirred overnight at room temperature. The solids were filtered out. The filtrate was concentrated under vacuum. This resulted was applied onto a silica gel column with ethyl acetate/petroleum ether (1:8). This resulted in 1.4 g (68%) of (1R)-1-[[(2S)-1-[[(2R)-1-(benzyloxy)-1-oxopropan-2-yl]oxy]-3-cyclopropyl-1-oxopropan-2-yl](methyl)carbamoyl]-2-[4-(oxan-4-yl)phenyl]ethyl (2S)-2-[[(tert-butoxy)carbonyl](methyl)amino]-4-fluoro-4-methylpentanoate as a white solid. MS (ESI, m/z): 783 [M+H]$^+$.

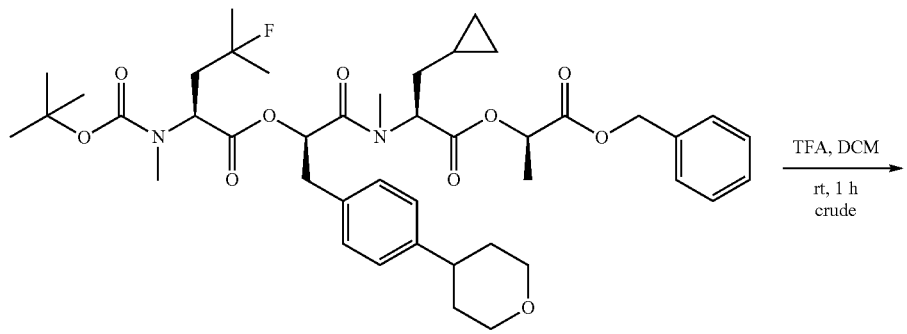

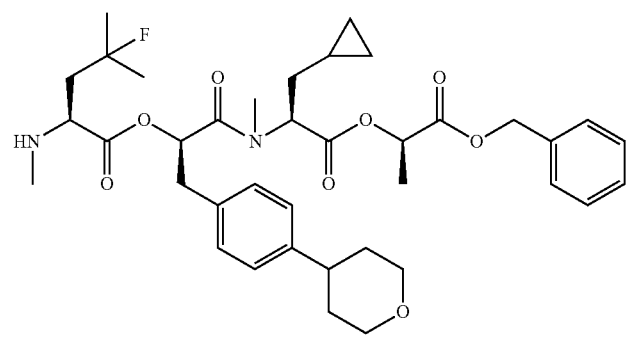

(1R)-1-[[(2S)-1-[[(2R)-1-(benzyloxy)-1-oxopropan-2-yl]oxy]-3-cyclopropyl-1-oxopropan-2-yl](methyl)carbamoyl]-2-[4-(oxan-4-yl)phenyl]ethyl (2S)-4-fluoro-4-methyl-2-(methylamino)pentanoate (TA7-34)

Into a 50-mL 3-necked round-bottom flask, was placed TP7-34 (700 mg, 0.89 mmol, 1.00 equiv), dichloromethane (15 mL). This was followed by the addition of trifluoroacetic acid (3 mL), dropwise with stirring at 0° C. The resulting solution was stirred for 1 h at room temperature. The pH value of the solution was adjusted to 8 with sodium bicarbonate (aq.). The resulting solution was extracted with 50 mL of dichloromethane and the organic layers combined. The organic layers were dried over anhydrous sodium sulfate and concentrated under vacuum. This resulted in 650 mg (crude) of (1R)-1-[[(2S)-1-[[(2R)-1-(benzyloxy)-1-oxopropan-2-yl]oxy]-3-cyclopropyl-1-oxopropan-2-yl](methyl)carbamoyl]-2-[4-(oxan-4-yl)phenyl]ethyl (2S)-4-fluoro-4-methyl-2-(methylamino)pentanoate (TA7-34) as a white solid. MS (ESI, m/z): 683 [M+H]$^+$.

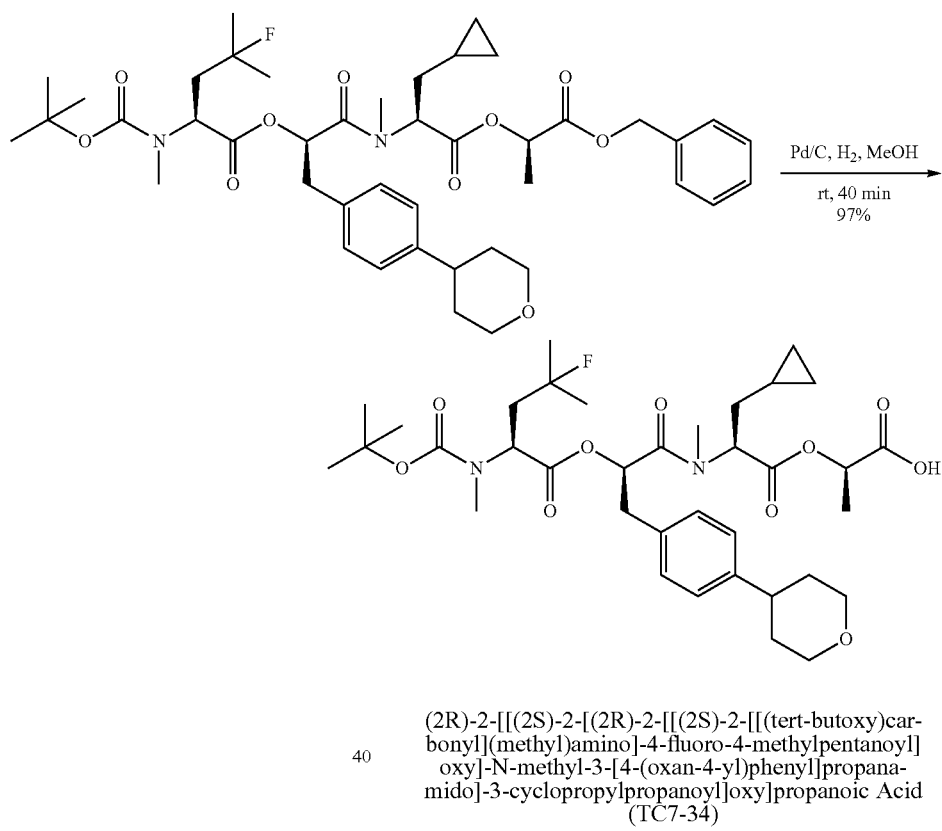

(2R)-2-[[(2S)-2-[(2R)-2-[[(2S)-2-[[(tert-butoxy)carbonyl](methyl)amino]-4-fluoro-4-methylpentanoyl]oxy]-N-methyl-3-[4-(oxan-4-yl)phenyl]propanamido]-3-cyclopropylpropanoyl]oxy]propanoic Acid (TC7-34)

Into a 100-mL round-bottom flask, was placed TP7-34 (700 mg, 0.89 mmol, 1.00 equiv), methanol (30 mL), Palladium carbon (100 mg). To the above mixture was introduced hydrogen. The resulting solution was stirred for 40 min at room temperature. The solids were filtered out. The filtrate was concentrated under vacuum. This resulted in 600 mg (97%) of (2R)-2-[[(2S)-2-[(2R)-2-[[(2S)-2-[[(tert-butoxy)carbonyl](methyl)amino]-4-fluoro-4-methylpentanoyl]oxy]-N-methyl-3-[4-(oxan-4-yl)phenyl]propanamido]-3-cyclopropylpropanoyl]oxy]propanoic acid as a white solid. MS (ESI, m/z): 693 [M+H]$^+$.

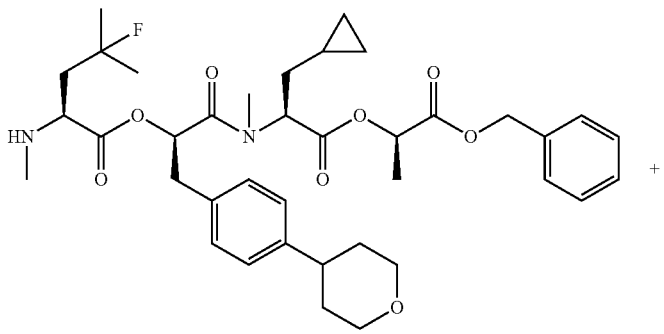

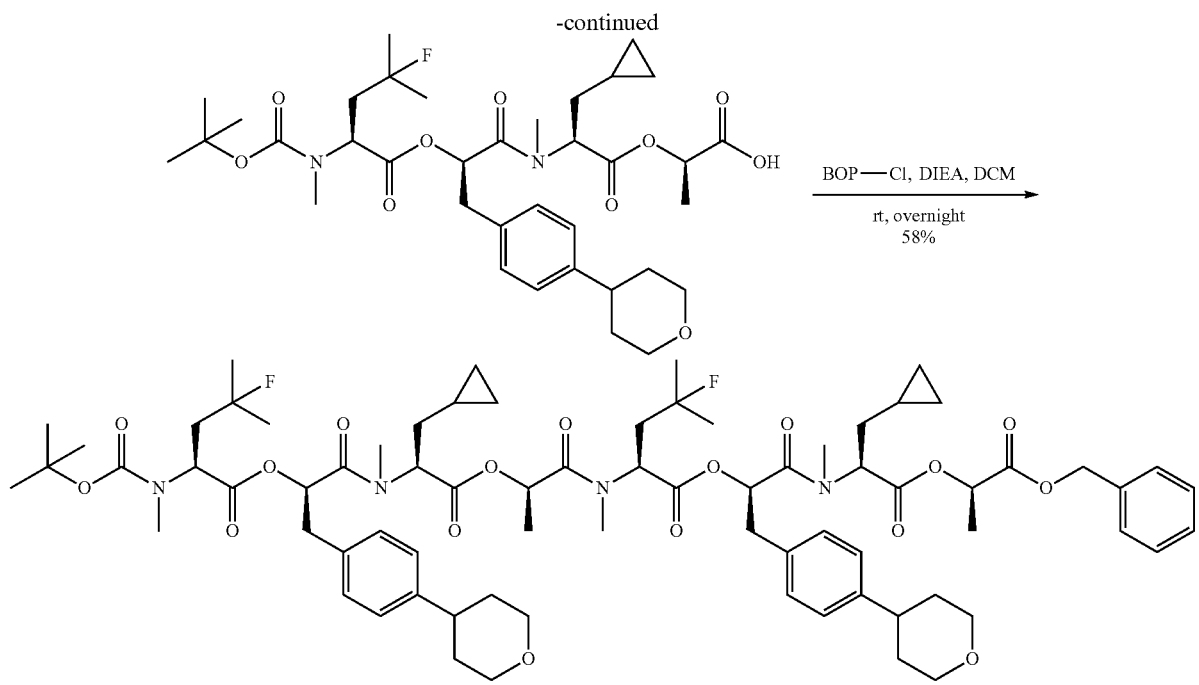

Compound OP7-34:

Into a 50-mL 3-necked round-bottom flask, was placed TA7-34 (650 mg, 0.95 mmol, 1.00 equiv), TC7-34 (600 mg, 0.87 mmol, 1.00 equiv), dichloromethane (15 mL). This was followed by the addition of BOP—Cl (486 mg, 2.00 equiv) in portions at 0° C. To this was added DIEA (246 mg, 1.90 mmol, 2.00 equiv) dropwise with stirring at 0° C. The resulting solution was stirred overnight at room temperature. The solids were filtered out. The filtrate was concentrated under vacuum. This resulted was applied onto a silica gel column and eluted with ethyl acetate/petroleum ether (1:3). This resulted in 750 mg (58%) of OP7-34 as a white solid. MS (ESI, m/z): 1358 [M+H]$^+$.

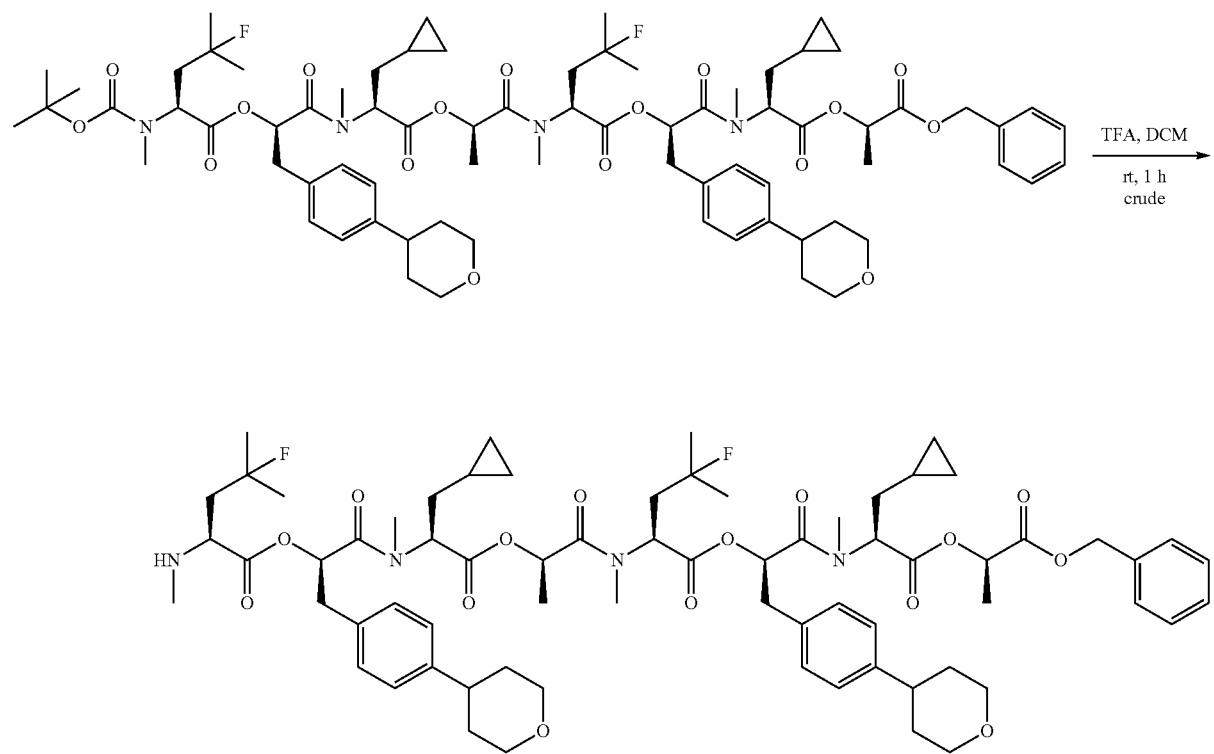 [SMILES: C[C@@H](OC(=O)[C@H](CC1CC1)N(C)C(=O)[C@@H](Cc1ccc(C2CCOCC2)cc1)OC(=O)[C@H](CC(C)(C)F)N(C)C(=O)[C@@H](C)OC(=O)[C@H](CC1CC1)N(C)C(=O)[C@@H](Cc1ccc(C2CCOCC2)cc1)OC(=O)[C@H](CC(C)(C)F)N(C)C(=O)OC(C)(C)C)C(=O)OCc1ccccc1 ; CN[C@@H](CC(C)(C)F)C(=O)O[C@H](Cc1ccc(C2CCOCC2)cc1)C(=O)N(C)[C@@H](CC1CC1)C(=O)O[C@H](C)C(=O)N(C)[C@@H](CC(C)(C)F)C(=O)O[C@H](Cc1ccc(C2CCOCC2)cc1)C(=O)N(C)[C@@H](CC1CC1)C(=O)O[C@H](C)C(=O)OCc1ccccc1]

(1R)-1-[[(2S)-1-[(1R)-1-[[(2S)-1-[(1R)-1-[[(2S)-1-[[(2R)-1-(benzyloxy)-1-oxopropan-2-yl]oxy]-3-cyclopropyl-1-oxopropan-2-yl](methyl)carbamoyl]-2-[4-(oxan-4-yl)phenyl]ethoxy]-4-fluoro-4-methyl-1-oxopentan-2-yl](methyl)carbamoyl]ethoxy]-3-cyclopropyl-1-oxopropan-2-yl](methyl)carbamoyl]-2-[4-(oxan-4-yl)phenyl]ethyl (2S)-4-fluoro-4-methyl-2-(methylamino)pentanoate (OA7-34)

Into a 50-mL 3-necked round-bottom flask, was placed OP7-34 (750 mg, 0.55 mmol, 1.00 equiv), dichloromethane (8 mL), This was followed by the additions of trifluoroacetic acid (2 mL) dropwise with stirring at 0° C. The resulting solution was stirred for 1 h at room temperature. The pH value of the solution was adjusted to 8 with sodium bicarbonate (aq.). The resulting solution was extracted with 30 mL of dichloromethane and the organic layers combined and dried in an oven under reduced pressure and concentrated under vacuum. This resulted in 700 mg of (1R)-1-[[(2S)-1-[(1R)-1-[[(2S)-1-[(1R)-1-[[(2S)-1-[[(2R)-1-(benzyloxy)-1-oxopropan-2-yl]oxy]-3-cyclopropyl-1-oxopro-pan-2-yl](methyl)carbamoyl]-2-[4-(oxan-4-yl)phenyl]ethoxy]-4-fluoro-4-methyl-1-oxopentan-2-yl](methyl)carbamoyl]ethoxy]-3-cyclopropyl-1-oxopropan-2-yl](methyl)carbamoyl]-2-[4-(oxan-4-yl)phenyl]ethyl (2S)-4-fluoro-4-methyl-2-(methylamino)pentanoate (OA7-34) as a white solid. MS (ESI, m/z): 1258 [M+H]$^+$.

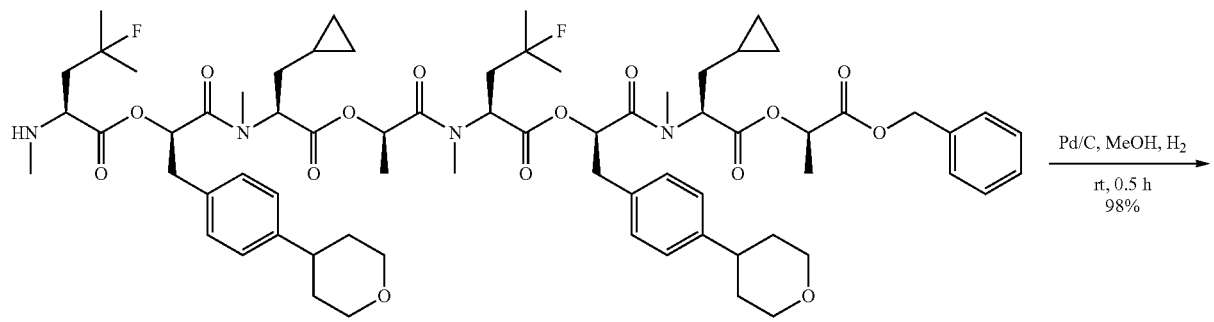

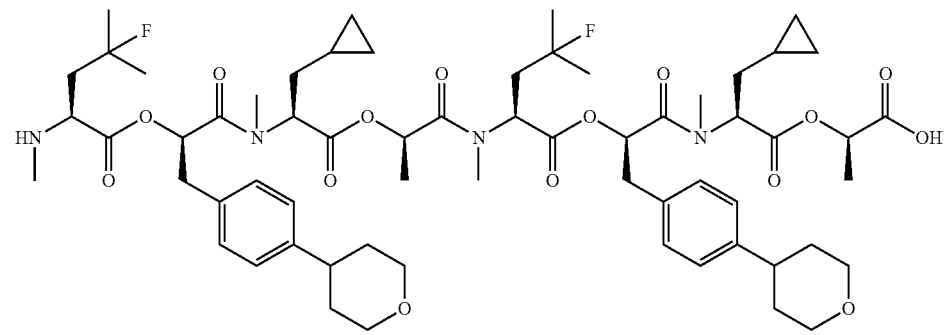

(2R)-2-[[(2S)-3-cyclopropyl-2-[(2R)-2-[[(2S)-2-[(2R)-2-[[(2S)-3-cyclopropyl-2-[(2R)-2-[[(2S)-4-fluoro-4-methyl-2-(methylamino)pentanoyl]oxy]-N-methyl-3-[4-(oxan-4-yl)phenyl]propanamido-]propanoyl]oxy]-N-methylpropanamido]-4-fluoro-4-methylpentanoyl]oxy]-N-methyl-3-[4-(oxan-4-yl)phenyl]propanamido]propanoyl]oxy]propanoic Acid (OAC7-34)

Into a 50-mL round-bottom flask, was placed OA7-34 (700 mg, 0.56 mmol, 1.00 equiv), methanol (30 mL), Palladium carbon (100 mg). To the above mixture was introduced hydrogen. The resulting solution was stirred for 0.5 h at room temperature. The solids were filtered out. The filtrate was concentrated under vacuum. This resulted in 640 mg (98%) of (2R)-2-[[(2S)-3-cyclopropyl-2-[(2R)-2-[[(2S)-2-[(2R)-2-[[(2S)-3-cyclopropyl-2-[(2R)-2-[[(2S)-4-fluoro-4-methyl-2-(methylamino)pentanoyl]oxy]-N-methyl-3-[4-(oxan-4-yl)phenyl]propanamido]propanoyl]oxy]-N-methylpropanamido]-4-fluoro-4-methylpentanoyl]oxy]-N-methyl-3-[4-(oxan-4-yl)phenyl]propanamido]propanoyl]oxy]propanoic acid (OAC7-30) as a white solid. MS (ESI, m/z): 1168 [M+H]+.

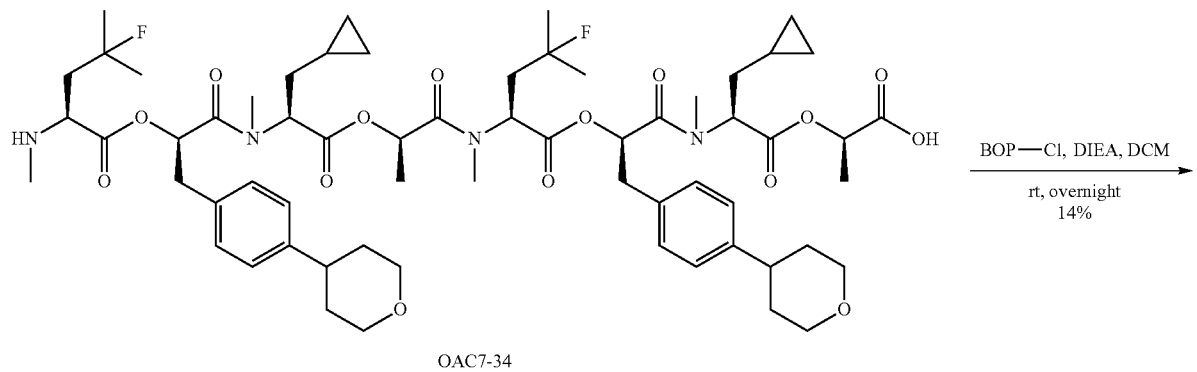

OAC7-34

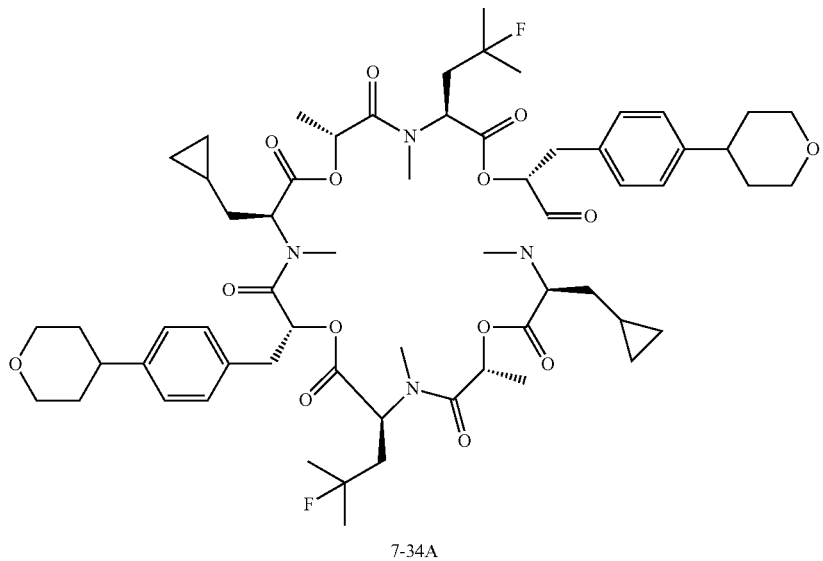

7-34A (3S,6R,9S,12R,15S,18R,21S,24R)-3,15-bis(cyclopropylmethyl)-9,21-bis(2-fluoro-2-methylpropyl)-4,10,12,16,22,24-hexamethyl-6,18-bis([[4-(oxan-4-yl)phenyl]methyl])-1,7,13,19-tetraoxa-4,10,16,22-tetraazacyclotetracosan-2,5S,11,14,17,20,23-octone (7-34A)

Into a 500-mL 3-necked round-bottom flask, was placed OAC7-34 (640 mg, 0.55 mmol, 1.00 equiv), dichloromethane (200 mL). This was followed by the addition of BOP—Cl (280 mg, 1.10 mmol, 2.00 equiv) in portions at 0° C. To this was added DIEA (141 mg, 1.09 mmol, 1.99 equiv) dropwise with stirring at 0° C. The resulting solution was stirred overnight at room temperature. The solids were filtered by filtration. The filtrate was concentrated under vacuum. The crude product was purified by Prep-HPLC with the following conditions (waters-2767): Column, SunFire Prep C18, 5 um, 19*150 mm; mobile phase, Water and $CH_3CN$ (70% $CH_3CN$ up to 80% in 8 min); Detector, UV 254 nm. This resulted in 85.8 mg (14%) of (3S,6R,9S,12R,15S,18R,21S,24R)-3,15-bis(cyclopropylmethyl)-9,21-bis(2-fluoro-2-methylpropyl)-4,10,12,16,22,24-hexamethyl-6,18-bis([[4-(oxan-4-yl)phenyl]methyl])-1,7,-13,19-tetraoxa-4,10,16,22-tetraazacyclotetracosan-2,5,8,11,14,17,20,23-octone (7-34A) as a white solid. $^1$H NMR ($CD_3OD$, 300 MHz) δ: 7.5-7.0 (m, 8H), 5.96-4.9 (m, 8H), 4.19-3.94 (m, 4H), 3.7-3.47 (m, 4H), 3.28-2.69 (m, 18H), 2.39-1.2 (m, 33H), 1.00-0.97 (m, 1H), 0.69-0.01 (m, 10H); MS (ESI, m/z): 1150 [M+H]+; [c]=−57.2°, T=27.2° C., C=1.0 g/100 mL in MeOH.

Preparation Example 38: Synthesis of Compound 7-30B in Table 7 Wherein $R^a$ and $R^b$ are Hydrogen, and R', R'', R''' and R'''' are Each Methyl
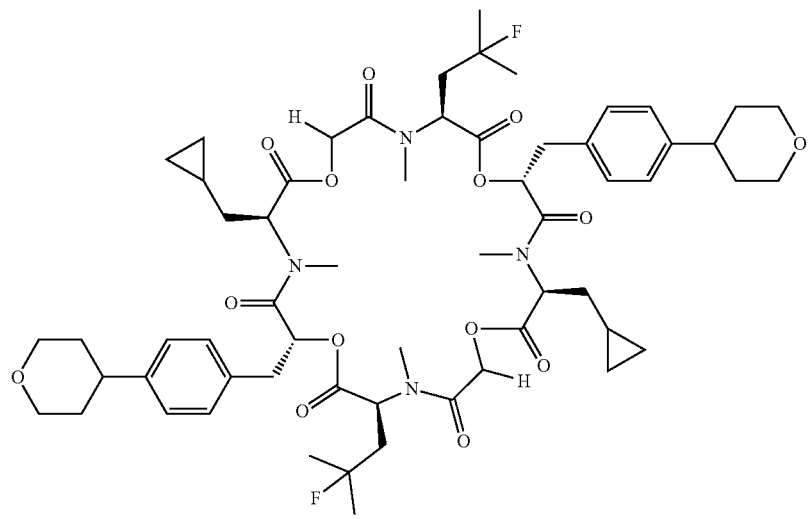 [SMILES: CN1C(=O)COC(=O)[C@H](CC2CC2)N(C)C(=O)[C@@H](Cc2ccc(C3CCOCC3)cc2)OC(=O)[C@H](CC(C)(C)F)N(C)C(=O)COC(=O)[C@H](CC2CC2)N(C)C(=O)[C@@H](Cc2ccc(C3CCOCC3)cc2)OC(=O)[C@@H]1CC(C)(C)F]
Compound 7-34B was prepared in a similar way to compound 6-7A according to Schemes 13 and 14 shown below.
Scheme 13
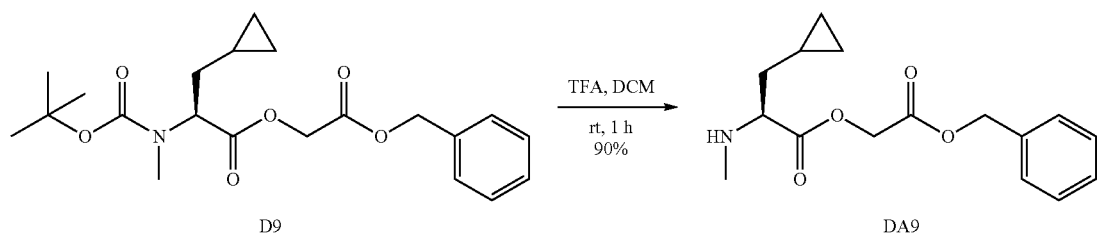
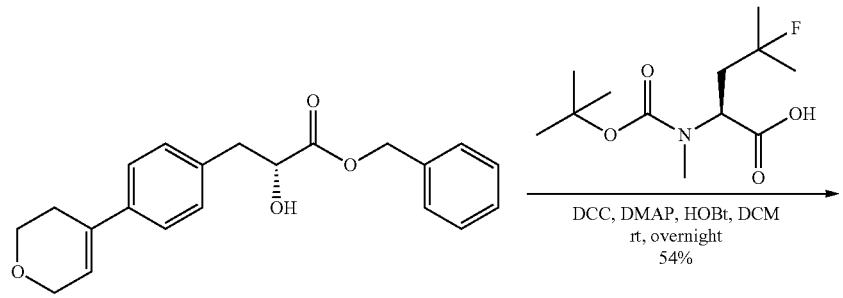

-continued
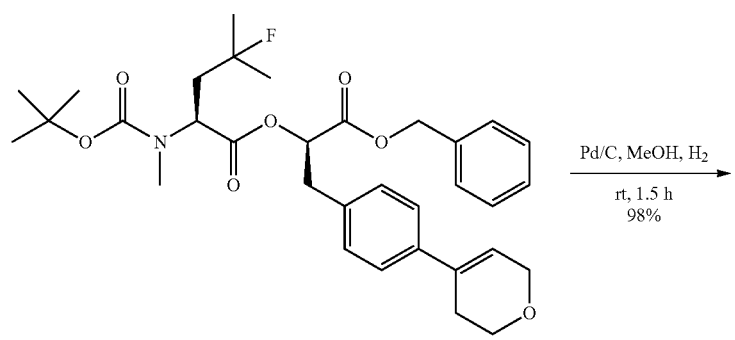
D6
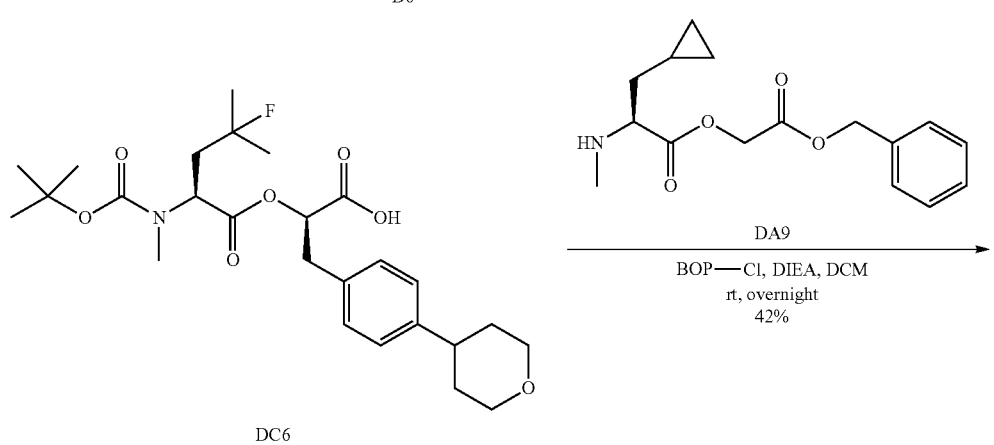
DC6
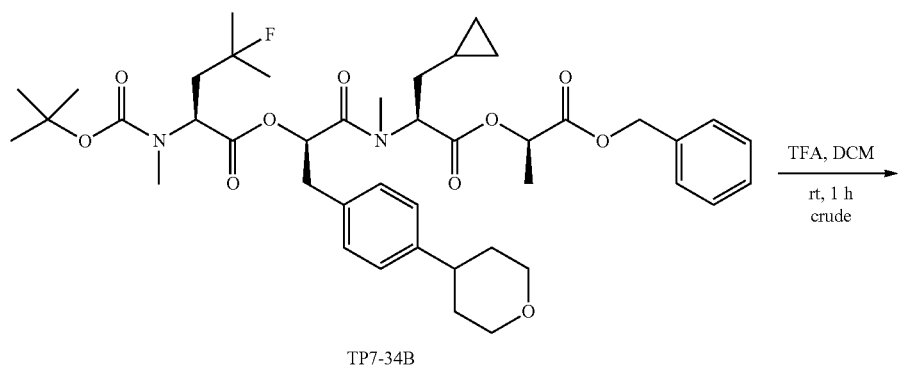
TP7-34B
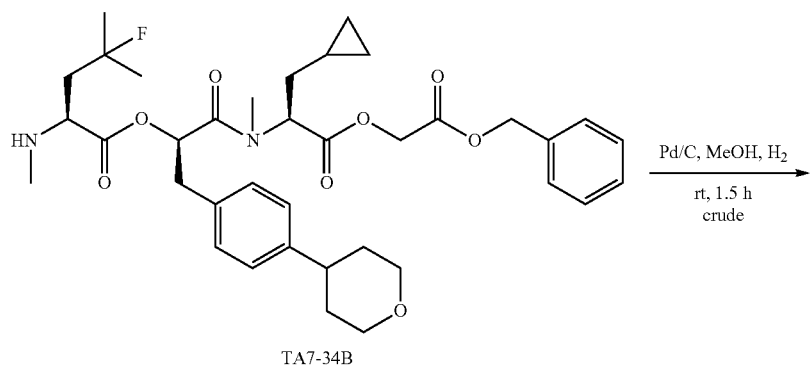
TA7-34B

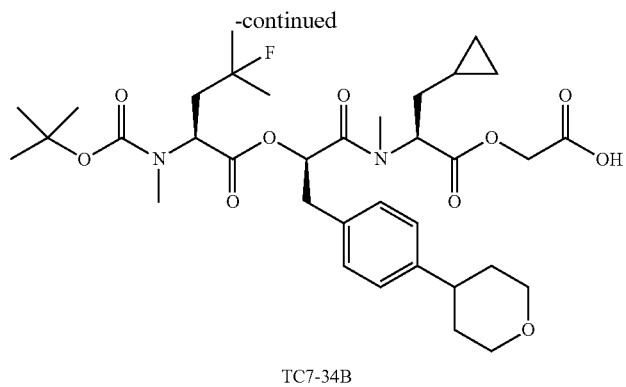
TC7-34B
Scheme 14
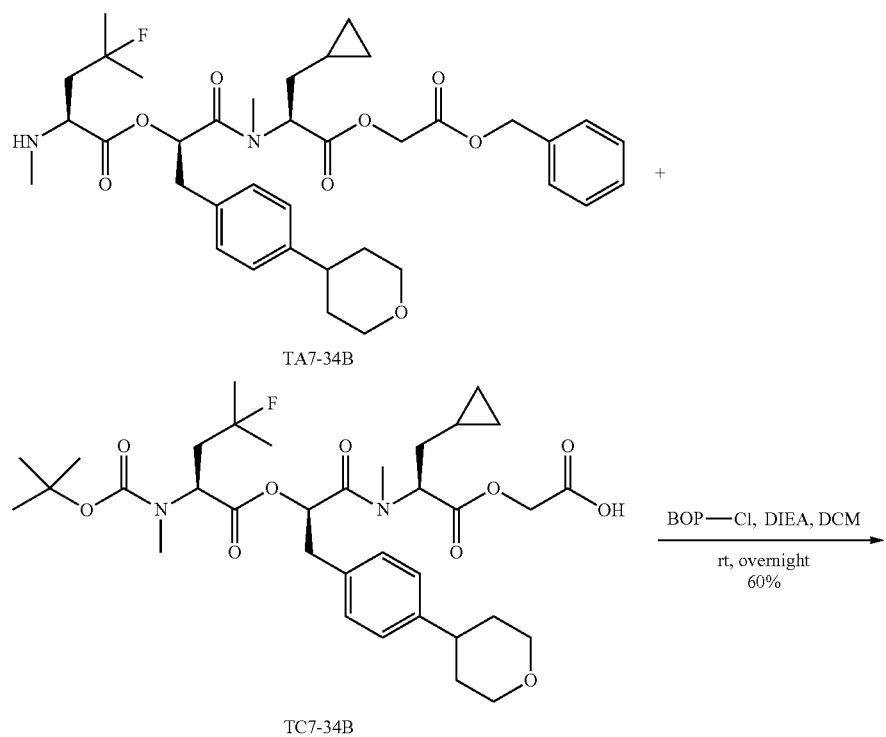
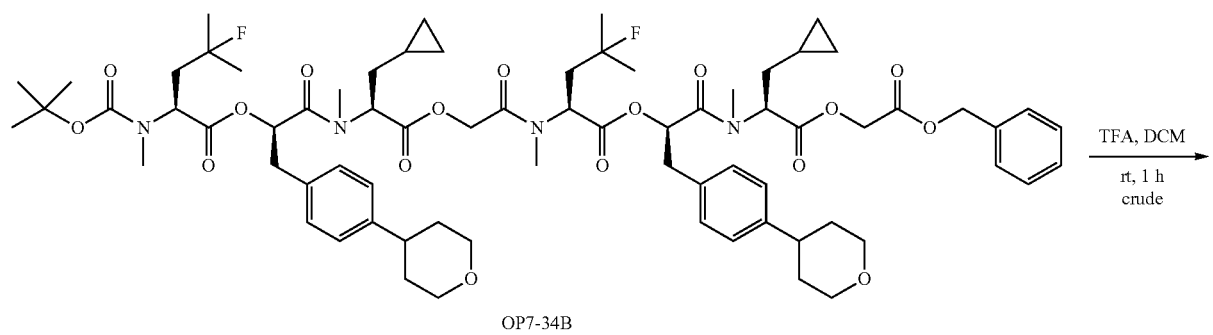

-continued
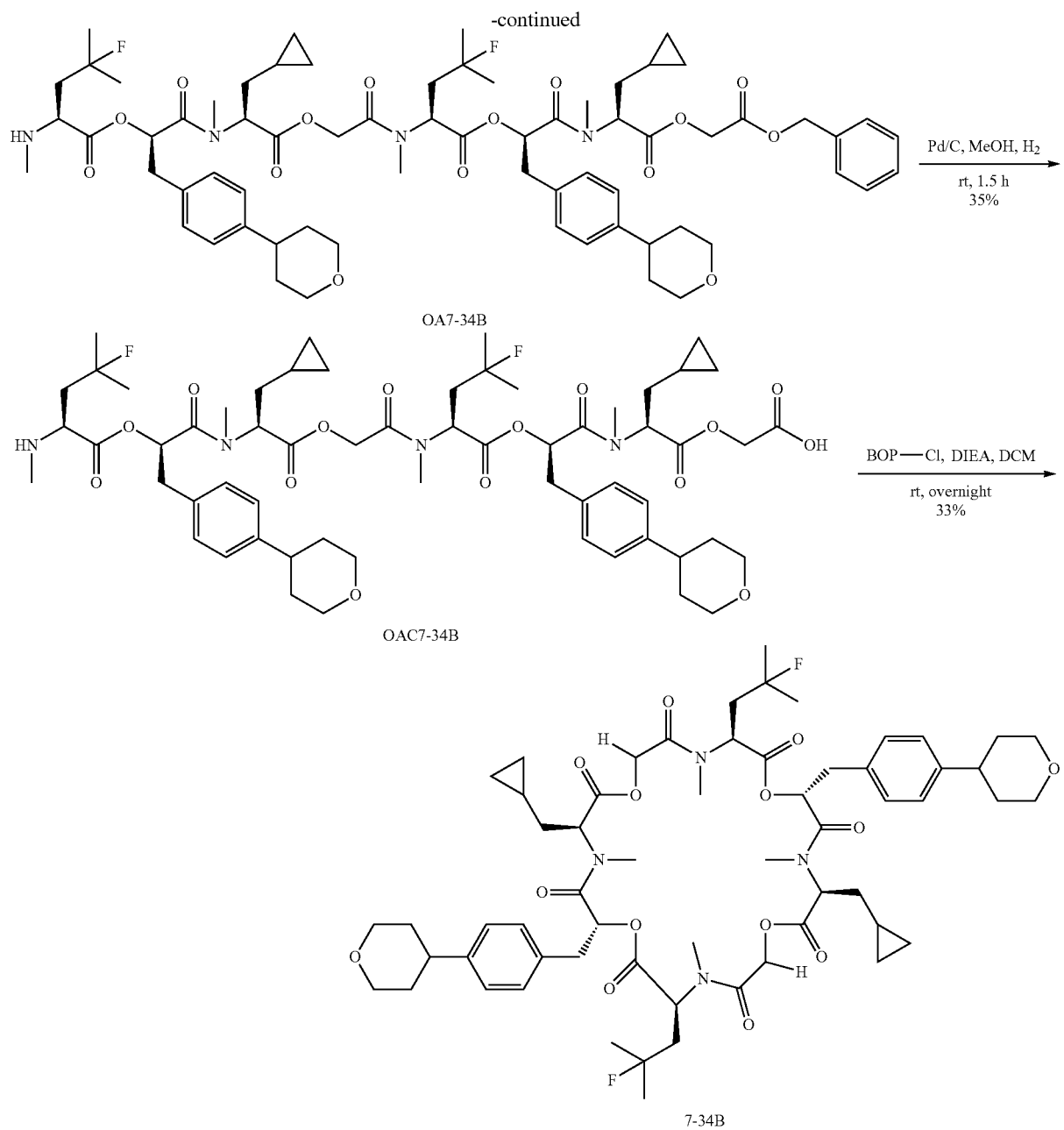
OA7-34B
OAC7-34B
7-34B
Experimental Details
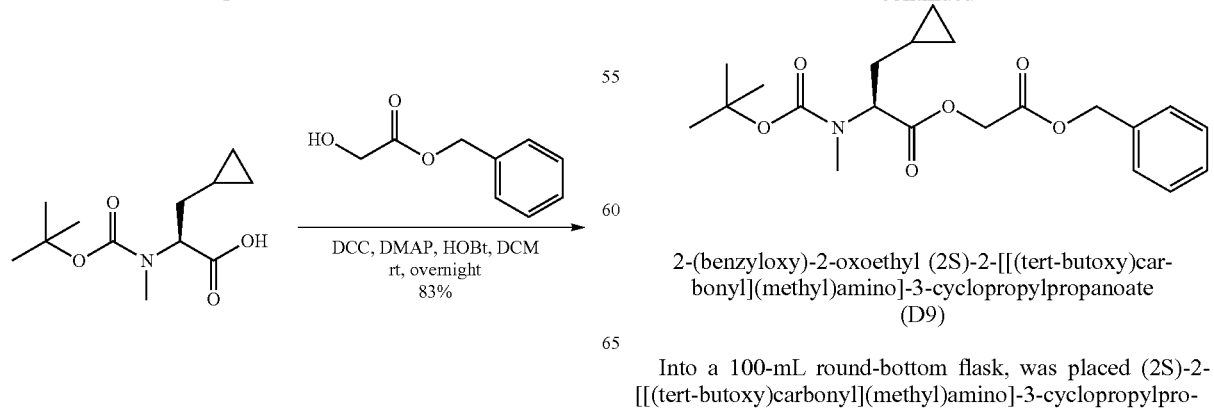
2-(benzyloxy)-2-oxoethyl (2S)-2-[[(tert-butoxy)carbonyl](methyl)amino]-3-cyclopropylpropanoate (D9)
Into a 100-mL round-bottom flask, was placed (2S)-2-[[(tert-butoxy)carbonyl](methyl)amino]-3-cyclopropylpropanoic acid (1.5 g, 6.17 mmol, 1.00 equiv), benzyl 2-hydroxyacetate (1.02 g, 6.14 mmol, 1.00 equiv) and dichloromethane (30 mL). This was followed by the addition of DCC (1.52 g, 7.37 mmol, 1.20 equiv), 4-dimethylaminopyridine (900 mg, 7.37 mmol, 1.20 equiv) and HOBt (1.0 g, 7.40 mmol, 1.20 equiv) in portions at 0° C. The resulting solution was stirred overnight at room temperature. The solids were filtered out. The filtrate was concentrated under vacuum. The residue was applied onto a silica gel column with ethyl acetate/petroleum ether (1:3). This resulted in 2 g (83%) of 2-(benzyloxy)-2-oxoethyl (2S)-2-[[(tert-butoxy)carbonyl](methyl)amino]-3-cyclopropylpropanoate as yellow oil. MS (ESI, m/z): 392 [M+H]+.

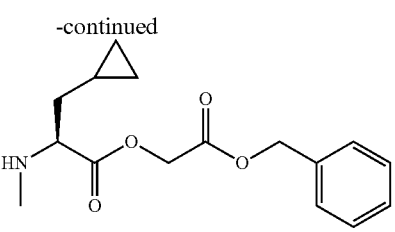

2-(benzyloxy)-2-oxoethyl (2S)-3-cyclopropyl-2-(methylamino)propanoate (DA9)

Into a 50-mL round-bottom flask, was placed 2-(benzyloxy)-2-oxoethyl (2S)-2-[[(tert-butoxy)carbonyl](methyl)amino]-3-cyclopropylpropanoate (D9, 1.8 g, 4.60 mmol, 1.00 equiv) and dichloromethane (16 mL). To this was added trifluoroacetic acid (3 mL) dropwise with stirring at 0° C. The resulting solution was stirred for 1 h at room temperature. The pH value of the solution was adjusted to 9 with sodium bicarbonate (aq.). The resulting solution was extracted with 2×20 mL of dichloromethane and the organic layers combined. The organic layers were dried over sodium sulfate and concentrated under vacuum. This resulted in 1.2 g (90%) of 2-(benzyloxy)-2-oxoethyl (2S)-3-cyclopropyl-2-(methylamino) propanoate as light yellow oil. MS (ESI, m/z): 292 [M+H]+.

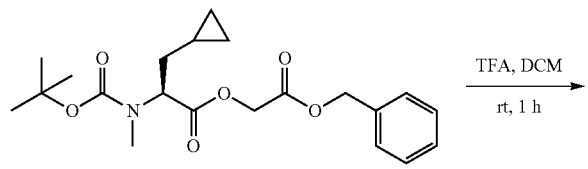

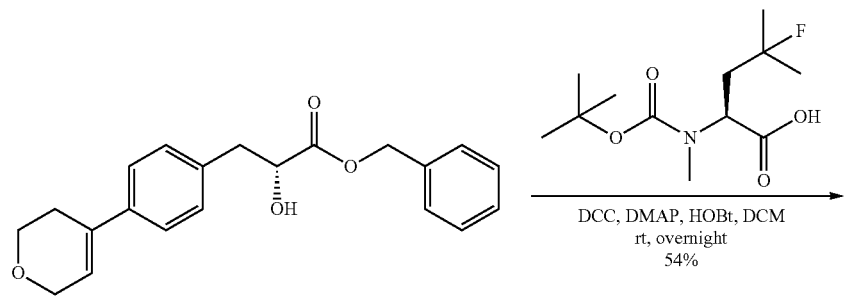

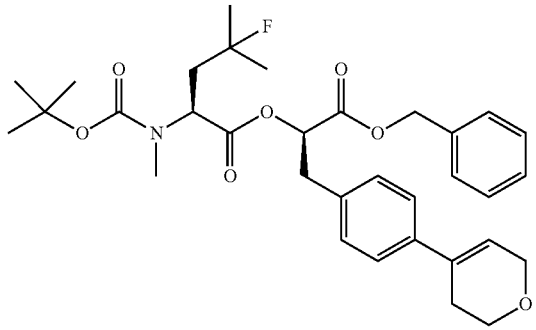

401

(2R)-1-(benzyloxy)-3-[4-(3,6-dihydro-2H-pyran-4-yl)phenyl]-1-oxopropan-2-yl (2S)-2-[[(tert-butoxy)carbonyl](methyl)amino]-4-fluoro-4-methylpentanoate (D6)

Into a 50-mL round-bottom flask, was placed (2S)-2-[[(tert-butoxy)carbonyl](methyl)amino]-4-fluoro-4-methylpentanoic acid (1 g, 3.80 mmol, 1.00 equiv), benzyl (2R)-3-[4-(3,6-dihydro-2H-pyran-4-yl)phenyl]-2-hydroxypropanoate (770 mg, 2.28 mmol, 1.00 equiv) and dichloromethane (20 mL), This was followed by the addition of DCC (730 mg, 3.54 mmol, 1.20 equiv), 4-dimethylaminopyridine (430 mg, 3.52 mmol, 1.20 equiv) and HOBt (480 mg, 3.55 mmol, 1.20 equiv). The resulting solution was stirred overnight at room temperature. The solids were filtered out. The filtrate was concentrated under vacuum. The residue was applied onto a silica gel column with ethyl acetate/petroleum ether (1:3). This resulted in 1.2 g (54%) of (2R)-1-(benzyloxy)-3-[4-(3,6-dihydro-2H-pyran-4-yl)phenyl]-1-oxopropan-2-yl (2S)-2-[[(tert-butoxy)carbonyl](methyl)amino]-4-fluoro-4-methylpentanoate as yellow oil. MS (ESI, m/z): 584 [M+H]$^+$.

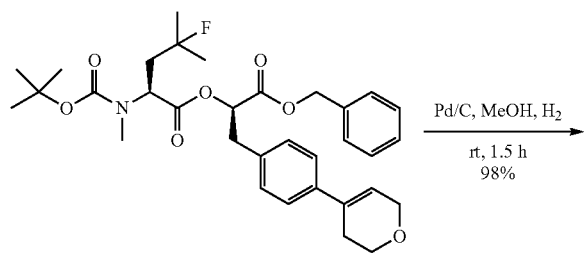

402

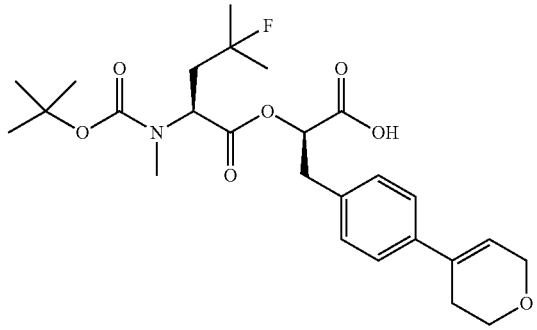

(2R)-2-[[(2S)-2-[[(tert-butoxy)carbonyl](methyl)amino]-4-fluoro-4-methylpentanoyl]oxy]-3-[4-(oxan-4-yl)phenyl]propanoic Acid (DC6)

Into a 50-mL round-bottom flask, was placed (2R)-1-(benzyloxy)-3-[4-(3,6-dihydro-2H-pyran-4-yl)phenyl]-1-oxopropan-2-yl (2S)-2-[[(tert-butoxy)carbonyl](methyl)amino]-4-fluoro-4-methylpentanoate (1.2 g, 2.06 mmol, 1.00 equiv), methanol (20 mL) and Palladium carbon (200 mg). To the above mixture was introduced hydrogen. The resulting solution was stirred for 1.5 h at room temperature. The solids were filtered out. The filtrate was concentrated under vacuum. This resulted in 1.0 g (98%) of (2R)-2-[[(2S)-2-[[(tert-butoxy)carbonyl](methyl)amino]-4-fluoro-4-methylpentanoyl]oxy]-3-[4-(oxan-4-yl)phenyl]propanoic acid as a white solid. MS (ESI, m/z): 496 [M+H]$^+$.

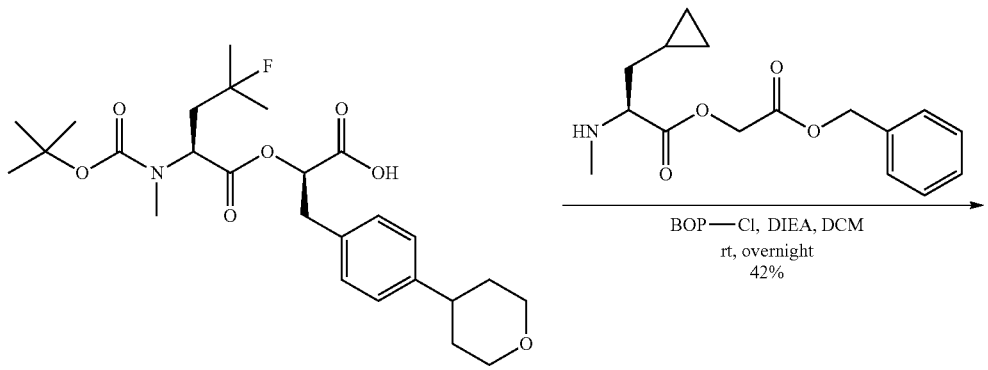

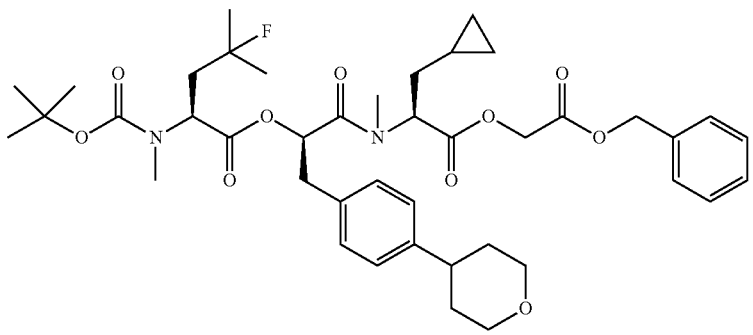

(1R)-1-[[(2S)-1-[2-(benzyloxy)-2-oxoethoxy]-3-cyclopropyl-1-oxopropan-2-yl](methyl)carbamoyl]-2-[4-(oxan-4-yl)phenyl]ethyl (2S)-2-[[(tert-butoxy)carbonyl](methyl)amino]-4-fluoro-4-methylpentanoate (TP7-34B)

Into a 50-mL round-bottom flask, was placed 2-(benzyloxy)-2-oxoethyl (2S)-3-cyclopropyl-2-(methylamino)propanoate (1.0 g, 3.43 mmol, 1.00 equiv), (2R)-1-(benzyloxy)-3-[4-(oxan-4-yl)phenyl]-1-oxopropan-2-yl (2S)-2-[[(tert-butoxy)carbonyl](methyl)amino]-4-fluoro-4-methylpentanoate (580 mg, 0.99 mmol, 1.00 equiv), dichloromethane (20 mL), The was followed by the addition of BOP—Cl (1.03 g, 4.05 mmol, 2.00 equiv) in portions at 0° C. To this was added DIEA (520 mg, 4.02 mmol, 2.00 equiv) dropwise with stirring at 0° C. The resulting solution was stirred overnight at room temperature. The solids were filtered out. The filtrate was concentrated under vacuum. The residue was applied onto a silica gel column with ethyl acetate/hexane (1:3). This resulted in 1.1 g (42%) of (1R)-1-[[(2S)-1-[2-(benzyloxy)-2-oxoethoxy]-3-cyclopropyl-1-oxopropan-2-yl](methyl)carbamoyl]-2-[4-(oxan-4-yl)phenyl]ethyl (2S)-2-[[(tert-butoxy)carbonyl](methyl)amino]-4-fluoro-4-methylpentanoate as yellow oil. MS (ESI, m/z): 769 [M+H]$^+$.

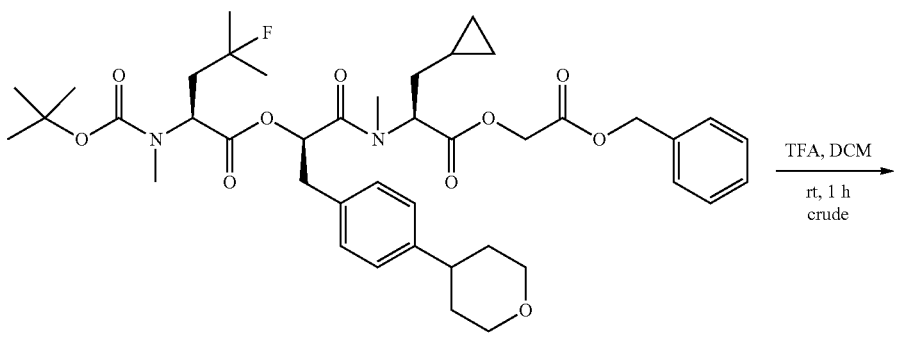

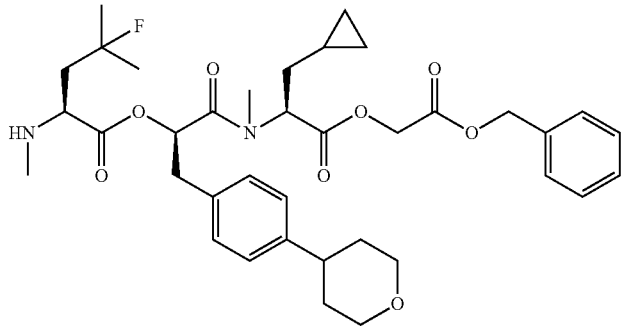

(1R)-1-[[(2S)-1-[2-(benzyloxy)-2-oxoethoxy]-3-cyclopropyl-1-oxopropan-2-yl](methyl)carbamoyl]-2-[4-(oxan-4-yl)phenyl]ethyl (2S)-4-fluoro-4-methyl-2-(methylamino)pentanoate (TA7-34B)

Into a 50-mL round-bottom flask, was placed (1R)-1-[[(2S)-1-[2-(benzyloxy)-2-oxoethoxy]-3-cyclopropyl-1-oxopropan-2-yl](methyl)carbamoyl]-2-[4-(oxan-4-yl)phenyl]ethyl (2S)-2-[[(tert-butoxy)carbonyl](methyl)amino]-4-fluoro-4-methylpentanoate (TP7-34B, 560 mg, 0.73 mmol, 1.00 equiv) and dichloromethane (20 mL). To this was added trifluoroacetic acid (3 mL) dropwise with stirring at 0° C. The resulting solution was stirred for 1 h at room temperature. The pH value of the solution was adjusted to 9 with sodium bicarbonate (aq.). The resulting solution was extracted with 2×20 mL of dichloromethane and the organic layers combined. The organic layers were dried over sodium sulfate and concentrated under vacuum. This resulted in 0.50 g (crude) of (1R)-1-[[(2S)-1-[2-(benzyloxy)-2-oxoethoxy]-3-cyclopropyl-1-oxopropan-2-yl](methyl)carbamoyl]-2-[4-(oxan-4-yl)phenyl]ethyl (2S)-4-fluoro-4-methyl-2-(methylamino)pentanoate as brown oil. MS (ESI, m/z): 669 [M+H]$^+$.

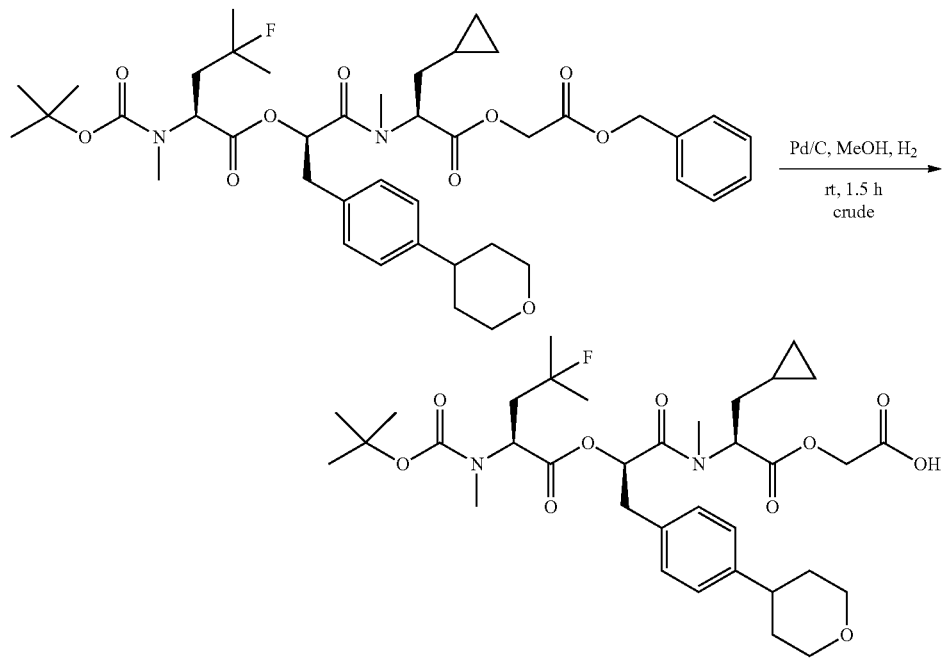

2-[[(2S)-2-[(2R)-2-[[(2S)-2-[[(tert-butoxy)carbonyl](methyl)amino]-4-fluoro-4-methylpentanoyl]oxy]-N-methyl-3-[4-(oxan-4-yl)phenyl]propanamido]-3-cyclopropylpropanoyl]oxy]acetic Acid (TC7-34B)

Into a 50-mL round-bottom flask, was placed (1R)-1-[[(2S)-1-[2-(benzyloxy)-2-oxoethoxy]-3-cyclopropyl-1-oxopropan-2-yl](methyl)carbamoyl]-2-[4-(oxan-4-yl)phenyl]ethyl (2S)-2-[[(tert-butoxy)carbonyl](methyl)amino]-4-fluoro-4-methylpentanoate (TP7-34B, 560 mg, 0.73 mmol, 1.00 equiv), methanol (20 mL) and Palladium carbon (50 mg). To the above mixture was introduced hydrogen. The resulting solution was stirred for 1.5 h at room temperature. The solids were filtered out. The filtrate was concentrated under vacuum. This resulted in 0.50 g (crude) of 2-[[(2S)-2-[(2R)-2-[[(2S)-2-[[(tert-butoxy)carbonyl](methyl)amino]-4-fluoro-4-methylpentanoyl]oxy]-N-methyl-3-[4-(oxan-4-yl)phenyl]propanamido]-3-cyclopropylpropanoyl]oxy] acetic acid as colorless oil. MS (ESI, m/z): 679 [M+H]$^+$.

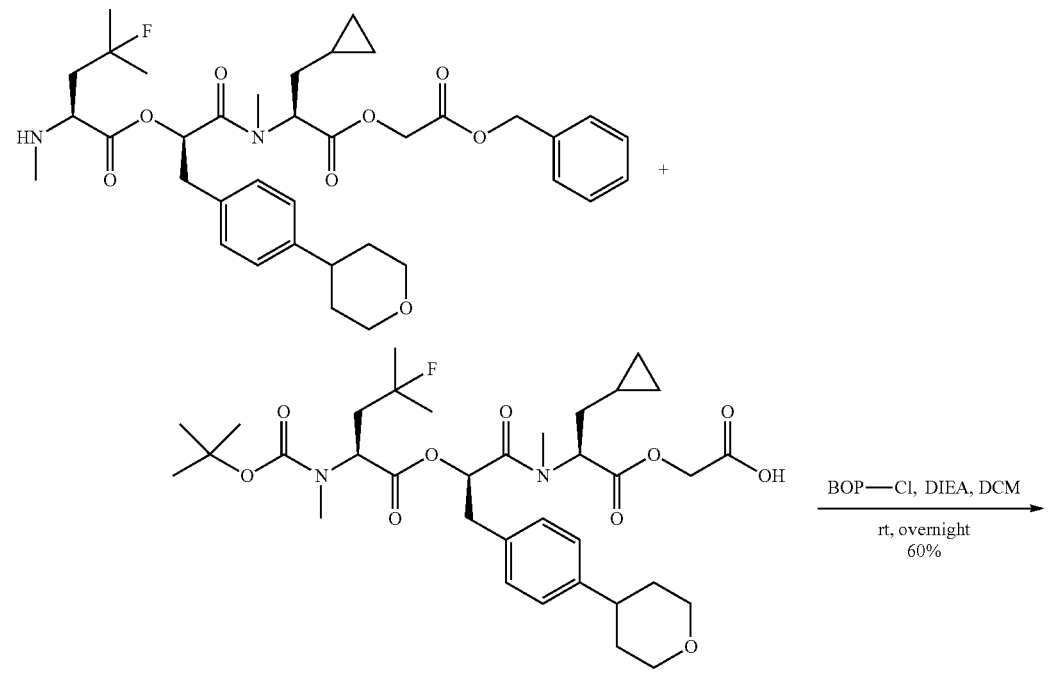

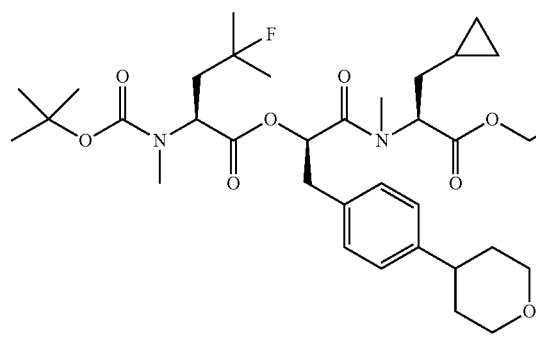
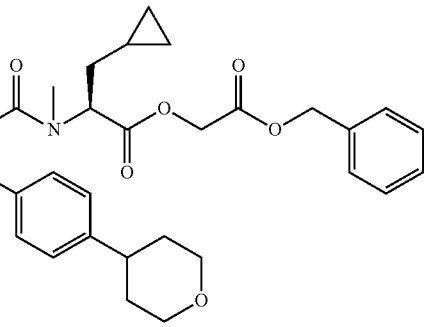

Compound OP7-34B:

Into a 50-mL round-bottom flask, was placed (1R)-1-[[(2S)-1-[2-(benzyloxy)-2-oxoethoxy]-3-cyclopropyl-1-oxopropan-2-yl](methyl)carbamoyl]-2-[4-(oxan-4-yl)phenyl]ethyl (2S)-4-fluoro-4-methyl-2-(methylamino)pentanoate (TA7-34B, 500 mg, 0.75 mmol, 1.00 equiv), 2-[[(2S)-2-[(2R)-2-[[(2S)-2-[[(tert-butoxy)carbonyl](methyl)amino]-4-fluoro-4-methylpentanoyl]oxy]-N-methyl-3-[4-(oxan-4-yl)phenyl]propanamido]-3-cyclopropylpropanoyl]oxy]acetic acid (TC7-34B, 500 mg, 0.74 mmol, 1.00 equiv), dichloromethane (20 mL), The was followed by the addition of BOP—Cl (420 mg, 1.65 mmol, 2.00 equiv) in portions at 0° C. To this was added DIEA (210 mg, 1.62 mmol, 2.00 equiv) dropwise with stirring at 0° C. The resulting solution was stirred overnight at room temperature. The solids were filtered out. The filtrate was concentrated under vacuum. The residue was applied onto a silica gel column with ethyl acetate/petroleum ether (1:10). This resulted in 0.6 g (60%) of OP7-34B as brown oil. MS (ESI, m/z): 1330 [M+H]⁺.

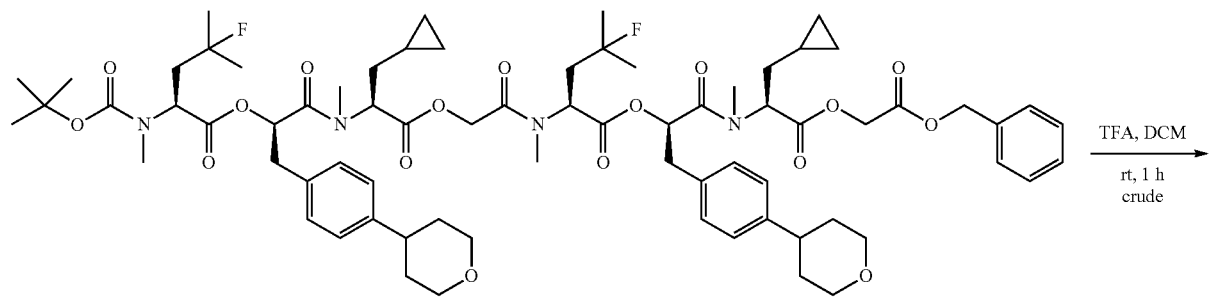

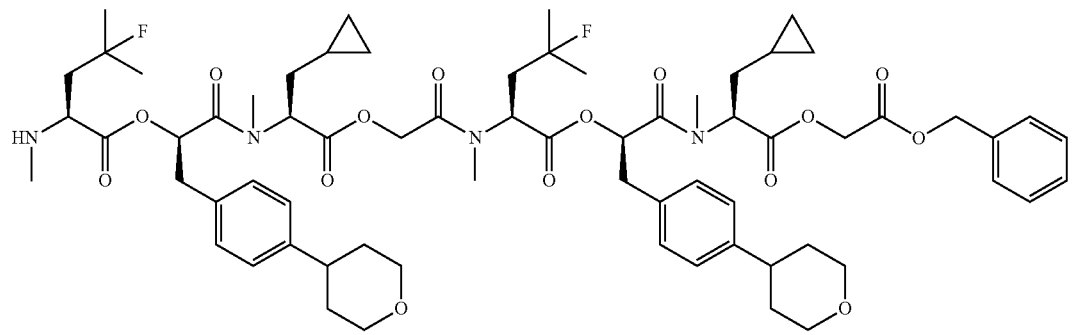

(1R)-1-[[(2S)-1-([[(2S)-1-[(1R)-1-[[(2S)-1-[2-(benzyloxy)-2-oxoethoxy]-3-cyclopropyl-1-oxopropan-2-yl](methyl)carbamoyl]-2-[4-(oxan-4-yl)phenyl]ethoxy]-4-fluoro-4-methyl-1-oxopentan-2-yl](methyl)carbamoyl]methoxy)-3-cyclopropyl-1-oxopropan-2-yl](methyl)carbamoyl]-2-[4-(oxan-4-yl)phenyl]ethyl (2S)-4-fluoro-4-methyl-2-(methylamino)pentanoate (OA7-34B)

Into a 50-mL round-bottom flask, was placed OP7-34B (600 mg, 0.45 mmol, 1.00 equiv) and dichloromethane (20 mL). To this was added trifluoroacetic acid (3 mL) dropwise with stirring at 0° C. The resulting solution was stirred for 1.5 h at room temperature. The pH value of the solution was adjusted to 9 with sodium bicarbonate (aq.). The resulting solution was extracted with 2×10 mL of dichloromethane and the organic layers combined. The organic layers were dried over sodium sulfate and concentrated under vacuum. This resulted in 560 mg (crude) of (1R)-1-[[(2S)-1-([[(2S)-1-[(1R)-1-[[(2S)-1-[2-(benzyloxy)-2-oxoethoxy]-3-cyclopropyl-1-oxopropan-2-yl](methyl)carbamoyl]-2-[4-(oxan-4-yl)phenyl]ethoxy]-4-fluoro-4-methyl-1-oxopentan-2-yl](methyl)carbamoyl]methoxy)-3-cyclopropyl-1-oxopropan-2-yl](methyl)carbamoyl]-2-[4-(oxan-4-yl)phenyl]ethyl (2S)-4-fluoro-4-methyl-2-(methylamino)pentanoate as yellow oil. MS (ESI, m/z): 1230 [M+H]$^+$.

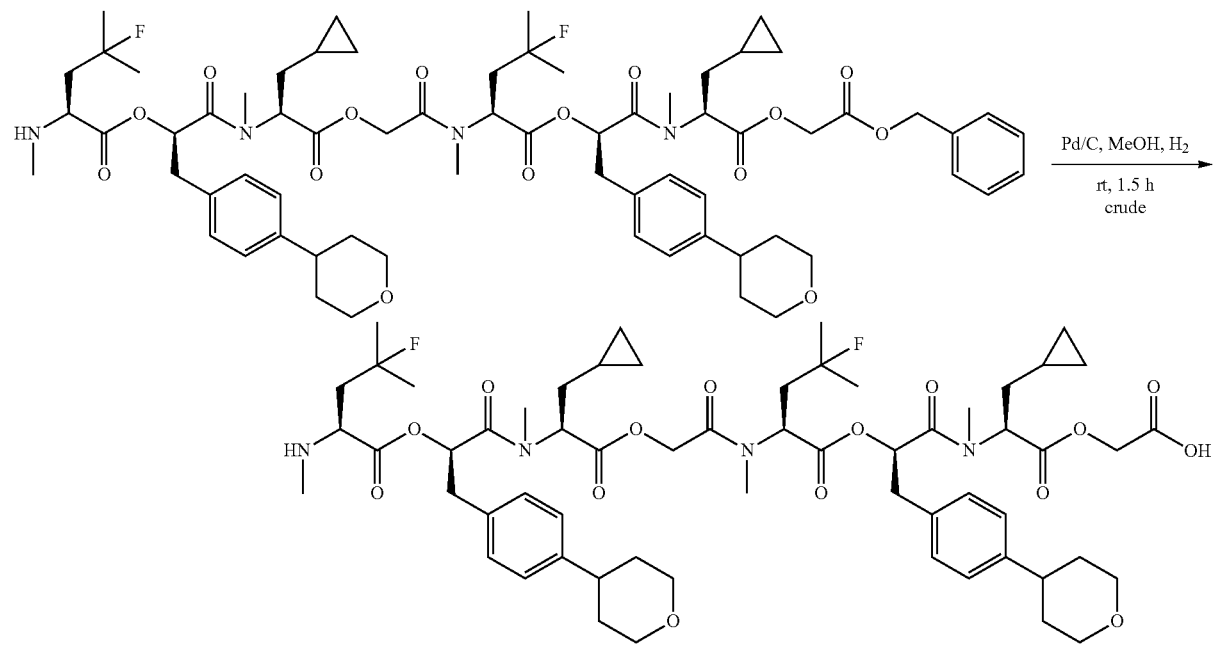

2-[[(2S)-2-[(2R)-2-[[(2S)-2-[2-[[(2S)-2-[(2R)-2-[[(2S)-2-[[(tert-butoxy)carbonyl](methyl)amino]-4-fluoro-4-methylpentanoyl]oxy]-N-methyl-3-[4-(oxan-4-yl)phenyl]propanamido]-3-cyclopropylpropanoyl]oxy]-N-methylacetamido)-4-fluoro-4-methylpentanoyl]oxy]-N-methyl-3-[4-(oxan-4-yl)phenyl]propanamido]-3-cyclopropylpropanoyl]oxy]acetic Acid (OAC7-34B)

Into a 50-mL round-bottom flask, was placed (1R)-1-[[(2S)-1-([[(2S)-1-[(1R)-1-[[(2S)-1-[2-(benzyloxy)-2-oxoethoxy]-3-cyclopropyl-1-oxopropan-2-yl](methyl)carbamoyl]-2-[4-(oxan-4-yl)phenyl]ethoxy]-4-fluoro-4-methyl-1-oxopentan-2-yl](methyl)carbamoyl]methoxy)-3-cyclopropyl-1-oxopropan-2-yl](methyl)carbamoyl]-2-[4-(oxan-4-yl)phenyl]ethyl (2S)-4-fluoro-4-methyl-2-(methylamino)pentanoate (OA7-34B, 560 mg, 0.46 mmol, 1.00 equiv), methanol (30 mL) and Palladium carbon (100 mg). To the above hydrogen was introduced. The resulting solution was stirred for 1.5 h at room temperature. The solids were filtered out. The filtrate was concentrated under vacuum. This resulted in 200 mg (35%) of 2-[[(2S)-2-[(2R)-2-[[(2S)-2-[2-[[(2S)-2-[(2R)-2-[[(2S)-2-[[(tert-butoxy)carbonyl](methyl)amino]-4-fluoro-4-methylpentanoyl]oxy]-N-methyl-3-[4-(oxan-4-yl)phenyl]propanamido]-3-cyclopropylpropanoyl]oxy]-N-methylacetamido)-4-fluoro-4-methylpentanoyl]oxy]-N-methyl-3-[4-(oxan-4-yl)phenyl]propanamido]-3-cyclopropylpropanoyl]oxy]acetic acid as light yellow oil. MS (ESI, m/z): 1140 [M+H]$^+$.

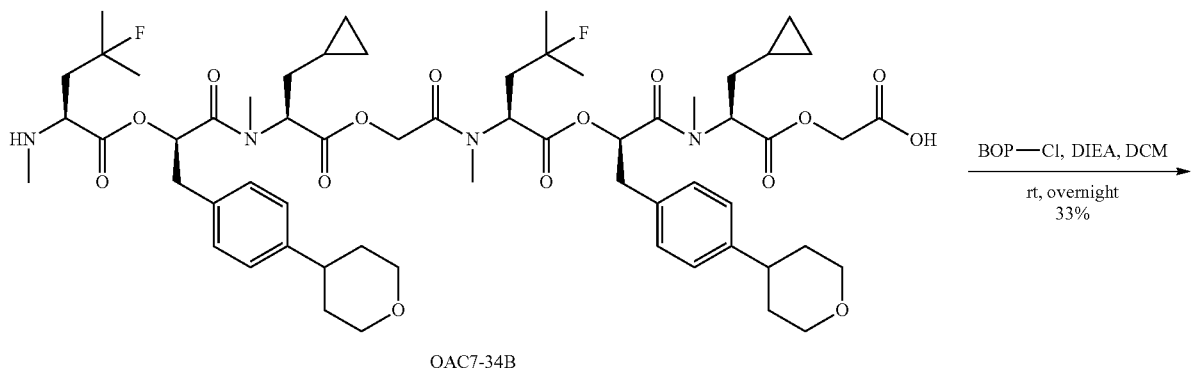

OAC7-34B

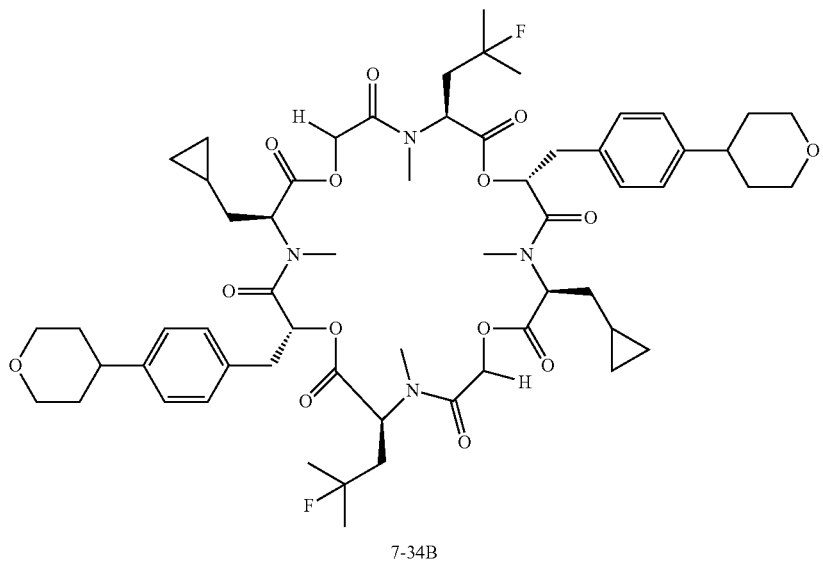

7-34B (3S,6R,9S,15S,18R,21S)-3,15-bis(cyclopropylmethyl)-9,21-bis(2-fluoro-2-methylpropyl)-4,10,16,22-tetramethyl-6,18-bis([[4-(oxan-4-yl)phenyl]methyl])-1,7,13,19-tetraoxa-4,10,16,22-tetraazacyclotetracosan-2,5,8,11,14,17,20,23-octone (7-34B)

Into a 250-mL round-bottom flask, was placed 2-[[(2S)-3-cyclopropyl-2-[(2R)-2-[[(2S)-2-(2-[[(2S)-3-cyclopropyl-2-[(2R)-2-[[(2S)-4-fluoro-4-methyl-2-(methylamino)pentanoyl]oxy]-N-methyl-3-[4-(oxan-4-yl)phenyl]propanamido]propanoyl]oxy]-N-methylacetamido)-4-fluoro-4-methylpentanoyl]oxy]-N-methyl-3-[4-(oxan-4-yl)phenyl]propanamido]propanoyl]oxy]acetic acid (OAC7-34B, 200 mg, 0.18 mmol, 1.00 equiv) and dichloromethane (70 mL). This was followed by the addition of BOP—Cl (89 mg, 0.35 mmol, 2.00 equiv) in portions at 0° C. To this was added DIEA (45 mg, 0.35 mmol, 2.00 equiv) dropwise with stirring at 0° C. The resulting solution was stirred overnight at room temperature. The resulting mixture was concentrated under vacuum. The crude product was purified by Prep-HPLC with the following conditions (waters-2767): Column, SunFire Prep C18, 5 um, 19*150 mm; mobile phase, Water and CH$_3$CN (70% CH$_3$CN up to 80% in 8 min); Detector, UV 254 nm. This resulted in 64 mg (33%) of (3S,6R,9S,15S,18R,21S)-3,15-bis(cyclopropylmethyl)-9,21-bis(2-fluoro-2-methylpropyl)-4,10,16,22-tetramethyl-6,18-bis([[4-(oxan-4-yl)phenyl]methyl])-1,7,13,19-tetraoxa-4,10,16,22-tetraazacyclotetracosan-2,5,8,11,14,17,20,23-octone as a white solid. $^1$H NMR (CD$_3$OD, 300 MHz) δ: 7.26-7.16 (m, 8H), 5.65-5.35 (m, 5H), 4.90-4.72 (m, 5H), 4.06-4.02 (m, 4H), 3.61-3.52 (m, 4H), 3.15-2.78 (m, 18H), 2.35-2.12 (m, 4H), 1.90-1.32 (m, 24H), 0.65-0.08 (m, 10H); MS (ESI, m/z): 1150 [M+H]+; [α]=−90.83°, T=27.2° C., C=0.48 g/100 mL in MeOH.

Preparation Example 39: Synthesis of Compound F4 wherein Cy$^1$ and Cy$^2$ are Each

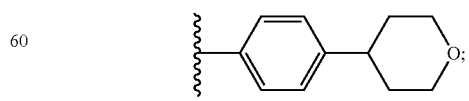

R and R are Each —CH$_2$CF(CH$_3$)$_2$; R$^2$ is —CH$_2$CH(CH$_3$)$_2$; R$^4$ is C27; and R$^a$, R$^b$, R', R", R'" and R"" are Each Methyl Compound 7-30B was prepared according to the process in Schemes 15 and 16 shown below.

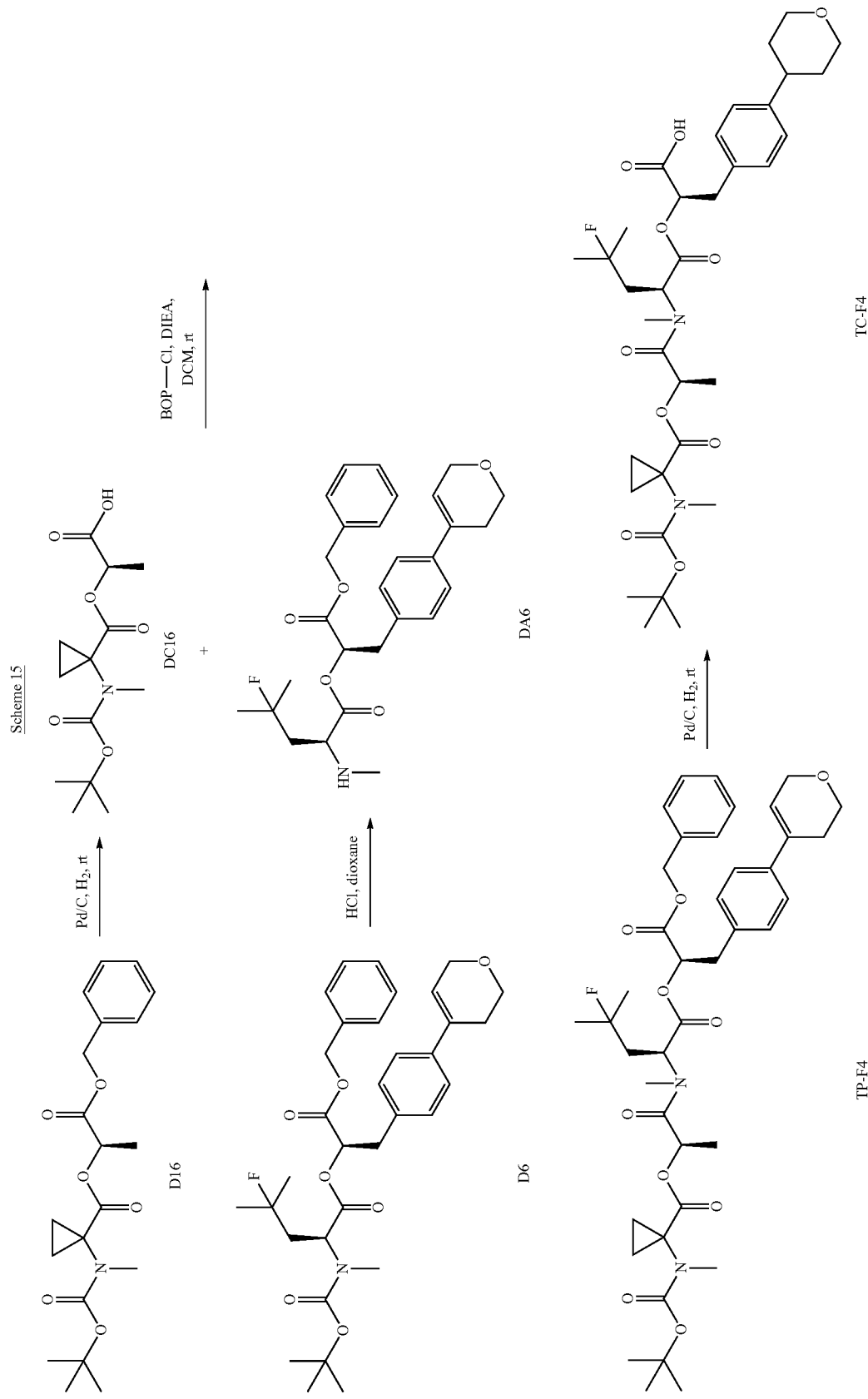

-continued
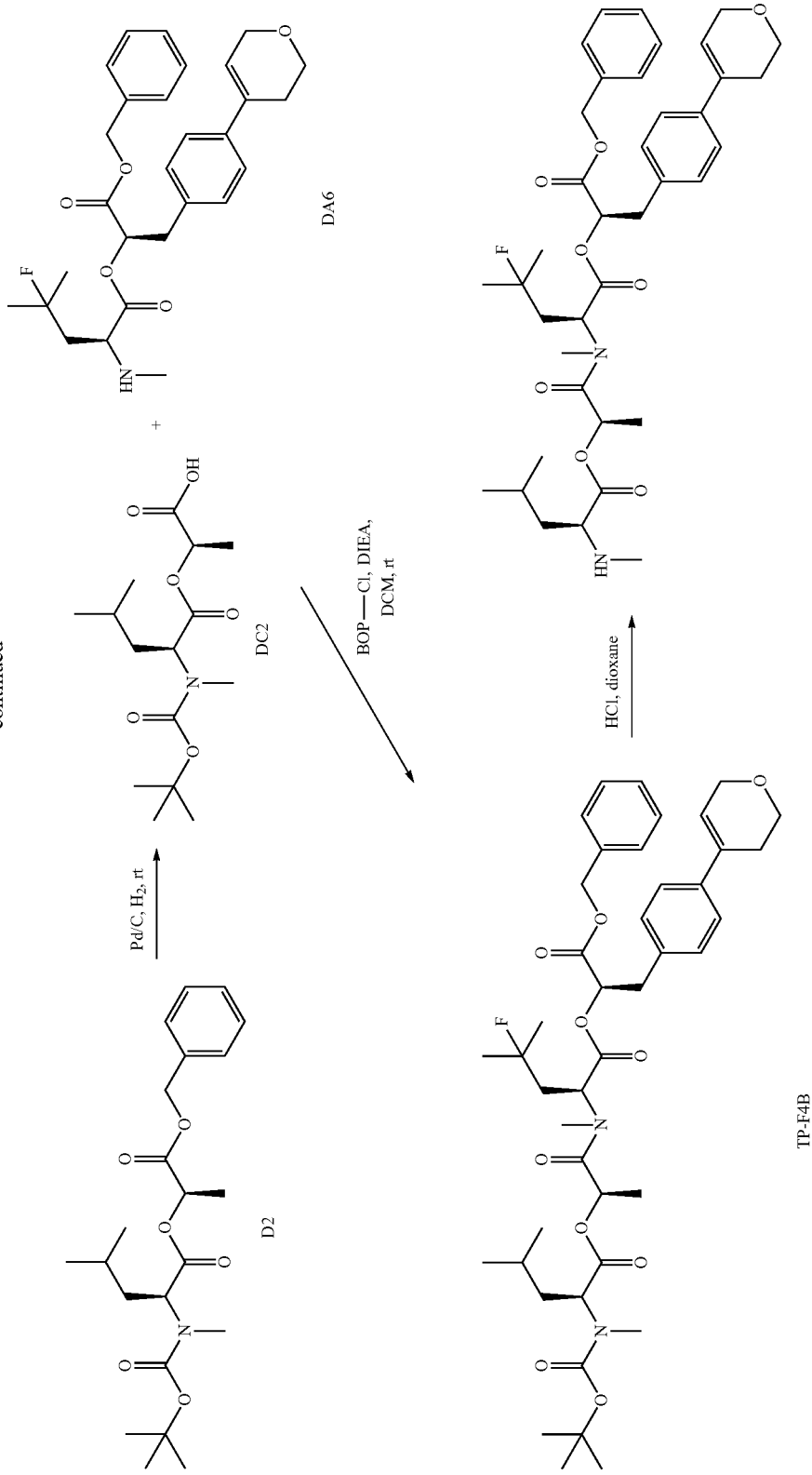

Scheme 16
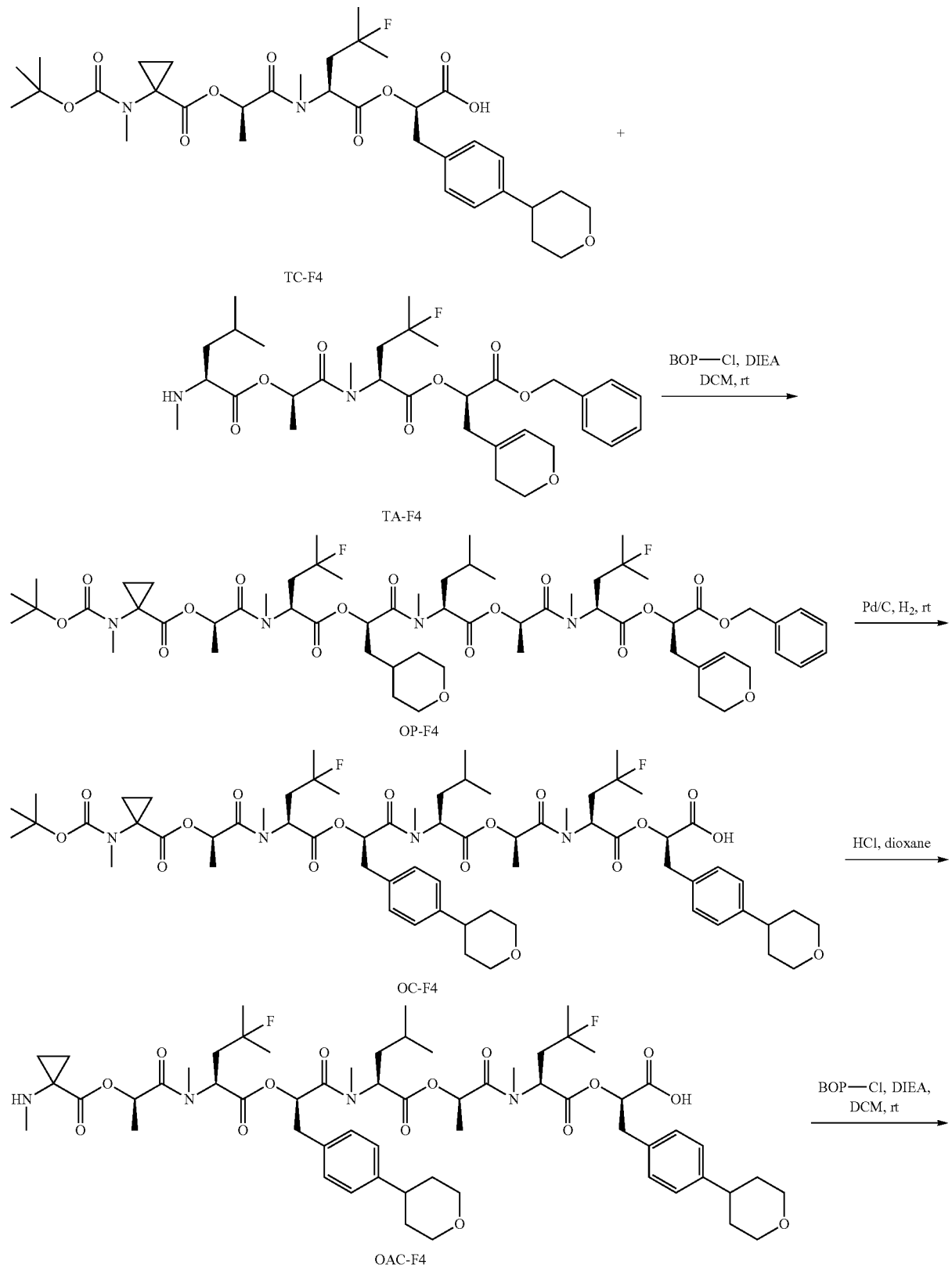

-continued

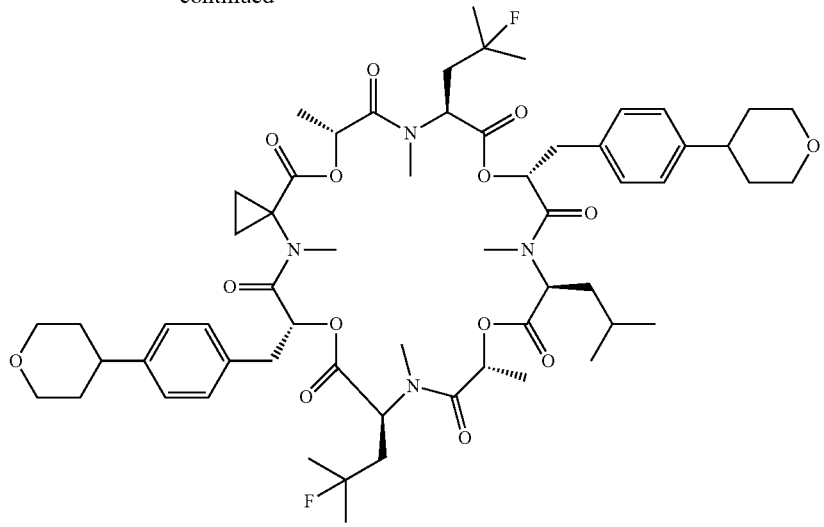

F4

Experimental Detail

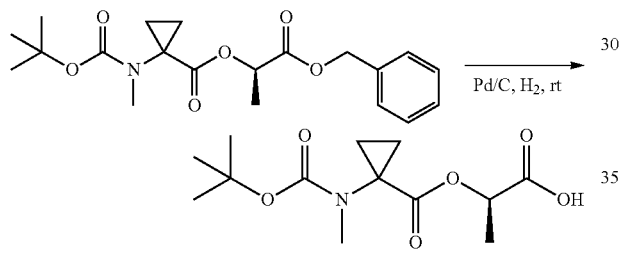

(2R)-2-[(1-[[(tert-butoxy)carbonyl](methyl)amino]
cyclopropyl)carbonyloxy]propanoic Acid (DC16)

Into a 100-mL round-bottom flask, was placed benzyl (2R)-2-[(1-[[(tert-butoxy)carbonyl](methyl)amino]cyclopropyl)carbonyloxy]propanoate (D16, 1 g, 2.65 mmol, 1.00 equiv), ethyl acetate (20 mL), Palladium carbon (400 mg). To the above mixture was introduced hydrogen. The resulting solution was stirred for 2 h at room temperature. The solids were filtered out. The filtrate was concentrated under vacuum. This resulted in 750 mg (99%) of (2R)-2-[(1-[[(tert-butoxy)carbonyl](methyl)amino]cyclopropyl)carbonyloxy]propanoic acid as pink oil. MS (ES, m/z): 288 (M+H).

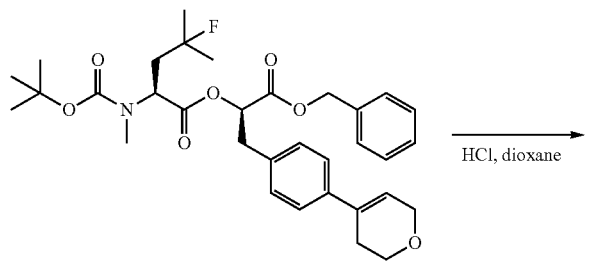

(2R)-1-(benzyloxy)-3-[4-(3,6-dihydro-2H-pyran-4-yl)phenyl]-1-oxopropan-2-yl (2S)-4-fluoro-4-methyl-2-(methylamino)pentanoate (DA6)

Into a 250-mL round-bottom flask, was placed (2R)-1-(benzyloxy)-3-[4-(3,6-dihydro-2H-pyran-4-yl)phenyl]-1-oxopropan-2-yl (2S)-2-[[(tert-butoxy)carbonyl](methyl)amino]-4-fluoro-4-methylpentanoate (D6, 2 g, 3.43 mmol, 1.00 equiv), DCM (10 mL), hydrogen chloride (dioxane, 20 mL). The resulting solution was stirred for 2 h at room temperature. The resulting mixture was concentrated under vacuum. The pH value of the solution was adjusted to 9 with aqueous sodium bicarbonate. The resulting solution was extracted with 2×30 mL of dichloromethane and the organic layers combined and washed with 40 mL of brine. The organic layer were collected and dried over sodium sulfate. The solids were filtered out. The filtrate was concentrated under vacuum. This resulted in 1.6 g (97%) of (2R)-1-(benzyloxy)-3-[4-(3,6-dihydro-2H-pyran-4-yl)phenyl]-1-oxopropan-2-yl (2S)-4-fluoro-4-methyl-2-(methylamino)pentanoate as yellow oil. MS (ES, m/z): 484 (M+H).

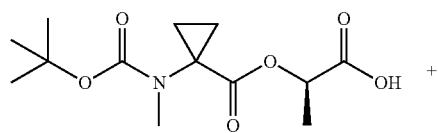

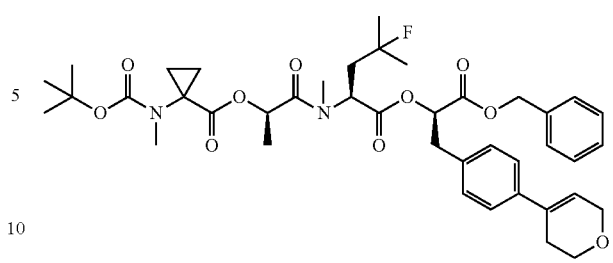

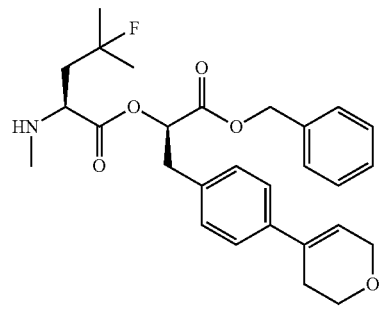

BOP—Cl, DIEA,
DCM, rt

Pd/C, H₂, rt

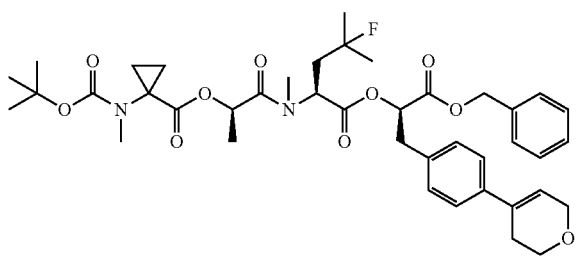

(2R)-1-(benzyloxy)-3-[4-(3,6-dihydro-2H-pyran-4-yl)phenyl]-1-oxopropan-2-yl (2S)-2-[(2R)-2-[(1-[[(tert-butoxy)carbonyl](methyl)amino]cyclopropyl)carbonyloxy]-N-methylpropanamido]-4-fluoro-4-methylpentanoate (TP-F4)

Into a 100-mL round-bottom flask, was placed (2R)-1-(benzyloxy)-3-[4-(3,6-dihydro-2H-pyran-4-yl)phenyl]-1-oxopropan-2-yl (2S)-4-fluoro-4-methyl-2-(methylamino)pentanoate (DA6, 1.5 g, 3.10 mmol, 1.00 equiv), (2R)-2-[(1-[[(tert-butoxy)carbonyl](methyl)amino]cyclopropyl)carbonyloxy]propanoic acid (DC16, 890 mg, 3.10 mmol, 1.00 equiv), dichloromethane (30 mL). This was followed by the addition of BOP—Cl (1.58 g, 6.21 mmol, 2.00 equiv) at 0° C. in 10 min. To this was added DIEA (800 mg, 6.19 mmol, 2.00 equiv) at 0° C. in 10 min. The resulting solution was stirred for 2 h at room temperature. The solids were filtered out. The filtrate was concentrated under vacuum. The residue was applied onto a silica gel column with ethyl acetate/petroleum ether (1:2). This resulted in 1.4 g (60%) of (2R)-1-(benzyloxy)-3-[4-(3,6-dihydro-2H-pyran-4-yl)phenyl]-1-oxopropan-2-yl (2S)-2-[(2R)-2-[(1-[[(tert-butoxy)carbonyl](methyl)amino]cyclopropyl)carbonyloxy]-N-methylpropanamido]-4-fluoro-4-methylpentanoate as yellow oil. MS (ES, m/z): 753 (M+H).

(2R)-2-[[(2S)-2-[(2R)-2-[(1-[[(tert-butoxy)carbonyl](methyl)amino]cyclopropyl)carbonyloxy]-N-methyl-propanamido]-4-fluoro-4-methylpentanoyl]oxy]-3-[4-(oxan-4-yl)phenyl]propanoic Acid (TC-F4)

Into a 100-mL round-bottom flask purged and maintained with an inert atmosphere of nitrogen, was placed (2R)-1-(benzyloxy)-3-[4-(3,6-dihydro-2H-pyran-4-yl)phenyl]-1-oxopropan-2-yl (2S)-2-[(2R)-2-[(1-[[(tert-butoxy)carbonyl](methyl)amino]cyclopropyl)carbonyloxy]-N-methylpropanamido]-4-fluoro-4-methylpentanoate (TP-F4, 900 mg, 1.20 mmol, 1.00 equiv), ethyl acetate (20 mL), Palladium carbon (200 mg). To the above mixture was introduced hydrogen. The resulting solution was stirred for 2 h at room temperature. The solids were filtered out. The filtrate was concentrated under vacuum. This resulted in 660 mg (83%) of (2R)-2-[[(2S)-2-[(2R)-2-[(1-[[(tert-butoxy)carbonyl](methyl)amino]cyclopropyl)carbonyloxy]-N-methylpropanamido]-4-fluoro-4-methylpentanoyl]oxy]-3-[4-(oxan-4-yl)phenyl]propanoic acid as a white solid. MS (ES, m/z): 665 (M+H).

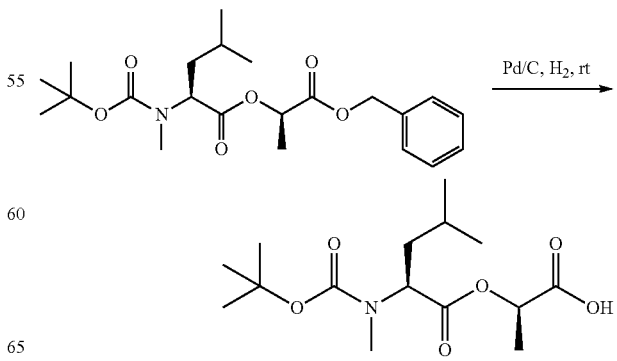

Pd/C, H₂, rt

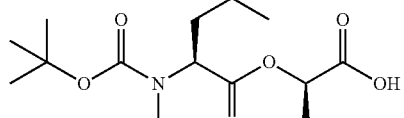

(R)-2-((S)-2-(tert-butoxycarbonyl(methyl)amino)-4-methylpentanoyloxy)propanoic Acid (DC2)

Into a 100-mL round-bottom flask, was placed (S)—((R)-1-(benzyloxy)-1-oxopropan-2-yl) 2-(tert-butoxycarbonyl(methyl)amino)-4-methylpentanoate (D2, 1 g, 2.40 mmol, 1.00 equiv), EA (30 mL), Palladium carbon (400 mg). To the above H$_2$ was introduced in. The resulting solution was stirred for 2 h at room temperature. The solids were filtered out. The filtrate was concentrated under vacuum. This resulted in 720 mg (crude) of (R)-2-((S)-2-(tert-butoxycarbonyl(methyl)amino)-4-methylpentanoyloxy)propanoic acid as yellow oil. MS (ES, m/z): 484 (M+H).

mmol, 2.00 equiv) at 0° C. in 5 min. The resulting solution was stirred for 2 h at room temperature. The resulting mixture was concentrated under vacuum. The residue was applied onto a silica gel column with ethyl acetate/petroleum ether (1:5). This resulted in 615 mg (76%) of (1R)-1-[[(2S)-1-[[(2R)-1-(benzyloxy)-3-[4-(oxan-4-yl)phenyl]-1-oxopropan-2-yl]oxy]-4-fluoro-4-methyl-1-oxopentan-2-yl](methyl)carbamoyl]ethyl (2S)-2-[[(tert-butoxy)carbonyl](methyl)amino]-4-methylpentanoate as yellow oil. MS (ES, m/z): 783 (M+H).

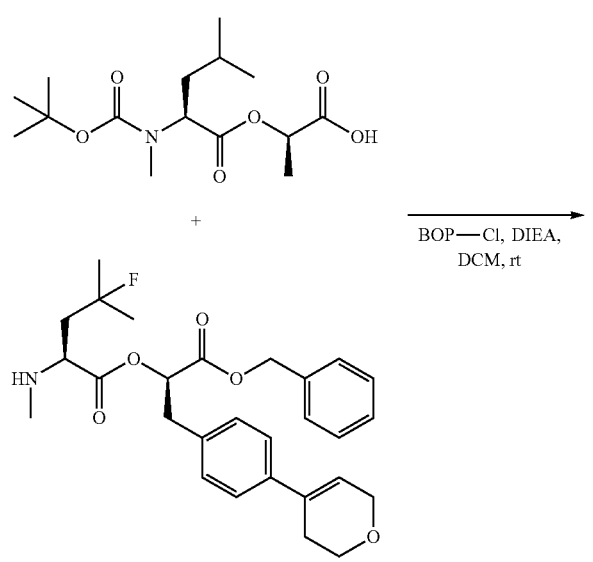

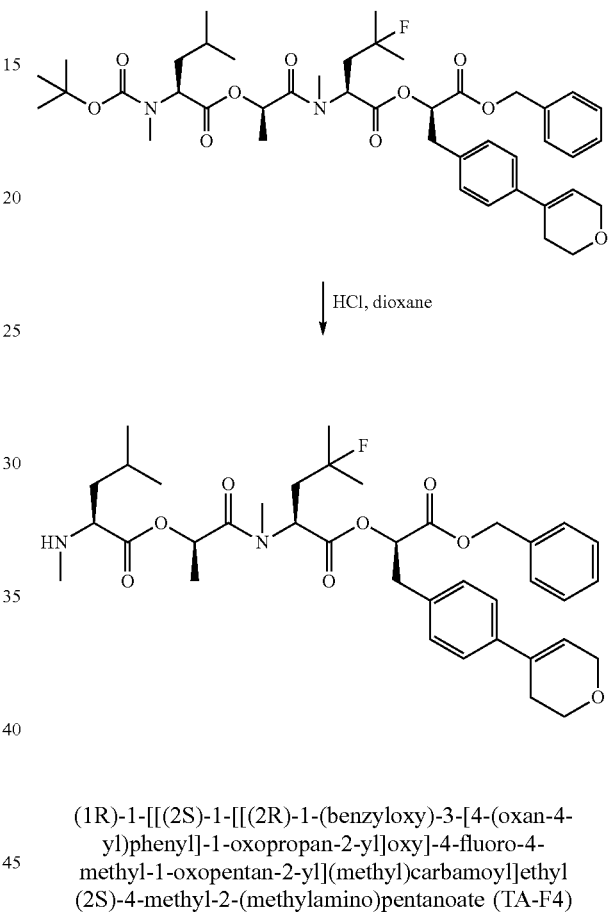

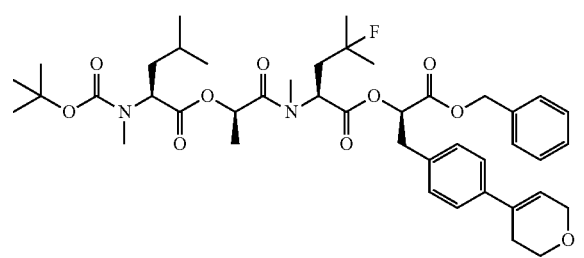

(1R)-1-[[(2S)-1-[[(2R)-1-(benzyloxy)-3-[4-(oxan-4-yl)phenyl]-1-oxopropan-2-yl]oxy]-4-fluoro-4-methyl-1-oxopentan-2-yl](methyl)carbamoyl]ethyl (2S)-2-[[(tert-butoxy)carbonyl](methyl)amino]-4-methylpentanoate (TP-F4B)

Into a 100-mL round-bottom flask, was placed (2R)-1-(benzyloxy)-3-[4-(3,6-dihydro-2H-pyran-4-yl)phenyl]-1-oxopropan-2-yl (2S)-4-fluoro-4-methyl-2-(methylamino)pentanoate (DA6, 500 mg, 1.03 mmol, 1.00 equiv), (R)-2-((S)-2-(tert-butoxycarbonyl(methyl)amino)-4-methylpentanoyloxy)propanoic acid (DC2, 330 mg, 1.03 mmol, 1.00 equiv) in DCM (30 mL). This was followed by the addition of BOP—Cl (528 mg, 2.06 mmol, 2.00 equiv) at 0° C. in 5 min. To this was added DIEA (267 mg, 2.06

(1R)-1-[[(2S)-1-[[(2R)-1-(benzyloxy)-3-[4-(oxan-4-yl)phenyl]-1-oxopropan-2-yl]oxy]-4-fluoro-4-methyl-1-oxopentan-2-yl](methyl)carbamoyl]ethyl (2S)-4-methyl-2-(methylamino)pentanoate (TA-F4)

Into a 100-mL round-bottom flask, was placed (1R)-1-[[(2S)-1-[[(2R)-1-(benzyloxy)-3-[4-(oxan-4-yl)phenyl]-1-oxopropan-2-yl]oxy]-4-fluoro-4-methyl-1-oxopentan-2-yl](methyl)carbamoyl]ethyl (2S)-2-[[(tert-butoxy)carbonyl](methyl)amino]-4-methylpentanoate (TP-F4B, 400 mg, 0.51 mmol, 1.00 equiv), hydrogen chloride (dioxane, 10 mL). The resulting solution was stirred for 2 h at room temperature. The resulting mixture was concentrated under vacuum. The pH value of the solution was adjusted to 9 with aqueous sodium bicarbonate. The resulting solution was extracted with 2×30 mL of dichloromethane and the organic layers combined and washed with 30 mL of brine. The organic phase was collected and dried over sodium sulfate. The solids were filtered out. The filtrate was concentrated under vacuum. This resulted in 400 mg (crude) of (1R)-1-[[(2S)-1-[[(2R)-1-(benzyloxy)-3-[4-(oxan-4-yl)phenyl]-1-oxopropan-2-yl]oxy]-4-fluoro-4-methyl-1-oxopentan-2-yl](methyl)carbamoyl]ethyl (2S)-4-methyl-2-(methylamino)pentanoate as yellow oil. MS (ES, m/z): 683 (M+H).

425

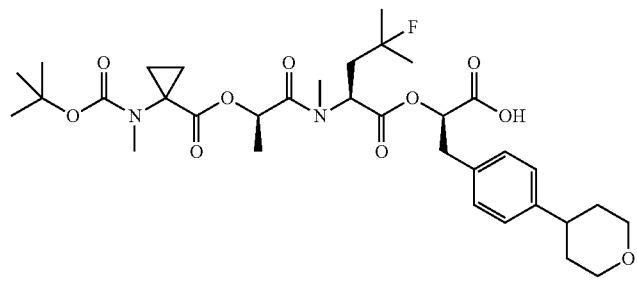

426

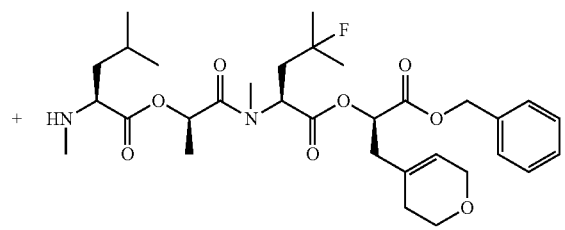

BOP—Cl, DIEA, DCM, rt

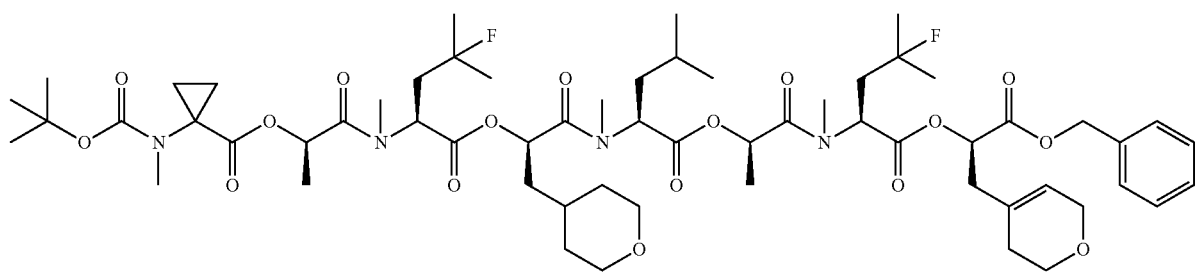

[(1R)-2-[[(1S)-1-[(1R)-2-[[(1S)-1-[(1R)-2-[[(1S)-1-[(1R)-2-benzyloxy-1-(3,6-dihydro-2H-pyran-4-ylmethyl)-2-oxo-ethoxy]carbonyl-3-fluoro-3-methyl-butyl]-methyl-amino]-1-methyl-2-oxo-ethoxy]carbonyl-3-methyl-butyl]-methyl-amino]-2-oxo-1-(tetrahydropyran-4-ylmethyl)ethoxy]carbonyl-3-fluoro-3-methyl-butyl]-methyl-amino]-1-methyl-2-oxo-ethyl]1-[tert-butoxycarbonyl(methyl)amino]cyclopropanecarboxylate (OP-F4)

Into a 100-mL round-bottom flask, was placed (2R)-2-[[(2S)-2-[(2R)-2-[(1-[[(tert-butoxy)carbonyl](methyl)amino]cyclopropyl)carbonyloxy]-N-methylpropanamido]-4-fluoro-4-methylpentanoyl]oxy]-3-[4-(oxan-4-yl)phenyl]propanoic acid (TC-F4, 340 mg, 0.51 mmol, 1.00 equiv), (1R)-1-[[(2S)-1-[[(2R)-1-(benzyloxy)-3-[4-(oxan-4-yl)phenyl]-1-oxopropan-2-yl]oxy]-4-fluoro-4-methyl-1-oxopentan-2-yl](methyl)carbamoyl]ethyl (2S)-4-methyl-2-(methylamino)pentanoate (TA-F4, 350 mg, 0.51 mmol, 1.00 equiv), dichloromethane (15 mL). This was followed by the addition of BOP—Cl (261 mg, 1.03 mmol, 2.00 equiv) at 0° C. in 5 min. To this was added DIEA (132 mg, 1.02 mmol, 2.00 equiv) at 0° C. in 5 min. The resulting solution was stirred for 2 h at room temperature. The resulting mixture was concentrated under vacuum. The crude product was purified by Flash-Prep-HPLC with the following conditions (IntelFlash-1): Column, C18 silica gel; mobile phase, $H_2O$ and $CH_3CN$ (50% $CH_3CN$ up to 80% in 15 min and 80% $CH_3CN$ up to 100% within 15 min); Detector, UV 220 nm. This resulted in 400 mg (59%) of OP-F4 as yellow oil. MS (ES, m/z): 1330 (M+H).

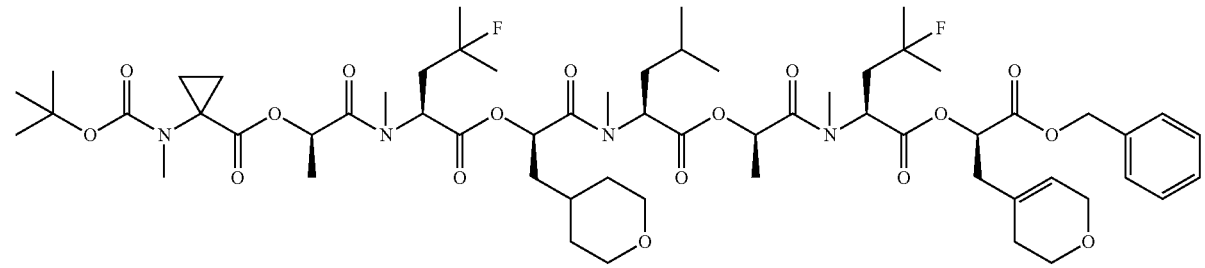

Pd/C, $H_2$, rt

-continued

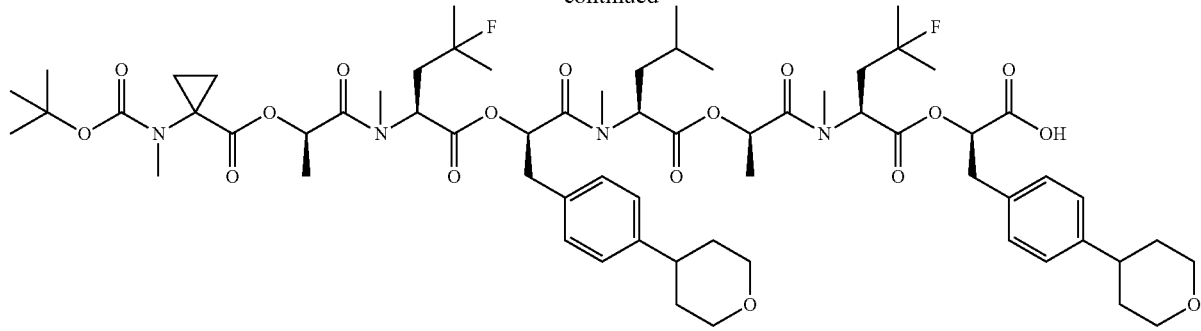

(2R)-2-[(2S)-2-[[(2R)-2-[(2S)-2-[[(2R)-2-[(2S)-2-[[(2R)-2-[1-[tert-butoxycarbonyl(methyl)amino]cyclopropanecarbonyl]oxypropanoyl]-methyl-amino]-4-fluoro-4-methyl-pentanoyl]oxy-3-(4-tetrahydropyran-4-ylphenyl)propanoyl]-methyl-amino]-4-methyl-pentanoyl]oxypropanoyl]-methyl-amino]-4-fluoro-4-methyl-pentanoyl]oxy-3-(4-tetrahydropyran-4-ylphenyl)propanoic Acid (OC-F4)

Into a 100-mL round-bottom flask, was placed OP-F4 (400 mg, 0.30 mmol, 1.00 equiv), ethyl acetate (15 mL), Palladium carbon (160 mg). To the above mixture was introduced hydrogen. The resulting solution was stirred for 2 h at room temperature. The solids were filtered out. The filtrate was concentrated under vacuum. This resulted in 350 mg (94%) of OC-F4 as yellow oil. MS (ES, m/z): 1242 (M+H).

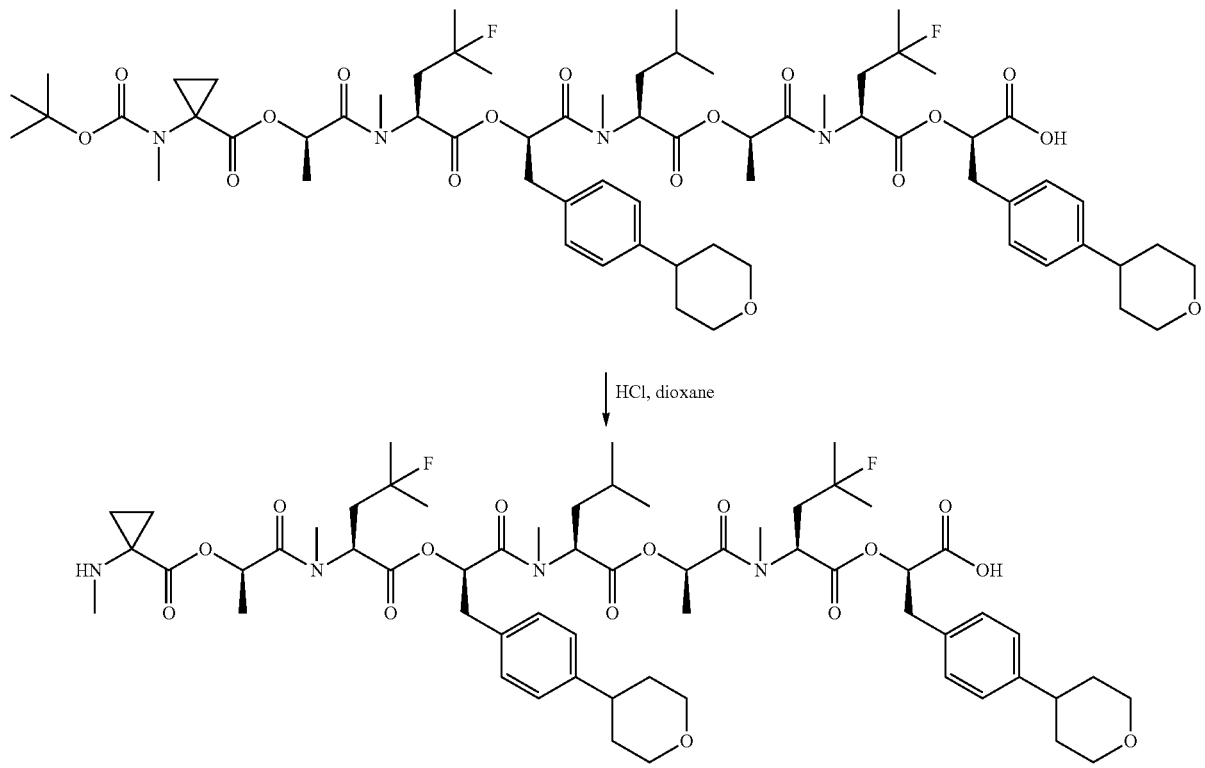

429

(2R)-2-[(2S)-4-fluoro-2-[[(2R)-2-[(2S)-2-[[(2R)-2-[(2S)-4-fluoro-4-methyl-2-[methyl-[(2R)-2-[1-(methylamino)cyclopropanecarbonyl]oxypropanoyl]amino]pentanoyl]oxy-3-(4-tetrahydropyran-4-ylphenyl)propanoyl]-methyl-amino]-4-methyl-pentanoyl]oxypropanoyl]-methyl-amino]-4-methyl-pentanoyl]oxy-3-(4-tetrahydropyran-4-ylphenyl)propanoic Acid (OAC-F4)

Into a 100-mL round-bottom flask, was placed OC-F4 (350 mg, 0.28 mmol, 1.00 equiv), DCM (5 mL), hydrogen chloride (dioxane, 10 mL). The resulting solution was stirred for 2 h at room temperature. The resulting mixture was concentrated under vacuum. The pH value of the solution was adjusted to 9 with aqueous sodium bicarbonate. The resulting solution was extracted with 2×30 mL of dichloromethane and the organic layers combined and washed with 40 mL of brine. The organic layer was collected and dried over sodium sulfate. The solids were filtered out. The filtrate was concentrated under vacuum. This resulted in 350 mg (crude) of OAC-F4 as yellow oil. MS (ES, m/z): 1142 (M+H).

430

(6R,9S,12R,15S,18R,21S,24R)-9,21-bis(2-fluoro-2-methylpropyl)-4,10,12,16,22,24-hexamethyl-15-(2-methylpropyl)-6,18-bis([[4-(oxan-4-yl)phenyl]methyl])-7,13,19,25-tetraoxa-4,10,16,22-tetraazaspiro[2.23]hexacosan-5,8,11,14,17,20,23,26-octone (F4)

Into a 250-mL round-bottom flask, was placed OAC-F4 (300 mg, 0.26 mmol, 1.00 equiv), dichloromethane (300 mL). This was followed by the addition of BOP—Cl (134 mg, 0.53 mmol, 2.00 equiv) at 0° C. in 5 min. To this was added DIEA (102 mg, 0.79 mmol, 3.00 equiv) at 0° C. in 5 min. The resulting solution was stirred overnight at room temperature. The resulting mixture was concentrated under vacuum. The crude product was purified by Prep-HPLC with the following conditions (Waters I): Column, X Bridge Prep RP18, 5 um, 19×150 mm; mobile phase, water and $CH_3CN$ (70% $CH_3CN$ up to 90% acetonitrile in 7 min); Detector, UV 220 nm. This resulted in 116.5 mg (39%) of (6R,9S,12R,15S,18R,21S,24R)-9,21-bis(2-fluoro-2-methylpropyl)-4,10,12,16,22,24-hexamethyl-15-(2-methylpropyl)-6,18-bis([[4-(oxan-4-yl)phenyl]methyl])-7,13,19,25-tetraoxa-4,10,16,

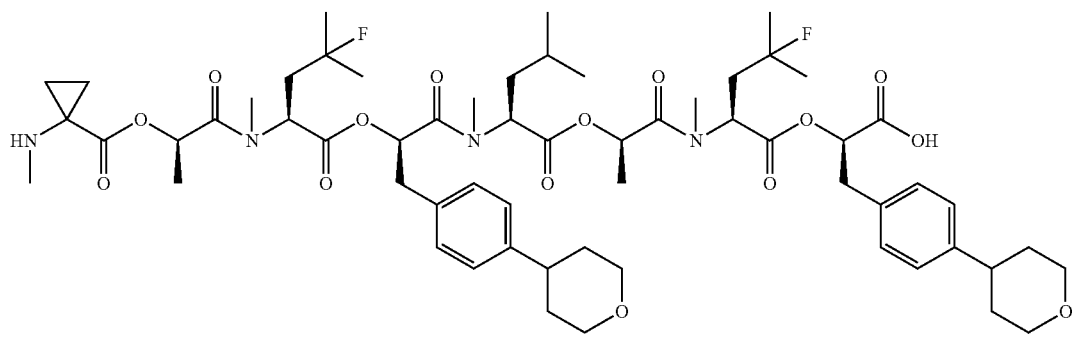

BOP—Cl, DIEA, DCM, rt

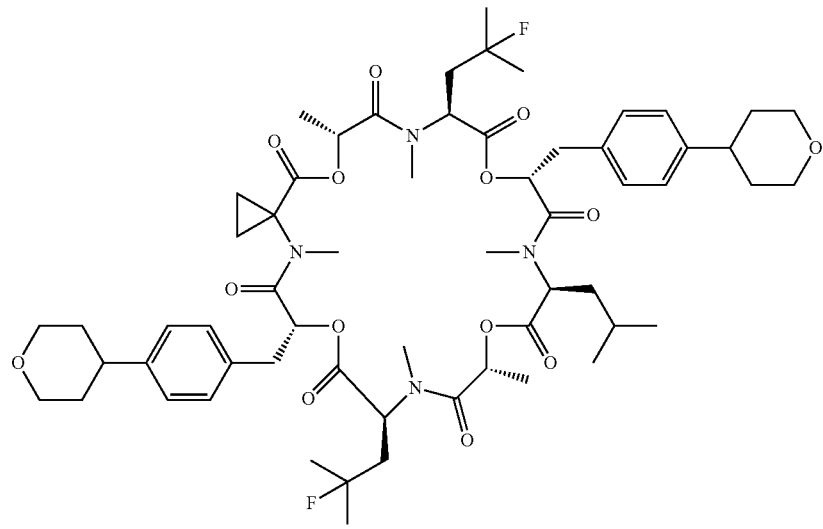

F4

22-tetraazaspiro[2.23]hexacosan-5,8,11,14,17,20,23,26-octone (F4) as a white solid. MS (ES, m/z): 1098.0 (M+H); $^1$H NMR (CD$_3$OD, 300 MHz, ppm): δ 7.31-7.23 (m, 8H), 5.96-5.83 (m, 1H), 5.81-5.72 (m, 1H), 5.71-5.60 (m, 1H), 5.59-5.31 (m, 2H), 5.31-5.09 (m, 2H), 4.18-3.95 (m, 4H), 3.71-3.43 (m, 4H), 3.21-3.09 (m, 6H), 3.06-2.94 (m, 6H), 2.85-2.77 (m, 6H), 2.26-2.18 (m, 4H), 2.05-1.61 (m, 11H), 1.49-1.26 (m, 18H), 1.18-0.97 (m, 4H), 0.96-0.75 (m, 6H); [α]=−89.93°, T=24.7° C., C=0.29 g/100 mL, MeOH.

Preparation Example 40: Synthesis of Compound 969-34A in Table 699 Wherein Each of R$^a$, R$^b$, R', R", R''' and R'''' are Methyl

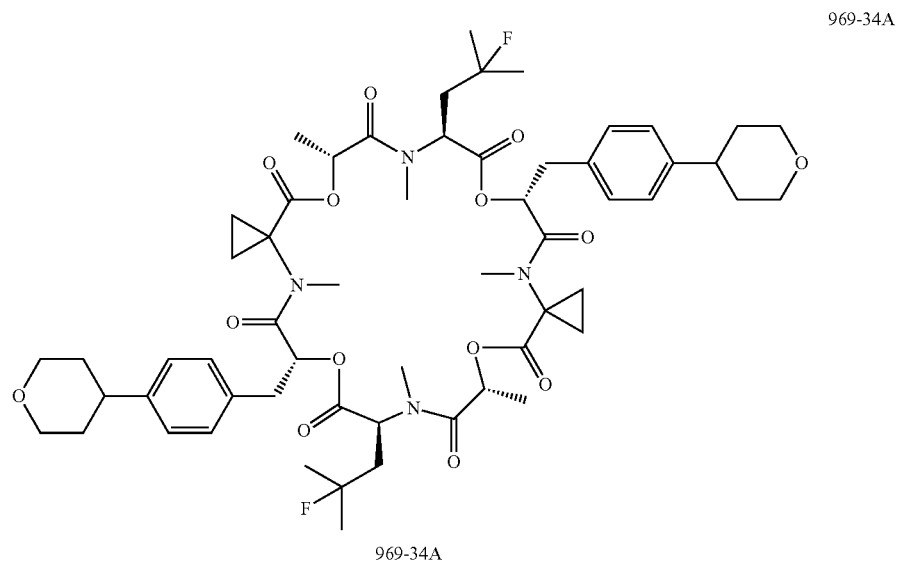 [SMILES: C[C@H]1OC(=O)C2(CC2)N(C)C(=O)[C@@H](Cc2ccc(C3CCOCC3)cc2)OC(=O)[C@H](CC(C)(C)F)N(C)C(=O)[C@@H](C)OC(=O)C2(CC2)N(C)C(=O)[C@@H](Cc2ccc(C3CCOCC3)cc2)OC(=O)[C@H](CC(C)(C)F)N(C)C1=O]

969-34A

Compound 969-34A was prepared in a similar way to compound 6-7A according to Scheme 17 shown below.

Scheme 17

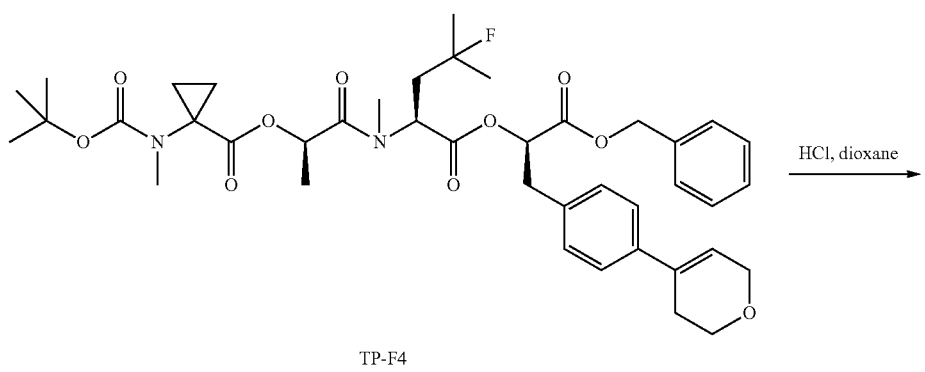

TP-F4    HCl, dioxane →

-continued
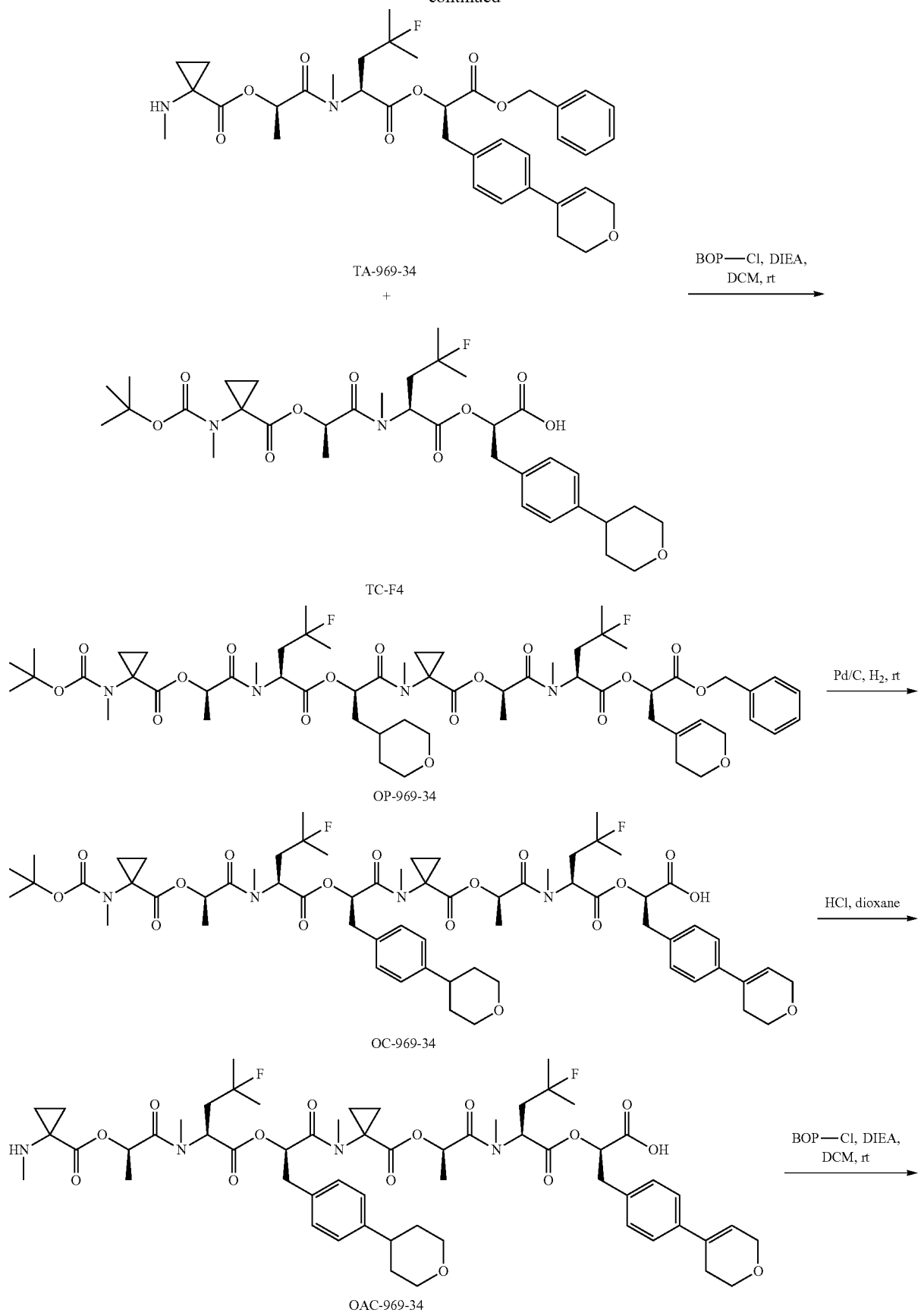

-continued

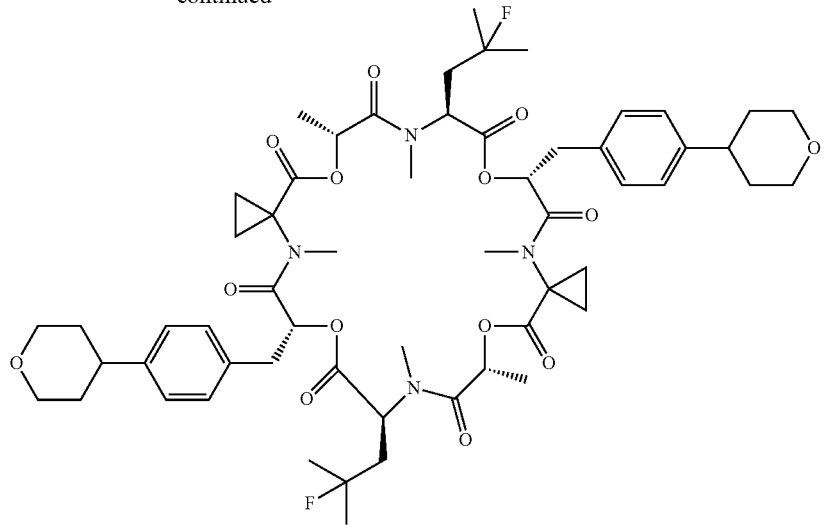

969-34A

Experimental Details

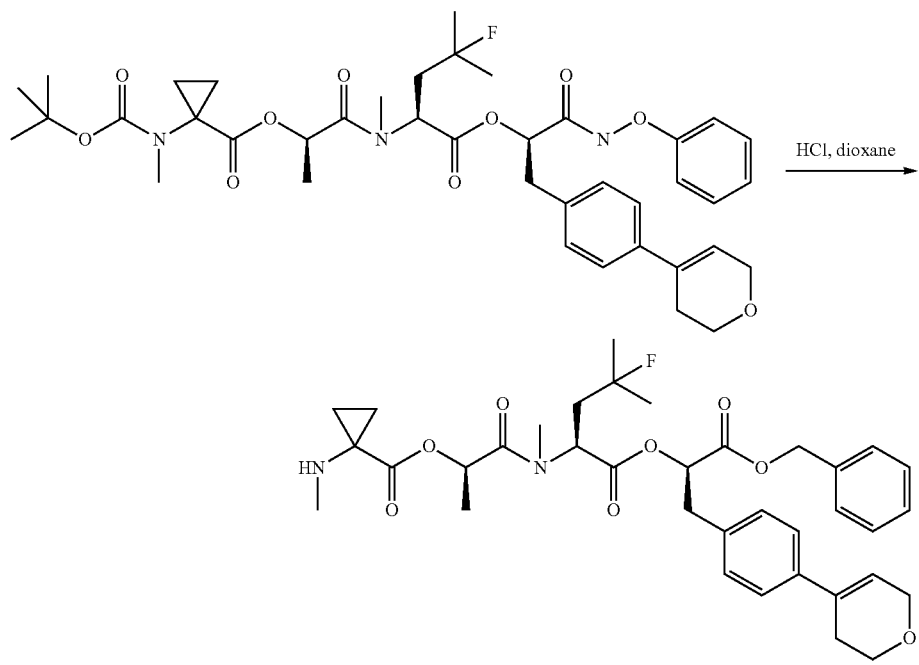

(2R)-1-(benzyloxy)-3-[4-(3,6-dihydro-2H-pyran-4-yl)phenyl]-1-oxopropan-2-yl (2S)-4-fluoro-4-methyl-2-[(2R)—N-methyl-2-[[1-(methylamino)cyclopropyl]carbonyloxy]propanamido]pentanoate (TA-969-34)

Into a 100-mL round-bottom flask, was placed (2R)-1-(benzyloxy)-3-[4-(3,6-dihydro-2H-pyran-4-yl)phenyl]-1-oxopropan-2-yl (2S)-2-[(2R)-2-[(1-[[(tert-butoxy)carbonyl](methyl)amino]cyclopropyl)carbonyloxy]-N-methylpropanamido]-4-fluoro-4-methylpentanoate (TP-F4) (300 mg, 0.40 mmol, 1.00 equiv), DCM (8 mL), hydrogen chloride (dioxane, 15 mL). The resulting solution was stirred for 2 h at room temperature. The resulting mixture was concentrated under vacuum. The pH value of the solution was adjusted to 9 with aqueous sodium bicarbonate. The resulting solution was extracted with 2×30 mL of dichloromethane and the organic layers combined and washed with 30 mL of brine. The organic layer was collected and dried over sodium sulfate. The solids were filtered out. The filtrate was concentrated under vacuum. This resulted in 350 mg (crude) of (2R)-1-(benzyloxy)-3-[4-(3,6-dihydro-2H-pyran-4-yl)phenyl]-1-oxopropan-2-yl (2S)-4-fluoro-4-methyl-2-[(2R)—N-methyl-2-[[1-(methylamino)cyclopropyl]carbonyloxy]propanamido]pentanoate as yellow oil. MS (ES, m/z): 653 (M+H).

437 438

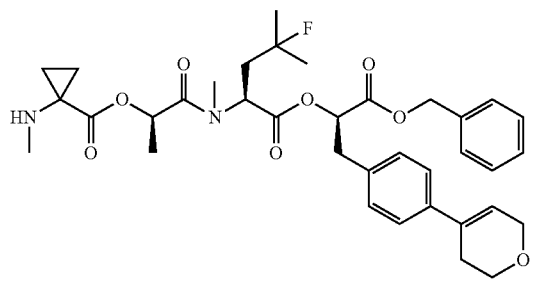 + 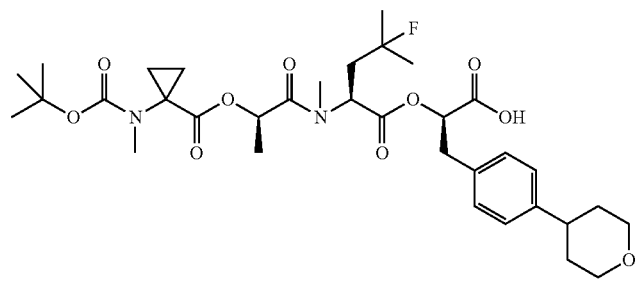

| BOP—Cl, DIEA,
DCM, rt

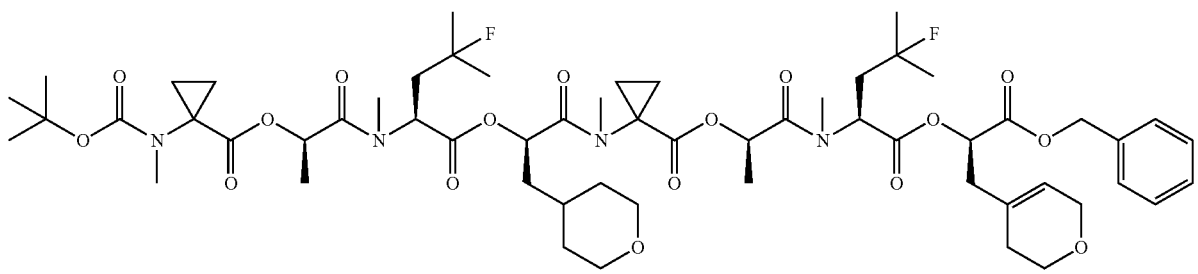

[(1R)-2-[[(1S)-1-[(1R)-2-benzyloxy-1-(3,6-dihydro-2H-pyran-4-ylmethyl)-2-oxo-ethoxy]carbonyl-3-fluoro-3-methyl-butyl]-methyl-amino]-1-methyl-2-oxo-ethyl]1-[[(2R)-2-[(2S)-2-[[(2R)-2-[1-[tert-butoxycarbonyl(methyl)amino]cyclopropanecarbonyl]oxypropanoyl]-methyl-amino]-4-fluoro-4-methyl-pentanoyl]oxy-3-tetrahydropyran-4-yl-propanoyl]-methyl-amino] cyclopropanecarboxylate (OP-969-34)

Into a 100-mL round-bottom flask, was placed (2R)-1-(benzyloxy)-3-[4-(3,6-dihydro-2H-pyran-4-yl)phenyl]-1-oxopropan-2-yl (2S)-4-fluoro-4-methyl-2-[(2R)—N-methyl-2-[[1-(methylamino)cyclopropyl]carbonyloxy] propanamido]pentanoate (TA-969-34) (350 mg, 0.54 mmol, 1.00 equiv), (2R)-2-[[(2S)-2-[(2R)-2-[(1-[[(tert-butoxy)carbonyl](methyl)amino]cyclopropyl)carbonyloxy]-N-methyl-propanamido]-4-fluoro-4-methylpentanoyl]oxy]-3-[4-(oxan-4-yl)phenyl]propanoic acid (TC-F4) (330 mg, 0.50 mmol, 1.00 equiv), dichloromethane (20 mL). This was followed by the addition of BOP—Cl (274 mg, 1.08 mmol, 2.00 equiv) at 0° C. in 5 min. To this was added DIEA (138 mg, 1.07 mmol, 2.00 equiv) at 0° C. in 5 min. The resulting solution was stirred for 2 h at room temperature. The solids were filtered out. The filtrate was concentrated under vacuum. The crude product was purified by Flash-Prep-HPLC with the following conditions (IntelFlash-1): Column, C18 silica gel; mobile phase, H₂O and CH₃CN (50% CH₃CN up to 100% in 20 min); Detector, UV 220 nm. This resulted in 220 mg (34%) of OP-969-34 as yellow oil. MS (ES, m/z): 1230 (M+H).

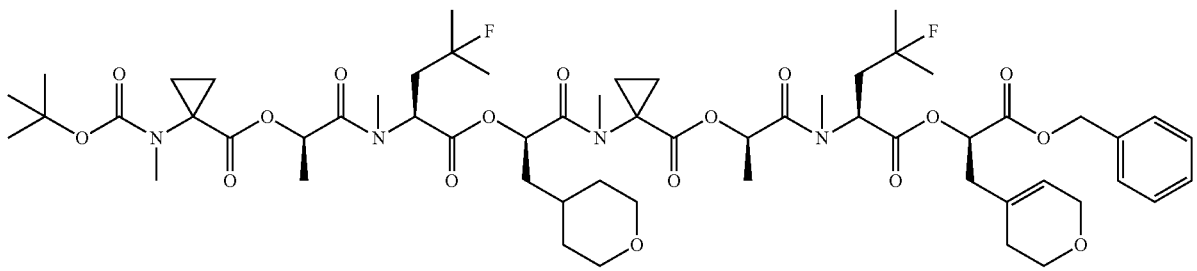

| Pd/C, H₂, rt

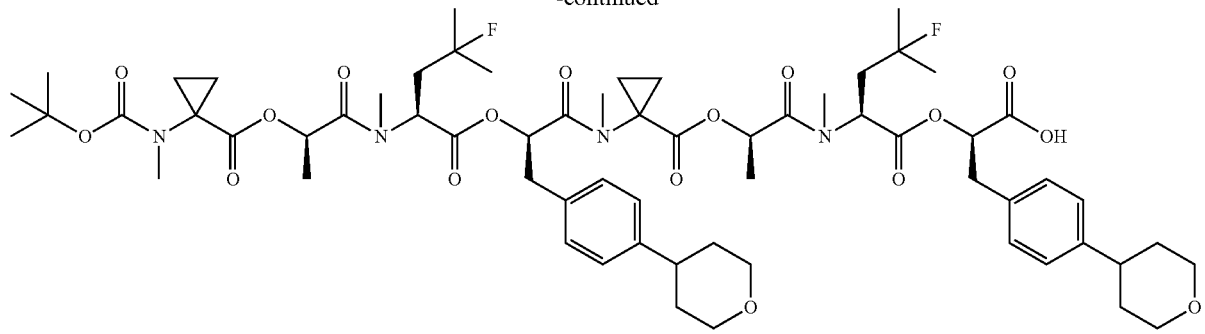

(2R)-2-[[(2S)-2-[(2R)-2-([1-[(2R)-2-[[(2S)-2-[(2R)-2-[(1-[[(tert-butoxy)carbonyl](methyl)amino]cyclopropyl)carbonyloxy]-N-methylpropanamido]-4-fluoro-4-methylpentanoyl]oxy]-N-methyl-3-[4-(oxan-4-yl)phenyl]propanamido]cyclopropyl]carbonyloxy)-N-methylpropanamido]-4-fluoro-4-methylpentanoyl]oxy]-3-[4-(oxan-4-yl)phenyl] propanoic Acid (OC-969-34)

Into a 100-mL round-bottom flask, was placed (2R)-1-(benzyloxy)-3-[4-(3,6-dihydro-2H-pyran-4-yl)phenyl]-1-oxopropan-2-yl (2S)-2-[(2R)-2-([1-[(2R)-2-[[(2S)-2-[(2R)-2-[(1-[[(tert-butoxy)carbonyl](methyl)amino]cyclopropyl)carbonyloxy]-N-methylpropanamido]-4-fluoro-4-methylpentanoyl]oxy]-N-methyl-3-[4-(oxan-4-yl)phenyl]propanamido]cyclopropyl]carbonyloxy)-N-methylpropanamido]-4-fluoro-4-methylpentanoate (OP-969-34) (200 mg, 0.15 mmol, 1.00 equiv), ethyl acetate (10 mL), Palladium carbon (80 mg). To the above mixture was introduced hydrogen. The resulting solution was stirred for 2 h at room temperature. The solids were filtered out. The filtrate was concentrated under vacuum. This resulted in 200 mg (crude) of (2R)-2-[[(2S)-2-[(2R)-2-([1-[(2R)-2-[[(2S)-2-[(2R)-2-[(1-[[(tert-butoxy)carbonyl](methyl)amino]cyclopropyl)carbonyloxy]-N-methylpropanamido]-4-fluoro-4-methylpentanoyl]oxy]-N-methyl-3-[4-(oxan-4-yl)phenyl]propanamido]cyclopropyl]carbonyloxy)-N-methylpropanamido]-4-fluoro-4-methylpentanoyl]oxy]-3-[4-(oxan-4-yl)phenyl]propanoic acid as yellow oil. MS (ES, m/z): 1212 (M+H).

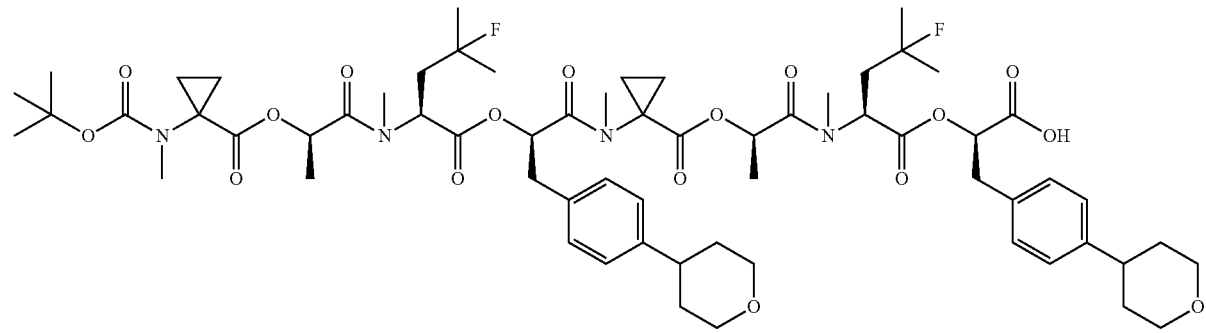

| HCl, dioxane ↓

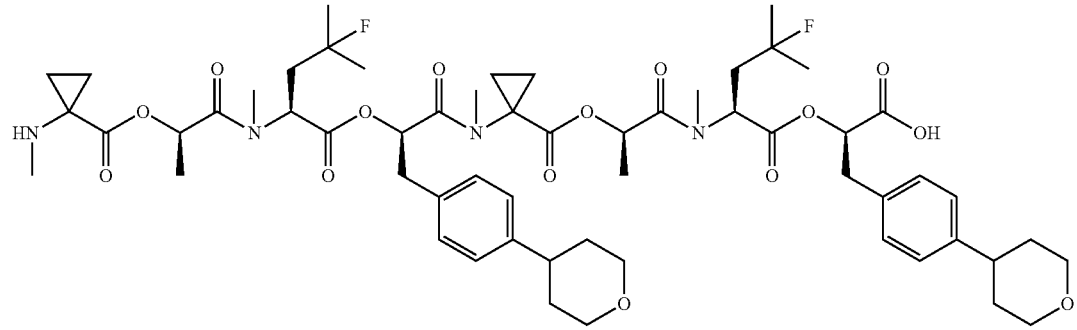

441

(2R)-2-[(2S)-4-fluoro-2-[[(2R)-2-[1-[[(2R)-2-[(2S)-4-fluoro-4-methyl-2-[methyl-[(2R)-2-[1-(methylamino)cyclopropanecarbonyl]oxypropanoyl]amino]pentanoyl]oxy-3-(4-tetrahydropyran-4-ylphenyl)propanoyl]-methyl-amino]cyclopropanecarbonyl]oxypropanoyl]-methyl-amino]-4-methyl-pentanoyl]oxy-3-(4-tetrahydropyran-4-ylphenyl)propanoic Acid (OAC-969-34)

Into a 100-mL round-bottom flask, was placed OC-969-34 (200 mg, 0.17 mmol, 1.00 equiv), DCM (5 mL), hydrogen

442 chloride (dioxane, 8 mL). The resulting solution was stirred for 2 h at room temperature. The resulting mixture was concentrated under vacuum. The pH value of the solution was adjusted to 9 with aqueous sodium bicarbonate. The resulting solution was extracted with 2×30 mL of dichloromethane and the organic layers combined and washed with 40 mL of brine. The organic layer was collected and dried over sodium sulfate. The solids were filtered out. The filtrate was concentrated under vacuum. This resulted in 200 mg (crude) of OAC-969-34 as yellow oil. MS (ES, m/z): 1112 (M+H).

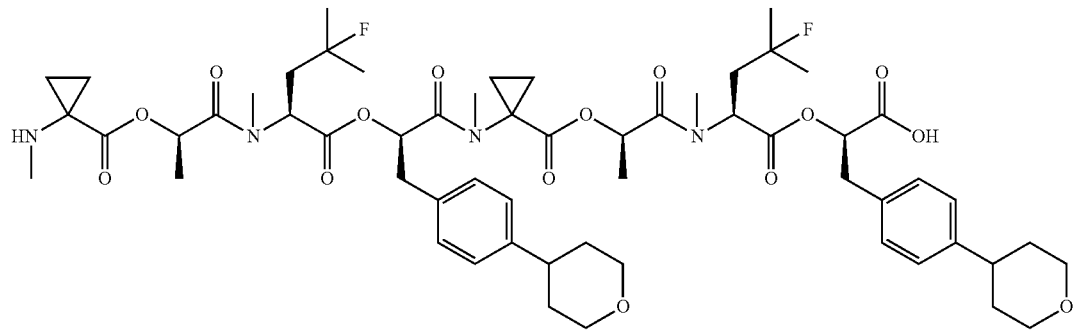

BOP—Cl, DIEA, DCM, rt

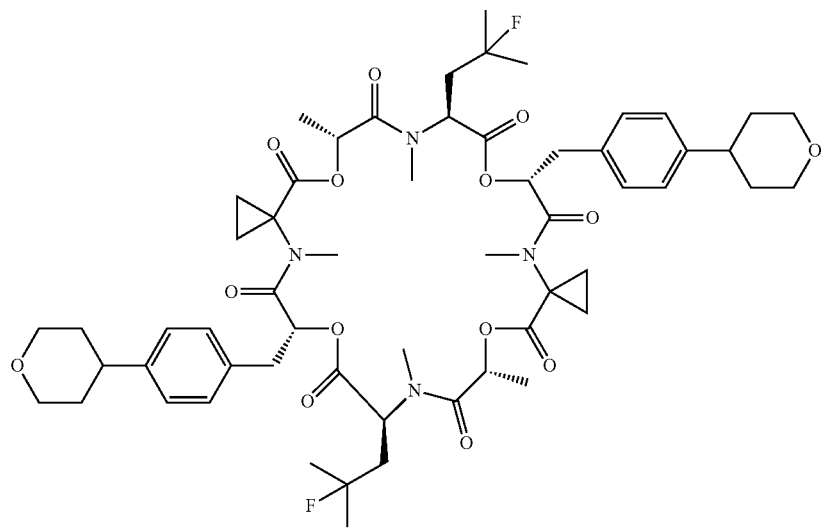

969-34A (6R,9S,12R,20R,23S,26R)-9,23-bis(2-fluoro-2-methylpropyl)-4,1,12,26-hexamethyl-6,20-bis([[4-(oxan-4-yl)phenyl]methyl])-7,13,21,27-tetraoxa-4,10,18,24-tetraazadispiro[2.11.2^[15].11^[3]]octacosan-5,8,11,14,19,22,25,28-octone (969-34A)

Into a 250-mL round-bottom flask, was placed OAC969-34 (180 mg, 0.16 mmol, 1.00 equiv), dichloromethane (50 mL). This was followed by the addition of BOP—Cl (83 mg, 0.33 mmol, 2.00 equiv) at 0° C. in 2 min. To this was added DIEA (63 mg, 0.49 mmol, 3.00 equiv) at 0° C. in 2 min. The resulting solution was stirred overnight at room temperature. The solids were filtered out. The filtrate was concentrated under vacuum. The crude product was purified by Prep-HPLC with the following conditions (Waters I): Column, X Bridge Prep RP18, 5 um, 19×150 mm; mobile phase, phase A: water and $CH_3CN$ (60% $CH_3CN$ up to 80% in 7 min); Detector, UV 220 nm. This resulted in 51.5 mg (29%) of (6R,9S,12R,20R,23S,26R)-9,23-bis(2-fluoro-2-methylpropyl)-4,10,12,18,24,26-hexamethyl-6,20-bis([[4-(oxan-4-yl)phenyl]methyl])-7,13,21,27-tetraoxa-4,10,18,24-tetraazadispiro[2.11.2^[15].11^[3]]octacosan-5,8,11,14,19,22,25,28-octone (969-34A) as a white solid. MS (ES, m/z): 1094 (M+H); $^1$H NMR ($CD_3OD$, 300 MHz, ppm): δ 7.22-7.20 (m, 8H), 5.93-4.93 (m, 6H), 4.07-4.03 (m, 4H), 3.61-3.53 (m, 4H), 3.11-2.79 (m, 18H), 2.41-2.08 (m, 4H), 2.05-1.81 (m, 1H), 1.81-1.76 (m, 9H), 1.76-1.24 (m, 20H), 1.08-1.06 (m, 3H), 0.85-0.72 (m, 1H); [α]=−62.98°, T=27.4° C., C=0.10 g/100 mL in MeOH.

In addition to depsipeptide compounds of the invention described in Examples 33-40, the additional numbered compounds shown in Table 1038 below (which are described above, wherein R', R", R"' and R"" are each methyl), were prepared in accordance with the synthetic procedures described in the examples with the exception that different dimer compounds having the desired functionality were selected to prepare the desired depsipeptide compounds. The selected dimers are prepared in turn from the required monomer compounds. It will be apparent to the skilled person that using this methodology additional depsipeptide compounds of the invention may be prepared using other monomer and dimer components.

TABLE 1038

Additional Compounds of Formula (I) Prepared

| Compound # | Observed Mass |
| --- | --- |
| 7-58B | 1122 |
| 229-34A | 1122 |
| 228-34A | 1124 |
| 6-58B | 1124 |
| 18-34A | 1094 |
| 4-34A | 1118 |
| 30-34A | 1188 |
| 32-34A | 1218 |
| 5-34A | 1150 |
| 35-34A | 1220 |
| 31-34A | 1186 |
| 303-34A | 1178 |
| SAX965250* | 1178 |

*$Cy^1$ and $Cy^2$ are p-THPphenyl (see Table 7); $R^1$, $R^3$ = —$CH_2CF(CH_3)_2$ and $R^2$, $R^4$ are —$CH_2CH_2$cyclopropyl Biological Activity Examples Method A: Screening Method to Test Activity of Compounds Against *Haemonchus contortus*.

Twenty L1 *Haemonchus contortus* larvae were added to wells of a microtitre plate containing a nutrient medium and the test compound in DMSO. An analysis was conducted at 4 days to determine the extent of development of the larvae. Larvae exposed to DMSO alone served as controls. Compounds 228-34A and 969-34A exhibited median $EC_{50}$ values between 1.0 and 10 μM, compound 7-58A exhibited a median $EC_{50}$ value between 0.1 μM and 1.0 μM, and compounds 4-34A, 5-34A, 7-34A, 18-34A, 30-34A, 32-34A, 35-34A, 229-34A, and 303-34A exhibited median $EC_{50}$ values of less than 0.1 μM when assessed at the 4 day time point. As a comparison, emodepside exhibits a median $EC_{50}$ value of between 1 μM and 10 μM in this assay.

Compound 6-1A exhibited a median $MIC_{90}$ value between 1.0 and 10 μM, compounds 6-7A and 6-34A exhibited median $MIC_{90}$ values between 0.1 μM and 1.0 μM, and compounds 7-34A and 7-58A exhibited median $MIC_{90}$ values of less than 0.1 μM when assessed at the 4 day time point. As a comparison, emodepside exhibits a median $EC_{50}$ value of between 0.1 μM and 1 μM in this assay. The $EC_{50}$ and $MIC_{90}$ recordings were obtained using different instruments.

Method B: Screening Method to Test Activity of Compounds Against Microfilaria of *Dirofilaria immitis*.

Microfilaria of *Dirofilaria immitis* were added to the wells of a microtitre plate containing buffer and the test compounds in DMSO. An assessment was conducted at 72 hours to determine survival of the microfilaria. Microfilaria exposed to DMSO alone served as controls. Compounds 6-58A, 9-7A, 31-34A, and 969-34A exhibited median $EC_{50}$ values of between 1 μM and 10 μM, compounds 6-1A, 6-7A, and 6-34A exhibited median $EC_{50}$ values of between 0.1 μM and 1.0 μM, and compounds 4-34A, 5-34A, 7-34A, 7-58A, 18-34A, 30-34A, 32-34A, 228-34A, 229-34A, and 303-34A exhibited median $EC_{50}$ values of less than 0.1 μM. As a comparison, emodepside exhibits a median $EC_{50}$ value of between 0.1 μM and 1 μM in this assay.

Method C: Screening Method to Evaluate the Efficacy of Compounds Against *Dirofilaria immitis* In Vivo.

Beagle dogs were tested for microfilaria and heartworm antigen and received a full physical examination prior to inclusion in the study. Each dog was inoculated with 50 infective third-stage *D. immitis* larvae on Day −30 using an isolate sensitive to macrocyclic lactones at standard doses. Antigen testing performed on blood collected on Day 90 confirmed that animals had not been exposed to *D. immitis* prior to the induced infection.

In the study, five blocks of four or five dogs each were formed based on descending Day −3 to Day 0 body weights. Within blocks, dogs were randomly allocated to one of five treatment groups by lottery and treated five times at monthly intervals with an oral solution of a compound of this invention according to table 1039 below. The control dogs were untreated. Treatment groups 2 and 3 included compounds outside the scope of this invention.

All animals were humanely euthanized on Day 159 and a necropsy was performed for parasite recovery and live *D. immitis* counts for individual dogs. The percent efficacies by treatment group are listed in Table 1039.

TABLE 1039

Efficacy against *D. immitis* in beagles.

| Trt. Group | # of Dogs | Investigational Material | Dose | Dosing Days | Efficacy |
|---|---|---|---|---|---|
| 1 | 5 | (—) control | n/a | n/a | n/a |
| 4 | 4 | 18-34A | 0.1 mg/kg | 0, 30, 60, 90, & 120 | 100% |
| 5 | 4 | 18-34A | 0.5 mg/kg | 0, 30, 60, 90, & 120 | 100% |

In this study, compound 18-34A from this invention (@ 0.1 and 0.5 mg/kg) administered orally (in solution) for five monthly doses, provided 100% efficacy against induced infections of a macrocyclic lactone susceptible isolate of *Dirofilaria immitis*.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for the treatment of a parasitic infection in a mammal caused by an endoparasite selected from group consisting of *Anaplocephala, Ancylostoma, Necator, Ascaris, Brugia, Bunostomum, Capillaria, Chabertia, Cooperia, Cyathostomum, Cylicocyclus, Cylicodontophorus, Cylicostephanus, Craterostomum, Dictyocaulus, Dipetalonema, Dipylidium, Dracunculus, Echinococcus, Enterobius, Fasciola, Filaroides, Habronema, Haemonchus, Metastrongylus, Moniezia, Nematodirus, Nippostrongylus, Oesophagostomum, Onchocerca, Ostertagia, Oxyuris, Parascaris, Schistosoma, Strongylus, Taenia, Toxocara, Strongyloides, Toxascaris, Trichinella, Trichuris, Trichostrongylus, Triodontophorus, Uncinaria* and *Wuchereria* comprising administering a parasiticidally effective amount of an anthelmintic cyclic depsipeptide of Formula (I) to the animal:

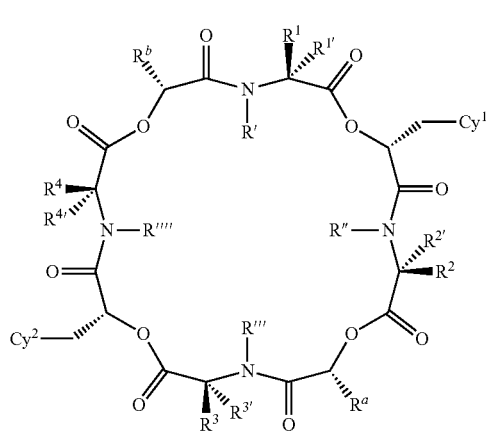

(I)

wherein:

$Cy^1$ and $Cy^2$ are independently aryl or heteroaryl, each of which is optionally substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —$NO_2$, cycloalkyl, heteroalkyl, heterocyclyl, aryl and heteroaryl, wherein each cycloalkyl, heteroalkyl, heterocyclyl, aryl or heteroaryl substituents of $Cy^1$ and $Cy^2$ is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5OC(O)$—, $R^5C(O)O$—, $R^5C(O)NR^6$—, —CN and —$NO_2$;

$R^5$ and $R^6$ are independently hydrogen, alkyl, haloalkyl, thioalkyl, alkylthio, alkylthioalkyl, hydroxyalkyl, alkoxyalkyl, alkenyl, haloalkenyl, alkynyl or haloalkynyl, or the group —$CH_2C(O)NHCH_2CF_3$; or $R^5$ and $R^6$ together with the atom(s) to which they are bonded form a $C_3$-$C_6$ cyclic group;

R', R'', R''' and R'''' are each independently hydrogen or $C_1$-$C_3$alkyl;

$R^a$ and $R^b$ are independently hydrogen, $C_1$-$C_3$alkyl or $C_1$-$C_3$haloalkyl; and (a) $R^1$ is $C_1$-$C_3$ alkyl or $C_1$-$C_3$ haloalkyl substituted by a 3- to 6-membered non-aromatic carbocyclic ring; wherein said 3- to 6-membered non-aromatic carbocyclic ring may be further substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and R'' is hydrogen or $C_1$-$C_3$alkyl; or $R^1$ and $R^{1'''}$ together form a 2-4-membered carbon chain to form a ring; and $R^2$, $R^{2'}$, $R^3$, $R^{3'}$, $R^4$ and $R^{4'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino; or (b) $R^2$ is $C_1$-$C_3$ alkyl or $C_1$-$C_3$ haloalkyl substituted by a 3- to 6-membered non-aromatic carbocyclic ring; wherein said 3- to 6-membered non-aromatic carbocyclic ring may be further substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{2'}$ is hydrogen or $C_1$-$C_3$alkyl; or $R^2$ and $R^{2'}$ together form a 2-4-membered carbon chain to form a ring; and $R^1$, $R^{1'''}$, $R^3$, $R^{3'}$, $R^4$ and $R^{4'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino; or (c) $R^3$ is $C_1$-$C_3$ alkyl or $C_1$-$C_3$ haloalkyl substituted by a 3- to 6-membered non-aromatic carbocyclic ring; wherein said 3- to 6-membered non-aromatic carbocyclic ring may be further substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{3'}$ is hydrogen or $C_1$-$C_3$alkyl; or $R^3$ and $R^{3'}$ together form a 2-4-membered carbon chain to form a ring; and $R^1$, $R^{1'}$, $R^2$, $R^{2'}$, $R^4$ and $R^{4'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino; or (d) $R^4$ is $C_1$-$C_3$ alkyl or $C_1$-$C_3$ haloalkyl substituted by a 3- to 6-membered non-aromatic carbocyclic ring; wherein said 3- to 6-membered non-aromatic carbocyclic ring may be further substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{4'}$ is hydrogen or $C_1$-$C_3$alkyl; or $R^4$ and $R^{4'}$ together form a 2-4-membered carbon chain to form a ring; and $R^1$, $R^{1'}$, $R^2$, $R^{2'}$, $R^3$ and $R^{3'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino; or (e) $R^1$ and $R^2$ are each independently $C_1$-$C_3$ alkyl or $C_1$-$C_3$ haloalkyl substituted by a 3- to 6-membered non-aromatic carbocyclic ring; wherein said 3- to 6-membered non-aromatic carbocyclic rings may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{1'}$ and $R^{2'}$ are independently hydrogen or $C_1$-$C_3$alkyl; or $R^1$ and $R^{1'}$ together and/or $R^2$ and $R^{2'}$ together independently form a 2-4-membered carbon chain to form a ring; and $R^3$, $R^{3'}$, $R^4$ and $R^{4'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkyl sulfonyl, haloalkylsulfonyl, alkoxyalkoxy, oxo, cyano, amino, alkylamino or dialkylamino; or (f) $R^1$ and $R^3$ are each independently $C_1$-$C_3$ alkyl or $C_1$-$C_3$ haloalkyl substituted by a 3- to 6-membered non-aromatic carbocyclic ring; wherein said 3- to 6-membered non-aromatic carbocyclic rings may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{1'}$ and $R^{3'}$ are independently hydrogen or $C_1$-$C_3$alkyl; or $R^1$ and $R^{1'}$ together and/or $R^3$ and $R^{3'}$ together independently form a 2-4-membered carbon chain to form a ring; and $R^2$, $R^{2'}$, $R^4$ and $R^{4'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkyl sulfonyl, haloalkylsulfonyl, alkoxyalkoxy, oxo, cyano, amino, alkylamino or dialkylamino; or (g) $R^1$ and $R^4$ are each independently $C_1$-$C_3$ alkyl or $C_1$-$C_3$ haloalkyl substituted by a 3- to 6-membered non-aromatic carbocyclic ring; wherein said 3- to 6-membered non-aromatic carbocyclic rings may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{1'}$ and $R^{4'}$ are independently hydrogen or $C_1$-$C_3$alkyl; or $R^1$ and $R^{1'}$ together and/or $R^4$ and $R^{4'}$ together independently form a 2-4-membered carbon chain to form a ring; and $R^2$, $R^{2'}$, $R^3$ and $R^{3'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkyl sulfonyl, haloalkylsulfonyl, alkoxyalkoxy, oxo, cyano, amino, alkylamino or dialkylamino; or (h) $R^2$ and $R^4$ are each independently $C_1$-$C_3$ alkyl or $C_1$-$C_3$ haloalkyl substituted by a 3- to 6-membered non-aromatic carbocyclic ring; wherein said 3- to 6-membered non-aromatic carbocyclic rings may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{2'}$ and $R^{4'}$ are independently hydrogen or $C_1$-$C_3$alkyl; or $R^2$ and $R^{2'}$ together and/or $R^4$ and $R^{4'}$ together independently form a 2-4-membered carbon chain to form a ring; and $R^1$, $R^{1'}$, $R^3$ and $R^{3'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkyl sulfonyl, haloalkylsulfonyl, alkoxyalkoxy, oxo, cyano, amino, alkylamino or dialkylamino; or (i) $R^2$ and $R^3$ are each independently $C_1$-$C_3$ alkyl or $C_1$-$C_3$ haloalkyl substituted by a 3- to 6-membered non-aromatic carbocyclic ring; wherein said 3- to 6-membered non-aromatic carbocyclic rings may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{2'}$ and $R^{3'}$ are independently hydrogen or $C_1$-$C_3$alkyl; or R$^2$ and R$^{2'}$ together and/or R$^3$ and R$^{3'}$ together independently form a 2-4-membered carbon chain to form a ring; and R$^1$, R$^{1'}$, R$^4$ and R$^{4'}$ are each independently hydrogen or C$_1$-C$_8$ alkyl, optionally substituted by one or more halogen, hydroxy, alkoxy, haloalkoxy, alkylthio, haloalkylthio, halothio, alkylsulfinyl, haloalkylsulfinyl, alkyl sulfonyl, haloalkylsulfonyl, alkoxyalkoxy, oxo, cyano, amino, alkylamino or dialkylamino; or (j) R$^3$ and R$^4$ are each independently C$_1$-C$_3$ alkyl or C$_1$-C$_3$ haloalkyl substituted by a 3- to 6-membered non-aromatic carbocyclic ring; wherein said 3- to 6-membered non-aromatic carbocyclic rings may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and R$^{3'}$ and R$^{4'}$ are independently hydrogen or C$_1$-C$_3$alkyl; or R$^3$ and R$^{3'}$ together and/or R$^4$ and R$^{4'}$ together independently form a 2-4-membered carbon chain to form a ring; and R$^1$, R$^{1'}$, R$^2$ and R$^{2'}$ are each independently hydrogen or C$_1$-C$_8$ alkyl, optionally substituted by one or more halogen, hydroxy, alkoxy, haloalkoxy, alkylthio, haloalkylthio, halothio, alkylsulfinyl, haloalkylsulfinyl, alkyl sulfonyl, haloalkylsulfonyl, alkoxyalkoxy, oxo, cyano, amino, alkylamino or dialkylamino; or (k) R$^1$, R$^2$ and R$^3$ are each independently C$_1$-C$_3$ alkyl or C$_1$-C$_3$ haloalkyl substituted by a 3- to 6-membered non-aromatic carbocyclic ring; wherein said 3- to 6-membered non-aromatic carbocyclic rings may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and R$^{1'}$, R$^{2'}$ and R$^{3'}$ are independently hydrogen or C$_1$-C$_3$alkyl; or R$^1$ and R$^{1'}$ together and/or R$^2$ and R$^{2'}$ together and/or R$^3$ and R$^{3'}$ together independently form a 2-4-membered carbon chain to form a ring; and R$^4$ and R$^{4'}$ are independently hydrogen or C$_1$-C$_8$ alkyl, optionally substituted by one or more halogen, hydroxy, alkoxy, haloalkoxy, alkylthio, haloalkylthio, halothio, alkylsulfinyl, haloalkylsulfinyl, alkyl sulfonyl, haloalkylsulfonyl, alkoxyalkoxy, oxo, cyano, amino, alkylamino or dialkylamino; or (l) R$^2$, R$^3$ and R$^4$ are each independently C$_1$-C$_3$ alkyl or C$_1$-C$_3$ haloalkyl substituted by a 3- to 6-membered non-aromatic carbocyclic ring; wherein said 3- to 6-membered non-aromatic carbocyclic rings may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and R$^{2'}$, R$^{3'}$ and R$^{4'}$ are independently hydrogen or C$_1$-C$_3$alkyl; or R$^2$ and R$^{2'}$ together and/or R$^3$ and R$^{3'}$ together and/or R$^4$ and R$^{4'}$ together independently form a 2-4-membered carbon chain to form a ring; and R$^1$ and R$^{1'}$ are independently hydrogen or C$_1$-C$_8$ alkyl, optionally substituted by one or more halogen, hydroxy, alkoxy, haloalkoxy, alkylthio, haloalkylthio, halothio, alkylsulfinyl, haloalkylsulfinyl, alkyl sulfonyl, haloalkylsulfonyl, alkoxyalkoxy, oxo, cyano, amino, alkylamino or dialkylamino; or (m) R$^1$, R$^3$ and R$^4$ are each independently C$_1$-C$_3$ alkyl or C$_1$-C$_3$ haloalkyl substituted by a 3- to 6-membered non-aromatic carbocyclic ring; wherein said 3- to 6-membered non-aromatic carbocyclic rings may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and R'', R$^{3'}$ and R$^{4'}$ are independently hydrogen or C$_1$-C$_3$alkyl; or R$^1$ and R$^{1''}$ together and/or R$^3$ and R$^{3'}$ together and/or R$^4$ and R$^{4'}$ together independently form a 2-4-membered carbon chain to form a ring; and R$^2$ and R$^{2'}$ are independently hydrogen or C$_1$-C$_8$ alkyl, optionally substituted by one or more halogen, hydroxy, alkoxy, haloalkoxy, alkylthio, haloalkylthio, halothio, alkylsulfinyl, haloalkylsulfinyl, alkyl sulfonyl, haloalkylsulfonyl, alkoxyalkoxy, oxo, cyano, amino, alkylamino or dialkylamino; or (n) R$^1$, R$^2$ and R$^4$ are each independently C$_1$-C$_3$ alkyl or C$_1$-C$_3$ haloalkyl substituted by a 3- to 6-membered non-aromatic carbocyclic ring; wherein said 3- to 6-membered non-aromatic carbocyclic rings may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino alkylamino and dialkylamino; and R$^{1'}$, R$^{2'}$ and R$^{4'}$ are independently hydrogen or C$_1$-C$_3$alkyl; or R$^1$ and R$^{1''}$ together and/or R$^2$ and R$^{2'}$ together and/or R$^4$ and R$^{4'}$ together independently form a 2-4-membered carbon chain to form a ring; and R$^3$ and R$^{3'}$ are independently hydrogen or C$_1$-C$_8$ alkyl, optionally substituted by one or more halogen, hydroxy, alkoxy, haloalkoxy, alkylthio, haloalkylthio, halothio, alkylsulfinyl, haloalkylsulfinyl, alkyl sulfonyl, haloalkylsulfonyl, alkoxyalkoxy, oxo, cyano, amino, alkylamino or dialkylamino; or (o) R$^1$, R$^2$, R$^3$ and R$^4$ are each independently C$_1$-C$_3$ alkyl or C$_1$-C$_3$ haloalkyl substituted by a 3- to 6-membered non-aromatic carbocyclic ring; wherein said 3- to 6-membered non-aromatic carbocyclic rings may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and R$^{1'}$, R$^{2'}$, R$^{3'}$ and R$^{4'}$ are independently hydrogen or C$_1$-C$_3$alkyl; or $R^1$ and $R^{1''}$ together and/or $R^2$ and $R^{2'}$ together and/or $R^3$ and $R^{3'}$ together and/or $R^4$ and $R^{4'}$ together independently form a 2-4-membered carbon chain to form a ring.

2. The method of claim 1, wherein
   (e) $R^1$ and $R^2$ are each independently $C_1$-$C_3$ alkyl or $C_1$-$C_3$ haloalkyl substituted by a 3- to 6-membered non-aromatic carbocyclic ring; wherein said 3- to 6-membered non-aromatic carbocyclic rings may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{1''}$ and $R^{2'}$ are independently hydrogen or $C_1$-$C_3$alkyl; or
   $R^1$ and $R^{1''}$ together and/or $R^2$ and $R^{2'}$ together independently form a 2-4-membered carbon chain to form a ring; and
   $R^3$, $R^{3'}$, $R^4$ and $R^{4'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkyl sulfonyl, haloalkylsulfonyl, alkoxyalkoxy, oxo, cyano, amino, alkylamino or dialkylamino; or
   (f) $R^1$ and $R^3$ are each independently $C_1$-$C_3$ alkyl or $C_1$-$C_3$ haloalkyl substituted by a 3- to 6-membered non-aromatic carbocyclic ring; wherein said 3- to 6-membered non-aromatic carbocyclic rings may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{1''}$ and $R^{3'}$ are independently hydrogen or $C_1$-$C_3$alkyl; or
   $R^1$ and $R^{1''}$ together and/or $R^3$ and $R^{3'}$ together independently form a 2-4-membered carbon chain to form a ring; and
   $R^2$, $R^{2'}$, $R^4$ and $R^{4'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkyl sulfonyl, haloalkylsulfonyl, alkoxyalkoxy, oxo, cyano, amino, alkylamino or dialkylamino; or
   (g) $R^1$ and $R^4$ are each independently $C_1$-$C_3$ alkyl or $C_1$-$C_3$ haloalkyl substituted by a 3- to 6-membered non-aromatic carbocyclic ring; wherein said 3- to 6-membered non-aromatic carbocyclic rings may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{1'}$ and $R^{4'}$ are independently hydrogen or $C_1$-$C_3$alkyl; or
   $R^1$ and $R^{1'}$ together and/or $R^4$ and $R^{4'}$ together independently form a 2-4-membered carbon chain to form a ring; and
   $R^2$, $R^{2'}$, $R^3$ and $R^{3'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkyl sulfonyl, haloalkylsulfonyl, alkoxyalkoxy, oxo, cyano, amino, alkylamino or dialkylamino; or
   (h) $R^2$ and $R^4$ are each independently $C_1$-$C_3$ alkyl or $C_1$-$C_3$ haloalkyl substituted by a 3- to 6-membered non-aromatic carbocyclic ring; wherein said 3- to 6-membered non-aromatic carbocyclic rings may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{2'}$ and $R^{4'}$ are independently hydrogen or $C_1$-$C_3$alkyl; or
   $R^2$ and $R^{2'}$ together and/or $R^4$ and $R^{4'}$ together independently form a 2-4-membered carbon chain to form a ring; and
   $R^1$, $R^{1'}$, $R^3$ and $R^{3'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkyl sulfonyl, haloalkylsulfonyl, alkoxyalkoxy, oxo, cyano, amino, alkylamino or dialkylamino; or
   (i) $R^2$ and $R^3$ are each independently $C_1$-$C_3$ alkyl or $C_1$-$C_3$ haloalkyl substituted by a 3- to 6-membered non-aromatic carbocyclic ring; wherein said 3- to 6-membered non-aromatic carbocyclic rings may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{2'}$ and $R^{3'}$ are independently hydrogen or $C_1$-$C_3$alkyl; or
   $R^2$ and $R^{2'}$ together and/or $R^3$ and $R^{3'}$ together independently form a 2-4-membered carbon chain to form a ring; and
   $R^1$, $R^{1'}$, $R^4$ and $R^{4'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkyl sulfonyl, haloalkylsulfonyl, alkoxyalkoxy, oxo, cyano, amino, alkylamino or dialkylamino; or
   (j) $R^3$ and $R^4$ are each independently $C_1$-$C_3$ alkyl or $C_1$-$C_3$ haloalkyl substituted by a 3- to 6-membered non-aromatic carbocyclic ring; wherein said 3- to 6-membered non-aromatic carbocyclic rings may be further independently substituted by one or more substituents selected from the group consisting of alkyl, haloalkyl, cycloalkyl, heterocyclyl, aryl, heteroaryl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and $R^{3'}$ and $R^{4'}$ are independently hydrogen or $C_1$-$C_3$alkyl; or
   $R^3$ and $R^{3'}$ together and/or $R^4$ and $R^{4'}$ together independently form a 2-4-membered carbon chain to form a ring; and
   $R'$, $R^{1'}$, $R^2$ and $R^{2'}$ are each independently hydrogen or $C_1$-$C_8$ alkyl, optionally substituted by one or more halogen, hydroxy, alkoxy, haloalkoxy, alkylthio, haloalkylthio, halothio, alkylsulfinyl, haloalkylsulfinyl, alkyl sulfonyl, haloalkylsulfonyl, alkoxyalkoxy, oxo, cyano, amino, alkylamino or dialkylamino.

3. The method of claim 1, wherein one, two, three or four of $R^1$ to $R^4$ is methylene or methylene substituted by one or two halogen atoms, which are further substituted by a 3- to 6-membered non-aromatic carbocyclic ring, wherein said 3- to 6-membered non-aromatic carbocyclic rings are independently optionally substituted by one or more substituents selected from the group consisting of alkyl, haloalkyl, halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino and dialkylamino; and the others of $R^1$ to $R^4$ are independently $C_1$-$C_6$ alkyl optionally independently substituted by one or more halogen, hydroxy, alkoxy, haloalkoxy, alkylthio, haloalkylthio, halothio, alkyl sulfinyl, haloalkylsulfinyl, alkylsulfonyl, haloalkylsulfonyl, alkoxyalkoxy, oxo, cyano, amino, alkylamino or dialkylamino.

4. The method of claim 3, wherein $R^1$ and $R^3$ are independently $C_2$-$C_6$ alkyl, optionally independently substituted by one or more halogen, hydroxy, alkoxy, haloalkoxy, alkylthio, haloalkylthio, halothio, alkylsulfinyl, haloalkylsulfinyl, alkylsulfonyl, haloalkylsulfonyl, alkoxyalkoxy, oxo, cyano, amino, alkylamino or dialkylamino.

5. The method of claim 4, wherein $R^1$ and $R^3$ are independently $C_2$-$C_6$ alkyl, optionally independently substituted by one or more of halogen.

6. The method of claim 5, wherein $R^1$ and $R^3$ are both independently $C_3$-$C_5$ alkyl independently substituted by one or more fluoro.

7. The method of claim 3, wherein one, two, three or four of $R^1$ to $R^4$ are one of C1 to C6, C9, C12-C16, C18, C19, C20, C27 or C28:

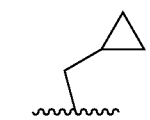
C1

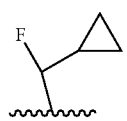
C2

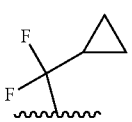
C3

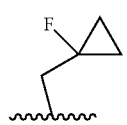
C4

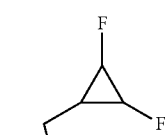
C5

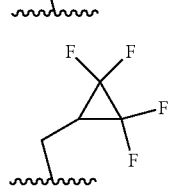
C6

-continued

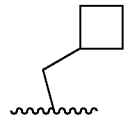
C9

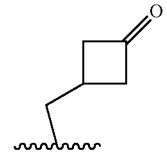
C12

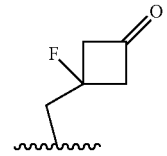
C13

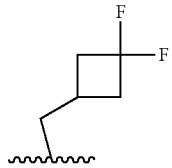
C14

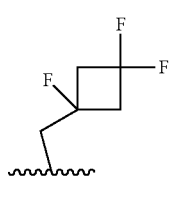
C15

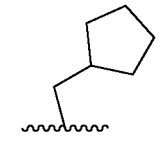
C16

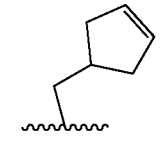
C18

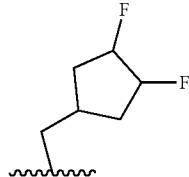
C19

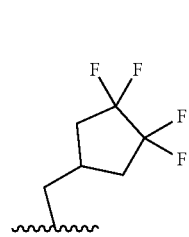
C20

-continued

C27
C28

8. The method of claim 7, wherein one, two, three or all four of $R^1$ to $R^4$ are each independently one of C1 to C6, C9, C12-C16, C18, C19, C20, C27 or C28; and the others of $R^1$ to $R^4$ are independently $C_2$-$C_6$ alkyl, optionally substituted by one or more halogen.

9. The method of claim 7, wherein $R^1$ and $R^3$ are each independently one of C1 to C6, C9, C12-C16, C18, C19, C20, C27 or C28; and $R^2$ and $R^4$ are independently 2,2-dimethylpropyl or 2-methylpropyl, substituted by one or more halogen.

10. The method of claim 7, wherein $R^2$ and $R^4$ are each independently one of C1 to C6, C9, C12-C16, C18, C19, C20, C27 or C28; and $R^1$ and $R^3$ are independently 2,2-dimethylpropyl or 2-methylpropyl, substituted by one or more halogen.

11. The method of claim 10, wherein $R^2$ and $R^4$ are each independently C1 or C9; and $R^1$ and $R^3$ are independently 2,2-dimethylpropyl or 2-methylpropyl, substituted by one or more fluorine.

12. The method of claim 9, wherein $R^1$ and $R^3$ are each independently C1 or C9; and $R^2$ and $R^4$ are independently 2,2-dimethylpropyl or 2-methylpropyl, substituted by one or more fluorine.

13. The method of claim 12, wherein $R^1$ and $R^3$ are $C_1$; and $R^2$ and $R^4$ are independently 2,2-dimethylpropyl or 2-methylpropyl substituted by one or more fluorine.

14. The method of claim 11, wherein $R^2$ and $R^4$ are $C_1$; and $R^1$ and $R^3$ are independently 2,2-dimethylpropyl or 2-methylpropyl substituted by one or more fluorine.

15. The method of claim 1, wherein $Cy^1$ and $Cy^2$ are independently phenyl or a 6-membered heteroaryl, each optionally independently substituted with one or more halogen, alkoxy, haloalkoxy, alkylthio, haloalkylthio, halothio, thioamido, amino, alkylamino, dialkylamino, alkyl, haloalkyl, $R^5S(O)$—, $R^5S(O)_2$—, $R^5C(O)$—, $R^5R^6NC(O)$—, $R_5R_6NC(O)NR^5$—, $R^5OC(O)$—, $R^5C(O)O$—, $R^5C(O)NR^6$—, —CN, —NO$_2$, cycloalkyl or heterocyclyl, wherein each cycloalkyl or heterocyclyl substituent is optionally further substituted with one or more substituents selected from the group consisting of halogen, hydroxy, alkoxy, haloalkoxy, alkylthio, haloalkylthio, halothio, thioamido, amino, alkylamino, dialkylamino, alkyl, haloalkyl, alkenyl, haloalkenyl, alkynyl, haloalkynyl, SF$_5$, $R^5S(O)$—, $R^5S(O)_2$—, $R^5C(O)$—, $R^5R^6NC(O)$—, $R_5R_6NC(O)NR^5$—, $R^5OC(O)$—, $R^5C(O)O$—, $R^5C(O)NR^6$—, —CN and —NO$_2$.

16. The method of claim 15, wherein $Cy^1$ and $Cy^2$ are independently phenyl, optionally independently substituted with halogen, —CN, alkyl, cycloalkyl, haloalkyl, alkoxy, haloalkoxy, alkylthio, haloalkylthio, halothio, $R^5R^6NC$ (O)— or heterocyclyl, wherein each cycloalkyl and heterocyclyl is optionally substituted with halogen.

17. The method of claim 15, wherein $Cy^1$ and $Cy^2$ are independently phenyl, optionally substituted with t-butyl, —CF$_3$, —OCF$_3$, —SCF$_3$, morpholinyl, piperidinyl, tetrahydropyranyl, cyclopentyl, cyclohexyl, fluoro or —SF$_5$, wherein said morpholinyl, piperidinyl, tetrahydropyranyl, cyclopentyl or cyclohexyl may be substituted with one or more halogen atoms.

18. The method of claim 17, wherein $Cy^1$ and $Cy^2$ are the same and are each

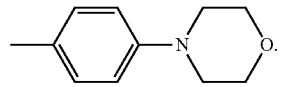

19. The method of claim 17, wherein $Cy^1$ and $Cy^2$ are the same and are each:

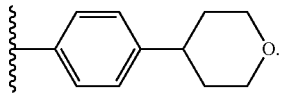

20. The anthelmintic cyclic depsipeptide of claim 17, wherein $Cy^1$ and $Cy^2$ are the same and are each para-t-butylphenyl.

21. The method of claim 1, wherein:
$R^1$ and $R^3$ are both independently selected from $C_3$-$C_5$ alkyl substituted with one or more fluoro;
$R^2$ and $R^4$ are each independently $C_1$-$C_3$ alkyl substituted by cyclopropyl or cyclobutyl;
$R^{1'}$, $R^{2'}$, $R^{3'}$ and $R^{4'}$ are H;
$Cy^1$ and $Cy^2$ are each independently phenyl substituted with halogen, $C_1$-$C_6$ alkyl, $C_1$-$C_6$haloalkyl, $C_3$-$C_6$ cycloalkyl, —OCF$_3$, —SCF$_3$, SF$_5$ or heterocyclyl, wherein said $C_3$-$C_6$ cycloalkyl or heterocyclyl may be substituted with one or more halogen atoms;
R', R'', R''' and R'''' are each independently $C_1$-$C_3$alkyl; and
$R^a$ and $R^b$ are independently $C_1$-$C_3$alkyl.

22. The method of claim 1, wherein:
$R^1$ and $R^3$ are —CH$_2$—C(CH$_3$)$_3$ or CH$_2$—CF(CH$_3$)$_2$;
$R^2$ and $R^4$ are each $C_1$-$C_3$ alkyl substituted by cyclopropyl or cyclobutyl;
$R^{1'}$, $R^{2'}$, $R^{3'}$ and $R^{4'}$ are H;
R', R'', R''' and R'''' are CH$_3$;
$Cy^1$ and $Cy^2$ are each independently phenyl substituted with halogen, t-butyl, CF$_3$, $C_3$-$C_6$ cycloalkyl, —OCF$_3$, —SCF$_3$, SF$_5$, morpholinyl, tetrahydropyranyl, piperidinyl, cyclopropyl, cyclobutyl, cyclopentyl or cyclohexyl, wherein said morpholinyl, tetrahydropyranyl, piperidinyl, cyclopropyl, cyclobutyl, cyclopentyl or cyclohexyl may be substituted with one or more halogen atoms; and
$R^a$ and $R^b$ are independently CH$_3$.

23. The method of claim 22, wherein:
$R^2$ and $R^4$ are each methylene or ethylene substituted by cyclopropyl; and
$Cy^1$ and $Cy^2$ are each independently phenyl substituted by morpholinyl, tetrahydropyranyl, t-butyl, —OCF$_3$ or CF$_3$.

24. The method of claim 22, wherein:
R² and R⁴ are each methylene or ethylene substituted by cyclobutyl; and
Cy¹ and Cy² are each independently phenyl substituted by morpholinyl, tetrahydropyranyl, t-butyl, —OCF₃ or CF₃.

25. The method of claim 1, wherein the endoparasite is *Haemonchus contortus, Ostertagia circumcincta* or *Trichostrongylus colubriformis*.

26. The method of claim 1, wherein the mammal is a human, a cat, a dog, cattle, a chicken, a bison, deer, a goat, a horse, a llama, a camel, a pig, sheep or a yak.

27. The method of claim 26, wherein the animal is a cattle or a horse.

28. A method for the treatment of a parasitic infection in a mammal comprising administering to the mammal a parasiticidally effective amount of an anthelmintic cyclic depsipeptide of Formula (I) to the animal:

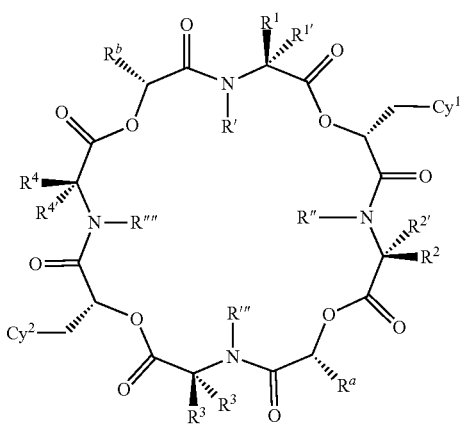

(I)

wherein:
R¹ and R³ are each —CH₂CF(CH₃)₂ and R² and R⁴ are independently C1 or C9; or
R² and R⁴ are each —CH₂CF(CH₃)₂; and R¹ and R³ are independently C1 or C9:

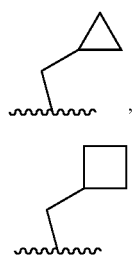

C1

C9

Rᵃ and Rᵇ are each methyl;
R', R'', R''' and R'''' are each methyl; and
Cy¹ and Cy² are independently selected from the group consisting of: Para-fluorophenyl, para-trifluoromethoxyphenyl, para-trifluoromethylphenyl, 3,4,5-trifluorophenyl, para-iodophenyl, para-bromophenyl, p-nitrophenyl, p-tert-butylphenyl, para-SF₅-phenyl, para-aminophenyl,

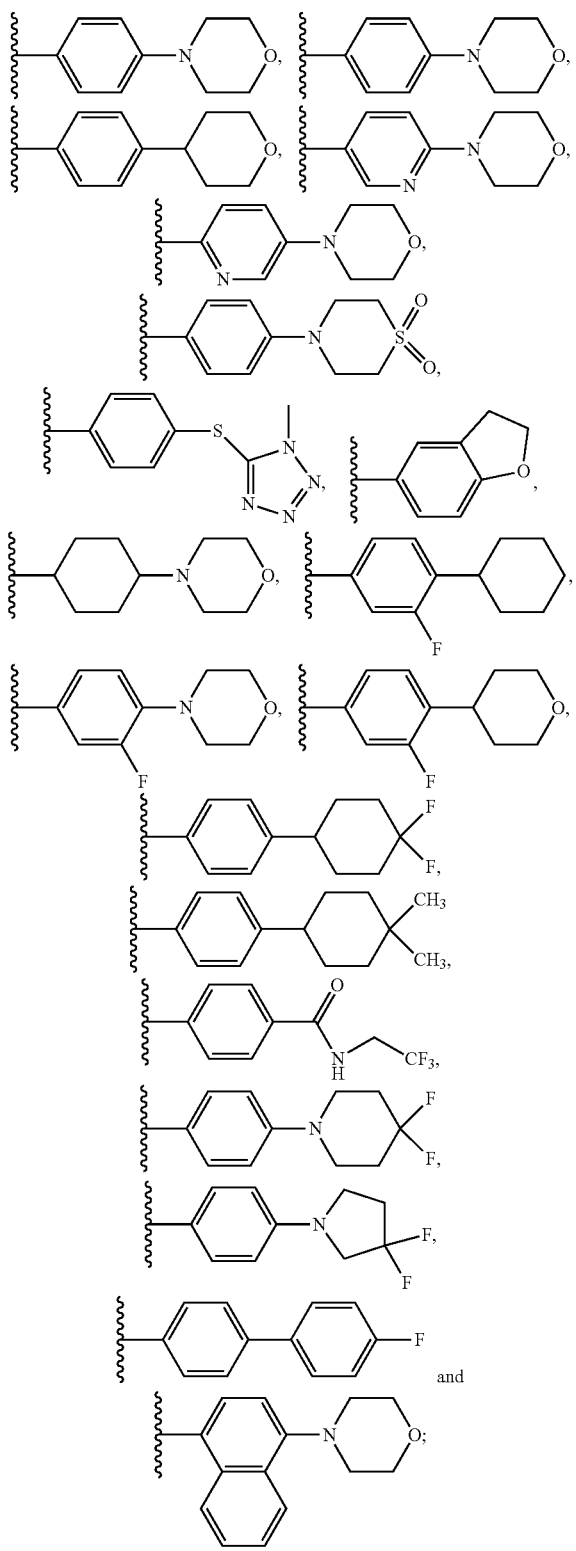

wherein the parasitic infection is caused by an endoparasite selected from group consisting of *Anaplocephala, Ancylostoma, Necator, Ascaris, Brugia, Bunostomum, Capillaria, Chabertia, Cooperia, Cyathostomum, Cylicocyclus, Cylicodontophorus, Cylicostephanus, Craterostomum, Dictyocaulus, Dipe-* talonema, Dipylidium, Dracunculus, Echinococcus, Enterobius, Fasciola, Filaroides, Habronema, Haemonchus, Metastrongylus, Moniezia, Necator, Nematodirus, Nippostrongylus, Oesophagostomum, Onchocerca, Ostertagia, Oxyuris, Parascaris, Schistosoma, Strongylus, Taenia, Toxocara, Strongyloides, Toxascaris, Trichinella, Trichuris, Trichostrongylus, Triodontophorus, Uncinaria and Wuchereria.

* * * * *